(12) United States Patent
Aikens et al.

(10) Patent No.: US 8,597,914 B2
(45) Date of Patent: Dec. 3, 2013

(54) METHOD OF PRODUCING A FERMENTABLE SUGAR

(71) Applicant: Proterro, Inc., Ewing, NJ (US)

(72) Inventors: John Aikens, La Grange Park, IL (US); Robert J. Turner, Aurora, IL (US)

(73) Assignee: Proterro, Inc., Ewing, NJ (US)

( * ) Notice: Subject to any disclaimer, the term of this patent is extended or adjusted under 35 U.S.C. 154(b) by 0 days.

(21) Appl. No.: 13/737,688

(22) Filed: Jan. 9, 2013

(65) Prior Publication Data

US 2013/0115660 A1  May 9, 2013

Related U.S. Application Data

(62) Division of application No. 12/348,887, filed on Jan. 5, 2009, now Pat. No. 8,367,379.

(60) Provisional application No. 61/018,798, filed on Jan. 3, 2008, provisional application No. 61/085,797, filed on Aug. 1, 2008.

(51) Int. Cl.
*C12P 19/12* (2006.01)

(52) U.S. Cl.
USPC ........ 435/100; 435/162; 435/105; 435/320.1; 435/252

(58) Field of Classification Search
None
See application file for complete search history.

(56) References Cited

U.S. PATENT DOCUMENTS

| | | | |
|---|---|---|---|
| 4,879,232 A | 11/1989 | MacDonald | |
| 5,151,347 A | 9/1992 | Delente et al. | |
| 5,162,051 A | 11/1992 | Hoeksema | |
| 5,534,417 A | 7/1996 | Arad et al. | |
| 6,133,034 A | 10/2000 | Strom et al. | |
| 6,632,602 B1 | 10/2003 | Sheen et al. | |
| 6,632,661 B2 | 10/2003 | Wickert | |
| 6,664,095 B1 | 12/2003 | Suryanarayan et al. | |
| 6,682,918 B1 | 1/2004 | Haselkorn et al. | |
| 6,699,696 B2 * | 3/2004 | Woods et al. | 435/161 |
| 6,833,490 B1 | 12/2004 | Goddijn et al. | |
| 7,247,770 B2 | 7/2007 | Goddijn et al. | |
| 7,745,201 B2 | 6/2010 | Melkonian et al. | |
| 7,803,601 B2 | 9/2010 | Nobles, Jr. et al. | |
| 7,973,214 B2 * | 7/2011 | Lee | 800/284 |
| 8,367,379 B2 * | 2/2013 | Aikens et al. | 435/105 |
| 2005/0014239 A1 | 1/2005 | Melis et al. | |
| 2005/0251882 A1 | 11/2005 | D'Ordine et al. | |
| 2007/0134790 A1 | 6/2007 | Gould et al. | |
| 2007/0166266 A1 | 7/2007 | Dillon et al. | |
| 2007/0166449 A1 | 7/2007 | Dillon et al. | |
| 2007/0166797 A1 | 7/2007 | Dillon et al. | |
| 2007/0167396 A1 | 7/2007 | Dillon et al. | |
| 2007/0167397 A1 | 7/2007 | Dillon et al. | |
| 2007/0167398 A1 | 7/2007 | Dillon et al. | |
| 2007/0191303 A1 | 8/2007 | Dillon et al. | |
| 2008/0044850 A1 | 2/2008 | Taylor et al. | |
| 2008/0124756 A1 | 5/2008 | Dillon | |
| 2008/0124767 A1 | 5/2008 | Nobles et al. | |
| 2008/0153080 A1 * | 6/2008 | Woods et al. | 435/4 |
| 2008/0274494 A1 | 11/2008 | Kertz | |
| 2008/0299147 A1 | 12/2008 | Dillon et al. | |
| 2009/0004715 A1 | 1/2009 | Trimbur et al. | |
| 2009/0011480 A1 | 1/2009 | Trimbur et al. | |
| 2009/0023180 A1 | 1/2009 | Dillon | |
| 2009/0035842 A1 | 2/2009 | Trimbur et al. | |
| 2009/0047721 A1 | 2/2009 | Trimbur et al. | |
| 2009/0061493 A1 | 3/2009 | Trimbur et al. | |
| 2009/0069213 A1 | 3/2009 | Avila et al. | |
| 2009/0087890 A1 | 4/2009 | Pyle et al. | |
| 2009/0123977 A1 | 5/2009 | Mendez et al. | |
| 2009/0126260 A1 | 5/2009 | Aravanis et al. | |
| 2009/0148918 A1 | 6/2009 | Trimbur et al. | |
| 2009/0181434 A1 | 7/2009 | Aikens et al. | |
| 2009/0246766 A1 | 10/2009 | Mayfield et al. | |
| 2009/0253169 A1 | 10/2009 | Mayfield et al. | |
| 2009/0269816 A1 | 10/2009 | Mendez et al. | |
| 2009/0274736 A1 | 11/2009 | Dillon et al. | |
| 2009/0280545 A1 | 11/2009 | Mendez et al. | |
| 2009/0285850 A1 | 11/2009 | Dillon et al. | |
| 2009/0291490 A1 | 11/2009 | Spradling | |

(Continued)

FOREIGN PATENT DOCUMENTS

| | | |
|---|---|---|
| SU | 1763484 | 9/1992 |
| WO | WO 98/03637 | 1/1998 |
| WO | WO 2004/076356 | 9/2004 |
| WO | WO 2007/035579 | 3/2007 |
| WO | WO 2007/076449 | 7/2007 |
| WO | WO 2008/042975 | 4/2008 |
| WO | WO 2008/130437 | 10/2008 |
| WO | WO 2009/089185 | 7/2009 |
| WO | WO 2009/111513 | 9/2009 |
| WO | WO 2009/129396 | 10/2009 |
| WO | WO 2010/048525 | 4/2010 |

OTHER PUBLICATIONS

Chen et al. (Nature Biotech), vol. 25, No. 7, Jul. 2007, pp. 759-761).*
Richert et al. (Current Microbiology, vol. 51, 2005, pp. 379-384).*
Dwi et al. (World Journal of Biotech., vol. 17, pp. 259-264, 2001).*
Australian Examination Report No. 1 dated Jun. 21, 2013 in related Application No. AU 2009204313, 5 pages.

(Continued)

*Primary Examiner* — Hope Robinson
(74) *Attorney, Agent, or Firm* — Dentons US LLP

(57) ABSTRACT

Provided herein is a transgenic bacteria engineered to accumulate carbohydrates, for example disaccharides. Also provided is a photobioreactor for cultivating photosynthetic microorganisms comprising a non-gelatinous, solid cultivation support suitable for providing nutrients and moisture to photosynthetic microorganisms and a physical barrier covering at least a portion of the surface of the cultivation support. Devices for the large scale and continuous cultivation of photosynthetic microorganisms incorporating photobioreactors and methods of use are disclosed. Also disclosed are methods of producing fermentable sugar from photosynthetic microorganisms using a photobioreactor of the invention.

20 Claims, 11 Drawing Sheets

(56) References Cited

U.S. PATENT DOCUMENTS

| | | | |
|---|---|---|---|
| 2009/0305942 A1 | 12/2009 | Day et al. |
| 2010/0050301 A1 | 2/2010 | Mendez et al. |
| 2010/0151112 A1 | 6/2010 | Franklin et al. |
| 2010/0151535 A1 | 6/2010 | Franklin et al. |
| 2010/0151538 A1 | 6/2010 | Franklin et al. |
| 2010/0151539 A1 | 6/2010 | Franklin et al. |
| 2010/0151567 A1 | 6/2010 | Franklin et al. |
| 2010/0170144 A1 | 7/2010 | Day et al. |
| 2010/0190235 A1 | 7/2010 | Schuring et al. |
| 2010/0239712 A1 | 9/2010 | Brooks et al. |

OTHER PUBLICATIONS

Cumino et al., Sucrose metabolism: Anabaena sucrose-phosphate synthase and sucrose-phosphate phosphatase define minimal functional domains shuffled during evolution, FEBS Letters, 2002, pp. 19-23, vol. 517.

Abad, Alignment, ATZ24631, Jun. 19, 2008, 8 pages.

Aichi et al., Role of Ntcb in Activation of Nitrate Assimilation Genes in the Cyanobacterium *Synechocystis* sp. Strain PCC 6803, J Bacteriol, 2001, pp. 5840-5847, vol. 183, No. 20.

Aoki et al., Circadian Expression of the *dnaK* Gene in the Cyanobacterium *Synechocystis* sp. Strain PCC 6803, J. Bacteriol., 1995, pp. 5606-5611, vol. 177, No. 19.

Blumwald et al., Studies of Osmoregulation in Salt Adaption of Cyanobacteria with ESR Spin-Probe Techniques, Proc Natl Acad Sci USA, 1983, pp. 2599-2602, vol. 80.

Cumino et al., Carbon Cycling in *Anabaena* sp. PCC 7120. Sucrose Synthesis in the Heterocysts and Possible Role in Nitrogen Fixation, Plant Physiol, 2007, pp. 1385-1397, vol. 143.

Curatti et al., Sucrose is involved in the diazotrophic metabolism of the heterocyst-forming cyanobacterium *Anabaena* sp., FEBS Letters, 2002, pp. 175-178, vol. 513.

Curtis et al., The Transcription Apparatus and the Regulation of Transcription Iinitiation, in The Molecular Biology of Cyanobacteria, Bryant, D. A. (ed), Kluwer Academic Publishers, 2001, pp. 613-639.

Database, GenBank, ABB56840.1, downloaded on Internet at http//www.uniprot.org/uniprot/Q31Q29 accessed Aug. 23, 2011, 4 pages.

Database, GenBank, BAA10782.1, downloaded on Internet at http//www.uniprot.org/uniprot/Q55440 accessed Aug. 23, 2011, 4 pages.

Database, GenBank, AAG31136.1, downloaded on Internet at http//www.uniprot.org/uniprot/P74325 accessed Aug. 23, 2011, 5 pages.

Database, GenBank, AAZ87937.1, downloaded on Internet at http//www.uniprot.org/uniprot/Q3Z2S5 accessed Aug. 23, 2011, 3 pages.

Database, GenBank, BAA18352.1, downloaded on Internet at http//www.uniprot.org/uniprot/P74258 accessed Aug. 23, 2011, 5 pages.

Database, GenBank, AAB41279.1, downloaded on Internet at http//www.uniprot.org/uniprot/Q55034 accessed Aug. 23, 2011, 5 pages.

Database, GenBank, ABU63292.1, downloaded on Internet at http//www.uniprot.org/uniprot/A7TZT2 accessed Aug. 23, 2011, 4 pages.

Database, GenBank, AAK86468.1, downloaded on Internet at URL:http//www.uniprot.org/uniprot/A9CK30 accessed Aug. 23, 2011, 4 pages.

Dillon et al., RNAi as an Experimental and Therapeutic Tool to Study and Regulate Physiological and Disease Processes, Annual Review of Physiology, 2005, pp. 147-173, vol. 67.

Dykxhoorn and Lieberman, The Silent Revolution: RNA Interference As Basic Biology, Research Tool, and Therapeutic, Annual Review of Medicine, 2005, 56:401-423.

Elhai et al., Conjugal Transfer of DNA to Cyanobacteria, Methods in Enzymology, 1988, pp. 747-754, vol. 167.

EMBL-Bank: U51113.1, Cloning vector pBeloBACI1, downloaded on internet at http//www.ebi.ac.uk/ena/data/view/U51113 accessed Aug. 23, 2011, 2 pages.

EMBL-Bank: CS176720.1, Sequence 24 from Patent W02005093080, downloaded on internet at http//www.ebi.ac.uk/enaldatalviewICS176720 accessed Aug. 23, 2011, 2 pages.

Eurasian Search Report dated May 13, 2011 issued in related application EA201070788, filed Jan. 5, 2009, in Russian, 2 pages.

Eurasian Search Report dated May 13, 2011 issued in related application EA201070788, filed Jan. 5, 2009, English translation, 2 pages.

Fanning et al., Gene-expressed RNA as a therapeutic: issues to consider, using ribozymes and small hairpin RNA as specific examples, Handbook Exp Pharmacol., 2006, pp. 289-303, vol. 173.

Ferino et al., A Promoter-Probe Vector-Host System for the Cyanobacterium, *Synechocystis* PCC6803, Gene, 1989, pp. 257-266, vol. 84.

Frey et al., Replication and Copy Number Control of the Broad-Host-Range Plasmid RSF1010, Gene, 1992, pp. 101-106, vol. 113.

Friedberg, Use of Reporter Genes in Cyanobacteria, Methods in Enzymology, 1988, pp. 736-747, vol. 167.

Furste et al., Molecular Cloning of the Plasmid RP4 Primase Region in a Multi-Host-Range *tac*P Expression Vector, Gene, 1986, pp. 119-131, vol. 48.

Ghadessy et al., Directed Evolution of Polymerase Function by Compartmentalized Self-Replication, Proc Natl Acad Sci USA, 2001, pp. 4552-4557, vol. 98, No. 8.

Golden et al., Optimal Conditions for Genetic Transformation of the Cyanobacterium *Anacystis nidulans* R2, Journal of Bacteriology, 1984, pp. 36-42, vol. 158, No. 1.

Golden et al., Expression of a Family of psbA Genes Encoding a Photosystem II Polypeptide in the Cyanobacterium *Anacystis nidulans* R2, EMBO Journal, 1986, pp. 2789-2798, vol. 5, No. 11.

Golden et al., Genetic Engineering of the Cyanobacterial Chromosome, Methods in Enzymology, 1987, pp. 215-231, vol. 153.

Gorelikova, Fundamentals of Modern Food Biotechnology, 2004, Kemerovo, in Russian, 100 pages.

Gormley et al., Transfer of Plasmid RSF1010 by Conjugation from *Escherichia coli* to *Streptomyces lividans* and *Mycobacterium smegmatis*, J Bacteriology, 1991, pp. 6705-6708, vol. 173, No. 21.

Gutierrez et al., Analysis and DNA sequence of the osmoregulated treA gene encoding the periplasmic trehalase of *Escherichia coli* K12, Mol Gen Genet., 1989, pp. 347-54, vol. 217.

Helene et al., Control of Gene Expression by Triple Helix-Forming Oligonucleotides, Ann. N.Y. Acad. Sci., 1992, pp. 27-36, vol. 660.

Hershkovitz et al., Accumulation of Trehalose and Sucrose in Cyanobacteria Exposed to Matric Water Stress, Appl Environ Microbiol, 1991, pp. 645-648, vol. 57, No. 3.

Ikeuchi et al., *Synechocystis* sp. PCC 680—A Useful Tool in the Study of the Genetics of Cyanobacteria, Photosynthesis Research, 2001, pp. 73-83, vol. 70.

International Search Report issued on May 22, 2009, in the related application PCT/US09/30162, 4 pages.

Jahreis et al., Adaptation of Sucrose Metabolism in the *Escherichia coli* Wild-Type Strain EC3132, J. Bacteriol., 2002, pp. 5307-5316, vol. 184, No. 19.

Kaneko et al., Sequence Analysis of the Genome of the Unicellular Cyanobacterium *Synechocystis* sp. Strain PCC6803. II. Sequence Determination of the Entire Genome and Assignment of Potential Protein-coding Regions, DNA Research, 1996, pp. 109-136, vol. 3.

Koksharova et al., Genetic Tools for cyanobacteria, Appl Microbiol Biotechnol, 2002, pp. 123-137, vol. 58, No. 2.

Koo et al., Regulation of Compatible Solute Accumulation in *Salmonella typhimurium*: Evidence for a Glycine Betaine Efflux System, J Gen Microbiol, 1991, pp. 2617-2625, vol. 137.

Kreps et al., Conjugative transfer and autonomous replication of a promiscuous IncQ plasmid in the cyanobacterium *Synechocystis* PCC 6803, Mol Gen Genet, 1990, pp. 129-133, vol. 221.

Kucho et al., Global Analysis of Circadian Expression in the Cyanobacterium *Synechocystis* sp. Strain PCC 6803, J Bacteriol, 2005, pp. 2190-2199, vol. 187, No. 6.

Labarre et al., Insertional Mutagenesis by Random Cloning of Antibiotic Resistance Genes into the Genome of the Cyanobacterium *Synechocystis* Strain PCC 6803, J Bacteriol, 1989, pp. 3449-3457, vol. 171, No. 6.

Lamark et al., Efflux of choline and glycine betaine from osmoregulating cells of *Escherichia coli*, FEMS Microbiol. Lett, 1992, pp. 149-154, vol. 96.

Lee et al., Aptamer Therapeutics Advance, Curr. Opin. Chem. Biol., 2006, pp. 282-289, vol. 10.

Link et al., Beyond Toothpicks: New Methods for Isolating Mutant Bacteria, Nature Reviews, 2007, pp. 680-688, vol. 5.

(56) References Cited

OTHER PUBLICATIONS

Lunn, Evolution of Sucrose Synthesis, Plant Physiol, 2002, pp. 1490-1500, vol. 128.
Ma et al., Exogenous expression of the wheat chloroplastic fructose-1,6-bisphosphatase gene enhances photosynthesis in the transgenic cyanobacterium, *Anabaena* PCC7120, Journal of Applied Phycology, 2005, pp. 273-280, vol. 17.
Machray et al., Characterisation of a Complementary DNA Encoding a Novel Plant Enzyme with Sucrolytic Activity, FEBS Lett, 1994, pp. 123-127, vol. 354.
Maeda et al., *cis*-Acting Sequences Required for NtcB-Dependent, Nitrite-Responsive Positive Regulation of the Nitrate Assimilation Operon in the Cyanobacterium *Synechococcus* sp. Strain PCC 7942, J. Bacteriol., 1998, pp. 4080-4088, vol. 180, No. 16.
Marraccini et al., A Conjugative Plasmid Vector for Promotor Analysis in Several Cyanobacteria of the Genera *Synechococcus* and *Synechocystis*, Plant Molecular Biology, 1993, pp. 905-909, vol. 23.
Mermet-Bouvier et al., A Conditional Expression Vector for the Cyanobacteria *Synechocystis* sp. Strains PCC6803 and PCC6714 or *Synechococcus* sp. Strains PCC7942 and PCC6301, Current Microbiology, 1994, pp. 145-148, vol. 28.
Mexican Official Office Action dated May 30, 2012 in related Application No. MX/a/2010/007319 filed Jan. 5, 2009, includes English translation, 4 pages.
Miao et al., Sucrose Accumulation in Salt-Stressed Cells of *agp* Gene Deletion-Mutant in Cyanobacterium *Synechocystis* sp. PCC6803, FEMS Microbiol. Lett., 2003, pp. 71-77, vol. 218.
Nitsch et al., Auxin-Dependent Growth of Excised *Helianthus tuberosus* Tissues. I., American Journal of Botany, 1956, pp. 839-851, vol. 43.
Pushparaj et al., Short Interfering RNA (siRNA) as a Novel Therapeutic, Clinical and Experimental Pharmacology and Physiology, 2006, pp. 504-510, vol. 33.
Reynolds et al., Rational siRNA Design for RNA Interference, Nature Biotechnology, 2004, pp. 326-330, vol. 22, No. 3.
Rose, The Nucleotide Sequence of pACYC177, Nucleic Acids Res, 1988, p. 356, vol. 16.
Sagner et al., Rapid Filter Assay for the Detection of DNA Polymerase Activity: Direct Identification of the Gene for the DNA Polymerase from *Thermus aquaticus*, Gene, 1991, pp. 119-123, vol. 97.
Sazuka et al., Sequence Features Surrounding the Translation Initiation Sites Assigned on the Genome Sequence of *Synechocystis* sp. Strain PCC6803 by Amino-Terminal Protein Sequencing, DNA Research, 1996, pp. 225-232, vol. 3.
Schleyer et al., Transient, Specific and Extremely Rapid Release of Osmolytes from Growing Cells of *Escherichia coli* K-12 Exposed to Hypoosmotic Shock, Arch Microbiol, 1993, pp. 424-443, vol. 160.
Shi et al., Removal of nitrogen and phosphorus from wastewater using microalgae immobilized on twin layers: an experimental study, J App Phyc, 2007, pp. 417-423, vol. 19.
SU1763484 Published Sep. 23, 1992, abstract only in English, 1 page.
Supplementary European Search Report dated Dec. 20, 2010, issued in related EP Application No. 09700920.3.
Studier, Protein Production by Auto-Induction in High-Density Shaking Cultures, Protein Expr Purif, 2005, pp. 207-234, vol. 41.
Wilson, Preparation of Genomic DNA from Bacteria, in Current Protocols in Molecular Biology, John Wiley and Sons, 1997, 2.4.1-2.4.5.
Zang et al., Optimum Conditions for Transformation of *Synechocystis* sp. PCC 6803, Journal of Microbiology, 2007, pp. 241-245, vol. 45.
Zhang et al., Photosynthetic performance of a cyanobacterium in a vertical flat-plate photobioreactor for outdoor microalgal production and fixation of $CO_2$, Biotechnology Letters, 2001, pp. 21-26, vol. 23.

* cited by examiner

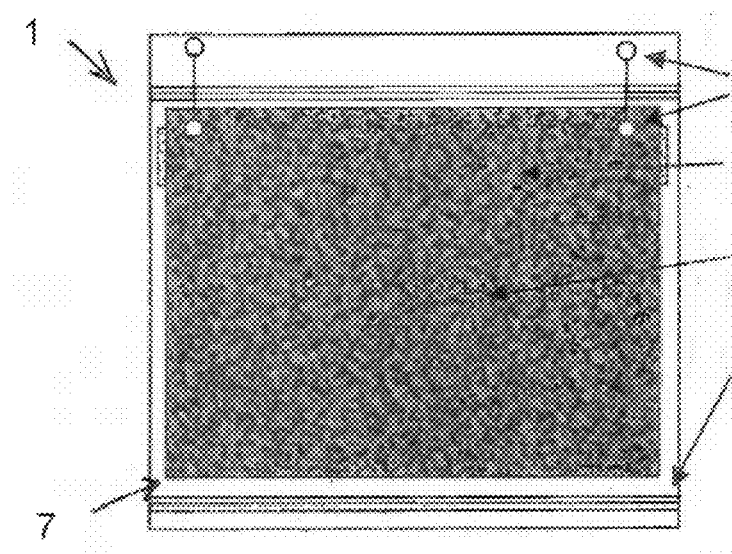
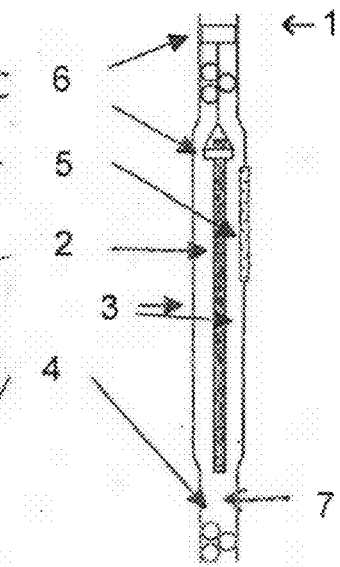
Figure 1                Figure 2
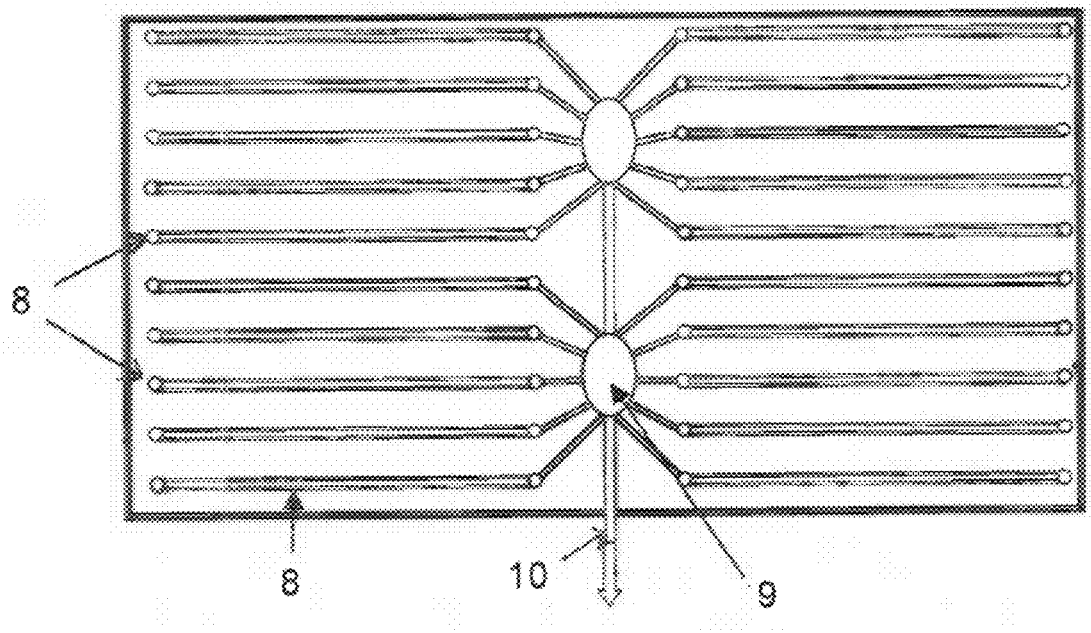
Figure 3

```
Ssp6803_SPS    MSYSSKYILLISVHGLIRGENLELGRDADTGGQTKYVLELARALVKNPQVARVDLLTRLI
Selo7942_ASF   MAAQNLYILHIQTHGLLRGQNLELGRDADTGGQTKYVLELAQAQAKSPQVQQVDIITRQI
Ssp6803_SPP    ------------------------------------------------------------

Ssp6803_SPS    KDPKVDADYAQPRELIGDRAQIVRIECGPEEYIAKEMLWDYLDNFADHALDYLKEQPELP
Selo7942_ASF   TDPRVSVGYSQAIEPFAPKGRIVRLPFGPKRYLRKELLWPHLYTFADAILQYLAQQKRTP
Ssp6803_SPP    ------------------------------------------------------------

Ssp6803_SPS    DVIHSHYADAGYVGTRLSHQLGIPLVHTGHSLGRSKRTRLLLSGIKADEIESRYNMARRI
Selo7942_ASF   TWIQAHYADAGQVGSLLSRWLNVPLIFTGHSLGRIKLKKLLEQDWPLEEIEAQFNIQQRI
Ssp6803_SPP    ------------------------------------------------------------

Ssp6803_SPS    NAEEETLGSAARVITSTHQEIAEQYAQYDYYQPDQMLVIPPGTDLEKFYPPKGNEWETPI
Selo7942_ASF   DAEEMTLTHADWIVASTQQEVEEQYRVYDRYNPERKLVIPPGVDTDRFRFQPLGDRGVVL
Ssp6803_SPP    ------------------------------------------------------------

Ssp6803_SPS    VQELQRFLRHPRKPIILALSRPDPRKNIHKLIAAYGQSPQLQAQANLVIVAGNRDDITDL
Selo7942_ASF   QQELSRFLRDPEKPQILCLCRPAPRKNVPALVRAFGEHPWLRKKANLVLVLGSRQDINQM
Ssp6803_SPP    ------------------------------------------------------------

Ssp6803_SPS    DQGPREVLTDLLLTIDRYDLYGKVAYPKQNQAEDVYALFRLTALSQGVFINPALTEPFGL
Selo7942_ASF   DRGSRQVFQEIFHLVDRYDLYGSVAYPKQHQADDVPEFYRLAAHSGGVFVNPALTEPFGL
Ssp6803_SPP    ------------------------------------------------------------

Ssp6803_SPS    TLIEAAACGVPIVATEDGGPVDIIKNCQNGYLINPLDEVDIADKLLKVLNDKQQWQFLSE
Selo7942_ASF   TILEAGSCGVPVVATHDGGPQEILKHCDFGTLVDVSRPANIATALATLLSDRDLWQCYHR
Ssp6803_SPP    ------------------------------------------------------------

DXDXT
Ssp6803_SPS    SGLEGVKRHYSWPSHVESYLEAINALTQQTSVLKRSDLKRRRTLYYNGALVTSLDQNLLG
Selo7942_ASF   NGIEKVPAHYSWDQHVNTLFERMETVALPRRRAVSFVRSRKRLIDAKRLVVSDIDNTLL-
Ssp6803_SPP    ---------------------------------------------MRQLLLISDLDNTWV-
                                                            :  :::.:*:. :

T
Ssp6803_SPS    ALQGGLPGDRQTLDELLEVLYQHRKNVGFCIATGRRLDSVLKILREYRIPQPDMLITSMG
Selo7942_ASF   -------GDRQGLENLMTYLDQYRDHFAFGIATGRRLDSAQEVLKEWGVPSPNFWVTSVG
Ssp6803_SPP    -------GDQQALEHLQEYLGDRRGNFYLAYATGRSYHSARELQKQVGLMEPDYWLTAVG
                      **:* *:.*   *   *  :. : ****  .*. ::  ::   : .*:  :*::*

Ssp6803_SPS    TEIYSSPDLIPDQSWRNHIDYLWNRNAIVRILGELPGLALQPKEELSAYKISYFYD-AAI
Selo7942_ASF   SEIHYGTDAEPDISWEKHINRNWNPQRIRAVMAQLPFLELQPEEDQTPFKVSFFVR-DRH
Ssp6803_SPP    SEIYHP--EGLDQHWADYLSEHWQRDILQAIADGFEALKPQSPLEQNPWKISYHLDPQAC
                :**:      *   * *.::.  *:  :    :    : *    *.  :  ..:*:*:.

K                          D
Ssp6803_SPS    APNLEEIRQLLHKGEQTVNTIISFGQFLDILPIRASKGYAVRWLSQQWNIPLEHVFTAGG
Selo7942_ASF   ETVLREVRQHLRRHRLRLKSIYSHQEFLDILPLAASKGDAIRHLSLRWRIPLENILVAGD
Ssp6803_SPP    PTVIDQLTEMLKETGIPVQVIFSSGKDVDLLPQRSNKGNATQYLQQHLAMEPSQTLVCGD
                 .  : :: ::   *:.      ::  * *  : *:**   : *  * *  :  ..*.

D
Ssp6803_SPS    SGADEDMMRGNTLSVVVANRHHEELSNLGEIEP--IYFSEKRYAAGILDGLAHYRFFELL
Selo7942_ASF   SGNDEEMLKGHNLGVVVGN-YSPELEPLRSYER--VYFAEGHYANGILEALKHYRFFEAI
Ssp6803_SPP    SGNDIGLFETSARGVIVRNAQPELLHWYDQWGDSRHYRAQSSHAGAILEAIAHFDFLS--
                ** *   ::.   .*:* *    .   *        *  :* .**.: *: *::  :.

Ssp6803_SPS    DPV
Selo7942_ASF   A--
Ssp6803_SPP    ---
```

A
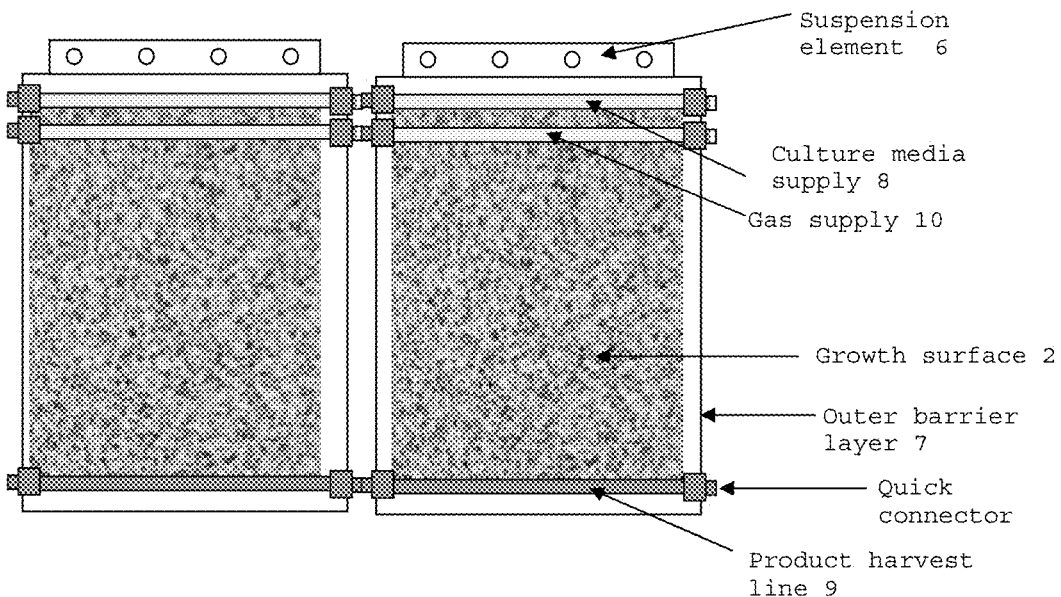
B
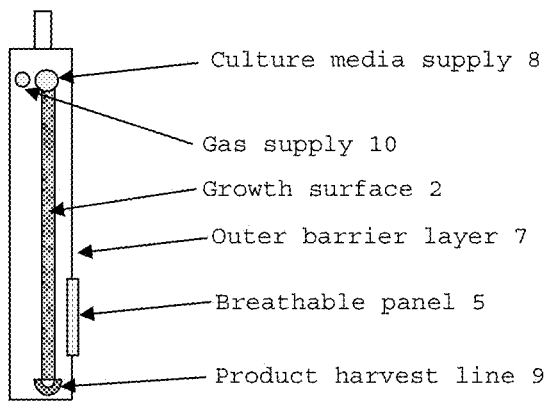
FIG. 12

A 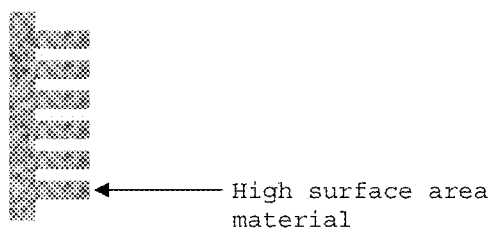 ← High surface area material
B 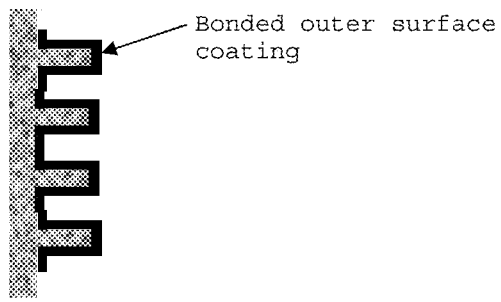 ← Bonded outer surface coating
FIG. 13

SEQUENCE LISTING

<160> NUMBER OF SEQ ID NOS: 138

<210> SEQ ID NO 1
<211> LENGTH: 2204
<212> TYPE: DNA
<213> ORGANISM: Synechococcus PCC7942

<400> SEQUENCE: 1

```
agactacaat tggggcgttt tctgtgaggc tgactagcgc gtggcagctc aaaatctcta      60
cattctgcac attcagaccc atggtctgct gcgagggcag aacttggaac tggggcgaga     120
tgccgacacc ggcgggcaga ccaagtacgt cttagaactg gctcaagccc aagctaaatc     180
cccacaagtc caacaagtcg acatcatcac ccgccaaatc accgaccccc gcgtcagtgt     240
tggttacagt caggcgatcg aacccttttgc gcccaaaggt cggattgtcc gtttgccttt     300
tggccccaaa cgctacctcc gtaaagagct gctttggccc catctctaca cctttgcgga     360
tgcaattctc caatatctgg ctcagcaaaa gcgcaccccg acttggattc aggcccacta     420
tgctgatgct ggccaagtgg gatcactgct gagtcgctgg ttgaatgtac cgctaatttt     480
cacagggcat tctctgggc ggatcaagct aaaaaagctg ttggagcaag actggccgct     540
tgaggaaatt gaagcgcaat tcaatattca acagcgaatt gatgcggagg agatgacgct     600
cactcatgct gactggattg tcgccagcac tcagcaggaa gtggaggagc aataccgcgt     660
ttacgatcgc tacaacccag agcgcaagct tgtcattcca ccgggtgtcg ataccgatcg     720
cttcaggttt cagcccttgg gcgatcgcgg tgttgttctc caacaggaac tgagccgctt     780
tctgcgcgac ccagaaaaac ctcaaattct ctgcctctgt cgccccgcac ctcgcaaaaa     840
tgtaccggcg ctggtgcgag cctttggcga acatccttgg ctgcgcaaaa aagccaacct     900
tgtcttagta ctgggcagcc gccaagacat caaccagatg gatcgcggca gtcggcaggt     960
gttccaagag attttccatc tggtcgatcg ctacgacctc tacggcagcg tcgcctatcc    1020
caaacagcat caggctgatg atgtgccgga gttctatcgc ctagcggctc attccggcgg    1080
ggtattcgtc aatccggcgc tgaccgaacc ttttggtttg acaattttgg aggcaggaag    1140
ctgcggcgtg ccggtggtgg caacccatga tggcggcccc caggaaattc tcaaacactg    1200
tgatttcggc actttagttg atgtcagccg acccgctaat atcgcgactg cactcgccac    1260
cctgctgagc gatcgcgatc tttggcagtg ctatcaccgc aatggcattg aaaaagttcc    1320
cgcccattac agctgggatc aacatgtcaa taccctgttt gagcgcatgg aaacggtggc    1380
tttgcctcgt cgtcgtgctg tcagtttcgt acggagtcgc aaacgcttga ttgatgccaa    1440
acgccttgtc gttagtgaca tcgacaacac actgttgggc gatcgtcaag gactcgagaa    1500
tttaatgacc tatctcgatc agtatcgcga tcattttgcc tttggaattg ccacggggcg    1560
tcgcctagac tctgcccaag aagtcttgaa agagtggggc gttccttcgc caaacttctg    1620
ggtgacttcc gtcggcagcg agattcacta tggcaccgat gctgaaccgg atatcagctg    1680
ggaaaagcat atcaatcgca actggaatcc tcagcgaatt cgggcagtaa tggcacaact    1740
accctttctt gaactgcagc cggaagagga tcaaacaccc ttcaaagtca gcttctttgt    1800
ccgcgatcgc cacgagactg tgctgcgaga agtacggcaa catcttcgcc gccatcgcct    1860
gcggctgaag tcaatctatt cccatcagga gtttcttgac attctgccgc tagctgcctc    1920 gaaagggggat gcgattcgcc acctctcact ccgctggcgg attcctcttg agaacatttt    1980
```

-continued

```
ggtggcaggc gattctggta acgatgagga aatgctcaag ggccataatc tcggcgttgt   2040
agttggcaat tactcaccgg aattggagcc actgcgcagc tacgagcgcg tctatttgc    2100 tgagggccac tatgctaatg gcattctgga agccttaaaa cactatcgct tttttgaggc   2160
gatcgcttaa cctttcaga atgagacgtt gatcggcacg taag                    2204
```

<210> SEQ ID NO 2
<211> LENGTH: 709
<212> TYPE: PRT
<213> ORGANISM: Synechococcus PCC7942

<400> SEQUENCE: 2

```
Met Ala Ala Gln Asn Leu Tyr Ile Leu His Ile Gln Thr His Gly Leu
1               5                   10                  15

Leu Arg Gly Gln Asn Leu Glu Leu Gly Arg Asp Ala Asp Thr Gly Gly
            20                  25                  30

Gln Thr Lys Tyr Val Leu Glu Leu Ala Gln Ala Gln Ala Lys Ser Pro
        35                  40                  45

Gln Val Gln Gln Val Asp Ile Ile Thr Arg Gln Ile Thr Asp Pro Arg
    50                  55                  60

Val Ser Val Gly Tyr Ser Gln Ala Ile Glu Pro Phe Ala Pro Lys Gly
65                  70                  75                  80

Arg Ile Val Arg Leu Pro Phe Gly Pro Lys Arg Tyr Leu Arg Lys Glu
                85                  90                  95

Leu Leu Trp Pro His Leu Tyr Thr Phe Ala Asp Ala Ile Leu Gln Tyr
            100                 105                 110

Leu Ala Gln Gln Lys Arg Thr Pro Thr Trp Ile Gln Ala His Tyr Ala
        115                 120                 125

Asp Ala Gly Gln Val Gly Ser Leu Leu Ser Arg Trp Leu Asn Val Pro
    130                 135                 140

Leu Ile Phe Thr Gly His Ser Leu Gly Arg Ile Lys Leu Lys Lys Leu
145                 150                 155                 160

Leu Glu Gln Asp Trp Pro Leu Glu Glu Ile Glu Ala Gln Phe Asn Ile
                165                 170                 175

Gln Gln Arg Ile Asp Ala Glu Glu Met Thr Leu Thr His Ala Asp Trp
            180                 185                 190

Ile Val Ala Ser Thr Gln Gln Glu Val Glu Glu Gln Tyr Arg Val Tyr
        195                 200                 205

Asp Arg Tyr Asn Pro Glu Arg Lys Leu Val Ile Pro Pro Gly Val Asp
    210                 215                 220

Thr Asp Arg Phe Arg Phe Gln Pro Leu Gly Asp Arg Gly Val Val Leu
225                 230                 235                 240

Gln Gln Glu Leu Ser Arg Phe Leu Arg Asp Pro Glu Lys Pro Gln Ile
                245                 250                 255

Leu Cys Leu Cys Arg Pro Ala Pro Arg Lys Asn Val Pro Ala Leu Val
            260                 265                 270

Arg Ala Phe Gly Glu His Pro Trp Leu Arg Lys Lys Ala Asn Leu Val
        275                 280                 285

Leu Val Leu Gly Ser Arg Gln Asp Ile Asn Gln Met Asp Arg Gly Ser
    290                 295                 300

Arg Gln Val Phe Gln Glu Ile Phe His Leu Val Asp Arg Tyr Asp Leu
305                 310                 315                 320

Tyr Gly Ser Val Ala Tyr Pro Lys Gln His Gln Ala Asp Asp Val Pro
                325                 330                 335
```

```
Glu Phe Tyr Arg Leu Ala Ala His Ser Gly Val Phe Val Asn Pro
                340                 345                 350

Ala Leu Thr Glu Pro Phe Gly Leu Thr Ile Leu Glu Ala Gly Ser Cys
            355                 360                 365

Gly Val Pro Val Val Ala Thr His Asp Gly Pro Gln Glu Ile Leu
    370                 375                 380

Lys His Cys Asp Phe Gly Thr Leu Val Asp Val Ser Arg Pro Ala Asn
385                 390                 395                 400

Ile Ala Thr Ala Leu Ala Thr Leu Leu Ser Asp Arg Asp Leu Trp Gln
                405                 410                 415

Cys Tyr His Arg Asn Gly Ile Glu Lys Val Pro Ala His Tyr Ser Trp
            420                 425                 430

Asp Gln His Val Asn Thr Leu Phe Glu Arg Met Glu Thr Val Ala Leu
        435                 440                 445

Pro Arg Arg Arg Ala Val Ser Phe Val Arg Ser Arg Lys Arg Leu Ile
    450                 455                 460

Asp Ala Lys Arg Leu Val Val Ser Asp Ile Asp Asn Thr Leu Leu Gly
465                 470                 475                 480

Asp Arg Gln Gly Leu Glu Asn Leu Met Thr Tyr Leu Asp Gln Tyr Arg
                485                 490                 495

Asp His Phe Ala Phe Gly Ile Ala Thr Gly Arg Arg Leu Asp Ser Ala
            500                 505                 510

Gln Glu Val Leu Lys Glu Trp Gly Val Pro Ser Pro Asn Phe Trp Val
        515                 520                 525

Thr Ser Val Gly Ser Glu Ile His Tyr Gly Thr Asp Ala Glu Pro Asp
    530                 535                 540

Ile Ser Trp Glu Lys His Ile Asn Arg Asn Trp Asn Pro Gln Arg Ile
545                 550                 555                 560

Arg Ala Val Met Ala Gln Leu Pro Phe Leu Glu Leu Gln Pro Glu Glu
                565                 570                 575

Asp Gln Thr Pro Phe Lys Val Ser Phe Phe Val Arg Asp Arg His Glu
            580                 585                 590

Thr Val Leu Arg Glu Val Arg Gln His Leu Arg Arg His Arg Leu Arg
        595                 600                 605

Leu Lys Ser Ile Tyr Ser His Gln Glu Phe Leu Asp Ile Leu Pro Leu
    610                 615                 620

Ala Ala Ser Lys Gly Asp Ala Ile Arg His Leu Ser Leu Arg Trp Arg
625                 630                 635                 640

Ile Pro Leu Glu Asn Ile Leu Val Ala Gly Asp Ser Gly Asn Asp Glu
                645                 650                 655

Glu Met Leu Lys Gly His Asn Leu Gly Val Val Val Gly Asn Tyr Ser
            660                 665                 670

Pro Glu Leu Glu Pro Leu Arg Ser Tyr Glu Arg Val Tyr Phe Ala Glu
        675                 680                 685

Gly His Tyr Ala Asn Gly Ile Leu Glu Ala Leu Lys His Tyr Arg Phe
    690                 695                 700

Phe Glu Ala Ile Ala
705
```

<210> SEQ ID NO 3
<211> LENGTH: 2163
<212> TYPE: DNA
<213> ORGANISM: Synechocystis PCC6803

<400> SEQUENCE: 3

```
atgagctatt catcaaaata cattttacta attagtgtcc atggtttaat tcggggagaa      60
aaccttgagt tgggcagaga tgccgacacc ggcgggcaaa ccaaatatgt gctggaactg     120
gcccgggcct tggtaaaaaa tccccaggtg gccagggtgg atttgctgac ccgtttaatt     180
aaagatccca agtagatgc agattatgcc cagcctagag aacttattgg cgatcgggcc      240
cagattgttc gcattgagtg cggcccggag gaatatattg ccaaggaaat gctctgggac     300
tatttggata attttgctga ccatgccctg gactatctca agaacagcc cgaactgccc      360
gatgtcatcc atagccatta cgccgatgcg ggttacgtgg caccagact ttctcaccaa      420
ttgggtattc ctttggtgca caccggacat tccctgggtc gtagtaagcg cacccgtctc     480
ctgctcagtg ggattaaagc cgacgaaatt gaaagccgtt acaatatggc ccgccggatt     540
aacgcggagg aagaaaccct aggatcagcg gcgagggtga ttaccagtac ccatcaggaa     600
atcgcagaac agtacgccca atacgactat taccagccag accagatgtt ggttattccc     660
cccggcactg atttagaaaa gttttatccc cccaaaggga acgagtggga aacgcccatt     720
gttcaagagt tgcaacgatt tctacggcat ccccgtaagc ctattatcct cgctttgtcc     780
cgaccggatc cccgcaaaaa tatccataaa ttaattgcag cctatggcca gtccccgcag     840
ttacaggccc aggccaattt ggtcattgtg gcgggcaatc gggatgacat cacgatcta     900
gaccaggggc cgagggaagt actgacggat ttactgttga ccattgaccg ttacgatctc     960
tacggcaaag tggcttaccc caaacagaat caggcggagg atgtgtatgc tttgtttcgc    1020
ctcactgctt tatcccaggg agtatttatc aatccggctt tgacggaacc ctttggttta    1080
actttgattg aagcggcggc ctgtggtgtg cccattgtgg ccacggagga tggggggccg    1140
gtggatatta tcaaaaattg tcagaatggc tatctaatta atcccctcga tgaagtggat    1200
attgcggata aattgctcaa agtactaaac gacaaacaac aatggcaatt cctttctgaa    1260
agtggtctag agggagttaa gcgccattat tcttggcctt cccacgttga agttatttta    1320
gaagccatca acgctctgac ccaacagact tcagtgctga aacgtagtga tttaaagcgg    1380
cggcggactt tgtactataa cggtgccctg gttactagtt tggaccaaaa tttactgggg    1440
gcattacagg ggggattacc gggcgatcgc cagacgttgg acgaattact ggaagtgctg    1500
tatcaacatc gaaaaaatgt cggcttttgc attgccactg ggagaagatt ggattcggtg    1560
ctgaaaattt tgcgggagta tcgcattccc caaccggata tgttgatcac cagcatgggc    1620
acggaaattt attcttcccc ggatttgatc cccgaccaga gttggcgcaa tcacattgat    1680
tatttgtgga accgtaacgc cattgtgcgt attttggggg aattacccgg tttagccctc    1740
caacccaagg aagaactgag cgcctataaa attagctatt tctacgatgc ggcgatcgcc    1800
cctaacctag aagaaattcg gcaactgttg cataaagggg aacaaaccgt aaataccatc    1860
atttcctttg gtcaattttt ggatattctg cccatccgag cttccaaagg ctatgctgtg    1920
cgttggttga gccaacagtg gaatattccc ctggagcacg ttttcaccgc cggaggatcg    1980
ggagccgacg aagatatgat gcggggtaac acccttttccg tcgtcgtggc taaccgtcac    2040
catgaggaac tttctaatct agggggagatc gaaccgattt attttttccga aaaacgttac   2100
gccgccggta ttctggacgg tctggcccat taccgcttct ttgagttgtt agaccccgtt    2160
taa                                                                    2163
```

<210> SEQ ID NO 4
<211> LENGTH: 720
<212> TYPE: PRT

<213> ORGANISM: Synechocystis PCC6803

<400> SEQUENCE: 4

```
Met Ser Tyr Ser Ser Lys Tyr Ile Leu Leu Ile Ser Val His Gly Leu
1               5                   10                  15

Ile Arg Gly Glu Asn Leu Glu Leu Gly Arg Asp Ala Asp Thr Gly Gly
            20                  25                  30

Gln Thr Lys Tyr Val Leu Glu Leu Ala Arg Ala Leu Val Lys Asn Pro
        35                  40                  45

Gln Val Ala Arg Val Asp Leu Leu Thr Arg Leu Ile Lys Asp Pro Lys
    50                  55                  60

Val Asp Ala Asp Tyr Ala Gln Pro Arg Glu Leu Ile Gly Asp Arg Ala
65                  70                  75                  80

Gln Ile Val Arg Ile Glu Cys Gly Pro Glu Glu Tyr Ile Ala Lys Glu
                85                  90                  95

Met Leu Trp Asp Tyr Leu Asp Asn Phe Ala Asp His Ala Leu Asp Tyr
            100                 105                 110

Leu Lys Glu Gln Pro Glu Leu Pro Asp Val Ile His Ser His Tyr Ala
        115                 120                 125

Asp Ala Gly Tyr Val Gly Thr Arg Leu Ser His Gln Leu Gly Ile Pro
    130                 135                 140

Leu Val His Thr Gly His Ser Leu Gly Arg Ser Lys Arg Thr Arg Leu
145                 150                 155                 160

Leu Leu Ser Gly Ile Lys Ala Asp Glu Ile Glu Ser Arg Tyr Asn Met
                165                 170                 175

Ala Arg Arg Ile Asn Ala Glu Glu Thr Leu Gly Ser Ala Ala Arg
            180                 185                 190

Val Ile Thr Ser Thr His Gln Glu Ile Ala Glu Gln Tyr Ala Gln Tyr
            195                 200                 205

Asp Tyr Tyr Gln Pro Asp Gln Met Leu Val Ile Pro Pro Gly Thr Asp
    210                 215                 220

Leu Glu Lys Phe Tyr Pro Pro Lys Gly Asn Glu Trp Glu Thr Pro Ile
225                 230                 235                 240

Val Gln Glu Leu Gln Arg Phe Leu Arg His Pro Arg Lys Pro Ile Ile
                245                 250                 255

Leu Ala Leu Ser Arg Pro Asp Pro Arg Lys Asn Ile His Lys Leu Ile
            260                 265                 270

Ala Ala Tyr Gly Gln Ser Pro Gln Leu Gln Ala Gln Ala Asn Leu Val
        275                 280                 285

Ile Val Ala Gly Asn Arg Asp Asp Ile Thr Asp Leu Asp Gln Gly Pro
    290                 295                 300

Arg Glu Val Leu Thr Asp Leu Leu Leu Thr Ile Asp Arg Tyr Asp Leu
305                 310                 315                 320

Tyr Gly Lys Val Ala Tyr Pro Lys Gln Asn Gln Ala Glu Asp Val Tyr
                325                 330                 335

Ala Leu Phe Arg Leu Thr Ala Leu Ser Gln Gly Val Phe Ile Asn Pro
            340                 345                 350

Ala Leu Thr Glu Pro Phe Gly Leu Thr Leu Ile Glu Ala Ala Ala Cys
        355                 360                 365

Gly Val Pro Ile Val Ala Thr Glu Asp Gly Gly Pro Val Asp Ile Ile
    370                 375                 380

Lys Asn Cys Gln Asn Gly Tyr Leu Ile Asn Pro Leu Asp Glu Val Asp
385                 390                 395                 400

Ile Ala Asp Lys Leu Leu Lys Val Leu Asn Asp Lys Gln Gln Trp Gln
```

```
                        405                 410                 415
Phe Leu Ser Glu Ser Gly Leu Glu Gly Val Lys Arg His Tyr Ser Trp
            420                 425                 430

Pro Ser His Val Glu Ser Tyr Leu Glu Ala Ile Asn Ala Leu Thr Gln
        435                 440                 445

Gln Thr Ser Val Leu Lys Arg Ser Asp Leu Lys Arg Arg Thr Leu
    450                 455                 460

Tyr Tyr Asn Gly Ala Leu Val Thr Ser Leu Asp Gln Asn Leu Leu Gly
465                 470                 475                 480

Ala Leu Gln Gly Gly Leu Pro Gly Asp Arg Gln Thr Leu Asp Glu Leu
                485                 490                 495

Leu Glu Val Leu Tyr Gln His Arg Lys Asn Val Gly Phe Cys Ile Ala
            500                 505                 510

Thr Gly Arg Arg Leu Asp Ser Val Leu Lys Ile Leu Arg Glu Tyr Arg
        515                 520                 525

Ile Pro Gln Pro Asp Met Leu Ile Thr Ser Met Gly Thr Glu Ile Tyr
    530                 535                 540

Ser Ser Pro Asp Leu Ile Pro Asp Gln Ser Trp Arg Asn His Ile Asp
545                 550                 555                 560

Tyr Leu Trp Asn Arg Asn Ala Ile Val Arg Ile Leu Gly Glu Leu Pro
                565                 570                 575

Gly Leu Ala Leu Gln Pro Lys Glu Leu Ser Ala Tyr Lys Ile Ser
            580                 585                 590

Tyr Phe Tyr Asp Ala Ala Ile Ala Pro Asn Leu Glu Glu Ile Arg Gln
        595                 600                 605

Leu Leu His Lys Gly Glu Gln Thr Val Asn Thr Ile Ile Ser Phe Gly
    610                 615                 620

Gln Phe Leu Asp Ile Leu Pro Ile Arg Ala Ser Lys Gly Tyr Ala Val
625                 630                 635                 640

Arg Trp Leu Ser Gln Gln Trp Asn Ile Pro Leu Glu His Val Phe Thr
                645                 650                 655

Ala Gly Gly Ser Gly Ala Asp Glu Asp Met Met Arg Gly Asn Thr Leu
            660                 665                 670

Ser Val Val Ala Asn Arg His His Glu Glu Leu Ser Asn Leu Gly
        675                 680                 685

Glu Ile Glu Pro Ile Tyr Phe Ser Glu Lys Arg Tyr Ala Ala Gly Ile
    690                 695                 700

Leu Asp Gly Leu Ala His Tyr Arg Phe Phe Glu Leu Leu Asp Pro Val
705                 710                 715                 720

<210> SEQ ID NO 5
<211> LENGTH: 735
<212> TYPE: DNA
<213> ORGANISM: Synechocystis PCC6803

<400> SEQUENCE: 5
atgcgacagt tattgctaat ttctgacctg gacaatacct gggtcggaga tcaacaagcc      60
ctggaacatt tgcaagaata tctaggcgat cgccggggaa attttatttt ggcctatgcc     120
acggggcgtt cctaccattc cgcgagggag ttgcaaaaac aggtgggact catggaaccg     180
gactattggc tcaccgcggt ggggagtgaa atttaccatc agaaggcct  ggaccaacat     240 tgggctgatt acctctctga gcattggcaa cgggatatcc tccaggcgat cgccgatggt     300
tttgaggcct aaaaccccca atctcccttg aacaaaaacc catggaaaat tagctatcat     360
ctcgatcccc aggcttgccc caccgtcatc gaccaattaa cggagatgtt gaaggaaacc     420
```

```
ggcatcccgg tgcaggtgat tttcagcagt ggcaaagatg tggatttatt gccccaacgg    480
agtaacaaag gtaacgccac ccaatatctg caacaacatt tagccatgga gccgtctcaa    540
accctggtgt gtggggactc cggcaatgat attggcttat ttgaaacttc cgctcggggt    600
gtcattgtcc gtaatgccca gccggaatta ttgcactggt atgaccaatg ggggattct    660 cgtcattatc gggcccaatc gagccatgct ggcgctatcc tagaggcgat cgcccatttc    720 gatttttga gctga                                                     735
```

```
<210> SEQ ID NO 6
<211> LENGTH: 244
<212> TYPE: PRT
<213> ORGANISM: Synechocystis PCC6803

<400> SEQUENCE: 6
```

```
Met Arg Gln Leu Leu Ile Ser Asp Leu Asp Asn Thr Trp Val Gly
1               5                   10                  15

Asp Gln Gln Ala Leu Glu His Leu Gln Glu Tyr Leu Gly Asp Arg Arg
            20                  25                  30

Gly Asn Phe Tyr Leu Ala Tyr Ala Thr Gly Arg Ser Tyr His Ser Ala
        35                  40                  45

Arg Glu Leu Gln Lys Gln Val Gly Leu Met Glu Pro Asp Tyr Trp Leu
    50                  55                  60

Thr Ala Val Gly Ser Glu Ile Tyr His Pro Glu Gly Leu Asp Gln His
65                  70                  75                  80

Trp Ala Asp Tyr Leu Ser Glu His Trp Gln Arg Asp Ile Leu Gln Ala
                85                  90                  95

Ile Ala Asp Gly Phe Glu Ala Leu Lys Pro Gln Ser Pro Leu Glu Gln
            100                 105                 110

Asn Pro Trp Lys Ile Ser Tyr His Leu Asp Pro Gln Ala Cys Pro Thr
        115                 120                 125

Val Ile Asp Gln Leu Thr Glu Met Leu Lys Glu Thr Gly Ile Pro Val
    130                 135                 140

Gln Val Ile Phe Ser Ser Gly Lys Asp Val Asp Leu Leu Pro Gln Arg
145                 150                 155                 160

Ser Asn Lys Gly Asn Ala Thr Gln Tyr Leu Gln Gln His Leu Ala Met
                165                 170                 175

Glu Pro Ser Gln Thr Leu Val Cys Gly Asp Ser Gly Asn Asp Ile Gly
            180                 185                 190

Leu Phe Glu Thr Ser Ala Arg Gly Val Ile Val Arg Asn Ala Gln Pro
        195                 200                 205

Glu Leu Leu His Trp Tyr Asp Gln Trp Gly Asp Ser Arg His Tyr Arg
    210                 215                 220

Ala Gln Ser Ser His Ala Gly Ala Ile Leu Glu Ala Ile Ala His Phe
225                 230                 235                 240

Asp Phe Leu Ser
```

```
<210> SEQ ID NO 7
<211> LENGTH: 28
<212> TYPE: DNA
<213> ORGANISM: Artificial
<220> FEATURE:
<223> OTHER INFORMATION: primer for amplificaiton of asf

<400> SEQUENCE: 7
```

```
agactacaat tggggcgttt tctgtgag                                       28
```

<210> SEQ ID NO 8
<211> LENGTH: 49
<212> TYPE: DNA
<213> ORGANISM: Artificial
<220> FEATURE:
<223> OTHER INFORMATION: primer for amplificaiton of asf

<400> SEQUENCE: 8
cttacgtgcc gatcaacgtc tcattctgaa aaggttaagc gatcgcctc                49

<210> SEQ ID NO 9
<211> LENGTH: 39
<212> TYPE: DNA
<213> ORGANISM: Artificial
<220> FEATURE:
<223> OTHER INFORMATION: Primer for amplifying cat gene from pBeloBAC11

<400> SEQUENCE: 9
ttatcgcgat cgtcaggagc taaggaagct aaaatggag                           39

<210> SEQ ID NO 10
<211> LENGTH: 29
<212> TYPE: DNA
<213> ORGANISM: Artificial
<220> FEATURE:
<223> OTHER INFORMATION: primer for amplificaiton of cat

<400> SEQUENCE: 10
cgaccaattc acgtgtttga cagcttatc                                      29

<210> SEQ ID NO 11
<211> LENGTH: 811
<212> TYPE: DNA
<213> ORGANISM: Artificial
<220> FEATURE:
<223> OTHER INFORMATION: cat gene amplified from pBeloBAC11

<400> SEQUENCE: 11
ttatcgcgat cgtcaggagc taaggaagct aaaatggaga aaaaaatcac tggatatacc     60
accgttgata tatcccaatg gcatcgtaaa gaacattttg aggcatttca gtcagttgct    120
caatgtacct ataaccagac cgttcagctg gatattacgg cctttttaaa gaccgtaaag    180
aaaaataagc acaagtttta tccggccttt attcacattc ttgcccgcct gatgaatgct    240
catccggaat tccgtatggc aatgaaagac ggtgagctgg tgatatggga tagtgttcac    300
ccttgttaca ccgttttcca tgagcaaact gaaacgtttt catcgctctg gagtgaatac    360
cacgacgatt tccggcagtt tctacacata tattcgcaag atgtggcgtg ttacggtgaa    420
aacctggcct atttccctaa agggtttatt gagaatatgt ttttcgtctc agccaatccc    480
tgggtgagtt tcaccagttt tgatttaaac gtggccaata tggacaactt cttcgccccc    540
gttttcacca tgggcaaata ttatacgcaa ggcgacaagg tgctgatgcc gctggcgatt    600
caggttcatc atgccgtttg tgatggcttc catgtcggca gaatgcttaa tgaattacaa    660
cagtactgcg atgagtggca gggcggggcg taattttttt aaggcagtta ttggtgccct    720
taaacgcctg gttgctacgc ctgaataagt gataataagc ggatgaatgg cagaaattcg    780
atgataagct gtcaaacacg tgaattggtc g                                   811

<210> SEQ ID NO 12
<211> LENGTH: 35
<212> TYPE: DNA
<213> ORGANISM: Artificial
<220> FEATURE:

-continued

```
<223> OTHER INFORMATION: primer for amplifying cat gene bearing the
      promoter from pBeloBAC11

<400> SEQUENCE: 12
ttttggcgat cgtgagacgt tgatcggcac gtaag                              35

<210> SEQ ID NO 13
<211> LENGTH: 29
<212> TYPE: DNA
<213> ORGANISM: Artificial
<220> FEATURE:
<223> OTHER INFORMATION: primer for amplifying cat gene bearing the
      promoter from pBeloBAC11

<400> SEQUENCE: 13
cgaccaattc acgtgtttga cagcttatc                                    29

<210> SEQ ID NO 14
<211> LENGTH: 901
<212> TYPE: DNA
<213> ORGANISM: Artificial
<220> FEATURE:
<223> OTHER INFORMATION: cat gene bearing the promoter amplified from
      pBeloBAC11

<400> SEQUENCE: 14
ttttggcgat cgtgagacgt tgatcggcac gtaagaggtt ccaactttca ccataatgaa    60
ataagatcac taccgggcgt atttttgag ttatcgagat tttcaggagc taaggaagct   120
aaaatggaga aaaaaatcac tggatatacc accgttgata tatcccaatg gcatcgtaaa   180
gaacattttg aggcatttca gtcagttgct caatgtacct ataaccagac cgttcagctg   240
gatattacgg cctttttaaa gaccgtaaag aaaaataagc acaagtttta tccggccttt   300
attcacattc ttgcccgcct gatgaatgct catccggaat tccgtatggc aatgaaagac   360
ggtgagctgg tgatatggga tagtgttcac ccttgttaca ccgttttcca tgagcaaact   420
gaaacgtttt catcgctctg gagtgaatac cacgacgatt tccggcagtt tctacacata   480
tattcgcaag atgtggcgtg ttacggtgaa aacctggcct atttccctaa agggtttatt   540
gagaatatgt ttttcgtctc agccaatccc tgggtgagtt tcaccagttt tgatttaaac   600
gtggccaata tggacaactt cttcgccccc gttttcacca tgggcaaata ttatacgcaa   660
ggcgacaagg tgctgatgcc gctggcgatt caggttcatc atgccgtttg tgatggcttc   720
catgtcggca gaatgcttaa tgaattacaa cagtactgcg atgagtggca gggcggggcg   780
taattttttt aaggcagtta ttggtgccct taaacgcctg gttgctacgc ctgaataagt   840
gataataagc ggatgaatgg cagaaattcg atgataagct gtcaaacacg tgaattggtc   900
g                                                                 901

<210> SEQ ID NO 15
<211> LENGTH: 30
<212> TYPE: DNA
<213> ORGANISM: Artificial
<220> FEATURE:
<223> OTHER INFORMATION: primer for sequence verification of cat/asf

<400> SEQUENCE: 15
gcttctgcgt tctgatttaa tctgtatcag                                   30

<210> SEQ ID NO 16
<211> LENGTH: 27
<212> TYPE: DNA
<213> ORGANISM: Artificial
```

```
<220> FEATURE:
<223> OTHER INFORMATION: primer for sequence verification of cat/asf

<400> SEQUENCE: 16
tatcacttat tcaggcgtag caaccag                                        27

<210> SEQ ID NO 17
<211> LENGTH: 27
<212> TYPE: DNA
<213> ORGANISM: Artificial
<220> FEATURE:
<223> OTHER INFORMATION: primer for sequence verification of cat/asf

<400> SEQUENCE: 17
gtcgttagtg acatcgacaa cacactg                                        27

<210> SEQ ID NO 18
<211> LENGTH: 26
<212> TYPE: DNA
<213> ORGANISM: Artificial
<220> FEATURE:
<223> OTHER INFORMATION: primer for sequence verification of cat/asf

<400> SEQUENCE: 18
gatcgcgata ctgatcgaga taggtc                                         26

<210> SEQ ID NO 19
<211> LENGTH: 10577
<212> TYPE: DNA
<213> ORGANISM: Artificial
<220> FEATURE:
<223> OTHER INFORMATION: Plasmid pLybAL11 containing ASF gene from
      Synechococcus elongatus PCC 7942

<400> SEQUENCE: 19
tgcatgcctg caggtcgact ctagaggatc cccgggtacc gagctcgaat tgggcgtttt       60
tctgtgaggc tgactagcgc gtggcagctc aaaatctcta cattctgcac attcagaccc      120
atggtctgct gcgagggcag aacttggaac tggggcgaga tgccgacacc ggcgggcaga      180
ccaagtacgt cttagaactg gctcaagccc aagctaaatc cccacaagtc aacaagtcg       240 acatcatcac ccgccaaatc accgaccccc gcgtcagtgt tggttacagt caggcgatcg      300 aacccttgc gcccaaaggt cggattgtcc gtttgccttt tggccccaaa cgctacctcc       360
gtaaagagct gctttggccc catctctaca cctttgcgga tgcaattctc caatatctgg      420
ctcagcaaaa gcgcacccg acttggattc aggcccacta tgctgatgct ggccaagtgg      480
gatcactgct gagtcgctgg ttgaatgtac cgctaatttt cacagggcat tctctggggc      540
ggatcaagct aaaaaagctg ttggagcaag actggccgct tgaggaaatt gaagcgcaat      600
tcaatattca acagcgaatt gatgcggagg agatgacgct cactcatgct gactggattg      660
tcgccagcac tcagcaggaa gtggaggagc aataccgcgt ttacgatcgc tacaacccag      720
agcgcaagct tgtcattcca ccgggtgtcg ataccgatcg cttcaggttt cagcccttgg      780
gcgatcgcgg tgttgttctc aacaggaac tgagccgctt tctgcgcgac ccagaaaaac      840
ctcaaattct ctgcctctgt cgccccgcac ctcgcaaaaa tgtaccggcg ctggtgcgag      900
cctttggcga acatccttgg ctgcgcaaaa aagccaacct tgtcttagta ctgggcagcc      960
gccaagacat caaccagatg gatcgcggca gtcggcaggt gttccaagag attttccatc     1020
tggtcgatcg ctacgacctc tacgcagcg tcgcctatcc caaacagcat caggctgatg     1080
atgtgccgga gttctatcgc ctagcggctc attccggcgg ggtattcgtc aatccggcgc     1140
```

```
tgaccgaacc ttttggtttg acaattttgg aggcaggaag ctgcggcgtg ccggtggtgg   1200
caacccatga tggcggcccc caggaaattc tcaaacactg tgatttcggc actttagttg   1260
atgtcagccg acccgctaat atcgcgactg cactcgccac cctgctgagc gatcgcgatc   1320
tttggcagtg ctatcaccgc aatggcattg aaaaagttcc cgcccattac agctgggatc   1380
aacatgtcaa tacccctgttt gagcgcatgg aaacggtggc tttgcctcgt cgtcgtgctg   1440
tcagtttcgt acggagtcgc aaacgcttga ttgatgccaa acgccttgtc gttagtgaca   1500
tcgacaacac actgttgggc gatcgtcaag gactcgagaa tttaatgacc tatctcgatc   1560
agtatcgcga tcatttttgcc tttggaattg ccacggggcg tcgcctagac tctgcccaag   1620
aagtcttgaa agagtggggc gttccttcgc caaacttctg ggtgacttcc gtcggcagcg   1680
agattcacta tggcaccgat gctgaaccgg atatcagctg ggaaaagcat atcaatcgca   1740
actggaatcc tcagcgaatt cgggcagtaa tggcacaact accctttctt gaactgcagc   1800
cggaagagga tcaaacaccc ttcaaagtca gcttctttgt ccgcgatcgc cacgagactg   1860
tgctgcgaga agtacggcaa catcttcgcc gccatcgcct gcggctgaag tcaatctatt   1920
cccatcagga gtttcttgac attctgccgc tagctgcctc gaaaggggat gcgattcgcc   1980
acctctcact ccgctggcgg attcctcttg agaacatttt ggtggcaggc gattctggta   2040
acgatgagga aatgctcaag ggccataatc tcggcgttgt agttggcaat tactcaccgg   2100
aattggagcc actgcgcagc tacgagcgcg tctatttgc tgagggccac tatgctaatg   2160
gcattctgga agccttaaaa cactatcgct tttttgaggc gatcgcttaa cctttcaga   2220 atgagacgtt gatcggcacg taagcgtcag gagctaagga agctaaaatg gagaaaaaaa   2280
tcactggata taccaccgtt gatatatccc aatggcatcg taaagaacat tttgaggcat   2340
ttcagtcagt tgctcaatgt acctataacc agaccgttca gctggatatt acggcctttt   2400
taaagaccgt aaagaaaaat aagcacaagt tttatccggc ctttattcac attcttgccc   2460
gcctgatgaa tgctcatccg gaattccgta tggcaatgaa agacggtgag ctggtgatat   2520
gggatagtgt tcacccttgt tacaccgttt tccatgagca aactgaaacg ttttcatcgc   2580
tctggagtga ataccacgac gatttccggc agtttctaca catatattcg caagatgtgg   2640
cgtgttacgg tgaaaacctg gcctatttcc ctaaagggtt tattgagaat atgttttcg   2700 tctcagccaa tccctgggtg agtttcacca gttttgattt aaacgtgcc aatatggaca   2760 acttcttcgc ccccgttttc accatgggca aatattatac gcaaggcgac aaggtgctga   2820
tgccgctggc gattcaggtt catcatgccg tttgtgatgg cttccatgtc ggcagaatgc   2880
ttaatgaatt acaacagtac tgcgatgagt ggcagggcgg ggcgtaattt ttttaaggca   2940
gttattggtg cccttaaacg cctggttgct acgcctgaat aagtgataat aagcggatga   3000
atggcagaaa ttcgatgata agctgtcaaa cacaaccacc atcaaacagg attttcgcct   3060 gctgggcaa accagcgtgg accgcttgct gcaactctct cagggccagg cggtgaaggg   3120
caatcagctg ttgcccgtct cactggtgaa aagaaaaacc accctggcgc ccaatacgca   3180
aaccgcctct ccccgcgcgt tggccgattc attaatgcag ctggcacgac aggtttcccg   3240
actggaaagc gggcagtgag cgcaacgcaa ttaatgtaag ttagcgcgaa ttgcaagctg   3300
gccgacgcgc tgggctacgt cttgctggcg ttcgggagca aagagcata catctggaag   3360 caaagccagg aaagcggcct atggagctgt gcggcagcgc tcagtaggca atttttcaaa   3420
atattgttaa gccttttctg agcatggtat ttttcatggt attaccaatt agcaggaaaa   3480
taagccattg aatataaaag ataaaaatgt cttgtttaca atagagtggg ggggtcagc   3540
```

```
ctgccgcctt gggccgggtg atgtcgtact tgcccgccgc gaactcggtt accgtccagc    3600
ccagcgcgac cagctccggc aacgcctcgc gcacccgctt gcggcgcttg cgcatggtcg    3660
aaccactggc ctctgacggc cagacatagc cgcacaaggt atctatggaa gccttgccgg    3720
ttttgccggg gtcgatccag ccacacagcc gctggtgcag caggcgggcg gtttcgctgt    3780
ccagcgcccg cacctcgtcc atgctgatgc gcacatgctg gccgccaccc atgacggcct    3840
gcgcgatcaa ggggttcagg gccacgtaca ggcgcccgtc cgcctcgtcg ctggcgtact    3900
ccgacagcag ccgaaacccc tgccgcttgc ggccattctg ggcgatgatg gataccttcc    3960
aaaggcgctc gatgcagtcc tgtatgtgct tgagcgcccc accactatcg acctctgccc    4020
cgatttcctt tgccagcgcc cgatagctac ctttgaccac atggcattca gcggtgacgg    4080
cctcccactt gggttccagg aacagccgga gctgccgtcc gccttcggtc ttgggttccg    4140
ggccaagcac taggccatta ggcccagcca tggccaccag cccttgcagg atgcgcagat    4200
catcagcgcc cagcggctcc gggccgctga actcgatccg cttgccgtcg ccgtagtcat    4260
acgtcacgtc cagcttgctg cgcttgcgct cgccccgctt gagggcacgg aacaggccgg    4320
gggccagaca gtcgccgggt cgtgccgga cgtggctgag gctgtgcttg ttcttaggct    4380
tcaccacggg gcaccccctt gctcttgcgc tgcctctcca gcacggcggg cttgagcacc    4440
ccgccgtcat gccgcctgaa ccaccgatca gcgaacggtg cgccatagtt ggccttgctc    4500
acaccgaagc ggacgaagaa ccggcgctgg tcgtcgtcca caccccattc ctcggcctcg    4560
gcgctggtca tgctcgacag gtaggactgc cagcggatgt tatcgaccag taccgagctg    4620
ccccggctgg cctgctgctg gtcgcctgcg cccatcatgg ccgcgccctt gctggcatgg    4680
tgcaggaaca cgatagagca cccggtatcg gcggcgatgg cctccatgcg accgatgacc    4740
tgggccatgg ggccgctggc gttttcttcc tcgatgtgga accggcgcag cgtgtccagc    4800
accatcaggc ggcggccctc ggcggcgcgc ttgaggccgt cgaaccactc cggggccatg    4860
atgttgggca ggctgccgat cagcggctgg atcagcaggc cgtcagccac ggcttgccgt    4920
tcctcggcgc tgaggtgcgc cccaaggggcg tgcaggcggt gatgaatggc ggtgggcggg    4980
tcttcggcgg gcaggtagat caccgggccg gtgggcagtt cgcccacctc cagcagatcc    5040
ggcccgcctg caatctgtgc ggccagttgc agggccagca tggatttacc ggcaccaccg    5100
ggcgacacca gcgccccgac cgtaccggcc accatgttgg gcaaaacgta gtccagcggt    5160
ggcggcgctg ctgcgaacgc ctccagaata ttgataggct tatgggtagc cattgattgc    5220
ctcctttgca ggcagttggt ggttaggcgc tggcggggtc actaccccccg ccctgcgccg    5280
ctctgagttc ttccaggcac tcgcgcagcg cctcgtattc gtcgtcggtc agccagaact    5340
tgcgctgacg catcccttttg gccttcatgc gctcggcata tcgcgcttgg cgtacagcgt    5400
cagggctggc cagcaggtcg ccggtctgct tgtccttttg gtctttcata tcagtcaccg    5460
agaaacttgc cggggccgaa aggcttgtct tcgcggaaca aggacaaggt gcagccgtca    5520
aggttaaggc tggccatatc agcgactgaa aagcggccag cctcggcctt gtttgacgta    5580
taaccaaagc caccgggcaa ccaatagccc ttgtcacttt tgatcaggta gaccgaccct    5640
gaagcgcttt tttcgtattc cataaaaccc ccttctgtgc gtgagtactc atagtataac    5700
aggcgtgagt accaacgcaa gcactacatg ctgaaatctg gcccgcccct gtccatgcct    5760
cgctggcggg gtgccggtgc ccgtgccagc tcggcccgcg caagctggac gctgggcaga    5820
cccatgacct tgctgacggt gcgctcgatg taatccgctt cgtggccggg cttgcgctct    5880
gccagcgctg ggctggcctc ggccatggcc ttgccgattt cctcggcact gcggccccgg    5940
```

```
ctggccagct tctgcgcggc gataaagtcg cacttgctga ggtcatgacc gaagcgcttg    6000
accagcccgg ccatctcgct gcggtactcg tccagcgccg tgcgccggtg gcggctaagc    6060
tgccgctcgg gcagttcgag gctggccagc ctgcgggcct tctcctgctg ccgctgggcc    6120
tgctcgatct gctggccagc ctgctgcacc agcgccgggc cagcggtggc ggtcttgccc    6180
ttggattcac gcagcagcac ccacggctga taaccggcgc gggtggtgtg cttgtccttg    6240
cggttggtga agcccgccaa gcggccatag tggcggctgt cggcgctggc cgggtcggcg    6300
tcgtactcgc tggccagcgt ccgggcaatc tgccccgaa gttcaccgcc tgcggcgtcg    6360
gccaccttga cccatgcctg atagttcttc gggctggttt ccactaccag ggcaggctcc    6420
cggccctcgg ctttcatgtc atccaggtca aactcgctga ggtcgtccac cagcaccaga    6480
ccatgccgct cctgctcggc gggcctgata tacacgtcat tgccctgggc attcatccgc    6540
ttgagccatg gcgtgttctg gagcacttcg gcggctgacc attcccggtt catcatctgg    6600
ccggtgggtg cgtccctgac gccgatatcg aagcgctcac agcccatggc cttgagctgt    6660
cggcctatgg cctgcaaagt cctgtcgttc ttcatcgggc caccaagcgc agccagatcg    6720
agccgtcctc ggttgtcagt ggcgtcaggt cgagcaagag caacgatgcg atcagcagca    6780
ccaccgtagg catcatggaa gccagcatca cggttagcca tagcttccag tgccaccccc    6840
gcgacgcgct ccgggcgctc tgcgcggcgc tgctcacctc ggcggctacc tcccgcaact    6900 cttttggccag ctccacccat gccgccctg tctggcgctg ggctttcagc cactccgccg    6960
cctgcgcctc gctggcctgc ttggtctggc tcatgacctg ccgggcttcg tcggccagtg    7020
tcgccatgct ctgggccagc ggttcgatct gctccgctaa ctcgttgatg cctctggatt    7080
tcttcactct gtcgattgcg ttcatggtct attgcctccc ggtattcctg taagtcgatg    7140
atctgggcgt tggcggtgtc gatgttcagg gccacgtctg cccggtcggt gcggatgccc    7200
cggccttcca tctccaccac gttcggcccc aggtgaacac cggcaggcg ctcgatgccc    7260 tgcgcctcaa gtgttctgtg gtcaatgcgg gcgtcgtggc cagcccgctc taatgcccgg    7320
ttggcatggt cggcccatgc ctcgcgggtc tgctcaagcc atgccttggg cttgagcgct    7380
tcggtcttct gtgccccgcc cttctccggg gtcttgccgt tgtaccgctt gaaccactga    7440
gcggcgggcc gctcgatgcc gtcattgatc cgctcggaga tcatcaggtg gcagtgcggg    7500
ttctcgccgc caccggcatg gatggccagc gtatacggca ggcgctcggc accggtcagg    7560
tgctgggcga actcggacgc cagcgccttc tgctggtcga gggtcagctc gaccggcagg    7620
gcaaattcga cctccttgaa cagccgccca ttggcgcgtt catacaggtc ggcagcatcc    7680
cagtagtcgg cgggccgctc gacgaactcc ggcatgtgcc cggattcggc gtgcaagact    7740
tcatccatgt cgcgggcata cttgccttcg cgctggatgt agtcggcctt ggccctggcc    7800
gattggccgc ccgacctgct gccggttttc gccgtaaggt gataaatcgc catgctgcct    7860
cgctgttgct tttgcttttc ggctccatgc aatggccctc ggagagcgca ccgcccgaag    7920
ggtggccgtt aggccagttt ctcgaagaga aaccggtaag tgcgccctcc cctacaaagt    7980
agggtcggga ttgccgccgc tgtgcctcca tgatagccta cgagacagca cattaacaat    8040
ggggtgtcaa gatggttaag gggagcaaca aggcggcgga tcggctggcc aagctcgaag    8100
aacaacgagc gcgaatcaat gccgaaattc agcgggagcg ggcaagggaa cagcagcaag    8160
agcgcaagaa cgaaacaagg cgcaaggtgc tggtgggggc catgattttg gccaaggtga    8220
acagcagcga gtgccggag gatcggctca tggcggcaat ggatgcgtac cttgaacgcg    8280
accacgaccg cgccttgttc ggtctgccgc cacgccagaa ggatgagccg ggctgaatga    8340
```

-continued

```
tcgaccgaga caggccctgc ggggctgcac acgcgccccc acccttcggg taggggaaa      8400
ggccgctaaa gcggctaaaa gcgctccagc gtatttctgc ggggtttggt gtggggttta      8460
gcgggctttg cccgcctttc ccctgccgc gcagcggtgg ggcggtgtgt agcctagcgc      8520
agcgaataga ccagctatcc ggcctctggc cgggcatatt gggcaagggc agcagcgccc      8580
cacaagggcg ctgataaccg cgcctagtgg attattctta gataatcatg gatggatttt      8640
tccaacaccc cgccagcccc cgccctgct gggtttgcag gtttggggc gtgacagtta       8700
ttgcaggggt tcgtgacagt tattgcaggg gggcgtgaca gttattgcag gggttcgtga      8760
cagttagtac gggagtgacg ggcactggct ggcaatgtct agcaacggca ggcatttcgg      8820
ctgagggtaa aagaactttc cgctaagcga tagactgtat gtaaacacag tattgcaagg      8880
acgcggaaca tgcctcatgt ggcggccagg acggccagcc gggatcggga tactggtcgt      8940
taccagagcc accgacccga gcaaaccctt ctctatcaga tcgttgacga gtattacccg      9000
gcattcgctg cgcttatggc agagcaggga aaggaattgc cgggctatgt gcaacgggaa      9060
tttgaagaat ttctccaatg cgggcggctg gagcatggct ttctacgggt tcgctgcgag      9120
tcttgccacg ccgagcacct ggtcgctttc agaaatcaat ctaaagtata tatgagtaaa      9180
cttggtctga cagttaccaa tgcttaatca gtgaggcacc tatctcagcg atctgtctat      9240
ttcgttcatc catagttgcc tgactccccg tcgtgtagat aactacgata cgggagggct      9300
taccatctgg ccccagtgct gcaatgatac cgcgagaccc acgctcaccg gctccagatt      9360
tatcagcaat aaaccagcca gccggaaggg ccgagcgcag aagtggtcct gcaactttat      9420
ccgcctccat ccagtctatt aattgttgcc gggaagctag agtaagtagt tcgccagtta      9480
atagtttgcg caacgttgtt gccattgcta caggcatcgt ggtgtcacgc tcgtcgtttg      9540
gtatggcttc attcagctcc ggttcccaac gatcaaggcg agttacatga tcccccatgt      9600
tgtgcaaaaa agcggttagc tccttcggtc ctccgatcgt tgtcagaagt aagttggccg      9660
cagtgttatc actcatggtt atggcagcac tgcataattc tcttactgtc atgccatccg      9720
taagatgctt ttctgtgact ggtgagtact caaccaagtc attctgagaa tagtgtatgc      9780
ggcgaccgag ttgctcttgc ccggcgtcaa cacgggataa taccgcgcca catagcagaa      9840
ctttaaaagt gctcatcatt ggaaaacgtt cttcggggcg aaaactctca aggatcttac      9900
cgctgttgag atccagttcg atgtaaccca ctcgtgcacc caactgatct tcagcatctt      9960
ttactttcac cagcgtttct gggtgagcaa aaacaggaag gcaaaatgcc gcaaaaaagg     10020
gaataagggc gacacggaaa tgttgaatac tcatactctt cctttttcaa tattattgaa     10080
gcatttatca gggttattgt ctcatgagcg gatacatatt tgaatgtatt tagaaaaata     10140
aacaaaagag tttgtagaaa cgcaaaaagg ccatccgtca ggatggcctt ctgcttaatt     10200
tgatgcctgg cagtttatgg cgggcgtcct gcccgccacc ctccgggccg ttgcttcgca     10260
acgttcaaat ccgctcccgg cggatttgtc tactcagga gagcgttcac cgacaaacaa      10320
cagataaaac gaaaggccca gtctttcgac tgagcctttc gttttatttg atgcctggca     10380
gttccctact ctcgcatggg gagacccac actaccatcg gcgctacggc gtttcacttc      10440
tgagttcggc atggggtcag gtgggaccac cgcgctactg ccgccaggca aattctgttt     10500
tatcagaccg cttctgcgtt ctgatttaat ctgtatcagg ctgaaaatct tctctcatcc     10560
gccaaaacag ccaagct                                                   10577
```

<210> SEQ ID NO 20
<211> LENGTH: 10667
<212> TYPE: DNA

<213> ORGANISM: Artificial
<220> FEATURE:
<223> OTHER INFORMATION: Plasmid pLybAL12 containing asf gene from
      Synechococcus elongatus PCC 7942

<400> SEQUENCE: 20

| | | | | | |
|---|---|---|---|---|---|
| tgcatgcctg | caggtcgact | ctagaggatc | cccgggtacc | gagctcgaat | tggggcgttt | 60 |
| tctgtgaggc | tgactagcgc | gtggcagctc | aaaatctcta | cattctgcac | attcagaccc | 120 |
| atggtctgct | gcgagggcag | aacttggaac | tggggcgaga | tgccgacacc | ggcgggcaga | 180 |
| ccaagtacgt | cttagaactg | gctcaagccc | aagctaaatc | cccacaagtc | caacaagtcg | 240 |
| acatcatcac | ccgccaaatc | accgaccccc | gcgtcagtgt | tggttacagt | caggcgatcg | 300 |
| aacccttttgc | gcccaaaggt | cggattgtcc | gtttgccttt | tggccccaaa | cgctacctcc | 360 |
| gtaaagagct | gctttggccc | catctctaca | cctttgcgga | tgcaattctc | caatatctgg | 420 |
| ctcagcaaaa | gcgcaccccg | acttggattc | aggcccacta | tgctgatgct | ggccaagtgg | 480 |
| gatcactgct | gagtcgctgg | ttgaatgtac | cgctaatttt | cacagggcat | tctctggggc | 540 |
| ggatcaagct | aaaaaagctg | ttggagcaag | actggccgct | tgaggaaatt | gaagcgcaat | 600 |
| tcaatattca | acagcgaatt | gatgcggagg | agatgacgct | cactcatgct | gactggattg | 660 |
| tcgccagcac | tcagcaggaa | gtggaggagc | aataccgcgt | ttacgatcgc | tacaacccag | 720 |
| agcgcaagct | tgtcattcca | ccgggtgtcg | ataccgatcg | cttcaggttt | cagcccttgg | 780 |
| gcgatcgcgg | tgttgttctc | caacaggaac | tgagccgctt | tctgcgcgac | ccagaaaaac | 840 |
| ctcaaattct | ctgcctctgt | cgccccgcac | ctcgcaaaaa | tgtaccggcg | ctggtgcgag | 900 |
| cctttggcga | catccttgg | ctgcgcaaaa | aagccaacct | tgtcttagta | ctgggcagcc | 960 |
| gccaagacat | caaccagatg | gatcgcggca | gtcggcaggt | gttccaagag | attttccatc | 1020 |
| tggtcgatcg | ctacgacctc | tacggcagcg | tcgcctatcc | caaacagcat | caggctgatg | 1080 |
| atgtgccgga | gttctatcgc | ctagcggctc | attccggcgg | ggtattcgtc | aatccggcgc | 1140 |
| tgaccgaacc | ttttggtttg | acaattttgg | aggcaggaag | ctgcggcgtg | ccggtggtgg | 1200 |
| caacccatga | tggcggcccc | caggaaattc | tcaaacactg | tgatttcggc | actttagttg | 1260 |
| atgtcagccg | acccgctaat | atcgcgactg | cactcgccac | cctgctgagc | gatcgcgatc | 1320 |
| tttggcagtg | ctatcaccgc | aatggcattg | aaaaagttcc | cgcccattac | agctgggatc | 1380 |
| aacatgtcaa | taccctgttt | gagcgcatgg | aaacggtggc | tttgcctcgt | cgtcgtgctg | 1440 |
| tcagtttcgt | acggagtcgc | aaacgcttga | ttgatgccaa | acgccttgtc | gttagtgaca | 1500 |
| tcgacaacac | actgttgggc | gatcgtcaag | gactcgagaa | tttaatgacc | tatctcgatc | 1560 |
| agtatcgcga | tcattttgcc | tttgaaattg | ccacggggcg | tcgcctagac | tctgcccaag | 1620 |
| aagtcttgaa | agagtggggc | gttccttcgc | caaacttctg | ggtgacttcc | gtcggcagcg | 1680 |
| agattcacta | tggcaccgat | gctgaaccgg | atatcagctg | ggaaaagcat | atcaatcgca | 1740 |
| actggaatcc | tcagcgaatt | cgggcagtaa | tggcacaact | accctttctt | gaactgcagc | 1800 |
| cggaagagga | tcaaacaccc | ttcaaagtca | gcttctttgt | ccgcgatcgc | cacgagactg | 1860 |
| tgctgcgaga | agtacggcaa | catcttcgcc | gccatcgcct | gcggctgaag | tcaatctatt | 1920 |
| cccatcagga | gtttcttgac | attctgccgc | tagctgcctc | gaaaggggat | gcgattcgcc | 1980 |
| acctctcact | ccgctggcgg | attcctcttg | agaacatttg | gtggcaggc | gattctggta | 2040 |
| acgatgagga | aatgctcaag | ggccataatc | tcggcgttgt | agttggcaat | tactcaccgg | 2100 |
| aattggagcc | actgcgcagc | tacgagcgcg | tctattttgc | tgagggccac | tatgctaatg | 2160 |
| gcattctgga | agccttaaaa | cactatcgct | ttttgaggc | gatcgcttaa | ccttttcaga | 2220 |

```
atgagacgtt gatcggcacg taagcgtgag acgttgatcg gcacgtaaga ggttccaact    2280
ttcaccataa tgaaataaga tcactaccgg gcgtattttt tgagttatcg agattttcag    2340
gagctaagga agctaaaatg gagaaaaaaa tcactggata taccaccgtt gatatatccc    2400
aatggcatcg taaagaacat tttgaggcat tcagtcagt tgctcaatgt acctataacc     2460
agaccgttca gctggatatt acggccttt taaagaccgt aaagaaaaat aagcacaagt     2520
tttatccggc ctttattcac attcttgccc gcctgatgaa tgctcatccg gaattccgta    2580
tggcaatgaa agacggtgag ctggtgatat gggatagtgt tcacccttgt tacaccgttt    2640
tccatgagca aactgaaacg ttttcatcgc tctggagtga ataccacgac gatttccggc    2700
agtttctaca catatattcg caagatgtgg cgtgttacgg tgaaaacctg gcctatttcc    2760
ctaaagggtt tattgagaat atgttttttcg tctcagccaa tccctgggtg agtttcacca    2820
gttttgattt aaacgtggcc aatatggaca acttcttcgc ccccgttttc accatgggca    2880
aatattatac gcaaggcgac aaggtgctga tgccgctggc gattcaggtt catcatgccg    2940
tttgtgatgg cttccatgtc ggcagaatgc ttaatgaatt acaacagtac tgcgatgagt    3000
ggcagggcgg ggcgtaattt ttttaaggca gttattggtg cccttaaacg cctggttgct    3060
acgcctgaat aagtgataat aagcggatga atggcagaaa ttcgatgata agctgtcaaa    3120
cacaaccacc atcaaacagg attttcgcct gctggggcaa accagcgtgg accgcttgct    3180
gcaactctct cagggccagg cggtgaaggg caatcagctg ttgcccgtct cactggtgaa    3240
aagaaaaacc accctggcgc ccaatacgca aaccgcctct ccccgcgcgt tggccgattc    3300
attaatgcag ctggcacgac aggtttcccg actggaaagc gggcagtgag cgcaacgcaa    3360
ttaatgtaag ttagcgcgaa ttgcaagctg gccgacgcgc tgggctacgt cttgctggcg    3420
ttcgggagca gaagagcata catctggaag caaagccagg aaagcggcct atggagctgt    3480
gcggcagcgc tcagtaggca atttttcaaa atattgttaa gccttttctg agcatggtat    3540
ttttcatggt attaccaatt agcaggaaaa taagccattg aatataaaag ataaaaatgt    3600
cttgtttaca atagagtggg gggggtcagc ctgccgcctt gggccgggtg atgtcgtact    3660
tgcccgccgc gaactcggtt accgtccagc ccagcgcgac cagctccggc aacgcctcgc    3720
gcacccgctt gcggcgcttg cgcatggtcg aaccactggc ctctgacggc cagacatagc    3780
cgcacaaggt atctatggaa gccttgccgg ttttgccggg gtcgatccag ccacacagcc    3840
gctggtgcag caggcgggcg gtttcgctgt ccagcgcccg cacctcgtcc atgctgatgc    3900
gcacatgctg gccgccaccc atgacggcct gcgcgatcaa ggggttcagg gccacgtaca    3960 ggcgccgtc cgcctcgtcg ctggcgtact ccgacagcag ccgaaacccc tgccgcttgc     4020
ggccattctg ggcgatgatg gataccttcc aaaggcgctc gatgcagtcc tgtatgtgct    4080
tgagcgcccc accactatcg acctctgccc cgatttcctt tgccagcgcc cgatagctac    4140
ctttgaccac atggcattca gcggtgacgg cctcccactt gggttccagg aacagccgga    4200
gctgccgtcc gccttcggtc ttgggttccg ggccaagcac taggccatta ggcccagcca    4260
tggccaccag cccttgcagg atgcgcagat catcagcgcc cagcggctcc gggccgctga    4320
actcgatccg cttgccgtcg ccgtagtcat acgtcacgtc cagcttgctg cgcttgcgct    4380
cgccccgctt gagggcacgg aacaggccgg gggccagaca gtgcgccggg tcgtgccgga    4440
cgtggctgag gctgtgcttg ttcttaggct tcaccacggg gcacccccttt gctcttgcgc    4500 tgcctctcca gcacggcggg cttgagcacc ccgccgtcat gccgcctgaa ccaccgatca    4560
gcgaacggtg cgccatagtt ggccttgctc acaccgaagc ggacgaagaa ccggcgctgg    4620
```

```
tcgtcgtcca cacccaattc ctcggcctcg gcgctggtca tgctcgacag gtaggactgc   4680
cagcggatgt tatcgaccag taccgagctg ccccggctgg cctgctgctg gtcgcctgcg   4740
cccatcatgg ccgcgccctt gctggcatgg tgcaggaaca cgatagagca cccggtatcg   4800
gcggcgatgg cctccatgcg accgatgacc tgggccatgg ggccgctggc gttttcttcc   4860
tcgatgtgga accggcgcag cgtgtccagc accatcaggc ggcggccctc ggcggcgcgc   4920
ttgaggccgt cgaaccactc cggggccatg atgttgggca ggctgccgat cagcggctgg   4980
atcagcaggc cgtcagccac ggcttgccgt tcctcggcgc tgaggtgcgc cccaagggcg   5040
tgcaggcggt gatgaatggc ggtgggcggg tcttcggcgg gcaggtagat caccgggccg   5100
gtgggcagtt cgcccacctc cagcagatcc ggcccgcctg caatctgtgc ggccagttgc   5160
agggccagca tggatttacc ggcaccaccg ggcgacacca gcgccccgac cgtaccggcc   5220
accatgttgg gcaaaacgta gtccagcggt ggcggcgctg ctgcgaacgc ctccagaata   5280
ttgataggct tatgggtagc cattgattgc ctcctttgca ggcagttggt ggttaggcgc   5340
tggcggggtc actaccccg ccctgcgccg ctctgagttc ttccaggcac tcgcgcagcg   5400
cctcgtattc gtcgtcggtc agccagaact tgcgctgacg catcccttty gccttcatgc   5460
gctcggcata tcgcgcttgg cgtacagcgt cagggctggc cagcaggtcg ccggtctgct   5520
tgtccttttg gtctttcata tcagtcaccg agaaacttgc cggggccgaa aggcttgtct   5580
tcgcggaaca aggacaaggt gcagccgtca aggttaaggc tggccatatc agcgactgaa   5640
aagcggccag cctcggcctt gtttgacgta taaccaaagc caccgggcaa ccaatagccc   5700
ttgtcacttt tgatcaggta gaccgaccct gaagcgcttt tttcgtattc cataaaaccc   5760
ccttctgtgc gtgagtactc atagtataac aggcgtgagt accaacgcaa gcactacatg   5820
ctgaaatctg gcccgcccct gtccatgcct cgctggcggg gtgccggtgc ccgtgccagc   5880
tcggcccgcg caagctggac gctgggcaga cccatgacct tgctgacggt gcgctcgatg   5940
taatccgctt cgtggccggg cttgcgctct gccagcgctg ggctggcctc ggccatggcc   6000
ttgccgattt cctcggcact gcggcccgg ctggccagct tctgcgcggc gataaagtcg   6060
cacttgctga ggtcatgacc gaagcgcttg accagcccgg ccatctcgct gcggtactcg   6120
tccagcgccg tgcgccggtg gcggctaagc tgccgctcgg gcagttcgag gctgccagc   6180 ctgcgggcct tctcctgctg ccgctgggcc tgctcgatct gctggccagc ctgctgcacc   6240
agcgccgggc cagcggtggc ggtcttgccc ttggattcac gcagcagcac ccacggctga   6300
taaccggcgc gggtggtgtg cttgtccttg cggttggtga agcccgccaa gcggccatag   6360
tggcggctgt cggcgctggc cgggtcggcg tcgtactcgc tggccagcgt ccgggcaatc   6420
tgcccccgaa gttcaccgcc tgcggcgtcg gccaccttga cccatgcctg atagttcttc   6480
gggctggttt ccactaccag ggcaggctcc cggccctcgg ctttcatgtc atccaggtca   6540
aactcgctga ggtcgtccac cagcaccaga ccatgccgct cctgctcggc gggcctgata   6600
tacacgtcat tgccctgggc attcatccgc ttgagccatg gcgtgttctg gagcacttcg   6660
gcggctgacc attcccggtt catcatctgg ccggtgggtg cgtccctgac gccgatatcg   6720
aagcgctcac agcccatggc cttgagctgt cggcctatgg cctgcaaagt cctgtcgttc   6780
ttcatcgggc caccaagcgc agccagatcg agccgtcctc ggttgtcagt ggcgtcaggt   6840
cgagcaagag caacgatgcg atcagcagca ccaccgtagg catcatggaa gccagcatca   6900
cggttagcca tagcttccag tgccacccccc gcgacgcgct ccgggcgctc tgcgcggcgc   6960
tgctcacctc ggcggctacc tcccgcaact ctttggccag ctccacccat gccgcccctg   7020
```

```
tctggcgctg ggcttcagc cactccgccg cctgcgcctc gctggcctgc ttggtctggc    7080
tcatgacctg ccgggcttcg tcggccagtg tcgccatgct ctgggccagc ggttcgatct    7140
gctccgctaa ctcgttgatg cctctggatt tcttcactct gtcgattgcg ttcatggtct    7200
attgcctccc ggtattcctg taagtcgatg atctgggcgt tggcggtgtc gatgttcagg    7260
gccacgtctg cccggtcggt gcggatgccc cggccttcca tctccaccac gttcggcccc    7320
aggtgaacac cgggcaggcg ctcgatgccc tgcgcctcaa gtgttctgtg gtcaatgcgg    7380
gcgtcgtggc cagcccgctc taatgcccgg ttggcatggt cggcccatgc ctcgcgggtc    7440
tgctcaagcc atgccttggg cttgagcgct tcggtcttct gtccccgcc cttctccggg     7500
gtcttgccgt tgtaccgctt gaaccactga gcggcgggcc gctcgatgcc gtcattgatc    7560
cgctcggaga tcatcaggtg gcagtgcggg ttctcgccgc caccggcatg gatggccagc    7620
gtatacggca ggcgctcggc accggtcagt tgctgggcga actcggacgc cagcgccttc    7680
tgctggtcga gggtcagctc gaccggcagg gcaaattcga cctccttgaa cagccgccca    7740
ttggcgcgtt catacaggtc ggcagcatcc cagtagtcgg cgggccgctc gacgaactcc    7800
ggcatgtgcc cggattcggc gtgcaagact tcatccatgt cgcgggcata cttgccttcg    7860
cgctggatgt agtcggcctt ggccctggcc gattggccgc ccgacctgct gccggttttc    7920
gccgtaaggt gataaatcgc catgctgcct cgctgttgct tttgcttttc ggctccatgc    7980
aatggccctc ggagagcgca ccgcccgaag ggtggccgtt aggccagttt ctcgaagaga    8040
aaccggtaag tgccgccctcc cctacaaagt agggtcggga ttgccgccgc tgtgcctcca    8100
tgatagccta cgagacagca cattaacaat ggggtgtcaa gatggttaag gggagcaaca    8160
aggcggcgga tcgctggcc aagctcgaag aacaacgagc gcgaatcaat gccgaaattc      8220
agcgggagcg ggcaagggaa cagcagcaag agcgcaagaa cgaaacaagg cgcaaggtgc    8280
tggtgggggc catgattttg gccaaggtga acagcagcga gtggccggag gatcggctca    8340
tggcggcaat ggatgcgtac cttgaacgcg accacgaccg cgccttgttc ggtctgccgc    8400
cacgccagaa ggatgagccg ggctgaatga tcgaccgaga caggccctgc ggggctgcac    8460
acgcgccccc acccttcggg tagggggaaa ggccgctaaa gcggctaaaa gcgctccagc    8520
gtatttctgc ggggtttggt gtggggttta gcgggctttg cccgcctttc ccctgccgc     8580
gcagcggtgg ggcggtgtgt agcctagcgc agcgaataga ccagctatcc ggcctctggc    8640
cgggcatatt gggcaagggc agcagcgccc cacaagggcg ctgataaccg cgcctagtgg    8700
attattctta gataatcatg gatggatttt tccaacaccc cgccagcccc cgccctgct     8760
gggtttgcag gtttggggc gtgacagtta ttgcaggggt tcgtgacagt tattgcaggg    8820
gggcgtgaca gttattgcag gggttcgtga cagttagtac gggagtgacg ggcactggct    8880
ggcaatgtct agcaacggca ggcatttcgg ctgagggtaa aagaactttc cgctaagcga    8940
tagactgtat gtaaacacag tattgcaagg acgcggaaca tgcctcatgt ggcggccagg    9000
acggccagcc gggatcggga tactggtcgt taccagagcc accgacccga gcaaacccttt   9060
ctctatcaga tcgttgacga gtattacccg gcattcgctg cgcttatggc agagcaggga    9120
aaggaattgc cgggctatgt gcaacgggaa tttgaagaat ttctccaatg cgggcggctg    9180
gagcatggct ttctacgggt tcgctgcgag tcttgccacg ccgagcacct ggtcgctttc    9240
agaaatcaat ctaaagtata tatgagtaaa cttggtctga cagttaccaa tgcttaatca    9300
gtgaggcacc tatctcagcg atctgtctat ttcgttcatc catagttgcc tgactccccg    9360
tcgtgtagat aactacgata cgggagggct taccatctgg ccccagtgct gcaatgatac    9420
```

-continued

```
cgcgagaccc acgctcaccg gctccagatt tatcagcaat aaaccagcca gccggaaggg    9480
ccgagcgcag aagtggtcct gcaactttat ccgcctccat ccagtctatt aattgttgcc    9540
gggaagctag agtaagtagt tcgccagtta atagtttgcg caacgttgtt gccattgcta    9600
caggcatcgt ggtgtcacgc tcgtcgtttg gtatggcttc attcagctcc ggttcccaac    9660
gatcaaggcg agttacatga tcccccatgt tgtgcaaaaa agcggttagc tccttcggtc    9720
ctccgatcgt tgtcagaagt aagttggccg cagtgttatc actcatggtt atggcagcac    9780
tgcataattc tcttactgtc atgccatccg taagatgctt ttctgtgact ggtgagtact    9840
caaccaagtc attctgagaa tagtgtatgc ggcgaccgag ttgctcttgc ccggcgtcaa    9900
cacgggataa taccgcgcca catagcagaa ctttaaaagt gctcatcatt ggaaaacgtt    9960
cttcggggcg aaaactctca aggatcttac cgctgttgag atccagttcg atgtaaccca   10020
ctcgtgcacc caactgatct tcagcatctt ttactttcac cagcgtttct gggtgagcaa   10080
aaacaggaag gcaaaatgcc gcaaaaaagg gaataagggc gacacggaaa tgttgaatac   10140
tcatactctt cctttttcaa tattattgaa gcatttatca gggttattgt ctcatgagcg   10200
gatacatatt tgaatgtatt tagaaaaata acaaaagag tttgtagaaa cgcaaaaagg    10260
ccatccgtca ggatggcctt ctgcttaatt tgatgcctgg cagtttatgg cgggcgtcct   10320
gcccgccacc ctccgggccg ttgcttcgca acgttcaaat ccgctcccgg cggatttgtc   10380
ctactcagga gagcgttcac cgacaaacaa cagataaaac gaaaggccca gtctttcgac   10440
tgagcctttc gttttatttg atgcctggca gttccctact ctcgcatggg gagaccccac   10500
actaccatcg gcgctacggc gtttcacttc tgagttcggc atggggtcag gtgggaccac   10560
cgcgctactg ccgccaggca aattctgttt tatcagaccg cttctgcgtt ctgatttaat   10620
ctgtatcagg ctgaaaatct tctctcatcc gccaaaacag ccaagct                 10667
```

```
<210> SEQ ID NO 21
<211> LENGTH: 28
<212> TYPE: DNA
<213> ORGANISM: Artificial
<220> FEATURE:
<223> OTHER INFORMATION: primer for amplifying Synechocystis spp. PCC
      6803 pyrR (SphI/KpnI)

<400> SEQUENCE: 21
cggtgtgcat gccgttattg atggaatg                                           28

<210> SEQ ID NO 22
<211> LENGTH: 32
<212> TYPE: DNA
<213> ORGANISM: Artificial
<220> FEATURE:
<223> OTHER INFORMATION: primer for amplifying Synechocystis spp. PCC
      6803 pyrR (SphI/KpnI)

<400> SEQUENCE: 22
tcactaggta cctaaattac ctgggaagcc ag                                      32

<210> SEQ ID NO 23
<211> LENGTH: 474
<212> TYPE: DNA
<213> ORGANISM: Synechocystis PCC6803

<400> SEQUENCE: 23
cggtgtgcat gccgttattg atggaatggg aagaagcaat ggtcacaata aactggaggt       60
tatgggtatg ttttttagcc ctaatgctcc aatcgccttg attgtatcga atgatgcagt      120
```

```
ctctaaaatt gtatccgtaa aagacctctg caccgccgac gggtctggat tatgggcaat    180
aatcacagtc gagccagact acccctggag gtaaactccg gggctggagc cataaagatt    240
aggaattcat taagaaatgt aacaatcgac gttctagatc ataccacgcc cccactgtcc    300
ggcagggtga acagaggaga ctttcccctg ttacagtgtc agtgacaaaa caactttttg    360
gcatcggtgc aggtggtgag ccatggcggc ccagatcatt gaaattcttt ccccggagga    420
aatccgacgt acccttaccc gtctggcttc ccaggtaatt taggtaccta gtga          474
```

<210> SEQ ID NO 24
<211> LENGTH: 35
<212> TYPE: DNA
<213> ORGANISM: Artificial
<220> FEATURE:
<223> OTHER INFORMATION: primer for amplifying Synechocystis spp. PCC
      6803 nirA (SphI/KpnI)

<400> SEQUENCE: 24

```
cccaaggcat gcaggaaaac aagctcagaa tgctg                                35
```

<210> SEQ ID NO 25
<211> LENGTH: 42
<212> TYPE: DNA
<213> ORGANISM: Artificial
<220> FEATURE:
<223> OTHER INFORMATION: primer for amplifying Synechocystis spp. PCC
      6803 nirA (SphI/KpnI)

<400> SEQUENCE: 25

```
tttattggta ccaacgcttc aagccagata acagtagaga tc                        42
```

<210> SEQ ID NO 26
<211> LENGTH: 384
<212> TYPE: DNA
<213> ORGANISM: Synechocystis PCC6803

<400> SEQUENCE: 26

```
cccaaggcat gcaggaaaac aagctcagaa tgctgcgggg agaagggcaa ctccccacca    60
gccccaaatt tttgctggcg ataaatattt ttcggtttaa ttgttcacaa agcttttga    120 atttgagttt atagaaattt attggctggt aatgctttt tgcccccctg caggacttca    180
ttgatccttg cctataccat caatatcatt ggtcaataat gatgatgatt gactaaaaca    240
tgtttaacaa aatttaacgc atatgctaaa tgcgtaaact gcatatgcct tggctgagtg    300
taatttacgt tacaaatttt aacgaaacgg gaaccctata ttgatctcta ctgttatctg    360
gcttgaagcg ttggtaccaa taaa                                          384
```

<210> SEQ ID NO 27
<211> LENGTH: 26
<212> TYPE: DNA
<213> ORGANISM: Artificial
<220> FEATURE:
<223> OTHER INFORMATION: primer for amplifying Synechococcus elongatus
      PCC 7942 psbAII (SphI/KpnI)

<400> SEQUENCE: 27

```
atctttgcgt tccgtgacgg ctactg                                          26
```

<210> SEQ ID NO 28
<211> LENGTH: 25
<212> TYPE: DNA
<213> ORGANISM: Artificial
<220> FEATURE:

<223> OTHER INFORMATION: primer for amplifying Synechococcus elongatus
PCC 7942 psbAII (SphI/KpnI)

<400> SEQUENCE: 28
gcagatggta ccggtcagca gagtg                                          25

<210> SEQ ID NO 29
<211> LENGTH: 676
<212> TYPE: DNA
<213> ORGANISM: Synechococcus PCC7942

<400> SEQUENCE: 29
atctttgcgt tccgtgacgg ctactgccag catgccgagc ctgatgtgtg acacctaaga    60
tcactccagt tctctttgga aactggctga tgagtgaaga caccatcttt ggcaagatca   120
tccggcgcga gattccagca gacattgttt atgaagatga tctctgtctg gcttttcgag   180
atgtggcacc ccaagcgccg gttcacattc tggtgattcc caagcaacca attgccaacc   240
ttttggaagc gacagcagaa catcaagcgc tgctgggtca tttgttgctg actgtaaagg   300
cgatcgcggc caagaagga ctcaccgagg gctaccgcac cgtgattaac acgggccctg    360
cgggtgggca aaccgtttac cacctgcata ttcacttact gggcgggcga tcgctggctt   420
ggccgcccgg ctgagaaaag tctgaaagtt ctttacaaaa ctcaatctgc ttgttagatt   480
ttactcacga ggctattaag tctcgtaaat agttcaacta aggactcatc gcaaaatgac   540
gactgcattg cagcggcgcg agagcgccag cctgtggcag cagttctgcg agtgggtaac   600
cagcaccgac aaccgcctct atgtgggttg gttcggcgtg ctgatgatcc ccactctgct   660
gaccggtacc atctgc                                                  676

<210> SEQ ID NO 30
<211> LENGTH: 40
<212> TYPE: DNA
<213> ORGANISM: Artificial
<220> FEATURE:
<223> OTHER INFORMATION: primer for amplifying Synechococcus elongatus
PCC 7942 nirA

<400> SEQUENCE: 30
cagccagcat gcataaattt ctgttttgac caaaccatcc                          40

<210> SEQ ID NO 31
<211> LENGTH: 34
<212> TYPE: DNA
<213> ORGANISM: Artificial
<220> FEATURE:
<223> OTHER INFORMATION: primer for amplifying Synechococcus elongatus
PCC 7942 nirA

<400> SEQUENCE: 31
gtggctggta ccatggattc atctgcctac aaag                                34

<210> SEQ ID NO 32
<211> LENGTH: 579
<212> TYPE: DNA
<213> ORGANISM: Synechococcus PCC7942

<400> SEQUENCE: 32
cagccagcat gcataaattt ctgttttgac caaaccatcc cgacataact cggtcagggc    60
ttgcaaaaca gcggggatgc gatcgtgctg ccagagactg caaaggtgag ccaataacca   120
ctgcgtctgc cagtcatcag gtatcgcttg gcagcgctgc aacccagctt cgaggacgcg   180
aacatcaact gttttggcca gttgctgaac ctgtcgccaa caatgttcaa aatcaccgct   240

```
tggccagccg tcactctctg caaacgctgc atcagtcatg tgcaatcaat acaggttaaa      300
aaccatgcta atggctccac ctaagcgggc ttcagagtca aggcttgtag caattgctac      360
taaaaactgc gatcgctgct gaaatgagct ggaattctgt ccctctcagc tcaaaaagta      420
tcaatgatta cttaatgttt gttctgcgca aacttcttgc agaacatgca tgatttacaa      480
aaagttgtag tttctgttac caattgcgaa tcgagaactg cctaatctgc cgagtatgca      540
agctgctttg taggcagatg aatccatggt accagccac                             579
```

```
<210> SEQ ID NO 33
<211> LENGTH: 35
<212> TYPE: DNA
<213> ORGANISM: Artificial
<220> FEATURE:
<223> OTHER INFORMATION: primer for amplifying gammaPR (XbaI/KpnI)

<400> SEQUENCE: 33
gtgcattcta gatggctacg agggcagaca gtaag                                 35
```

```
<210> SEQ ID NO 34
<211> LENGTH: 50
<212> TYPE: DNA
<213> ORGANISM: Artificial
<220> FEATURE:
<223> OTHER INFORMATION: primer for amplifying gammaPR (XbaI/KpnI)

<400> SEQUENCE: 34
ttctgtggta ccatatggat cctccttctt aagatgcaac cattatcacc                 50
```

```
<210> SEQ ID NO 35
<211> LENGTH: 1186
<212> TYPE: DNA
<213> ORGANISM: Artificial
<220> FEATURE:
<223> OTHER INFORMATION: gammaPR (XbaI/KpnI) promoter

<400> SEQUENCE: 35
gtgcattcta gatggctacg agggcagaca gtaagtggat ttaccataat cccttaattg      60
tacgcaccgc taaaacgcgt tcagcgcgat cacggcagca gacaggtaaa aatggcaaca      120
aaccacccta aaaactgcgc gatcgcgcct gataaatttt aaccgtatga ataccctatgc     180 aaccagaggg tacaggccac attaccccca cttaatccac tgaagctgcc atttttcatg     240
gtttcaccat cccagcgaag ggccatgcat gcatcgaaat taatacgacg aaattaatac     300
gactcactat agggcaattg ttatcagcta tgcgccgacc agaacacctt gccgatcagc     360
caaacgtctc ttcaggccac tgactagcga taactttccc cacaacggaa caactctcac     420
tgcatgggat cattgggtac tgtgggttta gtggttgtaa aaacacctga ccgctatccc     480
tgatcagttt cttgaaggta aactcatcac ccccaagtct ggctatgcag aaatcacctg     540
gctcaacagc ctgctcaggg tcaacgagaa ttaacattcc gtcaggaaag cttggcttgg    600
agcctgttgg tgcggtcatg gaattacctt caacctcaag ccagaatgca gaatcactgg   660 cttcttggt tgtgcttacc catctctccg catcaccttt ggtaaaggtt ctaagcttag     720
gtgagaacat ccctgcctga acatgagaaa aaacagggta ctcatactca cttctaagtg    780
acggctgcat actaaccgct tcatacatct cgtagatttc tctggcgatt gaagggctaa    840
attcttcaac gctaactttg agaattttttg taagcaatgc ggcgttataa gcatttaatg   900
cattgatgcc attaaataaa gcaccaacgc ctgactgccc catccccatc ttgtctgcga    960
cagattcctg ggataagcca agttcatttt tcttttttttc ataaattgct ttaaggcgac   1020
```

```
gtgcgtcctc aagctgctct tgtgttaatg gtttctttt tgtgctcata cgttaaatct    1080
atcaccgcaa gggataaata tctaacaccg tgcgtgttga ctattttacc tctggcggtg    1140
ataatggttg catcttaaga aggaggatcc atatggtacc acagaa                  1186
```

<210> SEQ ID NO 36
<211> LENGTH: 31
<212> TYPE: DNA
<213> ORGANISM: Artificial
<220> FEATURE:
<223> OTHER INFORMATION: primer for amplifying Synechocystis spp. PCC
      6803 dnaK (SphI/KpnI)

<400> SEQUENCE: 36

```
gccccagcat gcaccagtaa acataaatct c                                    31
```

<210> SEQ ID NO 37
<211> LENGTH: 30
<212> TYPE: DNA
<213> ORGANISM: Artificial
<220> FEATURE:
<223> OTHER INFORMATION: primer for amplifying Synechocystis spp. PCC
      6803 dnaK (SphI/KpnI)

<400> SEQUENCE: 37

```
attggtggta ccgaggtcaa tcccaacaac                                      30
```

<210> SEQ ID NO 38
<211> LENGTH: 895
<212> TYPE: DNA
<213> ORGANISM: Synechocystis PCC6803

<400> SEQUENCE: 38

```
gccccagcat gcaccagtaa acataaatct ccccggcgac gcaaaaaacg ggtgaccatc     60
aagccggtgc gcttcggcat ttttctgctt tgcctagcag gcattgtggg gggggcaact    120
gccctaatta tcaatcgtac tggcgatccc ctaggtgggt tgctagaaga ccccctagat    180
gttttcctgg accaaccttc agaatttatc cccgatgaag ccacgagccg gaatttgatt    240
ctcagtcaac ccaacttcaa tcagcaagtg ggtcagatgg tagtacaagg ctggcttgat    300
agtaaaaagt tagcctttgg ccaaaaactac gatgtcgggg cattgcagag tgttttagcc    360
cccaatctcc ttgcccaaca acggggtcgg gcccaacggg atcaagccca aaaggtctat    420
caccaatacg aacacaagtt gcagattta gcctatcaag ttaaccccca agaccccaac    480
cgagccaccg ttactgcccg ggtagaagaa attagccagc cctttaccct aggtaatcaa    540
cagcagaagg gctccgccac caaagatgac ttgactgtgc gctatcagct agtacgacac    600 caagggggttt ggaaaattga ccaaatacaa gtggtaaatg gccccgtta gtgcgtggcg    660 ttaactcccc ttttgaccaa tggcatacgg ctagatgccc ccataggtac ggaaacctgc    720
acttccgaga actaagcccc taccgtcact ataagagtgt gaacgtgtcg gccccaggca    780
atggattgga accatggctt ttcggcccat cgttgtgtct tatattctta cttgttaacg    840
ggagttaatt aaaattatgg gaaaagttgt tgggattgac ctcggtacca ccaat         895
```

<210> SEQ ID NO 39
<211> LENGTH: 28
<212> TYPE: DNA
<213> ORGANISM: Artificial
<220> FEATURE:
<223> OTHER INFORMATION: primer for amplifying Synechocystis spp. PCC
      6803 kiaA (SphI/KpnI)

```
<400> SEQUENCE: 39
gccagagcat gcaaagctca ctaactgg                                          28

<210> SEQ ID NO 40
<211> LENGTH: 31
<212> TYPE: DNA
<213> ORGANISM: Artificial
<220> FEATURE:
<223> OTHER INFORMATION: primer for amplifying Synechocystis spp. PCC
      6803 kiaA (SphI/KpnI)

<400> SEQUENCE: 40
ggaaaaggta cctgagtcta tgggcaacgt g                                      31

<210> SEQ ID NO 41
<211> LENGTH: 603
<212> TYPE: DNA
<213> ORGANISM: Synechocystis PCC6803

<400> SEQUENCE: 41
gccagagcat gcaaagctca ctaactgggc gggattttcc gggtccggtt gctgacggta       60
atagtcgtct aaaagtttgg ccacatccaa aaggctgtcg gcggggggat gctggccggc      120
gaggggatta ttctgcttg tcatatacaa aaattgtaaa aatggaggg cggcgatcag        180 gggcttagac acccaaatcc tagccaaaaa gggttaacta gccaagggct atccatgggc     240
aaagagataa aagaaaaagt ctccaaatcc ctggtcatag agaaaaaatt gccaaagtta     300
ccccaggcca tacacggccc agcgccaaga tggggagcac aaattcaaac tttgtaaaca     360
ggccggaagc tatccggcca aggagcactc agattgtgtt aacgttcagg ggagttgctt     420
aacacaattt tccaattaat agtattaata ttttcttaac ttgcaccgta ccatggtgag     480
aaagcctatc tgagcccttta tttgattaac cttcgactga ttattgatcc cctgtgcagt    540
ctcccctctc cctctgtctt tttgctcccg aacacgttgc ccatagactc aggtaccttt    600
tcc                                                                   603

<210> SEQ ID NO 42
<211> LENGTH: 30
<212> TYPE: DNA
<213> ORGANISM: Artificial
<220> FEATURE:
<223> OTHER INFORMATION: primer for sequence analysis of pLybAL

<400> SEQUENCE: 42
gcttctgcgt tctgatttaa tctgtatcag                                       30

<210> SEQ ID NO 43
<211> LENGTH: 27
<212> TYPE: DNA
<213> ORGANISM: Artificial
<220> FEATURE:
<223> OTHER INFORMATION: primer for sequence analysis of pLybAL

<400> SEQUENCE: 43
atgggtctga atgtgcagaa tgtagag                                          27

<210> SEQ ID NO 44
<211> LENGTH: 11090
<212> TYPE: DNA
<213> ORGANISM: Artificial
<220> FEATURE:
<223> OTHER INFORMATION: plasmid pLybAL15

<400> SEQUENCE: 44
```

```
tgcatgccgt tattgatgga atgggaagaa gcaatggtca aataaactg gaggttatgg     60 gtatgttttt tagccctaat gctccaatcg ccttgattgt atcgaatgat gcagtctcta    120
aaattgtatc cgtaaaagac ctctgcaccg ccgacgggtc tggattatgg gcaataatca    180
cagtcgagcc agactacccc tggaggtaaa ctccggggct ggagccataa agattaggaa    240
ttcattaaga aatgtaacaa tcgacgttct agatcatacc acgcccccac tgtccggcag    300
ggtgaacaga ggagactttc ccctgttaca gtgtcagtga caaaacaact ttttggcatc    360
ggtgcaggtg gtgagccatg gcggcccaga tcattgaaat tctttccccg gaggaaatcc    420
gacgtaccct tacccgtctg gcttcccagg taatttaggt accgagctcg aattggggcg    480
ttttctgtga ggctgactag cgcgtggcag ctcaaaatct ctacattctg cacattcaga    540
cccatggtct gctgcgaggg cagaacttgg aactggggcg agatgccgac accggcgggc    600
agaccaagta cgtcttagaa ctggctcaag cccaagctaa atccccacaa gtccaacaag    660
tcgacatcat cacccgccaa atcaccgacc ccgcgtcag tgttggttac agtcaggcga     720
tcgaaccctt tgcgcccaaa ggtcggattg tccgtttgcc ttttggcccc aaacgctacc    780
tccgtaaaga gctgctttgg ccccatctct acacctttgc ggatgcaatt ctccaatatc    840
tggctcagca aaagcgcacc ccgacttgga ttcaggccca ctatgctgat gctggccaag    900
tgggatcact gctgagtcgc tggttgaatg taccgctaat tttcacaggg cattctctgg    960
ggcggatcaa gctaaaaaag ctgttggagc aagactggcc gcttgaggaa attgaagcgc   1020
aattcaatat tcaacagcga attgatgcgg aggagatgac gctcactcat gctgactgga   1080
ttgtcgccag cactcagcag gaagtggagg agcaataccg cgtttacgat cgctacaacc   1140
cagagcgcaa gcttgtcatt ccaccgggtg tcgataccga tcgcttcagg tttcagccct   1200
tgggcgatcg cggtgttgtt ctccaacagg aactgagccg ctttctgcgc gacccagaaa   1260
aacctcaaat tctctgcctc tgtcgccccg cactcgcaa aaatgtaccg gcgctggtgc    1320
gagcctttgg cgaacatcct tggctgcgca aaaaagccaa ccttgtctta gtactgggca   1380
gccgccaaga catcaaccag atggatcgcg gcagtcggca ggtgttccaa agattttcc    1440 atctggtcga tcgctacgac ctctacggca gcgtcgccta tcccaaacag catcaggctg   1500
atgatgtgcc ggagttctat cgcctagcgg ctcattccgg cggggtattc gtcaatccgg   1560
cgctgaccga acctttggt ttgacaattt tggaggcagg aagctgcggc gtgccggtgg    1620 tgcaaccca tgatggcggc ccccaggaaa ttctcaaaca ctgtgatttc ggcactttag    1680
ttgatgtcag ccgacccgct aatatcgcga ctgcactcgc caccctgctg agcgatcgcg   1740
atctttggca gtgctatcac cgcaatggca ttgaaaaagt tcccgcccat tacagctggg   1800
atcaacatgt caatacctg tttgagcgca tggaaacggt ggctttgcct cgtcgtcgtg    1860
ctgtcagttt cgtacggagt cgcaaacgct tgattgatgc caaacgcctt gtcgttagtg   1920
acatcgacaa cacactgttg ggcgatcgtc aaggactcga gaatttaatg acctatctcg   1980
atcagtatcg cgatcatttt gcctttggaa ttgccacggg gcgtcgccta gactctgccc   2040
aagaagtctt gaaagagtgg ggcgttcctt cgccaaactt ctgggtgact ccgtcggca    2100 gcgagattca ctatggcacc gatgctgaac cggatatcag ctgggaaaag catatcaatc   2160
gcaactggaa tcctcagcga attcgggcag taatggcaca actacccttt cttgaactgc   2220
agccggaaga ggatcaaaca ccccttcaaag tcagcttctt tgtccgcgat cgccacgaga   2280
ctgtgctgcg agaagtacgg caacatcttc gccgccatcg cctgcggctg aagtcaatct   2340
attcccatca ggagtttctt gacattctgc cgctagctgc ctcgaaaggg gatgcgattc   2400
```

```
gccacctctc actccgctgg cggattcctc ttgagaacat tttggtggca ggcgattctg    2460
gtaacgatga ggaaatgctc aagggccata atctcggcgt tgtagttggc aattactcac    2520
cggaattgga gccactgcgc agctacgagc gcgtctattt tgctgagggc cactatgcta    2580
atggcattct ggaagcctta aaacactatc gcttttttga ggcgatcgct taaccttttc    2640
agaatgagac gttgatcggc acgtaagcgt gagacgttga tcggcacgta agaggttcca    2700
actttcacca taatgaaata agatcactac cgggcgtatt ttttgagtta tcgagatttt    2760
caggagctaa ggaagctaaa atggagaaaa aaatcactgg atataccacc gttgatatat    2820
cccaatggca tcgtaaagaa catttttgagg catttcagtc agttgctcaa tgtacctata    2880
accagaccgt tcagctggat attacggcct ttttaaagac cgtaaagaaa ataagcaca    2940 agttttatcc ggcctttatt cacattcttg cccgcctgat gaatgctcat ccggaattcc    3000
gtatggcaat gaaagacggt gagctggtga tatgggatag tgttcaccct tgttacaccg    3060
ttttccatga gcaaactgaa acgttttcat cgctctggag tgaataccac gacgatttcc    3120
ggcagtttct acacatatat tcgcaagatg tggcgtgtta cggtgaaaac ctggcctatt    3180
tccctaaagg gtttattgag aatatgtttt tcgtctcagc caatccctgg gtgagtttca    3240
ccagttttga tttaaacgtg gccaatatgg acaacttctt cgccccgtt ttcaccatgg    3300 gcaaatatta tacgcaaggc gacaaggtgc tgatgccgct ggcgattcag gttcatcatg    3360
ccgtttgtga tggcttccat gtcggcagaa tgcttaatga attacaacag tactgcgatg    3420
agtggcaggg cggggcgtaa ttttttaag gcagttattg gtgcccttaa acgcctggtt    3480
gctacgcctg aataagtgat aataagcgga tgaatggcag aaattcgatg ataagctgtc    3540
aaacacaacc accatcaaac aggattttcg cctgctgggg caaaccagcg tggaccgctt    3600
gctgcaactc tctcagggcc aggcggtgaa gggcaatcag ctgttgcccg tctcactggt    3660
gaaaagaaaa accaccctgg cgcccaatac gcaaaccgcc tctccccgcg cgttggccga    3720
ttcattaatg cagctggcac gacaggtttc ccgactggaa agcgggcagt gagcgcaacg    3780
caattaatgt aagttagcgc gaattgcaag ctggccgacg cgctgggcta cgtcttgctg    3840
gcgttcggga gcagaagagc atacatctgg aagcaaagcc aggaaagcgg cctatggagc    3900
tgtgcggcag cgctcagtag gcaatttttc aaaatattgt taagcctttt ctgagcatgg    3960
tatttttcat ggtattacca attagcagga aaataagcca ttgaatataa aagataaaaa    4020
tgtcttgttt acaatagagt ggggggggtc agcctgccgc cttgggccgg gtgatgtcgt    4080
acttgcccgc cgcgaactcg gttaccgtcc agcccagcgc gaccagctcc ggcaacgcct    4140
cgcgcacccg cttgcggcgc ttgcgcatgg tcgaaccact ggcctctgac ggccagacat    4200
agccgcacaa ggtatctatg gaagccttgc cggttttgcc ggggtcgatc cagccacaca    4260
gccgctggtg cagcaggcgg gcggtttcgc tgtccagcgc ccgcacctcg tccatgctga    4320
tgcgcacatg ctggccgcca cccatgacgg cctgcgcgat caagggggttc agggccacgt    4380 acaggcgccc gtccgcctcg tcgctggcgt actccgacag cagccgaaac ccctgccgct    4440
tgcggccatt ctgggcgatg atggatacct tccaaaggcg ctcgatgcag tcctgtatgt    4500
gcttgagcgc ccaccactac tcgacctctg ccccgatttc ctttgccagc gcccgatagc    4560
tacctttgac cacatggcat tcagcggtga cggcctccca cttgggttcc aggaacagcc    4620
ggagctgccg tccgccttcg gtcttgggtt ccgggccaag cactaggcca ttaggcccag    4680
ccatggccac cagcccttgc aggatgcgca gatcatcagc gcccagcggc tccgggccgc    4740
tgaactcgat ccgcttgccg tcgccgtagt catacgtcac gtccagcttg ctgcgcttgc    4800
```

```
gctcgccccg cttgagggca cggaacaggc cggggggccag acagtgcgcc gggtcgtgcc   4860
ggacgtggct gaggctgtgc ttgttcttag gcttcaccac ggggcacccc cttgctcttg   4920
cgctgcctct ccagcacggc gggcttgagc accccgccgt catgccgcct gaaccaccga   4980
tcagcgaacg gtgcgccata gttggccttg ctcacaccga agcggacgaa gaaccggcgc   5040
tggtcgtcgt ccacacccca ttcctcggcc tcggcgctgg tcatgctcga caggtaggac   5100
tgccagcgga tgttatcgac cagtaccgag ctgccccggc tggcctgctg ctggtcgcct   5160
gcgcccatca tggccgcgcc cttgctggca tggtgcagga acacgataga gcacccggta   5220
tcggcggcga tggcctccat gcgaccgatg acctgggcca tggggccgct ggcgttttct   5280
tcctcgatgt ggaaccggcg cagcgtgtcc agcaccatca ggcggcgcc ctcggcggcg   5340 cgcttgaggc cgtcgaacca ctccggggcc atgatgttgg gcaggctgcc gatcagcggc   5400
tggatcagca ggccgtcagc cacggcttgc cgttcctcgg cgctgaggtg cgccccaagg   5460
gcgtgcaggc ggtgatgaat ggcggtgggc gggtcttcgg cgggcaggta gatcaccggg   5520
ccggtgggca gttcgcccac ctccagcaga tccggcccgc ctgcaatctg tgcggccagt   5580
tgcagggcca gcatggattt accggcacca ccgggcgaca ccagcgcccc gaccgtaccg   5640
gccaccatgt tgggcaaaac gtagtccagc ggtggcggcg ctgctgcgaa cgcctccaga   5700
atattgatag gcttatgggt agccattgat tgcctccttt gcaggcagtt ggtggttagg   5760
cgctggcggg gtcactaccc ccgccctgcg ccgctctgag ttcttccagg cactcgcgca   5820
gcgcctcgta ttcgtcgtcg gtcagccaga acttgcgctg acgcatccct ttggccttca   5880
tgcgctcggc atatcgcgct tggcgtacag cgtcagggct ggccagcagg tcgccggtct   5940
gcttgtcctt ttggtctttc atatcagtca ccgagaaact tgccggggcc gaaaggcttg   6000
tcttcgcgga acaaggacaa ggtgcagccg tcaaggttaa ggctggccat atcagcgact   6060
gaaaagcggc cagcctcggc cttgtttgac gtataaccaa agccaccggg caaccaatag   6120
cccttgtcac ttttgatcag gtagaccgac cctgaagcgc ttttttcgta ttccataaaa   6180
cccccttctg tgcgtgagta ctcatagtat aacaggcgtg agtaccaacg caagcactac   6240
atgctgaaat ctggcccgcc cctgtccatg cctcgctggc ggggtgccgg tgcccgtgcc   6300
agctcggccc gcgcaagctg gacgctgggc agacccatga ccttgctgac ggtgcgctcg   6360
atgtaatccg cttcgtggcc gggcttgcgc tctgccagcg ctgggctggc ctcggccatg   6420
gccttgccga tttcctcggc actgcggccc cggctggcca gcttctgcgc ggcgataaag   6480
tcgcacttgc tgaggtcatg accgaagcgc ttgaccagcc cggccatctc gctgcggtac   6540
tcgtccagcg ccgtgcgccg gtggcggcta agctgccgct cggcagttc gaggctggcc   6600 agcctgcggg ccttctcctg ctgccgctgg gcctgctcga tctgctggcc agcctgctgc   6660
accagcgccg ggccagcggt ggcggtcttg cccttggatt cacgcagcag cacccacggc   6720
tgataaccgg cgcgggtggt gtgcttgtcc ttgcggttgg tgaagcccgc caagcggcca   6780
tagtggcggc tgtcgcgct ggccgggtcg gcgtcgtact cgctggccag cgtccgggca   6840
atctgccccc gaagttcacc gcctgcgcg tcggccacct tgacccatgc ctgatagttc   6900
ttcgggctgg tttccactac cagggcaggc tcccggccct cggctttcat gtcatccagg   6960
tcaaactcgc tgaggtcgtc caccagcacc agaccatgcc gctcctgctc ggcgggcctg   7020
atatacacgt cattgccctg ggcattcatc cgcttgagcc atggcgtgtt ctggagcact   7080
tcggcggctg accattcccg gttcatcatc tggccggtgg gtgcgtccct gacgccgata   7140
tcgaagcgct cacagcccat ggccttgagc tgtcggccta tggcctgcaa agtcctgtcg   7200
```

```
ttcttcatcg ggccaccaag cgcagccaga tcgagccgtc ctcggttgtc agtggcgtca   7260
ggtcgagcaa gagcaacgat gcgatcagca gcaccaccgt aggcatcatg gaagccagca   7320
tcacggttag ccatagcttc cagtgccacc ccgcgacgc gctccgggcg ctctgcgcgg    7380
cgctgctcac ctcggcggct acctcccgca actctttggc cagctccacc catgccgccc   7440
ctgtctggcg ctgggctttc agccactccg ccgcctgcgc ctcgctggcc tgcttggtct   7500
ggctcatgac ctgccgggct cgtcggcca gtgtcgccat gctctgggcc agcggttcga    7560
tctgctccgc taactcgttg atgcctctgg atttcttcac tctgtcgatt gcgttcatgg   7620
tctattgcct cccggtattc ctgtaagtcg atgatctggg cgttggcggt gtcgatgttc   7680
agggccacgt ctgcccggtc ggtgcggatg ccccggcctt ccatctccac cacgttcggc   7740
cccaggtgaa caccgggcag cgctcgatg ccctgcgcct caagtgttct gtggtcaatg    7800
cgggcgtcgt ggccagcccg ctctaatgcc cggttggcat ggtcggccca tgcctcgcgg   7860
gtctgctcaa gccatgcctt gggcttgagc gcttcggtct tctgtgcccc gcccttctcc   7920
ggggtcttgc cgttgtaccg cttgaaccac tgagcggcgg ccgctcgat gccgtcattg    7980 atccgctcgg agatcatcag gtggcagtgc gggttctcgc cgccaccggc atggatggcc   8040
agcgtatacg gcaggcgctc ggcaccggtc aggtgctggg cgaactcgga cgccagcgcc   8100
ttctgctggt cgagggtcag ctcgaccggc agggcaaatt cgacctcctt gaacagccgc   8160
ccattggcgc gttcatacag gtcggcagca tcccagtagt cggcgggccg ctcgacgaac   8220
tccggcatgt gccccggattc ggcgtgcaag acttcatcca tgtcgcgggc atacttgcct   8280
tcgcgctgga tgtagtcggc cttggccctg gccgattggc cgcccgacct gctgccggtt   8340
ttcgccgtaa ggtgataaat cgccatgctg cctcgctgtt gcttttgctt ttcggctcca   8400
tgcaatggcc ctcggagagc gcaccgcccg aagggtggcc gttaggccag tttctcgaag   8460
agaaaccggt aagtgcgccc tcccctacaa gtagggtcg ggattccgc cgctgtgcct     8520 ccatgatagc ctacgagaca gcacattaac aatggggtgt caagatggtt aaggggagca   8580
acaaggcggc ggatcggctg gccaagctcg aagaacaacg agcgcgaatc aatgccgaaa   8640
ttcagcggga gcgggcaagg gaacagcagc aagagcgcaa gaacgaaaca aggcgcaagg   8700
tgctggtggg ggccatgatt ttggccaagg tgaacagcag cgagtggccg gaggatcggc   8760
tcatggcggc aatggatgcg taccttgaac gcgaccacga ccgcgccttg ttcggtctgc   8820
cgccacgcca gaaggatgag ccgggctgaa tgatcgaccg agacaggccc tgcggggctg   8880
cacacgcgcc cccacccttc gggtaggggg aaaggccgct aaagcggcta aaagcgctcc   8940
agcgtatttc tgcggggttt ggtgtggggt ttagcgggct ttgcccgcct ttccccctgc   9000
cgcgcagcgg tggggcggtg tgtagcctag cgcagcgaat agaccagcta tccggcctct   9060
ggccgggcat attgggcaag gcagcagcg ccccacaagg gcgctgataa ccgcgcctag    9120
tggattattc ttagataatc atggatggat ttttccaaca ccccgccagc cccgcccct    9180 gctgggtttg caggtttggg ggcgtgacag ttattgcagg ggttcgtgac agttattgca   9240 gggggcgtg acagttattg cagggggttcg tgacagttag tacgggagtg acgggcactg   9300
gctggcaatg tctagcaacg gcaggcattt cggctgaggg taaaagaact ttccgctaag   9360
cgatagactg tatgtaaaca cagtattgca aggacgcgga acatgcctca tgtggcggcc   9420
aggacggcca gccgggatcg ggatactggt cgttaccaga gccaccgacc cgagcaaacc   9480
cttctctatc agatcgttga cgagtattac ccggcattcg ctgcgcttat ggcagagcag   9540
ggaaaggaat tgccgggcta tgtgcaacgg gaatttgaag aatttctcca atgcgggcgg   9600
```

```
ctggagcatg ctttctacg ggttcgctgc gagtcttgcc acgccgagca cctggtcgct    9660
ttcagaaatc aatctaaagt atatatgagt aaacttggtc tgacagttac caatgcttaa    9720
tcagtgaggc acctatctca gcgatctgtc tatttcgttc atccatagtt gcctgactcc    9780
ccgtcgtgta gataactacg atacgggagg gcttaccatc tggccccagt gctgcaatga    9840
taccgcgaga cccacgctca ccggctccag atttatcagc aataaaccag ccagccggaa    9900
gggccgagcg cagaagtggt cctgcaactt tatccgcctc catccagtct attaattgtt    9960
gccgggaagc tagagtaagt agttcgccag ttaatagttt gcgcaacgtt gttgccattg   10020
ctacaggcat cgtggtgtca cgctcgtcgt ttggtatggc ttcattcagc tccggttccc   10080
aacgatcaag gcgagttaca tgatccccca tgttgtgcaa aaaagcggtt agctccttcg   10140
gtcctccgat cgttgtcaga agtaagttgg ccgcagtgtt atcactcatg gttatggcag   10200
cactgcataa ttctcttact gtcatgccat ccgtaagatg cttttctgtg actggtgagt   10260
actcaaccaa gtcattctga aatagtgta tgcggcgacc gagttgctct tgcccggcgt   10320
caacacggga taataccgcg ccacatagca gaactttaaa agtgctcatc attggaaaac   10380
gttcttcggg gcgaaaactc tcaaggatct taccgctgtt gagatccagt tcgatgtaac   10440
ccactcgtgc acccaactga tcttcagcat cttttacttt caccagcgtt tctgggtgag   10500
caaaaacagg aaggcaaaat gccgcaaaaa agggaataag ggcgacacgg aaatgttgaa   10560
tactcatact cttccttttt caatattatt gaagcattta tcagggttat tgtctcatga   10620
gcggatacat atttgaatgt atttagaaaa ataaacaaaa gagtttgtag aaacgcaaaa   10680
aggccatccg tcaggatggc cttctgctta atttgatgcc tggcagttta tggcgggcgt   10740
cctgcccgcc accctccggg ccgttgcttc gcaacgttca aatccgctcc cggcggattt   10800
gtcctactca ggagagcgtt caccgacaaa caacagataa acgaaaggc ccagtctttc   10860 gactgagcct ttcgttttat ttgatgcctg gcagttccct actctcgcat ggggagaccc   10920
cacactacca tcggcgctac ggcgtttcac ttctgagttc ggcatggggt caggtgggac   10980
caccgcgcta ctgccgccag gcaaattctg ttttatcaga ccgcttctgc gttctgattt   11040
aatctgtatc aggctgaaaa tcttctctca tccgccaaaa cagccaagct              11090

<210> SEQ ID NO 45
<211> LENGTH: 11000
<212> TYPE: DNA
<213> ORGANISM: Artificial
<220> FEATURE:
<223> OTHER INFORMATION: plasmid pLybAL16

<400> SEQUENCE: 45
tgcatgcagg aaaacaagct cagaatgctg cggggagaag ggcaactccc caccagcccc      60 aaattttgc tggcgataaa tattttttcgg tttaattgtt cacaaagctt tttgaatttg     120
agtttataga aatttattgg ctggtaatgc ttttttgccc ccctgcagga cttcattgat     180
ccttgcctat accatcaata tcattggtca ataatgatga tgattgacta aaacatgttt     240
aacaaaattt aacgcatatg ctaaatgcgt aaactgcata tgccttggct gagtgtaatt     300
tacgttacaa atttaacga aacgggaacc ctatattgat ctctactgtt atctggcttg     360
aagcgttggt accgagctcg aattgggcg ttttctgtga ggctgactag cgcgtggcag     420
ctcaaaatct ctacattctg cacattcaga cccatggtct gctgcgaggg cagaacttgg     480
aactggggcg agatgccgac accggcgggc agaccaagta cgtcttagaa ctggctcaag     540
cccaagctaa atccccacaa gtccaacaag tcgacatcat cacccgccaa atcaccgacc     600
```

-continued

```
cccgcgtcag tgttggttac agtcaggcga tcgaacccct tgcgcccaaa ggtcggattg      660
tccgtttgcc ttttggcccc aaacgctacc tccgtaaaga gctgctttgg ccccatctct      720
acacctttgc ggatgcaatt ctccaatatc tggctcagca aaagcgcacc ccgacttgga      780
ttcaggccca ctatgctgat gctggccaag tgggatcact gctgagtcgc tggttgaatg      840
taccgctaat tttcacaggg cattctctgg ggcggatcaa gctaaaaaag ctgttggagc      900
aagactggcc gcttgaggaa attgaagcgc aattcaatat tcaacagcga attgatgcgg      960
aggagatgac gctcactcat gctgactgga ttgtcgccag cactcagcag gaagtggagg     1020
agcaataccg cgtttacgat cgctacaacc cagagcgcaa gcttgtcatt ccaccgggtg     1080
tcgataccga tcgcttcagg tttcagccct tgggcgatcg cggtgttgtt ctccaacagg     1140
aactgagccg ctttctgcgc gacccagaaa aacctcaaat tctctgcctc tgtcgccccg     1200
cacctcgcaa aaatgtaccg gcgctggtgc gagcctttgg cgaacatcct tggctgcgca     1260
aaaaagccaa ccttgtctta gtactgggca gccgccaaga catcaaccag atggatcgcg     1320
gcagtcggca ggtgttccaa gagattttcc atctggtcga tcgctacgac ctctacggca     1380
gcgtcgccta tcccaaacag catcaggctg atgatgtgcc ggagttctat cgcctagcgg     1440
ctcattccgg cggggtattc gtcaatccgg cgctgaccga accttttggt ttgacaattt     1500
tggaggcagg aagctgcggc gtgccggtgg tggcaaccca tgatggcggc ccccaggaaa     1560
ttctcaaaca ctgtgatttc ggcactttag ttgatgtcag ccgacccgct aatatcgcga     1620
ctgcactcgc caccctgctg agcgatcgcg atctttggca gtgctatcac cgcaatggca     1680
ttgaaaaagt tcccgcccat tacagctggg atcaacatgt caatacccctg tttgagcgca     1740 tggaaacggt ggctttgcct cgtcgtcgtg ctgtcagttt cgtacggagt cgcaaacgct     1800
tgattgatgc caaacgcctt gtcgttagtg acatcgacaa cacactgttg ggcgatcgtc     1860
aaggactcga gaatttaatg acctatctcg atcagtatcg cgatcatttt gcctttggaa     1920
ttgccacggg gcgtcgccta gactctgccc aagaagtctt gaaagagtgg ggcgttcctt     1980
cgccaaactt ctgggtgact tccgtcggca gcgagattca ctatggcacc gatgctgaac     2040
cggatatcag ctgggaaaag catatcaatc gcaactggaa tcctcagcga attcgggcag     2100
taatggcaca actacccttt cttgaactgc agccggaaga ggatcaaaca cccttcaaag     2160
tcagcttctt tgtccgcgat cgccacgaga ctgtgctgcg agaagtacgg caacatcttc     2220
gccgccatcg cctgcggctg aagtcaatct attcccatca ggagtttctt gacattctgc     2280
cgctagctgc ctcgaaaggg gatgcgattc gccacctctc actccgctgg cggattcctc     2340
ttgagaacat tttggtggca ggcgattctg gtaacgatga ggaaatgctc aagggccata     2400
atctcggcgt tgtagttggc aattactcac cggaattgga gccactgcgc agctacgagc     2460
gcgtctattt tgctgagggc cactatgcta atggcattct ggaagcctta aaacactatc     2520
gcttttttga ggcgatcgct taacctttc agaatgagac gttgatcggc acgtaagcgt     2580
gagacgttga tcggcacgta agaggttcca actttcacca taatgaaata agatcactac     2640
cgggcgtatt ttttgagtta tcgagatttt caggagctaa ggaagctaaa atggagaaaa     2700
aaatcactgg atataccacc gttgatatat cccaatggca tcgtaaagaa cattttgagg     2760
catttcagtc agttgctcaa tgtacctata accagaccgt tcagctggat attacggcct     2820
ttttaaagac cgtaaagaaa aataagcaca agttttatcc ggcctttatt cacattcttg     2880
cccgcctgat gaatgctcat ccggaattcc gtatggcaat gaaagacggt gagctggtga     2940
tatgggatag tgttcaccct tgttacaccg ttttccatga gcaaactgaa acgttttcat     3000
```

```
cgctctggag tgaataccac gacgatttcc ggcagtttct acacatatat tcgcaagatg    3060
tggcgtgtta cggtgaaaac ctggcctatt tccctaaagg gtttattgag aatatgtttt    3120
tcgtctcagc caatccctgg gtgagtttca ccagttttga tttaaacgtg gccaatatgg    3180
acaacttctt cgcccccgtt ttcaccatgg gcaaatatta tacgcaaggc gacaaggtgc    3240
tgatgccgct ggcgattcag gttcatcatg ccgtttgtga tggcttccat gtcggcagaa    3300
tgcttaatga attacaacag tactgcgatg agtggcaggg cggggcgtaa ttttttttaag    3360 gcagttattg gtgcccttaa acgcctggtt gctacgcctg aataagtgat aataagcgga    3420
tgaatggcag aaattcgatg ataagctgtc aaacacaacc accatcaaac aggattttcg    3480
cctgctgggg caaaccagcg tggaccgctt gctgcaactc tctcagggcc aggcggtgaa    3540
gggcaatcag ctgttgcccg tctcactggt gaaaagaaaa accaccctgg cgcccaatac    3600
gcaaaccgcc tctccccgcg cgttggccga ttcattaatg cagctggcac gacaggtttc    3660
ccgactggaa agcgggcagt gagcgcaacg caattaatgt aagttagcgc gaattgcaag    3720
ctggccgacg cgctgggcta cgtcttgctg gcgttcggga gcagaagagc atacatctgg    3780
aagcaaagcc aggaaagcgg cctatggagc tgtgcgcag cgctcagtag gcaatttttc    3840
aaaatattgt taagcctttt ctgagcatgg tattttttcat ggtattacca attagcagga    3900
aaataagcca ttgaatataa aagataaaaa tgtcttgttt acaatagagt gggggggggtc    3960 agcctgccgc cttgggccgg gtgatgtcgt acttgcccgc cgcgaactcg gttaccgtcc    4020
agcccagcgc gaccagctcc ggcaacgcct cgcgcacccg cttgcggcgc ttgcgcatgg    4080
tcgaaccact ggcctctgac ggccagacat agccgcacaa ggtatctatg gaagccttgc    4140
cggttttgcc ggggtcgatc cagccacaca gccgctggtg cagcaggcgg gcggtttcgc    4200
tgtccagcgc ccgcacctcg tccatgctga tgcgcacatg ctggccgcca cccatgacgg    4260
cctgcgcgat caaggggttc agggccacgt acaggcgccc gtccgcctcg tcgctggcgt    4320
actccgacag cagccgaaac ccctgccgct tgcggccatt ctgggcgatg atggatacct    4380
tccaaaggcg ctcgatgcag tcctgtatgt gcttgagcgc cccaccacta tcgacctctg    4440
ccccgatttc ctttgccagc gcccgatagc tacctttgac cacatggcat tcagcggtga    4500
cggcctccca cttgggttcc aggaacagcc ggagctgccg tccgccttcg gtcttgggtt    4560
ccgggccaag cactaggcca ttaggcccag ccatggccac cagcccttgc aggatgcgca    4620
gatcatcagc gccagcggc tccgggccgc tgaactcgat ccgcttgccg tcgccgtagt    4680
catacgtcac gtccagcttg ctgcgcttgc gctcgccccg cttgagggca cggaacaggc    4740 cggggggccag acagtgcgcc gggtcgtgcc ggacgtggct gaggctgtgc ttgttcttag    4800
gcttcaccac ggggcacccc cttgctcttg cgctgcctct ccagcacggc gggcttgagc    4860
accccgccgt catgccgcct gaaccaccga tcagcgaacg gtgcgccata gttggccttg    4920
ctcacaccga agcggacgaa gaaccggcgc tggtcgtcgt ccacacccca ttcctcggcc    4980
tcggcgctgg tcatgctcga caggtaggac tgccagcgga tgttatcgac cagtaccgag    5040
ctgccccggc tggcctgctg ctggtcgcct gcgcccatca tggccgcgcc cttgctggca    5100
tggtgcagga acacgataga gcacccggta tcggcggcga tggcctccat gcgaccgatg    5160
acctgggcca tggggccgct ggcgtttcct tcctcgatgt ggaaccggcg cagcgtgtcc    5220
agcaccatca ggcggcggcc ctcggcggcg cgcttgaggc cgtcgaacca ctccggggcc    5280
atgatgttgg gcaggctgcc gatcagcggc tggatcagca ggccgtcagc cacggcttgc    5340
cgttcctcgg cgctgaggtg cgccccaagg gcgtgcaggc ggtgatgaat ggcggtgggc    5400
```

```
gggtcttcgg cgggcaggta gatcaccggg ccggtgggca gttcgcccac ctccagcaga    5460
tccggcccgc ctgcaatctg tgcggccagt tgcagggcca gcatggattt accggcacca    5520
ccgggcgaca ccagcgcccc gaccgtaccg gccaccatgt tgggcaaaac gtagtccagc    5580
ggtggcggcg ctgctgcgaa cgcctccaga atattgatag gcttatgggt agccattgat    5640
tgcctccttt gcaggcagtt ggtggttagg cgctggcggg gtcactaccc cgccctgcg     5700 ccgctctgag ttcttccagg cactcgcgca gcgcctcgta ttcgtcgtcg gtcagccaga    5760
acttgcgctg acgcatccct ttggccttca tgcgctcggc atatcgcgct ggcgtacag     5820 cgtcagggct ggccagcagg tcgccggtct gcttgtcctt ttggtctttc atatcagtca    5880
ccgagaaact gccggggcc gaaaggcttg tcttcgcgga acaaggacaa ggtgcagccg     5940
tcaaggttaa ggctggccat atcagcgact gaaaagcggc cagcctcggc cttgtttgac    6000
gtataaccaa agccaccggg caaccaatag cccttgtcac ttttgatcag gtagaccgac    6060
cctgaagcgc ttttttcgta ttccataaaa ccccctcctg tgcgtgagta ctcatagtat    6120
aacaggcgtg agtaccaacg caagcactac atgctgaaat ctggcccgcc cctgtccatg    6180
cctcgctggc ggggtgccgg tgcccgtgcc agctcggccc gcgcaagctg gacgctgggc    6240
agacccatga ccttgctgac ggtgcgctcg atgtaatccg cttcgtggcc gggcttgcgc    6300
tctgccagcg ctgggctggc ctcggccatg gccttgccga tttcctcggc actgcggccc    6360
cggctggcca gcttctgcgc ggcgataaag tcgcacttgc tgaggtcatg accgaagcgc    6420
ttgaccagcc cggccatctc gctgcggtac tcgtccagcg ccgtgcgccg gtggcggcta    6480
agctgccgct cgggcagttc gaggctggcc agcctgcggg ccttctcctg ctgccgctgg    6540
gcctgctcga tctgctggcc agcctgctgc caccagcccg gccagcggt ggcggtcttg     6600 cccttggatt cacgcagcag cacccacggc tgataaccgg cgcgggtggt gtgcttgtcc    6660
ttgcggttgg tgaagcccgc caagcggcca tagtggcggc tgtcggcgct ggccgggtcg    6720
gcgtcgtact cgctggccag cgtccgggca atctgccccc gaagttcacc gcctgcggcg    6780
tcggccacct tgacccatgc ctgatagttc ttcgggctgg tttccactac cagggcaggc    6840
tcccggccct cggctttcat gtcatccagg tcaaactcgc tgaggtcgtc caccagcacc    6900
agaccatgcc gctcctgctc ggcgggcctg atatacacgt cattgccctg gcattcatc     6960 cgcttgagcc atggcgtgtt ctggagcact tcggcggctg accattcccg gttcatcatc    7020
tggccggtgg gtgcgtccct gacgccgata tcgaagcgct cacagcccat ggccttgagc    7080
tgtcggccta tggcctgcaa agtcctgtcg ttcttcatcg ggccaccaag cgcagccaga    7140
tcgagccgtc ctcggttgtc agtggcgtca ggtcgagcaa gagcaacgat gcgatcagca    7200
gcaccaccgt aggcatcatg gaagccagca tcacggttag ccatagcttc cagtgccacc    7260
cccgcgacgc gctccgggcg ctctgcgcg cgctgctcac ctcggcggct acctcccgca     7320
actctttggc cagctccacc catgccgccc ctgtctggcg ctgggctttc agccactccg    7380
ccgcctgcgc ctcgctggcc tgcttggtct ggctcatgac ctgccgggct tcgtcggcca    7440
gtgtcgccat gctctgggcc agcggttcga tctgctccgc taactcgttg atgcctctgg    7500
atttcttcac tctgtcgatt gcgttcatgg tctattgcct cccggtattc ctgtaagtcg    7560
atgatctggg cgttggcggt gtcgatgttc agggccacgt ctgcccggtc ggtgcggatg    7620
ccccggcctt ccatctccac cacgttcggc cccaggtgaa caccgggcag gcgctcgatg    7680
ccctgcgcct caagtgttct gtggtcaatg cgggcgtcgt ggccagcccg ctctaatgcc    7740
cggttggcat ggtcggccca tgcctcgcgg gtctgctcaa gccatgcctt gggcttgagc    7800
```

```
gcttcggtct tctgtgcccc gcccttctcc ggggtcttgc cgttgtaccg cttgaaccac    7860
tgagcggcgg gccgctcgat gccgtcattg atccgctcgg agatcatcag gtggcagtgc    7920
gggttctcgc cgccaccggc atggatggca gcgtatacg gcaggcgctc ggcaccggtc     7980
aggtgctggg cgaactcgga cgccagcgcc ttctgctggt cgagggtcag ctcgaccggc    8040
agggcaaatt cgacctcctt gaacagccgc ccattggcgc gttcatacag gtcggcagca    8100
tcccagtagt cggcgggccg ctcgacgaac tccggcatgt gcccggattc ggcgtgcaag    8160
acttcatcca tgtcgcgggc atacttgcct tcgcgctgga tgtagtcggc cttggccctg    8220
gccgattggc cgcccgacct gctgccggtt ttcgccgtaa ggtgataaat cgccatgctg    8280
cctcgctgtt gcttttgctt ttcggctcca tgcaatggcc ctcggagagc gcaccgcccg    8340
aagggtggcc gttaggccag tttctcgaag agaaaccggt aagtgcgccc tccctacaa     8400
agtagggtcg ggattgccgc cgctgtgcct ccatgatagc ctacgagaca gcacattaac    8460
aatggggtgt caagatggtt aagggagca acaaggcggg gatcggctg gccaagctcg      8520
aagaacaacg agcgcgaatc aatgccgaaa ttcagcggga gcgggcaagg gaacagcagc    8580
aagagcgcaa gaacgaaaca aggcgcaagg tgctggtggg ggccatgatt ttggccaagg    8640
tgaacagcag cgagtggccg gaggatcggc tcatggcggc aatggatgcg taccttgaac    8700
gcgaccacga ccgcgccttg ttcggtctgc cgccacgcca aaggatgag ccgggctgaa     8760
tgatcgaccg agacaggccc tgcggggctg cacacgcgcc cccacccttc gggtaggggg    8820
aaaggccgct aaagcggcta aaagcgctcc agcgtatttc tgcggggttt ggtgtggggt    8880
ttagcgggct ttgcccgcct ttcccctgc cgcgcagcgg tggggcggtg tgtagcctag     8940
cgcagcgaat agaccagcta tccggcctct ggccgggcat attgggcaag ggcagcagcg    9000
ccccacaagg gcgctgataa ccgcgcctag tggattattc ttagataatc atggatggat    9060
ttttccaaca ccccgccagc ccccgcccct gctgggtttg caggttggg ggcgtgacag     9120
ttattgcagg ggttcgtgac agttattgca ggggggcgtg acagttattg cagggggttcg   9180
tgacagttag tacgggagtg acgggcactg gctggcaatg tctagcaacg gcaggcattt    9240
cggctgaggg taaaagaact ttccgctaag cgatagactg tatgtaaaca cagtattgca    9300
aggacgcgga acatgcctca tgtggcggcc aggacggcca gccgggatcg ggatactggt    9360
cgttaccaga gccaccgacc cgagcaaacc cttctctatc agatcgttga cgagtattac    9420
ccggcattcg ctgcgcttat ggcagagcag ggaaaggaat tgccgggcta tgtgcaacgg    9480
gaatttgaag aatttctcca atgcgggcgg ctggagcatg gctttctacg ggttcgctgc    9540
gagtcttgcc acgccgagca cctggtcgct ttcagaaatc aatctaaagt atatatgagt    9600
aaacttggtc tgacagttac caatgcttaa tcagtgaggc acctatctca gcgatctgtc    9660
tatttcgttc atccatagtt gcctgactcc ccgtcgtgta gataactacg atacgggagg    9720
gcttaccatc tggccccagt gctgcaatga taccgcgaga cccacgctca ccggctccag    9780
atttatcagc aataaaccag ccagccgaa gggccgagcg cagaagtggt cctgcaactt     9840
tatccgcctc catccagtct attaattgtt gccgggaagc tagagtaagt agttcgccag    9900
ttaatagttt gcgcaacgtt gttgccattg ctacaggcat cgtggtgtca cgctcgtcgt    9960
ttggtatggc ttcattcagc tccggttccc aacgatcaag gcgagttaca tgatccccca    10020
tgttgtgcaa aaaagcggtt agctccttcg gtcctccgat cgttgtcaga agtaagttgg    10080
ccgcagtgtt atcactcatg gttatggcag cactgcataa ttctcttact gtcatgccat    10140
ccgtaagatg cttttctgtg actggtgagt actcaaccaa gtcattctga aatagtgta    10200
```

```
tgcggcgacc gagttgctct tgcccggcgt caacacggga taataccgcg ccacatagca   10260
gaactttaaa agtgctcatc attggaaaac gttcttcggg gcgaaaactc tcaaggatct   10320
taccgctgtt gagatccagt tcgatgtaac ccactcgtgc acccaactga tcttcagcat   10380
cttttacttt caccagcgtt tctgggtgag caaaaacagg aaggcaaaat gccgcaaaaa   10440
agggaataag ggcgacacgg aaatgttgaa tactcatact cttccttttt caatattatt   10500
gaagcattta tcagggttat tgtctcatga gcggatacat atttgaatgt atttagaaaa   10560
ataaacaaaa gagtttgtag aaacgcaaaa aggccatccg tcaggatggc cttctgctta   10620
atttgatgcc tggcagttta tggcgggcgt cctgcccgcc accctccggg ccgttgcttc   10680
gcaacgttca aatccgctcc cggcggattt gtcctactca ggagagcgtt caccgacaaa   10740
caacagataa aacgaaaggc ccagtctttc gactgagcct ttcgttttat ttgatgcctg   10800
gcagttccct actctcgcat ggggagaccc cacactacca tcggcgctac ggcgtttcac   10860
ttctgagttc ggcatggggt caggtgggac caccgcgcta ctgccgccag gcaaattctg   10920
ttttatcaga ccgcttctgc gttctgattt aatctgtatc aggctgaaaa tcttctctca   10980
tccgccaaaa cagccaagct                                              11000
```

<210> SEQ ID NO 46
<211> LENGTH: 11269
<212> TYPE: DNA
<213> ORGANISM: Artificial
<220> FEATURE:
<223> OTHER INFORMATION: plasmid pLybAL17

<400> SEQUENCE: 46

```
tgcatgccga gcctgatgtg tgacacctaa gatcactcca gttctctttg gaaactggct      60
gatgagtgaa gacaccatct ttggcaagat catccggcgc gagattccag cagacattgt     120
ttatgaagat gatctctgtc tggcttttcg agatgtggca ccccaagcgc cggttcacat     180
tctggtgatt cccaagcaac caattgccaa cctttttggaa gcgacagcag aacatcaagc    240
gctgctgggt catttgttgc tgactgtaaa ggcgatcgcg gccaagaag gactcaccga      300 gggctaccgc accgtgatta cacgggcccc tgcgggtggg caaaccgttt accacctgca    360
tattcactta ctgggcgggc gatcgctggc ttggccgccc ggctgagaaa agtctgaaag     420
ttctttacaa aactcaatct gcttgttaga ttttactcac gaggctatta agtctcgtaa     480
atagttcaac taaggactca tcgcaaaatg acgactgcat tgcagcggcg cgagagcgcc    540
agcctgtggc agcagttctg cgagtgggta accagcaccg acaaccgcct ctatgtgggt   600
tggttcggcg tgctgatgat cccccactctg ctgaccggta ccgagctcga attggggcgt    660
tttctgtgag gctgactagc gcgtggcagc tcaaaatctc tacattctgc acattcagac   720
ccatggtctg ctgcgagggc agaacttgga actgggggca gatgccgaca ccggcgggca    780
gaccaagtac gtcttagaac tggctcaagc ccaagctaaa tccccacaag tccaacaagt   840
cgacatcatc acccgccaaa tcaccgaccc ccgtcagt gttggttaca gtcaggcgat       900
cgaacccttt gcgcccaaag gtcggattgt ccgtttgcct tttggcccca aacgctacct    960
ccgtaaagag ctgctttggc cccatctcta cacctttgcg gatgcaattc tccaatatct   1020
ggctcagcaa aagcgcaccc cgacttggat tcaggcccac tatgctgatg ctggccaagt   1080
gggatcactg ctgagtcgct ggttgaatgt accgctaatt ttcacagggc attctctggg   1140
gcggatcaag ctaaaaaagc tgttggagca agactggccg cttgaggaaa ttgaagcgca   1200
attcaatatt caacagcgaa ttgatgcgga ggagatgacg ctcactcatg ctgactggat   1260
```

-continued

```
tgtcgccagc actcagcagg aagtggagga gcaataccgc gtttacgatc gctacaaccc   1320
agagcgcaag cttgtcattc caccgggtgt cgataccgat cgcttcaggt ttcagccctt   1380
gggcgatcgc ggtgttgttc tccaacagga actgagccgc tttctgcgcg acccagaaaa   1440
acctcaaatt ctctgcctct gtcgccccgc acctcgcaaa aatgtaccgg cgctggtgcg   1500
agcctttggc gaacatcctt ggctgcgcaa aaaagccaac cttgtcttag tactgggcag   1560
ccgccaagac atcaaccaga tggatcgcgg cagtcggcag gtgttccaag agattttcca   1620
tctggtcgat cgctacgacc tctacggcag cgtcgcctat cccaaacagc atcaggctga   1680
tgatgtgccg gagttctatc gcctagcggc tcattccggc ggggtattcg tcaatccggc   1740
gctgaccgaa ccttttggtt tgacaatttt ggaggcagga agctgcggcg tgccggtggt   1800
ggcaacccat gatggcggcc cccaggaaat tctcaaacac tgtgatttcg gcactttagt   1860
tgatgtcagc cgacccgcta atatcgcgac tgcactcgcc accctgctga gcgatcgcga   1920
tctttggcag tgctatcacc gcaatggcat tgaaaaagtt cccgcccatt acagctggga   1980
tcaacatgtc aataccctgt ttgagcgcat ggaaacggtg gctttgcctc gtcgtcgtgc   2040
tgtcagtttc gtacggagtc gcaaacgctt gattgatgcc aaacgccttg tcgttagtga   2100
catcgacaac acactgttgg gcgatcgtca aggactcgag aatttaatga cctatctcga   2160
tcagtatcgc gatcattttg cctttggaat tgccacgggg cgtcgcctag actctgccca   2220
agaagtcttg aaagagtggg gcgttccttc gccaaacttc tgggtgactt ccgtcggcag   2280
cgagattcac tatggcaccg atgctgaacc ggatatcagc tgggaaaagc atatcaatcg   2340
caactggaat cctcagcgaa ttcgggcagt aatggcacaa ctaccctttc ttgaactgca   2400
gccggaagag gatcaaacac ccttcaaagt cagcttcttt gtccgcgatc gccacgagac   2460
tgtgctgcga gaagtacggc aacatcttcg ccgccatcgc ctgcggctga agtcaatcta   2520
ttcccatcag gagtttcttg acattctgcc gctagctgcc tcgaaagggg atgcgattcg   2580
ccacctctca ctccgctggc ggattcctct tgagaacatt ttggtggcag gcgattctgg   2640
taacgatgag gaaatgctca agggccataa tctcggcgtt gtagttggca attactcacc   2700
ggaattggag ccactgcgca gctacgagcg cgtctatttt gctgagggcc actatgctaa   2760
tggcattctg gaagccttaa aacactatcg ctttttttgag gcgatcgctt aaccttttca   2820
gaatgagacg ttgatcggca cgtaagcgtg agacgttgat cggcacgtaa gaggttccaa   2880
ctttcaccat aatgaaataa gatcactacc gggcgtattt tttgagttat cgagattttc   2940
aggagctaag gaagctaaaa tggagaaaaa aatcactgga tataccaccg ttgatatatc   3000
ccaatggcat cgtaaagaac attttgaggc atttcagtca gttgctcaat gtacctataa   3060
ccagaccgtt cagctggata ttacggcctt tttaaagacc gtaaagaaaa ataagcacaa   3120
gttttatccg gcctttattc acattcttgc ccgcctgatg aatgctcatc cggaattccg   3180
tatggcaatg aaagacggtg agctggtgat atgggatagt gttcaccctt gttacaccgt   3240
tttccatgag caaactgaaa cgttttcatc gctctggagt gaataccacg acgatttccg   3300
gcagtttcta cacatatatt cgcaagatgt ggcgtgttac ggtgaaaacc tggcctattt   3360
ccctaaaggg tttattgaga atatgttttt cgtctcagcc aatccctggg tgagtttcac   3420
cagttttgat ttaaacgtgg ccaatatgga caacttcttc gcccccgttt tcaccatggg   3480
caaatattat acgcaaggcg acaaggtgct gatgccgctg gcgattcagg ttcatcatgc   3540
cgtttgtgat ggcttccatg tcggcagaat gcttaatgaa ttacaacagt actgcgatga   3600
gtggcagggc ggggcgtaat ttttttaagg cagttattgg tgcccttaaa cgcctggttg   3660
```

```
ctacgcctga ataagtgata ataagcggat gaatggcaga aattcgatga taagctgtca    3720
aacacaacca ccatcaaaca ggattttcgc ctgctggggc aaaccagcgt ggaccgcttg    3780
ctgcaactct ctcagggcca ggcggtgaag ggcaatcagc tgttgcccgt ctcactggtg    3840
aaaagaaaaa ccaccctggc gcccaatacg caaaccgcct ctccccgcgc gttggccgat    3900
tcattaatgc agctggcacg acaggtttcc cgactggaaa gcgggcagtg agcgcaacgc    3960
aattaatgta agttagcgcg aattgcaagc tggccgacgc gctgggctac gtcttgctgg    4020
cgttcgggag cagaagagca tacatctgga agcaaagcca ggaaagcggc ctatggagct    4080
gtgcggcagc gctcagtagg caattttttca aaatattgtt aagccttttc tgagcatggt    4140
atttttcatg gtattaccaa ttagcaggaa ataagccat tgaatataaa agataaaaat    4200
gtcttgttta caatagagtg ggggggggtca gcctgccgcc ttgggccggg tgatgtcgta    4260
cttgcccgcc gcgaactcgg ttaccgtcca gcccagcgcg accagctccg gcaacgcctc    4320
gcgcacccgc ttgcggcgct tgcgcatggt cgaaccactg gcctctgacg gccagacata    4380
gccgcacaag gtatctatgg aagccttgcc ggttttgccg gggtcgatcc agccacacag    4440
ccgctggtgc agcaggcggg cggtttcgct gtccagcgcc cgcacctcgt ccatgctgat    4500
gcgcacatgc tggccgccac ccatgacggc ctgcgcgatc aagggggttca gggccacgta    4560
caggcgcccg tccgcctcgt cgctggcgta ctccgacagc agccgaaacc cctgccgctt    4620
gcggccattc tgggcgatga tggatacctt ccaaaggcgc tcgatgcagt cctgtatgtg    4680
cttgagcgcc ccaccactat cgacctctgc cccgatttcc tttgccagcg cccgatagct    4740
acctttgacc acatggcatt cagcggtgac ggcctcccac ttgggttcca ggaacagccg    4800
gagctgccgt ccgccttcgg tcttgggttc cgggccaagc actaggccat taggcccagc    4860
catggccacc agcccttgca ggatgcgcag atcatcagcg cccagcggct ccgggccgct    4920
gaactcgatc cgcttgccgt cgccgtagtc atacgtcacg tccagcttgc tgcgcttgcg    4980
ctcgccccgc ttgagggcac ggaacaggcc gggggccaga cagtgcgccg ggtcgtgccg    5040
gacgtggctg aggctgtgct tgttcttagg cttcaccacg gggcaccccc ttgctcttgc    5100
gctgcctctc cagcacggcg ggcttgagca ccccgccgtc atgccgcctg aaccaccgat    5160
cagcgaacgg tgcgccatag ttggcctttgc tcacaccgaa gcggacgaag aaccggcgct    5220
ggtcgtcgtc cacacccccat tcctcggcct cggcgctggt catgctcgac aggtaggact    5280
gccagcggat gttatcgacc agtaccgagc tgccccggct ggcctgctgc tggtcgcctg    5340
cgcccatcat ggccgcgccc ttgctggcat ggtgcaggaa cacgatagag cacccggtat    5400
cggcggcgat ggcctccatg cgaccgatga cctgggccat ggggccgctg gcgttttctt    5460
cctcgatgtg gaaccggcgc agcgtgtcca gcaccatcag gcggcggccc tcggcggcgc    5520
gcttgaggcc gtcgaaccac tccggggcca tgatgttggg caggctgccg atcagcggct    5580
ggatcagcag gccgtcagcc acggcttgcc gttcctcggc gctgaggtgc gcccaagggg    5640
cgtgcaggcg gtgatgaatg gcggtgggcg ggtcttcggc gggcaggtag atcaccgggc    5700
cggtgggcag ttcgcccacc tccagcagat ccggcccgcc tgcaatctgt gcggccagtt    5760
gcagggccag catggattta ccggcaccac cgggcgacac cagcgccccg accgtaccgg    5820
ccaccatgtt gggcaaaacg tagtccgcg gtggcggcgc tgctgcgaac gcctccagaa    5880
tattgatagg cttatgggta gccattgatt gcctcctttg caggcagttg gtggttaggc    5940
gctgcgggg tcactacccc cgccctgcgc cgctctgagt tcttccaggc actcgcgcag    6000
cgcctcgtat tcgtcgtcgg tcagccagaa cttgcgctga cgcatcccctt tggccttcat    6060
```

```
gcgctcggca tatcgcgctt ggcgtacagc gtcagggctg ccagcaggt cgccggtctg    6120 cttgtcctttt tggtctttca tatcagtcac cgagaaactt gccggggccg aaaggcttgt   6180
cttcgcggaa caaggacaag gtgcagccgt caaggttaag gctggccata tcagcgactg   6240
aaaagcggcc agcctcggcc ttgtttgacg tataaccaaa gccaccgggc aaccaatagc    6300
ccttgtcact tttgatcagg tagaccgacc ctgaagcgct tttttcgtat tccataaaac    6360 cccettctgt gcgtgagtac tcatagtata acaggcgtga gtaccaacgc aagcactaca   6420
tgctgaaatc tggcccgccc ctgtccatgc ctcgctggcg gggtgccggt gcccgtgcca   6480
gctcggcccg cgcaagctgg acgctgggca gacccatgac cttgctgacg gtgcgctcga   6540
tgtaatccgc ttcgtggccg ggcttgcgct ctgccagcgc tgggctggcc tcggccatgg   6600
ccttgccgat ttcctcggca ctgcggcccc ggctggccag cttctgcgcg cgataaagt    6660 cgcacttgct gaggtcatga ccgaagcgct tgaccagccc ggccatctcg ctgcggtact   6720
cgtccagcgc cgtgcgccgg tggcggctaa gctgccgctc gggcagttcg aggctggcca   6780
gcctgcgggc cttctcctgc tgccgctggg cctgctcgat ctgctggcca gcctgctgca   6840
ccagcgccgg gccagcggtg gcggtcttgc ccttggattc acgcagcagc acccacggct   6900
gataaccggc gcgggtggtg tgcttgtcct tgcggttggt gaagcccgcc aagcggccat    6960
agtggcggct gtcggcgctg gccggtcgg cgtcgtactc gctggccagc gtccgggcaa     7020 tctgccccccg aagttcaccg cctgcggcgt cggccacctt gacccatgcc tgatagttct    7080
tcgggctggt ttccactacc agggcaggct cccggccctc ggctttcatg tcatccaggt    7140
caaactcgct gaggtcgtcc accagcacca gaccatgccg ctcctgctcg gcgggcctga   7200
tatacacgtc attgccctgg gcattcatcc gcttgagcca tggcgtgttc tggagcactt    7260
cggcggctga ccattcccgg ttcatcatct ggccggtggg tgcgtccctg acgccgatat    7320
cgaagcgctc acagcccatg gccttgagct gtcggcctat ggcctgcaaa gtcctgtcgt    7380
tcttcatcgg gccaccaagc gcagccagat cgagccgtcc tcggttgtca gtggcgtcag   7440
gtcgagcaag agcaacgatg cgatcagcag caccaccgta ggcatcatgg aagccagcat    7500
cacggttagc catagcttcc agtgccaccc ccgcgacgcg ctccgggcgc tctgcgcggc   7560
gctgctcacc tcggcggcta cctcccgcaa ctctttggcc agctccaccc atgccgcccc    7620
tgtctggcgc tgggctttca gccactccgc cgcctgcgcc tcgctggcct gcttggtctg   7680
gctcatgacc tgccgggctt cgtcggccag tgtcgccatg ctctgggcca gcggttcgat    7740
ctgctccgct aactcgttga tgcctctgga tttcttcact ctgtcgattg cgttcatggt    7800
ctattgcctc ccggtattcc tgtaagtcga tgatctgggc gttggcggtg tcgatgttca   7860
gggccacgtc tgcccggtcg gtgcggatgc cccggccttc catctccacc acgttcggcc    7920
ccaggtgaac accgggcagg cgctcgatgc cctgcgcctc aagtgttctg tggtcaatgc    7980
gggcgtcgtg ccagcccgc tctaatgccc ggttggcatg tcggccat gctcgcggg       8040 tctgctcaag ccatgccttg gcttgagcg cttcggtctt ctgtgcccg cccttctccg    8100 gggtcttgcc gttgtaccgc ttgaaccact gagcggcggg ccgctcgatg ccgtcattga    8160
tccgctcgga gatcatcagg tggcagtgcg ggttctcgcc gccaccggca tggatggcca    8220
gcgtatacgc caggcgctcg gcaccggtca ggtgctgggc gaactcggac gccagcgcct    8280
tctgctggtc gagggtcagc tcgaccggca gggcaaattc gacctccttg aacagccgcc    8340
cattggcgcg ttcatacagg tcggcagcat cccagtagtc ggcggccgc tcgacgaact    8400 ccggcatgtg cccggattcg gcgtgcaaga cttcatccat gtcgcgggca tacttgcctt    8460
```

```
cgcgctggat gtagtcggcc ttggccctgg ccgattggcc gcccgacctg ctgccggttt    8520
tcgccgtaag gtgataaatc gccatgctgc ctcgctgttg cttttgcttt tcggctccat    8580
gcaatggccc tcggagagcg caccgcccga agggtggccg ttaggccagt ttctcgaaga    8640
gaaaccggta agtgcgccct ccctacaaa gtagggtcgg gattgccgcc gctgtgcctc     8700
catgatagcc tacgagacag cacattaaca atggggtgtc aagatggtta aggggagcaa    8760
caaggcggcg gatcggctgg ccaagctcga agaacaacga gcgcgaatca atgccgaaat    8820
tcagcgggag cgggcaaggg aacagcagca agagcgcaag aacgaaacaa ggcgcaaggt    8880
gctggtgggg gccatgattt tggccaaggt gaacagcagc gagtggccgg aggatcggct    8940
catggcggca atggatgcgt accttgaacg cgaccacgac cgcgccttgt tcggtctgcc    9000
gccacgccag aaggatgagc cgggctgaat gatcgaccga gacaggccct gcggggctgc    9060
acacgcgccc ccaccttcg ggtaggggga aaggccgcta aagcggctaa aagcgctcca     9120
gcgtatttct gcgggttttg gtgtgggtt tagcgggctt tgcccgcctt tcccctgcc      9180 gcgcagcggt ggggcggtgt gtagcctagc gcagcgaata gaccagctat ccggcctctg    9240
gccgggcata ttgggcaagg gcagcagcgc cccacaaggg cgctgataac cgcgcctagt    9300
ggattattct tagataatca tggatggatt tttccaacac cccgccagcc cccgccctg     9360 ctgggtttgc aggtttgggg gcgtgacagt tattgcaggg gttcgtgaca gttattgcag    9420 ggggcgtga cagttattgc aggggttcgt gacagttagt acgggagtga cgggcactgg     9480
ctggcaatgt ctagcaacgg caggcatttc ggctgagggt aaaagaactt tccgctaagc    9540
gatagactgt atgtaaacac agtattgcaa ggacgcggaa catgcctcat gtggcggcca    9600
ggacggccag ccgggatcgg gatactggtc gttaccagag ccaccgaccc gagcaaaccc    9660
ttctctatca gatcgttgac gagtattacc cggcattcgc tgcgcttatg gcagagcagg    9720
gaaaggaatt gccgggctat gtgcaacggg aatttgaaga atttctccaa tgcgggcggc    9780
tggagcatgg cttttctacgg gttcgctgcg agtcttgcca cgccgagcac ctggtcgctt    9840
tcagaaatca atctaaagta tatatgagta aacttggtct gacagttacc aatgcttaat    9900
cagtgaggca cctatctcag cgatctgtct atttcgttca tccatagttg cctgactccc    9960
cgtcgtgtag ataactacga tacgggaggg cttaccatct ggccccagtg ctgcaatgat   10020
accgcgagac ccacgctcac cggctccaga tttatcagca ataaaccagc cagccggaag   10080
ggccgagcgc agaagtggtc ctgcaacttt atccgcctcc atccagtcta ttaattgttg   10140
ccgggaagct agagtaagta gttcgccagt taatagtttg cgcaacgttg ttgccattgc   10200
tacaggcatc gtggtgtcac gctcgtcgtt tggtatggct tcattcagct ccggttccca   10260
acgatcaagg cgagttacat gatcccccat gttgtgcaaa aaagcggtta gctccttcgg   10320
tcctccgatc gttgtcagaa gtaagttggc cgcagtgtta tcactcatgg ttatggcagc   10380
actgcataat tctcttactg tcatgccatc cgtaagatgc ttttctgtga ctggtgagta   10440
ctcaaccaag tcattctgag aatagtgtat gcggcgaccg agttgctctt gcccggcgtc   10500
aacacgggat aataccgcgc cacatagcag aactttaaaa gtgctcatca ttggaaaacg   10560
ttcttcgggg cgaaaactct caaggatctt accgctgttg agatccagtt cgatgtaacc   10620
cactcgtgca cccaactgat cttcagcatc ttttactttc accagcgttt ctgggtgagc   10680
aaaaacagga aggcaaaatg ccgcaaaaaa gggaataagg gcgacacgga aatgttgaat   10740
actcatactc ttcctttttc aatattattg aagcatttat cagggttatt gtctcatgag   10800
cggatacata tttgaatgta tttagaaaaa taaacaaaag agtttgtaga aacgcaaaaa   10860
```

```
ggccatccgt caggatggcc ttctgcttaa tttgatgcct ggcagtttat ggcgggcgtc    10920
ctgcccgcca ccctccgggc cgttgcttcg caacgttcaa atccgctccc ggcggatttg    10980
tcctactcag gagagcgttc accgacaaac aacagataaa acgaaaggcc cagtctttcg    11040
actgagcctt tcgttttatt tgatgcctgg cagttcccta ctctcgcatg gggagacccc    11100
acactaccat cggcgctacg gcgtttcact tctgagttcg gcatgggggtc aggtgggacc    11160 accgcgctac tgccgccagg caaattctgt tttatcagac cgcttctgcg ttctgattta    11220
atctgtatca ggctgaaaat cttctctcat ccgccaaaac agccaagct              11269

<210> SEQ ID NO 47
<211> LENGTH: 11195
<212> TYPE: DNA
<213> ORGANISM: Artificial
<220> FEATURE:
<223> OTHER INFORMATION: plasmid pLybAL18

<400> SEQUENCE: 47
tgcatgcata aatttctgtt ttgaccaaac catcccgaca taactcggtc agggcttgca      60
aaacagcggg gatgcgatcg tgctgccaga gactgcaaag gtgagccaat aaccactgcg     120
tctgccagtc atcaggtatc gcttggcagc gctgcaaccc agcttcgagg acgcgaacat     180
caactgtttt ggccagttgc tgaacctgtc gccaacaatg ttcaaaatca ccgcttggcc     240
agccgtcact ctctgcaaac gctgcatcag tcatgtgcaa tcaatacagg ttaaaaacca     300
tgctaatggc tccacctaag cgggcttcag agtcaaggct tgtagcaatt gctactaaaa     360
actgcgatcg ctgctgaaat gagctggaat tctgtccctc tcagctcaaa aagtatcaat     420
gattacttaa tgtttgttct gcgcaaactt cttgcagaac atgcatgatt tacaaaaagt     480
tgtagtttct gttaccaatt gcgaatcgag aactgcctaa tctgccgagt atgcaagctg     540
ctttgtaggc agatgaatcc atggtaccga gctcgaattg ggcgttttc tgtgaggctg     600 actagcgcgt ggcagctcaa atctctaca ttctgcacat tcagacccat ggtctgctgc     660
gagggcagaa cttggaactg gggcgagatg ccgacaccgg cgggcagacc aagtacgtct     720
tagaactggc tcaagcccaa gctaaatccc cacaagtcca acaagtcgac atcatcaccc     780
gccaaatcac cgaccccgc gtcagtgttg gttacagtca ggcgatcgaa cccttttgcgc    840 ccaaaggtcg gattgtccgt tgccttttg gccccaaacg ctacctccgt aaagagctgc     900
tttggcccca tctctacacc tttgcggatg caattctcca atatctggct cagcaaaagc     960
gcaccccgac ttggattcag gcccactatg ctgatgctgg ccaagtggga tcactgctga    1020
gtcgctggtt gaatgtaccg ctaattttca cagggcattc tctggggcgg atcaagctaa    1080
aaaagctgtt ggagcaagac tggccgcttg aggaaattga agcgcaattc aatattcaac    1140
agcgaattga tgcggaggag atgacgctca ctcatgctga ctggattgtc gccagcactc    1200
agcaggaagt ggaggagcaa taccgcgttt acgatcgcta caacccagag cgcaagcttg    1260
tcattccacc gggtgtcgat accgatcgct tcaggtttca gcccttgggc gatcgcggtg    1320
ttgttctcca acaggaactg agccgcttc tgcgcgaccc agaaaaacct caaattctct    1380
gcctctgtcg ccccgcacct cgcaaaaatg taccggcgct ggtgcgagcc tttggcgaac    1440
atccttggct gcgcaaaaaa gccaaccttg tcttagtact gggcagccgc caagacatca    1500
accagatgga tcgcggcagt cggcaggtgt tccaagagat tttccatctg gtcgatcgct    1560
acgacctcta cggcagcgtc gcctatccca aacagcatca ggctgatgat gtgccggagt    1620
tctatcgcct agcggctcat tccggcgggg tattcgtcaa tccggcgctg accgaacctt    1680
```

```
ttggtttgac aattttggag gcaggaagct gcggcgtgcc ggtggtggca acccatgatg   1740
gcggccccca ggaaattctc aaacactgtg atttcggcac tttagttgat gtcagccgac   1800
ccgctaatat cgcgactgca ctcgccaccc tgctgagcga tcgcgatctt tggcagtgct   1860
atcaccgcaa tggcattgaa aaagttcccg cccattacag ctgggatcaa catgtcaata   1920
ccctgtttga gcgcatggaa acggtggctt tgcctcgtcg tcgtgctgtc agtttcgtac   1980
ggagtcgcaa acgcttgatt gatgccaaac gccttgtcgt tagtgacatc gacaacacac   2040
tgttgggcga tcgtcaagga ctcgagaatt taatgaccta tctcgatcag tatcgcgatc   2100
attttgcctt tggaattgcc acggggcgtc gcctagactc tgcccaagaa gtcttgaaag   2160
agtggggcgt tccttcgcca aacttctggg tgacttccgt cggcagcgag attcactatg   2220
gcaccgatgc tgaaccggat atcagctggg aaaagcatat caatcgcaac tggaatcctc   2280
agcgaattcg ggcagtaatg gcacaactac cctttcttga actgcagccg aagaggatc    2340
aaacacccct caaagtcagc ttctttgtcc gcgatcgcca cgagactgtg ctgcgagaag   2400
tacggcaaca tcttcgccgc catcgcctgc ggctgaagtc aatctattcc catcaggagt   2460
ttcttgacat tctgccgcta gctgcctcga aggggatgc gattcgccac ctctcactcc    2520
gctggcggat tcctcttgag aacatttttgg tggcaggcga ttctggtaac gatgaggaaa  2580
tgctcaaggg ccataatctc ggcgttgtag ttggcaatta ctcaccggaa ttggagccac   2640
tgcgcagcta cgagcgcgtc tattttgctg agggccacta tgctaatggc attctggaag   2700
ccttaaaaca ctatcgcttt tttgaggcga tcgcttaacc ttttcagaat gagacgttga   2760
tcggcacgta agcgtgagac gttgatcggc acgtaagagg ttccaacttt caccataatg   2820
aaataagatc actaccgggc gtattttttg agttatcgag attttcagga gctaaggaag   2880
ctaaaatgga gaaaaaaatc actggatata ccaccgttga tatatcccaa tggcatcgta   2940
aagaacattt tgaggcattt cagtcagttg ctcaatgtac ctataaccag accgttcagc   3000
tggatattac ggccttttta aagaccgtaa agaaaaataa gcacaagttt tatccggcct   3060
ttattcacat tcttgcccgc ctgatgaatg ctcatccgga attccgtatg gcaatgaaag   3120
acggtgagct ggtgatatgg gatagtgttc acccttgtta caccgttttc catgagcaaa   3180
ctgaaacgtt tcatcgctc tggagtgaat accacgacga tttccggcag tttctacaca    3240
tatattcgca agatgtggcg tgttacggtg aaaacctggc ctatttccct aaagggttta   3300
ttgagaatat gttttttcgtc tcagccaatc cctgggtgag tttcaccagt tttgatttaa   3360
acgtggccaa tatggacaac ttcttcgccc ccgttttcac catgggcaaa tattatacgc   3420
aaggcgacaa ggtgctgatg ccgctggcga ttcaggttca tcatgccgtt tgtgatggct   3480
tccatgtcgg cagaatgctt aatgaattac aacagtactg cgatgagtgg cagggcgggg   3540
cgtaatttt  ttaaggcagt tattggtgcc cttaaacgcc tggttgctac gcctgaataa   3600
gtgataataa gcggatgaat ggcagaaatt cgatgataag ctgtcaaaca caaccaccat   3660
caaacaggat tttcgcctgc tggggcaaac cagcgtggac cgcttgctgc aactctctca   3720
gggccaggcg gtgaagggca atcagctgtt gcccgtctca ctggtgaaaa gaaaaaccac   3780
cctggcgccc aatacgcaaa ccgcctctcc ccgcgcgttg gccgattcat taatgcagct   3840
ggcacgacag gtttcccgac tggaaagcgg gcagtgagcg caacgcaatt aatgtaagtt   3900
agcgcgaatt gcaagctggc cgacgcgctg ggctacgtct tgctggcgtt cgggagcaga   3960
agagcataca tctggaagca aagccaggaa agcggcctat ggagctgtgc ggcagcgctc   4020
agtaggcaat ttttcaaaat attgttaagc cttttctgag catggtattt ttcatggtat   4080
```

```
taccaattag caggaaaata agccattgaa tataaaagat aaaaatgtct tgtttacaat    4140
agagtggggg gggtcagcct gccgccttgg gccgggtgat gtcgtacttg cccgccgcga    4200
actcggttac cgtccagccc agcgcgacca gctccggcaa cgcctcgcgc acccgcttgc    4260
ggcgcttgcg catggtcgaa ccactggcct ctgacggcca gacatagccg cacaaggtat    4320
ctatggaagc cttgccggtt ttgccggggt cgatccagcc acacagccgc tggtgcagca    4380
ggcgggcggt ttcgctgtcc agcgcccgca cctcgtccat gctgatgcgc acatgctggc    4440
cgccacccat gacggcctgc gcgatcaagg ggttcagggc cacgtacagg cgcccgtccg    4500
cctcgtcgct ggcgtactcc gacagcagcc gaaaccccctg ccgcttgcgg ccattctggg    4560
cgatgatgga taccttccaa aggcgctcga tgcagtcctg tatgtgcttg agcgccccac    4620
cactatcgac ctctgccccg atttcctttg ccagcgcccg atagctacct ttgaccacat    4680
ggcattcagc ggtgacggcc tcccacttgg gttccaggaa cagccggagc tgccgtccgc    4740
cttcggtctt gggttccggg ccaagcacta ggccattagg cccagccatg ccaccagcc    4800
cttgcaggat gcgcagatca tcagcgccca gcggctccgg ccgctgaac tcgatccgct    4860
tgccgtcgcc gtagtcatac gtcacgtcca gcttgctgcg cttgcgctcg ccccgcttga    4920
gggcacggaa caggccgggg ccagacagt gcgccgggtc gtgccggacg tggctgaggc    4980
tgtgcttgtt cttaggcttc accacggggc accccttgc tcttgcgctg cctctccagc    5040
acggcgggct tgagcacccc gccgtcatgc cgcctgaacc accgatcagc gaacggtgcg    5100
ccatagttgg ccttgctcac accgaagcgg acgaagaacc ggcgctggtc gtcgtccaca    5160
ccccattcct cggcctcggc gctggtcatg ctcgacaggt aggactgcca gcggatgtta    5220
tcgaccagta ccgagctgcc ccggctggcc tgctgctggt cgcctgcgcc catcatggcc    5280
gcgcccttgc tggcatggtg caggaacacg atagagcacc cggtatcggc ggcgatggcc    5340
tccatgcgac cgatgacctg ggccatgggg ccgctggcgt tttcttcctc gatgtggaac    5400
cggcgcagcg tgtccagcac catcaggcgg cggccctcgg cggcgcgctt gaggccgtcg    5460
aaccactccg gggccatgat gttgggcagg ctgccgatca gcggctggat cagcaggccg    5520
tcagccacgg cttgccgttc ctcggcgctg aggtgcgccc caagggcgtg caggcggtga    5580
tgaatggcgg tgggcgggtc ttcggcgggc aggtagatca ccgggccggt gggcagttcg    5640
cccacctcca gcagatccgg cccgcctgca atctgtgcgg ccagttgcag ggccagcatg    5700
gatttaccgg caccaccggg cgacaccagc gccccgaccg taccggccac catgttgggc    5760
aaaacgtagt ccagcggtgg cggcgctgct gcgaacgcct ccagaatatt gataggctta    5820
tgggtagcca ttgattgcct cctttgcagg cagttggtgg ttaggcgctg gcggggtcac    5880
taccccgcc ctgcgccgct ctgagttctt ccaggcactc gcgcagcgcc tcgtattcgt    5940
cgtcggtcag ccagaacttg cgctgacgca tcccctttggc cttcatgcgc tcggcatatc    6000
gcgcttggcg tacagcgtca gggctggcca gcaggtcgcc ggtctgcttg tcctttttggt    6060
ctttcatatc agtcaccgag aaacttgccg gggccgaaag gcttgtcttc gcggaacaag    6120
gacaaggtgc agccgtcaag gttaaggctg gccatatcag cgactgaaaa gcggccagcc    6180
tcggccttgt ttgacgtata accaaagcca ccgggcaacc aatagcccctt gtcacttttg    6240
atcaggtaga ccgaccctga agcgcttttt tcgtattcca taaaaccccc ttctgtgcgt    6300
gagtactcat agtataacag gcgtgagtac caacgcaagc actacatgct gaaatctggc    6360
ccgcccctgt ccatgcctcg ctggcggggt gccggtgccc gtgccagctc ggcccgcgca    6420
agctggacgc tgggcagacc catgaccttg ctgacggtgc gctcgatgta atccgcttcg    6480
```

```
tggccgggct tgcgctctgc cagcgctggg ctggcctcgg ccatggcctt gccgatttcc    6540
tcggcactgc ggccccggct ggccagcttc tgcgcggcga taaagtcgca cttgctgagg    6600
tcatgaccga agcgcttgac cagcccggcc atctcgctgc ggtactcgtc cagcgccgtg    6660
cgccggtggc ggctaagctg ccgctcgggc agttcgaggc tggccagcct gcgggccttc    6720
tcctgctgcc gctgggcctg ctcgatctgc tggccagcct gctgcaccag cgccgggcca    6780
gcggtggcgg tcttgccctt ggattcacgc agcagcaccc acggctgata accggcgcgg    6840
gtggtgtgct tgtccttgcg gttggtgaag cccgccaagc ggccatagtg gcggctgtcg    6900
gcgctggccg ggtcggcgtc gtactcgctg gccagcgtcc gggcaatctg cccccgaagt    6960
tcaccgcctg cggcgtcggc caccttgacc catgcctgat agttcttcgg gctggtttcc    7020
actaccaggg caggctcccg gccctcggct ttcatgtcat ccaggtcaaa ctcgctgagg    7080
tcgtccacca gcaccagacc atgccgctcc tgctcggcgg gcctgatata cacgtcattg    7140
ccctgggcat tcatccgctt gagccatggc gtgttctgga gcacttcggc ggctgaccat    7200
tcccggttca tcatctggcc ggtgggtgcg tccctgacgc cgatatcgaa gcgctcacag    7260
cccatggcct tgagctgtcg gcctatggcc tgcaaagtcc tgtcgttctt catcgggcca    7320
ccaagcgcag ccagatcgag ccgtcctcgg ttgtcagtgg cgtcaggtcg agcaagagca    7380
acgatgcgat cagcagcacc accgtaggca tcatggaagc cagcatcacg gttagccata    7440
gcttccagtg ccaccccgc gacgcgctcc gggcgctctg cgcggcgctg ctcacctcgg     7500
cggctacctc ccgcaactct ttggccagct ccacccatgc cgcccctgtc tggcgctggg    7560 cttttcagcca ctccgccgcc tgcgcctcgc tggcctgctt ggtctggctc atgacctgcc   7620
gggcttcgtc ggccagtgtc gccatgtctct gggccagcgg ttcgatctgc tccgctaact    7680
cgttgatgcc tctggatttc ttcactctgt cgattgcgtt catggtctat gcctcccgg     7740 tattcctgta agtcgatgat ctgggcgttg gcggtgtcga tgttcagggc cacgtctgcc    7800
cggtcggtgc ggatgccccg gccttccatc tccaccacgt tcggcccag gtgaacaccg     7860 ggcaggcgct cgatgccctg cgcctcaagt gttctgtggt caatgcgggc gtcgtggcca    7920
gcccgctcta atgcccggtt ggcatggtcg gcccatgcct cgcgggtctg ctcaagccat    7980
gccttgggct tgagcgcttc ggtcttctgt gccccgccct tctccgggt cttgccgttg     8040 taccgcttga accactgagc ggcgggccgc tcgatgccgt cattgatccg ctcggagatc    8100
atcaggtggc agtgcgggtt ctcgccgcca ccggcatgga tggccagcgt atacggcagg    8160
cgctcggcac cggtcaggtg ctgggcgaac tcggacgcca gcgccttctg ctggtcgagg    8220
gtcagctcga ccggcagggc aaattcgacc tccttgaaca gccgcccatt ggcgcgttca    8280
tacaggtcgg cagcatccca gtagtcggcg ggccgctcga cgaactccgg catgtgcccg    8340
gattcggcgt gcaagacttc atccatgtcg cgggcatact tgccttcgcg ctggatgtag    8400
tcggccttgg ccctggccga ttggccgccc gacctgctgc cggttttcgc cgtaaggtga    8460
taaatcgcca tgctgcctcg ctgttgcttt tgcttttcgg ctccatgcaa tggccctcgg    8520
agagcgcacc gcccgaaggg tggccgttag gccagtttct cgaagagaaa ccggtaagtg    8580
cgccctcccc tacaaagtag ggtcgggatt gccgccgctg tgcctccatg atagcctacg    8640
agacagcaca ttaacaatgg ggtgtcaaga tggttaaggg gagcaacaag gcggcggatc    8700
ggctggccaa gctcgaagaa caacgagcgc gaatcaatgc cgaaattcag cgggagcggg    8760
caagggaaca gcagcaagag cgcaagaacg aaacaaggcg caaggtgctg gtgggggcca    8820
tgattttggc caaggtgaac agcagcgagt ggccggagga tcggctcatg gcggcaatgg    8880
```

```
atgcgtacct tgaacgcgac cacgaccgcg ccttgttcgg tctgccgcca cgccagaagg    8940
atgagccggg ctgaatgatc gaccgagaca ggccctgcgg ggctgcacac gcgccccac    9000
ccttcgggta gggggaaagg ccgctaaagc ggctaaaagc gctccagcgt atttctgcgg    9060
ggtttggtgt ggggtttagc gggctttgcc cgcctttccc cctgccgcgc agcggtgggg    9120
cggtgtgtag cctagcgcag cgaatagacc agctatccgg cctctggccg ggcatattgg    9180
gcaagggcag cagcgcccca caagggcgct gataaccgcg cctagtggat tattcttaga    9240
taatcatgga tggattttc caacaccccg ccagccccg cccctgctgg gtttgcaggt    9300
ttggggcgt gacagttatt gcaggggttc gtgacagtta ttgcagggg gcgtgacagt    9360
tattgcaggg gttcgtgaca gttagtacgg gagtgacggg cactggctgg caatgtctag    9420
caacggcagg catttcggct gagggtaaaa gaactttccg ctaagcgata gactgtatgt    9480
aaacacagta ttgcaaggac gcggaacatg cctcatgtgg cggccaggac ggccagccgg    9540
gatcgggata ctggtcgtta ccagagccac cgacccgagc aaaccttct ctatcagatc    9600
gttgacgagt attacccggc attcgctgcg cttatggcag agcagggaaa ggaattgccg    9660
ggctatgtgc aacgggaatt tgaagaattt ctccaatgcg ggcggctgga gcatggcttt    9720
ctacgggttc gctgcgagtc ttgccacgcc gagcacctgg tcgctttcag aaatcaatct    9780
aaagtatata tgagtaaact tggtctgaca gttaccaatg cttaatcagt gaggcaccta    9840
tctcagcgat ctgtctattt cgttcatcca tagttgcctg actccccgtc gtgtagataa    9900
ctacgatacg ggagggctta ccatctggcc ccagtgctgc aatgataccg cgagacccac    9960
gctcaccggc tccagattta tcagcaataa accagccagc cggaagggcc gagcgcagaa    10020
gtggtcctgc aactttatcc gcctccatcc agtctattaa ttgttgccgg gaagctagag    10080
taagtagttc gccagttaat agtttgcgca acgttgttgc cattgctaca ggcatcgtgg    10140
tgtcacgctc gtcgtttggt atggcttcat tcagctccgg ttcccaacga tcaaggcgag    10200
ttacatgatc ccccatgttg tgcaaaaaag cggttagctc cttcggtcct ccgatcgttg    10260
tcagaagtaa gttggccgca gtgttatcac tcatggttat ggcagcactg cataattctc    10320
ttactgtcat gccatccgta agatgctttt ctgtgactgg tgagtactca accaagtcat    10380
tctgagaata gtgtatgcgg cgaccgagtt gctcttgccc ggcgtcaaca cgggataata    10440
ccgcgccaca tagcagaact ttaaaagtgc tcatcattgg aaaacgttct cgggggcgaa    10500
aactctcaag gatcttaccg ctgttgagat ccagttcgat gtaacccact cgtgcaccca    10560
actgatcttc agcatctttt actttcacca gcgtttctgg gtgagcaaaa acaggaaggc    10620
aaaatgccgc aaaaaaggga ataagggcga cacggaaatg ttgaatactc atactcttcc    10680
tttttcaata ttattgaagc atttatcagg gttattgtct catgagcgga tacatatttg    10740
aatgtattta gaaaaataaa caaaagagtt tgtagaaacg caaaaaggcc atccgtcagg    10800
atggccttct gcttaatttg atgcctggca gtttatggcg ggcgtcctgc ccgccaccct    10860
ccgggccgtt gcttcgcaac gttcaaatcc gctcccggcg gatttgtcct actcaggaga    10920
gcgttcaccg acaaacaaca gataaaacga aaggcccagt ctttcgactg agcctttcgt    10980
tttatttgat gcctggcagt tccctactct cgcatgggga daccccacac taccatcggc    11040
gctacggcgt ttcacttctg agttcggcat ggggtcaggt gggaccaccg cgctactgcc    11100
gccaggcaaa ttctgtttta tcagaccgct tctgcgttct gatttaatct gtatcaggct    11160
gaaaatcttc tctcatccgc caaaacagcc aagct                              11195
```

```
<210> SEQ ID NO 48
<211> LENGTH: 11820
<212> TYPE: DNA
<213> ORGANISM: Artificial
<220> FEATURE:
<223> OTHER INFORMATION: plasmid pLybAL19

<400> SEQUENCE: 48
tgcatgcctg caggtcgact ctagatggct acgagggcag acagtaagtg gatttaccat    60
aatcccttaa ttgtacgcac cgctaaaacg cgttcagcgc gatcacggca gcagacaggt   120
aaaaatggca acaaaccacc ctaaaaactg cgcgatcgcg cctgataaat tttaaccgta   180
tgaataccta tgcaaccaga gggtacaggc cacattaccc ccacttaatc cactgaagct   240 gccattttc atggtttcac catcccagcg aagggccatg catgcatcga aattaatacg   300
acgaaattaa tacgactcac tatagggcaa ttgttatcag ctatgcgccg accagaacac   360
cttgccgatc agccaaacgt ctcttcaggc cactgactag cgataacttt ccccacaacg   420
gaacaactct cactgcatgg gatcattggg tactgtgggt ttagtggttg taaaaacacc   480
tgaccgctat ccctgatcag tttcttgaag gtaaactcat caccccccaag tctggctatg   540 cagaaatcac ctggctcaac agcctgctca gggtcaacga gaattaacat tccgtcagga   600
aagcttggct tggagcctgt tggtgcggtc atggaattac cttcaacctc aagccagaat   660
gcagaatcac tggcttttctt ggttgtgctt acccatctct ccgcatcacc tttggtaaag   720
gttctaagct taggtgagaa catccctgcc tgaacatgag aaaaaacagg gtactcatac   780
tcacttctaa gtgacggctg catactaacc gcttcataca tctcgtagat ttctctggcg   840
attgaagggc taaattcttc aacgctaact ttgagaattt ttgtaagcaa tgcggcgtta   900
taagcattta atgcattgat gccattaaat aaagcaccaa cgcctgactg ccccatcccc   960
atcttgtctg cgacagattc ctgggataag ccaagttcat tttttctttt ttcataaatt  1020
gctttaaggc gacgtgcgtc ctcaagctgc tcttgtgtta atggtttctt ttttgtgctc  1080
atacgttaaa tctatcaccg caagggataa atatctaaca ccgtgcgtgt tgactatttt  1140
acctctggcg gtgataatgg ttgcatctta agaaggagga tccatatggt accgagctcg  1200
aattggggcg ttttctgtga ggctgactag cgcgtggcag ctcaaaatct ctacattctg  1260
cacattcaga cccatggtct gctgcgaggg cagaacttgg aactggggcg agatgccgac  1320
accggcgggc agaccaagta cgtcttagaa ctggctcaag cccaagctaa atccccacaa  1380
gtccaacaag tcgacatcat cacccgccaa atcaccgacc ccgcgtcag tgttggttac  1440 agtcaggcga tcgaaccctt tgcgcccaaa ggtcggattg tccgtttgcc ttttggcccc  1500
aaacgctacc tccgtaaaga gctgctttgg ccccatctct acacctttgc ggatgcaatt  1560
ctccaatatc tggctcagca aaagcgcacc ccgacttgga ttcaggccca ctatgctgat  1620
gctggccaag tgggatcact gctgagtcgc tggttgaatg taccgctaat tttcacaggg  1680
cattctctgg ggcggatcaa gctaaaaaag ctgttggagc aagactggcc gcttgaggaa  1740
attgaagcgc aattcaatat tcaacagcga attgatgcgg aggagatgac gctcactcat  1800
gctgactgga ttgtcgccag cactcagcag gaagtggagg agcaatacccg cgtttacgat  1860 cgctacaacc cagagcgcaa gcttgtcatt ccaccgggtg tcgataccga tcgcttcagg  1920 tttcagcccct tgggcgatcg cggtgttgtt ctccaacagg aactgagccg cttttctgcgc  1980 gacccagaaa aacctcaaat tctctgcctc tgtcgccccg cacctcgcaa aaatgtaccg  2040
gcgctggtgc gagcctttgg cgaacatcct tggctgcgca aaaaagccaa ccttgtctta  2100
gtactgggca gccgccaaga catcaaccag atggatcgcg gcagtcggca ggtgttccaa  2160
```

```
gagattttcc atctggtcga tcgctacgac ctctacggca gcgtcgccta tcccaaacag   2220
catcaggctg atgatgtgcc ggagttctat cgcctagcgg ctcattccgg cggggtattc   2280
gtcaatccgg cgctgaccga accttttggt ttgacaattt tggaggcagg aagctgcggc   2340
gtgccggtgg tggcaaccca tgatggcggc ccccaggaaa ttctcaaaca ctgtgatttc   2400
ggcactttag ttgatgtcag ccgacccgct aatatcgcga ctgcactcgc caccctgctg   2460
agcgatcgcg atctttggca gtgctatcac cgcaatggca ttgaaaaagt tcccgcccat   2520
tacagctggg atcaacatgt caatacctg tttgagcgca tggaaacggt ggctttgcct   2580
cgtcgtcgtg ctgtcagttt cgtacggagt cgcaaacgct tgattgatgc caaacgcctt   2640
gtcgttagtg acatcgacaa cacactgttg ggcgatcgtc aaggactcga gaatttaatg   2700
acctatctcg atcagtatcg cgatcatttt gcctttggaa ttgccacggg gcgtcgccta   2760
gactctgccc aagaagtctt gaaagagtgg ggcgttcctt cgccaaactt ctgggtgact   2820
tccgtcggca gcgagattca ctatggcacc gatgctgaac cggatatcag ctgggaaaag   2880
catatcaatc gcaactggaa tcctcagcga attcgggcag taatggcaca actacccttt   2940
cttgaactgc agccggaaga ggatcaaaca cccttcaaag tcagcttctt tgtccgcgat   3000
cgccacgaga ctgtgctgcg agaagtacgg caacatcttc gccgccatcg cctgcggctg   3060
aagtcaatct attcccatca ggagtttctt gacattctgc cgctagctgc ctcgaaaggg   3120
gatgcgattc gccacctctc actccgctgg cggattcctc ttgagaacat tttggtggca   3180
ggcgattctg gtaacgatga ggaaatgctc aagggccata atctcggcgt tgtagttggc   3240
aattactcac cggaattgga gccactgcgc agctacgagc gcgtctattt tgctgagggc   3300
cactatgcta atggcattct ggaagcctta aaacactatc gctttttga ggcgatcgct   3360 taacctttc agaatgagac gttgatcggc acgtaagcgt gagacgttga tcggcacgta   3420
agaggttcca actttcacca taatgaaata agatcactac cggcgtatt ttttgagtta   3480 tcgagatttt caggagctaa ggaagctaaa atggagaaaa aaatcactgg atataccacc   3540
gttgatatat cccaatggca tcgtaaagaa cattttgagg catttcagtc agttgctcaa   3600
tgtacctata accagaccgt tcagctggat attacggcct ttttaaagac cgtaaagaaa   3660
aataagcaca agttttatcc ggcctttatt cacattcttg cccgcctgat gaatgctcat   3720
ccggaattcc gtatggcaat gaaagacggt gagctggtga tatgggatag tgttcaccct   3780
tgttacaccg ttttccatga gcaaactgaa acgttttcat cgctctggag tgaataccac   3840
gacgatttcc ggcagtttct acacatatat tcgcaagatg tggcgtgtta cggtgaaaac   3900
ctggcctatt tccctaaagg gtttattgag aatatgtttt tcgtctcagc caatccctgg   3960
gtgagtttca ccagttttga tttaaacgtg gccaatatgg acaacttctt cgccccgtt   4020 ttcaccatgg gcaaatatta tacgcaaggc gacaaggtgc tgatgccgct ggcgattcag   4080
gttcatcatg ccgtttgtga tggcttccat gtcggcagaa tgcttaatga attacaacag   4140
tactgcgatg agtggcaggg cggggcgtaa ttttttaag gcagttattg gtgcccttaa   4200
acgcctggtt gctacgcctg aataagtgat aataagcgga tgaatggcag aaattcgatg   4260
ataagctgtc aaacacaacc accatcaaac aggattttcg cctgctgggg caaaccagcg   4320
tggaccgctt gctgcaactc tctcagggcc aggcggtgaa gggcaatcag ctgttgcccg   4380
tctcactggt gaaaagaaaa accaccctgg cgcccaatac gcaaaccgcc tctccccgcg   4440
cgttggccga ttcattaatg cagctggcac gacaggtttc ccgactggaa agcgggcagt   4500
gagcgcaacg caattaatgt aagttagcgc gaattgcaag ctggccgacg cgctgggcta   4560
```

```
cgtcttgctg gcgttcggga gcagaagagc atacatctgg aagcaaagcc aggaaagcgg    4620
cctatggagc tgtgcggcag cgctcagtag gcaattttc aaaatattgt taagcctttt    4680
ctgagcatgg tattttttcat ggtattacca attagcagga aaataagcca ttgaatataa    4740
aagataaaaa tgtcttgttt acaatagagt ggggggggtc agcctgccgc cttgggccgg    4800
gtgatgtcgt acttgcccgc cgcgaactcg gttaccgtcc agcccagcgc gaccagctcc    4860
ggcaacgcct cgcgcacccg cttgcggcgc ttgcgcatgg tcgaaccact ggcctctgac    4920
ggccagacat agccgcacaa ggtatctatg gaagccttgc cggttttgcc ggggtcgatc    4980
cagccacaca gccgctggtg cagcaggcgg gcggtttcgc tgtccagcgc ccgcacctcg    5040
tccatgctga tgcgcacatg ctggccgcca cccatgacgg cctgcgcgat caaggggttc    5100
agggccacgt acaggcgccc gtccgcctcg tcgctggcgt actccgacag cagccgaaac    5160
ccctgccgct gcggccatt ctgggcgatg atggatacct tccaaaggcg ctcgatgcag    5220
tcctgtatgt gcttgagcgc cccaccacta tcgacctctg ccccgatttc ctttgccagc    5280
gcccgatagc tacctttgac cacatggcat tcagcggtga cggcctccca cttgggttcc    5340
aggaacagcc ggagctgccg tccgccttcg gtcttgggtt ccgggccaag cactaggcca    5400
ttaggcccag ccatggccac cagcccttgc aggatgcgca gatcatcagc gcccagcggc    5460
tccgggccgc tgaactcgat ccgcttgccg tcgccgtagt catacgtcac gtccagcttg    5520
ctgcgcttgc gctcgccccg cttgagggca cggaacaggc cggggggccag acagtgcgcc    5580 gggtcgtgcc ggacgtggct gaggctgtgc ttgttcttag gcttcaccac ggggcacccc    5640
cttgctcttg cgctgcctct ccagcacggc gggcttgagc accccgccgt catgccgcct    5700
gaaccaccga tcagcgaacg gtgcgccata gttggccttg ctcacaccga agcggacgaa    5760
gaaccggcgc tggtcgtcgt ccacaccca ttcctcggcc tcggcgctgg tcatgctcga    5820
caggtaggac tgccagcgga tgttatcgac cagtaccgag ctgccccggc tggcctgctg    5880
ctggtcgcct gcgcccatca tggccgcgcc cttgctggca tggtgcagga acacgataga    5940
gcacccggta tcgcggcga tggcctccat gcgaccgatg acctgggcca tggggccgct    6000
ggcgttttct tcctcgatgt ggaaccggcg cagcgtgtcc agcaccatca ggcggcggcc    6060
ctcggcggcg cgcttgaggc cgtcgaacca ctccggggcc atgatgttgg gcaggctgcc    6120
gatcagcggc tggatcagca ggccgtcagc cacggcttgc cgttcctcgg cgctgaggtg    6180
cgccccaagg gcgtgcaggc ggtgatgaat ggcggtgggc gggtcttcgg cgggcaggta    6240
gatcaccggg ccggtgggca gttcgcccac ctccagcaga tccggcccgc ctgcaatctg    6300
tgcggccagt tgcagggcca gcatggattt accggcacca ccgggcgaca ccagcgcccc    6360
gaccgtaccg gccaccatgt tgggcaaaac gtagtccagc ggtggcggcg ctgctgcgaa    6420
cgcctccaga atattgatag gcttatgggt agccattgat tgcctccttt gcaggcagtt    6480
ggtggttagg cgctggcggg gtcactaccc ccgccctgcg ccgctctgag ttcttccagg    6540
cactcgcgca gcgcctcgta ttcgtcgtcg gtcagccaga acttgcgctg acgcatccct    6600
ttggccttca tgcgctcggc atatcgcgct tggcgtacag cgtcagggct ggccagcagg    6660
tcgccggtct gcttgtcctt ttggtctttc atatcagtca ccgagaaact tgccggggcc    6720
gaaaggcttg tcttcgcgga acaaggacaa ggtgcagccg tcaaggttaa ggctggccat    6780
atcagcgact gaaaagcggc cagcctcggc cttgtttgac gtataaccaa agccaccggg    6840
caaccaatag cccttgtcac ttttgatcag gtagaccgac cctgaagcgc ttttttcgta    6900
ttccataaaa cccccttctg tgcgtgagta ctcatagtat aacaggcgtg agtaccaacg    6960
```

```
caagcactac atgctgaaat ctggcccgcc cctgtccatg cctcgctggc ggggtgccgg    7020
tgcccgtgcc agctcggccc gcgcaagctg gacgctgggc agacccatga ccttgctgac    7080
ggtgcgctcg atgtaatccg cttcgtggcc gggcttgcgc tctgccagcg ctgggctggc    7140
ctcggccatg gccttgccga tttcctcggc actgcggccc cggctggcca gcttctgcgc    7200
ggcgataaag tcgcacttgc tgaggtcatg accgaagcgc ttgaccagcc cggccatctc    7260
gctgcggtac tcgtccagcg ccgtgcgccg gtggcggcta agctgccgct cgggcagttc    7320
gaggctggcc agcctgcggg ccttctcctg ctgccgctgg gcctgctcga tctgctggcc    7380
agcctgctgc accagcgccg ggccagcggt ggcggtcttg cccttggatt cacgcagcag    7440
cacccacggc tgataaccgg cgcgggtggt gtgcttgtcc ttgcggttgg tgaagcccgc    7500
caagcggcca tagtggcggc tgtcggcgct ggccgggtcg cgtcgtact cgctggccag    7560 cgtccgggca atctgccccc gaagttcacc gcctgcggcg tcggccacct tgacccatgc    7620
ctgatagttc ttcgggctgg tttccactac cagggcaggc tcccggccct cggctttcat    7680
gtcatccagg tcaaactcgc tgaggtcgtc caccagcacc agaccatgcc gctcctgctc    7740
ggcgggcctg atatacacgt cattgccctg gcattcatc cgcttgagcc atggcgtgtt    7800
ctggagcact tcggcggctg accattcccg gttcatcatc tggccggtgg gtgcgtccct    7860
gacgccgata tcgaagcgct cacagcccat ggccttgagc tgtcggccta ggcctgcaa    7920 agtcctgtcg ttcttcatcg ggccaccaag cgcagccaga tcgagccgtc ctcggttgtc    7980
agtggcgtca ggtcgagcaa gagcaacgat gcgatcagca gcaccaccgt aggcatcatg    8040
gaagccagca tcacggttag ccatagcttc cagtgccacc cccgcgacgc gctccgggcg    8100
ctctgcgcgg cgctgctcac ctcggcggct acctcccgca actctttggc cagctccacc    8160
catgccgccc ctgtctggcg ctgggctttc agccactccg ccgcctgcgc ctcgctggcc    8220
tgcttggtct ggctcatgac ctgccgggct tcgtcggcca gtgtcgccat gctctgggcc    8280
agcggttcga tctgctccgc taactcgttg atgcctctgg atttcttcac tctgtcgatt    8340
gcgttcatgg tctattgcct cccggtattc ctgtaagtcg atgatctggg cgttggcggt    8400
gtcgatgttc agggccacgt ctgcccggtc ggtgcggatg ccccggcctt ccatctccac    8460
cacgttcggc cccaggtgaa caccgggcag gcgctcgatg ccctgcgcct caagtgttct    8520
gtggtcaatg cgggcgtcgt ggccagcccg ctctaatgcc cggttggcat ggtcggccca    8580
tgcctcgcgg gtctgctcaa gccatgcctt gggcttgagc gcttcggtct tctgtgcccc    8640
gcccttctcc ggggtcttgc cgttgtaccg cttgaaccac tgagcggcgg gccgctcgat    8700
gccgtcattg atccgctcgg agatcatcag gtggcagtgc gggttctcgc cgccaccggc    8760
atggatggcc agcgtatacg gcaggcgctc ggcaccggtc aggtgctggg cgaactcgga    8820
cgccagcgcc ttctgctggt cgagggtcag ctcgaccggc agggcaaatt cgacctcctt    8880
gaacagccgc ccattggcgc gttcatacag gtcggcagca tcccagtagt cggcgggccg    8940
ctcgacgaac tccggcatgt gcccggattc ggcgtgcaag acttcatcca tgtcgcgggc    9000
atacttgcct tcgcgctgga tgtagtcggc cttggccctg gccgattggc cgcccgacct    9060
gctgccggtt ttcgccgtaa ggtgataaat cgccatgctg cctcgctgtt gcttttgctt    9120
ttcggctcca tgcaatggcc ctcggagagc gcaccgcccg aagggtggcc gttaggccag    9180
tttctcgaag agaaaccggt aagtgcgccc tcccctacaa agtagggtcg ggattgccgc    9240
cgctgtgcct ccatgatagc ctacgagaca gcacattaac aatgggtgt caagatggtt    9300 aaggggagca acaaggcggc ggatcggctg gccaagctcg aagaacaacg agcgcgaatc    9360
```

```
aatgccgaaa ttcagcggga gcgggcaagg gaacagcagc aagagcgcaa gaacgaaaca   9420
aggcgcaagg tgctggtggg ggccatgatt ttggccaagg tgaacagcag cgagtggccg   9480
gaggatcggc tcatggcggc aatggatgcg taccttgaac gcgaccacga ccgcgccttg   9540
ttcggtctgc cgccacgcca gaaggatgag ccgggctgaa tgatcgaccg agacaggccc   9600
tgcggggctg cacacgcgcc cccacccttc gggtaggggg aaaggccgct aaagcggcta   9660
aaagcgctcc agcgtatttc tgcgggtttt ggtgtggggt ttagcgggct ttgcccgcct   9720
ttccccctgc cgcgcagcgg tggggcggtg tgtagcctag cgcagcgaat agaccagcta   9780
tccggcctct ggccgggcat attgggcaag ggcagcagcg ccccacaagg gcgctgataa   9840
ccgcgcctag tggattattc ttagataatc atgatggat ttttccaaca ccccgccagc   9900
ccccgcccct gctgggtttg caggtttggg ggcgtgacga ttattgcagg ggttcgtgac   9960
agttattgca gggggggcgtg acagttattg caggggttcg tgacagttag tacgggagtg  10020
acgggcactg gctggcaatg tctagcaacg gcaggcattt cggctgaggg taaaagaact  10080
ttccgctaag cgatagactg tatgtaaaca cagtattgca aggacgcgga acatgcctca  10140
tgtggcggcc aggacggcca gccgggatcg ggatactggt cgttaccaga gccaccgacc  10200
cgagcaaacc cttctctatc agatcgttga cgagtattac ccggcattcg ctgcgcttat  10260
ggcagagcag ggaaaggaat tgccgggcta tgtgcaacgg gaatttgaag aatttctcca  10320
atgcgggcgg ctggagcatg gctttctacg ggttcgctgc gagtcttgcc acgccgagca  10380
cctggtcgct ttcagaaatc aatctaaagt atatatgagt aaacttggtc tgacagttac  10440
caatgcttaa tcagtgaggc acctatctca gcgatctgtc tatttcgttc atccatagtt  10500
gcctgactcc ccgtcgtgta gataactacg atacgggagg gcttaccatc tggccccagt  10560
gctgcaatga taccgcgaga cccacgctca ccggctccag atttatcagc aataaaccag  10620
ccagccggaa gggccgagcg cagaagtggt cctgcaactt tatccgcctc catccagtct  10680
attaattgtt gccgggaagc tagagtaagt agttcgccag ttaatagttt gcgcaacgtt  10740
gttgccattg ctacaggcat cgtggtgtca cgctcgtcgt ttggtatggc ttcattcagc  10800
tccggttccc aacgatcaag gcgagttaca tgatccccca tgttgtgcaa aaaagcggtt  10860
agctccttcg gtcctccgat cgttgtcaga agtaagttgg ccgcagtgtt atcactcatg  10920
gttatggcag cactgcataa ttctcttact gtcatgccat ccgtaagatg cttttctgtg  10980
actggtgagt actcaaccaa gtcattctga gaatagtgta tgcggcgacc gagttgctct  11040
tgcccggcgt caacacggga taataccgcg ccacatagca gaactttaaa agtgctcatc  11100
attggaaaac gttcttcggg gcgaaaactc tcaaggatct taccgctgtt gagatccagt  11160
tcgatgtaac ccactcgtgc acccaactga tcttcagcat cttttacttt caccagcgtt  11220
tctgggtgag caaaaacagg aaggcaaaat gccgcaaaaa agggaataag ggcgacacgg  11280
aaatgttgaa tactcatact cttccttttt caatattatt gaagcattta tcagggttat  11340
tgtctcatga gcggatacat atttgaatgt atttagaaaa ataaacaaaa gagtttgtag  11400
aaacgcaaaa aggccatccg tcaggatggc cttctgctta atttgatgcc tggcagttta  11460
tggcgggcgt cctgcccgcc accctccggg ccgttgcttc gcaacgttca aatccgctcc  11520
cggcggattt gtcctactca ggagagcgtt caccgacaaa caacagataa aacgaaaggc  11580
ccagtctttc gactgagcct ttcgttttat ttgatgcctg gcagttccct actctcgcat  11640
ggggagaccc cacactacca tcggcgctac ggcgtttcac ttctgagttc ggcatggggt  11700
caggtgggac caccgcgcta ctgccgccag gcaaattctg ttttatcaga ccgcttctgc  11760
```

```
gttctgattt aatctgtatc aggctgaaaa tcttctctca tccgccaaaa cagccaagct   11820
```

<210> SEQ ID NO 49
<211> LENGTH: 11511
<212> TYPE: DNA
<213> ORGANISM: Artificial
<220> FEATURE:
<223> OTHER INFORMATION: plasmid pLybAL21

<400> SEQUENCE: 49

```
tgcatgcacc agtaaacata aatctccccg gcgacgcaaa aaacgggtga ccatcaagcc     60
ggtgcgcttc ggcattttc tgctttgcct agcaggcatt gtgggggggg caactgccct    120
aattatcaat cgtactggcg atcccctagg tgggttgcta aaagaccccc tagatgtttt    180
cctggaccaa ccttcagaat ttatccccga tgaagccacg agccggaatt tgattctcag    240
tcaacccaac ttcaatcagc aagtgggtca gatggtagta caaggctggc ttgatagtaa    300
aaagttagcc tttggccaaa actacgatgt cggggcattg cagagtgttt tagcccccaa    360
tctccttgcc caacaacggg gtcgggccca acgggatcaa gcccaaaagg tctatcacca    420
atacgaacac aagttgcaga ttttagccta tcaagttaac ccccaagacc caaccgagc     480
caccgttact gcccgggtag aagaaattag ccagcccttt accctaggta atcaacagca    540
gaagggctcc gccaccaaag atgacttgac tgtgcgctat cagctagtac gacaccaagg    600
ggtttggaaa attgaccaaa tacaagtggt aaatggcccc cgttagtgcg tggcgttaac    660
tccccttttg accaatggca tacggctaga tgccccata ggtacggaaa cctgcacttc     720
cgagaactaa gccctaccg tcactataag agtgtgaacg tgtcggcccc aggcaatgga    780
ttggaaccat ggcttttcgg cccatcgttg tgtcttatat tcttacttgt taacgggagt    840
taattaaaat tatgggaaaa gttgttggga ttgaacctcgg taccgagctc gaattggggc    900
gttttctgtg aggctgacta gcgcgtggca gctcaaaatc tctacattct gcacattcag    960
acccatggtc tgctgcgagg gcagaacttg gaactggggc gagatgccga caccggcggg   1020
cagaccaagt acgtcttaga actggctcaa gcccaagcta aatcccccaca agtccaacaa   1080
gtcgacatca tcacccgcca aatcaccgac ccccgcgtca gtgttggtta cagtcaggcg   1140
atcgaaccct ttgcgcccaa aggtcggatt gtccgtttgc cttttggccc caaacgctac   1200
ctccgtaaag agctgctttg gccccatctc tacacctttg cggatgcaat tctccaatat   1260
ctggctcagc aaaagcgcac cccgacttgg attcaggccc actatgctga tgctggccaa   1320
gtgggatcac tgctgagtcg ctggttgaat gtaccgctaa ttttcacagg gcattctctg   1380
gggcggatca agctaaaaaa gctgttggag caagactggc cgcttgagga aattgaagcg   1440
caattcaata ttcaacagcg aattgatgcg gaggagatga cgctcactca tgctgactgg   1500
attgtcgcca gcactcagca ggaagtggag gagcaatacc gcgtttacga tcgctacaac   1560
ccagagcgca agcttgtcat tccaccgggt gtcgataccg atcgcttcag gtttcagccc   1620
ttgggcgatc gcggtgttgt tctccaacag gaactgagcc gctttctgcg cgacccagaa   1680
aaacctcaaa ttctctgcct ctgtcgcccc gcacctcgca aaaatgtacc ggcgctggtg   1740
cgagcctttg gcgaacatcc ttggctgcgc aaaaaagcca accttgtctt agtactgggc   1800
agccgccaag acatcaacca gatggatcgc ggcagtcggc aggtgttcca agagattttc   1860
catctggtcg atcgctacga cctctacggc agcgtcgcct atcccaaaca gcatcaggct   1920
gatgatgtgc cggagttcta tcgcctagcg gctcattccg gcggggtatt cgtcaatccg   1980
gcgctgaccg aaccttttgg tttgacaatt ttggaggcag gaagctgcgg cgtgccggtg   2040
```

-continued

```
gtggcaaccc atgatggcgg cccccaggaa attctcaaac actgtgattt cggcacttta    2100
gttgatgtca gccgacccgc taatatcgcg actgcactcg ccaccctgct gagcgatcgc    2160
gatctttggc agtgctatca ccgcaatggc attgaaaaag ttcccgccca ttacagctgg    2220
gatcaacatg tcaataccct gtttgagcgc atggaaacgg tggctttgcc tcgtcgtcgt    2280
gctgtcagtt tcgtacggag tcgcaaacgc ttgattgatg ccaaacgcct tgtcgttagt    2340
gacatcgaca acacactgtt gggcgatcgt caaggactcg agaatttaat gacctatctc    2400
gatcagtatc gcgatcattt tgcctttgga attgccacgg ggcgtcgcct agactctgcc    2460
caagaagtct tgaaagagtg gggcgttcct tcgccaaact tctgggtgac ttccgtcggc    2520
agcgagattc actatggcac cgatgctgaa ccggatatca gctgggaaaa gcatatcaat    2580
cgcaactgga atcctcagcg aattcgggca gtaatggcac aactacccct tcttgaactg    2640
cagccggaag aggatcaaac acccttcaaa gtcagcttct tgtccgcga tcgccacgag    2700 actgtgctgc gagaagtacg gcaacatctt cgccgccatc gcctgcggct gaagtcaatc    2760
tattcccatc aggagtttct tgacattctg ccgctagctg cctcgaaagg ggatgcgatt    2820
cgccacctct cactccgctg gcggattcct cttgagaaca ttttggtggc aggcgattct    2880
ggtaacgatg aggaaatgct caagggccat aatctcggcg ttgtagttgg caattactca    2940
ccggaattgg agccactgcg cagctacgag cgcgtctatt tgctgaggg ccactatgct    3000 aatggcattc tggaagcctt aaaacactat cgcttttttg aggcgatcgc ttaacctttt    3060
cagaatgaga cgttgatcgg cacgtaagcg tgagacgttg atcggcacgt aagaggttcc    3120
aactttcacc ataatgaaat aagatcacta ccgggcgtat tttttgagtt atcgagattt    3180
tcaggagcta aggaagctaa aatggagaaa aaaatcactg gatataccac cgttgatata    3240
tcccaatggc atcgtaaaga acattttgag gcatttcagt cagttgctca atgtacctat    3300
aaccagaccg ttcagctgga tattacggcc ttttttaaaga ccgtaaagaa aaataagcac    3360 aagtttatc cggcctttat tcacattctt gcccgcctga tgaatgctca tccggaattc    3420
cgtatggcaa tgaaagacgg tgagctggtg atatgggata gtgttcaccc ttgttacacc    3480
gttttccatg agcaaactga aacgttttca tcgctctgga gtgaatacca cgacgatttc    3540
cggcagtttc tacacatata ttcgcaagat gtggcgtgtt acggtgaaaa cctggcctat    3600
ttccctaaag ggtttattga gaatatgttt ttcgtctcag ccaatccctg ggtgagtttc    3660
accagttttg atttaaacgt ggccaatatg gacaacttct tcgcccccgt tttcaccatg    3720
ggcaaatatt atacgcaagg cgacaaggtg ctgatgccgc tggcgattca ggttcatcat    3780
gccgtttgtg atggcttcca tgtcggcaga atgcttaatg aattacaaca gtactgcgat    3840
gagtggcagg gcggggcgta atttttttaa ggcagttatt ggtgccctta aacgcctggt    3900
tgctacgcct gaataagtga taataagcgg atgaatggca gaaattcgat gataagctgt    3960
caaacacaac caccatcaaa caggattttc gcctgctggg gcaaaccagc gtggaccgct    4020
tgctgcaact ctctcagggc caggcggtga agggcaatca gctgttgccc gtctcactgg    4080
tgaaaagaaa accaccctg gcgcccaata cgcaaaccgc ctctccccgc gcgttggccg    4140
attcattaat gcagctggca cgacaggttt cccgactgga aagcgggcag tgagcgcaac    4200
gcaattaatg taagttagcg cgaattgcaa gctggcgac gcgctgggct acgtcttgct    4260
ggcgttcggg agcagaagag catacatctg gaagcaaagc caggaaagcg gcctatggag    4320
ctgtgcggca gcgctcagta ggcaatttt caaaatattt ttaagccttt tctgagcatg    4380
gtatttttca tggtattacc aattagcagg aaaataagcc attgaatata aagataaaa    4440
```

-continued

```
atgtcttgtt tacaatagag tgggggggt cagcctgccg ccttgggccg ggtgatgtcg   4500
tacttgcccg ccgcgaactc ggttaccgtc cagcccagcg cgaccagctc cggcaacgcc   4560
tcgcgcaccc gcttgcggcg cttgcgcatg gtcgaaccac tggcctctga cggccagaca   4620
tagccgcaca aggtatctat ggaagccttg ccggttttgc cggggtcgat ccagccacac   4680
agccgctggt gcagcaggcg ggcggtttcg ctgtccagcg cccgcacctc gtccatgctg   4740
atgcgcacat gctggccgcc acccatgacg gcctgcgcga tcaaggggtt cagggccacg   4800
tacaggcgcc cgtccgcctc gtcgctggcg tactccgaca gcagccgaaa cccctgccgc   4860
ttgcggccat tctgggcgat gatggatacc ttccaaaggc gctcgatgca gtcctgtatg   4920
tgcttgagcg ccccaccact atcgacctct gccccgattt cctttgccag cgcccgatag   4980
ctacctttga ccacatggca ttcagcggtg acggcctccc acttgggttc caggaacagc   5040
cggagctgcc gtccgccttc ggtcttgggt tccgggccaa gcactaggcc attaggccca   5100
gccatggcca ccagcccttg caggatgcgc agatcatcag cgcccagcgg ctccgggccg   5160
ctgaactcga tccgcttgcc gtcgccgtag tcatacgtca cgtccagctt gctgcgcttg   5220
cgctcgcccc gcttgagggc acggaacagg ccggggcca dacagtgcgc cgggtcgtgc   5280
cggacgtggc tgaggctgtg cttgttctta ggcttcacca cggggcaccc ccttgctctt   5340
gcgctgcctc tccagcacgg cgggcttgag caccccgccg tcatgccgcc tgaaccaccg   5400
atcagcgaac ggtgcgccat agttggcctt gctcacaccg aagcggacga agaaccggcg   5460
ctggtcgtcg tccacacccc attcctcggc ctcggcgctg gtcatgctcg acaggtagga   5520
ctgccagcgg atgttatcga ccagtaccga gctgccccgg ctggcctgct gctggtcgcc   5580
tgcgcccatc atgccgcgc ccttgctggc atggtgcagg aacacgatag agcacccggt   5640
atcggcggcg atggcctcca tgcgaccgat gacctgggcc atgggccgc tggcgttttc   5700 ttcctcgatg tggaaccggc gcagcgtgtc cagcaccatc aggcggcggc cctcggcggc   5760
gcgcttgagg ccgtcgaacc actccggggc catgatgttg ggcaggctgc cgatcagcgg   5820
ctggatcagc aggccgtcag ccacggcttg ccgttcctcg gcgctgaggt gcgccccaag   5880
ggcgtgcagg cggtgatgaa tggcggtggg cgggtcttcg gcgggcaggt agatcaccgg   5940
gccggtgggc agttcgccca cctccagcag atccggcccg cctgcaatct gtgcggccag   6000
ttgcagggcc agcatggatt taccggcacc accgggcgac accagcgccc cgaccgtacc   6060
ggccaccatg ttgggcaaaa cgtagtccag cggtggcggc gctgctgcga acgcctccag   6120
aatattgata ggcttatggg tagccattga ttgcctcctt tgcaggcagt tggtggttag   6180
gcgctggcgg ggtcactacc cccgccctgc gccgctctga gttcttccag gcactcgcgc   6240
agcgcctcgt attcgtcgtc ggtcagccag aacttgcgct gacgcatccc tttggccttc   6300
atgcgctcgg catatcgcgc ttggcgtaca gcgtcagggc tggccagcag gtcgccggtc   6360
tgcttgtcct tttggtcttt catatcagtc accgagaaac ttgccggggc cgaaaggctt   6420
gtcttcgcgg aacaaggaca aggtgcagcc gtcaaggtta aggctggcca tatcagcgac   6480
tgaaaagcgg ccagcctcgg ccttgtttga cgtataacca aagccaccgg caaccaata    6540 gcccttgtca ctttttgatca ggtagaccga ccctgaagcg cttttttcgt attccataaa   6600 accccttct gtgcgtgagt actcatagta taacaggcgt gagtaccaac gcaagcacta   6660
catgctgaaa tctggcccgc ccctgtccat gcctcgctgg cggggtgccg gtgcccgtgc   6720
cagctcggcc cgcgcaagct ggacgctggg cagacccatg accttgctga cggtgcgctc   6780
gatgtaatcc gcttcgtggc cgggcttgcg ctctgccagc gctgggctgg cctcggccat   6840
```

```
ggccttgccg atttcctcgg cactgcggcc ccggctggcc agcttctgcg cggcgataaa   6900
gtcgcacttg ctgaggtcat gaccgaagcg ctttgaccagc ccggccatct cgctgcggta   6960
ctcgtccagc gccgtgcgcc ggtggcggct aagctgccgc tcgggcagtt cgaggctggc   7020
cagcctgcgg gccttctcct gctgccgctg ggcctgctcg atctgctggc cagcctgctg   7080
caccagcgcc gggccagcgg tggcggtctt gcccttggat tcacgcagca gcacccacgg   7140
ctgataaccg gcgcgggtgg tgtgcttgtc cttgcggttg gtgaagcccg ccaagcggcc   7200
atagtggcgg ctgtcggcgc tggccgggtc ggcgtcgtac tcgctggcca gcgtccgggc   7260
aatctgcccc cgaagttcac cgcctgcggc gtcggccacc ttgacccatg cctgatagtt   7320
cttcgggctg gtttccacta ccagggcagg ctccccggccc tcggctttca tgtcatccag   7380
gtcaaactcg ctgaggtcgt ccaccagcac cagaccatgc cgctcctgct cggcgggcct   7440
gatatacacg tcattgccct gggcattcat ccgcttgagc catggcgtgt tctggagcac   7500
ttcggcggct gaccattccc ggttcatcat ctggccggtg ggtgcgtccc tgacgccgat   7560
atcgaagcgc tcacagccca tggccttgag ctgtcggcct atggcctgca aagtcctgtc   7620
gttcttcatc gggccaccaa gcgcagccag atcgagccgt cctcggttgt cagtggcgtc   7680
aggtcgagca agagcaacga tgcgatcagc agcaccaccg taggcatcat ggaagccagc   7740
atcacggtta gccatagctt ccagtgccac ccccgcgacg cgctccgggc gctctgcgcg   7800
gcgctgctca cctcggcggc tacctcccgc aactctttgg ccagctccac ccatgccgcc   7860
cctgtctggc gctgggcttt cagccactcc gccgctgcg cctcgctggc ctgcttggtc   7920
tggctcatga cctgccgggc ttcgtcggcc agtgtcgcca tgctctgggc agcggttcg   7980
atctgctccg ctaactcgtt gatgcctctg gatttcttca ctctgtcgat tgcgttcatg   8040
gtctattgcc tcccggtatt cctgtaagtc gatgatctgg gcgttggcgg tgtcgatgtt   8100
cagggccacg tctgcccggt cggtgcggat gccccggcct tccatctcca ccacgttcgg   8160
ccccaggtga acaccgggca ggcgctcgat gccctgcgcc tcaagtgttc tgtggtcaat   8220
gcgggcgtcg tggccagccc gctctaatgc ccggttggca tggtcggccc atgcctcgcg   8280
ggtctgctca agccatgcct tgggcttgag cgcttcggtc ttctgtgccc cgcccttctc   8340
cggggtcttg ccgttgtacc gcttgaacca ctgagcggcg ggccgctcga tgccgtcatt   8400
gatccgctcg gagatcatca ggtggcagtg cgggttctcg ccgccaccgg catggatggc   8460
cagcgtatac ggcaggcgct cggcaccggt caggtgctgg gcgaactcgg acgccagcgc   8520
cttctgctgg tcgagggtca gctcgaccgg cagggcaaat tcgacctcct tgaacagccg   8580
cccattggcg cgttcataca ggtcggcagc atcccagtag tcggcgggcc gctcgacgaa   8640
ctccggcatg tgcccggatt cggcgtgcaa gacttcatcc atgtcgcggg catacttgcc   8700
ttcgcgctgg atgtagtcgg ccttggccct ggccgattgg ccgcccgacc tgctgccggt   8760
tttcgccgta aggtgataaa tcgccatgct gcctcgctgt tgcttttgct tttcggctcc   8820
atgcaatggc cctcggagag cgcaccgccc gaagggtggc cgttaggcca gtttctcgaa   8880
gagaaaccgg taagtgcgcc ctcccctaca agtagggtc gggattgccg ccgctgtgcc   8940
tccatgatag cctacgagac agcacattaa caatggggtg tcaagatggt taaggggagc   9000
aacaaggcgg cggatcggct ggccaagctc gaagaacaac gagcgcgaat caatgccgaa   9060
attcagcggg agcgggcaag ggaacagcag caagagcgca agaacgaaac aaggcgcaag   9120
gtgctggtgg gggccatgat tttgccaagg gtgaacagca gcgagtggcc ggaggatcgg   9180
ctcatggcgg caatggatgc gtaccttgaa cgcgaccacg accgcgcctt gttcggtctg   9240
```

```
ccgccacgcc agaaggatga gccgggctga atgatcgacc gagacaggcc ctgcggggct    9300
gcacacgcgc ccccaccctt cgggtagggg gaaaggccgc taaagcggct aaaagcgctc    9360
cagcgtattt ctgcgggatt tggtgtgggg tttagcgggc tttgcccgcc tttcccctg     9420
ccgcgcagcg gtgggcggt gtgtagccta gcgcagcgaa tagaccagct atccggcctc    9480
tggccgggca tattgggcaa gggcagcagc gccccacaag ggcgctgata accgcgccta    9540
gtggattatt cttagataat catggatgga tttttccaac accccgccag ccccgcccc    9600
tgctgggttt gcaggtttgg gggcgtgaca gttattgcag gggttcgtga cagttattgc    9660
aggggggcgt gacagttatt gcaggggttc gtgacagtta gtacgggagt gacgggcact    9720
ggctggcaat gtctagcaac ggcaggcatt tcggctgagg gtaaaagaac tttccgctaa    9780
gcgatagact gtatgtaaac acagtattgc aaggacgcgg aacatgcctc atgtggcggc    9840
caggacggcc agccgggatc gggatactgg tcgttaccag agccaccgac ccgagcaaac    9900
ccttctctat cagatcgttg acgagtatta cccggcattc gctgcgctta tggcagagca    9960
gggaaaggaa ttgccgggct atgtgcaacg ggaatttgaa gaatttctcc aatgcgggcg   10020
gctggagcat ggctttctac gggttcgctg cgagtcttgc cacgccgagc acctggtcgc   10080
tttcagaaat caatctaaag tatatatgag taaacttggt ctgacagtta ccaatgctta   10140
atcagtgagg cacctatctc agcgatctgt ctatttcgtt catccatagt tgcctgactc   10200
cccgtcgtgt agataactac gatacgggag ggcttaccat ctggccccag tgctgcaatg   10260
ataccgcgag acccacgctc accggctcca gatttatcag caataaacca gccagccgga   10320
agggccgagc gcagaagtgg tcctgcaact ttatccgcct ccatccagtc tattaattgt   10380
tgccgggaag ctagagtaag tagttcgcca gttaatagtt tgcgcaacgt tgttgccatt   10440
gctacaggca tcgtggtgtc acgctcgtcg tttggtatgg cttcattcag ctccggttcc   10500
caacgatcaa ggcgagttac atgatccccc atgttgtgca aaaaagcggt tagctccttc   10560
ggtcctccga tcgttgtcag aagtaagttg gccgcagtgt tatcactcat ggttatggca   10620
gcactgcata attctcttac tgtcatgcca tccgtaagat gcttttctgt gactggtgag   10680
tactcaacca agtcattctg agaatagtgt atgcggcgac cgagttgctc ttgcccggcg   10740
tcaacacggg ataataccgc gccacatagc agaactttaa aagtgctcat cattggaaaa   10800
cgttcttcgg ggcgaaaact ctcaaggatc ttaccgctgt tgagatccag ttcgatgtaa   10860
cccactcgtg cacccaactg atcttcagca tcttttactt tcaccagcgt ttctgggtga   10920
gcaaaaacag gaaggcaaaa tgccgcaaaa aagggaataa gggcgacacg gaaatgttga   10980
atactcatac tcttcctttt tcaatattat tgaagcattt atcagggtta ttgtctcatg   11040
agcggataca tatttgaatg tatttagaaa aataaacaaa agagtttgta gaaacgcaaa   11100
aaggccatcc gtcaggatgg ccttctgctt aatttgatgc ctggcagttt atggcgggcg   11160
tcctgcccgc caccctccgg gccgttgctt cgcaacgttc aaatccgctc ccggcggatt   11220
tgtcctactc aggagagcgt tcaccgacaa acaacagata aaacgaaagg cccagtcttt   11280
cgactgagcc tttcgtttta tttgatgcct ggcagttccc tactctcgca tggggagacc   11340
ccacactacc atcggcgcta cggcgtttca cttctgagtt cggcatgggg tcaggtggga   11400
ccaccgcgct actgccgcca ggcaaattct gttttatcag accgcttctg cgttctgatt   11460
taatctgtat caggctgaaa atcttctctc atccgccaaa acagccaagc t             11511
```

<210> SEQ ID NO 50
<211> LENGTH: 11219

-continued

```
<212> TYPE: DNA
<213> ORGANISM: Artificial
<220> FEATURE:
<223> OTHER INFORMATION: plasmid pLybAL22

<400> SEQUENCE: 50
tgcatgcaaa gctcactaac tgggcgggat tttccgggtc cggttgctga cggtaatagt      60
cgtctaaaag tttggccaca tccaaaaggc tgtcggcggg gggatgctgg ccggcgaggg     120
gattaattct gcttgtcata tacaaaaatt gtaaaaaatg gagggcggcg atcagggggct    180
tagacaccca aatcctagcc aaaaagggtt aactagccaa gggctatcca tgggcaaaga    240
gataaaagaa aaagtctcca aatccctggt catagagaaa aaattgccaa agttacccca    300
ggccatacac ggcccagcgc caagatgggg agcacaaatt caaactttgt aaacaggccg    360
gaagctatcc ggccaaggag cactcagatt gtgttaacgt tcaggggagt tgcttaacac    420
aattttccaa ttaatagtat taatattttc ttaacttgca ccgtaccatg gtgagaaagc    480
ctatctgagc ccttatttga ttaaccttcg actgattatt gatccctgt gcagtctccc     540
ctctccctct gtcttttgc tcccgaacac gttgcccata gactcaggta ccgagctcga    600
attgggcgt tttctgtgag gctgactagc gcgtggcagc tcaaaatctc tacattctgc    660
acattcagac ccatggtctg ctgcgagggc agaacttgga actggggcga gatgccgaca    720
ccggcgggca gaccaagtac gtcttagaac tggctcaagc ccaagctaaa tccccacaag    780
tccaacaagt cgacatcatc acccgccaaa tcaccgaccc ccgcgtcagt gttggttaca    840
gtcaggcgat cgaacccttt gcgcccaaag gtcggattgt ccgtttgcct tttggcccca    900
aacgctacct ccgtaaagag ctgctttggc cccatctcta cacctttgcg gatgcaattc    960
tccaatatct ggctcagcaa aagcgcaccc gacttggat tcaggcccac tatgctgatg    1020
ctggccaagt gggatcactg ctgagtcgct ggttgaatgt accgctaatt ttcacagggc    1080
attctctggg gcggatcaag ctaaaaaagc tgttggagca agactggccg cttgaggaaa    1140
ttgaagcgca attcaatatt caacagcgaa ttgatgcgga ggagatgacg ctcactcatg    1200
ctgactggat tgtcgccagc actcagcagg aagtggagga gcaataccgc gtttacgatc    1260
gctacaaccc agagcgcaag cttgtcattc caccgggtgt cgataccgat cgcttcaggt    1320
ttcagccctt gggcgatcgc ggtgttgttc tccaacagga actgagccgc tttctgcgcg    1380
acccagaaaa acctcaaatt ctctgcctct gtcgcccgc acctcgcaaa aatgtaccgg    1440
cgctggtgcg agcctttggc gaacatcctt ggctgcgcaa aaaagccaac cttgtcttag    1500
tactgggcag ccgccaagac atcaaccaga tggatcgcgg cagtcggcag gtgttccaag    1560
agattttcca tctggtcgat cgctacgacc tctacggcag cgtcgcctat cccaaacagc    1620
atcaggctga tgatgtgccg gagttctatc gcctagcggc tcattccggc ggggtattcg    1680
tcaatccggc gctgaccgaa ccttttggtt tgacaatttt ggaggcagga agctgcggcg    1740
tgccggtggt ggcaacccat gatggcggcc cccaggaaat tctcaaacac tgtgatttcg    1800
gcactttagt tgatgtcagc cgacccgcta atatcgcgac tgcactcgcc accctgctga    1860
gcgatcgcga tctttggcag tgctatcacc gcaatggcat tgaaaaagtt cccgcccatt    1920
acagctggga tcaacatgtc aatacccgtt ttgagcgcat ggaacggtg gctttgcctc    1980
gtcgtcgtgc tgtcagtttc gtacggagtc gcaaacgctt gattgatgcc aaacgccttg    2040
tcgttagtga catcgacaac acactgttgg gcgatcgtca aggactcgag aatttaatga    2100
cctatctcga tcagtatcgc gatcattttg cctttggaat tgccacgggg cgtcgcctag    2160
actctgccca agaagtcttg aaagagtggg gcgttccttc gccaaacttc tgggtgactt    2220
```

```
ccgtcggcag cgagattcac tatggcaccg atgctgaacc ggatatcagc tgggaaaagc    2280
atatcaatcg caactggaat cctcagcgaa ttcgggcagt aatggcacaa ctacccttc    2340 ttgaactgca gccggaagag gatcaaacac ccttcaaagt cagcttcttt gtccgcgatc    2400
gccacgagac tgtgctgcga gaagtacggc aacatcttcg ccgccatcgc ctgcggctga    2460
agtcaatcta ttcccatcag gagtttcttg acattctgcc gctagctgcc tcgaaagggg    2520
atgcgattcg ccacctctca ctccgctggc ggattcctct tgagaacatt ttggtggcag    2580
gcgattctgg taacgatgag gaaatgctca agggccataa tctcggcgtt gtagttggca    2640
attactcacc ggaattggag ccactgcgca gctacgagcg cgtctatttt gctgagggcc    2700
actatgctaa tggcattctg gaagccttaa aacactatcg cttttttgag gcgatcgctt    2760
aaccttttca gaatgagacg ttgatcggca cgtaagcgtg agacgttgat cggcacgtaa    2820
gaggttccaa cttctcaccat aatgaaataa gatcactacc gggcgtattt tttgagttat    2880
cgagattttc aggagctaag gaagctaaaa tggagaaaaa aatcactgga tataccaccg    2940
ttgatatatc ccaatggcat cgtaaagaac attttgaggc atttcagtca gttgctcaat    3000
gtacctataa ccagaccgtt cagctggata ttacggcctt tttaaagacc gtaaagaaaa    3060
ataagcacaa gttttatccg gcctttattc acattcttgc ccgcctgatg aatgctcatc    3120
cggaattccg tatggcaatg aaagacgtg agctggtgat atgggatagt gttcacccctt    3180 gttacaccgt tttccatgag caaactgaaa cgttttcatc gctctggagt gaataccacg    3240
acgatttccg gcagtttcta cacatatatt cgcaagatgt ggcgtgttac ggtgaaaacc    3300
tggcctattt ccctaaaggg tttattgaga atatgttttt cgtctcagcc aatccctggg    3360
tgagtttcac cagttttgat ttaaacgtgg ccaatatgga aacttcttc gcccccgttt    3420 tcaccatggg caaatattat acgcaaggcg acaaggtgct gatgccgctg gcgattcagg    3480
ttcatcatgc cgtttgtgat ggcttccatg tcggcagaat gcttaatgaa ttacaacagt    3540
actgcgatga gtggcagggc ggggcgtaat ttttttaagg cagttattgg tgcccttaaa    3600
cgcctggttg ctacgcctga ataagtgata taagcggat gaatggcaga aattcgatga    3660
taagctgtca aacacaacca ccatcaaaca ggattttcgc ctgctggggc aaaccagcgt    3720
ggaccgcttg ctgcaactct ctcagggcca ggcggtgaag ggcaatcagc tgttgcccgt    3780
ctcactggtg aaaagaaaaa ccaccctggc gcccaatacg caaaccgcct ctccccgcgc    3840
gttggccgat tcattaatgc agctggcacg acaggtttcc cgactggaaa gcgggcagtg    3900
agcgcaacgc aattaatgta agttagcgcg aattgcaagc tggccgacgc gctgggctac    3960
gtcttgctgg cgttcgggag cagaagagca tacatctgga agcaaagcca ggaaagcggc    4020
ctatggagct gtgcggcagc gctcagtagg caattttca aaatattgtt aagccttttc    4080
tgagcatggt atttttcatg gtattaccaa ttagcaggaa aataagccat tgaatataaa    4140
agataaaaat gtcttgttta caatagagtg ggggggggtca gcctgccgcc ttgggccggg    4200
tgatgtcgta cttgcccgcc gcgaactcgg ttaccgtcca gcccagcgcg accagctccg    4260
gcaacgcctc gcgcacccgc ttgcggcgct tgcgcatggt cgaaccactg gcctctgacg    4320
gccagacata gccgcacaag gtatctatgg aagccttgcc ggttttgccg gggtcgatcc    4380
agccacacag ccgctggtgc agcaggcggg cggtttcgct gtccagcgcc cgcacctcgt    4440
ccatgctgat gcgcacatgc tggccgccac ccatgacggc ctgcgcgatc aaggggttca    4500
gggccacgta caggcgcccg tccgcctcgt cgctggcgta ctccgacagc agccgaaacc    4560
cctgccgctt gcggccattc tgggcgatga tggataccct ccaaaggcgc tcgatgcagt    4620
```

```
cctgtatgtg cttgagcgcc ccaccactat cgacctctgc cccgatttcc tttgccagcg   4680
cccgatagct acctttgacc acatggcatt cagcggtgac ggcctcccac ttgggttcca   4740
ggaacagccg gagctgccgt ccgccttcgg tcttgggttc cgggccaagc actaggccat   4800
taggcccagc catggccacc agcccttgca ggatgcgcag atcatcagcg cccagcggct   4860
ccgggccgct gaactcgatc cgcttgccgt cgccgtagtc atacgtcacg tccagcttgc   4920
tgcgcttgcg ctcgccccgc ttgagggcac ggaacaggcc gggggccaga cagtgcgccg   4980
ggtcgtgccg gacgtggctg aggctgtgct tgttcttagg cttcaccacg ggcaccccc    5040 ttgctcttgc gctgcctctc cagcacggcg ggcttgagca ccccgccgtc atgccgcctg   5100
aaccaccgat cagcgaacgg tgcgccatag ttggccttgc tcacaccgaa gcggacgaag   5160
aaccggcgct ggtcgtcgtc cacacccat tcctcggcct cggcgctggt catgctcgac    5220
aggtaggact gccagcggat gttatcgacc agtaccgagc tgccccggct ggcctgctgc   5280
tggtcgcctg cgcccatcat ggccgcgccc ttgctggcat ggtgcaggaa cacgatagag   5340
cacccggtat cggcggcgat ggcctccatg cgaccgatga cctgggccat ggggccgctg   5400
gcgttttctt cctcgatgtg gaaccggcgc agcgtgtcca gcaccatcag gcggcggccc   5460
tcggcggcgc gcttgaggcc gtcgaaccac tccggggcca tgatgttggg caggctgccg   5520
atcagcggct ggatcagcag gccgtcagcc acggcttgcc gttcctcggc gctgaggtgc   5580
gccccaaggg cgtgcaggcg gtgatgaatg gcggtgggcg ggtcttcggc gggcaggtag   5640
atcaccgggc cggtgggcag ttcgcccacc tccagcagat ccggcccgcc tgcaatctgt   5700
gcggccagtt gcagggccag catggattta ccggcaccac cgggcgacac cagcgccccg   5760
accgtaccgg ccaccatgtt gggcaaaacg tagtccagcg gtggcggcgc tgctgcgaac   5820
gcctccagaa tattgatagg cttatgggta gccattgatt gcctcctttg caggcagttg   5880
gtggttaggc gctggcgggg tcactacccc cgccctgcgc cgctctgagt tcttccaggc   5940
actcgcgcag cgcctcgtat tcgtcgtcgg tcagccagaa cttgcgctga cgcatccctt   6000
tggccttcat gcgctcggca tatcgcgctt ggcgtacagc gtcagggctg ccagcaggt    6060 cgccggtctg cttgtccttt tggtctttca tatcagtcac cgagaaactt gccggggccg   6120
aaaggcttgt cttcgcggaa caaggacaag gtgcagccgt caaggttaag gctgccata    6180 tcagcgactg aaaagcggcc agcctcggcc ttgtttgacg tataaccaaa gccaccgggc   6240
aaccaatagc ccttgtcact tttgatcagg tagaccgacc ctgaagcgct ttttcgtat    6300 tccataaaac ccccttctgt gcgtgagtac tcatagtata acaggcgtga gtaccaacgc   6360
aagcactaca tgctgaaatc tggcccgccc ctgtccatgc ctcgctggcg gggtgccggt   6420
gcccgtgcca gctcggcccg cgcaagctgg acgctgggca gacccatgac cttgctgacg   6480
gtgcgctcga tgtaatccgc ttcgtggccg ggcttgcgct ctgccagcgc tgggctggcc   6540
tcggccatgg ccttgccgat ttcctcggca ctgcggcccc ggctggccag cttctgcgcg   6600
gcgataaagt cgcacttgct gaggtcatga ccgaagcgct tgaccagccc ggccatctcg   6660
ctgcggtact cgtccagcgc cgtgcgccgg tggcggctaa gctgccgctc gggcagttcg   6720
aggctggcca gctgcgggc cttctcctgc tgccgctggg cctgctcgat ctgctggcca   6780
gcctgctgca ccagcgccgg gccagcggtg gcggtcttgc ccttggattc acgcagcagc   6840
acccacggct gataaccggc gcgggtggtg tgcttgtcct tgcggttggt gaagcccgcc   6900
aagcggccat agtggcggct gtcggcgctg gccgggtcgg cgtcgtactc gctgccagc    6960 gtccgggcaa tctgccccc aagttcaccg cctgcggcgt cggccacctt gacccatgcc    7020
```

```
tgatagttct tcgggctggt ttccactacc agggcaggct cccggccctc ggctttcatg    7080
tcatccaggt caaactcgct gaggtcgtcc accagcacca gaccatgccg ctcctgctcg    7140
gcgggcctga tatacacgtc attgccctgg gcattcatcc gcttgagcca tggcgtgttc    7200
tggagcactt cggcggctga ccattcccgg ttcatcatct ggccggtggg tgcgtccctg    7260
acgccgatat cgaagcgctc acagcccatg gccttgagct gtcggcctat ggcctgcaaa    7320
gtcctgtcgt tcttcatcgg gccaccaagc gcagccagat cgagccgtcc tcggttgtca    7380
gtggcgtcag gtcgagcaag agcaacgatg cgatcagcag caccaccgta ggcatcatgg    7440
aagccagcat cacggttagc catagcttcc agtgccaccc ccgcgacgcg ctccgggcgc    7500
tctgcgcggc gctgctcacc tcggcggcta cctcccgcaa ctctttggcc agctccaccc    7560
atgccgcccc tgtctggcgc tgggctttca gccactccgc cgcctgcgcc tcgctggcct    7620
gcttggtctg gctcatgacc tgccgggctt cgtcggccag tgtcgccatg ctctgggcca    7680
gcggttcgat ctgctccgct aactcgttga tgcctctgga tttcttcact ctgtcgattg    7740
cgttcatggt ctattgcctc ccggtattcc tgtaagtcga tgatctgggc gttggcggtg    7800
tcgatgttca gggccacgtc tgcccggtcg gtgcggatgc cccggccttc catctccacc    7860
acgttcggcc ccaggtgaac accgggcagg cgctcgatgc cctgcgcctc aagtgttctg    7920
tggtcaatgc gggcgtcgtg gccagcccgc tctaatgccc ggttggcatg gtcggcccat    7980
gcctcgcggg tctgctcaag ccatgccttg gcttgagcg cttcggtctt ctgtgccccg    8040
cccttctccg gggtcttgcc gttgtaccgc ttgaaccact gagcggcggg ccgctcgatg    8100
ccgtcattga tccgctcgga gatcatcagg tggcagtgcg ggttctcgcc gccaccggca    8160
tggatggcca gcgtatacgg caggcgctcg gcaccggtca ggtgctgggc gaactcggac    8220
gccagcgcct tctgctggtc gagggtcagc tcgaccggca gggcaaattc gacctccttg    8280
aacagccgcc cattggcgcg ttcatacagg tcggcagcat cccagtagtc ggcgggccgc    8340
tcgacgaact ccggcatgtg cccggattcg gcgtgcaaga cttcatccat gtcgcgggca    8400
tacttgcctt cgcgctggat gtagtcggcc ttggccctgg ccgattggcc gcccgacctg    8460
ctgccggttt tcgccgtaag gtgataaatc gccatgctgc ctcgctgttg cttttgcttt    8520
tcggctccat gcaatggccc tcggagagcg caccgcccga agggtggccg ttaggccagt    8580
ttctcgaaga gaaaccggta agtgcgccct ccctacaaa gtagggtcgg gattgccgcc    8640
gctgtgcctc catgatagcc tacgagacag cacattaaca atggggtgtc aagatggtta    8700
aggggagcaa caaggcggcg gatcggctgg ccaagctcga agaacaacga gcgcgaatca    8760
atgccgaaat tcagcgggag cgggcaaggg aacagcagca agagcgcaag aacgaaacaa    8820
ggcgcaaggt gctggtgggg gccatgattt tggccaaggt gaacagcagc gagtggccgg    8880
aggatcggct catggcggca atggatgcgt accttgaacg cgaccacgac cgcgccttgt    8940
tcggtctgcc gccacgccag aaggatgagc cgggctgaat gatcgaccga acaggccct    9000 gcggggctgc acacgcgccc ccacccttcg ggtaggggga aaggccgcta aagcggctaa    9060
aagcgctcca gcgtatttct gcggggtttg gtgtggggtt tagcgggctt tgcccgcctt    9120
tccccctgcc gcgcagcggt ggggcggtgt gtagcctagc gcagcgaata gaccagctat    9180
ccggcctctg gccgggcata ttgggcaagg gcagcagcgc cccacaaggg cgctgataac    9240
cgcgcctagt ggattattct tagataatca tggatggatt tttccaacac cccgccagcc    9300
cccgcccctg ctgggtttgc aggtttgggg gcgtgacagt tattgcaggg gttcgtgaca    9360
gttattgcag gggggcgtga cagttattgc aggggttcgt gacagttagt acgggagtga    9420
```

```
cgggcactgg ctggcaatgt ctagcaacgg caggcatttc ggctgagggt aaaagaactt    9480
tccgctaagc gatagactgt atgtaaacac agtattgcaa ggacgcggaa catgcctcat    9540
gtggcggcca ggacgccag ccgggatcgg gatactggtc gttaccagag ccaccgaccc     9600
gagcaaaccc ttctctatca gatcgttgac gagtattacc cggcattcgc tgcgcttatg    9660
gcagagcagg gaaaggaatt gccgggctat gtgcaacggg aatttgaaga atttctccaa    9720
tgcgggcggc tggagcatgg cttctacgg gttcgctgcg agtcttgcca cgccgagcac     9780
ctggtcgctt tcagaaatca atctaaagta tatatgagta aacttggtct gacagttacc    9840
aatgcttaat cagtgaggca cctatctcag cgatctgtct atttcgttca tccatagttg    9900
cctgactccc cgtcgtgtag ataactacga tacgggaggg cttaccatct ggccccagtg    9960
ctgcaatgat accgcgagac ccacgctcac cggctccaga tttatcagca ataaaccagc   10020
cagccggaag ggccgagcgc agaagtggtc ctgcaacttt atccgcctcc atccagtcta   10080
ttaattgttg ccgggaagct agagtaagta gttcgccagt taatagtttg cgcaacgttg   10140
ttgccattgc tacaggcatc gtggtgtcac gctcgtcgtt tggtatggct tcattcagct   10200
ccggttccca acgatcaagg cgagttacat gatcccccat gttgtgcaaa aaagcggtta   10260
gctccttcgg tcctccgatc gttgtcagaa gtaagttggc cgcagtgtta tcactcatgg   10320
ttatggcagc actgcataat tctcttactg tcatgccatc cgtaagatgc ttttctgtga   10380
ctggtgagta ctcaaccaag tcattctgag aatagtgtat gcggcgaccg agttgctctt   10440
gcccggcgtc aacacgggat aataccgcgc cacatagcag aactttaaaa gtgctcatca   10500
ttggaaaacg ttcttcgggg cgaaaactct caaggatctt accgctgttg agatccagtt   10560
cgatgtaacc cactcgtgca cccaactgat cttcagcatc ttttactttc accagcgttt   10620
ctgggtgagc aaaaacagga aggcaaaatg ccgcaaaaaa gggaataagg gcgacacgga   10680
aatgttgaat actcatactc ttcctttttc aatattattg aagcatttat cagggttatt   10740
gtctcatgag cggatacata tttgaatgta tttagaaaaa taaacaaaag agtttgtaga   10800
aacgcaaaaa ggccatccgt caggatggcc ttctgcttaa tttgatgcct ggcagtttat   10860
ggcgggcgtc ctgcccgcca ccctccgggc cgttgcttcg caacgttcaa atccgctccc   10920
ggcggatttg tcctactcag gagagcgttc accgacaaac aacagataaa acgaaaggcc   10980
cagtctttcg actgagcctt tcgttttatt tgatgcctgg cagttcccta ctctcgcatg   11040
gggagacccc acactaccat cggcgctacg gcgtttcact tctgagttcg gcatggggtc   11100
aggtgggacc accgcgctac tgccgccagg caaattctgt tttatcagac cgcttctgcg   11160
ttctgattta atctgtatca ggctgaaaat cttctctcat ccgccaaaac agccaagct   11219

<210> SEQ ID NO 51
<211> LENGTH: 4962
<212> TYPE: DNA
<213> ORGANISM: Artificial
<220> FEATURE:
<223> OTHER INFORMATION: plasmid pLybAL13f

<400> SEQUENCE: 51
cgaccaattc acgtgtttga cagcttatca tcgaatttct gccattcatc cgcttattat      60
cacttattca ggcgtagcaa ccaggcgttt aagggcacca ataactgcct taaaaaaatt     120
acgccccgcc ctgccactca tcgcagtact gttgtaattc attaagcatt ctgccgacat     180
ggaagccatc acaaacggca tgatgaacct gaatcgccag cggcatcagc accttgtcgc     240
cttgcgtata atatttgccc atggtgaaaa cgggggcgaa gaagttgtcc atattggcca     300
```

```
cgtttaaatc aaaactggtg aaactcaccc agggattggc tgagacgaaa aacatattct      360
caataaaccc tttagggaaa taggccaggt tttcaccgta acacgccaca tcttgcgaat      420
atatgtgtag aaactgccgg aaatcgtcgt ggtattcact ccagagcgat gaaaacgttt      480
cagtttgctc atggaaaacg gtgtaacaag ggtgaacact atcccatatc accagctcac      540
cgtctttcat tgccatacgg aattccggat gagcattcat caggcgggca agaatgtgaa      600
taaaggccgg ataaaacttg tgcttatttt tctttacggt cttttaaaaag gccgtaatat      660 ccagctgaac ggtctggtta taggtacatt gagcaactga ctgaaatgcc tcaaaatgtt      720
ctttacgatg ccattgggat atatcaacgg tggtatatcc agtgattttt ttctccattt      780
tagcttcctt agctcctgac gttctgaaaa ggttaagcga tcgcctcaaa aaagcgatag      840
tgttttaagg cttccagaat gccattagca tagtggccct cagcaaaata gacgcgctcg      900
tagctgcgca gtggctccaa ttccggtgag taattgccaa ctacaacgcc gagattatgg      960
cccttgagca tttcctcatc gttaccagaa tcgcctgcca ccaaaatgtt ctcaagagga     1020
atccgccagc ggagtgagag gtggcgaatc gcatcccctt tcgaggcagc tagcggcaga     1080
atgtcaagaa actcctgatg ggaatagatt gacttcagcc gcaggcgatg gcggcgaaga     1140
tgttgccgta cttctcgcag cacagtctcg tggcgatcgc ggacaaagaa gctgactttg     1200
aagggtgttt gatcctcttc cggctgcagt tcaagaaagg gtagttgtgc cattactgcc     1260
cgaattcgct gaggattcca gttgcgattg atatgctttt cccagctgat atccggttca     1320
gcatcggtgc catagtgaat ctcgctgccg acggaagtca cccagaagtt tggcgaagga     1380
acgccccact ctttcaagac ttcttgggca gagtctaggc gacgcccgt ggcaattcca     1440 aaggcaaaat gatcgcgata ctgatcgaga taggtcatta aattctcgag tccttgacga     1500
tcgcccaaca gtgtgttgtc gatgtcacta acgacaaggc gtttggcatc aatcaagcgt     1560
ttgcgactcc gtacgaaact gacagcacga cgacgaggca aagccaccgt ttccatgcgc     1620
tcaaacaggg tattgacatg ttgatcccag ctgtaatggg cgggaacttt ttcaatgcca     1680
ttgcggtgat agcactgcca aagatcgcga tcgctcagca gggtggcgag tgcagtcgcg     1740
atattagcgg gtcggctgac atcaactaaa gtgccgaaat cacagtgttt gagaatttcc     1800 tggggggccgc catcatgggt tgccaccacc ggcacgccgc agcttcctgc ctccaaaatt     1860
gtcaaaccaa aaggttcggt cagcgccgga ttgacgaata ccccgccgga atgagccgct     1920
aggcgataga actccggcac atcatcagcc tgatgctgtt tgggataggc gacgctgccg     1980
tagaggtcgt agcgatcgac cagatggaaa atctcttgga acacctgccg actgccgcga     2040
tccatctggt tgatgtcttg gcggctgccc agtactaaga caaggttggc tttttttgcgc     2100 agccaaggat gttcgccaaa ggctcgcacc agcgccggta cattttttgcg aggtgcgggg     2160 cgacagaggc agagaaattg aggtttttct gggtcgcgca gaaagcggct cagttcctgt     2220
tggagaacaa caccgcgatc gcccaagggc tgaaacctga agcgatcggt atcgacaccc     2280
ggtggaatga caagcttgcg ctctgggttg tagcgatcgt aaacgcggta ttgctcctcc     2340
acttcctgct gagtgctggc gacaatccag tcagcatgag tgagcgtcat ctcctccgca     2400
tcaattcgct gttgaatatt gaattgcgct tcaatttcct caagcggcca gtcttgctcc     2460
aacagctttt ttagcttgat ccgccccaga gaatgccctg tgaaaattag cggtacattc     2520
aaccagcgac tcagcagtga tcccacttgg ccagcatcag catagtgggc ctgaatccaa     2580
gtcggggtgc gcttttgctg agccagatat tggagaattg catccgcaaa ggtgtagaga     2640
tggggccaaa gcagctcttt acggaggtag cgtttggggc caaaaggcaa acggacaatc     2700
```

```
cgacctttgg gcgcaaaggg ttcgatcgcc tgactgtaac caacactgac gcggggtcg    2760 gtgatttggc gggtgatgat gtcgacttgt tggacttgtg gggatttagc ttgggcttga   2820
gccagttcta agacgtactt ggtctgcccg ccggtgtcgg catctcgccc cagttccaag   2880
ttctgccctc gcagcagacc atgggtctga atgtgcagaa tgtagagatt ttgagctgcc   2940
acgcgctagt cagcctcaca gaaaacgccc caattgtagt ctaacgaatt caagcttgat   3000
atcattcagg acgagcctca gactccagcg taactggact gcaatcaact cactggctca   3060
ccttcacggg tgggcctttc ttcggtagaa aatcaaagga tcttcttgag atcctttttt   3120
tctgcgcgta atctgctgct tgcaaacaaa aaaaccaccg ctaccagcgg tggtttgttt   3180
gccggatcaa gagctaccaa ctcttttttcc gaggtaactg gcttcagcag agcgcagata   3240
ccaaatactg ttcttctagt gtagccgtag ttaggccacc acttcaagaa ctctgtagca   3300
ccgcctacat acctcgctct gctaatcctg ttaccagtgg ctgctgccag tggcgataag   3360
tcgtgtctta ccgggttgga ctcaagacga tagttaccgg ataaggcgca gcggtcgggc   3420
tgaacggggg gttcgtgcac acagcccagc ttggagcgaa cgacctacac cgaactgaga   3480
tacctacagc gtgagctatg agaaagcgcc acgcttcccg aagggagaaa ggcggacagg   3540
tatccggtaa gcggcagggt cggaacagga gagcgcacga gggagcttcc agggggaaac   3600
gcctggtatc tttatagtcc tgtcgggttt cgccacctct gacttgagca tcgatttttg   3660
tgatgctcgt cagggggggcg gagcctatgg aaaaacgcca gcaacgcaga aaggcccacc   3720
cgaaggtgag ccaggtgatt acatttgggc cctcatcaga ggttttcacc gtcatcaccg   3780
aaacgcgcga ggcagctgcg gtaaagctca tcagcgtggt cgtgaagcga ttcacagatg   3840
tctgcctgtt catccgcgtc cagctcgttg agtttctcca gaagcgttaa tgtctggctt   3900
ctgataaagc gggccatgtt aagggcggtt ttttcctgtt tggtcattta gaaaaactca   3960
tcgagcatca agtgaaactg caatttattc atatcaggat tatcaatacc atattttga   4020 aaaagccgtt tctgtaatga aggagaaaac tcaccgaggc agttccatag gatggcaaga   4080
tcctggtatc ggtctgcgat tccgactcgt ccaacatcaa taaacctat taatttcccc   4140 tcgtcaaaaa taaggttatc aagtgagaaa tcaccatgag tgacgactga atccggtgag   4200
aatggcaaaa gcttatgcat ttcttttccag acttgttcaa caggccagcc attacgctcg   4260
tcatcaaaat cactcgcacc aaccaaaccg ttattcattc gtgattgcgc ctgagcgaga   4320
cgaaatacgc gatcgccgtt aaaaggacaa ttacaaacag gaatcgaatg caaccggcgc   4380
aggaacactg ccagcgcatc aacaatattt tcacctgaat caggatattc ttctaatacc   4440
tggaatgctg ttttcccctgg gatcgcagtg gtgagtaacc atgcatcatc aggagtacgg   4500
ataaaatgct tgatggtcgg aagaggcata aattccgtca gccagtttag cctgaccatc   4560
tcatctgtaa catcattggc aacgctacct ttgccatgtt tcagaaacaa ctctggcgca   4620
tcgggcttcc catacaatcg atagattgtc gcacctgatt gcccgacatt atcgcgagcc   4680
catttatacc catataaatc agcatccatg ttggaattta atcgcggcct cgagcaagac   4740
gtttcccgtt gaatatggct catttttagct tccttagctc ctgaaaatct cgataactca   4800
aaaaatacgc ccggtagtga tcttatttca ttatggtgaa agttggaacc tcttacgtgc   4860
cgatcaagtc aaaagcctcc ggtcggaggc ttttgacttt ctgctatgga ggtcaggtat   4920
gatttaaatg gtcagtattg agcgatatct agagaattcg tc                     4962
```

<210> SEQ ID NO 52
<211> LENGTH: 4962

```
<212> TYPE: DNA
<213> ORGANISM: Artificial
<220> FEATURE:
<223> OTHER INFORMATION: plasmid pLybAL13r

<400> SEQUENCE: 52
```

| | | | | | |
|---|---|---|---|---|---|
| agactacaat | tggggcgttt | tctgtgaggc | tgactagcgc | gtggcagctc | aaaatctcta | 60 |
| cattctgcac | attcagaccc | atggtctgct | gcgagggcag | aacttggaac | tggggcgaga | 120 |
| tgccgacacc | ggcgggcaga | ccaagtacgt | cttagaactg | gctcaagccc | aagctaaatc | 180 |
| cccacaagtc | caacaagtcg | acatcatcac | ccgccaaatc | accgaccccc | gcgtcagtgt | 240 |
| tggttacagt | caggcgatcg | aacccttttgc | gcccaaaggt | cggattgtcc | gtttgccttt | 300 |
| tggcccccaaa | cgctacctcc | gtaaagagct | gctttggccc | catctctaca | cctttgcgga | 360 |
| tgcaattctc | caatatctgg | ctcagcaaaa | gcgcaccccg | acttggattc | aggcccacta | 420 |
| tgctgatgct | ggccaagtgg | gatcactgct | gagtcgctgg | ttgaatgtac | cgctaatttt | 480 |
| cacagggcat | tctctggggc | ggatcaagct | aaaaaagctg | ttggagcaag | actggccgct | 540 |
| tgaggaaatt | gaagcgcaat | tcaatattca | acagcgaatt | gatgcggagg | agatgacgct | 600 |
| cactcatgct | gactggattg | tcgccagcac | tcagcaggaa | gtggaggagc | aataccgcgt | 660 |
| ttacgatcgc | tacaacccag | agcgcaagct | tgtcattcca | ccgggtgtcg | ataccgatcg | 720 |
| cttcaggtttt | cagcccttgg | gcgatcgcgg | tgttgttctc | caacaggaac | tgagccgctt | 780 |
| tctgcgcgac | ccagaaaaac | ctcaaattct | ctgcctctgt | cgccccgcac | ctcgcaaaaa | 840 |
| tgtaccggcg | ctggtgcgag | cctttggcga | acatccttgg | ctgcgcaaaa | aagccaacct | 900 |
| tgtcttagta | ctgggcagcc | gccaagacat | caaccagatg | gatcgcggca | gtcggcaggt | 960 |
| gttccaagag | attttccatc | tggtcgatcg | ctacgacctc | tacggcagcg | tcgcctatcc | 1020 |
| caaacagcat | caggctgatg | atgtgccgga | gttctatcgc | ctagcggctc | attccggcgg | 1080 |
| ggtattcgtc | aatccggcgc | tgaccgaacc | ttttggtttg | acaattttgg | aggcaggaag | 1140 |
| ctgcggcgtg | ccggtggtgg | caacccatga | tggcggcccc | caggaaattc | tcaaacactg | 1200 |
| tgatttcggc | actttagttg | atgtcagccg | accgctaat | atcgcgactg | cactcgccac | 1260 |
| cctgctgagc | gatcgcgatc | tttggcagtg | ctatcaccgc | aatggcattg | aaaaagttcc | 1320 |
| cgcccattac | agctgggatc | aacatgtcaa | taccctgttt | gagcgcatgg | aaacggtggc | 1380 |
| tttgcctcgt | cgtcgtgctg | tcagtttcgt | acggagtcgc | aaacgcttga | ttgatgccaa | 1440 |
| acgccttgtc | gttagtgaca | tcgacaacac | actgttgggc | gatcgtcaag | gactcgagaa | 1500 |
| tttaatgacc | tatctcgatc | agtatcgcga | tcattttgcc | tttggaattg | ccacggggcg | 1560 |
| tcgcctagac | tctgcccaag | aagtcttgaa | agagtggggc | gttccttcgc | caaacttctg | 1620 |
| ggtgacttcc | gtcggcagcg | agattcacta | tggcaccgat | gctgaaccgg | atatcagctg | 1680 |
| ggaaaagcat | atcaatcgca | actggaatcc | tcagcgaatt | cggcagtaa | tggcacaact | 1740 |
| acccttttctt | gaactgcagc | cggaagagga | tcaaacaccc | ttcaaagtca | gcttctttgt | 1800 |
| ccgcgatcgc | cacagagactg | tgctgcgaga | agtacggcaa | catcttcgcc | gccatcgcct | 1860 |
| gcggctgaag | tcaatctatt | cccatcagga | gtttcttgac | attctgccgc | tagctgcctc | 1920 |
| gaaaggggat | gcgattcgcc | acctctcact | ccgctggcgg | attcctcttg | agaacatttt | 1980 |
| ggtggcaggc | gattctggta | acgatgagga | aatgctcaag | ggccataatc | tcggcgttgt | 2040 |
| agttggcaat | tactcaccgg | aattggagcc | actgcgcagc | tacgagcgcg | tctattttgc | 2100 |
| tgagggccac | tatgctaatg | gcattctgga | agccttaaaa | cactatcgct | tttttggagcc | 2160 |
| gatcgcttaa | ccttttcaga | acgtcaggag | ctaaggaagc | taaaatggag | aaaaaaatca | 2220 |

```
ctggatatac caccgttgat atatcccaat ggcatcgtaa agaacatttt gaggcatttc    2280
agtcagttgc tcaatgtacc tataaccaga ccgttcagct ggatattacg gccttttaa     2340 agaccgtaaa gaaaataag cacaagtttt atccggcctt tattcacatt cttgcccgcc    2400
tgatgaatgc tcatccggaa ttccgtatgg caatgaaaga cggtgagctg gtgatatggg    2460
atagtgttca cccttgttac accgttttcc atgagcaaac tgaaacgttt tcatcgctct    2520
ggagtgaata ccacgacgat ttccggcagt ttctacacat atattcgcaa gatgtggcgt    2580
gttacggtga aaacctggcc tatttcccta aagggtttat tgagaatatg tttttcgtct    2640
cagccaatcc ctgggtgagt ttcaccagtt ttgatttaaa cgtggccaat atggacaact    2700
tcttcgcccc cgttttcacc atgggcaaat attatacgca aggcgacaag gtgctgatgc    2760
cgctggcgat tcaggttcat catgccgttt gtgatggctt ccatgtcggc agaatgctta    2820
atgaattaca acagtactgc gatgagtggc agggcggggc gtaatttttt taaggcagtt    2880
attggtgccc ttaaacgcct ggttgctacg cctgaataag tgataataag cggatgaatg    2940
gcagaaattc gatgataagc tgtcaaacac gtgaattggt cgaacgaatt caagcttgat    3000
atcattcagg acgagcctca gactccagcg taactggact gcaatcaact cactggctca    3060
ccttcacggg tgggcctttc ttcggtagaa aatcaaagga tcttcttgag atccttttt    3120 tctgcgcgta atctgctgct tgcaaacaaa aaaaccaccg ctaccagcgg tggtttgttt    3180
gccggatcaa gagctaccaa ctcttttcc gaggtaactg gcttcagcag agcgcagata    3240
ccaaatactg ttcttctagt gtagccgtag ttaggccacc acttcaagaa ctctgtagca    3300
ccgcctacat acctcgctct gctaatcctg ttaccagtgg ctgctgccag tggcgataag    3360
tcgtgtctta ccgggttgga ctcaagacga tagttaccgg ataaggcgca gcggtcgggc    3420
tgaacggggg gttcgtgcac acagcccagc ttggagcgaa cgacctacac cgaactgaga    3480
tacctacagc gtgagctatg agaaagcgcc acgcttcccg aagggagaaa ggcggacagg    3540
tatccggtaa gcggcagggt cggaacagga gagcgcacga gggagcttcc agggggaaac    3600
gcctggtatc tttatagtcc tgtcgggttt cgccacctct gacttgagca tcgattttg    3660 tgatgctcgt caggggggcg gagcctatgg aaaaacgcca gcaacgcaga aaggcccacc    3720
cgaaggtgag ccaggtgatt acatttgggc cctcatcaga ggttttcacc gtcatcaccg    3780
aaacgcgcga ggcagctgcg gtaaagctca tcagcgtggt cgtgaagcga ttcacagatg    3840
tctgcctgtt catccgcgtc cagctcgttg agtttctcca gaagcgttaa tgtctggctt    3900
ctgataaagc gggccatgtt aagggcggtt ttttcctgtt tggtcattta gaaaaactca    3960
tcgagcatca agtgaaactg caatttattc atatcaggat tatcaatacc atatttttga    4020
aaaagccgtt tctgtaatga aggagaaaac tcaccgaggc agttccatag gatggcaaga    4080
tcctggtatc ggtctgcgat tccgactcgt ccaacatcaa tacaacctat taatttcccc    4140
tcgtcaaaaa taaggttatc aagtgagaaa tcaccatgag tgacgactga atccggtgag    4200
aatggcaaaa gcttatgcat ttcttttccag acttgttcaa caggccagcc attacgctcg    4260
tcatcaaaat cactcgcacc aaccaaaccg ttattcattc gtgattgcgc ctgagcgaga    4320
cgaaatacgc gatcgccgtt aaaaggacaa ttacaaacag gaatcgaatg caaccggcgc    4380
aggaacactg ccagcgcatc aacaatattt tcacctgaat caggatattc ttctaatacc    4440
tggaatgctg ttttccctgg gatcgcagtg gtgagtaacc atgcatcatc aggagtacgg    4500
ataaaatgct tgatggtcgg aagaggcata aattccgtca gccagtttag cctgaccatc    4560
tcatctgtaa catcattggc aacgctacct ttgccatgtt tcagaaacaa ctctggcgca    4620
```

```
tcgggcttcc catacaatcg atagattgtc gcacctgatt gcccgacatt atcgcgagcc    4680
catttatacc catataaatc agcatccatg ttggaattta atcgcggcct cgagcaagac    4740
gtttcccgtt gaatatggct cattttagct tccttagctc ctgaaaatct cgataactca    4800
aaaaatacgc ccggtagtga tcttatttca ttatggtgaa agttggaacc tcttacgtgc    4860
cgatcaagtc aaaagcctcc ggtcggaggc ttttgacttt ctgctatgga ggtcaggtat    4920
gatttaaatg gtcagtattg agcgatatct agagaattcg tc                      4962
```

<210> SEQ ID NO 53
<211> LENGTH: 5052
<212> TYPE: DNA
<213> ORGANISM: Artificial
<220> FEATURE:
<223> OTHER INFORMATION: plasmid pLybAL14f

<400> SEQUENCE: 53

```
cgaccaattc acgtgtttga cagcttatca tcgaatttct gccattcatc cgcttattat      60
cacttattca ggcgtagcaa ccaggcgttt aagggcacca ataactgcct taaaaaaatt     120
acgccccgcc ctgccactca tcgcagtact gttgtaattc attaagcatt ctgccgacat     180
ggaagccatc acaaacggca tgatgaacct gaatcgccag cggcatcagc accttgtcgc     240
cttgcgtata atatttgccc atggtgaaaa cgggggcgaa gaagttgtcc atattggcca     300
cgtttaaatc aaaactggtg aaactcaccc agggattggc tgagacgaaa aacatattct     360
caataaaccc tttagggaaa taggccaggt tttcaccgta acacgccaca tcttgcgaat     420
atatgtgtag aaactgccgg aaatcgtcgt ggtattcact ccagagcgat gaaaacgttt     480
cagtttgctc atggaaaacg gtgtaacaag gtgaacact atcccatatc accagctcac     540
cgtctttcat tgccatacgg aattccggat gagcattcat caggcgggca agaatgtgaa     600
taaaggccgg ataaaacttg tgcttatttt tctttacggt cttttaaaaag gccgtaatat     660 ccagctgaac ggtctggtta taggtacatt gagcaactga ctgaaatgcc tcaaaatgtt     720
ctttacgatg ccattgggat atatcaacgg tggtatatcc agtgattttt ttctccattt     780
tagcttcctt agctcctgaa aatctcgata actcaaaaaa tacgcccggt agtgatctta     840
tttcattatg gtgaaagttg gaacctctta cgtgccgatc aacgtctcac gttctgaaaa     900
ggttaagcga tcgcctcaaa aaagcgatag tgttttaagg cttccagaat gccattagca     960
tagtggccct cagcaaaata gacgcgctcg tagctgcgca gtggctccaa ttccggtgag    1020
taattgccaa ctacaacgcc gagattatgg cccttgagca tttcctcatc gttaccagaa    1080
tcgcctgcca ccaaaatgtt ctcaagagga atccgccagc ggagtgagag gtggcgaatc    1140
gcatccccct tcgaggcagc tagcggcaga atgtcaagaa actcctgatg gaatagatt     1200 gacttcagcc gcaggcgatg gcggcgaaga tgttgccgta cttctcgcag cacagtctcg    1260
tggcgatcgc ggacaaagaa gctgactttg aagggtgttt gatcctcttc cggctgcagt    1320
tcaagaaagg gtagttgtgc cattactgcc gaattcgct gaggattcca gttgcgattg     1380
atatgctttt cccagctgat atccggttca gcatcggtgc catagtgaat ctcgctgccg    1440
acggaagtca cccagaagtt tggcgaagga acgccccact cttcaagac ttcttgggca     1500 gagtctaggc gacgccccgt ggcaattcca aaggcaaaat gatcgcgata ctgatcgaga    1560
taggtcatta aattctcgag tccttgacga tcgcccaaca gtgtgttgtc gatgtcacta    1620
acgacaaggc gtttggcatc aatcaagcgt ttgcgactcc gtacgaaact gacagcacga    1680
cgacgaggca aagccaccgt ttccatgcgc tcaaacaggg tattgacatg ttgatcccag    1740
```

```
ctgtaatggg cgggaacttt ttcaatgcca ttgcggtgat agcactgcca aagatcgcga   1800
tcgctcagca gggtggcgag tgcagtcgcg atattagcgg gtcggctgac atcaactaaa   1860
gtgccgaaat cacagtgttt gagaatttcc tgggggccgc catcatgggt tgccaccacc   1920
ggcacgccgc agcttcctgc ctccaaaatt gtcaaaccaa aaggttcggt cagcgccgga   1980
ttgacgaata ccccgccgga atgagccgct aggcgataga actccggcac atcatcagcc   2040
tgatgctgtt tgggataggc gacgctgccg tagaggtcgt agcgatcgac cagatggaaa   2100
atctcttgga acacctgccg actgccgcga tccatctggt tgatgtcttg gcggctgccc   2160
agtactaaga caaggttggc ttttttgcgc agccaaggat gttcgccaaa ggctcgcacc   2220
agcgccggta catttttgcg aggtgcgggg cgacagaggc agagaatttg aggtttttct   2280
gggtcgcgca gaaagcggct cagttcctgt tggagaacaa caccgcgatc gcccaagggc   2340
tgaaacctga agcgatcggt atcgacaccc ggtggaatga caagcttgcg ctctgggttg   2400
tagcgatcgt aaacgcggta ttgctcctcc acttcctgct gagtgctggc gacaatccag   2460
tcagcatgag tgagcgtcat ctcctccgca tcaattcgct gttgaatatt gaattgcgct   2520
tcaatttcct caagcggcca gtcttgctcc aacagctttt ttagcttgat ccgcccaga   2580 gaatgccctg tgaaaattag cggtacattc aaccagcgac tcagcagtga tcccacttgg   2640
ccagcatcag catagtgggc ctgaatccaa gtcggggtgc gcttttgctg agccagatat   2700
tggagaattg catccgcaaa ggtgtagaga tggggccaaa gcagctcttt acggaggtag   2760 cgtttgggc caaaggcaa acggacaatc cgacctttgg gcgcaaaggg ttcgatcgcc   2820
tgactgtaac caacactgac gcggggtcg gtgatttggc gggtgatgat gtcgacttgt   2880
tggacttgtg gggatttagc ttgggcttga gccagttcta agacgtactt ggtctgcccg   2940
ccggtgtcgg catctcgccc cagttccaag ttctgccctc gcagcagacc atgggtctga   3000
atgtgcagaa tgtagagatt ttgagctgcc acgcgctagt cagcctcaca gaaaacgccc   3060
caattgtagt ctaacgaatt caagcttgat atcattcagg acgagcctca gactccagcg   3120
taactggact gcaatcaact cactggctca ccttcacggg tgggcctttc ttcggtagaa   3180
aatcaaagga tcttcttgag atccttttt tctgcgcgta atctgctgct tgcaaacaaa   3240
aaaaccaccg ctaccagcgg tggtttgttt gccggatcaa gagctaccaa ctcttttcc   3300 gaggtaactg gcttcagcag agcgcagata ccaaatactg ttcttctagt gtagccgtag   3360
ttaggccacc acttcaagaa ctctgtagca ccgcctacat acctcgctct gctaatcctg   3420
ttaccagtgg ctgctgccag tggcgataag tcgtgtctta ccgggttgga ctcaagacga   3480
tagttaccgg ataaggcgca gcggtcgggc tgaacggggg gttcgtgcac acagcccagc   3540
ttggagcgaa cgacctacac cgaactgaga tacctacagc gtgagctatg agaaagcgcc   3600
acgcttcccg aagggagaaa ggcggacagg tatccggtaa gcggcagggt cggaacagga   3660
gagcgcacga gggagcttcc agggggaaac gcctggtatc tttatagtcc tgtcgggttt   3720
cgccacctct gacttgagca tcgattttg tgatgctcgt cagggggcg gagcctatgg   3780 aaaaacgcca gcaacgcaga aaggcccacc cgaaggtgag ccaggtgatt acatttgggc   3840
cctcatcaga ggttttcacc gtcatcaccg aaacgcgcga ggcagctgcg gtaaagctca   3900
tcagcgtggt cgtgaagcga ttcacagatg tctgcctgtt catccgcgtc cagctcgttg   3960
agtttctcca gaagcgttaa tgtctggctt ctgataaagc gggccatgtt aagggcggtt   4020
ttttcctgtt tggtcattta gaaaaactca tcgagcatca agtgaaactg caatttattc   4080
atatcaggat tatcaatacc atattttga aaaagccgtt tctgtaatga aggagaaaac   4140
```

```
tcaccgaggc agttccatag gatggcaaga tcctggtatc ggtctgcgat tccgactcgt    4200
ccaacatcaa tacaacctat taatttcccc tcgtcaaaaa taaggttatc aagtgagaaa    4260
tcaccatgag tgacgactga atccggtgag aatggcaaaa gcttatgcat ttctttccag    4320
acttgttcaa caggccagcc attacgctcg tcatcaaaat cactcgcacc aaccaaaccg    4380
ttattcattc gtgattgcgc ctgagcgaga cgaaatacgc gatcgccgtt aaaaggacaa    4440
ttacaaacag gaatcgaatg caaccggcgc aggaacactg ccagcgcatc aacaatattt    4500
tcacctgaat caggatattc ttctaatacc tggaatgctg ttttccctgg gatcgcagtg    4560
gtgagtaacc atgcatcatc aggagtacgg ataaaatgct tgatggtcgg aagaggcata    4620
aattccgtca gccagtttag cctgaccatc tcatctgtaa catcattggc aacgctacct    4680
ttgccatgtt tcagaaacaa ctctggcgca tcgggcttcc catacaatcg atagattgtc    4740
gcacctgatt gcccgacatt atcgcgagcc catttatacc catataaatc agcatccatg    4800
ttggaattta atcgcggcct cgagcaagac gtttcccgtt gaatatggct cattttagct    4860
tccttagctc ctgaaaatct cgataactca aaaaatacgc ccggtagtga tcttatttca    4920
ttatggtgaa agttggaacc tcttacgtgc cgatcaagtc aaaagcctcc ggtcggaggc    4980
ttttgacttt ctgctatgga ggtcaggtat gatttaaatg gtcagtattg agcgatatct    5040
agagaattcg tc                                                         5052

<210> SEQ ID NO 54
<211> LENGTH: 5052
<212> TYPE: DNA
<213> ORGANISM: Artificial
<220> FEATURE:
<223> OTHER INFORMATION: plasmid pLybAL14r

<400> SEQUENCE: 54
agactacaat tggggcgttt tctgtgaggc tgactagcgc gtggcagctc aaaatctcta      60
cattctgcac attcagaccc atggtctgct gcgagggcag aacttggaac tggggcgaga     120
tgccgacacc ggcgggcaga ccaagtacgt cttagaactg gctcaagccc aagctaaatc     180
cccacaagtc caacaagtcg acatcatcac ccgccaaatc accgaccccc gcgtcagtgt     240
tggttacagt caggcgatcg aacccttgc gcccaaaggt cggattgtcc gtttgccttt     300
tggccccaaa cgctacctcc gtaaagagct gctttggccc catctctaca cctttgcgga     360
tgcaattctc caatatctgg ctcagcaaaa gcgcaccccg acttggattc aggcccacta     420
tgctgatgct ggccaagtgg gatcactgct gagtcgctgg ttgaatgtac cgctaatttt     480
cacagggcat tctctggggc ggatcaagct aaaaaagctg ttggagcaag actggccgct     540
tgaggaaatt gaagcgcaat tcaatattca acagcgaatt gatgcggagg agatgacgct     600
cactcatgct gactggattg tcgccagcac tcagcaggaa gtggaggagc aataccgcgt     660
ttacgatcgc tacaacccag agcgcaagct tgtcattcca ccgggtgtcg ataccgatcg     720
cttcaggttt cagcccttgg gcgatcgcgg tgttgttctc caacaggaac tgagccgctt     780
tctgcgcgac ccagaaaaac ctcaaattct ctgcctctgt cgccccgcac ctcgcaaaaa     840
tgtaccggcg ctggtgcgag cctttggcga acatccttgg ctgcgcaaaa agccaacct     900
tgtcttagta ctgggcagcc gccaagacat caaccagatg gatcgcggca gtcggcaggt     960
gttccaagag atttccatc tggtcgatcg ctacgacctc tacggcagcg tcgcctatcc    1020
caaacagcat caggctgatg atgtgccgga gttctatcgc ctagcggctc attccggcgg    1080
ggtattcgtc aatccggcgc tgaccgaacc ttttggtttg acaattttgg aggcaggaag    1140
```

```
ctgcggcgtg ccggtggtgg caacccatga tggcggcccc caggaaattc tcaaacactg    1200
tgatttcggc actttagttg atgtcagccg acccgctaat atcgcgactg cactcgccac    1260
cctgctgagc gatcgcgatc tttggcagtg ctatcaccgc aatggcattg aaaaagttcc    1320
cgcccattac agctgggatc aacatgtcaa taccctgttt gagcgcatgg aaacggtggc    1380
tttgcctcgt cgtcgtgctg tcagtttcgt acggagtcgc aaacgcttga ttgatgccaa    1440
acgccttgtc gttagtgaca tcgacaacac actgttgggc gatcgtcaag gactcgagaa    1500
tttaatgacc tatctcgatc agtatcgcga tcattttgcc tttggaattg ccacggggcg    1560
tcgcctagac tctgcccaag aagtcttgaa agagtggggc gttccttcgc caaacttctg    1620
ggtgacttcc gtcggcagcg agattcacta tggcaccgat gctgaaccgg atatcagctg    1680
ggaaaagcat atcaatcgca actggaatcc tcagcgaatt cgggcagtaa tgcacaact     1740 acccttctt gaactgcagc cggaagagga tcaaacaccc ttcaaagtca gcttctttgt     1800
ccgcgatcgc cacgagactg tgctgcgaga agtacggcaa catcttcgcc gccatcgcct    1860
gcggctgaag tcaatctatt cccatcagga gtttcttgac attctgccgc tagctgcctc    1920
gaaaggggat gcgattcgcc acctctcact ccgctggcgg attcctcttg agaacatttt    1980
ggtggcaggc gattctggta acgatgagga aatgctcaag ggccataatc tcggcgttgt    2040
agttggcaat tactcaccgg aattggagcc actgcgcagc tacgagcgcg tctattttgc    2100
tgagggccac tatgctaatg gcattctgga agccttaaaa cactatcgct tttttgaggc    2160
gatcgcttaa ccttttcaga acgtgagacg ttgatcggca cgtaagaggt tccaactttc    2220
accataatga ataagatca ctaccgggcg tatttttga gttatcgaga ttttcaggag     2280
ctaaggaagc taaaatggag aaaaaaatca ctggatatac caccgttgat atatcccaat    2340
ggcatcgtaa agaacatttt gaggcatttc agtcagttgc tcaatgtacc tataaccaga    2400
ccgttcagct ggatattacg gcctttttaa agaccgtaaa gaaaaataag cacaagtttt    2460
atccggcctt tattcacatt cttgcccgcc tgatgaatgc tcatccggaa ttccgtatgg    2520
caatgaaaga cggtgagctg gtgatatggg atagtgttca cccttgttac accgttttcc    2580
atgagcaaac tgaaacgttt tcatcgctct ggagtgaata ccacgacgat ttccggcagt    2640
ttctacacat atattcgcaa gatgtggcgt gttacggtga aaacctggcc tatttcccta    2700
aagggtttat tgagaatatg ttttttcgtct cagccaatcc ctgggtgagt ttcaccagtt    2760
ttgatttaaa cgtggccaat atggacaact tcttcgcccc cgttttcacc atgggcaaat    2820
attatacgca aggcgacaag gtgctgatgc cgctggcgat tcaggttcat catgccgttt    2880
gtgatggctt ccatgtcggc agaatgctta atgaattaca acagtactgc gatgagtggc    2940 agggcgggc gtaattttt taaggcagtt attggtgccc ttaaacgcct ggttgctacg     3000
cctgaataag tgataataag cggatgaatg gcagaaattc gatgataagc tgtcaaacac    3060
gtgaattggt cgaacgaatt caagcttgat atcattcagg acgagcctca gactccagcg    3120
taactggact gcaatcaact cactggctca ccttcacggg tgggcctttc ttcggtagaa    3180
aatcaaagga tcttcttgag atcctttttt tctgcgcgta atctgctgct tgcaaacaaa    3240
aaaaccaccg ctaccagcgg tggtttgttt gccggatcaa gagctaccaa ctctttttcc    3300
gaggtaactg gcttcagcag agcgcagata ccaaatactg ttcttctagt gtagccgtag    3360
ttaggccacc acttcaagaa ctctgtagca ccgcctacat acctcgctct gctaatcctg    3420
ttaccagtgc tgctgccag tggcgataag tcgtgtctta ccgggttgga ctcaagacga    3480
tagttaccgg ataaggcgca gcggtcgggc tgaacggggg gttcgtgcac acagcccagc    3540
```

-continued

```
ttggagcgaa cgacctacac cgaactgaga tacctacagc gtgagctatg agaaagcgcc    3600
acgcttcccg aagggagaaa ggcggacagg tatccggtaa gcggcagggt cggaacagga    3660
gagcgcacga gggagcttcc aggggggaaac gcctggtatc tttatagtcc tgtcgggttt    3720
cgccacctct gacttgagca tcgattttttg tgatgctcgt caggggggcg gagcctatgg    3780
aaaaacgcca gcaacgcaga aaggcccacc cgaaggtgag ccaggtgatt acatttgggc    3840
cctcatcaga ggttttcacc gtcatcaccg aaacgcgcga ggcagctgcg gtaaagctca    3900
tcagcgtggt cgtgaagcga ttcacagatg tctgcctgtt catccgcgtc cagctcgttg    3960
agtttctcca gaagcgttaa tgtctggctt ctgataaagc gggccatgtt aagggcggtt    4020
ttttcctgtt tggtcattta gaaaaactca tcgagcatca agtgaaactg caatttattc    4080
atatcaggat tatcaatacc atattttttga aaaagccgtt tctgtaatga aggagaaaac    4140
tcaccgaggc agttccatag gatggcaaga tcctggtatc ggtctgcgat tccgactcgt    4200
ccaacatcaa tacaacctat taatttcccc tcgtcaaaaa taaggttatc aagtgagaaa    4260
tcaccatgag tgacgactga atccggtgag aatggcaaaa gcttatgcat ttctttccag    4320
acttgttcaa caggccagcc attacgctcg tcatcaaaat cactcgcacc aaccaaaccg    4380
ttattcattc gtgattgcgc ctgagcgaga cgaaatacgc gatcgccgtt aaaaggacaa    4440
ttacaaacag gaatcgaatg caaccggcgc aggaacactg ccagcgcatc aacaatattt    4500
tcacctgaat caggatattc ttctaatacc tggaatgctg ttttccctgg gatcgcagtg    4560
gtgagtaacc atgcatcatc aggagtacgg ataaaatgct tgatggtcgg aagaggcata    4620
aattccgtca gccagtttag cctgaccatc tcatctgtaa catcattggc aacgctacct    4680
ttgccatgtt tcagaaacaa ctctggcgca tcgggcttcc catacaatcg atagattgtc    4740
gcacctgatt gcccgacatt atcgcgagcc catttatacc catataaatc agcatccatg    4800
ttggaattta atcgcggcct cgagcaagac gtttcccgtt gaatatggct cattttagct    4860
tccttagctc ctgaaaatct cgataactca aaaaatacgc ccggtagtga tcttatttca    4920
ttatggtgaa agttggaacc tcttacgtgc cgatcaagtc aaaagcctcc ggtcggaggc    4980
ttttgacttt ctgctatgga ggtcaggtat gatttaaatg gtcagtattg agcgatatct    5040
agagaattcg tc                                                        5052
```

<210> SEQ ID NO 55
<211> LENGTH: 24
<212> TYPE: DNA
<213> ORGANISM: Artificial
<220> FEATURE:
<223> OTHER INFORMATION: primer for detection of plasmid in
      cyanobacteria

<400> SEQUENCE: 55

```
ggtggttgtg tttgacagct tatc                                             24
```

<210> SEQ ID NO 56
<211> LENGTH: 651
<212> TYPE: DNA
<213> ORGANISM: Synechocystis PCC6803

<400> SEQUENCE: 56

```
atggcttctc aattacgtgt ttatgtgccg gagcatcctc taattaagca ttggttgggg    60
gtagctaggg atgaaaacac gccgccggtt ttgtttaaaa ctgccatggg ggaattggga    120
cgttggttga cctatgaggc cgctcgttat tggttgccga cggtggatac ggaagtgaaa    180
```

| | |
|---|---|
| actccctgg cgatcgccaa ggccagtctt attgacccc aaacgccctt tgtcattgtg | 240 |
| cccatttgc gggcggggtt ggctctggtg aaggggccc aggggttgtt gcccctggca | 300 |
| aaaatttacc atctgggttt agtgcgcaat gaaactaccc tggaacctag tctgtatctg | 360 |
| aacaagttgc cggagcggtt tgccccggt acccatcttt tgttgctaga tcccatgttg | 420 |
| gctacgggta ataccatcat ggctgctttg gatttgctga tggcccggga cattgatgcc | 480 |
| aatttaatcc gtttggtctc cgtggtggcc gcccccactg ccctgcaaaa attaagtaat | 540 |
| gcccatccca atttgaccat ctacaccgcc atgattgacg aacaactcaa tgaccggggt | 600 |
| tacattgtgc ccggcctagg ggatgcaggc gatcgttgct ttggtacttg a | 651 |

<210> SEQ ID NO 57
<211> LENGTH: 216
<212> TYPE: PRT
<213> ORGANISM: Synechocystis PCC6803

<400> SEQUENCE: 57

Met Ala Ser Gln Leu Arg Val Tyr Val Pro Glu His Pro Leu Ile Lys
1               5                   10                  15

His Trp Leu Gly Val Ala Arg Asp Glu Asn Thr Pro Val Leu Phe
            20                  25                  30

Lys Thr Ala Met Gly Glu Leu Gly Arg Trp Leu Thr Tyr Glu Ala Ala
        35                  40                  45

Arg Tyr Trp Leu Pro Thr Val Asp Thr Glu Val Lys Thr Pro Leu Ala
    50                  55                  60

Ile Ala Lys Ala Ser Leu Ile Asp Pro Gln Thr Pro Phe Val Ile Val
65                  70                  75                  80

Pro Ile Leu Arg Ala Gly Leu Ala Leu Val Glu Gly Ala Gln Gly Leu
                85                  90                  95

Leu Pro Leu Ala Lys Ile Tyr His Leu Gly Leu Val Arg Asn Glu Thr
            100                 105                 110

Thr Leu Glu Pro Ser Leu Tyr Leu Asn Lys Leu Pro Glu Arg Phe Ala
        115                 120                 125

Pro Gly Thr His Leu Leu Leu Leu Asp Pro Met Leu Ala Thr Gly Asn
    130                 135                 140

Thr Ile Met Ala Ala Leu Asp Leu Leu Met Ala Arg Asp Ile Asp Ala
145                 150                 155                 160

Asn Leu Ile Arg Leu Val Ser Val Val Ala Ala Pro Thr Ala Leu Gln
                165                 170                 175

Lys Leu Ser Asn Ala His Pro Asn Leu Thr Ile Tyr Thr Ala Met Ile
            180                 185                 190

Asp Glu Gln Leu Asn Asp Arg Gly Tyr Ile Val Pro Gly Leu Gly Asp
        195                 200                 205

Ala Gly Asp Arg Cys Phe Gly Thr
    210                 215

<210> SEQ ID NO 58
<211> LENGTH: 654
<212> TYPE: DNA
<213> ORGANISM: Synechococcus PCC7942

<400> SEQUENCE: 58

| | |
|---|---|
| atggctcctc aactgcgtat cttcgtgccg cccatccct taattcggca ctggctgggc | 60 |
| attgcccgcg atcgccagac gccgacgcct ctgtttcgca ccgcgatcgc agagctgggc | 120 |
| cgctggctcg cctatgaggc tgtgcgggaa tggctaccaa cgattccagc ggcggtgcaa | 180 |

-continued

```
actcctcttg cagaaacccc agcggagttc gtcgattttt cgcaacccct tggcgatcgtg      240 ccgattctgc gcgcaggtct gggtttagtg gagtctgtcc aacaggtttt gccgactgcc      300 cgcattttc acgtgggtct caagcgggat gaagtcagtc ttgaaccgcg ctgctacctc       360
aatcacctgc cagagcaact tgaagtgaac agtcgcgttc tggttctcga cccgatgctg     420
gcgacaggtg gctcgctgct ctataccctt gatttgctgc gcgatcgcgg tgtctctgct     480
gagcaagtgc gggtgctttc aattgtggct gccccgccag cgctacaaaa actcagtcaa    540
gcctacccgg cgttgacgat ttacagcgcc atcattgatg agcagctgaa cgacaaaggc     600
tttatcgtgc cggggctggg ggatgctggc gatcgcctgt tggtactcc ttga            654
```

<210> SEQ ID NO 59
<211> LENGTH: 217
<212> TYPE: PRT
<213> ORGANISM: Synechococcus PCC7942

<400> SEQUENCE: 59

```
Met Ala Pro Gln Leu Arg Ile Phe Val Pro His Pro Leu Ile Arg
 1               5                  10                  15

His Trp Leu Gly Ile Ala Arg Asp Arg Gln Thr Pro Thr Pro Leu Phe
                20                  25                  30

Arg Thr Ala Ile Ala Glu Leu Gly Arg Trp Leu Ala Tyr Glu Ala Val
            35                  40                  45

Arg Glu Trp Leu Pro Thr Ile Pro Ala Ala Val Gln Thr Pro Leu Ala
        50                  55                  60

Glu Thr Pro Ala Glu Phe Val Asp Phe Ser Gln Pro Leu Ala Ile Val
65                  70                  75                  80

Pro Ile Leu Arg Ala Gly Leu Gly Leu Val Glu Ser Val Gln Gln Val
                85                  90                  95

Leu Pro Thr Ala Arg Ile Phe His Val Gly Leu Lys Arg Asp Glu Val
            100                 105                 110

Ser Leu Glu Pro Arg Cys Tyr Leu Asn His Leu Pro Glu Gln Leu Glu
        115                 120                 125

Val Asn Ser Arg Val Leu Val Leu Asp Pro Met Leu Ala Thr Gly Gly
    130                 135                 140

Ser Leu Leu Tyr Thr Leu Asp Leu Leu Arg Asp Arg Gly Val Ser Ala
145                 150                 155                 160

Glu Gln Val Arg Val Leu Ser Ile Val Ala Ala Pro Pro Ala Leu Gln
                165                 170                 175

Lys Leu Ser Gln Ala Tyr Pro Ala Leu Thr Ile Tyr Ser Ala Ile Ile
            180                 185                 190

Asp Glu Gln Leu Asn Asp Lys Gly Phe Ile Val Pro Gly Leu Gly Asp
        195                 200                 205

Ala Gly Asp Arg Leu Phe Gly Thr Pro
    210                 215
```

<210> SEQ ID NO 60
<211> LENGTH: 33
<212> TYPE: DNA
<213> ORGANISM: Artificial
<220> FEATURE:
<223> OTHER INFORMATION: primer for amplifying upp gene from Bacillus subtilis 168

<400> SEQUENCE: 60

```
aagaagcaag acagcgtgta gctgctctga ctg                                     33
```

```
<210> SEQ ID NO 61
<211> LENGTH: 50
<212> TYPE: DNA
<213> ORGANISM: Artificial
<220> FEATURE:
<223> OTHER INFORMATION: primer for amplifying upp gene from Bacillus
      subtilis 168

<400> SEQUENCE: 61
tcccgggatt tggtacctta ttttgttcca aacatgcggt cacccgcatc        50

<210> SEQ ID NO 62
<211> LENGTH: 849
<212> TYPE: DNA
<213> ORGANISM: Bacillus subtilis

<400> SEQUENCE: 62
aagaagcaag acagcgtgta gctgctctga ctgataaatt tcctttatat aaagaattag    60
attattaaga tcctaaaacc cgcttgggct tatgcccggc gggttttttg acgatgttct   120
tgaaactcaa tgtcttttt tgtagaatca atagaagtgt gtaattgttg atgggacaat   180
aaaaaaggag ctgaaacaca gtatgggaaa ggtttatgta tttgatcatc ctttaattca   240
gcacaagctg acatatatac ggaatgaaaa tacaggtacg aaggatttta gagagttagt   300
agatgaagtg gctacactca tggcatttga aattacccgc gatcttcctc tggaagaagt   360
ggatatcaat acaccggttc aggctgcgaa atcgaaagtc atctcaggga aaaaactcgg   420
agtggttcct atcctcagag caggattggg aatggttgac ggcattttaa agctgattcc   480
tgcggcaaaa gtgggacatg tcggccttta ccgtgatcca gaaaccttaa aacccgtgga   540
atactatgtc aagcttcctt ctgatgtgga agagcgtgaa ttcatcgtgg ttgacccgat   600
gctcgctaca ggcggttccg cagttgaagc cattcacagc cttaaaaaac gcggtgcgaa   660
aaatatccgt ttcatgtgtc ttgtagcagc gccggagggt gtggaagaat tgcagaagca   720
tcattcggac gttgatattt acattgcggc gctagatgaa aaattaaatg aaaaaggata   780
tattgttcca ggtctcggag atgcgggtga ccgcatgttt ggaacaaaat aaggtaccaa   840
atcccggga                                                         849

<210> SEQ ID NO 63
<211> LENGTH: 22
<212> TYPE: DNA
<213> ORGANISM: Artificial
<220> FEATURE:
<223> OTHER INFORMATION: primer for sequence verification of pLybAL7f

<400> SEQUENCE: 63
gtaatacgac tcactatagg gc                                           22

<210> SEQ ID NO 64
<211> LENGTH: 24
<212> TYPE: DNA
<213> ORGANISM: Artificial
<220> FEATURE:
<223> OTHER INFORMATION: primer for sequence verification of pLybAL7f

<400> SEQUENCE: 64
cacacaggaa acagctatga ccat                                         24

<210> SEQ ID NO 65
<211> LENGTH: 8988
<212> TYPE: DNA
<213> ORGANISM: Artificial
<220> FEATURE:
```

<223> OTHER INFORMATION: plasmid pLybAL7f

<400> SEQUENCE: 65

```
gcggccgcaa ggggttcgcg tcagcgggtg ttggcgggtg tcggggctgg cttaactatg      60
cggcatcaga gcagattgta ctgagagtgc accatatgcg gtgtgaaata ccgcacagat     120
gcgtaaggag aaaataccgc atcaggcgcc attcgccatt cagctgcgca actgttggga     180
agggcgatcg gtgcgggcct cttcgctatt acgccagctg gcgaaagggg gatgtgctgc     240
aaggcgatta agttgggtaa cgccagggtt ttcccagtca cgacgttgta aaacgacggc     300
cagtgaattg taatacgact cactataggg cgaattcgag ctcggtaccc ggggatccca     360
ctcccgggat ttggtacctt attttgttcc aaacatgcgg tcacccgcat ctccgagacc     420
tggaacaata tatccttttt catttaattt ttcatctagc gccgcaatgt aaatatcaac     480
gtccgaatga tgcttctgca attcttccac accctccggc gctgctacaa gacacatgaa     540
acggatattt ttcgcaccgc gttttttaag gctgtgaatg gcttcaactg cggaaccgcc     600
tgtagcgagc atcgggtcaa ccacgatgaa ttcacgctct tccacatcag aaggaagctt     660
gacatagtat tccacgggtt ttaaggtttc tggatcacgg taaaggccga catgtcccac     720
ttttgccgca ggaatcagct ttaaaatgcc gtcaaccatt cccaatcctg ctctgaggat     780
aggaaccact ccgagttttt tccctgagat gactttcgat ttcgcagcct gaaccggtgt     840
attgatatcc acttcttcca gaggaagatc gcgggtaatt tcaaatgcca tgagtgtagc     900
cacttcatct actaactctc taaaatcctt cgtacctgta ttttcattcc gtatatatgt     960
cagcttgtgc tgaattaaag gatgatcaaa tacataaacc tttcccatac tgtgtttcag    1020
ctcctttttt attgtcccat caacaattac acacttctat tgattctaca aaaaagaca    1080
ttgagtttca agaacatcgt caaaaaaccc gccgggcata agcccaagcg ggttttagga    1140
tcttaataat ctaattcttt atataaagga aatttatcag tcagagcagc tacacgctgt    1200
cttgcttctt gtgggatcct ctagagtcga cctgcaggca tgcaagcttg agtattctat    1260
agtctcacct aaatagcttg gcgtaatcat ggtcatagct gtttcctgtg tgaaattgtt    1320
atccgctcac aattccacac aacatacgag ccggaagcat aaagtgtaaa gcctggggtg    1380
cctaatgagt gagctaactc acattaattg cgttgcgctc actgcccgct ttccagtcgg    1440
gaaacctgtc gtgccagctg cattaatgaa tcggccaacg cgaacccctt gcggccgccc    1500
gggccgtcga ccaattctca tgtttgacag cttatcatcg aatttctgcc attcatccgc    1560
ttattatcac ttattcaggc gtagcaacca ggcgtttaag ggcaccaata actgccttaa    1620
aaaaattacg ccccgccctg ccactcatcg cagtactgtt gtaattcatt aagcattctg    1680
ccgacatgga agccatcaca aacggcatga tgaacctgaa tcgccagcgg catcagcacc    1740
ttgtcgcctt gcgtataata tttgcccatg gtgaaaacgg gggcgaagaa gttgtccata    1800
ttggccacgt ttaaatcaaa actggtgaaa ctcacccagg gattggctga acgaaaaac    1860
atattctcaa taaaccccttt agggaaatag gccaggtttt caccgtaaca cgccacatct    1920
tgcgaatata tgtgtagaaa ctgccggaaa tcgtcgtggt attcactcca gagcgatgaa    1980
aacgtttcag tttgctcatg gaaaacggtg taacaagggt gaacactatc ccatatcacc    2040
agctcaccgt ctttcattgc catacgaaat tccggatgag cattcatcag gcgggcaaga    2100
atgtgaataa aggccggata aaacttgtgc ttattttct ttacggtctt taaaaaggcc    2160
gtaatatcca gctgaacggt ctggttatag gtacattgag caactgactg aaatgcctca    2220
aaatgttctt tacgatgcca ttgggatata tcaacggtgg tatatccagt gattttttc    2280
```

```
tccatttag   cttccttagc   tcctgaaaat   ctcgataact   caaaaaatac   gcccggtagt   2340
gatcttattt  cattatggtg   aaagttggaa   cctcttacgt   gccgatcaac   gtctcatttt   2400
cgccaaaagt  tggcccaggg   cttcccggta   tcaacaggga   caccaggatt   tatttattct   2460
gcgaagtgat  cttccgtcac   aggtatttat   tcgcgataag   ctcatggagc   ggcgtaaccg   2520
tcgcacagga  aggacagaga   aagcgcggat   ctgggaagtg   acggacagaa   cggtcaggac   2580
ctggattggg  gaggcggttg   ccgccgctgc   tgctgacggt   gtgacgttct   ctgttccggt   2640
cacaccacat  acgttccgcc   attcctatgc   gatgcacatg   ctgtatgccg   gtataccgct   2700
gaaagttctg  caaagcctga   tgggacataa   gtccatcagt   tcaacggaag   tctacacgaa   2760
ggttttgcg   ctggatgtgg   ctgcccggca   ccgggtgcag   tttgcgatgc   cggagtctga   2820
tgcggttgcg  atgctgaaac   aattatcctg   agaataaatg   ccttggcctt   tatatggaaa   2880
tgtggaactg  agtggatatg   ctgttttgt   ctgttaaaca   gagaagctgg   ctgttatcca   2940
ctgagaagcg  aacgaaacag   tcgggaaaat   ctcccattat   cgtagagatc   cgcattatta   3000
atctcaggag  cctgtgtagc   gtttatagga   agtagtgttc   tgtcatgatg   cctgcaagcg   3060
gtaacgaaaa  cgatttgaat   atgccttcag   gaacaataga   atcttcgtg   cggtgttacg   3120
ttgaagtgga  gcggattatg   tcagcaatgg   acagaacaac   ctaatgaaca   cagaaccatg   3180
atgtggtctg  tccttttaca   gccagtagtg   ctcgccgcag   tcgagcgaca   gggcgaagcc   3240
ctcggctggt  tgccctcgcc   gctgggctgg   cggccgtcta   tggccctgca   aacgcgccag   3300
aaacgccgtc  gaagccgtgt   gcgagacacc   gcggccggcc   gccggcgttg   tggataccct   3360
gcggaaaact  tggccctcac   tgacagatga   ggggcggacg   ttgacacttg   aggggccgac   3420
tcacccggcg  cggcgttgac   agatgagggg   caggctcgat   ttcggccggc   gacgtggagc   3480
tggccagcct  cgcaaatcgg   cgaaaacgcc   tgattttacg   cgagtttccc   acagatgatg   3540
tggacaagcc  tggggataag   tgccctgcgg   tattgacact   tgaggggcgc   gactactgac   3600
agatgagggg  cgcgatcctt   gacacttgag   gggcagagtg   ctgacagatg   aggggcgcac   3660
ctattgacat  ttgagggct   gtccacaggc   agaaaatcca   gcatttgcaa   gggtttccgc   3720
ccgttttcg   gccaccgcta   acctgtcttt   taacctgctt   ttaaaccaat   atttataaac   3780
cttgtttta   accagggctg   cgccctgtgc   gcgtgaccgc   gcacgccgaa   ggggggtgcc   3840
cccccttctc  gaaccctccc   ggtcgagtga   gcgaggaagc   accagggaac   agcacttata   3900
tattctgctt  acacacgatg   cctgaaaaaa   cttcccttgg   ggttatccac   ttatccacgg   3960
ggatatttt   ataattattt   tttttatagt   ttttagatct   tctttttag   agcgccttgt   4020
aggcctttat  ccatgctggt   tctagagaag   gtgttgtgac   aaattgccct   ttcagtgtga   4080
caaatcaccc  tcaaatgaca   gtcctgtctg   tgacaaattg   cccttaaccc   tgtgacaaat   4140
tgccctcaga  agaagctgtt   ttttcacaaa   gttatccctg   cttattgact   ctttttatt   4200
tagtgtgaca  atctaaaaac   ttgtcacact   tcacatggat   ctgtcatggc   ggaaacagcg   4260
gttatcaatc  acaagaaacg   taaaaatagc   ccgcgaatcg   tccagtcaaa   cgacctcact   4320
gaggcggcat  atagtctctc   ccgggatcaa   aaacgtatgc   tgtatctgtt   cgttgaccag   4380
atcagaaaat  ctgatggcac   cctacaggaa   catgacggta   tctgcgagat   ccatgttgct   4440
aaatatgctg  aaatattcgg   attgacctct   gcggaagcca   gtaaggatat   acggcaggca   4500
ttgaagagtt  tcgcggggaa   ggaagtggtt   ttttatcgcc   ctgaagagga   tgccggcgat   4560
gaaaaaggct  atgaatcttt   tccttggttt   atcaaacgtg   cgcacagtcc   atccagaggg   4620
ctttacagtg  tacatatcaa   cccatatctc   attcccttct   ttatcgggtt   acagaaccgg   4680
```

```
tttacgcagt tcggcttag tgaaacaaaa gaaatcacca atccgtatgc catgcgttta    4740
tacgaatccc tgtgtcagta tcgtaagccg gatggctcag gcatcgtctc tctgaaaatc    4800
gactggatca tagagcgtta ccagctgcct caaagttacc agcgtatgcc tgacttccgc    4860
cgccgcttcc tgcaggtctg tgttaatgag atcaacagca gaactccaat gcgcctctca    4920
tacattgaga aaagaaagg ccgccagacg actcatatcg tattttcctt ccgcgatatc    4980
acttccatga cgacaggata gtctgagggt tatctgtcac agatttgagg gtggttcgtc    5040
acatttgttc tgacctactg agggtaattt gtcacagttt tgctgtttcc ttcagcctgc    5100
atggattttc tcatactttt tgaactgtaa tttttaagga agccaaattt gagggcagtt    5160
tgtcacagtt gatttccttc tctttccctt cgtcatgtga cctgatatcg ggggttagtt    5220
cgtcatcatt gatgagggtt gattatcaca gtttattact ctgaattggc tatccgcgtg    5280
tgtacctcta cctggagttt ttcccacggt ggatatttct tcttgcgctg agcgtaagag    5340
ctatctgaca gaacagttct tctttgcttc ctcgccagtt cgctcgctat gctcggttac    5400
acggctgcgg cgagcgctag tgataataag tgactgaggt atgtgctctt cttatctcct    5460
tttgtagtgt tgctcttatt ttaaacaact ttgcggtttt tgatgacttt tgcgattttg    5520
ttgttgcttt gcagtaaatt gcaagattta ataaaaaaac gcaaagcaat gattaaagga    5580
tgttcagaat gaaactcatg gaaacactta accagtgcat aaacgctggt catgaaatga    5640
cgaaggctat cgccattgca cagtttaatg atgacagccc ggaagcgagg aaaataaccc    5700
ggcgctggag aataggtgaa gcagcggatt tagttgggt ttcttctcag gctatcagag    5760
atgccgagaa agcagggcga ctaccgcacc cggatatgga aattcgagga cgggttgagc    5820
aacgtgttgg ttatacaatt gaacaaatta atcatatgcg tgatgtgttt ggtacgcgat    5880
tgcgacgtgc tgaagacgta tttccaccgg tgatcggggt tgctgcccat aaaggtggcg    5940
tttacaaaac ctcagtttct gttcatcttg ctcaggatct ggctctgaag gggctacgtg    6000
ttttgctcgt ggaaggtaac gaccccccagg gaacagcctc aatgtatcac ggatgggtac    6060
cagatcttca tattcatgca gaagacactc tcctgccttt ctatcttggg gaaaaggacg    6120
atgtcactta tgcaataaag cccacttgct ggccggggct tgacattatt ccttcctgtc    6180
tggctctgca ccgtattgaa actgagttaa tgggcaaatt tgatgaaggt aaactgccca    6240
ccgatccaca cctgatgctc cgactggcca ttgaaactgt tgctcatgac tatgatgtca    6300
tagttattga cagcgcgcct aacctgggta tcggcacgat taatgtcgta tgtgctgctg    6360
atgtgctgat tgttcccacg cctgctgagt tgtttgacta cacctccgca ctgcagtttt    6420
tcgatatgct tcgtgatctg ctcaagaacg ttgatcttaa agggttcgag cctgatgtac    6480 gtatttgct taccaaatac agcaatagta atggctctca gtccccgtgg atggaggagc    6540
aaattcggga tgcctgggga agcatggttc taaaaaatgt tgtacgtgaa acggatgaag    6600
ttggtaaagg tcagatccgg atgagaactg tttttgaaca ggccattgat caacgctctt    6660
caactggtgc ctggagaaat gctctttcta tttgggaacc tgtctgcaat gaaatttttcg    6720 atcgtctgat taaaccacgc tgggagatta gataatgaag cgtgcgcctg ttattccaaa    6780
acatacgctc aatactcaac cggttgaaga tacttcgtta tcgacaccag ctgccccgat    6840
ggtggattcg ttaattgcgc gcgtaggagt aatggctcgc ggtaatgcca ttactttgcc    6900
tgtatgtggt cgggatgtga agtttactct tgaagtgctc cggggtgata tgttgagaa    6960 gacctctcgg gtatggtcag gtaatgaacg tgaccaggag ctgcttactg aggacgcact    7020
ggatgatctc atcccttctt ttctactgac tggtcaacag acaccggcgt tcggtcgaag    7080
```

```
agtatctggt gtcatagaaa ttgccgatgg gagtcgccgt cgtaaagctg ctgcacttac    7140
cgaaagtgat tatcgtgttc tggttggcga gctggatgat gagcagatgg ctgcattatc    7200
cagattgggt aacgattatc gcccaacaag tgcttatgaa cgtggtcagc gttatgcaag    7260
ccgattgcag aatgaatttg ctggaaatat ttctgcgctg gctgatgcgg aaaatatttc    7320
acgtaagatt attacccgct gtatcaacac cgccaaattg cctaaatcag ttgttgctct    7380
tttttctcac cccggtgaac tatctgcccg gtcaggtgat gcacttcaaa agcctttac     7440
agataaagag gaattactta agcagcaggc atctaacctt catgagcaga aaaagctgg     7500
ggtgatattt gaagctgaag aagttatcac tcttttaact tctgtgctta aaacgtcatc    7560
tgcatcaaga actagtttaa gctcacgaca tcagtttgct cctggagcga cagtattgta    7620
taagggcgat aaaatggtgc ttaacctgga caggtctcgt gttccaactg agtgtataga    7680
gaaaattgag gccattctta aggaacttga aaagccagca ccctgatgcg accacgtttt    7740
agtctacgtt tatctgtctt tacttaatgt cctttgttac aggccagaaa gcataactgg    7800
cctgaatatt ctctctgggc ccactgttcc acttgtatcg tcggtctgat aatcagactg    7860
ggaccacgt cccactcgta tcgtcggtct gattattagt ctgggaccac ggtcccactc     7920
gtatcgtcgg tctgattatt agtctgggac cacggtccca ctcgtatcgt cggtctgata    7980
atcagactgg gaccacggtc ccactcgtat cgtcggtctg attattagtc tgggaccatg    8040
gtcccactcg tatcgtcggt ctgattatta gtctgggacc acggtcccac tcgtatcgtc    8100
ggtctgatta ttagtctgga accacggtcc cactcgtatc gtcggtctga ttattagtct    8160
gggaccacgg tcccactcgt atcgtcggtc tgattattag tctgggacca cgatcccact    8220
cgtgttgtcg gtctgattat cggtctggga ccacggtccc acttgtattg tcgatcagac    8280
tatcagcgtg agactacgat tccatcaatg cctgtcaagg gcaagtattg acatgtcgtc    8340
gtaacctgta gaacggagta acctcggtgt gcggttgtat gcctgctgtg gattgctgct    8400
gtgtcctgct tatccacaac attttgcgca cggttatgtg gacaaaatac ctggttaccc    8460
aggccgtgcc ggcacgttaa ccgggctgca tccgatgcaa gtgtgtcgct gtcgacgagc    8520
tcgcgagctc ggacatgagg ttgccccgta ttcagtgtcg ctgatttgta ttgtctgaag    8580
ttgtttttac gttaagttga tgcagatcaa ttaatacgat acctgcgtca taattgatta    8640
tttgacgtgg tttgatggcc tccacgcacg ttgtgatatg tagatgataa tcattatcac    8700
tttacgggtc ctttccggtg atccgacagg ttacggggcg gcgacctcgc gggttttcgc    8760
tatttatgaa aattttccgg tttaaggcgt ttccgttctt cttcgtcata acttaatgtt    8820
tttatttaaa ataccctctg aaaagaaagg aaacgacagg tgctgaaagc gagcttttg     8880
gcctctgtcg tttcctttct ctgttttgt ccgtggaatg aacaatggaa gtccgagctc     8940
atcgctaata acttcgtata gcatacatta tacgaagtta tattcgat               8988
```

<210> SEQ ID NO 66  
<211> LENGTH: 31  
<212> TYPE: DNA  
<213> ORGANISM: Artificial  
<220> FEATURE:  
<223> OTHER INFORMATION: primer for amplifying kanamycin resistance marker vector pLybAA1

<400> SEQUENCE: 66
gtcagtgcac tgctctgcca gtgttacaac c                               31

<210> SEQ ID NO 67  
<211> LENGTH: 38

```
<212> TYPE: DNA
<213> ORGANISM: Artificial
<220> FEATURE:
<223> OTHER INFORMATION: primer for amplifying kanamycin resistance
      marker vector pLybAA1

<400> SEQUENCE: 67
ctcagtggcg ccaaaactca cgttaaggga ttttggtc                         38

<210> SEQ ID NO 68
<211> LENGTH: 950
<212> TYPE: DNA
<213> ORGANISM: Artificial
<220> FEATURE:
<223> OTHER INFORMATION: kanamycin resistance marker from vector
      pLybAA1, originally derived from pACYC177

<400> SEQUENCE: 68
gtcagtgcac tgctctgcca gtgttacaac caattaacca attctgatta gaaaaactca     60
tcgagcatca aatgaaactg caatttattc atatcaggat tatcaatacc atatttttga    120
aaaagccgtt tctgtaatga aggagaaaac tcaccgaggc agttccatag gatggcaaga    180
tcctggtatc ggtctgcgat tccgactcgt ccaacatcaa taacctat taatttcccc     240 tcgtcaaaaa taaggttatc aagtgagaaa tcaccatgag tgacgactga atccggtgag    300
aatggcaaaa gcttatgcat ttctttccag acttgttcaa caggccagcc attacgctcg    360
tcatcaaaat cactcgcatc aaccaaaccg ttattcattc gtgattgcgc ctgagcgaga    420
cgaaatacgc gatcgctgtt aaaaggacaa ttacaaacag gaatcgaatg caaccggcgc    480
aggaacactg ccagcgcatc aacaatattt tcacctgaat caggatattc ttctaatacc    540
tggaatgctg ttttcccggg gatcgcagtg gtgagtaacc atgcatcatc aggagtacgg    600
ataaaatgct tgatggtcgg aagaggcata aattccgtca gccagtttag tctgaccatc    660
tcatctgtaa catcattggc aacgctacct ttgccatgtt tcagaaacaa ctctggcgca    720
tcgggcttcc catacaatcg atagattgtc gcacctgatt gcccgacatt atcgcgagcc    780
catttatacc catataaatc agcatccatg ttggaattta atcgcggcct cgagcaagac    840
gtttcccgtt gaatatggct cataacaccc cttgtattac tgtttatgta agcagacagt    900
tttattgttc atgaccaaaa tcccttaacg tgagttttgg cgccactgag                950

<210> SEQ ID NO 69
<211> LENGTH: 9864
<212> TYPE: DNA
<213> ORGANISM: Artificial
<220> FEATURE:
<223> OTHER INFORMATION: plasmid pLybAL8f (kanamycin resistance marker
      plus pLybAL7f)

<400> SEQUENCE: 69
gcggccgcaa ggggttcgcg tcagcggggtg ttggcgggtg tcggggctgg cttaactatg     60
cggcatcaga gcagattgta ctgagagtgc actgctctgc cagtgttaca accaattaac    120
caattctgat tagaaaaact catcgagcat caaatgaaac tgcaatttat tcatatcagg    180
attatcaata ccatattttt gaaaaagccg tttctgtaat gaaggagaaa actcaccgag    240
gcagttccat aggatggcaa gatcctggta tcggtctgcg attccgactc gtccaacatc    300
aatacaacct attaatttcc cctcgtcaaa aataaggtta tcaagtgaga aatcaccatg    360
agtgacgact gaatccggtg agaatggcaa aagcttatgc atttctttcc agacttgttc    420
aacaggccag ccattacgct cgtcatcaaa atcactcgca tcaaccaaac cgttattcat    480
```

-continued

```
tcgtgattgc gcctgagcga gacgaaatac gcgatcgctg ttaaaaggac aattacaaac    540
aggaatcgaa tgcaaccggc gcaggaacac tgccagcgca tcaacaatat tttcacctga    600
atcaggatat tcttctaata cctggaatgc tgttttcccg gggatcgcag tggtgagtaa    660
ccatgcatca tcaggagtac ggataaaatg cttgatggtc ggaagaggca taaattccgt    720
cagccagttt agtctgacca tctcatctgt aacatcattg gcaacgctac ctttgccatg    780
tttcagaaac aactctggcg catcgggctt cccatacaat cgatagattg tcgcacctga    840
ttgcccgaca ttatcgcgag cccatttata cccatataaa tcagcatcca tgttggaatt    900
taatcgcggc ctcgagcaag acgtttcccg ttgaatatgg ctcataacac cccttgtatt    960
actgtttatg taagcagaca gttttattgt tcatgaccaa aatcccttaa cgtgagtttt   1020
ggcgccattc gccattcagc tgcgcaactg ttgggaaggg cgatcggtgc gggcctcttc   1080
gctattacgc cagctggcga aggggggatg tgctgcaagg cgattaagtt gggtaacgcc   1140
agggttttcc cagtcacgac gttgtaaaac gacggccagt gaattgtaat acgactcact   1200
atagggcgaa ttcgagctcg gtacccgggg atcccactcc cgggatttgg taccttattt   1260
tgttccaaac atgcggtcac ccgcatctcc gagacctgga acaatatatc cttttcatt    1320 taattttca tctagcgccg caatgtaaat atcaacgtcc gaatgatgct tctgcaattc    1380
ttccacaccc tccggcgctg ctacaagaca catgaaacgg atattttcg caccgcgttt     1440 tttaaggctg tgaatggctt caactgcgga accgcctgta gcgagcatcg ggtcaaccac   1500
gatgaattca cgctcttcca catcagaagg aagcttgaca tagtattcca cgggttttaa   1560
ggtttctgga tcacggtaaa ggccgacatg tcccactttt gccgcaggaa tcagctttaa   1620
aatgccgtca accattccca atcctgctct gaggatagga accactccga gtttttttccc   1680 tgagatgact ttcgatttcg cagcctgaac cggtgtattg atatccactt cttccagagg   1740
aagatcgcgg gtaatttcaa atgccatgag tgtagccact tcatctacta actctctaaa   1800
atccttcgta cctgtatttt cattccgtat atatgtcagc ttgtgctgaa ttaaaggatg   1860
atcaaataca taaaccttc ccatactgtg tttcagctcc ttttttattg tcccatcaac     1920
aattacacac ttctattgat tctacaaaaa agacattga gtttcaagaa catcgtcaaa    1980
aaacccgccg ggcataagcc caagcgggtt taggatctt aataatctaa ttctttatat     2040
aaaggaaatt tatcagtcag agcagctaca cgctgtcttg cttcttgtgg gatcctctag   2100
agtcgacctg caggcatgca agcttgagta ttctatagtc tcacctaaat agcttggcgt   2160
aatcatggtc atagctgttt cctgtgtgaa attgttatcc gctcacaatt ccacacaaca   2220
tacgagccgg aagcataaag tgtaaagcct ggggtgccta atgagtgagc taactcacat   2280
taattgcgtt gcgctcactg cccgctttcc agtcgggaaa cctgtcgtgc cagctgcatt   2340
aatgaatcgg ccaacgcgaa ccccttgcgg ccgcccgggc cgtcgaccaa ttctcatgtt   2400
tgacagctta tcatcgaatt tctgccattc atccgcttat tatcacttat tcaggcgtag   2460
caaccaggcg tttaagggca ccaataactg ccttaaaaaa attacgcccc gccctgccac   2520
tcatcgcagt actgttgtaa ttcattaagc attctgccga catggaagcc atcacaaacg   2580
gcatgatgaa cctgaatcgc cagcggcatc agcaccttgt cgccttgcgt ataatatttg   2640
cccatggtga aaacggggc gaagaagttg tccatattgg ccacgtttaa atcaaaactg    2700
gtgaaactca cccagggatt ggctgagacg aaaaacatat tctcaataaa cccttagggg   2760
aaataggcca ggttttcacc gtaacacgcc acatcttgcg aatatatgtg tagaaactgc   2820
cggaaatcgt cgtggtattc actccagagc gatgaaaacg tttcagtttg ctcatggaaa   2880
```

```
acggtgtaac aagggtgaac actatcccat atcaccagct caccgtcttt cattgccata   2940
cgaaattccg gatgagcatt catcaggcgg gcaagaatgt gaataaaggc cggataaaac   3000
ttgtgcttat ttttctttac ggtctttaaa aaggccgtaa tatccagctg aacggtctgg   3060
ttataggtac attgagcaac tgactgaaat gcctcaaaat gttctttacg atgccattgg   3120
gatatatcaa cggtggtata tccagtgatt tttttctcca ttttagcttc cttagctcct   3180
gaaaatctcg ataactcaaa aaatacgccc ggtagtgatc ttatttcatt atggtgaaag   3240
ttggaacctc ttacgtgccg atcaacgtct cattttcgcc aaaagttggc ccagggcttc   3300
ccggtatcaa cagggacacc aggatttatt tattctgcga agtgatcttc cgtcacaggt   3360
atttattcgc gataagctca tggagcggcg taaccgtcgc acaggaagga cagagaaagc   3420
gcggatctgg gaagtgacgg acagaacggt caggacctgg attggggagg cggttgccgc   3480
cgctgctgct gacggtgtga cgttctctgt tccggtcaca ccacatacgt tccgccattc   3540
ctatgcgatg cacatgctgt atgccggtat accgctgaaa gttctgcaaa gcctgatggg   3600
acataagtcc atcagttcaa cggaagtcta cacgaaggtt tttgcgctgg atgtggctgc   3660
ccggcaccgg gtgcagtttg cgatgccgga gtctgatgcg gttgcgatgc tgaaacaatt   3720
atcctgagaa taaatgcctt ggcctttata tggaaatgtg gaactgagtg gatatgctgt   3780
ttttgtctgt taaacagaga agctggctgt tatccactga gaagcgaacg aaacagtcgg   3840
gaaaatctcc cattatcgta gagatccgca ttattaatct caggagcctg tgtagcgttt   3900
ataggaagta tgttctgtc atgatgcctg caagcggtaa cgaaaacgat ttgaatatgc   3960
cttcaggaac aatagaaatc ttcgtgcggt gttacgttga agtggagcgg attatgtcag   4020
caatggacag aacaacctaa tgaacacaga accatgatgt ggtctgtcct tttacagcca   4080
gtagtgctcg ccgcagtcga gcgacagggc gaagccctcg gctggttgcc ctcgccgctg   4140
ggctggcggc cgtctatggc cctgcaaacg cgccagaaac gccgtcgaag ccgtgtgcga   4200
gacaccgcgg ccggccgccg gcgttgtgga tacctcgcgg aaaacttggc cctcactgac   4260
agatgagggg cggacgttga cacttgaggg gccgactcac ccggcgcggc gttgacagat   4320
gaggggcagg ctcgatttcg gccggcgacg tggagctggc cagcctcgca aatcggcgaa   4380
aacgcctgat tttacgcgag ttccccacag atgatgtgga caagcctggg gataagtgcc   4440
ctgcggtatt gacacttgag gggcgcgact actgacagat gaggggcgcg atccttgaca   4500
cttgagggc agagtgctga cagatgaggg gcgcacctat tgacatttga ggggctgtcc   4560
acaggcagaa aatccagcat ttgcaagggt ttccgcccgt ttttcggcca ccgctaacct   4620
gtcttttaac ctgcttttaa accaatattt ataaaccttg tttttaacca gggctgcgcc   4680
ctgtgcgcgt gaccgcgcac gccgaagggg ggtgcccccc cttctcgaac cctcccggtc   4740
gagtgagcga ggaagcacca gggaacagca cttatatatt ctgcttacac acgatgcctg   4800
aaaaaacttc ccttggggtt atccactat ccacggggga attttataa ttattttttt   4860
tatagttttt agatcttctt ttttagagcg ccttgtaggc ctttatccat gctggttcta   4920
gagaaggtgt tgtgacaaat tgcccttca gtgtgacaaa tcaccctcaa atgacagtcc   4980
tgtctgtgac aaattgccct taaccctgtg acaaattgcc ctcagaagaa gctgtttttt   5040
cacaaagtta tccctgctta ttgactcttt tttatttagt gtgacaatct aaaaacttgt   5100
cacacttcac atggatctgt catggcggaa acagcggtta tcaatcacaa gaaacgtaaa   5160
aatagcccgc gaatcgtcca gtcaaacgac tcactgaggg cggcatatag tctctcccgg   5220
gatcaaaaac gtatgctgta tctgttcgtt gaccagatca gaaaatctga tggcaccta   5280
```

```
caggaacatg acggtatctg cgagatccat gttgctaaat atgctgaaat attcggattg   5340
acctctgcgg aagccagtaa ggatatacgg caggcattga agagtttcgc ggggaaggaa   5400
gtggtttttt atcgccctga agaggatgcc ggcgatgaaa aaggctatga atctttcct    5460
tggtttatca aacgtgcgca cagtccatcc agagggcttt acagtgtaca tatcaaccca   5520
tatctcattc ccttctttat cgggttacag aaccggttta cgcagtttcg cttagtgaa    5580
acaaaagaaa tcaccaatcc gtatgccatg cgtttatacg aatccctgtg tcagtatcgt   5640
aagccggatg gctcaggcat cgtctctctg aaaatcgact ggatcataga gcgttaccag   5700
ctgcctcaaa gttaccagcg tatgcctgac ttccgccgcc gcttcctgca ggtctgtgtt   5760
aatgagatca acagcagaac tccaatgcgc ctctcataca ttgagaaaaa gaaaggccgc   5820
cagacgactc atatcgtatt ttccttccgc gatatcactt ccatgacgac aggatagtct   5880
gagggttatc tgtcacagat ttgagggtgg ttcgtcacat ttgttctgac ctactgaggg   5940
taatttgtca cagttttgct gtttccttca gcctgcatgg atttctcat acttttgaa     6000
ctgtaatttt taaggaagcc aaatttgagg gcagtttgtc acagttgatt ccttctctt    6060
tcccttcgtc atgtgacctg atatcgggg ttagttcgtc atcattgatg agggttgatt    6120
atcacagttt attactctga attggctatc cgcgtgtgta cctctacctg gagtttttcc   6180
cacggtggat atttcttctt gcgctgagcg taagagctat ctgacagaac agttcttctt   6240
tgcttcctcg ccagttcgct cgctatgctc ggttacacgg ctgcggcgag cgctagtgat   6300
aataagtgac tgaggtatgt gctcttctta tctccttttg tagtgttgct cttatttaa    6360
acaactttgc ggttttttga tgactttgcg attttgttgt tgctttgcag taaattgcaa   6420
gatttaataa aaaacgcaaa agcaatgatt aaaggatgtt cagaatgaaa ctcatggaaa   6480
cacttaacca gtgcataaac gctggtcatg aaatgacgaa ggctatcgcc attgcacagt   6540
ttaatgatga cagcccggaa gcgaggaaaa taacccggcg ctggagaata ggtgaagcag   6600
cggatttagt tggggtttct tctcaggcta tcagagatgc cgagaaagca gggcgactac   6660
cgcacccgga tatggaaatt cgaggacggg ttgagcaacg tgttggttat acaattgaac   6720
aaattaatca tatgcgtgat gtgtttggta cgcgattgcg acgtgctgaa gacgtatttc   6780
caccggtgat cggggttgct gcccataaag gtggcgttta caaaacctca gtttctgttc   6840
atcttgctca ggatctggct ctgaaggggc tacgtgtttt gctcgtggaa ggtaacgacc   6900
cccagggaac agcctcaatg tatcacggat gggtaccaga tcttcatatt catgcagaag   6960
acactctcct gcctttctat cttggggaaa aggacgatgt cacttatgca ataaagccca   7020
cttgctggcc ggggcttgac attattcctt cctgtctggc tctgcaccgt attgaaactg   7080
agttaatggg caaatttgat gaaggtaaac tgcccaccga tccacacctg atgctccgac   7140
tggccattga aactgttgct catgactatg atgtcatagt tattgacagc gcgcctaacc   7200
tgggtatcgg cacgattaat gtcgtatgtg ctgctgatgt gctgattgtt cccacgcctg   7260
ctgagttgtt tgactacacc tccgcactgc agttttcga tatgcttcgt gatctgctca   7320
agaacgttga tcttaaaggg ttcgagcctg atgtacgtat tttgcttacc aaatacagca   7380
atagtaatgg ctctcagtcc ccgtggatgg aggagcaaat tcgggatgcc tggggaagca   7440
tggttctaaa aaatgttgta cgtgaaacgg atgaagttgg taaaggtcag atccggatga   7500
gaactgtttt tgaacaggcc attgatcaac gctcttcaac tggtgcctgg agaaatgctc   7560
tttctatttg ggaacctgtc tgcaatgaaa ttttcgatcg tctgattaaa ccacgctggg   7620
agattagata atgaagcgtg cgcctgttat tccaaaacat acgctcaata ctcaaccggt   7680
```

```
tgaagatact tcgttatcga caccagctgc cccgatggtg gattcgttaa ttgcgcgcgt   7740
aggagtaatg gctcgcggta atgccattac tttgcctgta tgtggtcggg atgtgaagtt   7800
tactcttgaa gtgctccggg gtgatagtgt tgagaagacc tctcgggtat ggtcaggtaa   7860
tgaacgtgac caggagctgc ttactgagga cgcactggat gatctcatcc cttcttttct   7920
actgactggt caacagacac cggcgttcgg tcgaagagta tctggtgtca tagaaattgc   7980
cgatgggagt cgccgtcgta aagctgctgc acttaccgaa agtgattatc gtgttctggt   8040
tggcgagctg gatgatgagc agatggctgc attatccaga ttgggtaacg attatcgccc   8100
aacaagtgct tatgaacgtg gtcagcgtta tgcaagccga ttgcagaatg aatttgctgg   8160
aaatatttct gcgctggctg atgcggaaaa tatttcacgt aagattatta cccgctgtat   8220
caacaccgcc aaattgccta atcagttgt tgctcttttt tctcaccccg gtgaactatc   8280
tgcccggtca ggtgatgcac ttcaaaaagc ctttacagat aaagaggaat tacttaagca   8340
gcaggcatct aaccttcatg agcagaaaaa agctgggtg atatttgaag ctgaagaagt   8400
tatcactctt ttaacttctg tgcttaaaac gtcatctgca tcaagaacta gtttaagctc   8460
acgacatcag tttgctcctg gagcgacagt attgtataag ggcgataaaa tggtgcttaa   8520
cctggacagg tctcgtgttc caactgagtg tatagagaaa attgaggcca ttcttaagga   8580
acttgaaaag ccagcaccct gatgcgacca cgttttagtc tacgtttatc tgtctttact   8640
taatgtcctt tgttacaggc cagaaagcat aactggcctg aatattctct ctgggcccac   8700
tgttccactt gtatcgtcgg tctgataatc agactgggac cacggtccca ctcgtatcgt   8760
cggtctgatt attagtctgg gaccacggtc ccactcgtat cgtcggtctg attattagtc   8820
tgggaccacg gtcccactcg tatcgtcggt ctgataatca gactgggacc acggtcccac   8880
tcgtatcgtc ggtctgatta ttagtctggg accatggtcc cactcgtatc gtcggtctga   8940
ttattagtct gggaccacgg tcccactcgt atcgtcggtc tgattattag tctggaacca   9000
cggtcccact cgtatcgtcg gtctgattat tagtctggga ccacggtccc actcgtatcg   9060
tcggtctgat tattagtctg gaccacgat cccactcgtg ttgtcggtct gattatcggt   9120
ctgggaccac ggtcccactt gtattgtcga tcagactatc agcgtgagac tacgattcca   9180
tcaatgcctg tcaagggcaa gtattgacat gtcgtcgtaa cctgtagaac ggagtaacct   9240
cggtgtgcgg ttgtatgcct gctgtggatt gctgctgtgt cctgcttatc cacaacattt   9300
tgcgcacggt tatgtggaca aaatacctgg ttacccaggc cgtgccggca cgttaaccgg   9360
gctgcatccg atgcaagtgt gtcgctgtcg acgagctcgc gagctcggac atgaggttgc   9420
cccgtattca gtgtcgctga tttgtattgt ctgaagttgt ttttacgtta agttgatgca   9480
gatcaattaa tacgatacct gcgtcataat tgattatttg acgtggtttg atggcctcca   9540
cgcacgttgt gatatgtaga tgataatcat tatcacttta cgggtccttt ccggtgatcc   9600
gacaggttac gggcggcga cctcgcgggt tttcgctatt tatgaaaatt ttccggttta   9660
aggcgtttcc gttcttcttc gtcataactt aatgttttta tttaaaatac cctctgaaaa   9720
gaaaggaaac gacaggtgct gaaagcgagc ttttttggcct ctgtcgtttc ctttctctgt   9780
ttttgtccgt ggaatgaaca atggaagtcc gagctcatcg ctaataactt cgtatagcat   9840
acattatacg aagttatatt cgat                                         9864
```

<210> SEQ ID NO 70
<211> LENGTH: 1470
<212> TYPE: DNA
<213> ORGANISM: Synechocystis PCC6803

-continued

```
<400> SEQUENCE: 70
atgaaatccc cccaggctca acaaatccta gaccaggccc gccgtttgct ctacgaaaaa      60
gccatggtca aaatcaatgg gcaatacgtg gggacggtgg cggccattcc ccaatcggat     120
caccatgatt tgaactatac ggaagttttc attcgggaca atgtgccggt gatgatcttc     180
ttgttactgc aaaatgaaac ggaaattgtc caaaactttt tggaaatttg cctcacccctc    240
caaagtaagg gctttcccac ctacggcatt tttcccacta gttttgtgga aacgaaaaac     300
catgaactca aggcagacta tggccaacgg gcgatcggtc gagtttgctc ggtggatgcg     360
tccctctggt ggcctatttt ggcctattac tacgtgcaaa gaaccggcaa tgaagcctgg     420
gctagacaaa cccatgtgca attggggcta caaaagtttt taaacctcat tctccatcca     480
gtctttcggg atgcacccac tttgtttgtg cccgacgggg cctttatgat tgaccgcccc     540
atggatgtgt ggggagcgcc gttggaaatc caaaccctgc tctacggagc cctgaaaagt     600
gcggcgggt tactgttaat cgacctcaag gcgaagggt attgcagcaa taaagaccat       660
ccttttgaca gcttcacgat ggagcagagt catcaattta acctgagtgt ggattggctc     720
aaaaaactcc gcacctatct gctcaagcat tattggatta attgcaatat tgtccaagct     780
ctccgccgcc gtcccacgga acagtacggt gaagaagcca gcaacgaaca taatgtccac     840
acagaaacca ttcccaactg gctccaggat tggctcggcg atcggggagg ctatttaatc     900
ggcaatatcc gcacgggtcg ccccgatttt cgcttttttct ccctgggtaa ttgcttgggg    960
gcaattttcg atgtcactag cttggcccag caacgttcct ttttccgttt ggtattaaat    1020
aatcagcggg agttatgtgc ccaaatgccc ctgaggattt gccatccccc cctcaaagat    1080
gacgattggc gcagtaaaac cggctttgac cgcaaaaatt taccctggtg ctaccacaac    1140
gccggccatt ggccctgttt attttggttt ctggtggtgg cggtgctccg ccatagctgc    1200
cattccaact acggcacggt ggagtatgcg gaaatgggga acctaattcg caataactat    1260
gaggtgcttt tgcgccgttt gcccaagcat aaatgggctg aatattttga tggccccacg    1320
ggctttgggg tcgggcaaca atcccgttcc taccaaacct ggaccattgt gggcctattg    1380
ctagtacacc atttcacaga gttaacccc gacgatgctt tgatgttcga tttgcctagt    1440
ttgaaaagtt tgcatcaagc gctgcattaa                                     1470

<210> SEQ ID NO 71
<211> LENGTH: 489
<212> TYPE: PRT
<213> ORGANISM: Synechocystis PCC6803

<400> SEQUENCE: 71

Met Lys Ser Pro Gln Ala Gln Gln Ile Leu Asp Gln Ala Arg Arg Leu
1               5                   10                  15

Leu Tyr Glu Lys Ala Met Val Lys Ile Asn Gly Gln Tyr Val Gly Thr
            20                  25                  30

Val Ala Ala Ile Pro Gln Ser Asp His His Asp Leu Asn Tyr Thr Glu
        35                  40                  45

Val Phe Ile Arg Asp Asn Val Pro Val Met Ile Phe Leu Leu Leu Gln
    50                  55                  60

Asn Glu Thr Glu Ile Val Gln Asn Phe Leu Glu Ile Cys Leu Thr Leu
65                  70                  75                  80

Gln Ser Lys Gly Phe Pro Thr Tyr Gly Ile Phe Pro Thr Ser Phe Val
                85                  90                  95

Glu Thr Glu Asn His Glu Leu Lys Ala Asp Tyr Gly Gln Arg Ala Ile
            100                 105                 110
```

Gly Arg Val Cys Ser Val Asp Ala Ser Leu Trp Trp Pro Ile Leu Ala
            115                 120                 125

Tyr Tyr Tyr Val Gln Arg Thr Gly Asn Glu Ala Trp Ala Arg Gln Thr
        130                 135                 140

His Val Gln Leu Gly Leu Gln Lys Phe Leu Asn Leu Ile Leu His Pro
145                 150                 155                 160

Val Phe Arg Asp Ala Pro Thr Leu Phe Val Pro Asp Gly Ala Phe Met
                165                 170                 175

Ile Asp Arg Pro Met Asp Val Trp Gly Ala Pro Leu Glu Ile Gln Thr
            180                 185                 190

Leu Leu Tyr Gly Ala Leu Lys Ser Ala Gly Leu Leu Leu Ile Asp
        195                 200                 205

Leu Lys Ala Lys Gly Tyr Cys Ser Asn Lys Asp His Pro Phe Asp Ser
210                 215                 220

Phe Thr Met Glu Gln Ser His Gln Phe Asn Leu Ser Val Asp Trp Leu
225                 230                 235                 240

Lys Lys Leu Arg Thr Tyr Leu Leu Lys His Tyr Trp Ile Asn Cys Asn
                245                 250                 255

Ile Val Gln Ala Leu Arg Arg Pro Thr Glu Gln Tyr Gly Glu Glu
            260                 265                 270

Ala Ser Asn Glu His Asn Val His Thr Glu Thr Ile Pro Asn Trp Leu
        275                 280                 285

Gln Asp Trp Leu Gly Asp Arg Gly Gly Tyr Leu Ile Gly Asn Ile Arg
    290                 295                 300

Thr Gly Arg Pro Asp Phe Arg Phe Phe Ser Leu Gly Asn Cys Leu Gly
305                 310                 315                 320

Ala Ile Phe Asp Val Thr Ser Leu Ala Gln Gln Arg Ser Phe Phe Arg
                325                 330                 335

Leu Val Leu Asn Asn Gln Arg Glu Leu Cys Ala Gln Met Pro Leu Arg
            340                 345                 350

Ile Cys His Pro Pro Leu Lys Asp Asp Asp Trp Arg Ser Lys Thr Gly
        355                 360                 365

Phe Asp Arg Lys Asn Leu Pro Trp Cys Tyr His Asn Ala Gly His Trp
    370                 375                 380

Pro Cys Leu Phe Trp Phe Leu Val Val Ala Val Leu Arg His Ser Cys
385                 390                 395                 400

His Ser Asn Tyr Gly Thr Val Glu Tyr Ala Glu Met Gly Asn Leu Ile
                405                 410                 415

Arg Asn Asn Tyr Glu Val Leu Leu Arg Arg Leu Pro Lys His Lys Trp
            420                 425                 430

Ala Glu Tyr Phe Asp Gly Pro Thr Gly Phe Trp Val Gly Gln Gln Ser
        435                 440                 445

Arg Ser Tyr Gln Thr Trp Thr Ile Val Gly Leu Leu Leu Val His His
    450                 455                 460

Phe Thr Glu Val Asn Pro Asp Asp Ala Leu Met Phe Asp Leu Pro Ser
465                 470                 475                 480

Leu Lys Ser Leu His Gln Ala Leu His
                485

<210> SEQ ID NO 72
<211> LENGTH: 1392
<212> TYPE: DNA
<213> ORGANISM: Synechococcus PCC7942

<400> SEQUENCE: 72

-continued

```
atgcccgatt ctgttgtgct gcccgctacg ctgcagaccg cgctgcaaac agcggagcag    60
ttactttggg atcgggcctt ggttcgctat cacgatcagt gggcgggggc gatcgcggca   120
ctgcctgaag atcaggagtt ggcggcagcg aactaccgcg aaatctttat tcgcgacaac   180
gtgccggtga tgctctacct gctgttgcag ggcaaaactg acgttgtccg cgacttcttg   240
caactgtcgc tttctctcca gagccaggca ctgcaaacct atggcattct gccgaccagt   300
ttcgtctgtg aggaaaccca ctgcgttgct gactatggtc agcgggcgat cgggcgggtg   360
gtttctgctg accctagcct tggtggccgt gtgctgctac aggcctatcg gcgggcctcc   420
catgatgatg cctttgtcca cagtccgact gttcagcagg ggttacagcg gttgctggct   480
ttcctgctgc gtccggtttt caaccaaaac ccactgctcg aggtgcccga tggggccttc   540
atggtcgatc gtcccttgga tgtggcgggc gcacctttag aaattcaagt cctgctctac   600
ggggcactgc gggcttgtgg gcagttgctg caatacaccg aagcggccaa tgctgcccat   660
gtgcaagccc gtcgcctgcg gcagtatctc tgctggcact actgggtgac gcccgatcgc   720
ctgcgacgct ggcagcagtg gcccaccgaa gaatttggcg atcgcagcca taaccCctac   780
aacattcagc cgatcgccat ccctgactgg gttgaacctt ggctgggtga gtcgggtggc   840
tacttcctag gaacatacg ggcaggacgt cctgacttcc gcttttttag ccttggcaat   900
tgctggcga tcgttttcga tgtgcttccg ctcaatcagc agggtgcgat ctgcgcttg   960
atttgcaga acgaagccca gattttgggc caagtgccgt tgcggctctg ctatcccgct  1020
ttaaccggat cggcgtggaa atcctgacgg gttgcgatc ctaaaaatca gccttggtcc  1080
tatcacaacg gtggtagttg gccatccctg ctttggtatc tcagtgcggc ggtcttgcac  1140
taccaacagc ggggaggcga tcgcaatctc tgtcaggtct ggctgaataa gcttcagcac  1200
taccacactc agcagtgcga gcaactccct ggcgatgagt ggccagagta ctacgagggt  1260
caggactcgg tccagattgc tactcgcgcc tgccgttatc agacttggac gtttacggga  1320
ttgctgctga atcacgcact gctctcgcag ccccagggca ttcaactgct gagtctgcgg  1380
ggcttaccct aa                                                     1392
```

<210> SEQ ID NO 73
<211> LENGTH: 463
<212> TYPE: PRT
<213> ORGANISM: Synechococcus PCC7942

<400> SEQUENCE: 73

```
Met Pro Asp Ser Val Val Leu Pro Ala Thr Leu Gln Thr Ala Leu Gln
1               5                  10                  15

Thr Ala Glu Gln Leu Leu Trp Asp Arg Ala Leu Val Arg Tyr His Asp
            20                  25                  30

Gln Trp Ala Gly Ala Ile Ala Ala Leu Pro Glu Asp Gln Glu Leu Ala
        35                  40                  45

Ala Ala Asn Tyr Arg Glu Ile Phe Ile Arg Asp Asn Val Pro Val Met
    50                  55                  60

Leu Tyr Leu Leu Leu Gln Gly Lys Thr Asp Val Val Arg Asp Phe Leu
65                  70                  75                  80

Gln Leu Ser Leu Ser Leu Gln Ser Gln Ala Leu Gln Thr Tyr Gly Ile
                85                  90                  95

Leu Pro Thr Ser Phe Val Cys Glu Glu Thr His Cys Val Ala Asp Tyr
            100                 105                 110

Gly Gln Arg Ala Ile Gly Arg Val Val Ser Ala Asp Pro Ser Leu Trp
        115                 120                 125
```

Trp Pro Val Leu Leu Gln Ala Tyr Arg Arg Ala Ser His Asp Asp Ala
    130                 135                 140

Phe Val His Ser Pro Thr Val Gln Gln Gly Leu Gln Arg Leu Leu Ala
145                 150                 155                 160

Phe Leu Leu Arg Pro Val Phe Asn Gln Asn Pro Leu Leu Glu Val Pro
                165                 170                 175

Asp Gly Ala Phe Met Val Asp Arg Pro Leu Asp Val Ala Gly Ala Pro
            180                 185                 190

Leu Glu Ile Gln Val Leu Leu Tyr Gly Ala Leu Arg Ala Cys Gly Gln
        195                 200                 205

Leu Leu Gln Tyr Thr Glu Ala Ala Asn Ala Ala His Val Gln Ala Arg
    210                 215                 220

Arg Leu Arg Gln Tyr Leu Cys Trp His Tyr Trp Val Thr Pro Asp Arg
225                 230                 235                 240

Leu Arg Arg Trp Gln Gln Trp Pro Thr Glu Glu Phe Gly Asp Arg Ser
                245                 250                 255

His Asn Pro Tyr Asn Ile Gln Pro Ile Ala Ile Pro Asp Trp Val Glu
            260                 265                 270

Pro Trp Leu Gly Glu Ser Gly Gly Tyr Phe Leu Gly Asn Ile Arg Ala
        275                 280                 285

Gly Arg Pro Asp Phe Arg Phe Phe Ser Leu Gly Asn Leu Leu Ala Ile
    290                 295                 300

Val Phe Asp Val Leu Pro Leu Asn Gln Gln Gly Ala Ile Leu Arg Leu
305                 310                 315                 320

Ile Leu Gln Asn Glu Ala Gln Ile Leu Gly Gln Val Pro Leu Arg Leu
                325                 330                 335

Cys Tyr Pro Ala Leu Thr Gly Ser Ala Trp Lys Ile Leu Thr Gly Cys
            340                 345                 350

Asp Pro Lys Asn Gln Pro Trp Ser Tyr His Asn Gly Gly Ser Trp Pro
        355                 360                 365

Ser Leu Leu Trp Tyr Leu Ser Ala Ala Val Leu His Tyr Gln Gln Arg
    370                 375                 380

Gly Gly Asp Arg Asn Leu Cys Gln Val Trp Leu Asn Lys Leu Gln His
385                 390                 395                 400

Tyr His Thr Gln Gln Cys Glu Gln Leu Pro Gly Asp Glu Trp Pro Glu
                405                 410                 415

Tyr Tyr Glu Gly Gln Asp Ser Val Gln Ile Ala Thr Arg Ala Cys Arg
            420                 425                 430

Tyr Gln Thr Trp Thr Phe Thr Gly Leu Leu Leu Asn His Ala Leu Leu
        435                 440                 445

Ser Gln Pro Gln Gly Ile Gln Leu Leu Ser Leu Arg Gly Leu Pro
    450                 455                 460

<210> SEQ ID NO 74
<211> LENGTH: 966
<212> TYPE: DNA
<213> ORGANISM: Synechocystis PCC6803

<400> SEQUENCE: 74
atgattaatt gtcaattttg ttccgttatt tccaaatcta acggggaaga tcctatcggc      60
acagcaaatt caagtgatcg ttggttaatt atggaattac cccaaccttg dacagaggaa    120
cgctttcatc atgaccccat tcttaaacca attcatgatc tttttcatca actttctgat    180
caaggagtta aagtatctcc aatggcgatc gcctcagatc acgagtattc tcaatcagga    240

-continued

```
tttagtcgta ttattcacta ccaaaagttt aatttgctct tttccagttt tataaaagaa    300
gaatatttag ttcctgatga tcaaaggtgg gatcttatca aaaatttatg ttatcaatct    360
ccagagttag aaaattttcg taactataaa ctgtcagatg ttgttgatcg agatatgatg    420
gtatgtactc atgaaacat tgatgtggct tgttcgagat ttggttatcc tatttataaa     480
caattacgac aaaaatatgc atcaaaaaat ttaagaatat ggcgctgctc tcattttggg    540
ggacatcagt ttgctccgac tttaattgat tttccaaatg gcaagtttg gggacatctt     600
gagtctgaag ttttagataa tctggtaagg caagaaggtc aagttaaaca actttataaa    660
ttttatcgag gttgggtagg cgtaacaaaa tttgcccaga ttgttgagcg tgaaatttgg    720
actcaacgag gttggcaatg gttaaattat caaaaatcag ctcaaatatt gaacatggat    780
gataatcagc atgatcccaa ttgggtagag gttcaatttg attttatttc tcccgataaa    840
gttaaaggag cttatttttgc aagagttgaa gtcaatgggt cagtgatgac tgctagaaat    900
tcaggagatg aacttatttc tgtcaagcag tatagtgtca gctacttaaa agaaattgat    960
aaataa                                                               966
```

<210> SEQ ID NO 75
<211> LENGTH: 321
<212> TYPE: PRT
<213> ORGANISM: Synechocystis PCC6803

<400> SEQUENCE: 75

```
Met Ile Asn Cys Gln Phe Cys Ser Val Ile Ser Lys Ser Asn Gly Glu
1               5                   10                  15

Asp Pro Ile Gly Thr Ala Asn Ser Ser Asp Arg Trp Leu Ile Met Glu
            20                  25                  30

Leu Pro Gln Pro Trp Thr Glu Glu Arg Phe His His Asp Pro Ile Leu
        35                  40                  45

Lys Pro Ile His Asp Leu Phe His Gln Leu Ser Asp Gln Gly Val Lys
    50                  55                  60

Val Ser Pro Met Ala Ile Ala Ser Asp His Glu Tyr Ser Gln Ser Gly
65                  70                  75                  80

Phe Ser Arg Ile Ile His Tyr Gln Lys Phe Asn Leu Leu Phe Ser Ser
                85                  90                  95

Phe Ile Lys Glu Glu Tyr Leu Val Pro Asp Asp Gln Arg Trp Asp Leu
            100                 105                 110

Ile Lys Asn Leu Cys Tyr Gln Ser Pro Glu Leu Glu Asn Phe Arg Asn
        115                 120                 125

Tyr Lys Leu Ser Asp Val Val Asp Arg Asp Met Met Val Cys Thr His
    130                 135                 140

Gly Asn Ile Asp Val Ala Cys Ser Arg Phe Gly Tyr Pro Ile Tyr Lys
145                 150                 155                 160

Gln Leu Arg Gln Lys Tyr Ala Ser Lys Asn Leu Arg Ile Trp Arg Cys
                165                 170                 175

Ser His Phe Gly Gly His Gln Phe Ala Pro Thr Leu Ile Asp Phe Pro
            180                 185                 190

Asn Gly Gln Val Trp Gly His Leu Glu Ser Glu Val Leu Asp Asn Leu
        195                 200                 205

Val Arg Gln Glu Gly Gln Val Lys Gln Leu Tyr Lys Phe Tyr Arg Gly
    210                 215                 220

Trp Val Gly Val Thr Lys Phe Ala Gln Ile Val Glu Arg Glu Ile Trp
225                 230                 235                 240

Thr Gln Arg Gly Trp Gln Trp Leu Asn Tyr Gln Lys Ser Ala Gln Ile
```

```
                        245                 250                 255
Leu Asn Met Asp Asp Asn Gln His Asp Pro Asn Trp Val Glu Val Gln
                260                 265                 270

Phe Asp Phe Ile Ser Pro Asp Lys Val Lys Gly Ala Tyr Phe Ala Arg
            275                 280                 285

Val Glu Val Asn Gly Ser Val Met Thr Ala Arg Asn Ser Gly Asp Glu
        290                 295                 300

Leu Ile Ser Val Lys Gln Tyr Ser Val Ser Tyr Leu Lys Glu Ile Asp
305                 310                 315                 320

Lys

<210> SEQ ID NO 76
<211> LENGTH: 1425
<212> TYPE: DNA
<213> ORGANISM: Escherichia coli

<400> SEQUENCE: 76
atgagtcgtt tagtcgtagt atctaaccgg attgcaccac cagacgagca cgccgccagt      60
gccggtggcc ttgccgttgg catactgggg gcactgaaag ccgcaggcgg actgtggttt     120
ggctggagtg gtgaaacagg gaatgaggat cagccgctaa aaaaggtgaa aaaaggtaac     180
attacgtggg cctcttttaa cctcagcgaa caggaccttg acgaatacta caaccaattc     240
tccaatgccg ttctctggcc cgcttttcat tatcggctcg atctggtgca atttcagcgt     300
cctgcctggg acggctatct acgcgtaaat gcgttgctgg cagataaatt actgccgctg     360
ttgcaagacg atgacattat ctggatccac gattatcacc tgttgccatt tgcgcatgaa     420
ttacgcaaac ggggagtgaa taatcgcatt ggtttctttc tgcatattcc tttcccgaca     480
ccggaaatct tcaacgcgct gccgacatat gacaccttgc ttgaacagct tgtgattat      540 gatttgctgg tttccagac agaaaacgat cgtctggcgt tcctggattg tctttctaac     600
ctgacccgcg tcacgacacg tagcgcaaaa agccatacag cctggggcaa agcatttcga     660
acagaagtct acccgatcgg cattgaaccg aaagaaatag ccaaacaggc tgccgggcca     720
ctgccgccaa actggcgca acttaaagcg gaactgaaaa acgtacaaaa tatcttttct     780
gtcgaacggc tggattattc caaaggtttg ccagagcgtt ttctcgccta tgaagcgttg     840
ctggaaaaat atccgcagca tcatggtaaa attcgttata cccagattgc accaacgtcg     900
cgtggtgatg tgcaagccta tcaggatatt cgtcatcagc tcgaaaatga agctggacga     960
attaatggta aatacgggca attaggctgg acgccgcttt attatttgaa tcagcatttt    1020
gaccgtaaat tactgatgaa aatattccgc tactctgacg tgggcttagt gacgccactg    1080
cgtgacggga tgaacctggt agcaaaagag tatgttgctg ctcaggaccc agccaatccg    1140
ggcgttcttg ttctttcgca atttgcggga gcggcaaacg agttaacgtc ggcgttaatt    1200
gttaacccct acgatcgtga cgaagttgca gctgcgctgg atcgtgcatt gactatgtcg    1260
ctggcggaac gtatttcccg tcatgcagaa atgctggacg ttatcgtgaa aaacgatatt    1320
aaccactggc aggagtgctt cattagcgac ctaaagcaga tagttccgcg aagcgcggaa    1380
agccagcagc gcgataaagt tgctacccttt ccaaagcttg cgtag                   1425

<210> SEQ ID NO 77
<211> LENGTH: 474
<212> TYPE: PRT
<213> ORGANISM: Escherichia coli

<400> SEQUENCE: 77
```

-continued

```
Met Ser Arg Leu Val Val Ser Asn Arg Ile Ala Pro Pro Asp Glu
1               5                   10                  15

His Ala Ala Ser Ala Gly Gly Leu Ala Val Gly Ile Leu Gly Ala Leu
            20                  25                  30

Lys Ala Ala Gly Gly Leu Trp Phe Gly Trp Ser Gly Glu Thr Gly Asn
        35                  40                  45

Glu Asp Gln Pro Leu Lys Lys Val Lys Lys Gly Asn Ile Thr Trp Ala
    50                  55                  60

Ser Phe Asn Leu Ser Glu Gln Asp Leu Asp Glu Tyr Tyr Asn Gln Phe
65                  70                  75                  80

Ser Asn Ala Val Leu Trp Pro Ala Phe His Tyr Arg Leu Asp Leu Val
                85                  90                  95

Gln Phe Gln Arg Pro Ala Trp Asp Gly Tyr Leu Arg Val Asn Ala Leu
            100                 105                 110

Leu Ala Asp Lys Leu Leu Pro Leu Leu Gln Asp Asp Ile Ile Trp
        115                 120                 125

Ile His Asp Tyr His Leu Leu Pro Phe Ala His Glu Leu Arg Lys Arg
    130                 135                 140

Gly Val Asn Asn Arg Ile Gly Phe Phe Leu His Ile Pro Phe Pro Thr
145                 150                 155                 160

Pro Glu Ile Phe Asn Ala Leu Pro Thr Tyr Asp Thr Leu Leu Glu Gln
                165                 170                 175

Leu Cys Asp Tyr Asp Leu Leu Gly Phe Gln Thr Glu Asn Asp Arg Leu
            180                 185                 190

Ala Phe Leu Asp Cys Leu Ser Asn Leu Thr Arg Val Thr Thr Arg Ser
        195                 200                 205

Ala Lys Ser His Thr Ala Trp Gly Lys Ala Phe Arg Thr Glu Val Tyr
    210                 215                 220

Pro Ile Gly Ile Glu Pro Lys Glu Ile Ala Lys Gln Ala Ala Gly Pro
225                 230                 235                 240

Leu Pro Pro Lys Leu Ala Gln Leu Lys Ala Glu Leu Lys Asn Val Gln
                245                 250                 255

Asn Ile Phe Ser Val Glu Arg Leu Asp Tyr Ser Lys Gly Leu Pro Glu
            260                 265                 270

Arg Phe Leu Ala Tyr Glu Ala Leu Leu Glu Lys Tyr Pro Gln His His
        275                 280                 285

Gly Lys Ile Arg Tyr Thr Gln Ile Ala Pro Thr Ser Arg Gly Asp Val
    290                 295                 300

Gln Ala Tyr Gln Asp Ile Arg His Gln Leu Asn Glu Ala Gly Arg
305                 310                 315                 320

Ile Asn Gly Lys Tyr Gly Gln Leu Gly Trp Thr Pro Leu Tyr Tyr Leu
            325                 330                 335

Asn Gln His Phe Asp Arg Lys Leu Leu Met Lys Ile Phe Arg Tyr Ser
        340                 345                 350

Asp Val Gly Leu Val Thr Pro Leu Arg Asp Gly Met Asn Leu Val Ala
    355                 360                 365

Lys Glu Tyr Val Ala Ala Gln Asp Pro Ala Asn Pro Gly Val Leu Val
    370                 375                 380

Leu Ser Gln Phe Ala Gly Ala Ala Asn Glu Leu Thr Ser Ala Leu Ile
385                 390                 395                 400

Val Asn Pro Tyr Asp Arg Asp Glu Val Ala Ala Leu Asp Arg Ala
            405                 410                 415

Leu Thr Met Ser Leu Ala Glu Arg Ile Ser Arg His Ala Glu Met Leu
        420                 425                 430
```

```
Asp Val Ile Val Lys Asn Asp Ile Asn His Trp Gln Glu Cys Phe Ile
        435                 440                 445

Ser Asp Leu Lys Gln Ile Val Pro Arg Ser Ala Glu Ser Gln Gln Arg
        450                 455                 460

Asp Lys Val Ala Thr Phe Pro Lys Leu Ala
465                 470
```

<210> SEQ ID NO 78
<211> LENGTH: 746
<212> TYPE: DNA
<213> ORGANISM: Escherichia coli

<400> SEQUENCE: 78

```
atgatcttga tggaacgctg gcggaaatca aaccgcatcc cgatcaggtc gtcgtgcctg      60
acaatattct gcaaggacta cagctactgg caaccgcaag tgatggtgca ttggcattga     120
tatcagggcg ctcaatggtg gagcttgacg cactggcaaa accttatcgc ttcccgttag     180
cgggcgtgca tggggcggag cgccgtgaca tcaatggtaa acacatatc gttcatctgc      240
cggatgcgat tgcgcgtgat attagcgtgc aactgcatac agtcatcgct cagtatcccg     300
gcgcggagct ggaggcgaaa gggatggctt ttgcgctgca ttatcgtcag gctccgcagc     360
atgaagacgc attaatgaca ttagcgcaac gtattactca gatctggcca caaatggcgt     420
tacagcaggg aaagtgtgtt gtcgagatca aaccgagagg taccagtaaa ggtgaggcaa     480
ttgcagcttt tatgcaggaa gctcccttta tcgggcgaac gcccgtatt ctgggcgatg      540
atttaaccga tgaatctggc ttcgcagtcg ttaaccgact gggcggaatg tcagtaaaaa     600
ttggcacagg tgcaactcag gcatcatggc gactggcggg tgtgccggat gtctggagct     660
ggcttgaaat gataaccacc gcattacaac aaaaaagaga aaataacagg agtgatgact     720
atgagtcgtt tagtcgtagt atctaa                                          746
```

<210> SEQ ID NO 79
<211> LENGTH: 266
<212> TYPE: PRT
<213> ORGANISM: Escherichia coli

<400> SEQUENCE: 79

```
Met Thr Glu Pro Leu Thr Glu Thr Pro Glu Leu Ser Ala Lys Tyr Ala
1               5                   10                  15

Trp Phe Phe Asp Leu Asp Gly Thr Leu Ala Glu Ile Lys Pro His Pro
            20                  25                  30

Asp Gln Val Val Val Pro Asp Asn Ile Leu Gln Gly Leu Gln Leu Leu
        35                  40                  45

Ala Thr Ala Ser Asp Gly Ala Leu Ala Leu Ile Ser Gly Arg Ser Met
    50                  55                  60

Val Glu Leu Asp Ala Leu Ala Lys Pro Tyr Arg Phe Pro Leu Ala Gly
65                  70                  75                  80

Val His Gly Ala Glu Arg Arg Asp Ile Asn Gly Lys Thr His Ile Val
                85                  90                  95

His Leu Pro Asp Ala Ile Ala Arg Asp Ile Ser Val Gln Leu His Thr
            100                 105                 110

Val Ile Ala Gln Tyr Pro Gly Ala Glu Leu Glu Ala Lys Gly Met Ala
        115                 120                 125

Phe Ala Leu His Tyr Arg Gln Ala Pro Gln His Glu Asp Ala Leu Met
    130                 135                 140

Thr Leu Ala Gln Arg Ile Thr Gln Ile Trp Pro Gln Met Ala Leu Gln
```

```
                145                 150                 155                 160
            Gln Gly Lys Cys Val Val Glu Ile Lys Pro Arg Gly Thr Ser Lys Gly
                            165                 170                 175
            Glu Ala Ile Ala Ala Phe Met Gln Glu Ala Pro Phe Ile Gly Arg Thr
                            180                 185                 190
            Pro Val Phe Leu Gly Asp Asp Leu Thr Asp Glu Ser Gly Phe Ala Val
                            195                 200                 205
            Val Asn Arg Leu Gly Gly Met Ser Val Lys Ile Gly Thr Gly Ala Thr
                            210                 215                 220
            Gln Ala Ser Trp Arg Leu Ala Gly Val Pro Asp Val Trp Ser Trp Leu
            225                 230                 235                 240
            Glu Met Ile Thr Thr Ala Leu Gln Gln Lys Arg Glu Asn Asn Arg Ser
                            245                 250                 255
            Asp Asp Tyr Glu Ser Phe Ser Arg Ser Ile
                            260                 265
```

<210> SEQ ID NO 80
<211> LENGTH: 1500
<212> TYPE: DNA
<213> ORGANISM: Synechocystis PCC6803

<400> SEQUENCE: 80

| | | | | | |
|---|---|---|---|---|---|
| atgaattcat | cccttgtgat | cctttaccac | cgtgagccct | acgacgaagt | tagggaaaat | 60 |
| ggcaaaacgg | tgtatcgaga | gaaaaagagt | cccaacggga | ttttgcccac | cctcaaaagt | 120 |
| ttttttgccg | atgcggaaca | gagcacctgg | gtcgcatgga | aacaggtttc | gccgaagcaa | 180 |
| aaggatgatt | ttcaggcgga | tatgtccatt | gaaggccttg | gcgatcgttg | tacggtgcgc | 240 |
| cgggtgcccc | tgacggcgga | gcaggtaaaa | aacttctatc | acatcacttc | caaggaagcc | 300 |
| ttttggccca | ttctccactc | tttcccctgg | cagttcacct | acgattcttc | tgattgggat | 360 |
| aattttcagc | acattaaccg | cttatttgcc | gaggcggcct | gtgccgatgc | cgatgacaat | 420 |
| gcattgtttt | gggtccacga | ctataaccctc | tggttagcgc | ccctttacat | tcgtcagctc | 480 |
| aagcccaacg | ccaagattgc | cttttttccac | cacaccccct | tccccagcgt | tgatattttc | 540 |
| aatattttgc | cctggcggga | ggcgatcgta | gaaagcttgc | tggcctgtga | tctctgtggt | 600 |
| tttcatattc | cccgctacgt | agaaaatttt | gtcgccgtgg | cccgtagtct | caagccggtg | 660 |
| gaaatcacca | gacgggttgt | ggtagaccaa | gcctttaccc | cctacggtac | ggccctggcg | 720 |
| gaaccggaac | tcaccaccca | gttgcgttat | ggcgatcgcc | tcattaacct | cgatgcgttt | 780 |
| cccgtgggca | ccaatccggc | aaatatccgg | gcgatcgtgg | ccaaagaaag | tgtgcaacaa | 840 |
| aaagttgctg | aaattaaaca | agatttaggc | ggtaagaggc | taattgtttc | cgctgggcgg | 900 |
| gtggattacg | tgaagggcac | caaggaaatg | ttgatgtgct | atgaacgtct | actggagcgt | 960 |
| cgcccccgaat | tgcaggggga | aattagcctg | gtagtccccg | tagccaaggc | cgctgaggga | 1020 |
| atgcgtattt | atcgcaacgc | ccaaaacgaa | attgaacgac | tggcagggaa | aattaacggt | 1080 |
| cgctttgcca | aactgtcctg | gacaccagtg | atgctgttca | cctctccttt | agcctatgag | 1140 |
| gagctcattg | ccctgttctg | tgccgccgac | attgcctgga | tcactcccct | gcgggatggg | 1200 |
| ctaaacctgg | tggctaagga | gtatgtggtg | gctaaaaatg | gcgaagaagg | agttctgatc | 1260 |
| ctctcggaat | ttgccggttg | tgcggtgaaa | ctacccgatg | cggtgttgac | taaccccctac | 1320 |
| gcttccagcc | gtatggacga | atccattgac | caggccctgg | ccatggacaa | agacgaacag | 1380 |
| aaaaaacgca | tggggagaat | gtacgccgcc | attaagcgtt | acgacgttca | acaatgggcc | 1440 |
| aatcacctac | tgcgggaagc | ctacgccgat | gtggtactgg | gagagccccc | ccaaatgtag | 1500 |

<210> SEQ ID NO 81
<211> LENGTH: 499
<212> TYPE: PRT
<213> ORGANISM: Synechocystis PCC6803

<400> SEQUENCE: 81

Met Asn Ser Ser Leu Val Ile Leu Tyr His Arg Glu Pro Tyr Asp Glu
1               5                   10                  15

Val Arg Glu Asn Gly Lys Thr Val Tyr Arg Glu Lys Ser Pro Asn
            20                  25                  30

Gly Ile Leu Pro Thr Leu Lys Ser Phe Phe Ala Asp Ala Glu Gln Ser
        35                  40                  45

Thr Trp Val Ala Trp Lys Gln Val Ser Pro Lys Gln Lys Asp Asp Phe
    50                  55                  60

Gln Ala Asp Met Ser Ile Glu Gly Leu Gly Asp Arg Cys Thr Val Arg
65                  70                  75                  80

Arg Val Pro Leu Thr Ala Glu Gln Val Lys Asn Phe Tyr His Ile Thr
                85                  90                  95

Ser Lys Glu Ala Phe Trp Pro Ile Leu His Ser Phe Pro Trp Gln Phe
            100                 105                 110

Thr Tyr Asp Ser Ser Asp Trp Asp Asn Phe Gln His Ile Asn Arg Leu
        115                 120                 125

Phe Ala Glu Ala Ala Cys Ala Asp Ala Asp Asp Asn Ala Leu Phe Trp
130                 135                 140

Val His Asp Tyr Asn Leu Trp Leu Ala Pro Leu Tyr Ile Arg Gln Leu
145                 150                 155                 160

Lys Pro Asn Ala Lys Ile Ala Phe Phe His His Thr Pro Phe Pro Ser
                165                 170                 175

Val Asp Ile Phe Asn Ile Leu Pro Trp Arg Glu Ala Ile Val Glu Ser
            180                 185                 190

Leu Leu Ala Cys Asp Leu Cys Gly Phe His Ile Pro Arg Tyr Val Glu
        195                 200                 205

Asn Phe Val Ala Val Ala Arg Ser Leu Lys Pro Val Glu Ile Thr Arg
    210                 215                 220

Arg Val Val Asp Gln Ala Phe Thr Pro Tyr Gly Thr Ala Leu Ala
225                 230                 235                 240

Glu Pro Glu Leu Thr Thr Gln Leu Arg Tyr Gly Asp Arg Leu Ile Asn
                245                 250                 255

Leu Asp Ala Phe Pro Val Gly Thr Asn Pro Ala Asn Ile Arg Ala Ile
            260                 265                 270

Val Ala Lys Glu Ser Val Gln Gln Lys Val Ala Glu Ile Lys Gln Asp
        275                 280                 285

Leu Gly Gly Lys Arg Leu Ile Val Ser Ala Gly Arg Val Asp Tyr Val
    290                 295                 300

Lys Gly Thr Lys Glu Met Leu Met Cys Tyr Glu Arg Leu Leu Glu Arg
305                 310                 315                 320

Arg Pro Glu Leu Gln Gly Glu Ile Ser Leu Val Val Pro Val Ala Lys
                325                 330                 335

Ala Ala Glu Gly Met Arg Ile Tyr Arg Asn Ala Gln Asn Glu Ile Glu
            340                 345                 350

Arg Leu Ala Gly Lys Ile Asn Gly Arg Phe Ala Lys Leu Ser Trp Thr
        355                 360                 365

Pro Val Met Leu Phe Thr Ser Pro Leu Ala Tyr Glu Glu Leu Ile Ala
    370                 375                 380

```
Leu Phe Cys Ala Ala Asp Ile Ala Trp Ile Thr Pro Leu Arg Asp Gly
385                 390                 395                 400

Leu Asn Leu Val Ala Lys Glu Tyr Val Val Ala Lys Asn Gly Glu Glu
            405                 410                 415

Gly Val Leu Ile Leu Ser Glu Phe Ala Gly Cys Ala Val Glu Leu Pro
            420                 425                 430

Asp Ala Val Leu Thr Asn Pro Tyr Ala Ser Ser Arg Met Asp Glu Ser
            435                 440                 445

Ile Asp Gln Ala Leu Ala Met Asp Lys Asp Glu Gln Lys Lys Arg Met
450                 455                 460

Gly Arg Met Tyr Ala Ala Ile Lys Arg Tyr Asp Val Gln Gln Trp Ala
465                 470                 475                 480

Asn His Leu Leu Arg Glu Ala Tyr Ala Asp Val Val Leu Gly Glu Pro
            485                 490                 495

Pro Gln Met

<210> SEQ ID NO 82
<211> LENGTH: 1269
<212> TYPE: DNA
<213> ORGANISM: Synechocystis PCC6803

<400> SEQUENCE: 82
atggtattac accaacaacg tttctccctc gaccatggag cttttgtca aaccttagcc      60 caaactgaaa atttactcat tgtccaagac ttggatgggg tctgcatgga attagtgcaa    120
gatcccctca gtcgccgcct ggatgccgat tatgtccggg ccaccaccct gtttgctgaa    180 cattttacg tgttgaccaa tggggagcac gtgggaaaaa gaggagtaca gggcattgtg     240
gaacaatcct ttggggatgc ttcctttgtg caacaggaag gcctatattt gcccggtttg    300
gcggccgggg gagtgcagtg gcaggatcgc catggcaaag taagtcatcc tggagtgggg    360
caaacggagc tggagttttt agcggcggtg cccgaaaaaa tcactaattg tttaaaaacc    420
ttttttggcg atcgcccca ttccctatcc ccagagcaat tacaaacggg cattgaagct     480
tcggttttag ataatgtggc ttcccccacc gccaatttaa ataccttggc caatctgtta    540
caagactttc cgcaaattta ccgagatttg caggaaacca tggctcaatt attggatcag    600 ttgatggcg aagccgttgc ccagggttg gggaatagtt ttttgtcca ctatgctccc       660 aatttaggta gggatgaacg aggtaaggaa attattcgtt gggccaaagc tggggattcc    720
ggcaccaccg atttcaatt tatgttgcgg ggtgggttca aagaagccgg ggttttggct    780
ttgctaaatc gttactatca caatcggaca gggcaatatc ctctgggaga aagttttagt    840
gctcgccaag cgcccccatc ccaccaggac ttgttgcatt tggtgaaagc gcaatttgat    900
ccggccttga tgccgctgat cattggagtt ggggatacgg tcaccagtca ggtggatgaa    960
gctaccgggg aaattcgacg tggcgggagc gatcgccaat ttttgcaatt aatccaagat   1020
tggggggatt ggggaaatca cggtaactta gtggtgtatg tggacagttc ccaggggag    1080 gtgaaaaatc gccaacctct acaactagaa accgtggcgg gcaaaccca gtggtggct    1140 ggccctgggg atatgcggga cagggaagag ccattgaaga tcaatgtggc ttttcctggt    1200
ggccatgacc aatatgtagc ggcgtttaag caggcggccc agcgccgaag agtccattt    1260 tcccagtag                                                            1269

<210> SEQ ID NO 83
<211> LENGTH: 422
<212> TYPE: PRT
```

-continued

<213> ORGANISM: Synechocystis PCC6803

<400> SEQUENCE: 83

```
Met Val Leu His Gln Gln Arg Phe Ser Leu Asp His Gly Ala Phe Cys
1               5                   10                  15

Gln Thr Leu Ala Gln Thr Glu Asn Leu Leu Ile Val Gln Asp Leu Asp
            20                  25                  30

Gly Val Cys Met Glu Leu Val Gln Asp Pro Leu Ser Arg Arg Leu Asp
        35                  40                  45

Ala Asp Tyr Val Arg Ala Thr Thr Leu Phe Ala Glu His Phe Tyr Val
    50                  55                  60

Leu Thr Asn Gly Glu His Val Gly Lys Arg Gly Val Gln Gly Ile Val
65                  70                  75                  80

Glu Gln Ser Phe Gly Asp Ala Ser Phe Val Gln Gln Glu Gly Leu Tyr
                85                  90                  95

Leu Pro Gly Leu Ala Ala Gly Gly Val Gln Trp Gln Asp Arg His Gly
            100                 105                 110

Lys Val Ser His Pro Gly Val Gly Gln Thr Glu Leu Glu Phe Leu Ala
        115                 120                 125

Ala Val Pro Glu Lys Ile Thr Asn Cys Leu Lys Thr Phe Phe Gly Asp
    130                 135                 140

Arg Pro His Ser Leu Ser Pro Glu Gln Leu Gln Thr Gly Ile Glu Ala
145                 150                 155                 160

Ser Val Leu Asp Asn Val Ala Ser Pro Thr Ala Asn Leu Asn Thr Leu
                165                 170                 175

Ala Asn Leu Leu Gln Asp Phe Pro Gln Ile Tyr Arg Asp Leu Gln Glu
            180                 185                 190

Thr Met Ala Gln Leu Leu Asp Gln Leu Met Ala Glu Ala Val Ala Gln
        195                 200                 205

Gly Leu Gly Asn Ser Phe Phe Val His Tyr Ala Pro Asn Leu Gly Arg
    210                 215                 220

Asp Glu Arg Gly Lys Glu Ile Ile Arg Trp Ala Lys Ala Gly Asp Ser
225                 230                 235                 240

Gly Thr Thr Asp Phe Gln Phe Met Leu Arg Gly Gly Val Lys Glu Ala
                245                 250                 255

Gly Val Leu Ala Leu Leu Asn Arg Tyr Tyr His Asn Arg Thr Gly Gln
            260                 265                 270

Tyr Pro Leu Gly Glu Ser Phe Ser Ala Arg Gln Ala Pro Ser His
        275                 280                 285

Gln Asp Leu Leu His Leu Val Lys Ala Gln Phe Asp Pro Ala Leu Met
    290                 295                 300

Pro Leu Ile Ile Gly Val Gly Asp Thr Val Thr Ser Gln Val Asp Glu
305                 310                 315                 320

Ala Thr Gly Glu Ile Arg Arg Gly Gly Ser Asp Arg Gln Phe Leu Gln
                325                 330                 335

Leu Ile Gln Asp Leu Gly Asp Trp Gly Asn His Gly Asn Leu Val Val
            340                 345                 350

Tyr Val Asp Ser Ser Gln Gly Glu Val Lys Asn Arg Gln Pro Leu Gln
        355                 360                 365

Leu Glu Thr Val Ala Gly Gln Thr Gln Val Ala Gly Pro Gly Asp
    370                 375                 380

Met Arg Asp Arg Glu Glu Pro Leu Lys Ile Asn Val Ala Phe Pro Gly
385                 390                 395                 400

Gly His Asp Gln Tyr Val Ala Ala Phe Lys Gln Ala Ala Gln Arg Arg
```

Arg Val His Phe Ser Gln
        420

<210> SEQ ID NO 84
<211> LENGTH: 1365
<212> TYPE: DNA
<213> ORGANISM: Agrobacterium tumefaciens

<400> SEQUENCE: 84

```
ttggaaaaat taccaagat gggacccatg acaaccacga gcgaaactga acgctatccg      60
cggatagctc tcatatcgac gcatggctat gtcgccgcac acccgcccct gggcgctgcc     120
gataccgggg ggcaggtggt ttatgtgctt gagcttgcac gaaaaactcgg ccaactcggt    180
tataccgtcg atctttacac ccgacgcttc gaagaccagc cggaattcga cgaggtcgat    240
gagcgcgtcc gtgtggtgcg cattccctgc ggcgggcgcg atttcattcc caaggaatat    300
ctgcaccggc acctgatgga atggtgcgag aacgcgctac gcttcatcaa aaaaaacgac    360
ctcaattact ccttcatcaa cagccactac tgggatgccg cgtggccgg gcagcggctc     420
tccgaagcac tgaaaatccc ccatctgcac acgccgcact cgctcggcat ctggaagaag    480
cgccagatgg agaccgatta tccggaaaag gccgatacgt tcgagcttga gttcaacttc    540
aaggagcgca tccagcacga gctgatcatc tatcgcagct gcgacatggt gatcgccacc    600
acgccggtgc agctggacgt gctgatcgaa gattatggcc tgaagcgcaa acatatccac    660
atgatcccgc cggggttatga cgacaaccgc ttcttccccg tctcggatgc gacgcgtcag    720
atgatccggc agcgtttcgg ttttgaaggc aaagtggtgc tggcactcgg tcggctcgcc    780
accaacaagg gctacgacct gctgatcgac ggcttttccg tgcttgccga gcgcgagccg    840
gaagcccgcc tgcatctggc cgtcggcggc gagaatatgg acgagcagga aaccaccatt    900
ctcaaccagc tgaaggagcg ggtgaaatcg ctcgggctgg aagacaaggt ggctttctct    960
ggttatgtcg cggacgagga tttgccggat atctatcggg ctgccgatct cttcgtgctt   1020
tccagccgct acgagccctt cggcatgacc gccatcgagg ccatggcgag cggcacgccg   1080
accgtcgtca ccatccatgg cgggctgttc cgcgccatca gctatgggcg acatgcgctg   1140
tttgccgatc ctttcgacaa ggaagatctc ggcattacca tgatgaagcc gttcaagcat   1200
gaacggctct acgggcggct ttcgcgcatg ggagcccaca aggcacgcag cctgttcaca   1260
tggaccggaa ttgcccagca acttctcgcg ctcgtggaag caggaccat gatgccggtt    1320
ctggaagaag ccgactgggc cgaaccatgg aatgacggcg attga                   1365
```

<210> SEQ ID NO 85
<211> LENGTH: 454
<212> TYPE: PRT
<213> ORGANISM: Agrobacterium tumefaciens

<400> SEQUENCE: 85

Met Glu Lys Phe Thr Lys Met Gly Pro Met Thr Thr Thr Ser Glu Thr
1               5                   10                  15

Glu Arg Tyr Pro Arg Ile Ala Leu Ile Ser Thr His Gly Tyr Val Ala
            20                  25                  30

Ala His Pro Pro Leu Gly Ala Ala Asp Thr Gly Gly Gln Val Val Tyr
        35                  40                  45

Val Leu Glu Leu Ala Arg Lys Leu Gly Gln Leu Gly Tyr Thr Val Asp
    50                  55                  60

Leu Tyr Thr Arg Arg Phe Glu Asp Gln Pro Glu Phe Asp Glu Val Asp

```
            65                  70                  75                  80
Glu Arg Val Arg Val Val Arg Ile Pro Cys Gly Gly Arg Asp Phe Ile
                    85                  90                  95

Pro Lys Glu Tyr Leu His Arg His Leu Met Glu Trp Cys Glu Asn Ala
                100                 105                 110

Leu Arg Phe Ile Lys Lys Asn Asp Leu Asn Tyr Ser Phe Ile Asn Ser
                115                 120                 125

His Tyr Trp Asp Ala Gly Val Ala Gly Gln Arg Leu Ser Glu Ala Leu
            130                 135                 140

Lys Ile Pro His Leu His Thr Pro His Ser Leu Gly Ile Trp Lys Lys
145                 150                 155                 160

Arg Gln Met Glu Thr Asp Tyr Pro Glu Lys Ala Asp Thr Phe Glu Leu
                165                 170                 175

Glu Phe Asn Phe Lys Glu Arg Ile Gln His Glu Leu Ile Ile Tyr Arg
                180                 185                 190

Ser Cys Asp Met Val Ile Ala Thr Thr Pro Val Gln Leu Asp Val Leu
                195                 200                 205

Ile Glu Asp Tyr Gly Leu Lys Arg Lys His Ile His Met Ile Pro Pro
            210                 215                 220

Gly Tyr Asp Asp Asn Arg Phe Phe Pro Val Ser Asp Ala Thr Arg Gln
225                 230                 235                 240

Met Ile Arg Gln Arg Phe Gly Phe Glu Gly Lys Val Val Leu Ala Leu
                245                 250                 255

Gly Arg Leu Ala Thr Asn Lys Gly Tyr Asp Leu Leu Ile Asp Gly Phe
                260                 265                 270

Ser Val Leu Ala Glu Arg Glu Pro Glu Ala Arg Leu His Leu Ala Val
                275                 280                 285

Gly Gly Glu Asn Met Asp Glu Gln Glu Thr Thr Ile Leu Asn Gln Leu
            290                 295                 300

Lys Glu Arg Val Lys Ser Leu Gly Leu Glu Asp Lys Val Ala Phe Ser
305                 310                 315                 320

Gly Tyr Val Ala Asp Glu Asp Leu Pro Asp Ile Tyr Arg Ala Ala Asp
                325                 330                 335

Leu Phe Val Leu Ser Ser Arg Tyr Glu Pro Phe Gly Met Thr Ala Ile
                340                 345                 350

Glu Ala Met Ala Ser Gly Thr Pro Thr Val Val Thr Ile His Gly Gly
                355                 360                 365

Leu Phe Arg Ala Ile Ser Tyr Gly Arg His Ala Leu Phe Ala Asp Pro
            370                 375                 380

Phe Asp Lys Glu Asp Leu Gly Ile Thr Met Met Lys Pro Phe Lys His
385                 390                 395                 400

Glu Arg Leu Tyr Gly Arg Leu Ser Arg Met Gly Ala His Lys Ala Arg
                405                 410                 415

Ser Leu Phe Thr Trp Thr Gly Ile Ala Gln Gln Leu Leu Ala Leu Val
                420                 425                 430

Glu Gly Arg Thr Met Met Pro Val Leu Glu Glu Ala Asp Trp Ala Glu
            435                 440                 445

Pro Trp Asn Asp Gly Asp
        450

<210> SEQ ID NO 86
<211> LENGTH: 747
<212> TYPE: DNA
<213> ORGANISM: Agrobacterium tumefaciens
```

<400> SEQUENCE: 86

```
ttgaaaccgc ttcgtcttct ttccaccgat cttgacggaa ccgtcgtcgg cgataatgac      60
gccacgcggc ggttccgcga tttctggcac gcactgccgg atgatcttcg cccggttctg     120
gtcttcaaca gcggccggtt gatcgacgat cagcttgccc ttttggaaga ggtgccgctg     180
ccgcagccgg actacatcat cggcggtgtc ggcaccatgc tgcatgcaaa aaaacgcagc     240
gaactggaaa ccgcctatac acagtcgctc ggcaccggtt ttgacccgcg gaagattgcc     300
gatgtcatga accgcattgc gggcgtgacg atgcaggagg agcgttatca gcacggcctg     360
aaatcgagct ggttcctgca tgacgccgat gccgccgcgc tcggcgagat cgaggccgcg     420
cttctggccg ccgatattga cgctcgtatc gtttattcca gcgatcgcga cctcgacata     480
ttgccgaagg ccgccgacaa aggcgcggca cttgcatggt tgtgtggaca attgcgcatc     540
ggcctcgacg aatcagtggt ctcgggtgat actggcaatg accgtgcgat gtttgagttg     600
aagactatcc gcggcgtgat cgtgggcaat gccctgcctg agcttgtctc gctggcgcat     660
caggacaatc gcttttttca ctcgaccgcg aaagaagcgg atggcgtgat cgaaggcctg     720
cggcactggg gactgaaccc ccgctaa                                          747
```

<210> SEQ ID NO 87
<211> LENGTH: 248
<212> TYPE: PRT
<213> ORGANISM: Agrobacterium tumefaciens

<400> SEQUENCE: 87

```
Met Lys Pro Leu Arg Leu Leu Ser Thr Asp Leu Asp Gly Thr Val Val
1               5                   10                  15

Gly Asp Asn Asp Ala Thr Arg Arg Phe Arg Asp Phe Trp His Ala Leu
            20                  25                  30

Pro Asp Asp Leu Arg Pro Val Leu Val Phe Asn Ser Gly Arg Leu Ile
        35                  40                  45

Asp Asp Gln Leu Ala Leu Leu Glu Glu Val Pro Leu Pro Gln Pro Asp
    50                  55                  60

Tyr Ile Ile Gly Gly Val Gly Thr Met Leu His Ala Lys Lys Arg Ser
65                  70                  75                  80

Glu Leu Glu Thr Ala Tyr Thr Gln Ser Leu Gly Thr Gly Phe Asp Pro
                85                  90                  95

Arg Lys Ile Ala Asp Val Met Asn Arg Ile Ala Gly Val Thr Met Gln
            100                 105                 110

Glu Glu Arg Tyr Gln His Gly Leu Lys Ser Ser Trp Phe Leu His Asp
        115                 120                 125

Ala Asp Ala Ala Ala Leu Gly Glu Ile Glu Ala Ala Leu Leu Ala Ala
    130                 135                 140

Asp Ile Asp Ala Arg Ile Val Tyr Ser Ser Arg Asp Leu Asp Ile
145                 150                 155                 160

Leu Pro Lys Ala Ala Asp Lys Gly Ala Ala Leu Ala Trp Leu Cys Gly
                165                 170                 175

Gln Leu Arg Ile Gly Leu Asp Glu Ser Val Ser Gly Asp Thr Gly
            180                 185                 190

Asn Asp Arg Ala Met Phe Glu Leu Lys Thr Ile Arg Gly Val Ile Val
        195                 200                 205

Gly Asn Ala Leu Pro Glu Leu Val Ser Leu Ala His Gln Asp Asn Arg
    210                 215                 220

Phe Phe His Ser Thr Ala Lys Glu Ala Asp Gly Val Ile Glu Gly Leu
225                 230                 235                 240
```

Arg His Trp Gly Leu Asn Pro Arg
             245

<210> SEQ ID NO 88
<211> LENGTH: 35
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (7)..(12)
<223> OTHER INFORMATION: BamHI restriction site

<400> SEQUENCE: 88
tctcagggat cccataccat gattaaaaaa agtac                          35

<210> SEQ ID NO 89
<211> LENGTH: 26
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (7)..(12)
<223> OTHER INFORMATION: SacI restriction site

<400> SEQUENCE: 89
ggccgtgagc tcagaaccag gtttcc                                    26

<210> SEQ ID NO 90
<211> LENGTH: 1546
<212> TYPE: DNA
<213> ORGANISM: Artificial Sequence
<220> FEATURE:
<223> OTHER INFORMATION: PCR product
<220> FEATURE:
<221> NAME/KEY: misc_feature
<222> LOCATION: (7)..(12)
<223> OTHER INFORMATION: BamHI restriction site
<220> FEATURE:
<221> NAME/KEY: misc_feature
<222> LOCATION: (1535)..(1540)
<223> OTHER INFORMATION: SacI restriction site

<400> SEQUENCE: 90
tctcagggat cccataccat gattaaaaaa agtacgcttg cccttaccct tggcttaatg    60
gccggtactc ccgccgcctt tgccgacagc aatatgtcca gcattgaggc gcgtctcgcc   120
gcgctggaac aacgtcttca ggcggctgaa cagcgcgcca gcgggcgga aacccgcgct   180 gaagccgcag agcgtcaggc acaggcgctt gccgcgcaac aaaaagcgca gccgccggtt   240
cagcctgtcg ccgcgcaacc tgcgccgcag cccgccacgc aaacggcgga taacagcggg   300
tttgaattcc acggctacgc ccgctcgggc ctgctgatga cgattccgc cgcgaaaacg   360 cagggcggcc cgtccttcac gccagcgggt gaaaccggcg gtcacgtcgg gcgtctcggc   420
aatgagccgg acacttacct tgaaatgaac ctagagcaca acagacgct cgcgaacggc   480 gccaccacgc gctttaaagt gatggtcgct gacggtcagc gcagctataa cgactggacg   540
gcctccacca gcgatctcaa cgtgcgccag gcgtttaccg aactcggcca cctgccgacc   600
ttcatcggcg cgtttaaaga tgccaccgtc tgggccggta acgcttcga tcgtgataac   660 ttcgatatcc actggattga ctccgacgtg gtgttcctcg ccggtacggg tgcgggtatc   720
tacgacatgc gctggagcga taacgcccgc agtaacttct cgctgtatgg ccgcaccttc   780

```
ggcgatatcg aaaacagcga aaacaccgcc cagaactata tccttacgct taataactac      840
gtcgggccgg tacagctgat ggtgagcggg atgcgcgcca agataacga agaccgcgtg      900 gatatcgagg gtaaccgcgt gaaaaagac gcggcggaag atggcgtgca tgcgctgctc      960
ggcctgcata acgacagctt ctacggtctg agcgacggct cctcgaaaac cgcactgctg     1020
tatggacatg gcctgggcgc ggaagtgaaa tccatcggct ccgatggcgc gctgctgccg     1080
caggccgata cctggcgtct cgcgacctac ggcatgacac cgctcggcgg cggctggcat     1140
atcgcaccgg cggtgctggc gcagagcagt aaagatcgct acgtcaaagg cgacagctac     1200
cagtgggcga ccgccaacct cgcctcatt caggagatta accagaactt tgagctgcag      1260
tatgagggca gctatcagta catggatctg cgcccgaaag gttacaacga ccgcaacgcg     1320
gtcagcggca acttctataa gctgaccttt gcgccgacgc tgaaagcggg cgacgtgggc     1380
gaattcctca gcgtcctga actgcgcctg ttcgccacct ggatggactg ggatcatcgc      1440
ctggataact acgccagcaa tgatgccttt ggcagcaccg gctttaccgc cggcggtgaa     1500
tggaacttcg gcgtacagat ggaaacctgg ttctgagctc acggcc                    1546

<210> SEQ ID NO 91
<211> LENGTH: 13332
<212> TYPE: DNA
<213> ORGANISM: Artificial Sequence
<220> FEATURE:
<223> OTHER INFORMATION: artifical plasmid pLybAL32 containing scrY

<400> SEQUENCE: 91
aggcccagtc tttcgactga gcctttcgtt ttatttgatg cctggcagtt ccctactctc       60
gcatggggag accccacact accatcggcg ctacggcgtt tcacttctga gttcggcatg      120
gggtcaggtg ggaccaccgc gctactgccg ccaggcaaat tctgttttat cagaccgctt      180
ctgcgttctg atttaatctg tatcaggctg aaaatcttct ctcatccgcc aaaacagcca      240
agcttgcatg cctgcaggtc gactctagat ggctacgagg gcagacagta agtggattta      300
ccataatccc ttaattgtac gcaccgctaa aacgcgttca gcgcgatcac ggcagcagac      360
aggtaaaaat ggcaacaaac caccctaaaa actgcgcgat cgcgcctgat aaatttttaac     420 cgtatgaata cctatgcaac cagagggtac aggccacatt accccactt aatccactga      480 agctgccatt tttcatggtt tcaccatccc agcgaaggc catgcatgca tcgaaattaa      540
tacgacgaaa ttaatacgac tcactatagg gcaattgtta tcagctatgc gccgaccaga      600
acaccttgcc gatcagccaa acgtctcttc aggccactga ctagcgataa ctttccccac      660
aacggaacaa ctctcactgc atgggatcat tgggtactgt gggtttagtg gttgtaaaaa      720
cacctgaccg ctatccctga tcagtttctt gaaggtaaac tcatcacccc caagtctggc      780
tatgcagaaa tcacctggct caacagcctg ctcagggtca acgagaatta acattccgtc      840
aggaaagctt ggcttggagc ctgttggtgc ggtcatggaa ttaccttcaa cctcaagcca      900
gaatgcagaa tcactggctt tcttggttgt gcttacccat ctctccgcat cacctttggt      960
aaaggttcta agcttaggtg agaacatccc tgcctgaaca tgagaaaaaa cagggtactc     1020
atactcactt ctaagtgacg gctgcatact aaccgcttca tacatctcgt agatttctct     1080
ggcgattgaa gggctaaatt cttcaacgct aactttgaga attttgtaa gcaatgcggc     1140 gttataagca tttaatgcat tgatgccatt aaataaagca ccaacgcctg actgccccat    1200
ccccatcttg tctgcgacag attcctggga taagccaagt tcattttttct ttttttcata   1260 aattgcttta aggcgacgtg cgtcctcaag ctgctcttgt gttaatggtt tcttttttgt     1320
```

```
gctcatacgt taaatctatc accgcaaggg ataaatatct aacaccgtgc gtgttgacta    1380 tttttacctct ggcggtgata atggttgcat cttaagaagg aggatcccat accatgatta   1440
aaaaaagtac gcttgccctt acccttggct taatggccgg tactcccgcc gcctttgccg    1500
acagcaatat gtccagcatt gaggcgcgtc tcgccgcgct ggaacaacgt cttcaggcgg    1560
ctgaacagcg cgccagcgcg gcggaaaccc gcgctgaagc cgcagagcgt caggcacagg    1620
cgcttgccgc gcaacaaaaa gcgcagccgc cggttcagcc tgtcgccgcg caacctgcgc    1680
cgcagcccgc cacgcaaacg gcggataaca gcgggtttga attccacggc tacgcccgct    1740
cgggcctgct gatgaacgat tccgccgcga aaacgcaggg cggcccgtcc ttcacgccag    1800
cgggtgaaac cggcggtcac gtcgggcgtc tcggcaatga gccggacact taccttgaaa    1860
tgaacctaga gcacaaacag acgctcgcga acggcgccac cacgcgcttt aaagtgatgg    1920
tcgctgacgg tcagcgcagc tataacgact ggacggcctc caccagcgat ctcaacgtgc    1980
gccaggcgtt taccgaactc ggccacctgc cgaccttcat cggcgcgttt aaagatgcca    2040
ccgtctgggc cggtaaacgc ttcgatcgtg ataacttcga tatccactgg attgactccg    2100
acgtggtgtt cctcgccggt acgggtgcgg gtatctacga catgcgctgg agcgataacg    2160
cccgcagtaa cttctcgctg tatggccgca ccttcggcga tatcgaaaac agcgaaaaca    2220
ccgcccagaa ctatatcctt acgcttaata actacgtcgg gccggtacag ctgatggtga    2280
gcgggatgcg cgccaaagat aacgaagacc gcgtggatat cgagggtaac cgcgtgaaaa    2340
aagacgcggc ggaagatggc gtgcatgcgc tgctcggcct gcataacgac agcttctacg    2400
gtctgagcga cggctcctcg aaaaccgcac tgctgtatgg acatggcctg ggcgcggaag    2460
tgaaatccat cggctccgat ggcgcgctgc tgccgcaggc cgatacctgg cgtctcgcga    2520
cctacggcat gacaccgctc ggcggcggct ggcatatcgc accggcggtg ctggcgcaga    2580
gcagtaaaga tcgctacgtc aaaggcgaca gctaccagtg ggcgaccgcc aacctgcgcc    2640
tcattcagga gattaaccag aactttgagc tgcagtatga gggcagctat cagtacatgg    2700
atctgcgccc gaaaggttac aacgaccgca acgcggtcag cggcaacttc tataagctga    2760
cctttgcgcc gacgctgaaa gcgggcgacg tgggcgaatt cctcaagcgt cctgaactgc    2820
gcctgttcgc cacctggatg gactgggatc atcgcctgga taactacgcc agcaatgatg    2880
cctttggcag caccggcttt accgccggcg gtgaatggaa cttcggcgta cagatggaaa    2940
cctggttctg agctcgaatt ggggcgtttt ctgtgaggct gactagcgcg tggcagctca    3000
aaatctctac attctgcaca ttcagaccca tggtctgctg cgagggcaga acttggaact    3060
ggggcgagat gccgacaccg gcgggcagac caagtacgtc ttagaactgg ctcaagccca    3120
agctaaatcc ccacaagtcc aacaagtcga catcatcacc cgccaaatca ccgaccccg     3180 cgtcagtgtt ggttacagtc aggcgatcga acccttttgcg cccaaaggtc ggattgtccg    3240
tttgcctttt ggccccaaac gctacctccg taaagagctg cttttggcccc atctctacac   3300 cttttgcggat gcaattctcc aatatctggc tcagcaaaag cgcaccccga cttggattca    3360
ggcccactat gctgatgctg gccaagtggg atcactgctg agtcgctggt tgaatgtacc    3420
gctaattttc acagggcatt ctctggggcg gatcaagcta aaaagctgt tggagcaaga     3480 ctggccgctt gaggaaattg aagcgcaatt caatattcaa cagcgaattg atgcggagga    3540
gatgacgctc actcatgctg actggattgt cgccagcact cagcaggaag tggaggagca    3600
ataccgcgtt tacgatcgct acaacccaga gcgcaagctt gtcattccac cgggtgtcga    3660
taccgatcgc ttcaggtttc agcccttggg cgatcgcggt gttgttctcc aacaggaact    3720
```

```
gagccgcttt ctgcgcgacc cagaaaaacc tcaaattctc tgcctctgtc gccccgcacc   3780
tcgcaaaaat gtaccggcgc tggtgcgagc ctttggcgaa catccttggc tgcgcaaaaa   3840
agccaacctt gtcttagtac tgggcagccg ccaagacatc aaccagatgg atcgcggcag   3900
tcggcaggtg ttccaagaga ttttccatct ggtcgatcgc tacgacctct acggcagcgt   3960
cgcctatccc aaacagcatc aggctgatga tgtgccggag ttctatcgcc tagcggctca   4020
ttccggcggg gtattcgtca atccggcgct gaccgaacct tttggtttga caattttgga   4080
ggcaggaagc tgcggcgtgc cggtggtggc aacccatgat ggcggccccc aggaaattct   4140
caaacactgt gatttcggca ctttagttga tgtcagccga cccgctaata tcgcgactgc   4200
actcgccacc ctgctgagcg atcgcgatct ttggcagtgc tatcaccgca atggcattga   4260
aaaagttccc gcccattaca gctgggatca acatgtcaat ccctgtttg agcgcatgga    4320
aacggtggct ttgcctcgtc gtcgtgctgt cagtttcgta cggagtcgca aacgcttgat   4380
tgatgccaaa cgccttgtcg ttagtgacat cgacaacaca ctgttgggcg atcgtcaagg   4440
actcgagaat ttaatgacct atctcgatca gtatcgcgat cattttgcct tggaattgc    4500
cacggggcgt cgcctagact ctgcccaaga agtcttgaaa gagtggggcg ttccttcgcc   4560
aaacttctgg gtgacttccg tcggcagcga gattcactat ggcaccgatg ctgaaccgga   4620
tatcagctgg gaaaagcata tcaatcgcaa ctggaatcct cagcgaattc gggcagtaat   4680
ggcacaacta cccttcttg aactgcagcc ggaagaggat caaacaccct tcaaagtcag    4740
cttctttgtc cgcgatcgcc acgagactgt gctgcgagaa gtacggcaac atcttcgccg   4800
ccatcgcctg cggctgaagt caatctattc ccatcaggag tttcttgaca ttctgccgct   4860
agctgcctcg aaaggggatg cgattcgcca cctctcactc cgctggcgga ttcctcttga   4920
gaacattttg gtggcaggcg attctggtaa cgatgaggaa atgctcaagg ccataatct    4980
cggcgttgta gttggcaatt actcaccgga attggagcca ctgcgcagct acgagcgcgt   5040
ctattttgct gagggccact atgctaatgg cattctggaa gccttaaaac actatcgctt   5100
ttttgaggcg atcgcttaac cttttcagaa tgagacgttg atcggcacgt aagcgtgaga   5160
cgttgatcgg cacgtaagag gttccaactt tcaccataat gaaataagat cactaccggg   5220
cgtattttt gagttatcga gattttcagg agctaaggaa gctaaatgg agaaaaaat     5280
cactggatat accaccgttg atatatccca atggcatcgt aaagaacatt ttgaggcatt   5340
tcagtcagtt gctcaatgta cctataacca gaccgttcag ctggatatta cggcctttt   5400
aaagaccgta aagaaaaata agcacaagtt ttatccggcc tttattcaca ttcttgcccg   5460
cctgatgaat gctcatccgg aattccgtat ggcaatgaaa gacggtgagc tggtgatatg   5520
ggatagtgtt caccctgtt acaccgtttt ccatgagcaa actgaaacgt ttcatcgct    5580
ctggagtgaa taccacgacg atttccggca gtttctacac atatattcgc aagatgtggc   5640
gtgttacggt gaaaacctgg cctatttccc taaagggttt attgagaata tgttttcgt    5700
ctcagccaat ccctgggtga gtttcaccag ttttgattta aacgtggcca atatggacaa   5760
cttcttcgcc cccgttttca ccatgggcaa atattatacg caaggcgaca aggtgctgat   5820
gccgctggcg attcaggttc atcatgccgt ttgtgatggc ttccatgtcg cagaatgct    5880
taatgaatta caacagtact gcgatgagtg gcagggcggg gcgtaatttt tttaaggcag   5940
ttattggtgc ccttaaacgc ctggttgcta cgcctgaata agtgataata gcggatgaa    6000
tgcagaaaat tcgatgataa gctgtcaaac acaaccacca tcaaacagga ttttcgcctg   6060
ctggggcaaa ccagcgtgga ccgcttgctg caactctctc agggccaggc ggtgaagggc   6120
```

```
aatcagctgt tgcccgtctc actggtgaaa agaaaaacca ccctggcgcc caatacgcaa    6180
accgcctctc cccgcgcgtt ggccgattca ttaatgcagc tggcacgaca ggtttcccga    6240
ctggaaagcg ggcagtgagc gcaacgcaat taatgtaagt tagcgcgaat tgcaagctgg    6300
ccgacgcgct gggctacgtc ttgctggcgt tcgggagcag aagagcatac atctggaagc    6360
aaagccagga aagcggccta tggagctgtg cggcagcgct cagtaggcaa ttttttcaaaa   6420 tattgttaag ccttttctga gcatggtatt tttcatggta ttaccaatta gcaggaaaat    6480
aagccattga atataaaaga taaaaatgtc ttgtttacaa tagagtgggg gggtcagcc     6540 tgccgccttg ggccgggtga tgtcgtactt gcccgccgcg aactcggtta ccgtccagcc    6600
cagcgcgacc agctccggca acgcctcgcg cacccgcttg cggcgcttgc gcatggtcga    6660
accactggcc tctgacggcc agacatagcc gcacaaggta tctatggaag ccttgccggt    6720
tttgccgggg tcgatccagc cacacagccg ctggtgcagc aggcgggcgg tttcgctgtc    6780
cagcgcccgc acctcgtcca tgctgatgcg cacatgctgg ccgccaccca tgacggcctg    6840
cgcgatcaag gggttcaggg ccacgtacag gcgcccgtcc gcctcgtcgc tggcgtactc    6900
cgacagcagc cgaaacccct gccgcttgcg gccattctgg gcgatgatgg ataccttcca    6960
aaggcgctcg atgcagtcct gtatgtgctt gagcgcccca ccactatcga cctctgcccc    7020
gatttccttt gccagcgccc gatagctacc tttgaccaca tggcattcag cggtgacggc    7080
ctcccacttg ggttccagga acagccggag ctgccgtccg ccttcggtct tgggttccgg    7140
gccaagcact aggccattag gcccagccat ggccaccagc ccttgcagga tgcgcagatc    7200
atcagcgccc agcggctccg ggccgctgaa ctcgatccgc ttgccgtcgc cgtagtcata    7260
cgtcacgtcc agcttgctgc gcttgcgctc gccccgcttg agggcacgga acaggccggg    7320
ggccagacag tgcgccgggt cgtgccggac gtggctgagg ctgtgcttgt tcttaggctt    7380
caccacgggg cacccccttg ctcttgcgct gcctctccag cacggcgggc ttgagcaccc    7440
cgccgtcatg ccgcctgaac caccgatcag cgaacggtgc gccatagttg gccttgctca    7500
caccgaagcg gacgaagaac cggcgctggt cgtcgtccac accccattcc tcggcctcgg    7560
cgctggtcat gctcgacagg taggactgcc agcggatgtt atcgaccagt accgagctgc    7620
cccggctggc ctgctgctgg tcgcctgcgc ccatcatggc cgcgcccttg ctggcatggt    7680
gcaggaacac gatagagcac ccggtatcgg cggcgatggc ctccatgcga ccgatgacct    7740
gggccatggg gccgctggcg ttttcttcct cgatgtggaa ccggcgcagc gtgtccagca    7800
ccatcaggcg gcgccctcg gcggcgcgct tgaggccgtc gaaccactcc ggggccatga    7860
tgttgggcag gctgccgatc agcggctgga tcagcaggcc gtcagccacg gcttgccgtt    7920
cctcggcgct gaggtgcgcc caagggcgt gcaggcggtg atgaatggcg gtgggcgggt    7980
cttcggcggg caggtagatc accgggccgg tgggcagttc gcccacctcc agcagatccg    8040
gcccgcctgc aatctgtgcg gccagttgca gggccagcat ggatttaccg gcaccaccgg    8100
gcgacaccag cgccccgacc gtaccggcca ccatgttggg caaaacgtag tccagcggtg    8160
gcggcgctgt gcgaacgcc tccagaatat tgataggctt atgggtagcc attgattgcc    8220
tcctttgcag gcagttggtg gttaggcgct ggcgggtca ctaccccgc cctgcgccgc    8280 tctgagttct tccaggcact cgcgcagcgc ctcgtattcg tcgtcggtca gccagaactt    8340
gcgctgacgc atcccttttgg ccttcatgcg ctcggcatat cgcgcttggc gtacagcgtc    8400
agggctggcc agcaggtcgc cggtctgctt gtccttttgg tctttcatat cagtcaccga    8460
gaaacttgcc ggggccgaaa ggcttgtctt cgcggaacaa ggacaaggtg cagccgtcaa    8520
```

```
ggttaaggct ggccatatca gcgactgaaa agcggccagc ctcggccttg tttgacgtat   8580
aaccaaagcc accgggcaac caatagccct tgtcactttt gatcaggtag accgaccctg   8640
aagcgctttt ttcgtattcc ataaaacccc cttctgtgcg tgagtactca tagtataaca   8700
ggcgtgagta ccaacgcaag cactacatgc tgaaatctgg cccgcccctg tccatgcctc   8760
gctggcgggg tgccggtgcc cgtgccagct cggcccgcgc aagctggacg ctgggcagac   8820
ccatgacctt gctgacggtg cgctcgatgt aatccgcttc gtggccgggc ttgcgctctg   8880
ccagcgctgg gctggcctcg gccatggcct tgccgatttc tcggcactg cggccccggc    8940 tggccagctt ctgcgcggcg ataaagtcgc acttgctgag gtcatgaccg aagcgcttga   9000
ccagcccggc catctcgctg cggtactcgt ccagcgccgt gcgccggtgg cggctaagct   9060
gccgctcggg cagttcgagg ctggccagcc tgcgggcctt ctcctgctgc cgctgggcct   9120
gctcgatctg ctggccagcc tgctgcacca gcgccgggcc agcggtggcg gtcttgccct   9180
tggattcacg cagcagcacc cacggctgat aaccggcgcg ggtggtgtgc ttgtccttgc   9240
ggttggtgaa gcccgccaag cggccatagt ggcggctgtc ggcgctggcc gggtcggcgt   9300
cgtactcgct ggccagcgtc cgggcaatct gcccccgaag ttcaccgcct gcggcgtcgg   9360
ccaccttgac ccatgcctga tagttcttcg ggctggtttc cactaccagg gcaggctccc   9420
ggccctcggc tttcatgtca tccaggtcaa actcgctgag gtcgtccacc agcaccagac   9480
catgccgctc ctgctcggcg ggcctgatat acacgtcatt gccctgggca ttcatccgct   9540
tgagccatgg cgtgttctgg agcacttcgg cggctgacca ttcccggttc atcatctggc   9600
cggtgggtgc gtccctgacg ccgatatcga agcgctcaca gcccatggcc ttgagctgtc   9660
ggcctatggc ctgcaaagtc ctgtcgttct tcatcgggcc accaagcgca gccagatcga   9720
gccgtcctcg gttgtcagtg gcgtcaggtc gagcaagagc aacgatgcga tcagcagcac   9780
caccgtaggc atcatggaag ccagcatcac ggttagccat agcttccagt gccacccccg   9840
cgacgcgctc cgggcgctct gcgcggcgct gctcacctcg gcggctacct cccgcaactc   9900
tttggccagc tccacccatg ccgcccctgt ctggcgctgg gctttcagcc actccgccgc   9960
ctgcgcctcg ctgcctgct tggtctggct catgacctgc cgggcttcgt cggccagtgt   10020
cgccatgctc tgggccagcg gttcgatctg ctccgctaac tcgttgatgc ctctggattt   10080
cttcactctg tcgattgcgt tcatggtcta ttgcctcccg gtattcctgt aagtcgatga   10140
tctgggcgtt ggcggtgtcg atgttcaggg ccacgtctgc ccggtcggtg cggatgcccc   10200
ggccttccat ctccaccacg ttcggcccca ggtgaacacc gggcaggcgc tcgatgccct   10260
gcgcctcaag tgttctgtgg tcaatgcggg cgtcgtggcc agcccgctct aatgcccggt   10320
tggcatggtc ggcccatgcc tcgcgggtct gctcaagcca tgccttgggc ttgagcgctt   10380
cggtcttctg tgccccgccc ttctccgggg tcttgccgtt gtaccgcttg aaccactgag   10440
cggcgggccg ctcgatgccg tcattgatcc gctcggagat catcaggtgg cagtgcgggt   10500
tctcgccgcc accggcatgg atggccagcg tatacggcag gcgctcggca ccggtcaggt   10560
gctgggcgaa ctcggacgcc agcgccttct gctggtcgag ggtcagctcg accggcaggg   10620
caaattcgac ctccttgaac agccgcccat ggcgcgttc atacaggtcg gcagcatccc   10680
agtagtcggc gggccgctcg acgaactccg gcatgtgccc ggattcggcg tgcaagactt   10740
catccatgtc gcgggcatac ttgccttcgc gctggatgta gtcggccttg ccctggccg    10800 attggccgcc cgacctgctg ccggttttcg ccgtaaggtg ataaatcgcc atgctgcctc   10860
gctgttgctt ttgcttttcg gctccatgca atggccctcg gagagcgcac cgcccgaagg   10920
```

```
gtggccgtta ggccagtttc tcgaagagaa accggtaagt gcgccctccc ctacaaagta   10980
gggtcgggat tgccgccgct gtgcctccat gatagcctac gagacagcac attaacaatg   11040
gggtgtcaag atggttaagg ggagcaacaa ggcggcggat cggctggcca agctcgaaga   11100
acaacgagcg cgaatcaatg ccgaaattca gcgggagcgg gcaagggaac agcagcaaga   11160
gcgcaagaac gaaacaaggc gcaaggtgct ggtgggggcc atgattttgg ccaaggtgaa   11220
cagcagcgag tggccggagg atcggctcat ggcggcaatg gatgcgtacc ttgaacgcga   11280
ccacgaccgc gccttgttcg gtctgccgcc acgccagaag gatgagccgg gctgaatgat   11340
cgaccgagac aggccctgcg gggctgcaca cgcgccccca cccttcgggt aggggggaaag   11400 gccgctaaag cggctaaaag cgctccagcg tatttctgcg gggtttggtg tggggtttag   11460
cgggctttgc ccgccttttcc ccctgccgcg cagcggtggg gcggtgtgta gcctagcgca   11520
gcgaatagac cagctatccg gcctctggcc gggcatattg ggcaagggca gcagcgcccc   11580
acaagggcgt tgataaccgc gcctagtgga ttattcttag ataatcatgg atggattttt   11640
ccaacacccc gccagccccc gcccctgctg ggtttgcagg tttgggggcg tgacagttat   11700
tgcaggggtt cgtgacagtt attgcagggg ggcgtgacag ttattgcagg ggttcgtgac   11760
agttagtacg ggagtgacgg gcactggctg gcaatgtcta gcaacggcag gcatttcggc   11820
tgagggtaaa agaactttcc gctaagcgat agactgtatg taaacacagt attgcaagga   11880
cgcggaacat gcctcatgtg gcggccagga cggccagccg ggatcgggat actggtcgtt   11940
accagagcca ccgacccgag caaacccttc tctatcagat cgttgacgag tattacccgg   12000
cattcgctgc gcttatggca gagcagggaa aggaattgcc gggctatgtg caacgggaat   12060
ttgaagaatt tctccaatgc gggcggctgg agcatggctt tctacgggtt cgctgcgagt   12120
cttgccacgc cgagcacctg gtcgctttca gaaatcaatc taaagtatat atgagtaaac   12180
ttggtctgac agttaccaat gcttaatcag tgaggcacct atctcagcga tctgtctatt   12240
tcgttcatcc atagttgcct gactccccgt cgtgtagata actacgatac gggagggctt   12300
accatctggc cccagtgctg caatgatacc gcgagaccca cgctcaccgg ctccagattt   12360
atcagcaata accagccagc ccggaagggc cgagcgcaga agtggtcctg caactttatc   12420
cgcctccatc cagtctatta attgttgccg ggaagctaga gtaagtagtt cgccagttaa   12480
tagtttgcgc aacgttgttg ccattgctac aggcatcgtg gtgtcacgct cgtcgtttgg   12540
tatggcttca ttcagctccg gttcccaacg atcaaggcga gttacatgat cccccatgtt   12600
gtgcaaaaaa gcggttagct ccttcggtcc tccgatcgtt gtcagaagta agttggccgc   12660
agtgttatca ctcatggtta tggcagcact gcataattct cttactgtca tgccatccgt   12720
aagatgcttt tctgtgactg gtgagtactc aaccaagtca ttctgagaat agtgtatgcg   12780
gcgaccgagt tgctcttgcc cggcgtcaac acgggataat accgcgccac atagcagaac   12840
tttaaaagtg ctcatcattg gaaaacgttc ttcggggcga aaactctcaa ggatcttacc   12900
gctgttgaga tccagttcga tgtaacccac tcgtgcaccc aactgatctt cagcatcttt   12960
tactttcacc agcgtttctg ggtgagcaaa aacaggaagg caaaatgccg caaaaaaggg   13020
aataagggcg acacggaaat gttgaatact catactcttc cttttttcaat attattgaag   13080 catttatcag ggttattgtc tcatgagcgg atacatattt gaatgtattt agaaaaataa   13140
acaaaagagt ttgtagaaac gcaaaaaggc catccgtcag gatggccttc tgcttaattt   13200
gatgcctggc agtttatggc gggcgtcctg cccgccaccc tccggccgt tgcttcgcaa   13260 cgttcaaatc cgctcccggc ggatttgtcc tactcaggag agcgttcacc gacaaacaac   13320
```
agataaaacg aa                                                          13332

<210> SEQ ID NO 92
<211> LENGTH: 21
<212> TYPE: DNA
<213> ORGANISM: Artificial Sequence
<220> FEATURE:
<223> OTHER INFORMATION: PCR primer

<400> SEQUENCE: 92
gcagtaactt ctcgctgtat g                                                    21

<210> SEQ ID NO 93
<211> LENGTH: 23
<212> TYPE: DNA
<213> ORGANISM: Artificial Sequence
<220> FEATURE:
<223> OTHER INFORMATION: PCR primer

<400> SEQUENCE: 93
gtgttttcgc tgttttcgat atc                                                  23

<210> SEQ ID NO 94
<211> LENGTH: 1518
<212> TYPE: DNA
<213> ORGANISM: Enterobacter sakazakii

<400> SEQUENCE: 94
atgattaaaa aaagtacgct tgcccttacc cttggcttaa tggccggtac tcccgccgcc         60
tttgccgaca gcaatatgtc cagcattgag gcgcgtctcg ccgcgctgga acaacgtctt        120
caggcggctg aacagcgcgc cagcgcggcg gaaacccgcg ctgaagccgc agagcgtcag        180
gcacaggcgc ttgccgcgca acaaaaagcg cagccgccgg ttcagcctgt cgccgcgcaa        240
cctgcgccgc agcccgccac gcaaacggcg gataacagcg ggtttgaatt ccacggctac        300
gcccgctcgg gcctgctgat gaacgattcc gccgcgaaaa cgcagggcgg cccgtccttc        360
acgccagcgg gtgaaaccgg cggtcacgtc gggcgtctcg gcaatgagcc ggacacttac        420
cttgaaatga acctagagca caaacagacg ctcgcgaacg cgccaccac gcgcttaaa         480
gtgatggtcg ctgacggtca gcgcagctat aacgactgga cggcctccac cagcgatctc        540
aacgtgcgcc aggcgtttac cgaactcggc cacctgccga ccttcatcgg cgcgtttaaa        600
gatgccaccg tctgggccgg taaacgcttc gatcgtgata acttcgatat ccactggatt        660
gactccgacg tggtgttcct cgccggtacg ggtgcgggta tctacgacat cgctggagc         720
gataacgccc gcagtaactt ctcgctgtat ggccgcacct tcggcgatat cgaaaacagc        780
gaaaacaccg cccagaacta tatccttacg cttaataact acgtcgggcc ggtacagctg        840
atggtgagcg ggatgcgcgc caaagataac gaagaccgcg tggatatcga gggtaaccgc        900
gtgaaaaaag acgcggcgga agatggcgtg catgcgctgc tcggcctgca taacgacagc        960
ttctacggtc tgagcgacgg ctcctcgaaa accgcactgc tgtatggaca tggcctgggc       1020
gcggaagtga aatccatcgg ctccgatggc gcgctgctgc cgcaggccga tacctggcgt       1080
ctcgcgacct acggcatgac accgctcggc ggcggctggc atatcgcacc ggcggtgctg       1140
gcgcagagca gtaaagatcg ctacgtcaaa ggcgacagct accagtgggc gaccgccaac       1200
ctgcgcctca ttcaggagat taaccagaac tttgagctgc agtatgaggg cagctatcag       1260
tacatggatc tgcgcccgaa aggttacaac gaccgcaacg cggtcagcgg caacttctat       1320
aagctgacct ttgcgccgac gctgaaagcg ggcgacgtgg gcgaattcct caagcgtcct       1380

```
gaactgcgcc tgttcgccac ctggatggac tgggatcatc gcctggataa ctacgccagc    1440
aatgatgcct ttggcagcac cggctttacc gccggcggtg aatggaactt cggcgtacag    1500
atggaaacct ggttctga                                                  1518
```

<210> SEQ ID NO 95
<211> LENGTH: 505
<212> TYPE: PRT
<213> ORGANISM: Enterobacter sakazakii

<400> SEQUENCE: 95

```
Met Ile Lys Lys Ser Thr Leu Ala Leu Thr Leu Gly Leu Met Ala Gly
1               5                   10                  15

Thr Pro Ala Ala Phe Ala Asp Ser Asn Met Ser Ser Ile Glu Ala Arg
            20                  25                  30

Leu Ala Ala Leu Glu Gln Arg Leu Gln Ala Ala Glu Gln Arg Ala Ser
        35                  40                  45

Ala Ala Glu Thr Arg Ala Glu Ala Ala Glu Arg Gln Ala Gln Ala Leu
    50                  55                  60

Ala Ala Gln Gln Lys Ala Gln Pro Pro Val Gln Pro Val Ala Ala Gln
65                  70                  75                  80

Pro Ala Pro Gln Pro Ala Thr Gln Thr Ala Asp Asn Ser Gly Phe Glu
                85                  90                  95

Phe His Gly Tyr Ala Arg Ser Gly Leu Leu Met Asn Asp Ser Ala Ala
            100                 105                 110

Lys Thr Gln Gly Gly Pro Ser Phe Thr Pro Ala Gly Glu Thr Gly Gly
        115                 120                 125

His Val Gly Arg Leu Gly Asn Glu Pro Asp Thr Tyr Leu Glu Met Asn
    130                 135                 140

Leu Glu His Lys Gln Thr Leu Ala Asn Gly Ala Thr Thr Arg Phe Lys
145                 150                 155                 160

Val Met Val Ala Asp Gly Gln Arg Ser Tyr Asn Asp Trp Thr Ala Ser
                165                 170                 175

Thr Ser Asp Leu Asn Val Arg Gln Ala Phe Thr Glu Leu Gly His Leu
            180                 185                 190

Pro Thr Phe Ile Gly Ala Phe Lys Asp Ala Thr Val Trp Ala Gly Lys
        195                 200                 205

Arg Phe Asp Arg Asp Asn Phe Asp Ile His Trp Ile Asp Ser Asp Val
    210                 215                 220

Val Phe Leu Ala Gly Thr Gly Ala Gly Ile Tyr Asp Met Arg Trp Ser
225                 230                 235                 240

Asp Asn Ala Arg Ser Asn Phe Ser Leu Tyr Gly Arg Thr Phe Gly Asp
                245                 250                 255

Ile Glu Asn Ser Glu Asn Thr Ala Gln Asn Tyr Ile Leu Thr Leu Asn
            260                 265                 270

Asn Tyr Val Gly Pro Val Gln Leu Met Val Ser Gly Met Arg Ala Lys
        275                 280                 285

Asp Asn Glu Asp Arg Val Asp Ile Glu Gly Asn Arg Val Lys Lys Asp
    290                 295                 300

Ala Ala Glu Asp Gly Val His Ala Leu Leu Gly Leu His Asn Asp Ser
305                 310                 315                 320

Phe Tyr Gly Leu Ser Asp Gly Ser Ser Lys Thr Ala Leu Leu Tyr Gly
                325                 330                 335

His Gly Leu Gly Ala Glu Val Lys Ser Ile Gly Ser Asp Gly Ala Leu
            340                 345                 350
```

```
Leu Pro Gln Ala Asp Thr Trp Arg Leu Ala Thr Tyr Gly Met Thr Pro
        355                 360                 365
Leu Gly Gly Gly Trp His Ile Ala Pro Ala Val Leu Ala Gln Ser Ser
    370                 375                 380
Lys Asp Arg Tyr Val Lys Gly Asp Ser Tyr Gln Trp Ala Thr Ala Asn
385                 390                 395                 400
Leu Arg Leu Ile Gln Glu Ile Asn Gln Asn Phe Glu Leu Gln Tyr Glu
                405                 410                 415
Gly Ser Tyr Gln Tyr Met Asp Leu Arg Pro Lys Gly Tyr Asn Asp Arg
            420                 425                 430
Asn Ala Val Ser Gly Asn Phe Tyr Lys Leu Thr Phe Ala Pro Thr Leu
        435                 440                 445
Lys Ala Gly Asp Val Gly Glu Phe Leu Lys Arg Pro Glu Leu Arg Leu
    450                 455                 460
Phe Ala Thr Trp Met Asp Trp Asp His Arg Leu Asp Asn Tyr Ala Ser
465                 470                 475                 480
Asn Asp Ala Phe Gly Ser Thr Gly Phe Thr Ala Gly Glu Trp Asn
                485                 490                 495
Phe Gly Val Gln Met Glu Thr Trp Phe
            500                 505

<210> SEQ ID NO 96
<211> LENGTH: 30
<212> TYPE: DNA
<213> ORGANISM: Artificial Sequence
<220> FEATURE:
<223> OTHER INFORMATION: PCR primer

<400> SEQUENCE: 96
ccacaatgga ctgccagccg tcaaaggatg                                         30

<210> SEQ ID NO 97
<211> LENGTH: 30
<212> TYPE: DNA
<213> ORGANISM: Artificial Sequence
<220> FEATURE:
<223> OTHER INFORMATION: PCR primer

<400> SEQUENCE: 97
gcccaactgg tcacggacat cgtcgataac                                         30

<210> SEQ ID NO 98
<211> LENGTH: 29
<212> TYPE: DNA
<213> ORGANISM: Artificial Sequence
<220> FEATURE:
<223> OTHER INFORMATION: PCR primer

<400> SEQUENCE: 98
tgcaatggct ccaggaagcc cgatcgatg                                          29

<210> SEQ ID NO 99
<211> LENGTH: 30
<212> TYPE: DNA
<213> ORGANISM: Artificial Sequence
<220> FEATURE:
<223> OTHER INFORMATION: PCR primer

<400> SEQUENCE: 99
ggcagcatta cggctcagac cttggtcatg                                         30

<210> SEQ ID NO 100
```

<211> LENGTH: 1246
<212> TYPE: DNA
<213> ORGANISM: Synechocystis PCC6803

<400> SEQUENCE: 100

| | | | | | |
|---|---|---|---|---|---|
| ccacaatgga | ctgccagccg | tcaaaggatg | gttgtttgct | cataatgctt | gcctgtctgt | 60 |
| cgttgaactt | gggggaaatc | cctgcccaaa | gtatggcaga | aaacctttcc | cttcccaatg | 120 |
| ccccaacttc | cggtaacccg | atctgagcta | cagtggagtt | ccgcggtgaa | ttgttaccga | 180 |
| cggtgagacc | acgtcctaac | ttttagccca | tttttcggtt | ccccaacggc | caagattaac | 240 |
| aaaattaaat | tttagatatt | aacttttaag | ttttcccatg | gcttctcaat | tacgtgttta | 300 |
| tgtgccggag | catcctctaa | ttaagcattg | gttggggta | gctagggatg | aaaacacgcc | 360 |
| gccggttttg | tttaaaactg | ccatggggga | attgggacgt | tggttgacct | atgaggccgc | 420 |
| tcgttattgg | ttgccgacgg | tggatacgga | agtgaaaact | cccctggcga | tcgccaaggc | 480 |
| cagtcttatt | gaccccaaa | cgcccttgt | cattgtgccc | attttgcggg | cggggttggc | 540 |
| tctggtggaa | ggggcccagg | ggttgttgcc | cctggcaaaa | atttaccatc | tgggtttagt | 600 |
| gcgcaatgaa | actaccctgg | aacctagtct | gtatctgaac | aagttgccgg | agcggtttgc | 660 |
| ccccggtacc | catcttttgt | tgctagatcc | catgttggct | acgggtaata | ccatcatggc | 720 |
| tgctttggat | ttgctgatgg | cccgggacat | tgatgccaat | ttaatccgtt | tggtctccgt | 780 |
| ggtggccgcc | cccactgccc | tgcaaaaatt | aagtaatgcc | catcccaatt | tgaccatcta | 840 |
| caccgccatg | attgacgaac | aactcaatga | ccggggttac | attgtgcccg | gcctagggga | 900 |
| tgcaggcgat | cgttgctttg | gtacttgata | acaccattaa | actagtgatc | aaataattac | 960 |
| aaattcaccc | ccaaacgtta | acaacaggag | taaagtcatg | gctcaaaaag | ataacttcgc | 1020 |
| cggaggattt | ttattaggta | cggtcattgg | tggcgtagtg | ggggaatttt | tgggttctgt | 1080 |
| cctggccaat | cgagctgcta | cccaaagccc | cgaccgggaa | aaattagaca | ctgaggggt | 1140 |
| aggaaatctc | gatagtgagg | aaaatattga | gttggctcgc | cgtcgcctgg | aagacaaaat | 1200 |
| tgcccaactt | aatttggtta | tcgacgatgt | ccgtgaccag | ttgggc | | 1246 |

<210> SEQ ID NO 101
<211> LENGTH: 1281
<212> TYPE: DNA
<213> ORGANISM: Synechococcus PCC7942

<400> SEQUENCE: 101

| | | | | | |
|---|---|---|---|---|---|
| tgcaatggct | ccaggaagcc | cgatcgatgg | gatttcaagt | cgctttagat | gattttggga | 60 |
| cgggttattc | cagccttggt | tacctcaagc | gtttgcccat | caatgctctc | aaaattgatc | 120 |
| gcagctttat | tcgcgatctg | ccgcacgacc | atgacgatca | agcgatcgtg | caggcgattg | 180 |
| ttgcaatggc | caaggtcttg | aaacttcgca | cgatcgcaga | aggcgtagaa | cgcctcgagc | 240 |
| aagccgcctt | cttagaagcg | attggttgtg | atgctgtgca | agggttcttc | tatgcccac | 300 |
| cactgcccga | agcagaagcg | cttgccttcc | tgcaccgttc | cgcttcccct | ggggtctgaa | 360 |
| cgttaaaatc | aggagctgtc | ttctgctgat | tggcatggct | cctcaactgc | gtatcttcgt | 420 |
| gccgccccat | cccttaattc | ggcactggct | gggcattgcc | cgcgatcgcc | agacgccgac | 480 |
| gcctctgttt | cgcaccgcga | tcgcagagct | gggccgctgg | ctcgcctatg | aggctgtgcg | 540 |
| ggaatggcta | ccaacgattc | cagcggcggt | gcaaactcct | cttgcagaaa | ccccagcgga | 600 |
| gttcgtcgat | ttttcgcaac | ccttggcgat | cgtgccgatt | ctgcgcgcag | gtctgggttt | 660 |
| agtggagtct | gtccaacagg | ttttgccgac | tgcccgcatt | tttcacgtgg | gtctcaagcg | 720 |

```
ggatgaagtc agtcttgaac cgcgctgcta cctcaatcac ctgccagagc aacttgaagt      780
gaacagtcgc gttctggttc tcgacccgat gctggcgaca ggtggctcgc tgctctatac      840
ccttgatttg ctgcgcgatc gcggtgtctc tgctgagcaa gtgcgggtgc tttcaattgt      900
ggctgccccg ccagcgctac aaaaactcag tcaagcctac ccggcgttga cgatttacag      960
cgccatcatt gatgagcagc tgaacgacaa aggctttatc gtgccggggc tgggggatgc     1020
tggcgatcgc ctgtttggta ctccttgatc tgctgactga attcgctagg cttcagcgtt     1080
gagcaaagcc tgaacggcct gccgaatgaa gctttcatcc tgcggatttt ggctggggtt     1140
gcccgcgcgg tgaccccaga tcgagggaat tgggcaatag tgcgccttag gaatcaactg     1200
cgcttcggcc tcacaatcct ctggggtgaa gtagagatct gttgtcgagg gcatgaccaa     1260
ggtctgagcc gtaatgctgc c                                               1281
```

<210> SEQ ID NO 102
<211> LENGTH: 9385
<212> TYPE: DNA
<213> ORGANISM: Artificial Sequence
<220> FEATURE:
<223> OTHER INFORMATION: plasmid pLybAL3f containing Synechocystis upp gene

<400> SEQUENCE: 102

```
gcggccgcaa ggggttcgcg tcagcgggtg ttggcgggtg tcggggctgg cttaactatg       60
cggcatcaga gcagattgta ctgagagtgc accatatgcg gtgtgaaata ccgcacagat      120
gcgtaaggag aaaataccgc atcaggcgcc attcgccatt cagctgcgca actgttggga      180
agggcgatcg gtgcgggcct cttcgctatt acgccagctg gcgaaagggg gatgtgctgc      240
aaggcgatta agttgggtaa cgccagggtt ttcccagtca cgacgttgta aaacgacggc      300
cagtgaattg taatacgact cactataggg cgaattcgag ctcggtaccc ggggatccca      360
cgcccaactg gtcacggaca tcgtcgataa ccaaattaag ttgggcaatt ttgtcttcca      420
ggcgacggcg agccaactca atattttcct cactatcgag atttcctacc ccctcagtgt      480 ctaattttc ccggtcgggg ctttgggtag cagctcgatt ggccaggaca gaacccaaaa      540 ttcccccac tacgccacca atgaccgtac ctaataaaaa tcctccggcg aagttatctt      600
tttgagccat gactttactc ctgttgttaa cgtttggggg tgaatttgta attatttgat      660 cactagtta atggtgttat caagtaccaa agcaacgatc gcctgcatcc cctaggccgg      720
gcacaatgta accccggtca ttgagttgtt cgtcaatcat ggcggtgtag atggtcaaat      780
tgggatgggc attacttaat ttttgcaggg cagtggggc ggccaccacg agaccaaac      840 ggattaaatt ggcatcaatg tcccgggcca tcagcaaatc caaagcagcc atgatggtat      900
tacccgtagc caacatggga tctagcaaca aaagatgggt accggggca aaccgctccg      960 gcaacttgtt cagatacaga ctaggttcca gggtagtttc attgcgcact aaacccagat     1020
ggtaaatttt tgccagggc aacaacccct gggcccttc caccagagcc aaccccgccc     1080
gcaaaatggg cacaatgaca aagggcgttt gggggtcaat aagactggcc ttggcgatcg     1140
ccaggggagt tttcacttcc gtatccaccg tcggcaacca ataacgagcg gcctcatagg     1200
tcaaccaacg tcccaattcc cccatgcag ttttaaacaa accggcggc gtgttttcat     1260 ccctagctac ccccaaccaa tgcttaatta gaggatgctc cggcacataa acacgtaatt     1320
gagaagccat gggaaaactt aaaagttaat atctaaaatt taattttgtt aatcttggcc     1380
gttggggaac cgaaaaatgg gctaaaagtt aggacgtggt ctcaccgtcg gtaacaattc     1440
accgcggaac tccactgtag ctcagatcgg gttaccggaa gttggggcat tgggaaggga     1500
```

```
aaggttttct gccatacttt gggcagggat ttcccccaag ttcaacgaca gacaggcaag    1560
cattatgagc aaacaaccat cctttgacgg ctggcagtcc attgtgggtg ggatcctcta    1620
gagtcgacct gcaggcatgc aagcttgagt attctatagt ctcacctaaa tagcttggcg    1680
taatcatggt catagctgtt tcctgtgtga aattgttatc cgctcacaat tccacacaac    1740
atacgagccg gaagcataaa gtgtaaagcc tggggtgcct aatgagtgag ctaactcaca    1800
ttaattgcgt tgcgctcact gcccgctttc cagtcgggaa acctgtcgtg ccagctgcat    1860
taatgaatcg gccaacgcga accccttgcg gccgcccggg ccgtcgacca attctcatgt    1920
ttgacagctt atcatcgaat ttctgccatt catccgctta ttatcactta ttcaggcgta    1980
gcaaccaggc gtttaagggc accaataact gccttaaaaa aattacgccc cgccctgcca    2040
ctcatcgcag tactgttgta attcattaag cattctgccg acatggaagc catcacaaac    2100
ggcatgatga acctgaatcg ccagcggcat cagcaccttg tcgccttgcg tataatattt    2160
gcccatggtg aaaacggggg cgaagaagtt gtccatattg gccacgttta aatcaaaact    2220
ggtgaaactc acccagggat tggctgagac gaaaaacata ttctcaataa acccttaagg    2280
gaaataggcc aggttttcac cgtaacacgc cacatcttgc gaatatatgt gtagaaactg    2340
ccggaaatcg tcgtggtatt cactccagag cgatgaaaac gtttcagttt gctcatggaa    2400
aacggtgtaa caagggtgaa cactatccca tatcaccagc tcaccgtctt tcattgccat    2460
acgaaattcc ggatgagcat tcatcaggcg gcaagaatg tgaataaagg ccggataaaa    2520
cttgtgctta ttttttctta cggtctttaa aaaggccgta atatccagct gaacggtctg    2580
gttataggta cattgagcaa ctgactgaaa tgcctcaaaa tgttctttac gatgccattg    2640
ggatatatca acggtggtat atccagtgat ttttttctcc attttagctt ccttagctcc    2700
tgaaaatctc gataactcaa aaaatacgcc cggtagtgat cttatttcat tatggtgaaa    2760
gttggaacct cttacgtgcc gatcaacgtc tcattttcgc caaaagttgg cccagggctt    2820
cccggtatca acagggacac caggatttat ttattctgcg aagtgatctt ccgtcacagg    2880
tatttattcg cgataagctc atggagcggc gtaaccgtcg cacaggaagg acagagaaag    2940
cgcggatctg ggaagtgacg gacagaacgg tcaggacctg gattggggag gcggttgccg    3000
ccgctgctgc tgacggtgtg acgttctctg ttccggtcac accacatacg ttccgccatt    3060
cctatgcgat gcacatgctg tatgccggta taccgctgaa agttctgcaa agcctgatgg    3120
gacataagtc catcagttca acggaagtct acacgaaggt ttttcgctg atgtggctg    3180 cccggcaccg ggtgcagttt gcgatgccgg agtctgatgc ggttgcgatg ctgaaacaat    3240
tatcctgaga ataaatgcct tggcctttat atggaaatgt ggaactgagt ggatatgctg    3300
tttttgtctg ttaaacagag aagctggctg ttatccactg agaagcgaac gaaacagtcg    3360
ggaaaatctc ccattatcgt agagatccgc attattaatc tcaggagcct gtgtagcgtt    3420
tataggaagt agtgttctgt catgatgcct gcaagcggta acgaaaacga tttgaatatg    3480
ccttcaggaa caatagaaat cttcgtgcgg tgttacgttg aagtggagcg gattatgtca    3540
gcaatggaca gaacaaccta atgaacacag aaccatgatg tggtctgtcc ttttacagcc    3600
agtagtgctc gccgcagtcg agcgacaggg cgaagccctc ggctggttgc cctcgccgct    3660
gggctggcgg ccgtctatgg ccctgcaaac gcgccagaaa cgccgtcgaa gccgtgtgcg    3720
agacaccgcg gccggccgcc ggcgttgtgg atacctcgcg gaaaacttgg ccctcactga    3780
cagatgaggg gcggacgttg acacttgagg gccgactcca cccggcgcgg cgttgacaga    3840
tgaggggcag gctcgatttc ggccggcgac gtggagctgg ccagcctcgc aaatcggcga    3900
```

```
aaacgcctga ttttacgcga gtttcccaca gatgatgtgg acaagcctgg ggataagtgc    3960
cctgcggtat tgacacttga ggggcgcgac tactgacaga tgagggcgc gatccttgac     4020 acttgagggg cagagtgctg acagatgagg ggcgcaccta ttgacatttg aggggctgtc    4080
cacaggcaga aaatccagca tttgcaaggg tttccgcccg ttttcggcc accgctaacc     4140 tgtcttttaa cctgctttta aaccaatatt tataaacctt gttttaacc agggctgcgc     4200 cctgtgcgcg tgaccgcgca cgccgaaggg gggtgccccc ccttctcgaa ccctcccggt    4260
cgagtgagcg aggaagcacc agggaacagc acttatatat tctgcttaca cacgatgcct    4320
gaaaaaactt cccttggggt tatccactta tccacgggga tattttttata attatttttt   4380 ttatagttttt tagatcttct tttttagagc gccttgtagg cctttatcca tgctggttct   4440
agagaaggtg ttgtgacaaa ttgccctttc agtgtgacaa atcaccctca aatgacagtc    4500
ctgtctgtga caaattgccc ttaaccctgt gacaaattgc cctcagaaga agctgttttt    4560
tcacaaagtt atccctgctt attgactctt ttttatttag tgtgacaatc taaaaacttg    4620
tcacacttca catggatctg tcatggcgga aacagcggtt atcaatcaca agaaacgtaa    4680
aaatagcccg cgaatcgtcc agtcaaacga cctcactgag gcggcatata gtctctcccg    4740
ggatcaaaaa cgtatgctgt atctgttcgt tgaccagatc agaaaatctg atggcaccct    4800
acaggaacat gacggtatct gcgagatcca tgttgctaaa tatgctgaaa tattcggatt    4860
gacctctgcg gaagccagta aggatatacg gcaggcattg aagagtttcg cggggaagga    4920
agtggttttt tatcgccctg aagaggatgc cggcgatgaa aaaggctatg aatcttttcc    4980
ttggtttatc aaacgtgcgc acagtccatc cagagggctt tacagtgtac atatcaaccc    5040
atatctcatt cccttcttta tcgggttaca gaaccggttt acgcagtttc ggcttagtga    5100
aacaaaagaa atcaccaatc cgtatgccat gcgtttatac gaatccctgt gtcagtatcg    5160
taagccggat ggctcaggca tcgtctctct gaaaatcgac tggatcatag agcgttacca    5220
gctgcctcaa agttaccagc gtatgcctga cttccgccgc cgcttcctgc aggtctgtgt    5280
taatgagatc aacagcagaa ctccaatgcg cctctcatac attgagaaaa agaaaggccg    5340
ccagacgact catatcgtat tttccttccg cgatatcact tccatgacga caggatagtc    5400
tgagggttat ctgtcacaga tttgagggtg gttcgtcaca tttgttctga cctactgagg    5460
gtaatttgtc acagttttgc tgtttccttc agcctgcatg gattttctca ctttttttga   5520
actgtaattt ttaaggaagc caaatttgag ggcagtttgt cacagttgat ttccttctct    5580
ttcccttcgt catgtgacct gatatcgggg gttagttcgt catcattgat gagggttgat    5640
tatcacagtt tattactctg aattggctat ccgcgtgtgt acctctacct ggagtttttc    5700
ccacggtgga tatttcttct tgcgctgagc gtaagagcta tctgacagaa cagttcttct    5760
ttgcttcctc gccagttcgc tcgctatgct cggttacacg gctgcggcga gcgctagtga    5820
taataagtga ctgaggtatg tgctcttctt atctcctttt gtagtgttgc tcttatttta    5880
aacaactttg cggttttttg atgactttgc gattttgttg ttgctttgca gtaaattgca    5940
agatttaata aaaaaacgca aagcaatgat taaaggatgt tcagaatgaa actcatggaa    6000
acacttaacc agtgcataaa cgctggtcat gaaatgacga aggctatcgc cattgcacag    6060
tttaatgatg acagcccgga agcgaggaaa ataacccggc gctggagaat aggtgaagca    6120
gcggatttag ttggggtttc ttctcaggct atcagagatg ccgagaaagc agggcgacta    6180
ccgcacccgg atatggaaat tcgaggacgg gttgagcaac gtgttggtta tacaattgaa    6240
caaattaatc atatgcgtga tgtgtttggt acgcgattgc gacgtgctga agacgtattt    6300
```

```
ccaccggtga tcggggttgc tgcccataaa ggtggcgttt acaaaacctc agtttctgtt    6360
catcttgctc aggatctggc tctgaagggg ctacgtgttt tgctcgtgga aggtaacgac    6420
ccccagggaa cagcctcaat gtatcacgga tgggtaccag atcttcatat tcatgcagaa    6480
gacactctcc tgcctttcta tcttggggaa aaggacgatg tcacttatgc aataaagccc    6540
acttgctggc cggggcttga cattattcct tcctgtctgg ctctgcaccg tattgaaact    6600
gagttaatgg gcaaatttga tgaaggtaaa ctgcccaccg atccacacct gatgctccga    6660
ctggccattg aaactgttgc tcatgactat gatgtcatag ttattgacag cgcgcctaac    6720
ctgggtatcg gcacgattaa tgtcgtatgt gctgctgatg tgctgattgt tcccacgcct    6780
gctgagttgt ttgactacac ctccgcactg cagttttcg atatgcttcg tgatctgctc     6840
aagaacgttg atcttaaagg gttcgagcct gatgtacgta ttttgcttac caaatacagc    6900
aatagtaatg gctctcagtc cccgtggatg gaggagcaaa ttcgggatgc ctggggaagc    6960
atggttctaa aaatgttgt acgtgaaacg gatgaagttg gtaaaggtca gatccggatg     7020
agaactgttt ttgaacaggc cattgatcaa cgctcttcaa ctggtgcctg agaaatgct     7080 cttttctattt gggaacctgt ctgcaatgaa attttcgatc gtctgattaa ccacgctgg    7140 gagattagat aatgaagcgt gcgcctgtta ttccaaaaca tacgctcaat actcaaccgg    7200
ttgaagatac ttcgttatcg acaccagctg ccccgatggt ggattcgtta attgcgcgcg    7260
taggagtaat ggctcgcggt aatgccatta ctttgcctgt atgtggtcgg atgtgaagt     7320 ttactcttga agtgctccgg ggtgatagtg ttgagaagac ctctcgggta tggtcaggta    7380
atgaacgtga ccaggagctg cttactgagg acgcactgga tgatctcatc ccttcttttc    7440
tactgactgg tcaacagaca ccggcgttcg gtcgaagagt atctggtgtc atagaaattg    7500
ccgatgggag tcgccgtcgt aaagctgctg cacttaccga aagtgattat cgtgttctgg    7560
ttggcgagct ggatgatgag cagatggctg cattatccag attgggtaac gattatcgcc    7620
caacaagtgc ttatgaacgt ggtcagcgtt atgcaagccg attgcagaat gaatttgctg    7680
gaaatatttc tgcgctggct gatgcggaaa atatttcacg taagattatt acccgctgta    7740
tcaacaccgc caaattgcct aaatcagttg ttgctctttt ttctcacccc ggtgaactat    7800
ctgcccggtc aggtgatgca cttcaaaaag cctttacaga taaagaggaa ttacttaagc    7860
agcaggcatc taaccttcat gagcagaaaa aagctggggt gatatttgaa gctgaagaag    7920
ttatcactct tttaacttct gtgcttaaaa cgtcatctgc atcaagaact agtttaagct    7980
cacgacatca gtttgctcct ggagcgacag tattgtataa gggcgataaa atggtgctta    8040
acctggacag gtctcgtgtt ccaactgagt gtatagagaa aattgaggcc attcttaagg    8100
aacttgaaaa gccagcaccc tgatgcgacc acgttttagt ctacgtttat ctgtctttac    8160
ttaatgtcct ttgttacagg ccagaaagca taactggcct gaatattctc tctgggccca    8220
ctgttccact tgtatcgtcg gtctgataat cagactggga ccacggtccc actcgtatcg    8280
tcggtctgat tattagtctg gaccacggt cccactcgta tcgtcggtct gattattagt     8340
ctgggaccac ggtcccactc gtatcgtcgg tctgataatc agactggac cacggtccca     8400 ctcgtatcgt cggtctgatt attagtctgg accatggtc ccactcgtat cgtcggtctg     8460
attattagtc tgggaccacg gtcccactcg tatcgtcggg ctgattatta gtctggaacc    8520
acggtcccac tcgtatcgtc ggtctgatta ttagtctggg accacggtcc cactcgtatc    8580
gtcggtctga ttattagtct gggaccacga tcccactcgt gttgtcggtc tgattatcgg    8640
tctgggacca cggtcccact tgtattgtcg atcagactat cagcgtgaga ctacgattcc    8700
```

```
atcaatgcct gtcaagggca agtattgaca tgtcgtcgta acctgtagaa cggagtaacc    8760
tcggtgtgcg gttgtatgcc tgctgtggat tgctgctgtg tcctgcttat ccacaacatt    8820
ttgcgcacgg ttatgtggac aaaatacctg gttacccagg ccgtgccggc acgttaaccg    8880
ggctgcatcc gatgcaagtg tgtcgctgtc gacgagctcg cgagctcgga catgaggttg    8940
ccccgtattc agtgtcgctg atttgtattg tctgaagttg tttttacgtt aagttgatgc    9000
agatcaatta atacgatacc tgcgtcataa ttgattattt gacgtggttt gatggcctcc    9060
acgcacgttg tgatatgtag atgataatca ttatcacttt acgggtcctt tccggtgatc    9120
cgacaggtta cggggcggcg acctcgcggg ttttcgctat ttatgaaaat tttccggttt    9180
aaggcgtttc cgttcttctt cgtcataact taatgttttt atttaaaata ccctctgaaa    9240
agaaaggaaa cgacaggtgc tgaaagcgag cttttttggcc tctgtcgttt cctttctctg    9300
tttttgtccg tggaatgaac aatggaagtc cgagctcatc gctaataact tcgtatagca    9360
tacattatac gaagttatat tcgat                                          9385
```

<210> SEQ ID NO 103
<211> LENGTH: 9420
<212> TYPE: DNA
<213> ORGANISM: Artificial Sequence
<220> FEATURE:
<223> OTHER INFORMATION: plasmid pLybAL5f containing Synechococcus upp gene

<400> SEQUENCE: 103

```
gcggccgcaa ggggttcgcg tcagcgggtg ttggcgggtg tcggggctgg cttaactatg     60
cggcatcaga gcagattgta ctgagagtgc accatatgcg gtgtgaaata ccgcacagat    120
gcgtaaggag aaaataccgc atcaggcgcc attcgccatt cagctgcgca actgttggga    180
agggcgatcg gtgcgggcct cttcgctatt acgccagctg gcgaaagggg gatgtgctgc    240
aaggcgatta agttgggtaa cgccagggtt ttcccagtca cgacgttgta aaacgacggc    300
cagtgaattg taatacgact cactataggg cgaattcgag ctcggtaccc ggggatccca    360
cggcagcatt acggctcaga ccttggtcat gccctcgaca acagatctct acttcacccc    420
agaggattgt gaggccgaag cgcagttgat tcctaaggcg cactattgcc caattccctc    480
gatctggggt caccgcgcgg gcaaccccag ccaaaatccg caggatgaaa gcttcattcg    540
gcaggccgtt caggctttgc tcaacgctga agcctagcga attcagtcag cagatcaagg    600
agtaccaaac aggcgatcgc cagcatcccc cagccccggc acgataaagc ctttgtcgtt    660
cagctgctca tcaatgatgg cgctgtaaat cgtcaacgcc gggtaggctt gactgagttt    720
ttgtagcgct ggcggggcag ccacaattga agcacccgc acttgctcag cagagacacc     780
gcgatcgcgc agcaaatcaa gggtatagag cagcgagcca cctgtcgcca gcatcgggtc    840
gagaaccaga acgcgactgt tcacttcaag ttgctctggc aggtgattga ggtagcagcg    900
cggttcaaga ctgacttcat cccgcttgag acccacgtga aaaatgcggg cagtcggcaa    960
aacctgttgg acagactcca ctaaacccag acctgcgcgc agaatcggca cgatcgccaa   1020
gggttgcgaa aaatcgacga actccgctgg ggtttctgca agaggagttt gcaccgccgc   1080
tggaatcgtt ggtagccatt cccgcacagc ctcataggcg agccagcggc ccagctctgc   1140
gatcgcggtg cgaaacagag gcgtcggcgt ctggcgatcg cgggcaatgc ccagccagtg   1200
ccgaattaag ggatgggcg gcacgaagat acgcagttga ggagccatgc caatcagcag   1260
aagacagctc ctgattttaa cgttcagacc ccaggggaag cggaacggtg caggaaggca   1320
```

-continued

```
agcgcttctg cttcgggcag tggtgggcca tagaagaacc cttgcacagc atcacaacca    1380
atcgcttcta agaaggcggc ttgctcgagg cgttctacgc cttctgcgat cgtgcgaagt    1440
ttcaagacct tggccattgc aacaatcgcc tgcacgatcg cttgatcgtc atggtcgtgc    1500
ggcagatcgc gaataaagct gcgatcaatt ttgagagcat tgatgggcaa acgcttgagg    1560
taaccaaggc tggaataacc cgtcccaaaa tcatctaaag cgacttgaaa tcccatcgat    1620
cgggcttcct ggagccattg cagtgggatc ctctagagtc gacctgcagg catgcaagct    1680
tgagtattct atagtctcac ctaaatagct tggcgtaatc atggtcatag ctgtttcctg    1740
tgtgaaattg ttatccgctc acaattccac acaacatacg agccggaagc ataaagtgta    1800
aagcctgggg tgcctaatga gtgagctaac tcacattaat tgcgttgcgc tcactgcccg    1860
ctttccagtc gggaaacctg tcgtgccagc tgcattaatg aatcggccaa cgcgaacccc    1920
ttgcggccgc ccgggccgtc gaccaattct catgtttgac agcttatcat cgaatttctg    1980
ccattcatcc gcttattatc acttattcag gcgtagcaac caggcgttta agggcaccaa    2040
taactgcctt aaaaaaatta cgccccgccc tgccactcat cgcagtactg ttgtaattca    2100
ttaagcattc tgccgacatg gaagccatca caaacggcat gatgaacctg aatcgccagc    2160
ggcatcagca ccttgtcgcc ttgcgtataa tatttgccca tggtgaaaac ggggggcgaag    2220
aagttgtcca tattggccac gtttaaatca aaactggtga aactcaccca gggattggct    2280
gagacgaaaa acatattctc aataaaccct ttagggaaat aggccaggtt ttcaccgtaa    2340
cacgccacat cttgcgaata tatgtgtaga actgccgga atcgtcgtg gtattcactc    2400
cagagcgatg aaaacgtttc agtttgctca tggaaaacgg tgtaacaagg gtgaacacta    2460
tcccatatca ccagctcacc gtctttcatt gccatacgaa attccggatg agcattcatc    2520
aggcgggcaa gaatgtgaat aaaggccgga taaaacttgt gcttattttt ctttacggtc    2580
tttaaaaagg ccgtaatatc cagctgaacg gtctggttat aggtacattg agcaactgac    2640
tgaaatgcct caaaatgttc tttacgatgc cattgggata tatcaacggt ggtatatcca    2700
gtgatttttt tctccatttt agcttcctta gctcctgaaa atctcgataa ctcaaaaaat    2760
acgcccggta gtgatcttat ttcattatgg tgaaagttgg aacctcttac gtgccgatca    2820
acgtctcatt ttcgccaaaa gttggcccag ggcttcccgg tatcaacagg gacaccagga    2880
tttatttatt ctgcgaagtg atcttccgtc acaggtattt attcgcgata agctcatgga    2940
gcggcgtaac cgtcgcacag gaaggacaga gaaagcgcgg atctgggaag tgacggacag    3000
aacggtcagg acctggattg gggaggcggt tgccgccgct gctgctgacg gtgtgacgtt    3060
ctctgttccg gtcacaccac atacgttccg ccattcctat gcgatgcaca tgctgtatgc    3120
cggtataccg ctgaaagttc tgcaaagcct gatgggacat aagtccatca gttcaacgga    3180
agtctacacg aaggttttg cgctggatgt ggctgcccgg caccgggtgc agtttgcgat    3240
gccgagtct gatgcggttg cgatgctgaa acaattatcc tgagaataaa tgccttggcc    3300
tttatatgga aatgtggaac tgagtggata tgctgttttt gtctgttaaa cagagaagct    3360
ggctgttatc cactgagaag cgaacgaaac agtcggaaa atctcccatt atcgtagaga    3420
tccgcattat taatctcagg agcctgtgta gcgtttatag gaagtagtgt tctgtcatga    3480
tgcctgcaag cggtaacgaa aacgatttga atatgccttc aggaacaata gaaatcttcg    3540
tgcggtgtta cgttgaagtg gagcggatta tgtcagcaat ggacagaaca acctaatgaa    3600
cacagaacca tgatgtggtc tgtccttta cagccagtag tgctcgccgc agtcgagcga    3660
cagggcgaag ccctcggctg gttgccctcg ccgctgggct ggcggccgtc tatggccctg    3720
```

```
caaacgcgcc agaaacgccg tcgaagccgt gtgcgagaca ccgcggccgg ccgccggcgt    3780
tgtggatacc tcgcggaaaa cttggccctc actgacagat gaggggcgga cgttgacact    3840
tgaggggccg actcacccgg cgcggcgttg acagatgagg ggcaggctcg atttcggccg    3900
gcgacgtgga gctggccagc ctcgcaaatc ggcgaaaacg cctgatttta cgcgagtttc    3960
ccacagatga tgtggacaag cctggggata agtgccctgc ggtattgaca cttgaggggc    4020
gcgactactg acagatgagg ggcgcgatcc ttgacacttg aggggcagag tgctgacaga    4080 tgagggggcgc acctattgac atttgagggg ctgtccacag gcagaaaatc cagcatttgc    4140
aagggtttcc gcccgttttt cggccaccgc taacctgtct tttaacctgc ttttaaacca    4200
atatttataa accttgtttt taaccagggc tgcgccctgt gcgcgtgacc gcgcacgccg    4260 aagggggggtg ccccccccttc tcgaaccctc ccggtcgagt gagcgaggaa gcaccaggga    4320
acagcactta tatattctgc ttacacacga tgcctgaaaa aacttcccctt ggggttatcc    4380 acttatccac ggggatattt ttataattat ttttttttata gttttttagat cttctttttt    4440 agagcgcctt gtaggccttt atccatgctg gttctagaga aggtgttgtg acaaattgcc    4500
ctttcagtgt gacaaatcac cctcaaatga cagtcctgtc tgtgacaaat tgcccttaac    4560
cctgtgacaa attgccctca gaagaagctg ttttttcaca aagttatccc tgcttattga    4620 ctcttttta tttagtgtga caatctaaaa acttgtcaca cttcacatgg atctgtcatg    4680
gcggaaacag cggttatcaa tcacaagaaa cgtaaaaata gcccgcgaat cgtccagtca    4740
aacgacctca ctgaggcggc atatagtctc tcccgggatc aaaaacgtat gctgtatctg    4800
ttcgttgacc agatcagaaa atctgatggc accctacagg aacatgacgg tatctgcgag    4860
atccatgttg ctaaatatgc tgaaatattc ggattgacct ctgcggaagc cagtaaggat    4920
atacggcagg cattgaagag tttcgcgggg aaggaagtgg ttttttatcg ccctgaagag    4980
gatgccggcg atgaaaaagg ctatgaatct tttccttggt ttatcaaacg tgcgcacagt    5040
ccatccagag ggctttacag tgtacatatc aacccatatc tcattcccctt ctttatcggg    5100 ttacagaacc ggtttacgca gtttcggctt agtgaaacaa aagaaatcac caatccgtat    5160
gccatgcgtt tatacgaatc cctgtgtcag tatcgtaagc cggatggctc aggcatcgtc    5220
tctctgaaaa tcgactggat catagagcgt taccagctgc ctcaaagtta ccagcgtatg    5280
cctgacttcc gccgccgctt cctgcaggtc tgtgttaatg agatcaacag cagaactcca    5340
atgcgcctct catacattga gaaaagaaa ggccgccaga cgactcatat cgtattttcc    5400
ttccgcgata tcacttccat gacgacagga tagtctgagg gttatctgtc acagatttga    5460
gggtggttcg tcacatttgt tctgacctac tgagggtaat ttgtcacagt tttgctgttt    5520
ccttcagcct gcatggattt tctcatactt tttgaactgt aatttttaag gaagccaaat    5580
ttgagggcag tttgtcacag ttgatttcct tctctttccc ttcgtcatgt gacctgatat    5640 cggggggttag ttcgtcatca ttgatgaggg ttgattatca cagtttatta ctctgaattg    5700
gctatccgcg tgtgtacctc tacctggagt tttttcccacg gtggatattt cttcttgcgc    5760
tgagcgtaag agctatctga cagaacagtt cttctttgct tcctcgccag ttcgctcgct    5820
atgctcggtt acacggctgc ggcgagcgct agtgataata agtgactgag gtatgtgctc    5880
ttcttatctc cttttgtagt gttgctctta ttttaaacaa ctttgcggtt ttttgatgac    5940
tttgcgattt tgttgttgct ttgcagtaaa ttgcaagatt taataaaaaa acgcaaagca    6000
atgattaaag gatgttcaga atgaaactca tggaaacact taaccagtgc ataaacgctg    6060
gtcatgaaat gacgaaggct atcgccattg cacagtttaa tgatgacagc ccggaagcga    6120
```

```
ggaaaataac ccggcgctgg agaataggtg aagcagcgga tttagttggg gtttcttctc    6180
aggctatcag agatgccgag aaagcagggc gactaccgca cccggatatg gaaattcgag    6240
gacgggttga gcaacgtgtt ggttatacaa ttgaacaaat taatcatatg cgtgatgtgt    6300
ttggtacgcg attgcgacgt gctgaagacg tatttccacc ggtgatcggg gttgctgccc    6360
ataaaggtgg cgtttacaaa acctcagttt ctgttcatct tgctcaggat ctggctctga    6420
aggggctacg tgttttgctc gtggaaggta acgaccccca gggaacagcc tcaatgtatc    6480
acggatgggt accagatctt catattcatg cagaagacac tctcctgcct ttctatcttg    6540
gggaaaagga cgatgtcact tatgcaataa agcccacttg ctggccgggg cttgacatta    6600
ttccttcctg tctggctctg caccgtattg aaactgagtt aatgggcaaa tttgatgaag    6660
gtaaactgcc caccgatcca cacctgatgc tccgactggc cattgaaact gttgctcatg    6720
actatgatgt catagttatt gacagcgcgc ctaacctggg tatcggcacg attaatgtcg    6780
tatgtgctgc tgatgtgctg attgttccca cgcctgctga gttgtttgac tacacctccg    6840
cactgcagtt tttcgatatg cttcgtgatc tgctcaagaa cgttgatctt aaagggttcg    6900
agcctgatgt acgtattttg cttaccaaat acagcaatag taatggctct cagtccccgt    6960
ggatggagga gcaaattcgg gatgcctggg gaagcatggt tctaaaaaat gttgtacgtg    7020
aaacggatga agttggtaaa ggtcagatcc ggatgagaac tgtttttgaa caggccattg    7080
atcaacgctc ttcaactggt gcctggagaa atgctctttc tatttgggaa cctgtctgca    7140
atgaaatttt cgatcgtctg attaaaccac gctgggagat tagataatga agcgtgcgcc    7200
tgttattcca aaacatacgc tcaatactca accggttgaa gatacttcgt tatcgacacc    7260
agctgccccg atggtggatt cgttaattgc gcgcgtagga gtaatggctc gcggtaatgc    7320
cattactttg cctgtatgtg gtcgggatgt gaagtttact cttgaagtgc tccggggtga    7380
tagtgttgag aagacctctc gggtatggtc aggtaatgaa cgtgaccagg agctgcttac    7440
tgaggacgca ctggatgatc tcatcccttc ttttctactg actggtcaac agacaccggc    7500
gttcggtcga agagtatctg tgtcataga aattgccgat gggagtcgcc gtcgtaaagc    7560
tgcctgcactt accgaaagtg attatcgtgt tctggttggc gagctggatg atgagcagat    7620
ggctgcatta tccagattgg gtaacgatta tcgcccaaca agtgcttatg aacgtggtca    7680
gcgttatgca agccgattgc agaatgaatt tgctggaaat atttctgcgc tggctgatgc    7740
ggaaaatatt tcacgtaaga ttattacccg ctgtatcaac accgccaaat tgcctaaatc    7800
agttgttgct ctttttttctc accccggtga actatctgcc cggtcaggtg atgcacttca    7860
aaaagccttt acagataaag aggaattact taagcagcag gcatctaacc ttcatgagca    7920
gaaaaaagct ggggtgatat ttgaagctga agaagttatc actcttttaa cttctgtgct    7980
taaaacgtca tctgcatcaa gaactagttt aagctcacga catcagtttg ctcctggagc    8040
gacagtattg tataagggcg ataaaatggt gcttaacctg gacaggtctc gtgttccaac    8100
tgagtgtata gagaaaattg aggccattct taaggaactt gaaaagccag caccctgatg    8160
cgaccacgtt ttagtctacg tttatctgtc tttacttaat gtcctttgtt acaggccaga    8220
aagcataact ggcctgaata ttctctctgg gcccactgtt ccacttgtat cgtcggtctg    8280
ataatcagac tggaccacg gtcccactcg tatcgtcggt ctgattatta gtctgggacc    8340
acggtcccac tcgtatcgtc ggtctgatta ttagtctggg accacggtcc cactcgtatc    8400
gtcggtctga taatcagact gggaccacg tcccactcgt atcgtcggtc tgattattag    8460
tctgggacca tggtcccact cgtatcgtcg gtctgattat tagtctggga ccacggtccc    8520
```

```
actcgtatcg tcggtctgat tattagtctg gaaccacggt cccactcgta tcgtcggtct    8580
gattattagt ctgggaccac ggtcccactc gtatcgtcgg tctgattatt agtctgggac    8640
cacgatccca ctcgtgttgt cggtctgatt atcggtctgg gaccacggtc ccacttgtat    8700
tgtcgatcag actatcagcg tgagactacg attccatcaa tgcctgtcaa gggcaagtat    8760
tgacatgtcg tcgtaacctg tagaacggag taacctcggt gtgcggttgt atgcctgctg    8820
tggattgctg ctgtgtcctg cttatccaca acatttgcg cacggttatg tggacaaaat    8880
acctggttac ccaggccgtg ccggcacgtt aaccgggctg catccgatgc aagtgtgtcg    8940
ctgtcgacga gctcgcgagc tcggacatga ggttgccccg tattcagtgt cgctgatttg    9000
tattgtctga agttgttttt acgttaagtt gatgcagatc aattaatacg atacctgcgt    9060
cataattgat tatttgacgt ggtttgatgg cctccacgca cgttgtgata tgtagatgat    9120
aatcattatc actttacggg tcctttccgg tgatccgaca ggttacgggg cggcgacctc    9180
gcgggttttc gctatttatg aaaattttcc ggtttaaggc gtttccgttc ttcttcgtca    9240
taacttaatg ttttttattta aaatacccctc tgaaaagaaa ggaaacgaca ggtgctgaaa    9300
gcgagctttt tggcctctgt cgtttccttt ctctgttttt gtccgtggaa tgaacaatgg    9360
aagtccgagc tcatcgctaa taacttcgta tagcatacat tatacgaagt tatattcgat    9420
```

<210> SEQ ID NO 104
<211> LENGTH: 22
<212> TYPE: DNA
<213> ORGANISM: Artificial Sequence
<220> FEATURE:
<223> OTHER INFORMATION: PCR primer
<400> SEQUENCE: 104

```
gtaatacgac tcactatagg gc                                             22
```

<210> SEQ ID NO 105
<211> LENGTH: 24
<212> TYPE: DNA
<213> ORGANISM: Artificial Sequence
<220> FEATURE:
<223> OTHER INFORMATION: PCR primer
<400> SEQUENCE: 105

```
cacacaggaa acagctatga ccat                                           24
```

<210> SEQ ID NO 106
<211> LENGTH: 5641
<212> TYPE: DNA
<213> ORGANISM: Artificial Sequence
<220> FEATURE:
<223> OTHER INFORMATION: plasmid pLybAL4f containing Synechocystis upp
       gene <400> SEQUENCE: 106

```
tgcaccatat gcggtgtgaa ataccgcaca gatgcgtaag gagaaaatac cgcatcaggc     60
gccattcgcc attcagctgc gcaactgttg gaagggcga tcggtgcggg cctcttcgct    120
attacgccag ctggcgaaag ggggatgtgc tgcaaggcga ttaagttggg taacgccagg    180
gttttcccag tcacgacgtt gtaaaacgac ggccagtgaa ttgtaatacg actcactata    240
gggcgaattc gagctcggta cccggggatc ccacgcccaa ctggtcacgg acatcgtcga    300
taaccaaatt aagttgggca attttgtctt ccaggcgacg gcgagccaac tcaatatttt    360
cctcactatc gagatttcct acccccctcag tgtctaattt ttcccggtcg ggctttggg    420 tagcagctcg attggccagg acagaaccca aaattccccc cactacgcca ccaatgaccg    480
```

```
tacctaataa aaatcctccg gcgaagttat cttttttgagc catgacttta ctcctgttgt    540
taacgtttgg gggtgaattt gtaattattt gatcactagt ttaatggtgt tatcaagtac    600
caaagcaacg atcgcctgca tccctaggc cgggcacaat gtaaccccgg tcattgagtt     660
gttcgtcaat catggcggtg tagatggtca aattgggatg ggcattactt aattttttgca    720
gggcagtggg ggcggccacc acggagacca aacggattaa attggcatca atgtcccggg   780
ccatcagcaa atccaaagca gccatgatgg tattacccgt agccaacatg ggatctagca    840
acaaaagatg ggtaccgggg gcaaaccgct ccggcaactt gttcagatac agactaggtt    900
ccagggtagt ttcattgcgc actaaaccca gatggtaaat ttttgccagg ggcaacaacc    960
cctgggcccc ttccaccaga gccaacccccg cccgcaaaat gggcacaatg acaaagggcg   1020
tttgggggtc aataagactg gccttggcga tcgccagggg agttttcact tccgtatcca    1080
ccgtcggcaa ccaataacga gcggcctcat aggtcaacca acgtcccaat tcccccatgg    1140
cagttttaaa caaaaccggc ggcgtgtttt catccctagc tacccccaac caatgcttaa    1200
ttagaggatg ctccggcaca taaacacgta attgagaagc catgggaaaa cttaaaagtt    1260
aatatctaaa atttaattt gttaatcttg gccgttgggg aaccgaaaaa tgggctaaaa    1320
gttaggacgt ggtctcaccg tcggtaacaa ttcaccgcgg aactccactg tagctcagat    1380
cgggttaccg gaagttgggg cattgggaag ggaaaggttt tctgccatac tttgggcagg    1440
gatttccccc aagttcaacg acagacaggc aagcattatg agcaaacaac catcctttga    1500
cggctggcag tccattgtgg gtgggatcct ctagagtcga cctgcaggca tgcaagcttg    1560
agtattctat agtctcacct aaatagcttg gcgtaatcat ggtcatagct gtttcctgtg    1620
tgaaattgtt atccgctcac aattccacac aacatacgag ccggaagcat aaagtgtaaa    1680
gcctggggtg cctaatgagt gagctaactc acattaattg cgttgcgctc actgcccgct    1740
ttccagtcgg gaaacctgtc gtgccagctg cattaatgaa tcggccaacg cgaacccctt    1800
gcggccgccc gggccgtcga ccaattctca tgtttgacag cttatcatcg aatttctgcc    1860
attcatccgc ttattatcac ttattcaggc gtagcaacca ggcgtttaag ggcaccaata    1920
actgccttaa aaaaattacg ccccgccctg ccactcatcg cagtactgtt gtaattcatt    1980
aagcattctg ccgacatgga agccatcaca aacggcatga tgaacctgaa tcgccagcgg    2040
catcagcacc ttgtcgcctt gcgtataata tttgcccatg gtgaaaacgg ggcgaagaa    2100
gttgtccata ttggccacgt ttaaatcaaa actggtgaaa ctcacccagg gattggctga    2160
gacgaaaaac atattctcaa taaacccttt agggaaatag gccaggtttt caccgtaaca    2220
cgccacatct gcgaatata tgtgtagaaa ctgccgaaa tcgtcgtggt attcactcca     2280
gagcgatgaa aacgtttcag tttgctcatg gaaaacggtg taacaagggt gaacactatc    2340
ccatatcacc agctcaccgt ctttcattgc catacgaaat tccggatgag cattcatcag    2400
gcgggcaaga atgtgaataa aggccggata aaacttgtgc ttattttttct ttacggtctt    2460
taaaaaggcc gtaatatcca gctgaacggt ctggttatag gtacattgag caactgactg    2520
aaatgcctca aaatgttctt tacgatgcca ttgggatata tcaacggtgg tatatccagt    2580
gatttttttc tccattttag cttccttagc tcctgaaaat ctcgataact caaaaaatac    2640
gcccggtagt gatcttattt cattatggtg aaagttggaa cctcttacgt gccgatcaac    2700
gtctcatttt cgccaaaagt tggcccaggg cttccggta tcaacaggga caccaggatt    2760
tatttattct gcgaagtgat cttccgtcac aggtatttat tcgcgataag ctcatggagc    2820
ggcgtaaccg tcgcacagga aggacagaga aagcgcggat ctgggaagtg acggacagaa    2880
```

```
cggtcaggac ctggattggg gaggcggttg ccgccgctgc tgctgacggt gtgacgttct  2940
ctgttccggt cacaccacat acgttccgcc attcctatgc gatgcacatg ctgtatgccg  3000
gtataccgct gaaagttctg caaagcctga tgggacataa gtccatcagt tcaacggaag  3060
tctacacgaa ggttttttgcg ctggatgtgg ctgcccggca ccggtgcag tttgcgatgc  3120
cggagtctga tgcggttgcg atgctgaaac aattatcctg agaataaatg ccttggcctt  3180
tatatggaaa tgtggaactg agtggatatg ctgttttttgt ctgttaaaca gagaagctgg  3240
ctgttatcca ctgagaagcg aacgaaacag tcgggaaaat ctcccattat cgtagagatc  3300
cgcattatta atctcaggag cctgtgtagc gtttatagga agtagtgttc tgtcatgatg  3360
cctgcaagcg gtaacgaaaa cgatttgaat atgccttcag gaacaataga aatcttcgtg  3420
cggtgttacg ttgaagtgga gcggattatg tcagcaatgg acagaacaac ctaatgaaca  3480
cagaaccatg atgtggtctg tccttttaca gccagtagtg ctcgccgcag tcgagcgaca  3540
gggcgaagcc ctcggctggt tgccctcgcc gctgggctgg cggccgtcta tggccctgca  3600
aacgcgccag aaacgccgtc gaagccgtgt gcgagacacc gcggccggcc gccggcgttg  3660
tggatacctc gcgaaaaact tggccctcac tgacagatga ggggcggacg ttgacacttg  3720
aggggccgac tcacccggcg cggcgttgac agatgagggg caggctcgat tcggccggc  3780
gacgtggagc tggccagcct cgcaaatcgg cgaaaacgcc tgattttacg cgagtttccc  3840
acagatgatg tggacaagcc tggggataag tgccctgcgg tattgacact tgaggggcgc  3900
gactactgac agatgagggg cgcgatcctt gacacttgag gggcagagtg ctgacagatg  3960
aggggcgcac ctattgacat ttgaggggct gtccacaggc agaaaatcca gcatttgcaa  4020
gggtttccgc ccgttttttcg gccaccgcta acctgtcttt taacctgctt ttaaaccaat  4080
atttataaac cttgttttta accagggctg cgccctgtgc gcgtgaccgc gcacgccgaa  4140
gggggggtgcc cccccttctc gaaccctccc ggtcgagtga gcgaggaagc accagggaac  4200
agcacttata tattctgctt acacacgatg cctgaaaaaa cttcccttgg ggttatccac  4260
ttatccacgg ggatattttt ataattattt tttttatagt ttttagatct tcttttttag  4320
agcgccttgt aggccttttat ccatgctggt tctagagaag gtgttgtgac aaattgccct  4380
ttcagtgtga caaatcaccc tcaaatgaca gtcctgtctg tgacaaattg cccttaaccc  4440
tgtgacaaat tgccctcaga agaagctgtt ttttcacaaa gttatccctg cttattgact  4500
cttttttatt tagtgtgaca atctaaaaac ttgtcacact tcacatggat ctgtcatggc  4560
ggaaacagcg gttatcaatc acaagaaacg taaaaatagc ccgcgaatcg tccagtcaaa  4620
cgacctcact gaggcggcat atagtctctc ccgggatcaa aaacgtatgc tgtatctgtt  4680
cgttgaccag atcagaaaat ctgatggcac cctacaggaa catgacggta tctgcgagat  4740
ccatgttgct aaatatgctg aaatattcgg attgacctct gcggaagcca gtaaggatat  4800
acggcaggca ttgaagagtt cgcgggggaa ggaagtggtt ttttatcgcc ctgaagagga  4860
tgccggcgat gaaaaaggct atgaatcttt tccttggttt atcaaacgtg cgcacagtcc  4920
atccagaggg ctttacagtg tacatatcaa cccatatctc attcccttct ttatcgggtt  4980
acagaaccgg tttacgcagt ttcggcttag tgaaacaaaa gaaatcacca atccgtatgc  5040
catgcgttta tacgaatccc tgtgtcagta tcgtaagccg gatggctcag gcatcgtctc  5100
tctgaaaatc gactggatca tagagcgtta ccagctgcct caaagttacc agcgtatgcc  5160
tgacttccgc cgccgcttcc tgcaggtctg tgttaatgag atcaacagca gaactccaat  5220
gcgcctctca tacattgaga aaaagaaagg ccgccagacg actcatatcg tatttccctt  5280
```

```
ccgcgatatc acttccatga cgacaggata gtctgagggt tatctgtcac agatttgagg      5340
gtggttcgtc acatttgttc tgacctactg agggtaattt gtcacagttt tgctgtttcc      5400
ttcagcctgc atggattttc tcatactttt tgaactgtaa ttttaagga agccaaattt        5460 gagggcagtt tgtcacagtt gatttccttc tctttcccctt cgtcatgtga cctgatatcg     5520
ggggttagtt cgtcatcatt gatgagggtt gattatcaca gtttattact ctgaattggc      5580
tatccgcgtg tgtacctcta cctggagttt ttcccacggt ggatatttct tcttgcgctg      5640
a                                                                      5641
```

<210> SEQ ID NO 107
<211> LENGTH: 5218
<212> TYPE: DNA
<213> ORGANISM: Artificial Sequence
<220> FEATURE:
<223> OTHER INFORMATION: plasmid pLybAL9f containing partially deleted
      Synechocystis upp gene

<400> SEQUENCE: 107

```
tgcaccatat gcggtgtgaa ataccgcaca gatgcgtaag gagaaaatac cgcatcaggc      60
gccattcgcc attcagctgc gcaactgttg ggaagggcga tcggtgcggg cctcttcgct     120
attacgccag ctggcgaaag ggggatgtgc tgcaaggcga ttaagttggg taacgccagg     180
gttttcccag tcacgacgtt gtaaaacgac ggccagtgaa ttgtaatacg actcactata     240
gggcgaattc gagctcggta cccggggatc cacgcccaa ctggtcacgg acatcgtcga     300
taaccaaatt aagttgggca attttgtctt ccaggcgacg gcgagccaac tcaatatttt     360
cctcactatc gagatttcct accccctcag tgtctaattt ttcccggtcg gggctttggg     420
tagcagctcg attggccagg acagaaccca aaattccccc cactacgcca ccaatgaccg     480
tacctaataa aaatcctccg gcgaagttat cttttttgagc catgacttta ctcctgttgt     540
taacgtttgg gggtgaattt gtaattattt gatcactagt ttaatggtgt tatcaagtac     600
caaagcaacg atcgcctgca tccctagcg ccaggggagt tttcacttcc gtatccaccg     660
tcggcaacca ataacgagcg gcctcatagg tcaaccaacg tcccaattcc cccatggcag     720
ttttaaacaa aaccggcggc gtgttttcat ccctagctac ccccaaccaa tgcttaatta     780
gaggatgctc cggcacataa acacgtaatt gagaagccat gggaaaactt aaaagttaat     840
atctaaaatt taattttgtt aatcttggcc gttggggaac cgaaaaatgg gctaaaagtt     900
aggacgtggt ctcaccgtcg gtaacaattc accgcgaaac tccactgtag ctcagatcgg     960
gttaccggaa gttggggcat tgggaaggga aaggttttct gccatacttt gggcagggat    1020
ttcccccaag ttcaacgaca gacaggcaag cattatgagc aaacaaccat cctttgacgg    1080
ctggcagtcc attgtgggtg ggatcctcta gagtcgacct gcaggcatgc aagcttgagt    1140
attctatagt ctcacctaaa tagcttggcg taatcatggt catagctgtt tcctgtgtga    1200
aattgttatc cgctcacaat tccacacaac atacgagccg gaagcataaa gtgtaaagcc    1260
tggggtgcct aatgagtgag ctaactcaca ttaattgcgt tgcgctcact gcccgctttc    1320
cagtcgggaa acctgtcgtg ccagctgcat taatgaatcg gccaacgcga acccccttgcg   1380 gccgcccggg ccgtcgacca attctcatgt ttgacagctt atcatcgaat ttctgccatt    1440
catccgctta ttatcactta ttcaggcgta gcaaccaggc gtttaagggc accaataact    1500
gccttaaaaa aattacgccc cgccctgcca ctcatcgcag tactgttgta attcattaag    1560
cattctgccg acatggaagc catcacaaac ggcatgatga acctgaatcg ccagcggcat    1620
```

```
cagcaccttg tcgccttgcg tataatattt gcccatggtg aaaacggggg cgaagaagtt    1680
gtccatattg gccacgttta aatcaaaact ggtgaaactc acccagggat tggctgagac    1740
gaaaaacata ttctcaataa acccttttagg gaaataggcc aggttttcac cgtaacacgc   1800
cacatcttgc gaatatatgt gtagaaactg ccggaaatcg tcgtggtatt cactccagag    1860
cgatgaaaac gtttcagttt gctcatggaa aacggtgtaa caagggtgaa cactatccca    1920
tatcaccagc tcaccgtctt tcattgccat acgaaattcc ggatgagcat tcatcaggcg    1980
ggcaagaatg tgaataaagg ccggataaaa cttgtgctta ttttcttta cggtctttaa     2040 aaaggccgta atatccagct gaacggtctg gttataggta cattgagcaa ctgactgaaa    2100
tgcctcaaaa tgttctttac gatgccattg ggatatatca acggtggtat atccagtgat    2160
ttttttctcc attttagctt ccttagctcc tgaaaatctc gataactcaa aaaatacgcc    2220
cggtagtgat cttatttcat tatggtgaaa gttggaacct cttacgtgcc gatcaacgtc    2280 tcatttttcgc caaagttgg cccagggctt cccggtatca cagggacac caggattat    2340 ttattctgcg aagtgatctt ccgtcacagg tatttattcg cgataagctc atggagcggc    2400
gtaaccgtcg cacaggaagg acagagaaag cgcggatctg ggaagtgacg gacagaacgg    2460
tcaggacctg gattggggag gcggttgccg ccgctgctgc tgacggtgtg acgttctctg    2520
ttccggtcac accacatacg ttccgccatt cctatgcgat gcacatgctg tatgccggta    2580
taccgctgaa agttctgcaa agcctgatgg gacataagtc catcagttca acggaagtct    2640
acacgaaggt ttttgcgctg gatgtggctg cccggcaccg ggtgcagttt gcgatgccgg    2700
agtctgatgc ggttgcgatg ctgaaacaat tatcctgaga ataaatgcct tggcctttat    2760
atggaaatgt ggaactgagt ggatatgctg ttttgtctg ttaaacagag aagctggctg    2820
ttatccactg agaagcgaac gaaacagtcg ggaaaatctc ccattatcgt agagatccgc    2880
attattaatc tcaggagcct gtgtagcgtt tataggaagt agtgttctgt catgatgcct    2940
gcaagcggta acgaaaacga tttgaatatg ccttcaggaa caatagaaat cttcgtgcgg    3000
tgttacgttg aagtggagcg gattatgtca gcaatggaca gaacaaccta atgaacacag    3060
aaccatgatg tggtctgtcc ttttacagcc agtagtgctc gccgcagtcg agcgacaggg    3120
cgaagccctc ggctggttgc cctcgccgct gggctggcgg ccgtctatgg ccctgcaaac    3180
gcgccagaaa cgccgtcgaa gccgtgtgcg agacaccgcg gccggccgcc ggcgttgtgg    3240
atacctcgcg gaaaacttgg ccctcactga cagatgaggg gcggacgttg acacttgagg    3300
ggccgactca cccggcgcgg cgttgacaga tgaggggcag gctcgatttc ggccggcgac    3360
gtggagctgg ccagcctcgc aaatcggcga aaacgcctga ttttacgcga gtttcccaca    3420
gatgatgtgg acaagcctgg ggataagtgc cctgcggtat tgacacttga ggggcgcgac    3480
tactgacaga tgaggggcgc gatccttgac acttgagggg cagagtgctg acagatgagg    3540
ggcgcaccta ttgacatttg aggggctgtc cacaggcaga aaatccagca tttgcaaggg    3600
tttccgcccg ttttttcggcc accgctaacc tgtcttttaa cctgctttta aaccaatatt    3660
tataaacctt gttttttaacc agggctgcgc cctgtgcgcg tgaccgcgca cgccgaaggg   3720
gggtgccccc ccttctcgaa ccctcccggt cgagtgagcg aggaagcacc agggaacagc    3780
acttatatat tctgcttaca cacgatgcct gaaaaaactt cccttggggt tatccactta    3840
tccacgggga tattttttata attatttttt ttatagtttt tagatcttct ttttagagc    3900 gccttgtagg cctttatcca tgctggttct agagaaggt ttgtgacaaa ttgcccttc     3960 agtgtgacaa atcaccctca aatgacagtc ctgtctgtga caaattgccc ttaaccctgt    4020
```

```
gacaaattgc cctcagaaga agctgttttt tcacaaagtt atccctgctt attgactctt    4080
ttttatttag tgtgacaatc taaaaacttg tcacacttca catggatctg tcatggcgga    4140
aacagcggtt atcaatcaca agaaacgtaa aaatagcccg cgaatcgtcc agtcaaacga    4200
cctcactgag gcggcatata gtctctcccg ggatcaaaaa cgtatgctgt atctgttcgt    4260
tgaccagatc agaaaatctg atggcaccct acaggaacat gacggtatct gcgagatcca    4320
tgttgctaaa tatgctgaaa tattcggatt gacctctgcg gaagccagta aggatatacg    4380
gcaggcattg aagagtttcg cggggaagga agtggttttt tatcgccctg aagaggatgc    4440
cggcgatgaa aaaggctatg aatcttttcc ttggtttatc aaacgtgcgc acagtccatc    4500
cagagggctt tacagtgtac atatcaaccc atatctcatt cccttcttta tcgggttaca    4560
gaaccggttt acgcagtttc ggcttagtga acaaaagaa atcaccaatc cgtatgccat    4620
gcgtttatac gaatccctgt gtcagtatcg taagccggat ggctcaggca tcgtctctct    4680
gaaaatcgac tggatcatag agcgttacca gctgcctcaa agttaccagc gtatgcctga    4740
cttccgccgc cgcttcctgc aggtctgtgt taatgagatc aacagcagaa ctccaatgcg    4800
cctctcatac attgagaaaa agaaaggccg ccagacgact catatcgtat tttccttccg    4860
cgatatcact tccatgacga caggatagtc tgagggttat ctgtcacaga tttgagggtg    4920
gttcgtcaca tttgttctga cctactgagg gtaatttgtc acagttttgc tgtttccttc    4980
agcctgcatg gattttctca acttttttga actgtaattt ttaaggaagc caaatttgag    5040
ggcagtttgt cacagttgat ttccttctct ttcccttcgt catgtgacct gatatcgggg    5100
gttagttcgt catcattgat gagggttgat tatcacagtt tattactctg aattggctat    5160
ccgcgtgtgt acctctacct ggagtttttc ccacggtgga tatttcttct tgcgctga    5218
```

<210> SEQ ID NO 108
<211> LENGTH: 880
<212> TYPE: DNA
<213> ORGANISM: Artificial Sequence
<220> FEATURE:
<223> OTHER INFORMATION: sequence of partially deleted Synechocystis upp

<400> SEQUENCE: 108

```
gagctcggta cccggggatc ccacgcccaa ctggtcacgg acatcgtcga taaccaaatt     60
aagttgggca atttttgtctt ccaggcgacg gcgagccaac tcaatatttt cctcactatc    120
gagatttcct accccctcag tgtctaattt ttcccggtcg gggctttggg tagcagctcg    180
attggccagg acagaaccca aaattccccc cactacgcca ccaatgaccg tacctaataa    240
aaatcctccg gcgaagttat ctttttgagc catgacttta ctcctgttgt taacgtttgg    300
gggtgaattt gtaattattt gatcactagt ttaatggtgt tatcaagtac caaagcaacg    360
atcgcctgca tcccctagcg ccaggggagt tttcacttcc gtatccaccg tcggcaacca    420
ataacgagcg gcctcatagg tcaaccaacg tcccaattcc cccatggcag ttttaaacaa    480
aaccggcggc gtgttttcat ccctagctac ccccaaccaa tgcttaatta gaggatgctc    540
cggcacataa acacgtaatt gagaagccat gggaaaactt aaaagttaat atctaaaatt    600
taattttgtt aatcttggcc gttggggaac cgaaaaatgg gctaaaagtt aggacgtggt    660
ctcaccgtcg gtaacaattc accgcggaac tccactgtag ctcagatcgg gttaccggaa    720
gttggggcat tgggaaggga aaggttttct gccatacttt gggcagggat ttcccccaag    780
ttcaacgaca gacaggcaag cattatgagc aaacaaccat cctttgacgg ctggcagtcc    840
attgtgggtg ggatcctcta gagtcgacct gcaggcatgc                          880
```

<210> SEQ ID NO 109
<211> LENGTH: 5800
<212> TYPE: DNA
<213> ORGANISM: Artificial Sequence
<220> FEATURE:
<223> OTHER INFORMATION: plasmid pLybAL6fb containing Synechococcus upp gene

<400> SEQUENCE: 109

```
tgcaccatat gcggtgtgaa ataccgcaca gatgcgtaag gagaaaatac cgcatcaggc      60
gccattcgcc attcagctgc gcaactgttg ggaagggcga tcggtgcggg cctcttcgct     120
attacgccag ctggcgaaag ggggatgtgc tgcaaggcga ttaagttggg taacgccagg     180
gttttcccag tcacgacgtt gtaaaacgac ggccagtgaa ttgtaatacg actcactata     240
gggcgaattc gagctcggta cccggggatc ccacggcagc attacggctc agaccttggt     300
catgccctcg acaacagatc tctacttcac cccagaggat tgtgaggccg aagcgcagtt     360
gattcctaag gcgcactatt gcccaattcc ctcgatctgg ggtcaccgcg cgggcaaccc     420
cagccaaaat ccgcaggatg aaagcttcat tcggcaggcc gttcaggctt tgctcaacgc     480
tgaagcctag cgaattcagt cagcagatca aggagtacca acaggcgat cgccagcatc      540
ccccagcccc ggcacgataa agcctttgtc gttcagctgc tcatcaatga tggcgctgta     600
aatcgtcaac gccgggtagg cttgactgag ttttgtagc gctggcgggg cagccacaat      660
tgaaagcacc cgcacttgct cagcagagac accgcgatcg cgcagcaaat caagggtata     720
gagcagcgag ccacctgtcg ccagcatcgg gtcgagaacc agaacgcgac tgttcacttc     780
aagttgctct ggcaggtgat tgaggtagca gcgcggttca agactgactt catcccgctt     840
gagacccacg tgaaaaatgc gggcagtcgg caaaacctgt tggacagact ccactaaacc     900
cagacctgcg cgcagaatcg gcacgatcgc caagggttgc gaaaaatcga cgaactccgc     960
tggggtttct gcaagaggag tttgcaccgc cgctggaatc gttggtagcc attcccgcac    1020
agcctcatag gcgagccagc ggcccagctc tgcgatcgcg gtgcgaaaca gaggcgtcgg    1080
cgtctggcga tcgcgggcaa tgcccagcca gtgccgaatt aagggatggg gcggcacgaa    1140
gatacgcagt tgaggagcca tgccaatcag cagaagacag ctcctgattt taacgttcag    1200
accccagggg aagcggaacg gtgcaggaag gcaagcgctt ctgcttcggg cagtggtggg    1260
ccatagaaga accccttgcac agcatcacaa ccaatcgctt ctaagaaggc ggcttgctcg    1320
aggcgttcta cgccttctgc gatcgtgcga agtttcaaga ccttggccat tgcaacaatc    1380
gcctgcacga tcgcttgatc gtcatggtcg tgcggcagat cgcgaataaa gctgcgatca    1440
attttgagag cattgatggg caaacgcttg aggtaaccaa ggctggaata acccgtccca    1500
aaatcatcta agcgacttg aaatcccatc gatcgggctt cctggagcca ttgcagtggg     1560
atcctctaga gtcgacctgc aggcatgcaa gcttgagtat tctatagtct cacctaaata    1620
gcttggcgta atcatggtca tagctgtttc ctgtgtgaaa ttgttatccg ctcacaattc    1680
cacacaacat acgagccgga agcataaagt gtaaagcctg gggtgcctaa tgagtgagct    1740
aactcacatt aattgcgttg cgctcactgc ccgctttcca gtcgggaaac ctgtcgtgcc    1800
agctgcatta atgaatcggc caacgcgaac cccttgcggc cgcccgggcc gtcgaccaat    1860
tctcatgttt gacagcttat catcgaattt ctgccattca tccgcttatt atcacttatt    1920
caggcgtagc aaccaggcgt ttaagggcac caataactgc cttaaaaaaa ttacgccccg    1980
ccctgccact catcgcagta ctgttgtaat tcattaagca ttctgccgac atggaagcca    2040
tcacaaacgg catgatgaac ctgaatcgcc agcggcatca gcaccttgtc gccttgcgta    2100
```

```
taatatttgc cgatggtgaa aacgggggcg aagaagttgt ccatattggc cacgtttaaa   2160
tcaaaactgg tgaaactcac ccagggattg gctgagacga aaaacatatt ctcaataaac   2220
cctttaggga ataggccag gttttcaccg taacacgcca catcttgcga atatatgtgt    2280
agaaactgcc ggaaatcgtc gtggtattca ctccagagcg atgaaaacgt ttcagtttgc   2340
tcatggaaaa cggtgtaaca agggtgaaca ctatcccata tcaccagctc accgtctttc   2400
attgccatac gaaattccgg atgagcattc atcaggcggg caagaatgtg aataaaggcc   2460
ggataaaact tgtgcttatt tttcttacg gtctttaaaa aggccgtaat atccagctga    2520
acggtctggt tataggtaca ttgagcaact gactgaaatg cctcaaaatg ttctttacga   2580
tgccattggg atatatcaac ggtggtatat ccagtgattt ttttctccat tttagcttcc   2640
ttagctcctg aaaatctcga taactcaaaa aatacgcccg gtagtgatct tatttcatta   2700
tggtgaaagt tggaacctct tacgtgccga tcaacgtctc attttcgcca aaagttggcc   2760
cagggcttcc cggtatcaac agggacacca ggatttattt attctgcgaa gtgatcttcc   2820
gtcacaggta tttattcgcg ataagctcat ggagcggcgt aaccgtcgca caggaaggac   2880
agagaaagcg cggatctggg aagtgacgga cagaacggtc aggacctgga ttggggaggc   2940
ggttgccgcc gctgctgctg acggtgtgac gttctctgtt ccggtcacac cacatacgtt   3000
ccgccattcc tatgcgatgc acatgctgta tgccggtata ccgctgaaag ttctgcaaag   3060
cctgatggga cataagtcca tcagttcaac ggaagtctac acgaaggttt tgcgctgga    3120
tgtggctgcc cggcaccggg tgcagtttgc gatgccggag tctgatgcgg ttgcgatgct   3180
gaaacaatta tcctgagaat aaatgccttg gcctttatat ggaaatgtgg aactgagtgg   3240
atatgctgtt tttgtctgtt aaacagagaa gctggctgtt atccactgag aagcgaacga   3300
aacagtcggg aaaatctccc attatcgtag agatccgcat tattaatctc aggagcctgt   3360
gtagcgttta taggaagtag tgttctgtca tgatgcctgc aagcggtaac gaaaacgatt   3420
tgaatatgcc ttcaggaaca atagaaatct tcgtgcggtg ttacgttgaa gtggagcgga   3480
ttatgtcagc aatggacaga acaacctaat gaacacagaa ccatgatgtg gtctgtcctt   3540
ttacagccag tagtgctcgc cgcagtcgag cgacagggcg aagccctcgg ctggttgccc   3600
tcgccgctgg gctggcggcc gtctatggcc ctgcaaacgc gccagaaacg ccgtcgaagc   3660
cgtgtgcgag acaccgcggc cggccgccgg cgttgtggat acctcgcgga aaacttggcc   3720
ctcactgaca gatgagggc ggacgttgac acttgagggg ccgactcacc cggcgcggcg   3780
ttgacagatg aggggcaggc tcgatttcgg ccggcgacgt ggagctggcc agcctcgcaa   3840
atcggcgaaa acgcctgatt ttacgcgagt ttcccacaga tgatgtggac aagcctgggg   3900
ataagtgccc tgcggtattg acacttgagg ggcgcgacta ctgacagatg aggggcgcga   3960
tccttgacac ttgaggggca gagtgctgac agatgagggg cgcacctatt gacatttgag   4020
gggctgtcca caggcagaaa atccagcatt tgcaagggtt tccgcccgtt tttcggccac   4080
cgctaacctg tcttttaacc tgcttttaaa ccaatattta taaaccttgt ttttaaccag   4140
ggctgcgccc tgtgcgcgtg accgcgcacg ccgaggggg gtgccccccc ttctcgaacc   4200
ctcccggtcg agtgagcgag gaagcaccag ggaacagcac ttatatattc tgcttacaca   4260
cgatgcctga aaaaacttcc cttggggtta tccacttatc cacggggata ttttttataat   4320
tatttttttt atagttttta gatcttcttt tttagagcgc cttgtaggcc tttatccatg   4380
ctggttctag agaaggtgtt gtgacaaatt gccctttcag tgtgacaaat cacccctcaaa  4440
tgacagtcct gtctgtgaca aattgccctt aaccctgtga caaattgccc tcagaagaag   4500
```

```
ctgttttttc acaaagttat ccctgcttat tgactctttt ttatttagtg tgacaatcta    4560
aaaacttgtc acacttcaca tggatctgtc atggcggaaa cagcggttat caatcacaag    4620
aaacgtaaaa atagcccgcg aatcgtccag tcaaacgacc tcactgaggc ggcatatagt    4680
ctctcccggg atcaaaaacg tatgctgtat ctgttcgttg accagatcag aaaatctgat    4740
ggcaccctac aggaacatga cggtatctgc gagatccatg ttgctaaata tgctgaaata    4800
ttcggattga cctctgcgga agccagtaag gatatacggc aggcattgaa gagtttcgcg    4860
gggaaggaag tggtttttta tcgccctgaa gaggatgccg gcgatgaaaa aggctatgaa    4920
tcttttcctt ggtttatcaa acgtgcgcac agtccatcca gagggcttta cagtgtacat    4980
atcaacccat atctcattcc cttctttatc gggttacaga accggtttac gcagtttcgg    5040
cttagtgaaa caaaagaaat caccaatccg tatgccatgc gtttatacga atccctgtgt    5100
cagtatcgta agccggatgg ctcaggcatc gtctctctga aaatcgactg gatcatagag    5160
cgttaccagc tgcctcaaag ttaccagcgt atgcctgact ccgccgccg cttcctgcag     5220 gtctgtgtta atgagatcaa cagcagaact ccaatgcgcc tctcatacat tgagaaaaag    5280
aaaggccgcc agacgactca tatcgtattt tccttccgcg atatcacttc catgacgaca    5340
ggatagtctg agggttatct gtcacagatt tgagggtggt tcgtcacatt tgttctgacc    5400
tactgagggt aatttgtcac agttttgctg tttccttcag cctgcatgga tttctcata    5460 cttttgaac tgtaattttt aaggaagcca aatttgaggg cagtttgtca cagttgattt     5520
ccttctcttt cccttcgtca tgtgacctga tatcgggggt tagttcgtca tcattgatga    5580
gggttgatta tcacagttta ttactctgaa ttggctatcc gcgtgtgtac ctctacctgg    5640
agttttcccc acgtggata tttcttcttg cgctgagcgt aagagctatc tgacagaaca     5700
gttcttcttt gcttcctcgc cagttcgctc gctatgctcg gttacacggc tgcggcgagc    5760
gctagtgata ataagtgact gaggtatgtg ctcttcttat                          5800
```

<210> SEQ ID NO 110
<211> LENGTH: 5731
<212> TYPE: DNA
<213> ORGANISM: Artificial Sequence
<220> FEATURE:
<223> OTHER INFORMATION: plasmid pLybAL10fb containing partially deleted
      Synechococcus upp gene

<400> SEQUENCE: 110

```
tgcaccatat gcggtgtgaa ataccgcaca gatgcgtaag gagaaaatac cgcatcaggc      60
gccattcgcc attcagctgc gcaactgttg ggaagggcga tcggtgcggg cctcttcgct    120
attacgccag ctggcgaaag ggggatgtgc tgcaaggcga ttaagttggg taacgccagg    180
gttttcccag tcacgacgtt gtaaaacgac ggccagtgaa ttgtaatacg actcactata    240
gggcgaattc gagctcggta cccggggatc cacggcagc attacggctc agaccttggt    300
catgccctcg acaacagatc tctacttcac cccagaggat tgtgaggccg aagcgcagtt    360
gattcctaag gcgcactatt gcccaattcc ctcgatctgg ggtcaccgcg cgggcaaccc    420
cagccaaaat ccgcaggatg aaagcttcat tcggcaggcc gttcaggctt tgctcaacgc    480
tgaagcctag cgaattcagt cagcagatca aggagtacca acaggcgat cgccagcatc     540 ccccagcccc ggcacgataa agcctttgtc gttcagctgc tcatcaatga tggcgctgta    600
aatcgtcaac gccgggtagg cttgactgag ttttttgtagc gctggcgggg cagccacaat    660
tgaaagcacc cgcacttgct cagcagagac accgcgatcg cgcagcaaat caagggtata    720
```

```
gagcagcgag ccacctgtcg ccagcatcgg gtcgagaacc agaacgcgac tgttcacttc    780
aagttgctct ggcaggtgat tgaggtagca gcgcggttca agactgactt catcccgctc    840
gcgcagaatc ggcacgatcg ccaagggttg cgaaaaatcg acgaactccg ctggggtttc    900
tgcaagagga gtttgcaccg ccgctggaat cgttggtagc cattcccgca cagcctcata    960
ggcgagccag cggcccagct ctgcgatcgc ggtgcgaaac agaggcgtcg gcgtctggcg   1020
atcgcgggca atgcccagcc agtgccgaat aagggatgg ggcggcacga agatacgcag   1080
ttgaggagcc atgccaatca gcagaagaca gctcctgatt ttaacgttca gaccccaggg   1140
gaagcggaac ggtgcaggaa ggcaagcgct tctgcttcgg gcagtggtgg gccatagaag   1200
aacccttgca cagcatcaca accaatcgct tctaagaagg cggcttgctc gaggcgttct   1260
acgccttctg cgatcgtgcg aagtttcaag accttggcca ttgcaacaat cgcctgcacg   1320
atcgcttgat cgtcatggtc gtgcggcaga tcgcgaataa agctgcgatc aattttgaga   1380
gcattgatgg gcaaacgctt gaggtaacca aggctgaat aacccgtccc aaaatcatct   1440
aaagcgactt gaaatcccat cgatcgggct tcctggagcc attgcagtgg gatcctctag   1500
agtcgacctg caggcatgca agcttgagta ttctatagtc tcacctaaat agcttggcgt   1560
aatcatggtc atagctgttt cctgtgtgaa attgttatcc gctcacaatt ccacacaaca   1620
tacgagccgg aagcataaag tgtaaagcct ggggtgccta atgagtgagc taactcacat   1680
taattgcgtt gcgctcactg cccgctttcc agtcgggaaa cctgtcgtgc cagctgcatt   1740
aatgaatcgg ccaacgcgaa ccccttgcgg ccgcccgggc cgtcgaccaa ttctcatgtt   1800
tgacagctta tcatcgaatt tctgccattc atccgcttat tatcacttat tcaggcgtag   1860
caaccaggcg tttaagggca ccaataactg ccttaaaaaa attacgcccc gccctgccac   1920
tcatcgcagt actgttgtaa ttcattaagc attctgccga catggaagcc atcacaaacg   1980
gcatgatgaa cctgaatcgc cagcggcatc agcaccttgt cgccttgcgt ataatatttg   2040
cccatggtga aaacgggggc gaagaagttg tccatattgg ccacgtttaa atcaaaactg   2100
gtgaaactca cccagggatt ggctgagacg aaaaacatat tctcaataaa ccctttaggg   2160
aaataggcca ggttttcacc gtaacacgcc acatcttgcg aatatatgtg tagaaactgc   2220
cggaaatcgt cgtggtattc actccagagc gatgaaaacg tttcagtttg ctcatggaaa   2280
acggtgtaac aagggtgaac actatcccat atcaccagct caccgtcttt cattgccata   2340
cgaaattccg gatgagcatt catcaggcgg gcaagaatgt gaataaaggc cggataaaac   2400
ttgtgcttat ttttctttac ggtctttaaa aaggccgtaa tatccagctg aacggtctgg   2460
ttataggtac attgagcaac tgactgaaat gcctcaaaat gttctttacg atgccattgg   2520
gatatatcaa cggtggtata tccagtgatt tttttctcca ttttagcttc cttagctcct   2580
gaaaatctcg ataactcaaa aaatacgccc ggtagtgatc ttatttcatt atggtgaaag   2640
ttggaacctc ttacgtgccg atcaacgtct cattttcgcc aaaagttggc ccagggcttc   2700
ccggtatcaa caggacacc aggatttatt tattctgcga agtgatcttc cgtcacaggt   2760
atttattcgc gataagctca tggagcgcgc taaccgtcgc acaggaagga cagagaaagc   2820
gcggatctgg gaagtgacgg acagaacggt caggacctgg attggggagg cggttgccgc   2880
cgctgctgct gacggtgtga cgttctctgt tccggtcaca ccacatacgt tccgccattc   2940
ctatgcgatg cacatgctgt atgccggtat accgctgaaa gttctgcaaa gcctgatggg   3000
acataagtcc atcagttcaa cggaagtcta cacgaaggtt tttgcgctgg atgtggctgc   3060
ccggcaccgg gtgcagtttg cgatgccgga gtctgatgcg gttgcgatgc tgaaacaatt   3120
```

```
atcctgagaa taaatgcctt ggcctttata tggaaatgtg gaactgagtg gatatgctgt    3180
ttttgtctgt taaacagaga agctggctgt tatccactga gaagcgaacg aaacagtcgg    3240
gaaaatctcc cattatcgta gagatccgca ttattaatct caggagcctg tgtagcgttt    3300
ataggaagta gtgttctgtc atgatgcctg caagcgtaa cgaaaacgat ttgaatatgc     3360
cttcaggaac aatagaaatc ttcgtgcggt gttacgttga agtggagcgg attatgtcag    3420
caatggacag aacaacctaa tgaacacaga accatgatgt ggtctgtcct tttacagcca    3480
gtagtgctcg ccgcagtcga gcgacagggc gaagccctcg gctggttgcc ctcgccgctg    3540
ggctggcggc cgtctatggc cctgcaaacg cgccagaaac gccgtcgaag ccgtgtgcga    3600
gacaccgcgg ccggccgccg gcgttgtgga tacctcgcgg aaaacttggc cctcactgac    3660
agatgagggg cggacgttga cacttgaggg gccgactcac ccggcgcggc gttgacagat    3720
gaggggcagg ctcgatttcg gccggcgacg tggagctggc cagcctcgca aatcggcgaa    3780
aacgcctgat tttacgcgag tttcccacag atgatgtgga caagcctggg gataagtgcc    3840
ctgcggtatt gacacttgag gggcgcgact actgacagat gaggggcgcg atccttgaca    3900 cttgagggc agagtgctga cagatgaggg gcgcacctat tgacatttga ggggctgtcc    3960
acaggcagaa aatccagcat ttgcaagggt ttccgcccgt ttttcggcca ccgctaacct    4020
gtcttttaac ctgcttttaa accaatattt ataaaccttg ttttttaacca gggctgcgcc    4080 ctgtgcgcgt gaccgcgcac gccgaagggg ggtgccccccc cttctcgaac cctcccggtc    4140
gagtgagcga ggaagcacca gggaacagca cttatatatt ctgcttacac acgatgcctg    4200
aaaaaacttc ccttggggtt atccacttat ccacgtggat attttttataa ttatttttttt   4260 tatagttttt agatcttctt ttttagagcg ccttgtaggc ctttatccat gctggttcta    4320
gagaaggtgt tgtgacaaat tgcccttttca gtgtgacaaa tcaccctcaa atgacagtcc    4380
tgtctgtgac aaaattgccct taaccctgtg acaaattgcc ctcagaagaa gctgtttttt    4440
cacaaagtta tccctgctta ttgactcttt tttatttagt gtgacaatct aaaaacttgt    4500
cacacttcac atggatctgt catggcggaa acagcggtta tcaatcacaa gaaacgtaaa    4560
aatagcccgc gaatcgtcca gtcaaacgac ctcactgagg cggcatatag tctctcccgg    4620
gatcaaaaac gtatgctgta tctgttcgtt gaccagatca gaaaatctga tggcacccta    4680
caggaacatg acggtatctg cgagatccat gttgctaaat atgctgaaat attcggattg    4740
acctctgcgg aagccagtaa ggatatacgg caggcattga agagtttcgc ggggaaggaa    4800
gtggtttttt atcgccctga agaggatgcc ggcgatgaaa aaggctatga atcttttcct    4860
tggtttatca aacgtgcgca cagtccatcc agagggcttt acagtgtaca tatcaaccca    4920
tatctcattc ccttctttat cgggttacag aaccggttta cgcagtttcg cttagtgaa     4980 acaaaagaaa tcaccaatcc gtatgccatg cgtttatacg aatccctgtg tcagtatcgt    5040
aagccggatg gctcaggcat cgtctctctg aaaatcgact ggatcataga gcgttaccag    5100
ctgcctcaaa gttaccagcg tatgcctgac ttccgccgcc gcttcctgca ggtctgtgtt    5160
aatgagatca acagcagaac tccaatgcgc ctctcataca ttgagaaaaa gaaaggccgc    5220
cagacgactc atatcgtatt ttccttccgc gatatcactt ccatgacgac aggatagtct    5280
gagggttatc tgtcacagat ttgagggtgg ttcgtcacat ttgttctgac ctactgaggg    5340
taatttgtca cagttttgct gtttccttca gcctgcatgg attttctcat acttttttgaa    5400 ctgtaatttt taaggaagcc aaatttgagg gcagtttgtc acagttgatt tccttctctt    5460
tcccttcgtc atgtgacctg atatcggggg ttagttcgtc atcattgatg agggttgatt    5520
```

-continued

```
atcacagttt attactctga attggctatc cgcgtgtgta cctctacctg gagttttcc    5580 cacggtggat atttcttctt gcgctgagcg taagagctat ctgacagaac agttcttct    5640 tgcttcctcg ccagttcgct cgctatgctc ggttacacgg ctgcggcgag cgctagtgat    5700
aataagtgac tgaggtatgt gctcttctta t                                   5731
```

<210> SEQ ID NO 111
<211> LENGTH: 651
<212> TYPE: DNA
<213> ORGANISM: Synechocystis PCC6803

<400> SEQUENCE: 111

```
atggcttctc aattacgtgt ttatgtgccg gagcatcctc taattaagca ttggttgggg    60
gtagctaggg atgaaaacac gccgccggtt ttgtttaaaa ctgccatggg ggaattggga   120
cgttggttga cctatgaggc cgctcgttat tggttgccga cggtggatac ggaagtgaaa   180
actcccctgg cgatcgccaa ggccagtctt attgaccccc aaacgccctt tgtcattgtg   240
cccattttgc gggcggggtt ggctctggtg aaggggccc aggggttgtt gcccctggca    300
aaaatttacc atctgggttt agtgcgcaat gaaactaccc tggaacctag tctgtatctg   360
aacaagttgc cggagcggtt tgcccccggt acccatcttt tgttgctaga tcccatgttg   420
gctacgggta ataccatcat ggctgctttg gatttgctga tggcccggga cattgatgcc   480
aatttaatcc gtttggtctc cgtggtggcc gcccccactg ccctgcaaaa attaagtaat   540
gcccatccca atttgaccat ctacaccgcc atgattgacg aacaactcaa tgaccggggt   600
tacattgtgc ccggcctagg ggatgcaggc gatcgttgct ttggtacttg a            651
```

<210> SEQ ID NO 112
<211> LENGTH: 216
<212> TYPE: PRT
<213> ORGANISM: Synechocystis PCC6803

<400> SEQUENCE: 112

```
Met Ala Ser Gln Leu Arg Val Tyr Val Pro Glu His Pro Leu Ile Lys
1               5                   10                  15

His Trp Leu Gly Val Ala Arg Asp Glu Asn Thr Pro Pro Val Leu Phe
            20                  25                  30

Lys Thr Ala Met Gly Glu Leu Gly Arg Trp Leu Thr Tyr Glu Ala Ala
        35                  40                  45

Arg Tyr Trp Leu Pro Thr Val Asp Thr Glu Val Lys Thr Pro Leu Ala
    50                  55                  60

Ile Ala Lys Ala Ser Leu Ile Asp Pro Gln Thr Pro Phe Val Ile Val
65                  70                  75                  80

Pro Ile Leu Arg Ala Gly Leu Ala Leu Val Glu Gly Ala Gln Gly Leu
                85                  90                  95

Leu Pro Leu Ala Lys Ile Tyr His Leu Gly Leu Val Arg Asn Glu Thr
            100                 105                 110

Thr Leu Glu Pro Ser Leu Tyr Leu Asn Lys Leu Pro Glu Arg Phe Ala
        115                 120                 125

Pro Gly Thr His Leu Leu Leu Leu Asp Pro Met Leu Ala Thr Gly Asn
    130                 135                 140

Thr Ile Met Ala Ala Leu Asp Leu Leu Met Ala Arg Asp Ile Asp Ala
145                 150                 155                 160

Asn Leu Ile Arg Leu Val Ser Val Val Ala Ala Pro Thr Ala Leu Gln
                165                 170                 175

Lys Leu Ser Asn Ala His Pro Asn Leu Thr Ile Tyr Thr Ala Met Ile
```

-continued

```
              180                 185                 190
Asp Glu Gln Leu Asn Asp Arg Gly Tyr Ile Val Pro Gly Leu Gly Asp
        195                 200                 205

Ala Gly Asp Arg Cys Phe Gly Thr
        210                 215

<210> SEQ ID NO 113
<211> LENGTH: 654
<212> TYPE: DNA
<213> ORGANISM: Synechococcus PCC7942

<400> SEQUENCE: 113
atggctcctc aactgcgtat cttcgtgccg ccccatccct taattcggca ctggctgggc      60
attgcccgcg atcgccagac gccgacgcct ctgtttcgca ccgcgatcgc agagctgggc     120
cgctggctcg cctatgaggc tgtgcgggaa tggctaccaa cgattccagc ggcggtgcaa     180
actcctcttg cagaaacccc agcggagttc gtcgattttt cgcaacccct tgcgatcgtg     240
ccgattctgc gcgcaggtct gggtttagtg gagtctgtcc aacaggtttt gccgactgcc     300 cgcattttc acgtgggtct caagcgggat gaagtcagtc ttgaaccgcg ctgctacctc      360
aatcacctgc cagagcaact tgaagtgaac agtcgcgttc tggttctcga cccgatgctg     420
gcgacaggtg gctcgctgct ctataccctt gatttgctgc gcgatcgcgg tgtctctgct     480
gagcaagtgc gggtgctttc aattgtggct gccccgccag cgctacaaaa actcagtcaa     540
gcctacccgg cgttgacgat ttacagcgcc atcattgatg agcagctgaa cgacaaaggc     600
tttatcgtgc cggggctggg ggatgctggc gatcgcctgt ttggtactcc ttga           654

<210> SEQ ID NO 114
<211> LENGTH: 217
<212> TYPE: PRT
<213> ORGANISM: Synechococcus PCC7942

<400> SEQUENCE: 114

Met Ala Pro Gln Leu Arg Ile Phe Val Pro Pro His Pro Leu Ile Arg
1               5                   10                  15

His Trp Leu Gly Ile Ala Arg Asp Arg Gln Thr Pro Thr Pro Leu Phe
            20                  25                  30

Arg Thr Ala Ile Ala Glu Leu Gly Arg Trp Leu Ala Tyr Glu Ala Val
        35                  40                  45

Arg Glu Trp Leu Pro Thr Ile Pro Ala Ala Val Gln Thr Pro Leu Ala
    50                  55                  60

Glu Thr Pro Ala Glu Phe Val Asp Phe Ser Gln Pro Leu Ala Ile Val
65                  70                  75                  80

Pro Ile Leu Arg Ala Gly Leu Gly Leu Val Glu Ser Val Gln Gln Val
                85                  90                  95

Leu Pro Thr Ala Arg Ile Phe His Val Gly Leu Lys Arg Asp Glu Val
            100                 105                 110

Ser Leu Glu Pro Arg Cys Tyr Leu Asn His Leu Pro Glu Gln Leu Glu
        115                 120                 125

Val Asn Ser Arg Val Leu Val Leu Asp Pro Met Leu Ala Thr Gly Gly
    130                 135                 140

Ser Leu Leu Tyr Thr Leu Asp Leu Leu Arg Asp Arg Gly Val Ser Ala
145                 150                 155                 160

Glu Gln Val Arg Val Leu Ser Ile Val Ala Ala Pro Pro Ala Leu Gln
                165                 170                 175

Lys Leu Ser Gln Ala Tyr Pro Ala Leu Thr Ile Tyr Ser Ala Ile Ile
```

```
                180             185                190
Asp Glu Gln Leu Asn Asp Lys Gly Phe Ile Val Pro Gly Leu Gly Asp
        195                 200                 205

Ala Gly Asp Arg Leu Phe Gly Thr Pro
        210                 215

<210> SEQ ID NO 115
<211> LENGTH: 2184
<212> TYPE: DNA
<213> ORGANISM: Artificial Sequence
<220> FEATURE:
<223> OTHER INFORMATION: PCR product
<220> FEATURE:
<221> NAME/KEY: misc_feature
<222> LOCATION: (7)..(12)
<223> OTHER INFORMATION: AflI restriction site
<220> FEATURE:
<221> NAME/KEY: misc_feature
<222> LOCATION: (2173)..(2178)
<223> OTHER INFORMATION: NheI restriction site

<400> SEQUENCE: 115
ttgcatctta agaaggagga tccatatgat cttgatggaa cgctggcgga aatcaaaccg      60
catcccgatc aggtcgtcgt gcctgacaat attctgcaag gactacagct actggcaacc     120
gcaagtgatg gtgcattggc attgatatca gggcgctcaa tggtggagct tgacgcactg     180
gcaaaacctt atcgcttccc gttagcgggc gtgcatgggg cggagcgccg tgacatcaat     240
ggtaaaacac atatcgttca tctgccggat gcgattgcgc gtgatattag cgtgcaactg     300
catacagtca tcgctcagta tcccggcgcg gagctggagg cgaaagggat ggcttttgcg     360
ctgcattatc gtcaggctcc gcagcatgaa gacgcattaa tgacattagc gcaacgtatt     420
actcagatct ggccacaaat ggcgttacag cagggaaagt gtgttgtcga gatcaaaccg     480
agaggtacca gtaaaggtga ggcaattgca gctttatgc aggaagctcc ctttatcggg     540
cgaacgcccg tatttctggg cgatgattta accgatgaat ctggcttcgc agtcgttaac     600
cgactgggcg gaatgtcagt aaaaattggc acaggtgcaa ctcaggcatc atggcgactg     660
gcgggtgtgc cggatgtctg gagctggctt gaaatgataa ccaccgcatt acaacaaaaa     720
agagaaaata caggagtga tgactatgag tcgtttagtc gtagtatcta accggattgc      780
accaccagac gagcacgccg ccagtgccgg tggccttgcc gttggcatac tgggggcact     840
gaaagccgca ggcggactgt ggtttggctg gagtggtgaa acagggaatg aggatcagcc     900
gctaaaaaag gtgaaaaaag gtaacattac gtgggcctct tttaacctca gcaacagga     960 ccttgacgaa tactacaacc aattctccaa tgccgttctc tggcccgctt tcattatcg    1020 gctcgatctg gtgcaatttc agcgtcctgc ctgggacggc tatctacgcg taaatgcgtt    1080
gctggcagat aaattactgc cgctgttgca agacgatgac attatctgga tccacgatta    1140
tcacctgttg ccatttgcgc atgaattacg caaacgggga gtgaataatc gcattggttt    1200 cttctgcat attcctttcc cgacaccgga atcttcaac gcgctgccga catatgacac     1260
cttgcttgaa cagctttgtg attatgattt gctgggtttc cagacagaaa cgatcgtct     1320 ggcgttcctg gattgtcttt ctaacctgac ccgcgtcacg acacgtagcg caaaaagcca    1380
tacagcctgg ggcaaagcat ttcgaacaga agtctacccg atcggcattg aaccgaaaga    1440
aatagccaaa caggctgccg ggccactgcc gccaaaactg gcgcaactta agcggaact      1500 gaaaaacgta caaatatctc tttctgtcga acggctggat tattccaaag gtttgccaga    1560
gcgttttctc gcctatgaag cgttgctgga aaaatatccg cagcatcatg gtaaaattcg    1620
```

```
ttatacccag attgcaccaa cgtcgcgtgg tgatgtgcaa gcctatcagg atattcgtca    1680
tcagctcgaa aatgaagctg gacgaattaa tggtaaatac gggcaattag gctggacgcc    1740
gctttattat ttgaatcagc attttgaccg taaattactg atgaaaatat tccgctactc    1800
tgacgtgggc ttagtgacgc cactgcgtga cgggatgaac ctggtagcaa aagagtatgt    1860
tgctgctcag gacccagcca atccgggcgt tcttgttctt tcgcaatttg cgggagcggc    1920
aaacgagtta acgtcggcgt taattgttaa ccccctacgat cgtgacgaag ttgcagctgc    1980
gctggatcgt gcattgacta tgtcgctggc ggaacgtatt tcccgtcatg cagaaatgct    2040
ggacgttatc gtgaaaaacg atattaacca ctggcaggag tgcttcatta gcgacctaaa    2100
gcagatagtt ccgcgaagcg cggaaagcca gcagcgcgat aaagttgcta cctttccaaa    2160
gcttgcgtag gagctagcaa tctc                                           2184

<210> SEQ ID NO 116
<211> LENGTH: 46
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (7)..(12)
<223> OTHER INFORMATION: AflI restriction site

<400> SEQUENCE: 116
ttgcatctta agaaggagga tccatatgat cttgatggaa cgctgg                   46

<210> SEQ ID NO 117
<211> LENGTH: 28
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (7)..(12)
<223> OTHER INFORMATION: NheI restriction site

<400> SEQUENCE: 117
gagattgcta gctcctacgc aagctttg                                       28

<210> SEQ ID NO 118
<211> LENGTH: 12051
<212> TYPE: DNA
<213> ORGANISM: Artificial Sequence
<220> FEATURE:
<223> OTHER INFORMATION: plasmid pLybAL23 containing otsBA operon

<400> SEQUENCE: 118
aggcccagtc tttcgactga gcctttcgtt ttatttgatg cctggcagtt ccctactctc    60 gcatgggggag accccacact accatcggcg ctacggcgtt tcacttctga gttcggcatg   120
gggtcaggtg ggaccaccgc gctactgccg ccaggcaaat tctgttttat cagaccgctt   180
ctgcgttctg atttaatctg tatcaggctg aaaatcttct ctcatccgcc aaaacagcca   240
agcttgcatg cctgcaggtc gactctagat ggctacgagg gcagacagta agtggattta   300
ccataatccc ttaattgtac gcaccgctaa acgcgttca gcgcgatcac ggcagcagac    360
aggtaaaaat ggcaacaaac caccctaaaa actgcgcgat cgcgcctgat aaattttaac   420
cgtatgaata cctatgcaac cagagggtac aggccacatt accccacctt aatccactga   480
agctgccatt tttcatggtt tcaccatccc agcgaagggc catgcatgca tcgaaattaa   540
```

| | |
|---|---|
| tacgacgaaa ttaatacgac tcactatagg gcaattgtta tcagctatgc gccgaccaga | 600 |
| acaccttgcc gatcagccaa acgtctcttc aggccactga ctagcgataa cttccccac | 660 |
| aacggaacaa ctctcactgc atgggatcat tgggtactgt gggtttagtg gttgtaaaaa | 720 |
| cacctgaccg ctatccctga tcagtttctt gaaggtaaac tcatcacccc caagtctggc | 780 |
| tatgcagaaa tcacctggct caacagcctg ctcagggtca acgagaatta acattccgtc | 840 |
| aggaaagctt ggcttggagc ctgttggtgc ggtcatggaa ttaccttcaa cctcaagcca | 900 |
| gaatgcagaa tcactggctt tcttggttgt gcttacccat ctctccgcat cacctttggt | 960 |
| aaaggttcta agcttaggtg agaacatccc tgcctgaaca tgagaaaaaa cagggtactc | 1020 |
| atactcactt ctaagtgacg gctgcatact aaccgcttca tacatctcgt agatttctct | 1080 |
| ggcgattgaa gggctaaatt cttcaacgct aactttgaga attttgtaa gcaatgcggc | 1140 |
| gttataagca tttaatgcat tgatgccatt aaataaagca ccaacgcctg actgccccat | 1200 |
| ccccatcttg tctgcgacag attcctggga taagccaagt tcattttct tttttcata | 1260 |
| aattgcttta aggcgacgtg cgtcctcaag ctgctcttgt gttaatggtt tcttttttgt | 1320 |
| gctcatacgt taaatctatc accgcaaggg ataaatatct aacaccgtgc gtgttgacta | 1380 |
| ttttacctct ggcggtgata atggttgcat cttaagaagg aggatccata tgatcttgat | 1440 |
| ggaacgctgg cggaaatcaa accgcatccc gatcaggtcg tcgtgcctga caatattctg | 1500 |
| caaggactac agctactggc aaccgcaagt gatggtgcat tggcattgat atcagggcgc | 1560 |
| tcaatggtgg agcttgacgc actggcaaaa ccttatcgct tcccgttagc gggcgtgcat | 1620 |
| ggggcggagc gccgtgacat caatggtaaa acacatatcg ttcatctgcc ggatgcgatt | 1680 |
| gcgcgtgata ttagcgtgca actgcataca gtcatcgctc agtatcccgg cgcggagctg | 1740 |
| gaggcgaaag ggatggcttt tgcgctgcat tatcgtcagg ctccgcagca tgaagacgca | 1800 |
| ttaatgacat tagcgcaacg tattactcag atctggccac aaatggcgtt acagcaggga | 1860 |
| aagtgtgttg tcgagatcaa accgagaggt accagtaaag gtgaggcaat tgcagctttt | 1920 |
| atgcaggaag ctccctttat cgggcgaacg cccgtatttc tgggcgatga tttaaccgat | 1980 |
| gaatctggct tcgcagtcgt taaccgactg ggcggaatgt cagtaaaaat tggcacaggt | 2040 |
| gcaactcagg catcatggcg actggcgggt gtgccggatg tctggagctg gcttgaaatg | 2100 |
| ataaccaccg cattcaaaca aaaagagaa aataacagga gtgatgacta tgagtcgttt | 2160 |
| agtcgtagta tctaaccgga ttgcaccacc agacgagcac gccgccagtg ccggtggcct | 2220 |
| tgccgttggc atactggggg cactgaaagc cgcaggcgga ctgtggtttg gctggagtgg | 2280 |
| tgaaacaggg aatgaggatc agccgctaaa aaggtgaaa aaggtaaca ttacgtgggc | 2340 |
| ctctttaac ctcagcgaac aggaccttga cgaatactac aaccaattct ccaatgccgt | 2400 |
| tctctggccc gcttttcatt atcggctcga tctggtgcaa tttcagcgtc ctgcctggga | 2460 |
| cggctatcta cgcgtaaatg cgttgctggc agataaatta ctgccgctgt tgcaagacga | 2520 |
| tgacattatc tggatccacg attatcacct gttgccattt gcgcatgaat tacgcaaacg | 2580 |
| gggagtgaat aatcgcattg gtttctttct gcatattcct ttcccgacac cggaaatctt | 2640 |
| caacgcgctg ccgacatatg acaccttgct tgaacagctt tgtgattatg atttgctggg | 2700 |
| tttccagaca gaaacgatc gtctggcgtt cctggattgt cttctaacc tgacccgcgt | 2760 |
| cacgacacgt agcgcaaaaa gccatacagc ctggggcaaa gcatttcgaa cagaagtcta | 2820 |
| cccgatcggc attgaaccga agaaatagc caaacaggct gccgggccac tgccgccaaa | 2880 |
| actggcgcaa cttaaagcgg aactgaaaaa cgtacaaaat atcttttctg tcgaacggct | 2940 |

```
ggattattcc aaaggtttgc cagagcgttt tctcgcctat gaagcgttgc tggaaaaata    3000
tccgcagcat catggtaaaa ttcgttatac ccagattgca ccaacgtcgc gtggtgatgt    3060
gcaagcctat caggatattc gtcatcagct cgaaaatgaa gctggacgaa ttaatggtaa    3120
atacgggcaa ttaggctgga cgccgcttta ttatttgaat cagcattttg accgtaaatt    3180
actgatgaaa atattccgct actctgacgt gggcttagtg acgccactgc gtgacgggat    3240
gaacctggta gcaaaagagt atgttgctgc tcaggaccca gccaatccgg gcgttcttgt    3300
tctttcgcaa tttgcgggag cggcaaacga gttaacgtcg gcgttaattg ttaaccccta    3360
cgatcgtgac gaagttgcag ctgcgctgga tcgtgcattg actatgtcgc tggcggaacg    3420
tatttcccgt catgcagaaa tgctggacgt tatcgtgaaa aacgatatta accactggca    3480
ggagtgcttc attagcgacc taaagcagat agttccgcga agcgcggaaa gccagcagcg    3540
cgataaagtt gctacctttc caaagcttgc gtaggagcta gctgcctcga aggggatgc     3600
gattcgccac ctctcactcc gctggcggat tcctcttgag aacattttgg tggcaggcga    3660
ttctggtaac gatgaggaaa tgctcaaggg ccataatctc ggcgttgtag ttggcaatta    3720
ctcaccggaa ttggagccac tgcgcagcta cgagcgcgtc tattttgctg agggccacta    3780
tgctaatggc attctggaag ccttaaaaca ctatcgcttt tttgaggcga tcgcttaacc    3840
ttttcagaat gagacgttga tcggcacgta agcgtgagac gttgatcggc acgtaagagg    3900
ttccaacttt caccataatg aaataagatc actaccgggc gtattttttg agttatcgag    3960
attttcagga gctaaggaag ctaaaatgga gaaaaaatc actggatata ccaccgttga    4020
tatatcccaa tggcatcgta agaacatttt tgaggcattt cagtcagttg ctcaatgtac    4080
ctataaccag accgttcagc tggatattac ggcctttttta aagaccgtaa agaaaaataa    4140
gcacaagttt tatccggcct ttattcacat tcttgcccgc ctgatgaatg ctcatccgga    4200
attccgtatg gcaatgaaag acggtgagct ggtgatatgg gatagtgttc acccttgtta    4260
caccgttttc catgagcaaa ctgaaacgtt ttcatcgctc tggagtgaat accacgacga    4320
tttccggcag tttctacaca tatattcgca agatgtggcg tgttacggtg aaaacctggc    4380
ctatttccct aaagggttta ttgagaatat gttttttcgtc tcagccaatc cctgggtgag    4440
tttcaccagt tttgatttaa acgtggccaa tatggacaac ttcttcgccc ccgttttcac    4500
catgggcaaa tattatacgc aaggcgacaa ggtgctgatg ccgctggcga ttcaggttca    4560
tcatgccgtt tgtgatggct tccatgtcgg cagaatgctt aatgaattac aacagtactg    4620
cgatgagtgg cagggcgggg cgtaattttt ttaaggcagt tattggtgcc cttaaacgcc    4680
tggttgctac gcctgaataa gtgataataa gcggatgaat ggcagaaatt cgatgataag    4740
ctgtcaaaca caaccaccat caaacaggat tttcgcctgc tggggcaaac cagcgtggac    4800
cgcttgctgc aactctctca gggccaggcg gtgaagggca atcagctgtt gcccgtctca    4860
ctggtgaaaa gaaaaaccac cctggcgccc aatacgcaaa ccgcctctcc ccgcgcgttg    4920
gccgattcat taatgcagct ggcacgacag gtttcccgac tggaaagcgg gcagtgagcg    4980
caacgcaatt aatgtaagtt agcgcgaatt gcaagctggc cgacgcgctg gctacgtcct    5040
tgctggcgtt cgggagcaga agagcataca tctggaagca aagccaggaa agcggcctat    5100
ggagctgtgc ggcagcgctc agtaggcaat ttttcaaaat attgttaagc cttttctgag    5160
catggtattt ttcatggtat taccaattag caggaaaata agccattgaa tataaaagat    5220
aaaaatgtct tgtttacaat agagtggggg gggtcagcct gccgccttgg gccgggtgat    5280
gtcgtacttg cccgccgcga actcggttac cgtccagccc agcgcgacca gctccggcaa    5340
```

```
cgcctcgcgc acccgcttgc ggcgcttgcg catggtcgaa ccactggcct ctgacggcca    5400
gacatagccg cacaaggtat ctatggaagc cttgccggtt ttgccggggt cgatccagcc    5460
acacagccgc tggtgcagca ggcgggcggt ttcgctgtcc agcgcccgca cctcgtccat    5520
gctgatgcgc acatgctggc cgccacccat gacggcctgc gcgatcaagg ggttcagggc    5580
cacgtacagg cgcccgtccg cctcgtcgct ggcgtactcc gacagcagcc gaaaccccctg   5640 ccgcttgcgg ccattctggg cgatgatgga taccttccaa aggcgctcga tgcagtcctg    5700
tatgtgcttg agcgccccac cactatcgac ctctgccccg atttcctttg ccagcgcccg    5760
atagctacct ttgaccacat ggcattcagc ggtgacggcc tcccacttgg gttccaggaa    5820
cagccggagc tgccgtccgc cttcggtctt gggttccggg ccaagcacta ggccattagg    5880
cccagccatg gccaccagcc cttgcaggat gcgcagatca tcagcgccca gcggctccgg    5940
gccgctgaac tcgatccgct tgccgtcgcc gtagtcatac gtcacgtcca gcttgctgcg    6000
cttgcgctcg ccccgcttga gggcacggaa caggccgggg gccagacagt gcgccgggtc    6060
gtgccggacg tggctgaggc tgtgcttgtt cttaggcttc accacggggc accccccttgc   6120 tcttgcgctg cctctccagc acggcgggct gagcacccc gccgtcatgc cgcctgaacc     6180
accgatcagc gaacggtgcg ccatagttgg ccttgctcac accgaagcgg acgaagaacc    6240
ggcgctggtc gtcgtccaca ccccattcct cggcctcggc gctggtcatg ctcgacaggt    6300
aggactgcca gcggatgtta tcgaccagta ccgagctgcc ccggctggcc tgctgctggt    6360
cgcctgcgcc catcatggcc gcgcccttgc tggcatggtg caggaacacg atagagcacc    6420
cggtatcggc ggcgatggcc tccatgcgac cgatgacctg ggccatgggg ccgctggcgt    6480
tttcttcctc gatgtggaac cggcgcagcg tgtccagcac catcaggcgg cggccctcgg    6540
cggcgcgctt gaggccgtcg aaccactccg gggccatgat gttgggcagg ctgccgatca    6600
gcggctggat cagcaggccg tcagccacgg cttgccgttc ctcggcgctg aggtgcgccc    6660
caagggcgtg caggcggtga tgaatggcgg tgggcgggtc ttcggcgggc aggtagatca    6720 ccgggcggt gggcagttcg cccacctcca gcagatccgg cccgcctgca atctgtgcgg     6780
ccagttgcag ggccagcatg gatttaccgg caccaccggg cgacaccagc gccccgaccg    6840
taccggccac catgttgggc aaaacgtagt ccagcggtgg cggcgctgct gcgaacgcct    6900
ccagaatatt gataggctta tgggtagcca ttgattgcct cctttgcagg cagttggtgg    6960
ttaggcgctg gcggggtcac tacccccgcc ctgcgccgct ctgagttctt ccaggcactc    7020
gcgcagcgcc tcgtattcgt cgtcggtcag ccagaacttg cgctgacgca tcccctttggc   7080 cttcatgcgc tcggcatatc gcgcttggcg tacagcgtca gggctggcca gcaggtcgcc    7140
ggtctgcttg tccttttggt cttttcatatc agtcaccgag aaacttgccg gggccgaaag   7200
gcttgtcttc gcggaacaag gacaaggtgc agccgtcaag gttaaggctg gccatatcag    7260
cgactgaaaa gcgccagcc tcggccttgt ttgacgtata accaaagcca ccgggcaacc     7320
aatagccctt gtcactttg atcaggtaga ccgaccctga agcgcttttt tcgtattcca     7380
taaaaccccc ttctgtgcgt gagtactcat agtataacag gcgtgagtac caacgcaagc    7440
actacatgct gaaatctggc ccgcccctgt ccatgcctcg ctggcggggt gccggtgccc    7500
gtgccagctc ggcccgcgca agctggacgc tgggcagacc catgaccttg ctgacggtgc    7560
gctcgatgta atccgcttcg tggccgggct tgcgctctgc cagcgctggg ctggcctcgg    7620
ccatggcctt gccgatttcc tcggcactgc ggccccggct ggccagcttc tgcgcggcga    7680
taaagtcgca cttgctgagg tcatgaccga agcgcttgac cagcccggcc atctcgctgc    7740
```

```
ggtactcgtc cagcgccgtg cgccggtggc ggctaagctg ccgctcgggc agttcgaggc   7800
tggccagcct gcgggccttc tcctgctgcc gctgggcctg ctcgatctgc tggccagcct   7860
gctgcaccag cgccgggcca gcggtggcgg tcttgcccct tggattcacgc agcagcaccc   7920 acggctgata accggcgcgg gtggtgtgct tgtccttgcg gttggtgaag cccgccaagc   7980
ggccatagtg gcggctgtcg gcgctggccg ggtcggcgtc gtactcgctg ccagcgtcc    8040 gggcaatctg cccccgaagt tcaccgcctg cggcgtcggc caccttgacc catgcctgat   8100
agttcttcgg gctggtttcc actaccaggg caggctcccg gccctcggct ttcatgtcat   8160
ccaggtcaaa ctcgctgagg tcgtccacca gcaccagacc atgccgctcc tgctcggcgg   8220
gcctgatata cacgtcattg ccctgggcat tcatccgctt gagccatggc gtgttctgga   8280
gcacttcggc ggctgaccat tcccggttca tcatctggcc ggtgggtgcg tccctgacgc   8340
cgatatcgaa gcgctcacag cccatggcct tgagctgtcg gcctatggcc tgcaaagtcc   8400
tgtcgttctt catcgggcca ccaagcgcag ccagatcgag ccgtcctcgg ttgtcagtgg   8460
cgtcaggtcg agcaagagca acgatgcgat cagcagcacc accgtaggca tcatggaagc   8520
cagcatcacg gttagccata gcttccagtg ccaccccgc gacgcgctcc gggcgctctg    8580
cgcggcgctg ctcacctcgg cggctacctc ccgcaactct ttggccagct ccacccatgc   8640
cgcccctgtc tggcgctggg ctttcagcca ctccgccgcc tgcgcctcgc tggcctgctt   8700
ggtctggctc atgacctgcc gggcttcgtc ggccagtgtc gccatgctct gggccagcgg   8760
ttcgatctgc tccgctaact cgttgatgcc tctggatttc ttcactctgt cgattgcgtt   8820
catggtctat tgcctcccgg tattcctgta agtcgatgat ctgggcgttg gcggtgtcga   8880
tgttcagggc cacgtctgcc cggtcggtgc ggatgcccg gccttccatc tccaccacgt    8940 tcggcccag gtgaacaccg ggcaggcgct cgatgccctg cgcctcaagt gttctgtggt    9000
caatgcgggc gtcgtggcca gcccgctcta atgcccggtt ggcatggtcg cccatgcct    9060 cgcgggtctg ctcaagccat gccttgggct tgagcgcttc ggtcttctgt gccccgccct   9120
tctccggggt cttgccgttg taccgcttga accactgagc ggcgggccgc tcgatgccgt   9180
cattgatccg ctcggagatc atcaggtggc agtgcgggtt ctcgccgcca ccggcatgga   9240
tggccagcgt atacggcagg cgctcggcac cggtcaggtg ctgggcgaac tcggacgcca   9300
gcgccttctg ctggtcgagg gtcagctcga ccggcagggc aaattcgacc tccttgaaca   9360
gccgcccatt ggcgcgttca tacaggtcgg cagcatccca gtagtcggcg ggccgctcga   9420
cgaactccgg catgtgcccg gattcggcgt gcaagacttc atccatgtcg cggcatact    9480 tgccttcgcg ctggatgtag tcggccttgg ccctggccga ttggccgccc gacctgctgc   9540
cggttttcgc cgtaaggtga taaatcgcca tgctgcctcg ctgttgcttt tgcttttcgg   9600
ctccatgcaa tggccctcgg agagcgcacc gcccgaaggg tggccgttag ccagtttct    9660 cgaagagaaa ccggtaagtg cgccctcccc tacaaagtag ggtcgggatt gccgccgctg   9720
tgcctccatg atagcctacg agacagcaca ttaacaatgg ggtgtcaaga tggttaaggg   9780
gagcaacaag gcggcggatc ggctggccaa gctcgaagaa caacgagcgc gaatcaatgc   9840
cgaaattcag cgggagcggg caagggaaca gcagcaagag cgcaagaacg aaacaaggcg   9900
caaggtgctg gtgggggcca tgattttggc caaggtgaac agcagcgagt ggccggagga   9960
tcggctcatg gcggcaatgg atgcgtacct tgaacgcgac cacgaccgcg ccttgttcgg  10020
tctgccgcca cgccagaagg atgagccggg ctgaatgatc gaccgagaca ggccctgcgg  10080
ggctgcacac gcgcccccac ccttcgggta gggggaaagg ccgctaaagc ggctaaaagc  10140
```

-continued

| | |
|---|---|
| gctccagcgt atttctgcgg ggtttggtgt ggggtttagc gggctttgcc cgcctttccc | 10200 |
| cctgccgcgc agcggtgggg cggtgtgtag cctagcgcag cgaatagacc agctatccgg | 10260 |
| cctctggccg ggcatattgg gcaagggcag cagcgcccca caagggcgct gataaccgcg | 10320 |
| cctagtggat tattcttaga taatcatgga tggattttc caacacccg ccagcccccg | 10380 |
| cccctgctgg gtttgcaggt ttgggggcgt gacagttatt gcaggggttc gtgacagtta | 10440 |
| ttgcaggggg gcgtgacagt tattgcaggg gttcgtgaca gttagtacgg gagtgacggg | 10500 |
| cactggctgg caatgtctag caacggcagg catttcggct gagggtaaaa gaactttccg | 10560 |
| ctaagcgata gactgtatgt aaacacagta ttgcaaggac gcggaacatg cctcatgtgg | 10620 |
| cggccaggac ggccagccgg gatcgggata ctggtcgtta ccagagccac cgacccgagc | 10680 |
| aaaccttct ctatcagatc gttgacgagt attaccggc attcgctgcg cttatggcag | 10740 |
| agcagggaaa ggaattgccg ggctatgtgc aacgggaatt tgaagaattt ctccaatgcg | 10800 |
| ggcggctgga gcatggcttt ctacgggttc gctgcgagtc ttgccacgcc gagcacctgg | 10860 |
| tcgctttcag aaatcaatct aaagtatata tgagtaaact tggtctgaca gttaccaatg | 10920 |
| cttaatcagt gaggcaccta tctcagcgat ctgtctattt cgttcatcca tagttgcctg | 10980 |
| actccccgtc gtgtagataa ctacgatacg ggagggctta ccatctggcc ccagtgctgc | 11040 |
| aatgataccg cgagacccac gctcaccggc tccagattta tcagcaataa accagccagc | 11100 |
| cggaagggcc gagcgcagaa gtggtcctgc aactttatcc gcctccatcc agtctattaa | 11160 |
| ttgttgccgg gaagctagag taagtagttc gccagttaat agtttgcgca acgttgttgc | 11220 |
| cattgctaca ggcatcgtgg tgtcacgctc gtcgtttggt atggcttcat tcagctccgg | 11280 |
| ttcccaacga tcaaggcgag ttacatgatc ccccatgttg tgcaaaaaag cggttagctc | 11340 |
| cttcggtcct ccgatcgttg tcagaagtaa gttggccgca gtgttatcac tcatggttat | 11400 |
| ggcagcactg cataattctc ttactgtcat gccatccgta agatgctttt ctgtgactgg | 11460 |
| tgagtactca accaagtcat tctgagaata gtgtatgcgg cgaccgagtt gctcttgccc | 11520 |
| ggcgtcaaca cggataata ccgcgccaca tagcagaact ttaaaagtgc tcatcattgg | 11580 |
| aaaacgttct cggggcgaa aactctcaag gatcttaccg ctgttgagat ccagttcgat | 11640 |
| gtaacccact cgtgcaccca actgatcttc agcatctttt actttcacca gcgtttctgg | 11700 |
| gtgagcaaaa acaggaaggc aaaatgccgc aaaaaaggga ataagggcga cacggaaatg | 11760 |
| ttgaatactc atactcttcc tttttcaata ttattgaagc atttatcagg gttattgtct | 11820 |
| catgagcgga tacatatttg aatgtattta gaaaaataaa caaagagtt tgtagaaacg | 11880 |
| caaaaaggcc atccgtcagg atggccttct gcttaatttg atgcctggca gtttatggcg | 11940 |
| ggcgtcctgc ccgccaccct ccgggccgtt gcttcgcaac gttcaaatcc gctcccggcg | 12000 |
| gatttgtcct actcaggaga gcgttcaccg acaaacaaca gataaaacga a | 12051 |

<210> SEQ ID NO 119
<211> LENGTH: 23
<212> TYPE: DNA
<213> ORGANISM: Artificial Sequence
<220> FEATURE:
<223> OTHER INFORMATION: PCR primer

<400> SEQUENCE: 119
ttcattatcg gctcgatctg gtg        23

<210> SEQ ID NO 120
<211> LENGTH: 25
<212> TYPE: DNA

<213> ORGANISM: Artificial Sequence
<220> FEATURE:
<223> OTHER INFORMATION: PCR primer

<400> SEQUENCE: 120
caacaggtga taatcgtgga tccag                                         25

<210> SEQ ID NO 121
<211> LENGTH: 11348
<212> TYPE: DNA
<213> ORGANISM: Artificial Sequence
<220> FEATURE:
<223> OTHER INFORMATION: plasmid pLybAL28 containing otsBA operon

<400> SEQUENCE: 121

| | | |
|---|---|---|
| aggcccagtc tttcgactga gcctttcgtt ttatttgatg cctggcagtt ccctactctc | 60 |
| gcatggggag accccacact accatcggcg ctacggcgtt tcacttctga gttcggcatg | 120 |
| gggtcaggtg ggaccaccgc gctactgccg ccaggcaaat tctgttttat cagaccgctt | 180 |
| ctgcgttctg atttaatctg tatcaggctg aaaatcttct ctcatccgcc aaaacagcca | 240 |
| agcttgcatg ccgttattga tggaatggga agaagcaatg gtcacaataa actggaggtt | 300 |
| atgggtatgt ttttttagccc taatgctcca atcgccttga ttgtatcgaa tgatgcagtc | 360 |
| tctaaaattg tatccgtaaa agacctctgc accgccgacg ggtctggatt atgggcaata | 420 |
| atcacagtcg agccagacta cccctggagg taaactccgg ggctggagcc ataaagatta | 480 |
| ggaattcatt aagaaatgta acaatcgacg ttctagatca taccacgccc ccactgtccg | 540 |
| gcagggtgaa cagaggagac tttcccctgt tacagtgtca gtgacaaaac aacttttttgg | 600 |
| catcggtgca ggtggtgagc catggcggcc cagatcattg aaattctttc cccggaggaa | 660 |
| atccgacgta cccttacccg tctggcttcc caggtaattt aggtaccgtt aagaaggagg | 720 |
| atccatatga tcttgatgga acgctggcgg aaatcaaacc gcatcccgat caggtcgtcg | 780 |
| tgcctgacaa tattctgcaa ggactacagc tactggcaac cgcaagtgat ggtgcattgg | 840 |
| cattgatatc agggcgctca atggtggagc ttgacgcact ggcaaaacct tatcgcttcc | 900 |
| cgttagcggg cgtgcatggg gcggagcgcc gtgacatcaa tggtaaaaca catatcgttc | 960 |
| atctgccgga tgcgattgcg cgtgatatta gcgtgcaact gcatacagtc atcgctcagt | 1020 |
| atcccggcgc ggagctggag gcgaaaggga tggcttttgc gctgcattat cgtcaggctc | 1080 |
| cgcagcatga agacgcatta atgacattag cgcaacgtat tactcagatc tggccacaaa | 1140 |
| tggcgttaca gcagggaaag tgtgttgtcg agatcaaacc gagaggtacc agtaaaggtg | 1200 |
| aggcaattgc agcttttatg caggaagctc cctttatcgg gcgaacgccc gtatttctgg | 1260 |
| gcgatgattt aaccgatgaa tctggcttcg cagtcgttaa ccgactgggc ggaatgtcag | 1320 |
| taaaaattgg cacaggtgca actcaggcat catggcgact ggcgggtgtg ccggatgtct | 1380 |
| ggagctggct tgaaatgata accaccgcat acaacaaaa aagagaaaat aacaggagtg | 1440 |
| atgactatga gtcgtttagt cgtagtatct aaccggattg caccaccaga cgagcacgcc | 1500 |
| gccagtgccg gtggccttgc cgttggcata ctggggcac tgaaagccgc aggcggactg | 1560 |
| tggtttggct ggagtggtga acagggaat gaggatcagc cgctaaaaaa ggtgaaaaaa | 1620 |
| ggtaacatta cgtgggcctc ttttaacctc agcgaacagg accttgacga atactacaac | 1680 |
| caattctcca atgccgttct ctggcccgct tttcattatc ggctcgatct ggtgcaattt | 1740 |
| cagcgtcctg cctgggacgg ctatctacgc gtaaatgcgt tgctggcaga taaattactg | 1800 |
| ccgctgttgc aagacgatga cattatctgg atccacgatt atcacctgtt gccatttgcg | 1860 |

```
catgaattac gcaaacgggg agtgaataat cgcattggtt tctttctgca tattcctttc    1920
ccgacaccgg aaatcttcaa cgcgctgccg acatatgaca ccttgcttga acagctttgt    1980
gattatgatt tgctgggttt ccagacagaa aacgatcgtc tggcgttcct ggattgtctt    2040
tctaacctga cccgcgtcac gacacgtagc gcaaaaagcc atacagcctg ggcaaagca     2100
tttcgaacag aagtctaccc gatcggcatt gaaccgaaag aaatagccaa acaggctgcc    2160
gggccactgc cgccaaaact ggcgcaactt aaagcggaac tgaaaaacgt acaaaatatc    2220
ttttctgtcg aacggctgga ttattccaaa ggtttgccag agcgttttct cgcctatgaa    2280
gcgttgctgc aaaaatatcc gcagcatcat ggtaaaattc gttatcccca gattgcacca    2340
acgtcgcgtg gtgatgtgca agcctatcag gatattcgtc atcagctcga aaatgaagct    2400
ggacgaatta atggtaaata cggcaatta ggctggacgc cgctttatta tttgaatcag     2460
cattttgacc gtaaattact gatgaaaata ttccgctact ctgacgtggg cttagtgacg    2520
ccactgcgtg acgggatgaa cctggtagca aaagagtatg ttgctgctca ggacccagcc    2580
aatccgggcg ttcttgttct ttcgcaattt gcgggagcgg caaacgagtt aacgtcggcg    2640
ttaattgtta cccctacga tcgtgacgaa gttgcagctg cgctggatcg tgcattgact     2700
atgtcgctgg cggaacgtat ttcccgtcat gcagaaatgc tggacgttat cgtgaaaaac    2760
gatattaacc actggcagga gtgcttcatt agcgacctaa agcagatagt tccgcgaagc    2820
gcggaaagcc agcagcgcga taaagttgct acctttccaa agcttgcgta ggagctagct    2880
gcctcgaaag gggatgcgat cgccacctc tcactccgct ggcggattcc tcttgagaac     2940
attttggtgg caggcgattc tggtaacgat gaggaaatgc tcaagggcca taatctcggc    3000
gttgtagttg gcaattactc accggaattg gagccactgc gcagctacga gcgcgtctat    3060
tttgctgagg gccactatgc taatggcatt ctggaagcct taaaacacta tcgctttttt    3120
gaggcgatcg cttaaccttt tcagaatgag acgttgatcg gcacgtaagc gtgagacgtt    3180
gatcggcacg taagaggttc caactttcac cataatgaaa taagatcact accgggcgta    3240
ttttttgagt tatcgagatt ttcaggagct aaggaagcta aaatggagaa aaaaatcact    3300
ggatatacca ccgttgatat atcccaatgg catcgtaaag aacattttga ggcatttcag    3360
tcagttgctc aatgtaccta taaccagacc gttcagctgg atattacggc cttttttaaag   3420
accgtaaaga aaaataagca caagttttat ccggccttta ttcacattct tgcccgcctg    3480
atgaatgctc atccggaatt ccgtatggca atgaaagacg gtgagctggt gatatgggat    3540
agtgttcacc cttgttacac cgttttccat gagcaaactg aaacgttttc atcgctctgg    3600
agtgaatacc acgacgattt ccggcagttt ctacacatat attcgcaaga tgtggcgtgt    3660
tacggtgaaa acctggccta tttccctaaa gggtttattg agaatatgtt ttcgtctca    3720
gccaatccct gggtgagttt caccagtttt gatttaaacg tggccaatat ggacaacttc    3780
ttcgccccg ttttcaccat gggcaaatat tatacgcaag cgacaaggt gctgatgccg     3840
ctggcgattc aggttcatca tgccgtttgt gatggcttcc atgtcggcag aatgcttaat    3900
gaattacaac agtactgcga tgagtggcag ggcgggcgt aatttttta aggcagttat     3960
tggtgccctt aaacgcctgg ttgctacgcc tgaataagtg ataataagcg gatgaatggc    4020
agaaattcga tgataagctg tcaaacacaa ccaccatcaa acaggatttt cgcctgctgg    4080
ggcaaaccag cgtggaccgc ttgctgcaac tctctcaggg ccaggcggtg aagggcaatc    4140
agctgttgcc cgtctcactg gtgaaaagaa aaaccaccct ggcgcccaat acgcaaaccg    4200
cctctccccg cgcgttggcc gattcattaa tgcagctggc acgacaggtt cccgactgg     4260
```

```
aaagcgggca gtgagcgcaa cgcaattaat gtaagttagc gcgaattgca agctggccga   4320
cgcgctgggc tacgtcttgc tggcgttcgg gagcagaaga gcatacatct ggaagcaaag   4380
ccaggaaagc ggcctatgga gctgtgcggc agcgctcagt aggcaatttt tcaaaatatt   4440
gttaagcctt ttctgagcat ggtattttc atggtattac caattagcag gaaaataagc    4500
cattgaatat aaaagataaa aatgtcttgt ttacaataga gtgggggggg tcagcctgcc   4560
gccttgggcc gggtgatgtc gtacttgccc gccgcgaact cggttaccgt ccagcccagc   4620
gcgaccagct ccggcaacgc ctcgcgcacc cgcttgcggc gcttgcgcat ggtcgaacca   4680
ctggcctctg acggcagac atagccgcac aaggtatcta tggaagcctt gccggttttg    4740
ccggggtcga tccagccaca cagccgctgg tgcagcaggc gggcggtttc gctgtccagc   4800
gcccgcacct cgtccatgct gatgcgcaca tgctggccgc cacccatgac ggcctgcgcg   4860
atcaagggt tcagggccac gtacaggcgc ccgtccgcct cgtcgctggc gtactccgac    4920
agcagccgaa accctgccg cttgcggcca ttctgggcga tgatggatac cttccaaagg    4980
cgctcgatgc agtcctgtat gtgcttgagc gccccaccac tatcgacctc tgccccgatt   5040
tcctttgcca gcgcccgata gctacctttg accacatggc attcagcggt gacgcctcc    5100
cacttgggtt ccaggaacag ccggagctgc cgtccgcctt cggtcttggg ttccgggcca   5160
agcactaggc cattaggccc agccatggcc accagcccctt gcaggatgcg cagatcatca   5220
gcgcccagcg gctccgggcc gctgaactcg atccgcttgc cgtcgccgta gtcatacgtc   5280
acgtccagct tgctgcgctt gcgctcgccc cgcttgaggg cacggaacag gccggggcc    5340
agacagtgcg ccgggtcgtg ccggacgtgg ctgaggctgt gcttgttctt aggcttcacc   5400
acggggcacc cccttgctct tgcgctgcct ctccagcacg gcgggcttga gcaccccgcc   5460
gtcatgccgc ctgaaccacc gatcagcgaa cggtgcgcca gttggcct tgctcacacc    5520
gaagcggacg aagaaccggc gctggtcgtc gtccacaccc cattcctcgg cctcggcgct   5580
ggtcatgctc gacaggtagg actgccagcg gatgttatcg accagtaccg agctgccccg   5640
gctggcctgc tgctggtcgc ctgcgcccat catggccgcg cccttgctgg catggtgcag   5700
gaacacgata gagcacccgg tatcggcggc gatggcctcc atgcgaccga tgacctgggc   5760
catgggccg ctggcgtttt cttcctcgat gtggaaccgg cgcagcgtgt ccagcaccat    5820
caggcggcg ccctcggcgg cgcgcttgag gccgtcgaac cactccgggg ccatgatgtt    5880
gggcaggctg ccgatcagcg gctggatcag caggccgtca gccacggctt gccgttcctc   5940
ggcgctgagg tgcgccccaa gggcgtgcag gcggtgatga atggcggtgg gcgggtcttc   6000
ggcgggcagg tagatcaccg ggcggtggg cagttcgccc acctccagca gatccggccc    6060
gcctgcaatc tgtgcggcca gttgcagggc cagcatggat ttaccggcac caccgggcga   6120
caccagcgcc ccgaccgtac cggccaccat gttgggcaaa acgtagtcca gcggtggcgg   6180
cgctgctgcg aacgcctcca gaatattgat aggcttatgg gtagccattg attgcctcct   6240
ttgcaggcag ttggtggtta ggcgctggcg gggtcactac ccccgccctg cgccgctctg   6300
agttcttcca ggcactcgcg cagcgcctcg tattcgtcgt cggtcagcca gaacttgcgc   6360
tgacgcatcc cttttggcctt catgcgctcg gcatatcgcg cttggcgtac agcgtcaggg   6420
ctggccagca ggtcgccggt ctgcttgtcc ttttggtctt tcatatcagt caccgagaaa   6480
cttgccgggg ccgaaaggct tgtcttcgcg gaacaaggac aaggtgcagc cgtcaaggtt   6540
aaggctggcc atatcagcga ctgaaaagcg gccagcctcg gccttgtttg acgtataacc   6600
aaagccaccg ggcaaccaat agcccttgtc acttttgatc aggtagaccg accctgaagc   6660
```

```
gcttttttcg tattccataa aaccccctto tgtgcgtgag tactcatagt ataacaggcg    6720
tgagtaccaa cgcaagcact acatgctgaa atctggcccg ccctgtcca tgcctcgctg    6780 gcggggtgcc ggtgcccgtg ccagctcggc ccgcgcaagc tggacgctgg cagacccat    6840 gaccttgctg acggtgcgct cgatgtaatc cgcttcgtgg ccgggcttgc gctctgccag    6900
cgctgggctg gcctcggcca tggccttgcc gatttcctcg gcactgcggc cccggctggc    6960
cagcttctgc gcggcgataa agtcgcactt gctgaggtca tgaccgaagc gcttgaccag    7020
cccggccatc tcgctgcggt actcgtccag cgccgtgcgc cggtggcggc taagctgccg    7080
ctcgggcagt tcgaggctgg ccagcctgcg ggccttctcc tgctgccgct gggcctgctc    7140
gatctgctgg ccagcctgct gcaccagcgc cgggccagcg gtggcggtct tgcccttgga    7200
ttcacgcagc agcacccacg gctgataacc ggcgcgggtg gtgtgcttgt ccttgcggtt    7260
ggtgaagccc gccaagcggc catagtggcg gctgtcggcg ctggccgggt cggcgtcgta    7320
ctcgctggca agcgtccggg caatctgccc ccgaagttca ccgcctgcgg cgtcggccac    7380
cttgacccat gcctgatagt tcttcgggct ggtttccact accagggcag gctcccggcc    7440
ctcggctttc atgtcatcca ggtcaaactc gctgaggtcg tccaccagca ccagaccatg    7500
ccgctcctgc tcggcgggcc tgatatacac gtcattgccc tgggcattca tccgcttgag    7560
ccatggcgtg ttctggagca cttcggcggc tgaccattcc cggttcatca tctgccggt    7620 gggtgcgtcc ctgacgccga tatcgaagcg ctcacagccc atggccttga gctgtcggcc    7680
tatggcctgc aaagtcctgt cgttcttcat cgggccacca agcgcagcca gatcgagccg    7740
tcctcggttg tcagtggcgt caggtcgagc aagagcaacg atgcgatcag cagcaccacc    7800
gtaggcatca tggaagccag catcacggtt agccatagct tccagtgcca ccccgcgac    7860 gcgctccggg cgctctgcgc ggcgctgctc acctcggcgg ctacctcccg caactctttg    7920
gccagctcca cccatgccgc ccctgtctgg cgctgggctt tcagccactc cgccgcctgc    7980
gcctcgctgg cctgcttggt ctggctcatg acctgccggg cttcgtcggc cagtgtcgcc    8040
atgctctggg ccagcggttc gatctgctcc gctaactcgt tgatgcctct ggatttcttc    8100
actctgtcga ttgcgttcat ggtctattgc ctcccggtat tcctgtaagt cgatgatctg    8160
ggcgttggcg tgtcgatgt tcagggccac gtctgcccgg tcggtgcgga tgccccggcc    8220
ttccatctcc accacgttcg gcccaggtg aacaccgggc aggcgctcga tgccctgcgc    8280
ctcaagtgtt ctgtggtcaa tgcgggcgtc gtggccagcc cgctctaatg cccggttggc    8340
atggtcggcc catgcctcgc gggtctgctc aagccatgcc ttgggcttga gcgcttcggt    8400
cttctgtgcc ccgcccttct ccggggtctt gccgttgtac cgcttgaacc actgagcggc    8460
gggccgctcg atgccgtcat tgatccgctc ggagatcatc aggtggcagt gcgggttctc    8520
gccgccaccg gcatggatgg ccagcgtata cggcaggcgc tcggcaccgg tcaggtgctg    8580
ggcgaactcg gacgccagcg ccttctgctg gtcgagggtc agctcgaccg gcagggcaaa    8640
ttcgacctcc ttgaacagcc gcccattggc gcgttcatac aggtcggcag catcccagta    8700
gtcggcgggc cgctcgacga actccggcat gtgcccggat tcggcgtgca agacttcatc    8760
catgtcgcgg gcatacttgc cttcgcgctg gatgtagtcg gccttggccc tggccgattg    8820
gccgcccgac ctgctgccgg ttttcgccgt aaggtgataa atcgccatgc tgcctcgctg    8880
ttgcttttgc ttttcggctc catgcaatgg ccctcggaga gcgcaccgcc cgaagggtgg    8940
ccgttaggcc agtttctcga agagaaaccg gtaagtgcgc cctcccctac aaagtagggt    9000
cgggattgcc gccgctgtgc ctccatgata gcctacgaga cagcacatta acaatgggt    9060
```

```
gtcaagatgg ttaaggggag caacaaggcg gcggatcggc tggccaagct cgaagaacaa    9120
cgagcgcgaa tcaatgccga aattcagcgg gagcgggcaa gggaacagca gcaagagcgc    9180
aagaacgaaa caaggcgcaa ggtgctggtg ggggccatga ttttggccaa ggtgaacagc    9240
agcgagtggc cggaggatcg gctcatggcg gcaatgdatg cgtaccttga acgcgaccac    9300
gaccgcgcct tgttcggtct gccgccacgc cagaaggatg agccgggctg aatgatcgac    9360
cgagacaggc cctgcgggc tgcacacgcg cccccaccct tcgggtaggg ggaaaggccg    9420
ctaaagcggc taaaagcgct ccagcgtatt tctgcggggt ttggtgtggg gtttagcggg    9480
ctttgccccgc ctttcccct gccgcgcagc ggtggggcgg tgtgtagcct agcgcagcga    9540
atagaccagc tatccggcct ctggccgggc atattgggca agggcagcag cgccccacaa    9600
gggcgctgat aaccgcgcct agtggattat tcttagataa tcatggatgg atttttccaa    9660
caccccgcca gccccgccc ctgctgggtt tgcaggtttg ggggcgtgac agttattgca    9720
ggggttcgtg acagttattg cagggggcg tgacagttat tgcaggggtt cgtgacagtt    9780
agtacgggag tgacgggcac tggctggcaa tgtctagcaa cggcaggcat ttcggctgag    9840
ggtaaaagaa ctttccgcta agcgatagac tgtatgtaaa cacagtattg caaggacgcg    9900
gaacatgcct catgtggcgg ccaggacggc cagccgggat cgggatactg gtcgttacca    9960
gagccaccga cccgagcaaa cccttctcta tcagatcgtt gacgagtatt acccggcatt   10020
cgctgcgctt atggcagagc agggaaagga attgccgggc tatgtgcaac gggaatttga   10080
agaatttctc caatgcgggc ggctggagca tggctttcta cggttcgct gcgagtcttg   10140
ccacgccgag cacctggtcg cttcagaaa tcaatctaaa gtatatatga gtaaacttgg   10200
tctgacagtt accaatgctt aatcagtgag gcacctatct cagcgatctg tctatttcgt   10260
tcatccatag ttgcctgact ccccgtcgtg tagataacta cgatacggga gggcttacca   10320
tctggcccca gtgctgcaat gataccgcga gacccacgct caccggctcc agatttatca   10380
gcaataaacc agccagccgg aagggccgag cgcagaagtg gtcctgcaac tttatccgcc   10440
tccatccagt ctattaattg ttgccgggaa gctagagtaa gtagttcgcc agttaatagt   10500
ttgcgcaacg ttgttgccat tgctacaggc atcgtggtgt cacgctcgtc gtttggtatg   10560
gcttcattca gctccggttc ccaacgatca aggcgagtta catgatcccc catgttgtgc   10620
aaaaaagcgg ttagctcctt cggtcctccg atcgttgtca gaagtaagtt ggccgcagtg   10680
ttatcactca tggttatggc agcactgcat aattctctta ctgtcatgcc atccgtaaga   10740
tgcttttctg tgactggtga gtactcaacc aagtcattct gagaatagtg tatgcggcga   10800
ccgagttgct cttgcccggc gtcaacacgg gataataccg cgccacatag cagaacttta   10860
aaagtgctca tcattggaaa acgttcttcg ggcgaaaac tctcaaggat cttaccgctg   10920
ttgagatcca gttcgatgta acccactcgt gcacccaact gatcttcagc atcttttact   10980
ttcaccagcg tttctgggtg agcaaaaaca ggaaggcaaa atgccgcaaa aaagggaata   11040
agggcgacac ggaaatgttg aatactcata ctcttccttt ttcaatatta ttgaagcatt   11100
tatcagggtt attgtctcat gagcggatac atatttgaat gtatttagaa aaataaacaa   11160
aagagtttgt agaaacgcaa aaaggccatc cgtcaggatg gccttctgct taatttgatg   11220
cctggcagtt tatggcgggc gtcctgcccg ccacccctccg ggccgttgct tcgcaacgtt   11280
caaatccgct cccggcggat ttgtcctact caggagagcg ttcaccgaca aacaacagat   11340
aaaacgaa                                                             11348
```

<210> SEQ ID NO 122

<211> LENGTH: 11527
<212> TYPE: DNA
<213> ORGANISM: Artificial Sequence
<220> FEATURE:
<223> OTHER INFORMATION: plasmid pLybAL29 containing otsBA operon

<400> SEQUENCE: 122

| | | | | | |
|---|---|---|---|---|---|
| aggcccagtc | tttcgactga | gcctttcgtt | ttatttgatg | cctggcagtt | ccctactctc | 60 |
| gcatggggag | accccacact | accatcggcg | ctacggcgtt | tcacttctga | gttcggcatg | 120 |
| gggtcaggtg | ggaccaccgc | gctactgccg | ccaggcaaat | tctgttttat | cagaccgctt | 180 |
| ctgcgttctg | atttaatctg | tatcaggctg | aaaatcttct | ctcatccgcc | aaaacagcca | 240 |
| agcttgcatg | ccgagcctga | tgtgtgacac | ctaagatcac | tccagttctc | tttggaaact | 300 |
| ggctgatgag | tgaagacacc | atctttggca | agatcatccg | gcgcgagatt | ccagcagaca | 360 |
| ttgtttatga | agatgatctc | tgtctggctt | ttcgagatgt | ggcaccccaa | gcgccggttc | 420 |
| acattctggt | gattcccaag | caaccaattg | ccaacctttt | ggaagcgaca | gcagaacatc | 480 |
| aagcgctgct | gggtcatttg | ttgctgactg | taaaggcgat | cgcggcccaa | gaaggactca | 540 |
| ccgagggcta | ccgcaccgtg | attaacacgg | gccctgcggg | tggcaaaacc | gtttaccacc | 600 |
| tgcatattca | cttactgggc | gggcgatcgc | tggcttggcc | gcccggctga | gaaaagtctg | 660 |
| aaagttcttt | acaaaactca | atctgcttgt | tagattttac | tcacgaggct | attaagtctc | 720 |
| gtaaatagtt | caactaagga | ctcatcgcaa | aatgacgact | gcattgcagc | ggcgcgagag | 780 |
| cgccagcctg | tggcagcagt | tctgcgagtg | ggtaaccagc | accgacaacc | gcctctatgt | 840 |
| gggttggttc | ggcgtgctga | tgatccccac | tctgctgacc | ggtaccgtta | agaaggagga | 900 |
| tccatatgat | cttgatggaa | cgctggcgga | aatcaaaccg | catcccgatc | aggtcgtcgt | 960 |
| gcctgacaat | attctgcaag | gactacagct | actggcaacc | gcaagtgatg | gtgcattggc | 1020 |
| attgatatca | gggcgctcaa | tggtggagct | tgacgcactg | gcaaaacctt | atcgcttccc | 1080 |
| gttagcgggc | gtgcatgggg | cggagcgccg | tgacatcaat | ggtaaaacac | atatcgttca | 1140 |
| tctgccggat | gcgattgcgc | gtgatattag | cgtgcaactg | catacagtca | tcgctcagta | 1200 |
| tccccggcgcg | gagctggagg | cgaaagggat | ggcttttgcg | ctgcattatc | gtcaggctcc | 1260 |
| gcagcatgaa | gacgcattaa | tgacattagc | gcaacgtatt | actcagatct | ggccacaaat | 1320 |
| ggcgttacag | cagggaaagt | gtgttgtcga | gatcaaaccg | agaggtacca | gtaaggtgaa | 1380 |
| gcaattgca | gcttttatgc | aggaagctcc | ctttatcggg | cgaacgcccg | tatttctggg | 1440 |
| cgatgattta | accgatgaat | ctggcttcgc | agtcgttaac | cgactgggcg | gaatgtcagt | 1500 |
| aaaaattggc | acaggtgcaa | ctcaggcatc | atggcgactg | gcgggtgtgc | cggatgtctg | 1560 |
| gagctggctt | gaaatgataa | ccaccgcatt | acaacaaaaa | agagaaaata | acaggagtga | 1620 |
| tgactatgag | tcgtttagtc | gtagtatcta | accggattgc | accaccagac | gagcacgccg | 1680 |
| ccagtgccgg | tggccttgcc | gttggcatac | tgggggcact | gaaagccgca | ggcggactgt | 1740 |
| ggtttggctg | gagtggtgaa | acagggaatg | aggatcagcc | gctaaaaaag | gtgaaaaaag | 1800 |
| gtaacattac | gtgggcctct | tttaacctca | gcgaacagga | ccttgacgaa | tactacaacc | 1860 |
| aattctccaa | tgccgttctc | tggcccgctt | ttcattatcg | gctcgatctg | gtgcaatttc | 1920 |
| agcgtcctgc | ctgggacggc | tatctacgcg | taaatgcgtt | gctggcagat | aaattactgc | 1980 |
| cgctgttgca | agacgatgac | attatctgga | tccacgatta | tcacctgttg | ccatttgcgc | 2040 |
| atgaattacg | caaacgggga | gtgaataatc | gcattggttt | ctttctgcat | attccttttc | 2100 |
| cgacaccgga | aatcttcaac | gcgctgccga | catatgacac | cttgcttgaa | cagctttgtg | 2160 |

-continued

```
attatgattt gctgggtttc cagacagaaa acgatcgtct ggcgttcctg gattgtcttt    2220
ctaacctgac ccgcgtcacg acacgtagcg caaaaagcca tacagcctgg ggcaaagcat    2280
ttcgaacaga agtctacccg atcggcattg aaccgaaaga aatagccaaa caggctgccg    2340
ggccactgcc gccaaaactg gcgcaactta agcggaact gaaaaacgta caaaatatct     2400
tttctgtcga acggctggat tattccaaag gtttgccaga gcgttttctc gcctatgaag    2460
cgttgctgga aaaatatccg cagcatcatg gtaaaattcg ttatacccag attgcaccaa    2520
cgtcgcgtgg tgatgtgcaa gcctatcagg atattcgtca tcagctcgaa atgaagctg    2580 gacgaattaa tggtaaatac gggcaattag gctggacgcc gctttattat ttgaatcagc    2640
attttgaccg taaattactg atgaaaatat ccgctactc tgacgtgggc ttagtgacgc    2700
cactgcgtga cggatgaac ctggtagcaa aagagtatgt tgctgctcag gacccagcca     2760
atccgggcgt tcttgttctt tcgcaatttg cgggagcggc aaacgagtta acgtcggcgt    2820
taattgttaa cccctacgat cgtgacgaag ttgcagctgc gctggatcgt gcattgacta    2880
tgtcgctggc ggaacgtatt tcccgtcatg cagaaatgct ggacgttatc gtgaaaaacg    2940
atattaacca ctggcaggag tgcttcatta gcgacctaaa gcagatagtt ccgcgaagcg    3000
cggaaagcca gcagcgcgat aaagttgcta cctttccaaa gcttgcgtag gagctagctg    3060
cctcgaaagg ggatgcgatt cgccacctct cactccgctg gcggattcct cttgagaaca    3120
ttttggtggc aggcgattct ggtaacgatg aggaaatgct caagggccat aatctcggcg    3180
ttgtagttgg caattactca ccggaattgg agccactgcg cagctacgag cgcgtctatt    3240
ttgctgaggg ccactatgct aatggcattc tggaagcctt aaaacactat cgcttttttg    3300
aggcgatcgc ttaacctttt cagaatgaga cgttgatcgg cacgtaagcg tgagacgttg    3360
atcggcacgt aagaggttcc aactttcacc ataatgaaat aagatcacta ccgggcgtat    3420
tttttgagtt atcgagattt tcaggagcta aggaagctaa aatggagaaa aaaatcactg    3480
gatataccac cgttgatata tcccaatggc atcgtaaaga acattttgag gcatttcagt    3540
cagttgctca atgtacctat aaccagaccg ttcagctgga tattacggcc tttttaaaga    3600
ccgtaaagaa aaataagcac aagttttatc cggcctttat tcacattctt gcccgcctga    3660
tgaatgctca tccggaattc cgtatggcaa tgaaagacgg tgagctggtg atatgggata    3720
gtgttcaccc ttgttacacc gttttccatg agcaaactga aacgttttca tcgctctgga    3780
gtgaataccc acgacgattc cggcagtttc tacacatata ttcgcaagat gtggcgtgtt    3840
acggtgaaaa cctggcctat ttccctaaag ggtttattga gaatatgttt ttcgtctcag    3900
ccaatccctg ggtgagtttc accagttttg atttaaacgt ggccaatatg gacaacttct    3960
tcgcccccgt tttcaccatg gcaaatatt atacgcaagg cgacaaggtg ctgatgccgc     4020
tggcgattca ggttcatcat gccgtttgtg atggcttcca tgtcggcaga atgcttaatg    4080
aattacaaca gtactgcgat gagtggcagg gcggggcgta atttttttaa ggcagttatt    4140
ggtgccctta aacgcctggt tgctacgcct gaataagtga taataagcgg atgaatggca    4200
gaaattcgat gataagctgt caaacacaac caccatcaaa caggatttc gcctgctggg    4260 gcaaaccagc gtggaccgct tgctgcaact ctctcagggc caggcggtga agggcaatca    4320
gctgttgccc gtctcactgg tgaaaagaaa accaccctg gcgcccaata cgcaaaccgc     4380
ctctccccgc gcgttggccg attcattaat gcagctggca cgacaggttt cccgactgga    4440
aagcgggcag tgagcgcaac gcaattaatg taagttagcg cgaattgcaa gctgccgac     4500 gcgctgggct acgtcttgct ggcgttcggg agcagaagag catacatctg gaagcaaagc    4560
```

```
caggaaagcg gcctatggag ctgtgcggca gcgctcagta ggcaatttt caaaatattg   4620 ttaagccttt tctgagcatg gtattttca tggtattacc aattagcagg aaaataagcc   4680
attgaatata aaagataaaa atgtcttgtt tacaatagag tgggggggt cagcctgccg   4740 ccttgggccg ggtgatgtcg tacttgcccg ccgcgaactc ggttaccgtc cagcccagcg   4800
cgaccagctc cggcaacgcc tcgcgcaccc gcttgcggcg cttgcgcatg gtcgaaccac   4860
tggcctctga cggccagaca tagccgcaca aggtatctat ggaagccttg ccggttttgc   4920
cggggtcgat ccagccacac agccgctggt gcagcaggcg ggcggtttcg ctgtccagcg   4980
cccgcacctc gtccatgctg atgcgcacat gctggccgcc acccatgacg gcctgcgcga   5040
tcaaggggtt cagggccacg tacaggcgcc cgtccgcctc gtcgctggcg tactccgaca   5100
gcagccgaaa cccctgccgc ttgcggccat tctgggcgat gatggatacc ttccaaaggc   5160
gctcgatgca gtcctgtatg tgcttgagcg ccccaccact atcgacctct gccccgattt   5220
cctttgccag cgcccgatag ctacctttga ccacatggca ttcagcggtg acggcctccc   5280
acttgggttc caggaacagc cggagctgcc gtccgccttc ggtcttgggt tccgggccaa   5340
gcactaggcc attaggccca gccatggcca ccagcccttg caggatgcgc agatcatcag   5400
cgcccagcgg ctccgggccg ctgaactcga tccgcttgcc gtcgccgtag tcatacgtca   5460
cgtccagctt gctgcgcttg cgctcgcccc gcttgagggc acggaacagg ccggggccta   5520
gacagtgcgc cgggtcgtgc cggacgtggc tgaggctgtg cttgttctta ggcttcacca   5580
cggggcaccc ccttgctctt gcgctgcctc tccagcacgg cgggcttgag caccccgccg   5640
tcatgccgcc tgaaccaccg atcagcgaac ggtgcgccat agttggcctt gctcacaccg   5700
aagcggacga agaaccggcg ctggtcgtcg tccacacccc attcctcggc ctcggcgctg   5760
gtcatgctcg acaggtagga ctgccagcgg atgttatcga ccagtaccga gctgcccgg   5820 ctggcctgct gctggtcgcc tgcgcccatc atggccgcgc ccttgctggc atggtgcagg   5880
aacacgatag agcacccggt atcggcggcg atggcctcca tgcgaccgat gacctgggcc   5940
atggggccgc tggcgttttc ttcctcgatg tggaaccggc gcagcgtgtc cagcaccatc   6000
aggcggcggc cctcggcggc gcgcttgagg ccgtcgaacc actccggggc catgatgttg   6060
ggcaggctgc cgatcagcgg ctggatcagc aggccgtcag ccacggcttg ccgttcctcg   6120
gcgctgaggt gcgccccaag ggcgtgcagg cggtgatgaa tggcggtggg cgggtcttcg   6180
gcgggcaggt agatcaccgg gccggtgggc agttcgccca cctccagcag atccggcccg   6240
cctgcaatct gtgcgccag ttgcaggcc agcatggatt taccggcacc accgggcgac   6300
accagcgccc cgaccgtacc ggccaccatg ttgggcaaaa cgtagtccag cggtggcggc   6360
gctgctgcga acgcctccag aatattgata ggcttatggg tagccattga ttgcctcctt   6420
tgcaggcagt tggtggttag gcgctggcgg ggtcactacc cccgccctgc gccgctctga   6480
gttcttccag gcactcgcgc agcgcctcgt attcgtcgtc ggtcagccag aacttgcgct   6540
gacgcatccc tttggccttc atgcgctcgg catatcgcgc ttggcgtaca gcgtcagggc   6600
tggccagcag gtcgccggtc tgcttgtcct tttggtcttt catatcagtc accgagaaac   6660
ttgccggggc cgaaaggctt gtcttcgcgg aacaaggaca aggtgcagcc gtcaaggtta   6720
aggctggcca tatcagcgac tgaaaagcgg ccagcctcgg ccttgtttga cgtataacca   6780
aagccaccgg gcaaccaata gcccttgtca cttttgatca ggtagaccga ccctgaagcg   6840 ctttttcgt attccataaa acccccttct gtgcgtgagt actcatagta taacaggcgt   6900
gagtaccaac gcaagcacta catgctgaaa tctggcccgc cctgtccat gcctcgctgg   6960
```

```
cggggtgccg gtgcccgtgc cagctcggcc cgcgcaagct ggacgctggg cagacccatg    7020
accttgctga cggtgcgctc gatgtaatcc gcttcgtggc cgggcttgcg ctctgccagc    7080
gctgggctgg cctcggccat ggccttgccg atttcctcgg cactgcggcc ccggctggcc    7140
agcttctgcg cggcgataaa gtcgcacttg ctgaggtcat gaccgaagcg cttgaccagc    7200
ccggccatct cgctgcggta ctcgtccagc gccgtgcgcc ggtggcggct aagctgccgc    7260
tcgggcagtt cgaggctggc cagcctgcgg gccttctcct gctgccgctg ggcctgctcg    7320
atctgctggc cagcctgctg caccagcgcc gggccagcgg tggcggtctt gcccttggat    7380
tcacgcagca gcacccacgg ctgataaccg gcgcgggtgg tgtgcttgtc cttgcggttg    7440
gtgaagcccg ccaagcggcc atagtggcgg ctgtcggcgc tggccgggtc ggcgtcgtac    7500
tcgctggcca gcgtccgggc aatcgccccc gaagttcac cgcctgcggc gtcggccacc    7560
ttgacccatg cctgatagtt cttcgggctg gtttccacta ccagggcagg ctcccggccc    7620
tcggctttca tgtcatccag gtcaaactcg ctgaggtcgt ccaccagcac cagaccatgc    7680
cgctcctgct cggcgggcct gatatacacg tcattgccct gggcattcat ccgcttgagc    7740
catggcgtgt tctggagcac ttcggcggct gaccattccc ggttcatcat ctggccggtg    7800
ggtgcgtccc tgacgccgat atcgaagcgc tcacagccca tggccttgag ctgtcggcct    7860
atggcctgca aagtcctgtc gttcttcatc gggccaccaa gcgcagccag atcgagccgt    7920
cctcggttgt cagtggcgtc aggtcgagca agagcaacga tgcgatcagc agcaccaccg    7980
taggcatcat ggaagccagc atcacggtta gccatagctt ccagtgccac ccccgcgacg    8040
cgctccgggc gctctgcgcg gcgctgctca cctcggcggc tacctcccgc aactctttgg    8100
ccagctccac ccatgccgcc cctgtctggc gctgggcttt cagccactcc gccgcctgcg    8160
cctcgctggc ctgcttggtc tggctcatga cctgccgggc ttcgtcggcc agtgtcgcca    8220
tgctctgggc cagcggttcg atctgctccg ctaactcgtt gatgcctctg gatttcttca    8280
ctctgtcgat tgcgttcatg gtctattgcc tcccggtatt cctgtaagtc gatgatctgg    8340
gcgttggcgg tgtcgatgtt cagggccacg tctgcccggt cggtgcggat gccccggcct    8400
tccatctcca ccacgttcgg ccccaggtga acaccgggca ggcgctcgat gccctgcgcc    8460
tcaagtgttc tgtggtcaat gcgggcgtcg tggccagccc gctctaatgc ccggttggca    8520
tggtcggccc atgcctcgcg ggtctgctca agccatgcct gggcttgag cgcttcggtc    8580 ttctgtgccc cgcccttctc cggggtcttg ccgttgtacc gcttgaacca ctgagcggcg    8640
ggccgctcga tgccgtcatt gatccgctcg gagatcatca ggtggcagtg cgggttctcg    8700
ccgccaccgg catggatggc cagcgtatac ggcaggcgct cggcaccggt caggtgctgg    8760
gcgaactcga cgccagcgc cttctgctgg tcgagggtca gctcgaccgg cagggcaaat    8820
tcgacctcct tgaacagccg cccattggcg cgttcataca ggtcggcagc atcccagtag    8880
tcggcgggcc gctcgacgaa ctccggcatg tgcccggatt cggcgtgcaa gacttcatcc    8940
atgtcgcggg catacttgcc ttcgcgctgg atgtagtcgg ccttggccct ggccgattgg    9000
ccgcccgacc tgctgccggt tttcgccgta aggtgataaa tcgccatgct gcctcgctgt    9060
tgcttttgct tttcggctcc atgcaatggc cctcggagag cgcaccgccc gaagggtggc    9120
cgttaggcca gttctctcgaa gagaaaccgg taagtgcgcc ctccctaca aagtagggtc    9180 gggattgccg ccgctgtgcc tccatgatag cctacgagac agcacattaa caatgggtg    9240 tcaagatggt taaggggagc aacaaggcgg cggatcggct ggccaagctc gaagaacaac    9300
gagcgcgaat caatgccgaa attcagcggg agcgggcaag ggaacagcag caagagcgca    9360
```

| | | | | |
|---|---|---|---|---|
| agaacgaaac | aaggcgcaag | gtgctggtgg | gggccatgat | tttggccaag gtgaacagca | 9420 |
| gcgagtggcc | ggaggatcgg | ctcatggcgg | caatggatgc | gtaccttgaa cgcgaccacg | 9480 |
| accgcgcctt | gttcggtctg | ccgccacgcc | agaaggatga | gccgggctga atgatcgacc | 9540 |
| gagacaggcc | ctgcggggct | gcacacgcgc | ccccacccctt | cgggtagggg gaaaggccgc | 9600 |
| taaagcggct | aaaagcgctc | cagcgtattt | ctgcggggtt | tggtgtgggg tttagcgggc | 9660 |
| tttgcccgcc | tttccccctg | ccgcgcagcg | gtggggcggt | gtgtagccta gcgcagcgaa | 9720 |
| tagaccagct | atccggcctc | tggccgggca | tattgggcaa | gggcagcagc gccccacaag | 9780 |
| ggcgctgata | accgcgccta | gtggattatt | cttagataat | catggatgga tttttccaac | 9840 |
| accccgccag | cccccgcccc | tgctgggttt | gcaggtttgg | gggcgtgaca gttattgcag | 9900 |
| gggttcgtga | cagttattgc | agggggggcgt | gacagttatt | gcaggggttc gtgacagtta | 9960 |
| gtacgggagt | gacgggcact | ggctggcaat | gtctagcaac | ggcaggcatt tcggctgagg | 10020 |
| gtaaaagaac | tttccgctaa | gcgatagact | gtatgtaaac | acagtattgc aaggacgcgg | 10080 |
| aacatgcctc | atgtggcggc | caggacggcc | agccgggatc | gggatactgg tcgttaccag | 10140 |
| agccaccgac | ccgagcaaac | ccttctctat | cagatcgttg | acgagtatta cccggcattc | 10200 |
| gctgcgctta | tggcagagca | gggaaaggaa | ttgccgggct | atgtgcaacg ggaatttgaa | 10260 |
| gaatttctcc | aatgcgggcg | gctggagcat | ggctttctac | gggttcgctg cgagtcttgc | 10320 |
| cacgccgagc | acctggtcgc | tttcagaaat | caatctaaag | tatatatgag taaacttggt | 10380 |
| ctgacagtta | ccaatgctta | atcagtgagg | cacctatctc | agcgatctgt ctatttcgtt | 10440 |
| catccatagt | tgcctgactc | cccgtcgtgt | agataactac | gatacgggag ggcttaccat | 10500 |
| ctggccccag | tgctgcaatg | ataccgcgag | acccacgctc | accggctcca gatttatcag | 10560 |
| caataaacca | gccagccgga | agggccgagc | gcagaagtgg | tcctgcaact ttatccgcct | 10620 |
| ccatccagtc | tattaattgt | tgccgggaag | ctagagtaag | tagttcgcca gttaatagtt | 10680 |
| tgcgcaacgt | tgttgccatt | gctacaggca | tcgtggtgtc | acgctcgtcg tttggtatgg | 10740 |
| cttcattcag | ctccggttcc | caacgatcaa | ggcgagttac | atgatccccc atgttgtgca | 10800 |
| aaaaagcggt | tagctccttc | ggtcctccga | tcgttgtcag | aagtaagttg gccgcagtgt | 10860 |
| tatcactcat | ggttatggca | gcactgcata | attctcttac | tgtcatgcca tccgtaagat | 10920 |
| gcttttctgt | gactggtgag | tactcaacca | agtcattctg | agaatagtgt atgcggcgac | 10980 |
| cgagttgctc | ttgcccggcg | tcaacacggg | ataataccgc | gccacatagc agaactttaa | 11040 |
| aagtgctcat | cattggaaaa | cgttcttcgg | ggcgaaaact | ctcaaggatc ttaccgctgt | 11100 |
| tgagatccag | ttcgatgtaa | cccactcgtg | cacccaactg | atcttcagca tcttttactt | 11160 |
| tcaccagcgt | ttctgggtga | gcaaaaacag | gaaggcaaaa | tgccgcaaaa aagggaataa | 11220 |
| gggcgacacg | gaaatgttga | atactcatac | tcttcctttt | tcaatattat tgaagcattt | 11280 |
| atcagggtta | ttgtctcatg | agcggataca | tatttgaatg | tatttagaaa aataaacaaa | 11340 |
| agagtttgta | gaaacgcaaa | aaggccatcc | gtcaggatgg | ccttctgctt aatttgatgc | 11400 |
| ctggcagttt | atgcgcggcg | tcctgcccgc | caccctccgg | gccgttgctt cgcaacgttc | 11460 |
| aaatccgctc | ccggcggatt | tgtcctactc | aggagagcgt | tcaccgacaa acaacagata | 11520 |
| aaacgaa | | | | | 11527 |

<210> SEQ ID NO 123
<211> LENGTH: 11769
<212> TYPE: DNA
<213> ORGANISM: Artificial Sequence
<220> FEATURE:

<223> OTHER INFORMATION: plasmid pLybAL30 containing otsBA operon

<400> SEQUENCE: 123

```
aggcccagtc tttcgactga gcctttcgtt ttatttgatg cctggcagtt ccctactctc      60
gcatggggag accccacact accatcggcg ctacggcgtt tcacttctga gttcggcatg     120
gggtcaggtg ggaccaccgc gctactgccg ccaggcaaat tctgttttat cagaccgctt     180
ctgcgttctg atttaatctg tatcaggctg aaaatcttct ctcatccgcc aaaacagcca     240
agcttgcatg caccagtaaa cataaatctc cccggcgacg caaaaaacgg gtgaccatca     300
agccggtgcg cttcggcatt tttctgcttt gcctagcagg cattgtgggg ggcaactg      360
ccctaattat caatcgtact ggcgatcccc taggtgggtt gctagaagac cccctagatg     420
ttttcctgga ccaaccttca gaatttatcc ccgatgaagc cacgagccgg aatttgattc     480
tcagtcaacc caacttcaat cagcaagtgg gtcagatggt agtacaaggc tggcttgata     540
gtaaaaagtt agcctttggc caaaactacg atgtcgggc attgcagagt gttttagccc     600
ccaatctcct tgcccaacaa cggggtcggg cccaacggga tcaagcccaa aaggtctatc     660
accaatacga acacaagttg cagatttag cctatcaagt taaccccaa gaccccaacc     720
gagccaccgt tactgcccgg gtagaagaaa ttagccagcc ctttacccta ggtaatcaac     780
agcagaaggg ctccgccacc aaagatgact tgactgtgcg ctatcagcta gtacgacacc     840
aaggggtttg gaaaattgac caaatacaag tggtaaatgg ccccgttag tgcgtggcgt      900
taactcccct tttgaccaat ggcatacggc tagatgcccc cataggtacg aaacctgca     960
cttccgagaa ctaagcccct accgtcacta taagagtgtg aacgtgtcgg ccccaggcaa    1020
tggattggaa ccatggcttt tcggcccatc gttgtgtctt atattcttac ttgttaacgg    1080
gagttaatta aaattatggg aaaagttgtt gggattgacc tcggtaccgt taagaaggag    1140
gatccatatg atcttgatgg aacgctggcg gaaatcaaac cgcatcccga tcaggtcgtc    1200
gtgcctgaca atattctgca aggactacag ctactggcaa ccgcaagtga tggtgcattg    1260
gcattgatat cagggcgctc aatggtggag cttgacgcac tggcaaaacc ttatcgcttc    1320
ccgttagcgg gcgtgcatgg ggcggagcgc cgtgacatca atggtaaaac acatatcgtt    1380
catctgccgg atgcgattgc gcgtgatatt agcgtgcaac tgcatacagt catcgctcag    1440
tatcccggcg cggagctgga ggcgaaaggg atggcttttg cgctgcatta tcgtcaggct    1500
ccgcagcatg aagacgcatt aatgacatta gcgcaacgta ttactcagat ctggccacaa    1560
atggcgttac agcagggaaa gtgtgttgtc gagatcaaac cgagaggtac cagtaaaggt    1620
gaggcaattg cagctttttat gcaggaagct ccctttatcg ggcgaacgcc cgtatttctg    1680
ggcgatgatt taaccgatga atctggcttc gcagtcgtta accgactggg cggaatgtca    1740
gtaaaaattg gcacaggtgc aactcaggca tcatggcgac tggcgggtgt gccggatgtc    1800
tggagctggc ttgaaatgat aaccaccgca ttacaacaaa aaagagaaaa taacaggagt    1860
gatgactatg agtcgtttag tcgtagtatc taaccggatt gcaccaccag acgagcacgc    1920
cgccagtgcc ggtggccttg ccgttggcat actgggggca ctgaaagccg caggcggact    1980
gtggtttggc tggagtggtg aaacagggaa tgaggatcag ccgctaaaaa aggtgaaaaa    2040
aggtaacatt acgtgggcct cttttaacct cagcgaacag gaccttgacg aatactacaa    2100
ccaattctcc aatgccgttc tctggcccgc ttttcattat cggctcgatc tggtgcaatt    2160
tcagcgtcct gcctgggacg gctatctacg cgtaaatgcg ttgctggcag ataaattact    2220
gccgctgttg caagacgatg acattatctg gatccacgat tatcacctgt tgccatttgc    2280
```

```
gcatgaatta cgcaaacggg gagtgaataa tcgcattggt ttctttctgc atattccttt      2340
cccgacaccg gaaatcttca acgcgctgcc gacatatgac accttgcttg aacagctttg      2400
tgattatgat ttgctgggtt tccagacaga aaacgatcgt ctggcgttcc tggattgtct      2460
ttctaacctg acccgcgtca cgacacgtag cgcaaaaagc catacagcct ggggcaaagc      2520
atttcgaaca gaagtctacc cgatcggcat tgaaccgaaa gaaatagcca acaggctgc      2580 cgggccactg ccgccaaaac tggcgcaact taaagcggaa ctgaaaaacg tacaaaatat      2640
cttttctgtc gaacggctgg attattccaa aggtttgcca gagcgttttc tcgcctatga      2700
agcgttgctg gaaaaatatc cgcagcatca tggtaaaatt cgttataccc agattgcacc      2760
aacgtcgcgt ggtgatgtgc aagcctatca ggatattcgt catcagctcg aaaatgaagc      2820
tggacgaatt aatggtaaat acgggcaatt aggctggacg ccgctttatt atttgaatca      2880
gcattttgac cgtaaattac tgatgaaaat attccgctac tctgacgtgg gcttagtgac      2940
gccactgcgt gacgggatga acctggtagc aaaagagtat gttgctgctc aggacccagc      3000
caatccgggc gttcttgttc tttcgcaatt tgcgggagcg gcaaacgagt taacgtcggc      3060
gttaattgtt aaccgctacg atcgtgacga agttgcagct cgcgctggat cgtgcattgac      3120 tatgtcgctg gcggaacgta tttcccgtca tgcagaaatg ctggacgtta tcgtgaaaaa      3180
cgatattaac cactggcagg agtgcttcat tagcgaccta aagcagatag ttccgcgaag      3240
cgcggaaagc cagcagcgcg ataaagttgc taccttccca aagcttgcgt aggagctagc      3300
tgcctcgaaa ggggatgcga ttcgccacct ctcactccgc tggcggattc ctcttgagaa      3360
cattttggtg gcaggcgatt ctggtaacga tgaggaaatg ctcaagggcc ataatctcgg      3420
cgttgtagtt ggcaattact caccggaatt ggagccactg cgcagctacg agcgcgtcta      3480
ttttgctgag ggccactatg ctaatggcat tctggaagcc ttaaaacact atcgcttttt      3540
tgaggcgatc gcttaacctt ttcagaatga gacgttgatc ggcacgtaag cgtgagacgt      3600
tgatcggcac gtaagaggtt ccaactttca ccataatgaa ataagatcac taccgggcgt      3660
attttttgag ttatcgagat tttcaggagc taaggaagct aaaatggaga aaaaaatcac      3720
tggatatacc accgttgata tatcccaatg gcatcgtaaa gaacattttg aggcatttca      3780
gtcagttgct caatgtacct ataaccagac cgttcagctg gatattacgg cctttttaaa      3840
gaccgtaaag aaaaataagc acaagtttta tccggccttt attcacattc ttgcccgcct      3900
gatgaatgct catccggaat tccgtatggc aatgaaagac ggtgagctgg tgatatggga      3960
tagtgttcac ccttgttaca ccgttttcca tgagcaaact gaaacgtttt catcgctctg      4020
gagtgaatac cacgacgatt tccggcagtt tctacacata tattcgcaag atgtggcgtg      4080
ttacggtgaa aacctggcct atttccctaa agggtttatt gagaatatgt ttttcgtctc      4140
agccaatccc tgggtgagtt tcaccagttt tgatttaaac gtggccaata tggacaactt      4200
cttcgccccc gttttcacca tgggcaaata ttatacgcaa ggcgacaagg tgctgatgcc      4260
gctggcgatt caggttcatc atgccgtttg tgatggcttc catgtcggca gaatgcttaa      4320
tgaattacaa cagtactgcg atgagtggca gggcggggcg taatttttt aaggcagtta      4380 ttggtgccct taaacgcctg gttgctacgc ctgaataagt gataataagc ggatgaatgg      4440
cagaaattcg atgataagct gtcaaacaca accaccatca acaggatttt cgcctgctg      4500 gggcaaacca gcgtggaccg cttgctgcaa ctctctcagg gccaggcggt gaagggcaat      4560
cagctgttgc ccgtctcact ggtgaaaaga aaaccaccc tggcgcccaa tacgcaaacc      4620
gcctctcccc gcgcgttggc cgattcatta atgcagctgg cacgacaggt ttcccgactg      4680
```

```
gaaagcgggc agtgagcgca acgcaattaa tgtaagttag cgcgaattgc aagctggccg    4740
acgcgctggg ctacgtcttg ctggcgttcg ggagcagaag agcatacatc tggaagcaaa    4800
gccaggaaag cggcctatgg agctgtgcgg cagcgctcag taggcaattt ttcaaaatat    4860
tgttaagcct tttctgagca tggtattttt catggtatta ccaattagca ggaaaataag    4920
ccattgaata taaaagataa aaatgtcttg tttacaatag agtggggggg gtcagcctgc    4980
cgccttgggc cgggtgatgt cgtacttgcc cgccgcgaac tcggttaccg tccagcccag    5040
cgcgaccagc tccggcaacg cctcgcgcac ccgcttgcgg cgcttgcgca tggtcgaacc    5100
actggcctct gacggccaga catagccgca caaggtatct atggaagcct tgccggtttt    5160
gccggggtcg atccagccac acagccgctg gtgcagcagg cgggcggttt cgctgtccag    5220
cgcccgcacc tcgtccatgc tgatgcgcac atgctggccg ccacccatga cggcctgcgc    5280
gatcaagggg ttcagggcca cgtacaggcg cccgtccgcc tcgtcgctgg cgtactccga    5340
cagcagccga aacccctgcc gcttgcggcc attctgggcg atgatggata ccttccaaag    5400
gcgctcgatg cagtcctgta tgtgcttgag cgccccacca ctatcgacct ctgccccgat    5460
ttcctttgcc agcgcccgat agctacctttt gaccacatgg cattcagcgg tgacggcctc    5520
ccacttgggt tccaggaaca gccggagctg ccgtccgcct tcggtcttgg gttccgggcc    5580
aagcactagg ccattaggcc cagccatggc caccagccct tgcaggatgc gcagatcatc    5640
agcgcccagc ggctccgggc cgctgaactc gatccgcttg ccgtcgccgt agtcatacgt    5700
cacgtccagc ttgctgcgct tgcgctcgcc ccgcttgagg gcacggaaca ggccggggc    5760 cagacagtgc gccgggtcgt gccggacgtg gctgaggctg tgcttgttct taggcttcac    5820
cacggggcac ccccttgctc ttgcgctgcc tctccagcac ggcgggcttg agcaccccgc    5880
cgtcatgccg cctgaaccac cgatcagcga acggtgcgcc atagttggcc ttgctcacac    5940
cgaagcggac gaagaaccgg cgctggtcgt cgtccacacc ccattcctcg gcctcggcgc    6000
tggtcatgct cgacaggtag gactgccagc ggatgttatc gaccagtacc gagctgcccc    6060
ggctggcctg ctgctggtcg cctgcgccca tcatggccgc gcccttgctg gcatggtgca    6120
ggaacacgat agagcacccg gtatcggcgg cgatggcctc catgcgaccg atgacctggg    6180
ccatggggcc gctggcgttt tcttcctcga tgtggaaccg gcgcagcgtg tccagcacca    6240
tcaggcggcg gccctcggcg gcgcgcttga ggccgtcgaa ccactccggg gccatgatgt    6300
tgggcaggct gccgatcagc ggctggatca gcaggccgtc agccacggct tgccgttcct    6360
cggcgctgag gtgcgcccca agggcgtgca ggcggtgatg aatggcggtg gcgggtctt    6420 cggcgggcag gtagatcacc gggccggtgg gcagttcgcc cacctccagc agatccggcc    6480
cgcctgcaat ctgtgcggcc agttgcaggg ccagcatgga tttaccggca ccacggggcg    6540
acaccagcgc cccgaccgta ccggccacca tgttgggcaa aacgtagtcc agcggtggcg    6600
gcgctgctgc gaacgcctcc agaatattga taggcttatg ggtagccatt gattgcctcc    6660
tttgcaggca gttggtggtt aggcgctggc ggggtcacta ccccgccct gcgccgctct    6720 gagttcttcc aggcactcgc gcagcgcctc gtattcgtcg tcggtcagcc agaacttgcg    6780
ctgacgcatc cctttggcct tcatgcgctc ggcatatcgc gcttggcgta cagcgtcagg    6840 gctgccagc aggtcgccgg tctgcttgtc cttttggtct ttcatatcag tcaccgagaa    6900
acttgccggg gccgaaaggc ttgtcttcgc ggaacaagga caaggtgcag ccgtcaaggt    6960
taaggctggc catatcagcg actgaaaagc ggccagcctc ggccttgttt gacgtataac    7020
caaagccacc gggcaaccaa tagcccttgt cactttgat caggtagacc gaccctgaag    7080
```

```
cgcttttttc gtattccata aaaccccctt ctgtgcgtga gtactcatag tataacaggc    7140
gtgagtacca acgcaagcac tacatgctga aatctggccc gccctgtcc atgcctcgct     7200
ggcggggtgc cggtgcccgt gccagctcgg cccgcgcaag ctggacgctg ggcagaccca    7260
tgaccttgct gacggtgcgc tcgatgtaat ccgcttcgtg gccgggcttg cgctctgcca    7320
gcgctgggct ggcctcggcc atggccttgc cgatttcctc ggcactgcgg ccccggctgg    7380
ccagcttctg cgcggcgata aagtcgcact tgctgaggtc atgaccgaag cgcttgacca    7440
gcccggccat ctcgctgcgg tactcgtcca gcgccgtgcg ccggtggcgg ctaagctgcc    7500
gctcgggcag ttcgaggctg gccagcctgc gggccttctc ctgctgccgc tgggcctgct    7560
cgatctgctg gccagcctgc tgcaccagcg ccgggccagc ggtggcggtc ttgcccttgg    7620
attcacgcag cagcacccac ggctgataac cggcgcgggt ggtgtgcttg tccttgcggt    7680
tggtgaagcc cgccaagcgg ccatagtggc ggctgtcggc gctggccggg tcggcgtcgt    7740
actcgctggc cagcgtccgg gcaatctgcc cccgaagttc accgcctgcg gcgtcggcca    7800
ccttgaccca tgcctgatag ttcttcgggc tggtttccac taccagggca ggctcccggc    7860
cctcggcttt catgtcatcc aggtcaaact cgctgaggtc gtccaccagc accagaccat    7920
gccgctcctg ctcggcgggc ctgatataca cgtcattgcc ctgggcattc atccgcttga    7980
gccatggcgt gttctggagc acttcggcgg ctgaccattc ccggttcatc atctggccgg    8040
tgggtgcgtc cctgacgccg atatcgaagc gctcacagcc catggccttg agctgtcggc    8100
ctatggcctg caaagtcctg tcgttcttca tcgggccacc aagcgcagcc agatcgagcc    8160
gtcctcggtt gtcagtggcg tcaggtcgag caagagcaac gatgcgatca gcagcaccac    8220
cgtaggcatc atggaagcca gcatcacggt tagccatagc ttccagtgcc accccgcga    8280
cgcgctccgg gcgctctgcg cggcgctgct cacctcggcg gctacctccc gcaactcttt    8340
ggccagctcc acccatgccg ccctgtctg gcgctgggct ttcagccact ccgccgcctg    8400
cgcctcgctg gcctgcttgg tctggctcat gacctgccgg gcttcgtcgg ccagtgtcgc    8460
catgctctgg gccagcggtt cgatctgctc cgctaactcg ttgatgcctc tggatttctt    8520
cactctgtcg attgcgttca tggtctattg cctcccggta ttcctgtaag tcgatgatct    8580
gggcgttggc ggtgtcgatg ttcagggcca cgtctgcccg gtcggtgcgg atgccccggc    8640
cttccatctc caccacgttc ggccccaggt gaacaccggg caggcgctcg atgccctgcg    8700
cctcaagtgt tctgtggtca atgcgggcgt cgtggccagc ccgctctaat gcccggttgg    8760
catggtcggc ccatgcctcg cgggtctgct caagccatgc cttgggcttg agcgcttcgg    8820
tcttctgtgc cccgcccttc tccggggtct tgccgttgta ccgcttgaac cactgagcgg    8880
cgggccgctc gatgccgtca ttgatccgct cggagatcat caggtggcag tgcgggttct    8940
cgccgccacc ggcatggatg gccagcgtat acggcaggcg ctcggcaccg gtcaggtgct    9000
gggcgaactc ggacgccagc gccttctgct ggtcgagggt cagctcgacc ggcagggcaa    9060
attcgacctc cttgaacagc cgcccattgg cgcgttcata caggtcggca gcatcccagt    9120
agtcggcggg ccgctcgacg aactccggca tgtgcccgga ttcggcgtgc aagacttcat    9180
ccatgtcgcg ggcatacttg ccttcgcgct ggatgtagtc ggccttggcc ctggccgatt    9240
ggccgcccga cctgctgccg gttttcgccg taaggtgata aatcgccatg ctgcctcgct    9300
gttgcttttg cttttcggct ccatgcaatg gccctcggag agcgcaccgc ccgaagggtg    9360
gccgttaggc cagtttctcg aagagaaacc ggtaagtgcg ccctcccta caaagtaggg    9420
tcgggattgc cgccgctgtg cctccatgat agcctacgag acagcacatt aacaatgggg    9480
```

```
tgtcaagatg gttaagggga gcaacaaggc ggcggatcgg ctggccaagc tcgaagaaca    9540
acgagcgcga atcaatgccg aaattcagcg ggagcgggca agggaacagc agcaagagcg    9600
caagaacgaa acaaggcgca aggtgctggt gggggccatg attttggcca aggtgaacag    9660
cagcgagtgg ccggaggatc ggctcatggc ggcaatggat gcgtaccttg aacgcgacca    9720
cgaccgcgcc ttgttcggtc tgccgccacg ccagaaggat gagccgggct gaatgatcga    9780
ccgagacagg ccctgcgggg ctgcacacgc gcccccaccc ttcgggtagg gggaaaggcc    9840
gctaaagcgg ctaaaagcgc tccagcgtat ttctgcgggg tttggtgtgg ggtttagcgg    9900
gctttgcccg cctttccccc tgccgcgcag cggtggggcg gtgtgtagcc tagcgcagcg    9960
aatagaccag ctatccggcc tctggccggg catattgggc aagggcagca gcgccccaca   10020
agggcgctga taaccgcgcc tagtggatta ttcttagata atcatggatg gattttttcca  10080
acaccccgcc agcccccgcc cctgctgggt ttgcaggttt gggggcgtga cagttattgc   10140
agggggttcgt gacagttatt gcaggggggc ggtgacagtta ttgcaggggt tcgtgacagt  10200
tagtacggga gtgacgggca ctggctggca atgtctagca acggcaggca tttcggctga   10260
gggtaaaaga actttccgct aagcgataga ctgtatgtaa acacagtatt gcaaggacgc   10320
ggaacatgcc tcatgtggcg gccaggacgg ccagccggga tcgggatact ggtcgttacc   10380
agagccaccg acccgagcaa acccttctct atcagatcgt tgacgagtat tacccggcat   10440
tcgctgcgct tatggcagag cagggaaagg aattgccggg ctatgtgcaa cgggaatttg   10500
aagaatttct ccaatgcggg cggctggagc atggctttct acgggttcgc tgcgagtctt   10560
gccacgccga gcacctggtc gctttcagaa atcaatctaa agtatatatg agtaaacttg   10620
gtctgacagt taccaatgct taatcagtga ggcacctatc tcagcgatct gtctatttcg   10680
ttcatccata gttgcctgac tccccgtcgt gtagataact acgatacggg agggcttacc   10740
atctggcccc agtgctgcaa tgataccgcg agacccacgc tcaccggctc cagatttatc   10800
agcaataaac cagccagccg gaagggccga gcgcagaagt ggtcctgcaa ctttatccgc   10860
ctccatccag tctattaatt gttgccggga agctagagta agtagttcgc cagttaatag   10920
tttgcgcaac gttgttgcca ttgctacagg catcgtggtg tcacgctcgt cgtttggtat   10980
ggcttcattc agctccggtt cccaacgatc aaggcgagtt acatgatccc ccatgttgtg   11040
caaaaaagcg gttagctcct tcggtcctcc gatcgttgtc agaagtaagt tggccgcagt   11100
gttatcactc atggttatgg cagcactgca taattctctt actgtcatgc catccgtaag   11160
atgcttttct gtgactggtg agtactcaac caagtcattc tgagaatagt gtatgcggcg   11220
accgagttgc tcttgcccgg cgtcaacacg ggataatacc gcgccacata gcagaacttt   11280
aaaagtgctc atcattggaa aacgttcttc ggggcgaaaa ctctcaagga tcttaccgct   11340
gttgagatcc agttcgatgt aacccactcg tgcacccaac tgatcttcag catctttttac  11400
tttcaccagc gtttctgggt gagcaaaaac aggaaggcaa aatgccgcaa aaagggaat    11460
aagggcgaca cggaaatgtt gaatactcat actcttcctt tttcaatatt attgaagcat   11520
ttatcagggt tattgtctca tgagcggata catatttgaa tgtatttaga aaataaaca    11580
aaagagtttg tagaaacgca aaaaggccat ccgtcaggat ggccttctgc ttaatttgat   11640
gcctggcagt ttatgcgggc gtcctgcccg ccacccctcc gggccgttgc ttcgcaacgt   11700
tcaaatccgc tcccggcgga tttgtcctac tcaggagagc gttcaccgac aaacaacaga   11760
taaaacgaa                                                            11769
```

<210> SEQ ID NO 124

<211> LENGTH: 11477
<212> TYPE: DNA
<213> ORGANISM: Artificial Sequence
<220> FEATURE:
<223> OTHER INFORMATION: plasmid pLybAL31 containing otsBA operon

<400> SEQUENCE: 124

| | | | | | |
|---|---|---|---|---|---|
| aggcccagtc | tttcgactga | gcctttcgtt | ttatttgatg | cctggcagtt | ccctactctc | 60 |
| gcatggggag | accccacact | accatcggcg | ctacggcgtt | tcacttctga | gttcggcatg | 120 |
| gggtcaggtg | ggaccaccgc | gctactgccg | ccaggcaaat | tctgttttat | cagaccgctt | 180 |
| ctgcgttctg | atttaatctg | tatcaggctg | aaaatcttct | ctcatccgcc | aaaacagcca | 240 |
| agcttgcatg | caaagctcac | taactgggcg | ggattttccg | ggtccggttg | ctgacggtaa | 300 |
| tagtcgtcta | aaagtttggc | cacatccaaa | aggctgtcgg | cgggggatg | ctggccggcg | 360 |
| aggggattaa | ttctgcttgt | catatacaaa | aattgtaaaa | aatggagggc | ggcgatcagg | 420 |
| ggcttagaca | cccaaatcct | agccaaaaag | ggttaactag | ccaagggcta | tccatgggca | 480 |
| aagagataaa | agaaaaagtc | tccaaatccc | tggtcataga | gaaaaaattg | ccaaagttac | 540 |
| cccaggccat | acacggccca | gcgccaagat | ggggagcaca | aattcaaact | ttgtaaacag | 600 |
| gccggaagct | atccggccaa | ggagcactca | gattgtgtta | acgttcaggg | gagttgctta | 660 |
| acacaatttt | ccaattaata | gtattaatat | tttcttaact | tgcaccgtac | catggtgaga | 720 |
| aagcctatct | gagcccttat | ttgattaacc | ttcgactgat | tattgatccc | ctgtgcagtc | 780 |
| tccctctcc | ctctgtcttt | ttgctcccga | acacgttgcc | catagactca | ggtaccgtta | 840 |
| agaaggagga | tccatatgat | cttgatggaa | cgctggcgga | aatcaaaccg | catcccgatc | 900 |
| aggtcgtcgt | gcctgacaat | attctgcaag | gactacagct | actggcaacc | gcaagtgatg | 960 |
| gtgcattggc | attgatatca | gggcgctcaa | tggtggagct | tgacgcactg | gcaaaacctt | 1020 |
| atcgcttccc | gttagcgggc | gtgcatgggg | cggagcgccg | tgacatcaat | ggtaaaacac | 1080 |
| atatcgttca | tctgccggat | gcgattgcgc | gtgatattag | cgtgcaactg | catacagtca | 1140 |
| tcgctcagta | tcccggcgcg | gagctggagg | cgaaagggat | ggcttttgcg | ctgcattatc | 1200 |
| gtcaggctcc | gcagcatgaa | gacgcattaa | tgacattagc | gcaacgtatt | actcagatct | 1260 |
| ggccacaaat | ggcgttacag | cagggaaagt | gtgttgtcga | gatcaaaccg | agaggtacca | 1320 |
| gtaaaggtga | ggcaattgca | gctttttatgc | aggaagctcc | cttatcgggg | cgaacgcccg | 1380 |
| tatttctggg | cgatgattta | accgatgaat | ctggcttcgc | agtcgttaac | cgactgggcg | 1440 |
| gaatgtcagt | aaaaattggc | acaggtgcaa | ctcaggcatc | atggcgactg | gcgggtgtgc | 1500 |
| cggatgtctg | gagctggctt | gaaatgataa | ccaccgcatt | acaacaaaaa | agagaaaata | 1560 |
| acaggagtga | tgactatgag | tcgtttagtc | gtagtatcta | accggattgc | accaccagac | 1620 |
| gagcacgccg | ccagtgccgg | tggccttgcc | gttggcatac | tgggggcact | gaaagccgca | 1680 |
| ggcggactgt | ggtttggctg | gagtggtgaa | acagggaatg | aggatcagcc | gctaaaaaag | 1740 |
| gtgaaaaaag | gtaacattac | gtgggcctct | tttaacctca | gcgaacagga | ccttgacgaa | 1800 |
| tactacaacc | aattctccaa | tgccgttctc | tggcccgctt | ttcattatcg | gctcgatctg | 1860 |
| gtgcaatttc | agcgtcctgc | ctgggacggc | tatctacgcg | taaatgcgtt | gctggcagat | 1920 |
| aaattactgc | cgctgttgca | agacgatgac | attatctgga | tccacgatta | tcacctgttg | 1980 |
| ccatttgcgc | atgaattacg | caaacgggga | gtgaataatc | gcattggttt | ctttctgcat | 2040 |
| attccttttcc | cgacaccgga | aatcttcaac | gcgctgccga | catatgacac | cttgcttgaa | 2100 |
| cagctttgtg | attatgattt | gctgggtttc | cagacagaaa | acgatcgtct | ggcgttcctg | 2160 |

```
gattgtcttt ctaacctgac ccgcgtcacg acacgtagcg caaaaagcca tacagcctgg    2220
ggcaaagcat ttcgaacaga agtctacccg atcggcattg aaccgaaaga aatagccaaa    2280
caggctgccg ggccactgcc gccaaaactg gcgcaactta aagcggaact gaaaaacgta    2340
caaaatatct tttctgtcga acggctggat tattccaaag gtttgccaga gcgttttctc    2400
gcctatgaag cgttgctgga aaaatatccg cagcatcatg gtaaaattcg ttatacccag    2460
attgcaccaa cgtcgcgtgg tgatgtgcaa gcctatcagg atattcgtca tcagctcgaa    2520
aatgaagctg gacgaattaa tggtaaatac gggcaattag gctggacgcc gctttattat    2580
ttgaatcagc attttgaccg taaattactg atgaaaatat ccgctactc tgacgtgggc    2640 ttagtgacgc cactgcgtga cgggatgaac ctggtagcaa agagtatgt tgctgctcag     2700 gacccagcca atccgggcgt tcttgttctt tcgcaatttg cgggagcggc aaacgagtta    2760
acgtcggcgt taattgttaa cccctacgat cgtgacgaag ttgcagctgc gctggatcgt    2820
gcattgacta tgtcgctggc ggaacgtatt tcccgtcatg cagaaatgct ggacgttatc    2880
gtgaaaaacg atattaacca ctggcaggag tgcttcatta gcgacctaaa gcagatagtt    2940
ccgcgaagcg cggaaagcca gcagcgcgat aaagttgcta cctttccaaa gcttgcgtag    3000
gagctagctg cctcgaaagg ggatgcgatt cgccacctct cactccgctg gcggattcct    3060
cttgagaaca ttttggtggc aggcgattct ggtaacgatg aggaaatgct caagggccat    3120
aatctcggcg ttgtagttgg caattactca ccggaattgg agccactgcg cagctacgag    3180
cgcgtctatt ttgctgaggg ccactatgct aatggcattc tggaagcctt aaaacactat    3240
cgcttttttg aggcgatcgc ttaacctttt cagaatgaga cgttgatcgg cacgtaagcg    3300
tgagacgttg atcggcacgt aagaggttcc aactttcacc ataatgaaat aagatcacta    3360
ccgggcgtat ttttttgagtt atcgagattt tcaggagcta aggaagctaa aatggagaaa    3420
aaaatcactg gatataccac cgttgatata tcccaatggc atcgtaaaga acattttgag    3480
gcatttcagt cagttgctca atgtacctat aaccagaccg ttcagctgga tattacggcc    3540
tttttaaaga ccgtaaagaa aaataagcac aagttttatc cggcctttat tcacattctt    3600
gcccgcctga tgaatgctca tccggaattc cgtatgcaa tgaaagacgg tgagctggtg    3660
atatgggata gtgttcaccc ttgttacacc gttttccatg agcaaactga acgttttca    3720 tcgctctgga gtgaataca cgacgatttc cggcagtttc tacacatata ttcgcaagat    3780
gtggcgtgtt acggtgaaaa cctggcctat ttccctaaag ggtttattga gaatatgttt    3840
ttcgtctcag ccaatccctg ggtgagtttc accagttttg atttaaacgt ggccaatatg    3900
gacaacttct tcgccccgt tttcaccatg gcaaatatt atacgcaagg cgacaaggtg     3960
ctgatgccgc tggcgattca ggttcatcat gccgtttgtg atggcttcca tgtcggcaga    4020
atgcttaatg aattacaaca gtactgcgat gagtggcagg gcggggcgta attttttaa     4080 ggcagttatt ggtgccctta aacgcctggt tgctacgcct gaataagtga taataagcgg    4140
atgaatggca gaaattcgat gataagctgt caaacacaac caccatcaaa caggattttc    4200
gcctgctggg gcaaaccagc gtggaccgct tgctgcaact ctctcagggc caggcggtga    4260
agggcaatca gctgttgccc gtctcactgg tgaaaagaaa accaccctg gcgcccaata    4320 cgcaaaccgc ctctccccgc gcgttggccg attcattaat gcagctggca cgacaggttt    4380
cccgactgga aagcgggcag tgagcgcaac gcaattaatg taagttagcg cgaattgcaa    4440
gctggccgac gcgctgggct acgtcttgct ggcgttcggg agcagaagag catacatctg    4500
gaagcaaagc caggaaagcg gcctatggag ctgtgcggca gcgctcagta ggcaatttt     4560
```

```
caaaatattg ttaagccttt tctgagcatg gtatttttca tggtattacc aattagcagg    4620
aaaataagcc attgaatata aaagataaaa atgtcttgtt tacaatagag tgggggggggt    4680 cagcctgccg ccttgggccg ggtgatgtcg tacttgcccg ccgcgaactc ggttaccgtc    4740
cagcccagcg cgaccagctc cggcaacgcc tcgcgcaccc gcttgcggcg cttgcgcatg    4800
gtcgaaccac tggcctctga cggccagaca tagccgcaca aggtatctat ggaagccttg    4860
ccggttttgc cggggtcgat ccagccacac agccgctggt gcagcaggcg ggcggttttcg    4920 ctgtccagcg cccgcacctc gtccatgctg atgcgcacat gctggccgcc acccatgacg    4980
gcctgcgcga tcaaggggtt cagggccacg tacaggcgcc cgtccgcctc gtcgctggcg    5040
tactccgaca gcagccgaaa cccctgccgc ttgcggccat tctgggcgat gatggatacc    5100
ttccaaaggc gctcgatgca gtcctgtatg tgcttgagcg ccccaccact atcgacctct    5160
gccccgattt cctttgccag cgcccgatag ctacctttga ccacatggca ttcagcggtg    5220
acggcctccc acttgggttc caggaacagc cggagctgcc gtccgccttc ggtcttgggt    5280
tccgggccaa gcactaggcc attaggccca gccatggcca ccagcccttg caggatgcgc    5340
agatcatcag cgcccagcgg ctccgggccg ctgaactcga tccgcttgcc gtcgccgtag    5400
tcatacgtca cgtccagctt gctgcgcttg cgctcgcccc gcttgagggc acggaacagg    5460 ccggggggcca gacagtgcgc cgggtcgtgc cggacgtggc tgaggctgtg cttgttctta    5520
ggcttcacca cggggcaccc ccttgctctt gcgctgcctc tccagcacgg cgggcttgag    5580
caccccgccg tcatgccgcc tgaaccaccg atcagcgaac ggtgcgccat agttggcctt    5640
gctcacaccg aagcggacga agaaccggcg ctggtcgtcg tccacacccc attcctcggc    5700
ctcggcgctg gtcatgctcg acaggtagga ctgccagcgg atgttatcga ccagtaccga    5760
gctgccccgg ctggcctgct gctggtcgcc tgcgcccatc atggccgcgc ccttgctggc    5820
atggtgcagg aacacgatag agcacccggt atcggcggcg atggcctcca tgcgaccgat    5880
gacctgggcc atgggccgc tggcgttttc ttcctcgatg tggaaccggc gcagcgtgtc    5940
cagcaccatc aggcggcggc cctcggcggc gcgcttgagg ccgtcgaacc actccggggc    6000
catgatgttg ggcaggctgc cgatcagcgg ctggatcagc aggccgtcag ccacggcttg    6060
ccgttcctcg gcgctgaggt gcgccccaag ggcgtgcagg cggtgatgaa tggcggtggg    6120
cgggtcttcg gcgggcaggt agatcaccgg gccggtgggc agttcgccca cctccagcag    6180
atccggcccg cctgcaatct gtgcggccag ttgcagggcc agcatggatt taccggcacc    6240
accgggcgac accagcgccc cgaccgtacc ggccaccatg ttgggcaaaa cgtagtccag    6300
cggtggcggc gctgctgcga acgcctccag aatattgata ggcttatggg tagccattga    6360
ttgcctcctt tgcaggcagt tggtggttag gcgctggcgg ggtcactacc cccgccctgc    6420
gccgctctga gttcttccag gcactcgcgc agcgcctcgt attcgtcgtc ggtcagccag    6480
aacttgcgct gacgcatccc tttggccttc atgcgctcgg catatcgcgc ttggcgtaca    6540
gcgtcagggc tggccagcag gtcgccggtc tgcttgtcct tttggtcttt catatcagtc    6600
accgagaaac ttgccggggc cgaaaggctt gtcttcgcgg aacaaggaca aggtgcagcc    6660
gtcaaggtta aggctggcca tatcagcgac tgaaaagcgg ccagcctcgg ccttgtttga    6720
cgtataacca aagccaccgg gcaaccaata gcccttgtca cttttgatca ggtagaccga    6780
ccctgaagcg cttttttcgt attccataaa accccttct gtgcgtgagt actcatagta    6840
taacaggcgt gagtaccaac gcaagcacta catgctgaaa tctggcccgc ccctgtccat    6900
gcctcgctgg cggggtgccg gtgccgtgc cagctcggcc cgcgcaagct ggacgctggg    6960
```

```
cagacccatg accttgctga cggtgcgctc gatgtaatcc gcttcgtggc cgggcttgcg    7020
ctctgccagc gctgggctgg cctcggccat ggccttgccg atttcctcgg cactgcggcc    7080
ccggctggcc agcttctgcg cggcgataaa gtcgcacttg ctgaggtcat gaccgaagcg    7140
cttgaccagc ccgccatct cgctgcgta ctcgtccagc gccgtgcgcc ggtggcggct      7200
aagctgccgc tcgggcagtt cgaggctggc cagcctgcgg gccttctcct gctgccgctg    7260
ggcctgctcg atctgctggc cagcctgctg caccagcgcc gggccagcgg tggcggtctt    7320
gcccttggat tcacgcagca gcacccacgg ctgataaccg gcgcgggtgg tgtgcttgtc    7380
cttgcggttg gtgaagcccg ccaagcgcc atagtggcgg ctgtcggcgc tggccgggtc     7440
ggcgtcgtac tcgctggcca gcgtccgggc aatctgcccc cgaagttcac cgcctgcggc    7500 gtcgccacc ttgacccatg cctgatagtt cttcgggctg gtttccacta ccagggcagg     7560
ctcccggccc tcggctttca tgtcatccag gtcaaactcg ctgaggtcgt ccaccagcac    7620
cagaccatgc cgctcctgct cggcgggcct gatatacacg tcattgccct gggcattcat    7680
ccgcttgagc catggcgtgt tctggagcac ttcggcggct gaccattccc ggttcatcat    7740
ctggccggtg ggtgcgtccc tgacgccgat atcgaagcgc tcacagccca tggccttgag    7800
ctgtcggcct atggcctgca aagtcctgtc gttcttcatc gggccaccaa gcgcagccag    7860
atcgagccgt cctcggttgt cagtggcgtc aggtcgagca agagcaacga tgcgatcagc    7920
agcaccaccg taggcatcat ggaagccagc atcacggtta gccatagctt ccagtgccac    7980
ccccgcgacg cgctccgggc gctctgcgcg gcgctgctca cctcggcggc tacctcccgc    8040
aactctttgg ccagctccac ccatgccgcc cctgtctggc gctgggcttt cagccactcc    8100 gccgctgcg cctcgctggc ctgcttggtc tggctcatga cctgccgggc ttcgtcggcc     8160
agtgtcgcca tgctctgggc cagcggttcg atctgctccg ctaactcgtt gatgcctctg    8220
gatttcttca ctctgtcgat tgcgttcatg gtctattgcc tcccggtatt cctgtaagtc    8280
gatgatctgg gcgttggcgg tgtcgatgtt cagggccacg tctgcccggt cggtgcggat    8340
gccccggcct tccatctcca ccacgttcgg ccccaggtga acaccgggca ggcgctcgat    8400
gccctgcgcc tcaagtgttc tgtggtcaat gcgggcgtcg tggccagccc gctctaatgc    8460
ccggttggca tggtcggccc atgcctcgcg ggtctgctca agccatgcct gggcttgag    8520 cgcttcggtc ttctgtgccc cgcccttctc cggggtcttg ccgttgtacc gcttgaacca    8580
ctgagcggcg ggccgctcga tgccgtcatt gatccgctcg agatcatca ggtggcagtg     8640 cgggttctcg ccgccaccgg catggatggc cagcgtatac ggcaggcgct cggcaccggt    8700
caggtgctgg gcgaactcgg acgccagcgc cttctgctgg tcgagggtca gctcgaccgg    8760
cagggcaaat tcgacctcct tgaacagccg cccattggcg cgttcataca ggtcggcagc    8820
atcccagtag tcggcgggcc gctcgacgaa ctccggcatg tgcccggatt cggcgtgcaa    8880
gacttcatcc atgtcgcggg catacttgcc ttcgcgctgg atgtagtcgg ccttggccct    8940
ggccgattgg ccgcccgacc tgctgccggt tttcgccgta aggtgataaa tcgccatgct    9000
gcctcgctgt tgcttttgct tttcggctcc atgcaatggc cctcggagag cgcaccgccc    9060
gaagggtggc cgttaggcca gtttctcgaa gagaaaccgg taagtgcgcc ctcccctaca    9120
aagtagggtc gggattgccg ccgctgtgcc tccatgatag cctacgagac agcacattaa    9180
caatggggtg tcaagatggt taaggggagc aacaaggcgg cggatcggct ggccaagctc    9240
gaagaacaac gagcgcgaat caatgccgaa attcagcggg agcgggcaag gaacagcag     9300 caagagcgca agaacgaaac aaggcgcaag gtgctggtgg gggccatgat tttggccaag    9360
```

```
gtgaacagca gcgagtggcc ggaggatcgg ctcatggcgg caatggatgc gtaccttgaa   9420
cgcgaccacg accgcgcctt gttcggtctg ccgccacgcc agaaggatga gccgggctga   9480
atgatcgacc gagacaggcc ctgcggggct gcacacgcgc ccccacccct cgggtagggg   9540
gaaaggccgc taaagcggct aaaagcgctc cagcgtattt ctgcggggtt tggtgtgggg   9600
tttagcgggc tttgcccgcc tttcccctg ccgcgcagcg gtgggcggt gtgtagccta    9660 gcgcagcgaa tagaccagct atccggcctc tggccgggca tattgggcaa gggcagcagc   9720
gccccacaag ggcgctgata accgcgccta gtggattatt cttagataat catggatgga   9780
tttttccaac accccgccag cccccgcccc tgctgggttt gcaggtttgg gggcgtgaca   9840
gttattgcag gggttcgtga cagttattgc agggggcgt gacagttatt gcaggggttc    9900
gtgacagtta gtacgggagt gacgggcact ggctggcaat gtctagcaac ggcaggcatt   9960
tcggctgagg gtaaaagaac tttccgctaa gcgatagact gtatgtaaac acagtattgc   10020
aaggacgcgg aacatgcctc atgtggcggc caggacggcc agcccgggatc gggatactgg   10080 tcgttaccag agccaccgac ccgagcaaac ccttctctat cagatcgttg acgagtatta   10140
cccggcattc gctgcgctta tggcagagca gggaaaggaa ttgccgggct atgtgcaacg   10200
ggaatttgaa gaatttctcc aatgcgggcg gctggagcat ggctttctac gggttcgctg   10260
cgagtcttgc cacgccgagc acctggtcgc tttcagaaat caatctaaag tatatatgag   10320
taaacttggt ctgacagtta ccaatgctta atcagtgagg cacctatctc agcgatctgt   10380
ctatttcgtt catccatagt tgcctgactc ccgtcgtgt agataactac gatacgggag    10440
ggcttaccat ctggccccag tgctgcaatg ataccgcgag acccacgctc accggctcca   10500
gatttatcag caataaacca gccagccgga agggccgagc gcagaagtgg tcctgcaact   10560
ttatccgcct ccatccagtc tattaattgt tgccgggaag ctagagtaag tagttcgcca   10620
gttaatagtt tgcgcaacgt tgttgccatt gctacaggca tcgtggtgtc acgctcgtcg   10680
tttggtatgg cttcattcag ctccggttcc caacgatcaa ggcgagttac atgatccccc   10740
atgttgtgca aaaagcggt tagctccttc ggtcctccga tcgttgtcag aagtaagttg    10800
gccgcagtgt tatcactcat ggttatgca gcactgcata ttctcttac tgtcatgcca     10860 tccgtaagat gcttttctgt gactggtgag tactcaacca agtcattctg agaatagtgt   10920
atgcggcgac cgagttgctc ttgcccggcg tcaaacgggg ataataccgc gccacatagc   10980
agaactttaa aagtgctcat cattggaaaa cgttcttcgg ggcgaaaact ctcaaggatc   11040
ttaccgctgt tgagatccag ttcgatgtaa cccactcgtg cacccaactg atcttcagca   11100
tcttttactt tcaccagcgt ttctgggtga gcaaaaacag gaaggcaaaa tgccgcaaaa   11160
aagggaataa gggcgacacg gaaatgttga atactcatac tcttcctttt tcaatattat   11220
tgaagcattt atcagggtta ttgtctcatg agcggataca tatttgaatg tatttagaaa   11280
aataaacaaa agagtttgta gaaacgcaaa aaggccatcc gtcaggatgg ccttctgctt   11340
aatttgatgc ctggcagttt atggcgggcg tcctgcccgc caccctccgg gccgttgctt   11400
cgcaacgttc aaatccgctc ccggcggatt tgtcctactc aggagagcgt tcaccgacaa   11460
acaacagata aaacgaa                                                 11477
```

<210> SEQ ID NO 125  
<211> LENGTH: 11258  
<212> TYPE: DNA  
<213> ORGANISM: Artificial Sequence  
<220> FEATURE:  
<223> OTHER INFORMATION: plasmid pLybAL36 containing otsBA operon

<400> SEQUENCE: 125

```
aggcccagtc tttcgactga gcctttcgtt ttatttgatg cctggcagtt ccctactctc      60
gcatggggag accccacact accatcggcg ctacggcgtt tcacttctga gttcggcatg     120
gggtcaggtg ggaccaccgc gctactgccg ccaggcaaat tctgttttat cagaccgctt     180
ctgcgttctg atttaatctg tatcaggctg aaaatcttct ctcatccgcc aaaacagcca     240
agcttgcatg caggaaaaca agctcagaat gctgcgggga aagggcaac tccccaccag      300
ccccaaattt tgctggcga taaatatttt tcggtttaat tgttcacaaa gcttttgaa       360
tttgagttta tagaaattta ttggctggta atgcttttt gcccccctgc aggacttcat      420
tgatccttgc ctataccatc aatatcattg gtcaataatg atgatgattg actaaaacat     480
gtttaacaaa atttaacgca tatgctaaat gcgtaaactg catatgcctt ggctgagtgt     540
aatttacgtt acaaattttta acgaaacggg aaccctatat tgatctctac tgttatctgg    600
cttgaagcgt tggtaccgtt aagaaggagg atccatatga tcttgatgga acgctggcgg    660
aaatcaaacc gcatcccgat caggtcgtcg tgcctgacaa tattctgcaa ggactacagc    720
tactggcaac cgcaagtgat ggtgcattgg cattgatatc agggcgctca atggtggagc    780
ttgacgcact ggcaaaacct tatcgcttcc cgttagcggg cgtgcatggg gcggagcgcc    840
gtgacatcaa tggtaaaaca catatcgttc atctgccgga tgcgattgcg cgtgatatta    900
gcgtgcaact gcatacagtc atcgctcagt atcccggcgc ggagctggag gcgaaaggga    960
tggcttttgc gctgcattat cgtcaggctc cgcagcatga agacgcatta atgacattag   1020
cgcaacgtat tactcagatc tggccacaaa tggcgttaca gcagggaaag tgtgttgtcg   1080
agatcaaacc gagaggtacc agtaaaggtg aggcaattgc agcttttatg caggaagctc   1140
cctttatcgg gcgaacgccc gtatttctgg gcgatgattt aaccgatgaa tctggcttcg   1200
cagtcgttaa ccgactgggc ggaatgtcag taaaaattgg cacaggtgca actcaggcat   1260
catggcgact ggcgggtgtg ccggatgtct ggagctggct tgaaatgata accaccgcat   1320
tacaacaaaa aagagaaaat aacaggagtg atgactatga gtcgtttagt cgtagtatct   1380
aaccggattg caccaccaga cgagcacgcc gccagtgccg gtggccttgc cgttggcata   1440
ctggggcac tgaaagccgc aggcggactg tggtttggct ggagtggtga acagggaat    1500
gaggatcagc cgctaaaaaa ggtgaaaaaa ggtaacatta cgtgggcctc ttttaacctc   1560
agcgaacagg accttgacga atactacaac caattctcca atgccgttct ctggcccgct   1620
tttcattatc ggctcgatct ggtgcaattt cagcgtcctg cctgggacgg ctatctacgc   1680
gtaaatgcgt tgctggcaga taaattactg ccgctgttgc aagacgatga cattatctgg   1740
atccacgatt atcacctgtt gccatttgcg catgaattac gcaaacgggg agtgaataat   1800
cgcattggtt tctttctgca tattcctttc ccgacaccgg aaatcttcaa cgcgctgccg   1860
acatatgaca ccttgcttga acagctttgt gattatgatt tgctgggttt ccagacagaa   1920
aacgatcgtc tggcgttcct ggattgtctt tctaacctga cccgcgtcac gacacgtagc   1980
gcaaaaagcc atacagcctg ggcaaagca tttcgaacag aagtctaccc gatcggcatt    2040
gaaccgaaag aaatagccaa acaggctgcc gggccactgc cgccaaaact ggcgcaactt   2100
aaagcggaac tgaaaaacgt acaaaatatc ttttctgtcg aacggctgga ttattccaaa   2160
ggtttgccag agcgttttct cgcctatgaa gcgttgctgg aaaaatatcc gcagcatcat   2220
ggtaaaattc gttatccca gattgcacca acgtcgcgtg gtgatgtgca agcctatcag   2280
gatattcgtc atcagctcga aaatgaagct ggacgaatta atggtaaata cgggcaatta   2340
```

```
ggctggacgc cgctttatta tttgaatcag cattttgacc gtaaattact gatgaaaata    2400
ttccgctact ctgacgtggg cttagtgacg ccactgcgtg acgggatgaa cctggtagca    2460
aaagagtatg ttgctgctca ggacccagcc aatccgggcg ttcttgttct ttcgcaattt    2520
gcgggagcgc caaacgagtt aacgtcggcg ttaattgtta accoctacga tcgtgacgaa    2580 gttgcagctg cgctggatcg tgcattgact atgtcgctgg cggaacgtat ttcccgtcat    2640
gcagaaatgc tggacgttat cgtgaaaaac gatattaacc actggcagga gtgcttcatt    2700
agcgacctaa agcagatagt tccgcgaagc gcggaaagcc agcagcgcga taaagttgct    2760
acctttccaa agcttgcgta ggagctagct gcctcgaaag gggatgcgat cgccacctc    2820 tcactccgct ggcggattcc tcttgagaac attttggtgg caggcgattc tggtaacgat    2880
gaggaaatgc tcaagggcca taatctcggc gttgtagttg caattactc accgaaattg    2940 gagccactgc gcagctacga gcgcgtctat tttgctgagg gccactatgc taatggcatt    3000
ctggaagcct aaaacacta tcgcttttt gaggcgatcg cttaacctt tcagaatgag    3060 acgttgatcg gcacgtaagc gtgagacgtt gatcggcacg taagaggttc aactttcac    3120 cataatgaaa taagatcact accgggcgta tttttttgagt tatcgagatt ttcaggagct    3180
aaggaagcta aaatggagaa aaaaatcact ggatatacca ccgttgatat atcccaatgg    3240
catcgtaaag aacattttga ggcatttcag tcagttgctc aatgtaccta taaccagacc    3300
gttcagctgg atattacggc ctttttaaag accgtaaaga aaataagca caagttttat    3360 ccggccttta ttcacattct tgcccgcctg atgaatgctc atccggaatt ccgtatggca    3420
atgaaagacg gtgagctggt gatatgggat agtgttcacc cttgttacac cgtttttccat    3480 gagcaaactg aaacgttttc atcgctctgg agtgaatacc acgacgattt ccggcagttt    3540
ctacacatat attcgcaaga tgtggcgtgt tacggtgaaa acctggccta tttccctaaa    3600
gggtttattg agaatatgtt tttcgtctca gccaatccct gggtgagttt caccagtttt    3660
gatttaaacg tggccaatat ggacaacttc ttcgcccccg ttttcaccat gggcaaatat    3720
tatacgcaag cgacaaggt gctgatgccg ctggcgattc aggttcatca tgccgtttgt    3780
gatggcttcc atgtcggcag aatgcttaat gaattacaac agtactgcga tgagtggcag    3840
ggcggggcgt aattttttta aggcagttat tggtgccctt aaacgcctgg ttgctacgcc    3900
tgaataagtg ataataagcg gatgaatggc agaaattcga tgataagctg tcaaacacaa    3960
ccaccatcaa acaggatttt cgcctgctgg ggcaaaccag cgtggaccgc ttgctgcaac    4020
tctctcaggg ccaggcggtg aagggcaatc agctgttgcc cgtctcactg gtgaaaagaa    4080
aaaccaccct ggcgcccaat acgcaaaccg cctctccccg cgcgttggcc gattcattaa    4140
tgcagctggc acgacaggtt tcccgactgg aaagcgggca gtgagcgcaa cgcaattaat    4200
gtaagttagc gcgaattgca agctggccga cgcgctgggc tacgtcttgc tggcgttcgg    4260
gagcagaaga gcatacatct ggaagcaaag ccaggaaagc ggcctatgga gctgtgcggc    4320
agcgctcagt aggcaatttt tcaaaatatt gttaagcctt ttctgagcat ggtattttc    4380 atggtattac caattagcag gaaataagc cattgaatat aaaagataaa aatgtcttgt    4440
ttacaataga gtgggggggg tcagcctgcc gccttgggcc gggtgatgtc gtacttgccc    4500
gccgcgaact cggttaccgt ccagcccagc gcgaccagct ccggcaacgc ctcgcgcacc    4560
cgcttgcggc gcttgcgcat ggtcgaacca ctggcctctg acggcagac atagccgcac    4620 aaggtatcta tggaagcctt gccggttttg ccggggtcga tccagccaca cagccgctgg    4680
tgcagcaggc gggcggtttc gctgtccagc gcccgcacct cgtccatgct gatgcgcaca    4740
```

```
tgctggccgc cacccatgac ggcctgcgcg atcaaggggt tcagggccac gtacaggcgc    4800
ccgtccgcct cgtcgctggc gtactccgac agcagccgaa accctgccg cttgcggcca     4860 ttctgggcga tgatggatac cttccaaagg cgctcgatgc agtcctgtat gtgcttgagc    4920
gccccaccac tatcgacctc tgccccgatt cctttgcca cgcccgata gctacctttg      4980 accacatggc attcagcggt gacggcctcc cacttgggtt ccaggaacag ccggagctgc    5040
cgtccgcctt cggtcttggg ttccgggcca agcactaggc cattaggccc agccatggcc   5100
accagccctt gcaggatgcg cagatcatca gcgcccagcg gctccgggcc gctgaactcg    5160
atccgcttgc cgtcgccgta gtcatacgtc acgtccagct tgctgcgctt gcgctcgccc    5220
cgcttgaggg cacggaacag gccggggggcc agacagtgcg ccgggtcgtg ccggacgtgg   5280
ctgaggctgt gcttgttctt aggcttcacc acggggcacc cccttgctct tgcgctgcct   5340
ctccagcacg gcgggcttga gcaccccgcc gtcatgccgc ctgaaccacc gatcagcgaa   5400
cggtgcgcca tagttggcct tgctcacacc gaagcggacg aagaaccggc gctggtcgtc    5460
gtccacaccc cattcctcgg cctcggcgct ggtcatgctc gacaggtagg actgccagcg   5520
gatgttatcg accagtaccg agctgccccg gctggcctgc tgctggtcgc ctgcgcccat    5580
catggccgcg cccttgctgg catggtgcag gaacacgata gagcacccgg tatcggcggc    5640 gatgcctcc atgcgaccga tgacctgggc catggggccg ctggcgtttt cttcctcgat     5700
gtggaaccgg cgcagcgtgt ccagcaccat caggcggcgg ccctcggcgg cgcgcttgag   5760
gccgtcgaac cactccgggg ccatgatgtt gggcaggctg ccgatcagcg gctggatcag    5820
caggccgtca gccacggctt gccgttcctc ggcgctgagg tgcgcccaa gggcgtgcag     5880 gcggtgatga atggcggtgg gcgggtcttc ggcgggcagg tagatcaccg ggccggtggg    5940
cagttcgccc acctccagca gatccggccc gcctgcaatc tgtgcggcca gttgcagggc   6000
cagcatggat ttaccggcac caccgggcga caccagcgcc ccgaccgtac cggccaccat    6060
gttgggcaaa acgtagtcca gcggtggcgg cgctgctgcg aacgcctcca gaatattgat    6120
aggcttatgg gtagccattg attgcctcct ttgcaggcag ttggtggtta ggcgctggcg    6180
gggtcactac ccccgccctg cgccgctctg agttcttcca ggcactcgcg cagcgcctcg    6240
tattcgtcgt cggtcagcca gaacttgcgc tgacgcatcc cttggccctt catgcgctcg    6300
gcatatcgcg cttggcgtac agcgtcaggg ctggccagca ggtcgccggt ctgcttgtcc    6360
ttttggtctt tcatatcagt caccgagaaa cttgccgggg ccgaaaggct tgtcttcgcg    6420
gaacaaggac aaggtgcagc cgtcaaggtt aaggctggcc atatcagcga ctgaaaagcg    6480
gccagcctcg gccttgtttg acgtataacc aaagccaccg ggcaaccaat agcccttgtc   6540
acttttgatc aggtagaccg accctgaagc gctttttttcg tattccataa aacccccttc   6600
tgtgcgtgag tactcatagt ataacaggcg tgagtaccaa cgcaagcact acatgctgaa    6660
atctggcccg cccctgtcca tgcctcgctg gcggggtgcc ggtgcccgtg ccagctcggc    6720
ccgcgcaagc tggacgctgg gcagacccat gaccttgctg acggtgcgct cgatgtaatc   6780
cgcttcgtgg ccgggcttgc gctctgccag cgctgggctg gcctcggcca tggccttgcc   6840
gatttcctcg gcactgcggc cccggctggc cagcttctgc gcggcgataa agtcgcactt    6900
gctgaggtca tgaccgaagc gcttgaccag cccggccatc tcgctgcggt actcgtccag    6960
cgccgtgcgc cggtggcggc taagctgccg ctcgggcagt tcgaggctgg ccagcctgcg   7020
ggccttctcc tgctgccgct gggcctgctc gatctgctgg ccagcctgct gcaccagcgc    7080
cgggccagcg gtggcggtct tgcccttgga ttcacgcagc agcacccacg gctgataacc    7140
```

```
ggcgcgggtg gtgtgcttgt ccttgcggtt ggtgaagccc gccaagcggc catagtggcg    7200
gctgtcggcg ctggccgggt cggcgtcgta ctcgctggcc agcgtccggg caatctgccc    7260
ccgaagttca ccgcctgcgg cgtcggccac cttgacccat gcctgatagt tcttcgggct    7320
ggtttccact accagggcag gctcccgncc ctcggctttc atgtcatcca ggtcaaactc    7380
gctgaggtcg tccaccagca ccagaccatg ccgctcctgc tcggcgggcc tgatatacac    7440
gtcattgccc tgggcattca tccgcttgag ccatggcgtg ttctggagca cttcggcggc    7500
tgaccattcc cggttcatca tctggccggt gggtgcgtcc ctgacgccga tatcgaagcg    7560
ctcacagccc atggccttga gctgtcggcc tatggcctgc aaagtcctgt cgttcttcat    7620
cgggccacca agcgcagcca gatcgagccg tcctcggttg tcagtggcgt caggtcgagc    7680
aagagcaacg atgcgatcag cagcaccacc gtaggcatca tggaagccag catcacggtt    7740
agccatagct tccagtgcca cccccgcgac gcgctccggg cgctctgcgc ggcgctgctc    7800
acctcggcgg ctacctcccg caactctttg ccagctcca  cccatgccgc cctgtctgg     7860
cgctgggctt tcagccactc cgccgcctgc gcctcgctgg cctgcttggt ctggctcatg    7920
acctgccggg cttcgtcggc cagtgtcgcc atgctctggg ccagcggttc gatctgctcc    7980
gctaactcgt tgatgcctct ggatttcttc actctgtcga ttgcgttcat ggtctattgc    8040
ctcccggtat tcctgtaagt cgatgatctg ggcgttggcg gtgtcgatgt tcagggccac    8100
gtctgcccgg tcggtgcgga tgccccggcc ttccatctcc accacgttcg gccccaggtg    8160
aacaccgggc aggcgctcga tgccctgcgc ctcaagtgtt ctgtggtcaa tgcgggcgtc    8220
gtggccagcc cgctctaatg cccggttggc atggtcggcc catgcctcgc gggtctgctc    8280
aagccatgcc ttgggcttga gcgcttcggt cttctgtgcc ccgcccttct ccggggtctt    8340
gccgttgtac cgcttgaacc actgagcggc gggccgctcg atgccgtcat tgatccgctc    8400
ggagatcatc aggtggcagt gcgggttctc gccgccaccg gcatggatgg ccagcgtata    8460
cggcaggcgc tcggcaccgg tcaggtgctg ggcgaactcg gacgccagcg ccttctgctg    8520
gtcgagggtc agctcgaccg gcagggcaaa ttcgacctcc ttgaacagcc gcccattggc    8580
gcgttcatac aggtcggcag catcccagta gtcggcgggc cgctcgacga actccggcat    8640
gtgcccggat tcggcgtgca agacttcatc catgtcgcgg gcatacttgc cttcgcgctg    8700
gatgtagtcg gccttggccc tggccgattg ccgcccgac  ctgctgccgg ttttcgccgt    8760
aaggtgataa atcgccatgc tgcctcgctg ttgcttttgc ttttcggctc catgcaatgg    8820
ccctcggaga gcgcaccgcc cgaagggtgg ccgttaggcc agtttctcga agagaaaccg    8880
gtaagtgcgc cctcccctac aaagtagggt cgggattgcc gccgctgtgc ctccatgata    8940
gcctacgaga cagcacatta acaatggggt gtcaagatgg ttaaggggag caacaaggcg    9000
gcggatcggc tggccaagct cgaagaacaa cgagcgcgaa tcaatgccga aattcagcgg    9060
gagcgggcaa gggaacagca gcaagagcgc aagaacgaaa caaggcgcaa ggtgctggtg    9120
ggggccatga ttttggccaa ggtgaacagc agcgagtggc cggaggatcg gctcatggcg    9180
gcaatggatg cgtaccttga acgcgaccac gaccgcgcct tgttcggtct gccgccacgc    9240
cagaaggatg agccgggctg aatgatcgac cgagacaggc cctgcggggc tgcacacgcg    9300
cccccaccct tcgggtaggg ggaaaggccg ctaaagcggc taaaagcgct ccagcgtatt    9360
tctgcgggt  ttggtgtggg gtttagcggg cttgcccgc  ctttccccct gccgcgcagc    9420
ggtgggcgcg tgtgtagcct agcgcagcga atagaccagc tatccggcct ctggccgggc    9480
atattgggca agggcagcag cgccccacaa gggcgctgat aaccgcgcct agtggattat    9540
```

```
tcttagataa tcatggatgg attttttccaa cacccccgcca gcccccgccc ctgctgggtt   9600
tgcaggtttg ggggcgtgac agttattgca ggggttcgtg acagttattg caggggggcg   9660
tgacagttat tgcaggggtt cgtgacagtt agtacgggag tgacgggcac tggctggcaa   9720
tgtctagcaa cggcaggcat ttcggctgag ggtaaaagaa ctttccgcta agcgatagac   9780
tgtatgtaaa cacagtattg caaggacgcg gaacatgcct catgtggcgg ccaggacggc   9840
cagccgggat cgggatactg gtcgttacca gagccaccga cccgagcaaa cccttctcta   9900
tcagatcgtt gacgagtatt acccggcatt cgctgcgctt atggcagagc agggaaagga   9960
attgccgggc tatgtgcaac gggaatttga agaatttctc caatgcgggc ggctggagca  10020
tggctttcta cgggttcgct gcgagtcttg ccacgccgag cacctggtcg ctttcagaaa  10080
tcaatctaaa gtatatatga gtaaacttgg tctgacagtt accaatgctt aatcagtgag  10140
gcacctatct cagcgatctg tctatttcgt tcatccatag ttgcctgact ccccgtcgtg  10200
tagataacta cgatacggga gggcttacca tctggcccca gtgctgcaat gataccgcga  10260
gacccacgct caccggctcc agatttatca gcaataaacc agccagccgg aagggccgag  10320
cgcagaagtg gtcctgcaac tttatccgcc tccatccagt ctattaattg ttgccgggaa  10380
gctagagtaa gtagttcgcc agttaatagt ttgcgcaacg ttgttgccat tgctacaggc  10440
atcgtggtgt cacgctcgtc gtttggtatg gcttcattca gctccggttc ccaacgatca  10500
aggcgagtta catgatcccc catgttgtgc aaaaaagcgg ttagctcctt cggtcctccg  10560
atcgttgtca gaagtaagtt ggccgcagtg ttatcactca tggttatggc agcactgcat  10620
aattctctta ctgtcatgcc atccgtaaga tgcttttctg tgactggtga gtactcaacc  10680
aagtcattct gagaatagtg tatgcggcga ccgagttgct cttgcccggc gtcaacacgg  10740
gataataccg cgccacatag cagaacttta aaagtgctca tcattggaaa acgttcttcg  10800
gggcgaaaac tctcaaggat cttaccgctg ttgagatcca gttcgatgta acccactcgt  10860
gcacccaact gatcttcagc atcttttact ttcaccagcg tttctgggtg agcaaaaaca  10920
ggaaggcaaa atgccgcaaa aaagggaata aaggcgacac ggaaatgttg aatactcata  10980
ctcttccttt ttcaatatta ttgaagcatt tatcagggtt attgtctcat gagcggatac  11040
atatttgaat gtatttagaa aaataaacaa aagagtttgt agaaacgcaa aaaggccatc  11100
cgtcaggatg gccttctgct taatttgatg cctggcagtt tatggcgggc gtcctgcccg  11160
ccacccctccg ggccgttgct tcgcaacgtt caaatccgct cccggcggat tgtcctact  11220
caggagagcg ttcaccgaca acaacagat aaaacgaa                            11258
```

<210> SEQ ID NO 126  
<211> LENGTH: 11453  
<212> TYPE: DNA  
<213> ORGANISM: Artificial Sequence  
<220> FEATURE:  
<223> OTHER INFORMATION: plasmid pLybAL37 containing otsBA operon

<400> SEQUENCE: 126

```
aggcccagtc tttcgactga gcctttcgtt ttatttgatg cctggcagtt ccctactctc     60
gcatggggag accccacact accatcggcg ctacggcgtt tcacttctga gttcggcatg    120
gggtcaggtg ggaccaccgc gctactgccg ccagcaaat tctgtttttat cagaccgctt    180
ctgcgttctg atttaatctg tatcaggctg aaaatcttct ctcatccgcc aaaacagcca    240
agcttgcatg cataaatttc tgttttgacc aaaccatccc gacataactc ggtcagggct    300
tgcaaaacag cggggatgcg atcgtgctgc cagagactgc aaaggtgagc caataaccac    360
```

```
tgcgtctgcc agtcatcagg tatcgcttgg cagcgctgca acccagcttc gaggacgcga    420
acatcaactg ttttggccag ttgctgaacc tgtcgccaac aatgttcaaa atcaccgctt    480
ggccagccgt cactctctgc aaacgctgca tcagtcatgt gcaatcaata caggttaaaa    540
accatgctaa tggctccacc taagcgggct tcagagtcaa ggcttgtagc aattgctact    600
aaaaactgcg atcgctgctg aaatgagctg gaattctgtc cctctcagct caaaaagtat    660
caatgattac ttaatgtttg ttctgcgcaa acttcttgca gaacatgcat gatttacaaa    720
aagttgtagt ttctgttacc aattgcgaat cgagaactgc ctaatctgcc gagtatgcaa    780
gctgctttgt aggcagatga atccatggta ccgttaagaa ggaggatcca tatgatcttg    840
atggaacgct ggcggaaatc aaaccgcatc ccgatcaggt cgtcgtgcct gacaatattc    900
tgcaaggact acagctactg caaccgcaaa gtgatggtgc attggcattg atatcagggc    960
gctcaatggt ggagcttgac gcactggcaa aaccttatcg cttcccgtta gcgggcgtgc   1020
atggggcgga gcgccgtgac atcaatggta aaacacatat cgttcatctg ccggatgcga   1080
ttgcgcgtga tattagcgtg caactgcata cagtcatcgc tcagtatccc ggcgcggagc   1140
tggaggcgaa agggatggct tttgcgctgc attatcgtca ggctccgcag catgaagacg   1200
cattaatgac attagcgcaa cgtattactc agatctggcc acaaatggcg ttacagcagg   1260
gaaagtgtgt tgtcgagatc aaaccgagag gtaccagtaa aggtgaggca attgcagctt   1320
ttatgcagga agctcccttt atcgggcgaa cgcccgtatt tctgggcgat gatttaaccg   1380
atgaatctgg cttcgcagtc gttaaccgac tgggcggaat gtcagtaaaa attggcacag   1440
gtgcaactca ggcatcatgg cgactggcgg gtgtgccgga tgtctggagc tggcttgaaa   1500
tgataaccac cgcattacaa caaaaaagag aaaataacag gagtgatgac tatgagtcgt   1560
ttagtcgtag tatctaaccg gattgcacca ccagacgagc acgccgccag tgccggtggc   1620
cttgccgttg gcatactggg ggcactgaaa gccgcaggcg gactgtggtt tggctggagt   1680
ggtgaaacag ggaatgagga tcagccgcta aaaaaggtga aaaaaggtaa cattacgtgg   1740 gcctcttttta acctcagcga acaggacctt gacgaatact acaaccaatt ctccaatgcc   1800
gttctctggc ccgcttttca ttatcggctc gatctggtgc aatttcagcg tcctgcctgg   1860
gacggctatc tacgcgtaaa tgcgttgctg gcagataaat tactgccgct gttgcaagac   1920
gatgacatta tctggatcca cgattatcac ctgttgccat ttgcgcatga attacgcaaa   1980
cggggagtga ataatcgcat tggtttctttt ctgcatattc ctttcccgac accggaaatc   2040
ttcaacgcgc tgccgacata tgacaccttg cttgaacagc tttgtgatta tgatttgctg   2100
ggtttccaga cagaaaacga tcgtctggcg ttcctggatt gtctttctaa cctgacccgc   2160
gtcacgacac gtagcgcaaa aagccataca gcctggggca agcatttcg aacagaagtc   2220 tacccgatcg gcattgaacc gaaagaaata gccaaacagg ctgccgggcc actgccgcca   2280
aaactggcgc aacttaaagc ggaactgaaa aacgtacaaa atatcttttc tgtcgaacgg   2340
ctggattatt ccaaaggttt gccagagcgt tttctcgcct atgaagcgtt gctggaaaaa   2400
tatccgcagc atcatggtaa aattcgttat acccagattg caccaacgtc gcgtggtgat   2460
gtgcaagcct atcaggatat tcgtcatcag ctcgaaaatg aagctggacg aattaatggt   2520
aaatacgggc aattaggctg gacgccgctt tattatttga atcagcatttt tgaccgtaaa   2580 ttactgatga aaatattccg ctactctgac gtgggcttag tgacgccact gcgtgacggg   2640
atgaacctgg tagcaaaaga gtatgttgct gctcaggacc cagccaatcc gggcgttctt   2700
gttctttcgc aatttgcggg agcggcaaac gagttaacgt cggcgttaat tgttaaccccc   2760
```

```
tacgatcgtg acgaagttgc agctgcgctg gatcgtgcat tgactatgtc gctggcggaa   2820
cgtatttccc gtcatgcaga aatgctggac gttatcgtga aaaacgatat taaccactgg   2880
caggagtgct tcattagcga cctaaagcag atagttccgc gaagcgcgga aagccagcag   2940
cgcgataaag ttgctacctt tccaaagctt gcgtaggagc tagctgcctc gaaaggggat   3000
gcgattcgcc acctctcact ccgctggcgg attcctcttg agaacatttt ggtggcaggc   3060
gattctggta acgatgagga aatgctcaag ggccataatc tcggcgttgt agttggcaat   3120
tactcaccgg aattggagcc actgcgcagc tacgagcgcg tctattttgc tgagggccac   3180
tatgctaatg gcattctgga agccttaaaa cactatcgct tttttgaggc gatcgcttaa   3240 cctttcaga atgagacgtt gatcggcacg taagcgtgag acgttgatcg gcacgtaaga   3300
ggttccaact ttcaccataa tgaaataaga tcactaccgg gcgtattttt tgagttatcg   3360
agattttcag gagctaagga agctaaaatg gagaaaaaaa tcactggata taccaccgtt   3420
gatatatccc aatggcatcg taaagaacat tttgaggcat ttcagtcagt tgctcaatgt   3480
acctataacc agaccgttca gctggatatt acggcctttt taaagaccgt aaagaaaaat   3540
aagcacaagt tttatccggc ctttattcac attcttgccc gcctgatgaa tgctcatccg   3600
gaattccgta tggcaatgaa agacggtgag ctggtgatat gggatagtgt tcacccttgt   3660
tacaccgttt tccatgagca aactgaaacg ttttcatcgc tctggagtga ataccacgac   3720
gatttccggc agtttctaca catatattcg caagatgtgg cgtgttacgg tgaaaacctg   3780
gcctatttcc ctaaagggtt tattgagaat atgttttcg tctcagccaa tccctgggtg   3840
agtttcacca gttttgattt aaacgtggcc aatatggaca cttcttcgc ccccgttttc   3900 accatgggca atattatac gcaaggcgac aaggtgctga tgccgctggc gattcaggtt   3960
catcatgccg tttgtgatgg cttccatgtc ggcagaatgc ttaatgaatt acaacagtac   4020
tgcgatgagt ggcagggcgg ggcgtaattt ttttaaggca gttattggtg cccttaaacg   4080
cctggttgct acgcctgaat aagtgataat aagcggatga atggcagaaa ttcgatgata   4140
agctgtcaaa cacaaccacc atcaaacagg attttcgcct gctggggcaa accagcgtgg   4200
accgcttgct gcaactctct cagggccagg cggtgaaggg caatcagctg ttgcccgtct   4260
cactggtgaa aagaaaaacc accctggcgc ccaatacgca aaccgcctct ccccgcgcgt   4320
tggccgattc attaatgcag ctggcacgac aggtttcccg actggaaagc gggcagtgag   4380
cgcaacgcaa ttaatgtaag ttagcgcgaa ttgcaagctg gccgacgcgc tgggctacgt   4440
cttgctggcg ttcgggagca gaagagcata catctggaag caaagccagg aaagcggcct   4500
atggagctgt gcggcagcgc tcagtaggca attttttcaaa atattgttaa gccttttctg   4560
agcatggtat ttttcatggt attaccaatt agcaggaaaa taagccattg aatataaaag   4620
ataaaaatgt cttgtttaca atagagtggg ggggtcagc ctgccgcctt gggccgggtg   4680
atgtcgtact tgcccgccgc gaactcggtt accgtccagc ccagcgcgac cagctccggc   4740
aacgcctcgc gcacccgctt gcggcgcttg cgcatggtcg aaccactggc ctctgacggc   4800
cagacatagc cgcacaaggt atctatggaa gccttgccgg ttttgccggg gtcgatccag   4860
ccacacagcc gctggtgcag caggcgggcg gtttcgctgt ccagcgcccg cacctcgtcc   4920
atgctgatgc gcacatgctg gccgccaccc atgacggcct gcgcgatcaa ggggttcagg   4980
gccacgtaca ggcgcccgtc cgcctcgtcg ctggcgtact ccgacagcag ccgaaacccc   5040
tgccgcttgc ggccattctg ggcgatgatg gataccttcc aaaggcgctc gatgcagtcc   5100
tgtatgtgct tgagcgcccc accactatcg acctctgccc cgatttcctt tgccagcgcc   5160
```

```
cgatagctac ctttgaccac atggcattca gcggtgacgg cctcccactt gggttccagg      5220
aacagccgga gctgccgtcc gccttcggtc ttgggttccg ggccaagcac taggccatta      5280
ggcccagcca tggccaccag cccttgcagg atgcgcagat catcagcgcc cagcggctcc      5340
gggccgctga actcgatccg cttgccgtcg ccgtagtcat acgtcacgtc cagcttgctg      5400
cgcttgcgct cgccccgctt gagggcacgg aacaggccgg gggccagaca gtgcgccggg      5460
tcgtgccgga cgtggctgag gctgtgcttg ttcttaggct tcaccacggg gcacccctt      5520 gctcttgcgc tgcctctcca gcacggcggg cttgagcacc ccgccgtcat gccgcctgaa      5580
ccaccgatca gcgaacggtg cgccatagtt ggccttgctc acaccgaagc ggacgaagaa      5640
ccggcgctgg tcgtcgtcca caccccattc ctcggcctcg gcgctggtca tgctcgacag      5700
gtaggactgc cagcggatgt tatcgaccag taccgagctg ccccggctgg cctgctgctg      5760
gtcgcctgcg cccatcatgg ccgcgccctt gctggcatgg tgcaggaaca cgatagagca      5820
cccggtatcg gcgcgatgg cctccatgcg accgatgacc tgggccatgg gccgctggc       5880 gttttcttcc tcgatgtgga accggcgcag cgtgtccagc accatcaggc ggcggccctc      5940
ggcggcgcgc ttgaggccgt cgaaccactc cggggccatg atgttgggca ggctgccgat      6000
cagcggctgg atcagcaggc cgtcagccac ggcttgccgt cctcggcgc tgaggtgcgc       6060 cccaagggcg tgcaggcggt gatgaatggc ggtgggcggg tcttcggcgg gcaggtagat      6120
caccgggccg gtgggcagtt cgcccacctc cagcagatcc ggcccgcctg caatctgtgc      6180
ggccagttgc agggccagca tggatttacc ggcaccaccg ggcgacacca gcgcccgac       6240 cgtaccggcc accatgttgg gcaaaacgta gtccagcggt ggcggcgctg ctgcgaacgc      6300
ctccagaata ttgataggct tatgggtagc cattgattgc ctcctttgca ggcagttggt      6360
ggttaggcgc tggcggggtc actacccccg ccctgcgccg ctctgagttc ttccaggcac      6420
tcgcgcagcg cctcgtattc gtcgtcggtc agccagaact tgcgctgacg catcccttttg     6480 gccttcatgc gctcggcata tcgcgcttgg cgtacagcgt cagggctggc cagcaggtcg      6540
ccggtctgct tgtccttttg gtctttcata tcagtcaccg agaaacttgc cggggccgaa      6600
aggcttgtct tcgcggaaca aggacaaggt gcagccgtca aggttaaggc tggccatatc      6660
agcgactgaa aagcggccag cctcggcctt gtttgacgta taaccaaagc caccgggcaa      6720
ccaatagccc ttgtcacttt tgatcaggta gaccgaccct gaagcgcttt tttcgtattc      6780
cataaaaccc ccttctgtgc gtgagtactc atagtataac aggcgtgagt accaacgcaa      6840
gcactacatg ctgaaatctg gcccgcccct gtccatgcct cgctggcggg gtgccggtgc      6900
ccgtgccagc tcggcccgcg caagctggac gctgggcaga cccatgacct tgctgacggt      6960
gcgctcgatg taatccgctt cgtggccggg cttgcgctct gccagcgctg ggctggcctc      7020
ggccatggcc ttgccgattt cctcggcact gcggccccgg ctggccagct tctgcgcggc      7080
gataaagtcg cacttgctga ggtcatgacc gaagcgcttg accagcccgg ccatctcgct      7140
gcggtactcg tccagcgccg tgccgccgtg gcggctaagc tgccgctcgg gcagttcgag      7200 gctgccagc ctgcgggcct tctcctgctg ccgctgggcc tgctcgatct gctgccagc       7260 ctgctgcacc agcgccgggc cagcggtggc ggtcttgccc ttggattcac gcagcagcac      7320
ccacggctga taaccggcgc gggtggtgtg cttgtccttg cggttggtga agcccgccaa      7380
gcggccatag tggcggctgt cggcgctggc cgggtcggcg tcgtactcgc tggccagcgt      7440
ccgggcaatc tgccccgaa gttcaccgcc tgcggcgtcg gccaccttga cccatgcctg       7500
atagttcttc gggctggttt ccactaccag ggcaggctcc cggccctcgg ctttcatgtc      7560
```

```
atccaggtca aactcgctga ggtcgtccac cagcaccaga ccatgccgct cctgctcggc    7620
gggcctgata tacacgtcat tgccctgggc attcatccgc ttgagccatg gcgtgttctg    7680
gagcacttcg gcggctgacc attcccggtt catcatctgg ccggtgggtg cgtccctgac    7740
gccgatatcg aagcgctcac agcccatggc cttgagctgt cggcctatgg cctgcaaagt    7800
cctgtcgttc ttcatcgggc caccaagcgc agccagatcg agccgtcctc ggttgtcagt    7860
ggcgtcaggt cgagcaagag caacgatgcg atcagcagca ccaccgtagg catcatggaa    7920
gccagcatca cggttagcca tagcttccag tgccaccccc gcgacgcgct ccgggcgctc    7980
tgcgcggcgc tgctcacctc ggcggctacc tcccgcaact cttttggccag ctccacccat    8040
gccgcccctg tctggcgctg ggctttcagc cactccgccg cctgcgcctc gctggcctgc    8100
ttggtctggc tcatgacctg ccgggcttcg tcggccagtg tcgccatgct ctgggccagc    8160
ggttcgatct gctccgctaa ctcgttgatg cctctggatt tcttcactct gtcgattgcg    8220
ttcatggtct attgcctccc ggtattcctg taagtcgatg atctgggcgt ggcggtgtc    8280
gatgttcagg gccacgtctg cccggtcggt gcggatgccc cggccttcca tctccaccac    8340
gttcggcccc aggtgaacac cgggcaggcg ctcgatgccc tgcgcctcaa gtgttctgtg    8400
gtcaatgcgg gcgtcgtggc cagcccgctc taatgcccgg ttggcatggt cggcccatgc    8460
ctcgcgggtc tgctcaagcc atgccttggg cttgagcgct tcggtcttct gtgccccgcc    8520
cttctccggg gtcttgccgt tgtaccgctt gaaccactga gcggcgggcc gctcgatgcc    8580
gtcattgatc cgctcggaga tcatcaggtg gcagtgcggg ttctcgccgc caccggcatg    8640
gatggccagc gtatacggca ggcgctcggc accggtcagg tgctgggcga actcggacgc    8700
cagcgccttc tgctggtcga gggtcagctc gaccggcagg gcaaattcga cctccttgaa    8760
cagccgccca ttggcgcgtt catacaggtc ggcagcatcc cagtagtcgg cgggccgctc    8820
gacgaactcc ggcatgtgcc cggattcggc gtgcaagact tcatccatgt cgcgggcata    8880
cttgccttcg cgctggatgt agtcggcctt ggccctggcc gattggccgc ccgacctgct    8940
gccggttttc gccgtaaggt gataaatcgc catgctgcct cgctgttgct tttgcttttc    9000
ggctccatgc aatggccctc ggagagcgca ccgcccgaag ggtggccgtt aggccagttt    9060
ctcgaagaga aaccggtaag tgcgccctcc cctacaaagt agggtcggga ttgccgccgc    9120
tgtgccttca tgatagccta cgagacagca cattaacaat ggggtgtcaa gatggttaag    9180
gggagcaaca aggcggcgga tcggctggcc aagctcgaag aacaacgagc gcgaatcaat    9240
gccgaaattc agcgggagcg ggcaagggaa cagcagcaag agcgcaagaa cgaaacaagg    9300
cgcaaggtgc tggtgggggc catgattttg gccaaggtga acagcagcga gtggccggag    9360
gatcggctca tggcggcaat ggatgcgtac cttgaacgcg accacgaccg cgccttgttc    9420
ggtctgccgc cacgccagaa ggatgagccg ggctgaatga tcgaccgaga caggccctgc    9480
ggggctgcac acgcgccccc acccttcggg taggggaaa ggccgctaaa gcggctaaaa    9540
gcgctccagc gtatttctgc ggggtttggt gtggggttta gcgggctttg cccgcctttc    9600
cccctgccgc gcagcggtgg ggcggtgtgt agcctagcgc agcgaataga ccagctatcc    9660
ggcctctggc cgggcatatt gggcaagggc agcagcgccc cacaagggcg ctgataaccg    9720
cgcctagtgg attattctta gataatcatg gatggatttt tccaacaccc cgccagcccc    9780
cgcccctgct gggtttgcag gtttgggggc gtgacagtta ttgcaggggt tcgtgacagt    9840
tattgcaggg gggcgtgaca gttattgcag ggttcgtga cagttagtac gggagtgacg    9900
ggcactggct ggcaatgtct agcaacggca ggcatttcgg ctgagggtaa aagaactttc    9960
```

```
cgctaagcga tagactgtat gtaaacacag tattgcaagg acgcggaaca tgcctcatgt    10020
ggcggccagg acggccagcc gggatcggga tactggtcgt taccagagcc accgacccga    10080
gcaaacccct tctctatcaga tcgttgacga gtattacccg gcattcgctg cgcttatggc    10140
agagcaggga aggaattgc cgggctatgt gcaacgggaa tttgaagaat ttctccaatg    10200
cgggcggctg gagcatggct ttctacgggt tcgctgcgag tcttgccacg ccgagcacct    10260
ggtcgctttc agaaatcaat ctaaagtata tatgagtaaa cttggtctga cagttaccaa    10320
tgcttaatca gtgaggcacc tatctcagcg atctgtctat ttcgttcatc catagttgcc    10380
tgactccccg tcgtgtagat aactacgata cgggagggct taccatctgg ccccagtgct    10440
gcaatgatac cgcgagaccc acgctcaccg gctccagatt tatcagcaat aaaccagcca    10500
gccggaaggg ccgagcgcag aagtggtcct gcaactttat ccgcctccat ccagtctatt    10560
aattgttgcc gggaagctag agtaagtagt tcgccagtta atagtttgcg caacgttgtt    10620
gccattgcta caggcatcgt ggtgtcacgc tcgtcgtttg gtatggcttc attcagctcc    10680
ggttcccaac gatcaaggcg agttacatga tcccccatgt tgtgcaaaaa agcggttagc    10740
tccttcggtc ctccgatcgt tgtcagaagt aagttggccg cagtgttatc actcatggtt    10800
atggcagcac tgcataattc tcttactgtc atgccatccg taagatgctt ttctgtgact    10860
ggtgagtact caaccaagtc attctgagaa tagtgtatgc ggcgaccgag ttgctcttgc    10920
ccggcgtcaa cacgggataa taccgcgcca catagcagaa ctttaaaagt gctcatcatt    10980
ggaaaacgtt cttcggggcg aaaactctca aggatcttac cgctgttgag atccagttcg    11040
atgtaaccca ctcgtgcacc caactgatct tcagcatctt ttactttcac cagcgtttct    11100
gggtgagcaa aaacaggaag gcaaaatgcc gcaaaaaagg gaataagggc gacacggaaa    11160
tgttgaatac tcatactctt cctttttcaa tattattgaa gcatttatca gggttattgt    11220
ctcatgagcg gatacatatt tgaatgtatt tagaaaaata aacaaaagag tttgtagaaa    11280
cgcaaaaagg ccatccgtca ggatggcctt ctgcttaatt tgatgcctgg cagtttatgg    11340
cgggcgtcct gcccgccacc ctccgggccg ttgcttcgca acgttcaaat ccgctcccgg    11400
cggatttgtc ctactcagga gagcgttcac cgacaaacaa cagataaaac gaa           11453
```

<210> SEQ ID NO 127
<211> LENGTH: 1754
<212> TYPE: DNA
<213> ORGANISM: Artificial Sequence
<220> FEATURE:
<223> OTHER INFORMATION: PCR product
<220> FEATURE:
<221> NAME/KEY: misc_feature
<222> LOCATION: (7)..(12)
<223> OTHER INFORMATION: AflII restriction site
<220> FEATURE:
<221> NAME/KEY: misc_feature
<222> LOCATION: (1743)..(1748)
<223> OTHER INFORMATION: XbaI restriction site

<400> SEQUENCE: 127

```
tattcgctta agccaaagga gaatgattga tgaaatcccc cgcaccttct cgcccgcaaa      60
aaatggcgtt aattccagcc tgtatctttt tgtgtttcgc tgcgctatcg gtgcaggcag     120
aagaaacacc ggtaacacca cagccgcctg atatttatt agggccgctg tttaatgatg     180
tgcaaaacgc caaacttttt ccggaccaaa aaaccttgc cgatgccgtg ccgaacagcg     240
atccgctgat gatccttgct gattatcgga tgcagcaaaa ccagagcgga tttgatctgc     300
gccatttcgt taacgtcaat ttcaccctgc cgaaagaagg cgagaaatat gttccgccag    360
```

-continued

```
agggggcagtc actgcgcgaa catattgacg gactttggcc ggtattaacg cgttctaccg      420
aaaacaccga aaaatgggat tctctgttac cgctgccgga accttatgtc gtgccgggcg      480
gacgctttcg cgaggtatat tactgggaca gttacttcac catgttagga cttgccgaaa      540
gcggtcactg ggataaagtc gcggatatgg tggccaattt tgctcatgaa atagacactt      600
acggtcatat tcccaacggc aaccgcagtt actatttaag ccgctcgcaa ccgcccttct      660
ttgccctgat ggtagagtta ctggcgcagc atgaaggcga tgccgcgttg aagcaatacc      720
tgccgcaaat gcaaaagaa tatgcttact ggatggacgg tgttgaaaac ctgcaagccg      780
gacaacagga aaaacgcgtt gtcaaacttc aggatggtac ccttctcaac cgctactggg      840
acgatcgcga tacgccacga ccagagtcat gggtggaaga tattgccacc gccaaaagca      900
atccgaatcg acctgccact gaaatttacc gcgacctgcg ctctgccgct gcgtctggct      960
gggatttcag ctcgcgctgg atggacaacc cgcagcagtt aaatacctta cgcaccacca     1020
gcatcgtacc ggtcgatctg aacagcctga tgtttaaaat ggaaaaaatc ctcgcccgcg     1080
ccagcaaagc tgccggagat aacgcgatgg caaaccagta cgaaacgctg gcaaatgccc     1140
gtcaaaaagg gatcgaaaaa tacctgtgga acgatcaaca aggctggtat gccgattacg     1200
acctgaaaag tcataaagtg cgcaatcagt taaccgcggc cgccctgttc ccgctgtacg     1260
tcaatgcggc agcgaaagat cgcgccaaca aaatggcgac ggcgacgaaa acacatctgc     1320
tgcaacccgg cggcctgaac accacgtcgg tgaaaagtgg gcaacaatgg gatgcgccaa     1380
atggctgggc accgttacag tgggtcgcga cagaaggatt acaaaactac gggcaaaaag     1440
aggtggcgat ggacattagc tggcacttcc tgaccaatgt tcagcacacc tatgaccggg     1500
agaaaaagct ggtggaaaaa tatgatgtca gcaccaccgg aacgggggc ggcggtggcg      1560
aatatccatt acaggatggc tttggctgga ccaatggcgt gacgctgaaa atgctggatt     1620
tgatctgccc gaaagagcaa ccgtgtgaca atgttccggc gacgcgtccg accgttaagt     1680
cagcaacgac gcaaccctca accaaagagg cacaacccac accttaacca gcgcttactc     1740
cgtctagatc attc                                                      1754
```

<210> SEQ ID NO 128
<211> LENGTH: 29
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (7)..(12)
<223> OTHER INFORMATION: AflII restriction site

<400> SEQUENCE: 128
tattcgctta agccaaagga gaatgattg                                       29

<210> SEQ ID NO 129
<211> LENGTH: 27
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (7)..(12)
<223> OTHER INFORMATION: XbaI restriction site

<400> SEQUENCE: 129
gaatgatcta gacggagtaa gcgctgg                                         27

<210> SEQ ID NO 130
<211> LENGTH: 6282
<212> TYPE: DNA
<213> ORGANISM: Artificial Sequence
<220> FEATURE:
<223> OTHER INFORMATION: plasmid pLybAL24 containing treA

<400> SEQUENCE: 130

| | | | | | |
|---|---|---|---|---|---|
| tagtcatgcc | ccgcgcccac | cggaaggagc | tgactgggtt | gaaggctctc | aagggcatcg | 60 |
| gtcgataaat | attctgaaat | gagctgttga | caattaatca | tcgaactagt | taactttta c | 120 |
| gcaagttctt | aagccaaagg | agaatgattg | atgaaatccc | ccgcaccttc | tcgcccgcaa | 180 |
| aaaatggcgt | taattccagc | ctgtatcttt | ttgtgtttcg | ctgcgctatc | ggtgcaggca | 240 |
| gaagaaacac | cggtaacacc | acagccgcct | gatattttat | tagggccgct | gtttaatgat | 300 |
| gtgcaaaacg | ccaaactttt | tccggaccaa | aaaacctttg | ccgatgccgt | gccgaacagc | 360 |
| gatccgctga | tgatccttgc | tgattatcgg | atgcagcaaa | accagagcgg | atttgatctg | 420 |
| cgccatttcg | ttaacgtcaa | tttcaccctg | ccgaaagaag | gcgagaaata | tgttccgcca | 480 |
| gaggggcagt | cactgcgcga | acatattgac | ggactttggc | cggtattaac | gcgttctacc | 540 |
| gaaaacaccg | aaaaatggga | ttctctgtta | ccgctgccgg | aaccttatgt | cgtgccgggc | 600 |
| ggacgctttc | gcgaggtata | ttactgggac | agttacttca | ccatgttagg | acttgccgaa | 660 |
| agcggtcact | gggataaagt | cgcggatatg | gtggccaatt | ttgctcatga | aatagacact | 720 |
| tacggtcata | ttcccaacgg | caaccgcagt | tactatttaa | gccgctcgca | accgcccttc | 780 |
| tttgccctga | tggtagagtt | actggcgcag | catgaaggcg | atgccgcgtt | gaagcaatac | 840 |
| ctgccgcaaa | tgcaaaaaga | atatgcttac | tggatggacg | tgttgaaaa | cctgcaagcc | 900 |
| ggacaacagg | aaaaacgcgt | tgtcaaactt | caggatggta | cccttctcaa | ccgctactgg | 960 |
| gacgatcgcg | atacgccacg | accagagtca | tgggtggaag | atattgccac | cgccaaaagc | 1020 |
| aatccgaatc | gacctgccac | tgaaatttac | cgcgacctgc | gctctgccgc | tgcgtctggc | 1080 |
| tgggatttca | gctcgcgctg | gatggacaac | ccgcagcagt | taaatacctt | acgcaccacc | 1140 |
| agcatcgtac | cggtcgatct | gaacagcctg | atgtttaaaa | tggaaaaaat | cctcgcccgc | 1200 |
| gccagcaaag | ctgccggaga | taacgcgatg | caaaccagt | acgaaacgct | ggcaaatgcc | 1260 |
| cgtcaaaaag | ggatcgaaaa | atacctgtgg | aacgatcaac | aaggctggta | tgccgattac | 1320 |
| gacctgaaaa | gtcataaagt | gcgcaatcag | ttaaccgcgg | ccgccctgtt | cccgctgtac | 1380 |
| gtcaatgcgg | cagcgaaaga | tcgcgccaac | aaaatggcga | cggcgacgaa | acacatctg | 1440 |
| ctgcaacccg | gcggcctgaa | caccacgtcg | gtgaaaagtg | ggcaacaatg | ggatgcgcca | 1500 |
| aatggctggg | caccgttaca | gtgggtcgcg | acagaaggat | tacaaaacta | cgggcaaaaa | 1560 |
| gaggtggcga | tggacattag | ctggcacttc | ctgaccaatg | ttcagcacac | ctatgaccgg | 1620 |
| gagaaaaagc | tggtggaaaa | atatgatgtc | agcaccaccg | gaacgggggg | cggcggtggc | 1680 |
| gaatatccat | tacaggatgg | ctttggctgg | accaatggcg | tgacgctgaa | aatgctggat | 1740 |
| ttgatctgcc | cgaaagagca | accgtgtgac | aatgttccgg | cgacgcgtcc | gaccgttaag | 1800 |
| tcagcaacga | cgcaacccctc | aaccaaagag | gcacaaccca | caccttaacc | agcgcttact | 1860 |
| ccgtctagac | atcaccatca | ccatcattaa | ttaagtttgt | gtttaaactg | caggcatgca | 1920 |
| agcttctgtt | ttggcggatg | agagaagatt | ttcagcctga | tacagattaa | atcagaacgc | 1980 |
| agaagcggtc | tgataaaaca | gaatttgcct | ggcggcagta | gcgcggtggt | cccacctgac | 2040 |
| cccatgccga | actcagaagt | gaaacgccgt | agcgccgatg | gtagtgtggg | gtctccccat | 2100 |

-continued

```
gcgagagtag ggaactgcca ggcatcaaat aaaacgaaag gctcagtcga aagactgggc   2160
ctttcgtttt atctgttgtt tgtcggtgaa cgctctcctg agtaggacaa atccgccggg   2220
agcggatttg aacgttgcga agcaacggcc cggagggtgg cgggcaggac gcccgccata   2280
aactgccagg catcaaatta agcagaaggc catcctgacg gatggccttt ttgcgtttct   2340
acaaactctt ttgtttattt ttctaaatac attcaaatat gtatccgctc atgaaaaaa   2400 atccttacgt ttcgctaagg atgtcagcgt aatgctctgc cagtgttaca accaattaac   2460
caattctgat tagaaaaact catcgagcat caaatgaaac tgcaatttat tcatatcagg   2520
attatcaata ccatattttt gaaaaagccg tttctgtaat gaaggagaaa actcaccgag   2580
gcagttccat aggatggcaa gatcctggta tcggtctgcg attccgactc gtccaacatc   2640
aatacaacct attaatttcc cctcgtcaaa aataaggtta tcaagtgaga atcaccatg   2700 agtgacgact gaatccggtg agaatggcaa aagcttatgc atttctttcc agacttgttc   2760
aacaggccag ccattacgct cgtcatcaaa atcactcgca tcaaccaaac cgttattcat   2820
tcgtgattgc gcctgagcga gacgaaatac gcgatcgctg ttaaaaggac aattacaaac   2880
aggaatcgaa tgcaaccggc gcaggaacac tgccagcgca tcaacaatat tttcacctga   2940
atcaggatat tcttctaata cctggaatgc tgttttcccg gggatcgcag tggtgagtaa   3000
ccatgcatca tcaggagtac ggataaaatg cttgatggtc ggaagaggca taaattccgt   3060
cagccagttt agtctgacca tctcatctgt aacatcattg gcaacgctac ctttgccatg   3120
tttcagaaac aactctggcg catcgggctt cccatacaat cgatagattg tcgcacctga   3180
ttgcccgaca ttatcgcgag cccatttata cccatataaa tcagcatcca tgttggaatt   3240
taatcgcggc ctcgagcaag acgtttcccg ttgaatatgg ctcataacac cccttgtatt   3300
actgtttatg taagcagaca gttttattgt tcatgaccaa aatcccttaa cgtgagtttt   3360
cgttccactg agcgtcagac cccgtagaaa agatcaaagg atcttcttga tccttttt    3420 ttctgcgcgt aatctgctgc ttgcaaacaa aaaaaccacc gctaccagcg gtggtttgtt   3480
tgccggatca agagctacca actctttttc cgaaggtaac tggcttcagc agagcgcaga   3540
taccaaatac tgtccttcta gtgtagccgt agttaggcca ccacttcaag aactctgtag   3600
caccgcctac atacctcgct ctgctaatcc tgttaccagt ggctgctgcc agtggcgata   3660
agtcgtgtct taccgggttg gactcaagac gatagttacc ggataaggcg cagcggtcgg   3720
gctgaacggg gggttcgtgc acacagccca gcttggagcg aacgacctac accgaactga   3780
gatacctaca gcgtgagcta tgagaaagcg ccacgcttcc cgaagggaga aaggcggaca   3840
ggtatccggt aagcggcagg gtcggaacag gagagcgcac gagggagctt ccaggggga   3900 acgcctggta tctttatagt cctgtcgggt ttcgccacct ctgacttgag cgtcgatttt   3960
tgtgatgctc gtcagggggg cggagcctat ggaaaaacgc cagcaacgcg gcctttttac   4020
ggttcctggc cttttgctgg ccttttgctc acatgttctt tcctgcgtta tcccctgatt   4080
ctgtggataa ccgtattacc gcctttgagt gagctgatac cgctcgccgc agccgaacga   4140
ccgagcgcag cgagtcagtg agcgaggaag cggaagagcg cctgatgcgg tattttctcc   4200
ttacgcatct gtgcggtatt tcacaccgca tatatggtgc actctcagta caatctgctc   4260
tgatgccgca tagttaagcc agtatacact ccgctatcgc tacgtgactg ggtcatggct   4320
gcgccccgac acccgccaac acccgctgac gcgccctgac gggcttgtct gctcccggca   4380
tccgcttaca gacaagctgt gaccgtctcc gggagctgca tgtgtcagag gttttcaccg   4440
tcatcaccga aacgcgcgag gcagctgcgg taaagctcat cagcgtggtc gtgaagcgat   4500
```

```
tcacagatgt ctgcctgttc atccgcgtcc agctcgttga gtttctccag aagcgttaat    4560
gtctggcttc tgataaagcg ggccatgtta agggcggttt tttcctgttt ggtcacttga    4620
tgcctccgtg taaggggggaa tttctgttca tgggggtaat gataccgatg aaacgagaga    4680
ggatgctcac gatacgggtt actgatgatg aacatgcccg gttactggaa cgttgtgagg    4740
gtaaacaact ggcggtatgg atgcggcggg accagagaaa aatcactcag ggtcaatgcc    4800
agcgcttcgt taatacagat gtaggtgttc cacagggtag ccagcagcat cctgcgatgc    4860
agatccggaa cataatggtg cagggcgctg acttccgcgt ttccagactt tacgaaacac    4920
ggaaaccgaa gaccattcat gttgttgctc aggtcgcaga cgttttgcag cagcagtcgc    4980
ttcacgttcg ctcgcgtatc ggtgattcat tctgctaacc agtaaggcaa ccccgccagc    5040
ctagccgggt cctcaacgac aggagcacga tcatgcgcac ccgtggccag acccaacgc    5100 tgcccgagat gcgccgcgtg cggctgctgg agatggcgga cgcgatggat atgttctgcc    5160
aagggttggt ttgcgcattc acagttctcc gcaagaattg attggctcca attcttggag    5220
tggtgaatcc gttagcgagg tgccgccggc ttccattcag gtcgaggtgg cccggctcca    5280
tgcaccgcga cgcaacgcgg ggaggcagac aaggtatagg gcggcgccta caatccatgc    5340
caacccgttc catgtgctcg ccgaggcggc ataaatcgcc gtgacgatca gcggtccagt    5400
gatcgaagtt aggctggtaa gagccgcgag cgatccttga agctgtccct gatggtcgtc    5460
atctacctgc ctggacagca tggcctgcaa cgcgggcatc ccgatgccgc cggaagcgag    5520
aagaatcata tgggggaagg ccatccagcc tcgcgtcgcg aacgccagca agacgtagcc    5580
cagcgcgtcg gccgccatgc cggcgataat ggcctgcttc tcgccgaaac gtttggtggc    5640
gggaccagtg acgaaggctt gagcgagggc gtgcaagatt ccgaataccg caagcgacag    5700
gccgatcatc gtcgcgctcc agcgaaagcg gtcctcgccg aaaatgaccc agagcgctgc    5760
cggcacctgt cctacgagtt gcatgataaa aagacagtc ataagtgcgg cgacgatagt    5820
catgccccgc gcccaccgga aggagctgac tgggttgaag gctctcaagg gcatcggtcg    5880
acgctctccc ttatgcgact cctgcattag gaagcagccc agtagtaggt tgaggccgtt    5940
gagcaccgcc gccgcaagga atggtgcatg ctcgatggct acgagggcag acagtaagtg    6000
gatttaccat aatcccttaa ttgtacgcac cgctaaaacg cgttcagcgc gatcacggca    6060
gcagacaggt aaaaatggca acaaaccacc ctaaaaactg cgcgatcgcg cctgataaat    6120
tttaaccgta tgaataccta tgcaaccaga gggtacaggc cacattaccc ccacttaatc    6180
cactgaagct gccattttc atggtttcac catcccagcg aagggccatg catgcatcga    6240
aattaatacg acgaaattaa tacgactcac tatagggcaa tt                       6282
```

<210> SEQ ID NO 131
<211> LENGTH: 27
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (9)..(14)
<223> OTHER INFORMATION: AflII restriction site

<400> SEQUENCE: 131
cgcaagttct taagccaaag gagaatg                                          27

<210> SEQ ID NO 132
<211> LENGTH: 26
<212> TYPE: DNA

<213> ORGANISM: Artificial Sequence
<220> FEATURE:
<223> OTHER INFORMATION: PCR primer
<220> FEATURE:
<221> NAME/KEY: misc_feature
<222> LOCATION: (7)..(12)
<223> OTHER INFORMATION: XbaI restriction site

<400> SEQUENCE: 132
aagcgctcta gaaggtgtgg gttgtg                                   26

<210> SEQ ID NO 133
<211> LENGTH: 6264
<212> TYPE: DNA
<213> ORGANISM: Artificial Sequence
<220> FEATURE:
<223> OTHER INFORMATION: plasmid pLybAL33 containing 6-His tagged treA

<400> SEQUENCE: 133

| | | | | | |
|---|---|---|---|---|---|
| tagtcatgcc | ccgcgcccac | cggaaggagc | tgactgggtt | gaaggctctc | aagggcatcg | 60 |
| gtcgataaat | attctgaaat | gagctgttga | caattaatca | tcgaactagt | taacttttac | 120 |
| gcaagttctt | aagccaaagg | agaatgattg | atgaaatccc | ccgcaccttc | tcgcccgcaa | 180 |
| aaaatggcgt | taattccagc | ctgtatcttt | ttgtgtttcg | ctgcgctatc | ggtgcaggca | 240 |
| gaagaaacac | cggtaacacc | acagccgcct | gatattttat | tagggccgct | gtttaatgat | 300 |
| gtgcaaaacg | ccaaactttt | tccggaccaa | aaaacctttg | ccgatgccgt | gccgaacagc | 360 |
| gatccgctga | tgatccttgc | tgattatcgg | atgcagcaaa | accagagcgg | atttgatctg | 420 |
| cgccatttcg | ttaacgtcaa | tttcaccctg | ccgaaagaag | gcgagaaata | tgttccgcca | 480 |
| gagggcagt | cactgcgcga | acatattgac | ggactttggc | cggtattaac | gcgttctacc | 540 |
| gaaaacaccg | aaaaatggga | ttctctgtta | ccgctgccgg | aaccttatgt | cgtgccgggc | 600 |
| ggacgctttc | gcgaggtata | ttactgggac | agttacttca | ccatgttagg | acttgccgaa | 660 |
| agcggtcact | gggataaagt | cgcggatatg | gtggccaatt | ttgctcatga | aatagacact | 720 |
| tacggtcata | ttcccaacgg | caaccgcagt | tactatttaa | gccgctcgca | accgcccttc | 780 |
| tttgccctga | tggtagagtt | actggcgcag | catgaaggcg | atgccgcgtt | gaagcaatac | 840 |
| ctgccgcaaa | tgcaaaaaga | atatgcttac | tggatggacg | tgttgaaaa | cctgcaagcc | 900 |
| ggacaacagg | aaaaacgcgt | tgtcaaactt | caggatggta | cccttctcaa | ccgctactgg | 960 |
| gacgatcgcg | atacgccacg | accagagtca | tgggtggaag | atattgccac | cgccaaaagc | 1020 |
| aatccgaatc | gacctgccac | tgaaatttac | cgcgacctgc | gctctgccgc | tgcgtctggc | 1080 |
| tgggatttca | gctcgcgctg | gatggacaac | ccgcagcagt | taaataccct | acgcaccacc | 1140 |
| agcatcgtac | cggtcgatct | gaacagcctg | atgtttaaaa | tggaaaaaat | cctcgcccgc | 1200 |
| gccagcaaag | ctgccggaga | taacgcgatg | gcaaaccagt | acgaaacgct | ggcaaatgcc | 1260 |
| cgtcaaaaag | ggatcgaaaa | atacctgtgg | aacgatcaac | aaggctggta | tgccgattac | 1320 |
| gacctgaaaa | gtcataaagt | gcgcaatcag | ttaaccgcgg | ccgccctgtt | cccgctgtac | 1380 |
| gtcaatgcgg | cagcgaaaga | tcgcgccaac | aaaatggcga | cggcgacgaa | aacacatctg | 1440 |
| ctgcaacccg | gcggcctgaa | caccacgtcg | gtgaaaagtg | ggcaacaatg | ggatgcgcca | 1500 |
| aatggctggg | caccgttaca | gtgggtcgcg | acagaaggat | tacaaaacta | cgggcaaaaa | 1560 |
| gaggtggcga | tggacattag | ctggcacttc | ctgaccaatg | ttcagcacac | ctatgaccgg | 1620 |
| gagaaaaagc | tggtggaaaa | atatgatgtc | agcaccaccg | gaacgggggg | cggcggtggc | 1680 |
| gaatatccat | tacaggatgg | ctttggctgg | accaatggcg | tgacgctgaa | aatgctggat | 1740 |

```
ttgatctgcc cgaaagagca accgtgtgac aatgttccgg cgacgcgtcc gaccgttaag   1800
tcagcaacga cgcaaccctc aaccaaagag gcacaaccca caccttctag acatcaccat   1860
caccatcatt aattaagttt gtgtttaaac tgcaggcatg caagcttctg ttttggcgga   1920
tgagagaaga ttttcagcct gatacagatt aaatcagaac gcagaagcgg tctgataaaa   1980
cagaatttgc ctggcggcag tagcgcggtg gtcccacctg accccatgcc gaactcagaa   2040
gtgaaacgcc gtagcgccga tggtagtgtg gggtctcccc atgcgagagt agggaactgc   2100
caggcatcaa ataaaacgaa aggctcagtc gaaagactgg gcctttcgtt ttatctgttg   2160
tttgtcggtg aacgctctcc tgagtaggac aaatccgccg ggagcggatt tgaacgttgc   2220
gaagcaacgg cccggagggt ggcgggcagg acgcccgcca taaactgcca ggcatcaaat   2280
taagcagaag gccatcctga cggatggcct ttttgcgttt ctacaaactc ttttgtttat   2340
ttttctaaat acattcaaat atgtatccgc tcatgaaaaa aaatccttac gtttcgctaa   2400
ggatgtcagc gtaatgctct gccagtgtta caaccaatta accaattctg attagaaaaa   2460
ctcatcgagc atcaaatgaa actgcaattt attcatatca ggattatcaa taccatattt   2520
ttgaaaaagc cgtttctgta atgaaggaga aaactcaccg aggcagttcc ataggatggc   2580
aagatcctgg tatcggtctg cgattccgac tcgtccaaca tcaatacaac ctattaattt   2640
cccctcgtca aaataaggt tatcaagtga gaaatcacca tgagtgacga ctgaatccgg   2700
tgagaatggc aaaagcttat gcatttcttt ccagacttgt tcaacaggcc agccattacg   2760
ctcgtcatca aaatcactcg catcaaccaa accgttattc attcgtgatt gcgcctgagc   2820
gagacgaaat acgcgatcgc tgttaaaagg acaattacaa acaggaatcg aatgcaaccg   2880
gcgcaggaac actgccagcg catcaacaat attttcacct gaatcaggat attcttctaa   2940
tacctggaat gctgttttcc cggggatcgc agtggtgagt aaccatgcat catcaggagt   3000
acggataaaa tgcttgatgg tcggaagagg cataaattcc gtcagccagt ttagtctgac   3060
catctcatct gtaacatcat tggcaacgct acctttgcca tgtttcagaa acaactctgg   3120
cgcatcgggc ttcccataca atcgatagat tgtcgcacct gattgcccga cattatcgcg   3180
agcccattta tacccatata aatcagcatc catgttggaa tttaatcgcg gcctcgagca   3240
agacgtttcc cgttgaatat ggctcataac accccttgta ttactgttta tgtaagcaga   3300
cagttttatt gttcatgacc aaaatccctt aacgtgagtt ttcgttccac tgagcgtcag   3360
accccgtaga aaagatcaaa ggatcttctt gagatccttt ttttctgcgc gtaatctgct   3420
gcttgcaaac aaaaaaacca ccgctaccag cggtggtttg tttgccggat caagagctac   3480
caactctttt tccgaaggta actggcttca gcagagcgca gataccaaat actgtccttc   3540
tagtgtagcc gtagttaggc caccacttca agaactctgt agcaccgcct acatacctcg   3600
ctctgctaat cctgttacca gtggctgctg ccagtggcga taagtcgtgt cttaccgggt   3660
tggactcaag acgatagtta ccggataagg cgcagcggtc gggctgaacg gggggttcgt   3720
gcacacagcc cagcttggag cgaacgacct acaccgaact gagatacccta cagcgtgagc   3780 tatgagaaag cgccacgctt cccgaaggga gaaaggcgga caggtatccg gtaagcggca   3840
gggtcggaac aggagagcgc acgagggagc ttccagggg aaacgcctgg tatctttata   3900
gtcctgtcgg gtttcgccac ctctgacttg agcgtcgatt tttgtgatgc tcgtcagggg   3960
ggcggagcct atggaaaaac gccagcaacg cggccttttt acggttcctg gccttttgct   4020
ggccttttgc tcacatgttc tttcctgcgt tatcccctga ttctgtggat aaccgtatta   4080
ccgcctttga gtgagctgat accgctcgcc gcagccgaac gaccgagcgc agcgagtcag   4140
```

| | | |
|---|---|---|
| tgagcgagga agcggaagag cgcctgatgc ggtattttct ccttacgcat ctgtgcggta | 4200 | |
| tttcacaccg catatatggt gcactctcag tacaatctgc tctgatgccg catagttaag | 4260 | |
| ccagtataca ctccgctatc gctacgtgac tgggtcatgg ctgcgcccg acacccgcca | 4320 | |
| acaccgctg acgcgccctg acgggcttgt ctgctcccgg catccgctta cagacaagct | 4380 | |
| gtgaccgtct ccgggagctg catgtgtcag aggttttcac cgtcatcacc gaaacgcgcg | 4440 | |
| aggcagctgc ggtaaagctc atcagcgtgg tcgtgaagcg attcacagat gtctgcctgt | 4500 | |
| tcatccgcgt ccagctcgtt gagtttctcc agaagcgtta atgtctggct tctgataaag | 4560 | |
| cgggccatgt taagggcggt ttttcctgt ttggtcactt gatgcctccg tgtaagggg | 4620 | |
| aatttctgtt catgggggta atgataccga tgaaacgaga gaggatgctc acgatacggg | 4680 | |
| ttactgatga tgaacatgcc cggttactgg aacgttgtga gggtaaacaa ctggcggtat | 4740 | |
| ggatgcggcg ggaccagaga aaaatcactc agggtcaatg ccagcgcttc gttaatacag | 4800 | |
| atgtaggtgt tccacaggt agccagcagc atcctgcgat gcagatccgg aacataatgg | 4860 | |
| tgcagggcgc tgacttccgc gtttccagac tttacgaaac acggaaaccg aagaccattc | 4920 | |
| atgttgttgc tcaggtcgca gacgttttgc agcagcagtc gcttcacgtt cgctcgcgta | 4980 | |
| tcggtgattc attctgctaa ccagtaaggc aaccccgcca gcctagccgg gtcctcaacg | 5040 | |
| acaggagcac gatcatgcgc acccgtggcc aggacccaac gctgcccgag atgcgccgcg | 5100 | |
| tgcggctgct ggagatggcg gacgcgatgg atatgttctg ccaagggttg gtttgcgcat | 5160 | |
| tcacagttct ccgcaagaat tgattggctc caattcttgg agtggtgaat ccgttagcga | 5220 | |
| ggtgccgccg gcttccattc aggtcgaggt ggcccggctc catgcaccgc gacgcaacgc | 5280 | |
| ggggaggcag acaaggtata gggcggcgcc tacaatccat gccaacccgt tccatgtgct | 5340 | |
| cgccgaggcg gcataaatcg ccgtgacgat cagcggtcca gtgatcgaag ttaggctggt | 5400 | |
| aagagccgcg agcgatcctt gaagctgtcc ctgatggtcg tcatctacct gcctggacag | 5460 | |
| catggcctgc aacgcgggca tcccgatgcc gccggaagcg agaagaatca taatgggaa | 5520 | |
| ggccatccag cctcgcgtcg cgaacgccag caagacgtag cccagcgcgt cggccgccat | 5580 | |
| gccggcgata atggcctgct tctcgccgaa acgtttggtg gcgggaccag tgacgaaggc | 5640 | |
| ttgagcgagg gcgtgcaaga ttccgaatac cgcaagcgac aggccgatca tcgtcgcgct | 5700 | |
| ccagcgaaag cggtcctcgc cgaaaatgac ccagagcgct gccggcacct gtcctacgag | 5760 | |
| ttgcatgata aagaagacag tcataagtgc ggcgacgata gtcatgcccc gcgcccaccg | 5820 | |
| gaaggagctg actgggttga aggctctcaa gggcatcggt cgacgctctc ccttatgcga | 5880 | |
| ctcctgcatt aggaagcagc ccagtagtag gttgaggccg ttgagcaccg ccgccgcaag | 5940 | |
| gaatggtgca tgctcgatgg ctacgagggc agacagtaag tggatttacc ataatccctt | 6000 | |
| aattgtacgc accgctaaaa cgcgttcagc gcgatcacgg cagcagacag gtaaaaatgg | 6060 | |
| caacaaacca ccctaaaaac tgcgcgatcg cgcctgataa atttaaccg tatgaatacc | 6120 | |
| tatgcaacca gagggtacag gccacattac ccccacttaa tccactgaag ctgccatttt | 6180 | |
| tcatggtttc accatcccag cgaagggcca tgcatgcatc gaaattaata cgacgaaatt | 6240 | |
| aatacgactc actatagggc aatt | 6264 | |

<210> SEQ ID NO 134
<211> LENGTH: 1698
<212> TYPE: DNA
<213> ORGANISM: Escherichia coli -continued

```
<400> SEQUENCE: 134
atgaaatccc cgcgcaccttc tcgcccgcaa aaaatggcgt taattccagc ctgtatcttt      60
ttgtgtttcg ctgcgctatc ggtgcaggca gaagaaacac cggtaacacc acagccgcct     120
gatattttat tagggccgct gtttaatgat gtgcaaaacg ccaaactttt tccggaccaa     180
aaaacctttg ccgatgccgt gccgaacagc gatccgctga tgatccttgc tgattatcgg     240
atgcagcaaa accagagcgg atttgatctg cgccatttcg ttaacgtcaa tttcaccctg     300
ccgaaagaag gcgagaaata tgttccgcca gaggggcagt cactgcgcga acatattgac     360
ggactttggc cggtattaac gcgttctacc gaaaacaccg aaaaatggga ttctctgtta     420
ccgctgccgg aaccttatgt cgtgccgggc ggacgctttc gcgaggtata ttactgggac     480
agttacttca ccatgttagg acttgccgaa agcggtcact gggataaagt cgcggatatg     540
gtggccaatt tgctcatga atagacact tacggtcata ttcccaacgg caaccgcagt     600
tactatttaa gccgctcgca accgcccttc tttgccctga tggtagagtt actggcgcag     660
catgaaggcg atgccgcgtt gaagcaatac ctgccgcaaa tgcaaaaaga atatgcttac     720
tggatggacg tgttgaaaa cctgcaagcc ggacaacagg aaaaacgcgt tgtcaaactt     780
caggatggta ccccttctcaa ccgctactgg gacgatcgcg atacgccacg accagagtca     840
tgggtggaag atattgccac cgccaaaagc aatccgaatc gacctgccac tgaaatttac     900
cgcgacctgc gctctgccgc tgcgtctggc tgggatttca gctcgcgctg gatggacaac     960
ccgcagcagt taaatacctt acgcaccacc agcatcgtac cggtcgatct gaacagcctg    1020
atgtttaaaa tggaaaaaat cctcgcccgc gccagcaaag ctgccggaga taacgcgatg    1080
gcaaaccagt acgaaacgct ggcaaatgcc cgtcaaaaag ggatcgaaaa atacctgtgg    1140
aacgatcaac aaggctggta tgccgattac gacctgaaaa gtcataaagt gcgcaatcag    1200
ttaaccgcgg ccgccctgtt cccgctgtac gtcaatgcgg cagcgaaaga tcgcgccaac    1260
aaaatggcga cggcgacgaa aacacatctg ctgcaacccg gcggcctgaa caccacgtcg    1320
gtgaaaagtg gcaacaatg ggatgcgcca aatggctggg caccgttaca gtgggtcgcg    1380
acagaaggat tacaaaacta cgggcaaaaa gaggtggcga tggacattag ctggcacttc    1440
ctgaccaatg ttcagcacac ctatgaccgg gagaaaaagc tggtggaaaa atatgatgtc    1500
agcaccaccg gaacgggggg cggcggtggc gaatatccat tacaggatgg ctttggctgg    1560
accaatggcg tgacgctgaa aatgctggat ttgatctgcc cgaaagagca accgtgtgac    1620
aatgttccgg cgacgcgtcc gaccgttaag tcagcaacga cgcaaccctc aaccaaagag    1680
gcacaaccca caccttaa                                                  1698

<210> SEQ ID NO 135
<211> LENGTH: 565
<212> TYPE: PRT
<213> ORGANISM: Escherichia coli

<400> SEQUENCE: 135

Met Lys Ser Pro Ala Pro Ser Arg Pro Gln Lys Met Ala Leu Ile Pro
1               5                   10                  15

Ala Cys Ile Phe Leu Cys Phe Ala Ala Leu Ser Val Gln Ala Glu Glu
            20                  25                  30

Thr Pro Val Thr Pro Gln Pro Pro Asp Ile Leu Leu Gly Pro Leu Phe
        35                  40                  45

Asn Asp Val Gln Asn Ala Lys Leu Phe Pro Asp Gln Lys Thr Phe Ala
    50                  55                  60
```

```
Asp Ala Val Pro Asn Ser Asp Pro Leu Met Ile Leu Ala Asp Tyr Arg
 65                  70                  75                  80

Met Gln Gln Asn Gln Ser Gly Phe Asp Leu Arg His Phe Val Asn Val
                 85                  90                  95

Asn Phe Thr Leu Pro Lys Glu Gly Lys Tyr Val Pro Pro Glu Gly
            100                 105                 110

Gln Ser Leu Arg Glu His Ile Asp Gly Leu Trp Pro Val Leu Thr Arg
            115                 120                 125

Ser Thr Glu Asn Thr Glu Lys Trp Asp Ser Leu Leu Pro Leu Pro Glu
130                 135                 140

Pro Tyr Val Val Pro Gly Gly Arg Phe Arg Glu Val Tyr Tyr Trp Asp
145                 150                 155                 160

Ser Tyr Phe Thr Met Leu Gly Leu Ala Glu Ser Gly His Trp Asp Lys
                165                 170                 175

Val Ala Asp Met Val Ala Asn Phe Ala His Glu Ile Asp Thr Tyr Gly
                180                 185                 190

His Ile Pro Asn Gly Asn Arg Ser Tyr Tyr Leu Ser Arg Ser Gln Pro
            195                 200                 205

Pro Phe Phe Ala Leu Met Val Glu Leu Leu Ala Gln His Glu Gly Asp
210                 215                 220

Ala Ala Leu Lys Gln Tyr Leu Pro Gln Met Gln Lys Glu Tyr Ala Tyr
225                 230                 235                 240

Trp Met Asp Gly Val Glu Asn Leu Gln Ala Gly Gln Gln Glu Lys Arg
                245                 250                 255

Val Val Lys Leu Gln Asp Gly Thr Leu Leu Asn Arg Tyr Trp Asp Asp
            260                 265                 270

Arg Asp Thr Pro Arg Pro Glu Ser Trp Val Glu Asp Ile Ala Thr Ala
            275                 280                 285

Lys Ser Asn Pro Asn Arg Pro Ala Thr Glu Ile Tyr Arg Asp Leu Arg
            290                 295                 300

Ser Ala Ala Ala Ser Gly Trp Asp Phe Ser Ser Arg Trp Met Asp Asn
305                 310                 315                 320

Pro Gln Gln Leu Asn Thr Leu Arg Thr Thr Ser Ile Val Pro Val Asp
                325                 330                 335

Leu Asn Ser Leu Met Phe Lys Met Glu Lys Ile Leu Ala Arg Ala Ser
                340                 345                 350

Lys Ala Ala Gly Asp Asn Ala Met Ala Asn Gln Tyr Glu Thr Leu Ala
            355                 360                 365

Asn Ala Arg Gln Lys Gly Ile Glu Lys Tyr Leu Trp Asn Asp Gln Gln
            370                 375                 380

Gly Trp Tyr Ala Asp Tyr Asp Leu Lys Ser His Lys Val Arg Asn Gln
385                 390                 395                 400

Leu Thr Ala Ala Ala Leu Phe Pro Leu Tyr Val Asn Ala Ala Ala Lys
                405                 410                 415

Asp Arg Ala Asn Lys Met Ala Thr Ala Thr Lys Thr His Leu Leu Gln
            420                 425                 430

Pro Gly Gly Leu Asn Thr Thr Ser Val Lys Ser Gly Gln Gln Trp Asp
            435                 440                 445

Ala Pro Asn Gly Trp Ala Pro Leu Gln Trp Val Ala Thr Glu Gly Leu
450                 455                 460

Gln Asn Tyr Gly Gln Lys Glu Val Ala Met Asp Ile Ser Trp His Phe
465                 470                 475                 480

Leu Thr Asn Val Gln His Thr Tyr Asp Arg Glu Lys Lys Leu Val Glu
                485                 490                 495
```

```
Lys Tyr Asp Val Ser Thr Thr Gly Thr Gly Gly Gly Gly Glu Tyr
            500                 505                 510
Pro Leu Gln Asp Gly Phe Gly Trp Thr Asn Gly Val Thr Leu Lys Met
        515                 520                 525
Leu Asp Leu Ile Cys Pro Lys Glu Gln Pro Cys Asp Asn Val Pro Ala
    530                 535                 540
Thr Arg Pro Thr Val Lys Ser Ala Thr Thr Gln Pro Ser Thr Lys Glu
545                 550                 555                 560
Ala Gln Pro Thr Pro
                565

<210> SEQ ID NO 136
<211> LENGTH: 1738
<212> TYPE: DNA
<213> ORGANISM: Artificial Sequence
<220> FEATURE:
<223> OTHER INFORMATION: PCR product
<220> FEATURE:
<221> NAME/KEY: misc_feature
<222> LOCATION: (9)..(14)
<223> OTHER INFORMATION: AflII restriction site
<220> FEATURE:
<221> NAME/KEY: misc_feature
<222> LOCATION: (1727)..(1732)
<223> OTHER INFORMATION: XbaI restriction site

<400> SEQUENCE: 136
cgcaagttct taagccaaag gagaatgatt gatgaaatcc cccgcacctt ctcgcccgca      60
aaaaatggcg ttaattccag cctgtatctt tttgtgtttc gctgcgctat cggtgcaggc     120
agaagaaaca ccggtaacac cacagccgcc tgatatttta ttagggccgc tgtttaatga     180
tgtgcaaaac gccaaacttt ttccggacca aaaaaccttt gccgatgccg tgccgaacag     240
cgatccgctg atgatccttg ctgattatcg gatgcagcaa aaccagagcg atttgatct     300 gcgccatttc gttaacgtca atttcaccct gccgaaagaa ggcgagaaat atgttccgcc     360 agagggcag tcactgcgcg aacatattga cggactttgg ccggtattaa cgcgttctac     420
cgaaaacacc gaaaaatggg attctctgtt accgctgccg gaaccttatg tcgtgccggg     480
cggacgcttt cgcgaggtat attactggga cagttacttc accatgttag acttgccga     540 aagcggtcac tgggataaag tcgcggatat ggtggccaat tttgctcatg aaatagacac     600
ttacggtcat attcccaacg gcaaccgcag ttactattta agccgctcgc aaccgccctt     660
cttgcccctg atggtagagt tactggcgca gcatgaaggc gatgccgcgt tgaagcaata     720
cctgccgcaa atgcaaaaag aatatgctta ctggatggac ggtgttgaaa acctgcaagc     780
cggacaacag gaaaaacgcg ttgtcaaact tcaggatggt acccttctca accgctactg     840
ggacgatcgc gatacgccac gaccagagtc atgggtggaa gatattgcca ccgccaaaag     900
caatccgaat cgacctgcca ctgaaattta ccgcgacctg cgctctgccg ctgcgtctgg     960
ctgggatttc agctcgcgct ggatggacaa cccgcagcag ttaaatacct tacgcaccac    1020
cagcatcgta ccggtcgatc tgaacagcct gatgtttaaa atggaaaaaa tcctcgcccg    1080
cgccagcaaa gctgccggag ataacgcgat ggcaaaccag tacgaaacgc tggcaaatgc    1140
ccgtcaaaaa gggatcgaaa atacctgtg gaacgatcaa caaggctggt atgccgatta    1200
cgacctgaaa agtcataaag tgcgcaatca gttaaccgcg gccgccctgt cccgctgta    1260 cgtcaatgcg gcagcgaaag atcgcgccaa caaatggcg acggcgacga aaacacatct    1320
gctgcaaccc ggcggcctga acaccacgtc ggtgaaaagt gggcaacaat gggatgcgcc    1380
aaatggctgg gcaccgttac agtgggtcgc gacagaagga ttacaaaact acgggcaaaa    1440
```

```
agaggtggcg atggacatta gctggcactt cctgaccaat gttcagcaca cctatgaccg   1500
ggagaaaaag ctggtggaaa atatgatgt cagcaccacc ggaacggggg gcggcggtgg   1560
cgaatatcca ttacaggatg gctttggctg gaccaatggc gtgacgctga aaatgctgga   1620
tttgatctgc ccgaaagagc aaccgtgtga caatgttccg cgacgcgtc cgaccgttaa   1680 gtcagcaacg acgcaaccct caaccaaaga ggcacaaccc acaccttcta gagcgctt   1738
```

<210> SEQ ID NO 137
<211> LENGTH: 573
<212> TYPE: PRT
<213> ORGANISM: Artificial Sequence
<220> FEATURE:
<223> OTHER INFORMATION: treA with 6-His tag

<400> SEQUENCE: 137

```
Met Lys Ser Pro Ala Pro Ser Arg Pro Gln Lys Met Ala Leu Ile Pro
1               5                   10                  15

Ala Cys Ile Phe Leu Cys Phe Ala Ala Leu Ser Val Gln Ala Glu Glu
            20                  25                  30

Thr Pro Val Thr Pro Gln Pro Pro Asp Ile Leu Leu Gly Pro Leu Phe
        35                  40                  45

Asn Asp Val Gln Asn Ala Lys Leu Phe Pro Asp Gln Lys Thr Phe Ala
    50                  55                  60

Asp Ala Val Pro Asn Ser Asp Pro Leu Met Ile Leu Ala Asp Tyr Arg
65                  70                  75                  80

Met Gln Gln Asn Gln Ser Gly Phe Asp Leu Arg His Phe Val Asn Val
                85                  90                  95

Asn Phe Thr Leu Pro Lys Glu Gly Glu Lys Tyr Val Pro Pro Glu Gly
            100                 105                 110

Gln Ser Leu Arg Glu His Ile Asp Gly Leu Trp Pro Val Leu Thr Arg
        115                 120                 125

Ser Thr Glu Asn Thr Glu Lys Trp Asp Ser Leu Leu Pro Leu Pro Glu
    130                 135                 140

Pro Tyr Val Val Pro Gly Gly Arg Phe Arg Glu Val Tyr Tyr Trp Asp
145                 150                 155                 160

Ser Tyr Phe Thr Met Leu Gly Leu Ala Glu Ser Gly His Trp Asp Lys
                165                 170                 175

Val Ala Asp Met Val Ala Asn Phe Ala His Glu Ile Asp Thr Tyr Gly
            180                 185                 190

His Ile Pro Asn Gly Asn Arg Ser Tyr Tyr Leu Ser Arg Ser Gln Pro
        195                 200                 205

Pro Phe Phe Ala Leu Met Val Glu Leu Leu Ala Gln His Glu Gly Asp
    210                 215                 220

Ala Ala Leu Lys Gln Tyr Leu Pro Gln Met Gln Lys Glu Tyr Ala Tyr
225                 230                 235                 240

Trp Met Asp Gly Val Glu Asn Leu Gln Ala Gly Gln Gln Glu Lys Arg
                245                 250                 255

Val Val Lys Leu Gln Asp Gly Thr Leu Leu Asn Arg Tyr Trp Asp Asp
            260                 265                 270

Arg Asp Thr Pro Arg Pro Glu Ser Trp Val Glu Asp Ile Ala Thr Ala
        275                 280                 285

Lys Ser Asn Pro Asn Arg Pro Ala Thr Glu Ile Tyr Arg Asp Leu Arg
    290                 295                 300

Ser Ala Ala Ala Ser Gly Trp Asp Phe Ser Ser Arg Trp Met Asp Asn
305                 310                 315                 320
```

```
Pro Gln Gln Leu Asn Thr Leu Arg Thr Thr Ser Ile Val Pro Val Asp
                325                 330                 335

Leu Asn Ser Leu Met Phe Lys Met Glu Lys Ile Leu Ala Arg Ala Ser
            340                 345                 350

Lys Ala Ala Gly Asp Asn Ala Met Ala Asn Gln Tyr Glu Thr Leu Ala
        355                 360                 365

Asn Ala Arg Gln Lys Gly Ile Glu Lys Tyr Leu Trp Asn Asp Gln Gln
    370                 375                 380

Gly Trp Tyr Ala Asp Tyr Asp Leu Lys Ser His Lys Val Arg Asn Gln
385                 390                 395                 400

Leu Thr Ala Ala Ala Leu Phe Pro Leu Tyr Val Asn Ala Ala Lys
                405                 410                 415

Asp Arg Ala Asn Lys Met Ala Thr Ala Thr Lys Thr His Leu Leu Gln
            420                 425                 430

Pro Gly Gly Leu Asn Thr Thr Ser Val Lys Ser Gly Gln Gln Trp Asp
        435                 440                 445

Ala Pro Asn Gly Trp Ala Pro Leu Gln Trp Val Ala Thr Glu Gly Leu
    450                 455                 460

Gln Asn Tyr Gly Gln Lys Glu Val Ala Met Asp Ile Ser Trp His Phe
465                 470                 475                 480

Leu Thr Asn Val Gln His Thr Tyr Asp Arg Glu Lys Lys Leu Val Glu
                485                 490                 495

Lys Tyr Asp Val Ser Thr Thr Gly Thr Gly Gly Gly Gly Glu Tyr
            500                 505                 510

Pro Leu Gln Asp Gly Phe Gly Trp Thr Asn Gly Val Thr Leu Lys Met
        515                 520                 525

Leu Asp Leu Ile Cys Pro Lys Glu Gln Pro Cys Asp Asn Val Pro Ala
    530                 535                 540

Thr Arg Pro Thr Val Lys Ser Ala Thr Thr Gln Pro Ser Thr Lys Glu
545                 550                 555                 560

Ala Gln Pro Thr Pro Ser Arg His His His His His His
                565                 570

<210> SEQ ID NO 138
<211> LENGTH: 1269
<212> TYPE: DNA
<213> ORGANISM: Artificial Sequence
<220> FEATURE:
<223> OTHER INFORMATION: sequence of partially deleted Synechococcus upp

<400> SEQUENCE: 138
gagctcggta cccggggatc ccacggcagc attacggctc agaccttggt catgccctcg      60
acaacagatc tctacttcac ccagaggat tgtgaggccg aagcgcagtt gattcctaag      120
gcgcactatt gcccaattcc ctcgatctgg ggtcaccgcg cgggcaaccc cagccaaaat    180
ccgcaggatg aaagcttcat tcggcaggcc gttcaggctt tgctcaacgc tgaagcctag    240
cgaattcagt cagcagatca aggagtacca aacaggcgat cgccagcatc ccccagcccc    300
ggcacgataa agcctttgtc gttcagctgc tcatcaatga tggcgctgta atcgtcaac     360 gccgggtagg cttgactgag tttttgtagc gctggcgggg cagccacaat tgaaagcacc    420
cgcacttgct cagcagagac accgcgatcg cgcagcaaat caagggtata gagcagcgag    480
ccacctgtcg ccagcatcgg gtcgagaacc agaacgcgac tgttcacttc aagttgctct    540
ggcaggtgat tgaggtagca gcgcggttca agactgactt catcccgctc gcgcagaatc    600
ggcacgatcg ccaagggttg cgaaaaatcg acgaactccg ctggggtttc tgcaagagga    660
```

```
gtttgcaccg ccgctggaat cgttggtagc cattcccgca cagcctcata ggcgagccag    720
cggcccagct ctgcgatcgc ggtgcgaaac agaggcgtcg gcgtctggcg atcgcgggca    780
atgcccagcc agtgccgaat taagggatgg ggcggcacga agatacgcag ttgaggagcc    840
atgccaatca gcagaagaca gctcctgatt ttaacgttca gaccccaggg gaagcggaac    900
ggtgcaggaa ggcaagcgct tctgcttcgg gcagtggtgg gccatagaag aacccttgca    960
cagcatcaca accaatcgct tctaagaagg cggcttgctc gaggcgttct acgccttctg   1020
cgatcgtgcg aagtttcaag accttggcca ttgcaacaat cgcctgcacg atcgcttgat   1080
cgtcatggtc gtgcggcaga tcgcgaataa agctgcgatc aattttgaga gcattgatgg   1140
gcaaacgctt gaggtaacca aggctggaat aacccgtccc aaaatcatct aaagcgactt   1200
gaaatcccat cgatcgggct tcctggagcc attgcagtgg gatcctctag agtcgacctg   1260
caggcatgc                                                           1269
```

METHOD OF PRODUCING A FERMENTABLE SUGAR

CROSS-REFERENCE TO RELATED APPLICATIONS

The present application is a Divisional of U.S. application Ser. No. 12/348,887 (filed 5 Jan. 2009, published as U.S. App. Publication No. 2009/0181434 on 16 Jul. 2009, and issued as U.S. Pat. No. 8,367,379 on 16 Jan. 2013), which claims priority to U.S. Prov. App. Ser. No. 61/085,797 (filed 1 Aug. 2008) and U.S. Prov. App. Ser. No. 61/018,798 (filed 3 Jan. 2008), each of which is incorporated herein by reference in its entirety.

INCORPORATION-BY-REFERENCE OF MATERIAL SUBMITTED IN COMPUTER READABLE FORM

The Sequence Listing, which is a part of the present disclosure, includes a computer readable form and a written sequence listing comprising nucleotide and/or amino acid sequences of the present invention. The sequence listing information recorded in computer readable form is identical to the written sequence listing. The subject matter of the Sequence Listing is incorporated herein by reference in its entirety.

FIELD OF THE INVENTION

The present invention generally relates to transgenic microorganisms and methods and devices for their cultivation.

BACKGROUND

To address the world's increasing energy requirements, efficient and environmentally sound alternatives to the use of fossil fuels are sought after. Alternative fuels, such as ethanol or biodiesel, can be produced from plant biomass. For example, the key ingredient used to produce ethanol from current processes is termed fermentable sugar. Most often, fermentable sugar is in the form of sucrose, glucose, or high-fructose corn syrup. Plants currently grown to produce such biomass include corn, sugarcane, soybeans, canola, jatropha, and so forth. But much of the plant biomass used to produce fermentable sugar requires extensive energy-intensive pre-processing. Further, use of such plant biomass can lead to soil depletion, erosion, and diversion of the food supply.

It is known that some cyanobacteria produce sucrose through the action of sucrose phosphate synthase and sucrose phosphate phosphatase, where it has been studied exclusively as an osmoprotectant. With respect to salt tolerance, cyanobacteria can be divided into three groups. Strains having low tolerance (less than 700 mM) synthesize either sucrose, as is the case with *Synechococcus elongatus* PCC 7942, or another dissaccharide known as trehalose [Blumwald et al., Proc Natl Acd Sci USA (1983) 80:2599-2602 and Reed et al., FEMS Microbiol Rev (1986) 39:51-56]. Glucosylglycerol is produced by strains having moderate halotolerance (0.7-1.8 mM), such as *Synechocystis* sp. PCC 6803. High salt tolerance (up to 2.5 M) results from the accumulation of either glycine betaine or glutamate betaine. Miao et al. [FEMS Microbiol Lett (2003) 218:71-77] determined that when glucosylglycerol biosynthesis is blocked by deletion of the agp gene, however, *Synechocystis* sp. PCC 6803 produces sucrose as its osmoprotectant. Desiccation tolerant cyanobacteria also produce sucrose and trehalose in response to matric water stress [Hershkovitz et al., Appl Environ Microbiol (1991) 57:645-648].

*Synechocystis* spp. PCC 6803 (ATCC 27184) and *Synechococcus elongatus* PCC 7942 (ATCC 33912) are relatively well-studied, have genetic tools available and the sequences of their genomes are known (see e.g., Koksharova, O. A. and Wolk, C. P. 2002. Appl Microbiol Biotechnol 58, 123-137; Ikeuchil, M. and Satoshi Tabata, S. 2001. Photosynthesis Research 70, 73-83; Golden, S. S., Brusslan, J. and Haselkorn, R. 1987. Methods in Enzymology 153, 215-231; Friedberg, D. 1988. Methods in Enzymology 167, 736-747; Kaneko, T. et al. 1996. DNA Research 3, 109-136).

The commercial cultivation of photosynthetic microorganisms such as *Spirulina maximum*, *Spirulina platensis*, *Dunaliella salina*, *Botrycoccus braunii*, *Chlorella vulgaris*, *Chlorella pyrenoidosa*, *Serenastrum capricomutum*, *Scenedesmus auadricauda*, *Porphyridium cruentum*, *Scenedesmus acutus*, *Dunaliella* sp., *Scenedesmus obliquus*, *Anabaenopsis*, *Aulosira*, *Cylindrospermum*, *Scenecoccus* sp., *Scenecosystis* sp., and *Tolypothrix* is desirable for numerous applications including the production of fine chemicals, pharmaceuticals, cosmetic pigments, fatty acids, antioxidants, proteins with prophylactic action, growth factors, antibiotics, vitamins and polysaccharides. The algic biomass can also be useful, in a low dose, to replace or decrease the level of antibiotics in animal food or be useful as a source of proteins. Furthermore, the algic biomass provided in a wet form, as opposed to a dried form, can be fermented or liquefied by thermal processes to produce fuel. Thus, there is great interest in the ability to increase the efficiency of cultivating such organisms.

In general, current photosynthetic bioreactors rely on the cultivation of microorganisms in a liquid phase system to produce biomass. These systems are usually open-air pond-type reactors or enclosed tank-type reactors. Enclosed bioreactors, however, typically are considered to be an improvement over pond type reactors in many respects. Importantly, enclosed systems provide a barrier against environmental contamination. In addition, these systems allow for greater control of temperature and gas content of the liquid media.

Still, the uses of enclosed photobioreactors tend to be limited by photosynthetic microorganisms' requirement for light (i.e., actinic radiation provides the energy required by photosynthetic microorganisms to fix carbon dioxide into organic molecules). Thus, sufficient illumination of the photosynthetic microorganisms is an unyielding requirement. Nevertheless, as the cell density in a liquid phase photobioreactor increases, the ability of light to penetrate into the media decreases, which typically limits the cell density that may be achieved. Additionally, some type of agitation of the liquid media is generally required to prevent unwanted sedimentation of the organisms, a process that requires the input of energy.

Numerous attempts have been made to devise a method of bringing light to the organisms in liquid phase systems. For example, some systems involve circulating the liquid culture media through transparent tubes. Other attempts involve placing a light source within the media or introducing reflecting particles into the culture media to adjust the radiation absorbance of the culture. Despite these efforts, a significant increase in the ability to culture organisms in liquid phase systems at higher cell densities has not yet been achieved.

In addition to the aforementioned light requirement, the use of liquid phase photobioreactors has been burdened with providing the photosynthetic microorganisms enough carbon dioxide for photosynthesis. Typically, these systems generally incorporate some type of additional aeration system to increase the concentration of carbon dioxide dissolved in the media. Eliminating the need for aeration would greatly simplify the system thus reducing operating costs.

Liquid phase photobioreactors also tend not to be well suited for conventional methods of continuous production. In general, the transportation of large volumes of liquid is complex and burdensome. Further, because liquid phase systems usually require mechanisms for circulation, agitation, aeration, and the like, it is generally simpler and more cost effective to operate only one or a few large cultivation devices rather than numerous smaller ones. Therefore, currently practiced methods involve processing relatively large batches (i.e., a batch of photosynthetic microorganisms is cultivated and the entire resulting biomass is then harvested).

Thus, there is a great need in the art for advancement in photosynthetic bioreactor design. Providing a new type of photosynthetic bioreactor capable of efficiently cultivating and harvesting relatively high densities of photosynthetic microorganisms without large volumes of water or other liquid media, without the aforementioned extraordinary measures for supplying adequate light and carbon dioxide, and at a reasonable cost would represent a substantial advance in the art, and benefit industry and consumers alike.

SUMMARY OF THE INVENTION

Provided herein is a photobioreactor for cultivating photosynthetic microorganisms comprising a non-gelatinous, solid cultivation support suitable for providing nutrients and moisture to photosynthetic microorganisms and a physical barrier covering at least a portion of the surface of the cultivation support. Devices for the large scale and continuous cultivation of photosynthetic microorganisms incorporating photobioreactors and methods of use are disclosed.

One aspect provides a photobioreactor for cultivating photosynthetic microorganisms. The photobioreactor comprises a non-gelatinous, solid cultivation support suitable for providing nutrients and moisture to photosynthetic microorganisms on at least a portion of a surface thereof, wherein said portion of the surface has a topography that allows photosynthetic microorganisms to adhere thereto when said portion of the surface is oriented non-horizontally; and a physical barrier covering at least said portion of the surface of the cultivation support, wherein the physical barrier is configured so as to allow inoculation of said portion of the surface of the cultivation support, formation and maintenance of an environment suitable for the cultivation of such photosynthetic microorganisms, and harvesting of such cultivated photosynthetic microorganisms.

In some embodiments, the photobioreactor comprises photosynthetic microorganisms on said portion of the surface of the cultivation support. In some embodiments, the photobioreactor further comprises a cell engineered to accumulate a disaccharide, as described further below, wherein the cell is adhered to the solid cultivation support. In some embodiments, said portion of the surface of the cultivation support is capable of cultivating photosynthetic microorganisms at a density of at least about 50 grams of dry biomass per liter equivalent.

In some embodiments, the cultivation support is flexible. In some embodiments, the cultivation support comprises one or more rigid materials. In some embodiments, the cultivation support of the photobioreactor comprises at least two layers, a first layer adjacent to a second layer, wherein material of the at least two layers is the same material or different materials. In some embodiments, the first layer comprises a high surface area growth material and the second layer a permeable type material. In some embodiments, the cultivation support of the photobioreactor comprises flexibly connected rigid portions, wherein the rigid portions are comprised of the one or more rigid materials. In some embodiments, the photobioreactor comprises a single cultivation support. In some embodiments, the photobioreactor comprises a plurality of cultivation supports.

In some embodiments, the cultivation support comprises a fabric. In some embodiments, the fabric is comprised of fibers that are natural, modified natural, synthetic, or a combination thereof. In some embodiments, the fabric is a woven fabric, a knitted fabric, a felt, a mesh of cross-linked fiber polymers, or a combination thereof. In some embodiments, the natural fibers are selected from the group consisting of cotton, wool, hemp, tree fiber, other cellulosic fibers, and combinations thereof. In some embodiments, the modified natural fibers are selected from the group consisting of nitrocellulose, cellulose acetate, cellulose sulfonate, crosslinked starches, and combinations thereof. In some embodiments, the synthetic fibers are selected from the group consisting of polyester, polyacrylate, polyamine, polyamide, polysulfone, and combinations thereof.

In some embodiments, the cultivation support is coated with a moisture absorbent polymer. In some embodiments, the fabric, the fiber of the fabric, or both, are coated with a moisture absorbent polymer. In some embodiments, the moisture absorbent polymer is selected from the group consisting of agar, polyacrylate, polyamide, polyamine, polyethylene glycol, modified starches, and combinations thereof.

In some embodiments, the physical barrier of the photobioreactor is at least substantially impermeable to solid particulate and liquid but does not prevent the transport of gas or vapor to and from the space proximate to said portion of the surface of the cultivation support nor actinic irradiation of said portion of the surface of the cultivation support. In some embodiments, the physical barrier is sufficiently impermeable to water vapor so that the cultivation support upon being moistened will retain enough of the moisture so the photosynthetic microorganisms remain adequately hydrated during cultivation. In some embodiments, the barrier is configured to enclose the cultivation support and any photosynthetic microorganisms thereon, and to be releasably sealed during at least a portion of the cultivation of the photosynthetic microorganisms. In some embodiments, the physical barrier is flexible. In some embodiments, the physical barrier further comprises a first portion that is at least substantially impermeable to solid particulate, liquid, gas, and vapor, and a second portion that is permeable to gas and vapor but at least substantially impermeable to solid particulate and liquid. In some embodiments, the second portion of the barrier has a gas or vapor exchange rate that is from at least about 5 Gurley seconds to no greater than about 10,000 Gurley seconds. In some embodiments, the second portion of the barrier comprises a selective membrane comprising olefin fiber or polyethylene fiber material, polytetrafluoroethylene filtration media, cellulosic filter material, fiberglass filter material, polyester filter material, polyacrylate filter material, polysulfone membranes, or nylon membranes. In some embodiments, the first portion is at least substantially transparent to actinic radiation and the second portion is not at least substantially transparent to actinic radiation, and the configuration of the first and second portions relative to each other and at least said portion of the surface of the cultivation support is such that there a sufficient amount of actinic radiation and gas exchange to support photosynthesis by photosynthetic microorganisms.

In some embodiments, the photobioreactor further comprises a source of actinic radiation situated between the cultivation support and the physical barrier. In some embodiments, the physical barrier is between the cultivation support and a source of actinic radiation and is sufficiently transparent to such actinic radiation and sufficiently gas permeable to allow for photosynthesis by the photosynthetic microorganisms during cultivation.

In some embodiments, the photobioreactor further comprises water, nutrients, or a combination thereof on, within, or on and within, the cultivation support. In some embodiments, the photobioreactor further comprises one or more attachment points for attaching the photobioreactor to a structure. In some embodiments, the solid cultivation support further comprises one or more attachment points for attaching the cultivation support. In some embodiments, the photobioreactor further comprises at least one of a fluid supply system, a nutrient supply system, a gas supply system, and a microorgansim supply system.

In some embodiments, the photobioreactor further comprises a conveyance system, wherein the conveyance system moves the solid cultivation support so as to optimize position of the solid cultivation support for receiving light. In some embodiments, the photobioreactor comprises a plurality of solid cultivation supports, wherein the plurality of solid cultivation supports radiate outward from a central point. In some embodiments, one or more solid cultivation supports of the plurality of solid cultivation supports comprises a sheet in which the depth of the solid cultivation support is substantially less than length and width of the solid cultivation support. In some embodiments, the photobioreactor comprises a conveyance system, wherein the conveyance system moves one or more solid cultivation supports of the plurality of solid cultivation supports so as to optimize position thereof for receiving light. In some embodiments, the conveyance system moves the plurality of solid cultivation supports around the central point so as to optimize position of one or more solid cultivation supports for receiving light. In some embodiments, the physical barrier comprises at least a portion sufficiently transparent to actinic radiation for the cultivation of photosynthetic organisms and the position of the transparent portion of the physical barrier is movable to optimize receipt of light by the solid cultivation support. In some embodiments, at least a portion of the solid cultivation support is configured so as to be exposed to an external source of actinic radiation. In some embodiments, the photobioreactor comprises a source of artificial actinic radiation. In some embodiments, the solid cultivation support comprises a material having loops, such as terry cloth.

Another aspect provides a device for cultivating photosynthetic microorganisms. Such device comprises at least one photobioreactor as described above, and a structure to which the at least one photobioreactor is attached that orientates at least one cultivation support of the at least one photobioreactor non-horizontally. In some embodiments, the at least one photobioreactor is suspended from the structure. In some embodiments, the structure is substantially covered by the physical barrier. In some embodiments, the structure comprises a conveyor system or a component thereof such that the at least one cultivation support is capable of being conveyed along the path of the conveyor system. In some embodiments, the device further comprises one, two, or three of the following: an inoculation station such that each cultivation support as it is conveyed along the path of the conveyor system may be inoculated with photosynthetic microorganisms; a cultivating station such that the photosynthetic microorganisms on each inoculated cultivation support are cultivated as each cultivation support is conveyed along the path of the conveyor system; and a harvesting station to which the cultivation support is conveyed so that at least a portion of the cultivated photosynthetic microorganisms may be harvested from each cultivation support. In some embodiments, the inoculation station and the harvesting station are substantially adjacent to each other or are substantially coextensive. In some embodiments, the device further comprises an inducing station for inducing the synthesis of fermentable sugar by photosynthetic microorganisms on each cultivation support. In some embodiments, the device further comprises at least one of a fluid supply system, a nutrient supply system, a gas supply system, or a microorgansim supply system. In some embodiments, the device further comprises a photosynthetic microorganisms adhered on the solid cultivation support. In some embodiments, the device further comprises a cell engineered to accumulate a disaccharide, as described further below, wherein the cell is adhered to the solid cultivation support.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

FIG. 1 illustrates a front view of the photobioreactor of the invention including a solid cultivation support, an outer protective transparent barrier layer, a selective panel, resealable closures, and support elements for suspending the device.

FIG. 2 illustrates a side view of the photobioreactor of the invention including a solid cultivation support, an outer protective transparent barrier layer, a selective panel, resealable closures, and support elements for suspending the device.

FIG. 3 illustrates an arrangement of multiple photobioreactors or cultivation supports of the invention along multiple closed loop conveyor systems radiating out from common inoculation and harvesting centers to comprise a photobioreactor farm.

FIG. 5 is a polypeptide sequence alignment of the *Synechocystis* spp. PCC 6803 (Ssp6803) sucrose phosphate synthase (SPS) (SEQ ID NO: 4) and sucrose phosphate phosphatase (SPP) (SEQ ID NO: 6) proteins with the *Synechococcus elongatus* PCC 7942 (Selo7942) active SPS/SPP fusion (ASF) (SEQ ID NO: 2). Ssp6803 contains separate genes encoding SPS and SPP activities. The SPS protein from *Synechocystis* spp. PCC 6803 bears a presumably inactive SPP domain, as many of the active site residues are not conserved. The canonical HAD hydrolase active site residues are shown above the alignment with conserved amino acids shown underlined and non-conserved residues double underlined. An eight amino acid insertion within the inactive SPP domain of *Synechocystis* spp. PCC 6803 SPS is italicized. Further details regarding methodology are provided in Example 4.

FIG. 10 is a sequence listing showing a possible promoter within *Synechococcus elongatus* PCC 7942 asf (polynucleotide of SEQ ID NO: 1, polypeptide of SEQ ID NO: 2). Shown is the amplified PCR product containing the asf gene from *Synechococcus elongatus* PCC 7942 that was cloned upstream of the chloramphenicol resistance marker. The regions of asf encoding the sucrose phosphate synthase and sucrose phosphate phosphatase polypeptide activities are single underlined and double underlined, respectively. All DNA sequence elements are italicized and labeled above. Start and Stop represent the start and stop codons, respectively. SD represents the Shine-Delgarno sequence. The −35 and −10 regions of the putative promoters are highlighted in gray. Further details regarding methodology are provided in Example 8.

FIG. 12 is a schematic diagram of a photobioreactor embodiment. FIG. 12A provides a front view while FIG. 12B provides a side view. The photobioreactor includes suspension element (6); culture media supply (8); gas supply (10); growth surface (2); outer barrier layer (7); quick connector; and product harvest line (9).

FIG. 13 is a schematic diagram of a growth surface in a single material format (FIG. 13A) and a hybrid material format (FIG. 13B).

DETAILED DESCRIPTION OF THE INVENTION

Figure 4:
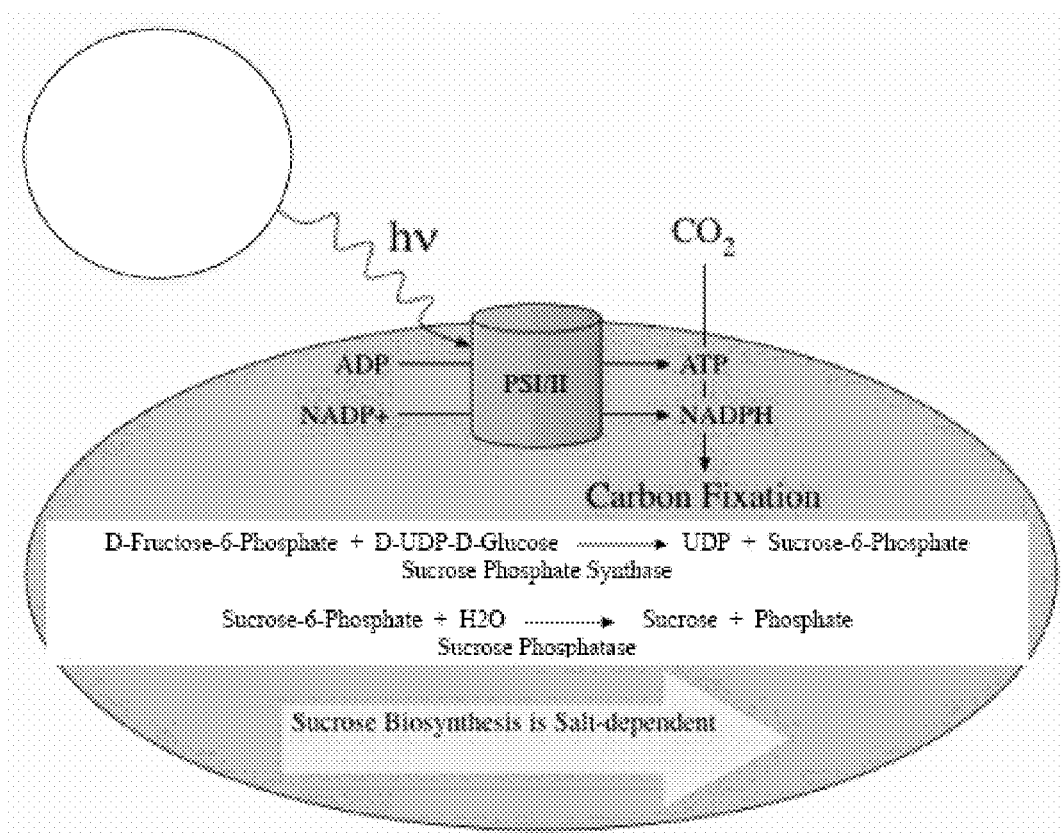
FIG. 4 is a cartoon depicting photosynthetic production of sucrose in cyanobacteria.

The present application relates to fermentable sugar accumulating photosynthetic microorganisms, solid-phase photoreactor devices, and methods of using each.

In the fermentable sugar accumulating photosynthetic microorganisms, it may be preferable to produce a dissaccharide sugar not generally utilized by the photosynthetic microorganisms, which therefore can accumulate within the cultivated biomass (e.g., sucrose, trehalose). In some embodiments, photosynthetic microorganisms are genetically engineered to synthesize a dissaccharide sugar normally produced according to osmotic stress pathways (e.g., sucrose or trehalose) such that the sugar is produced in the absence of, or at reduced levels of, osmotic stress. Because of the greater efficiency and lower environmental impact of growing photosynthetic microorganisms compared to higher plants, the method represents important improvements in sustainability over current biofuel production practices. Advantageously, the foregoing method of synthesizing a dissaccharide sugar has been adapted to occur within the photobioreactor(s) of the present invention.

The photobioreactor described herein utilizes a solid cultivation support. Advantageously, the difficulty of providing adequate light exposures is alleviated, at least in part. Utilizing the aforementioned solid cultivation support in a photobioreactor can allow for cultivation and growth of photosynthetic microorganisms at cell densities greater than those of commercial-scale liquid phase bioreactors (e.g., cell densities in excess of 200 grams of dry biomass per liter equivalent). In addition, various embodiments of the photobioreactor described herein can be operated using less energy and more simply than conventional commercial-scale liquid phase photobioreactors.

Embodiments of the photobioreactor described herein provide additional benefits over conventional liquid phase photobioreactors. For example, liquid systems typically require special equipment to deliver adequate concentrations/amount of carbon dioxide to the photosynthetic microorganisms to support their growth and photosynthesis. In contrast, by growing the microorganisms on a solid cultivation support, carbon dioxide can be provided in a relatively simple, less costly manner, such as exposure to surrounding air. If additional carbon dioxide is desired, it can easily be delivered by, for example, adding it to the atmosphere (e.g., air) surrounding or in contact with the cultivation support. Another benefit is ease of transport. Liquid phase photobioreactors can be a pond (completely immobile) or bulky tanks or collections of tubing. In contrast, in various embodiments, the photobioreactor is flat and flexible, which allows for it or a multiplicity of them to be stacked, rolled up, folded, and/or configured in a similar manner for relatively easy transport. In various embodiments, the photobioreactor can be configured in a manner such that it is suspended from a system that allows for easy conveyance of one or more photobioreactors from one location to another. This portability may be utilized on a commercial scale to allow for efficient methods of handling and processing large numbers of photobioreactors in a continuous-type manner.

One aspect of the application is directed to a method of fermentable sugar feedstock production by photosynthetic microorganisms. Preferably, the fermentable sugar is a fermentable disaccharide sugar. Examples of fermentable disaccharide sugars include, but are not limited to sucrose and trehalose. The fermentable sugar can be a disaccharide not generally utilized by photosynthetic microorganisms. For example, trehalose is not generally utilized by cyanobacteria and therefore can accumulate within the cultivated biomass without substantial degradation by endogenous metabolic pathways. The fermentable sugar can be a disaccharide that is generally utilized by photosynthetic microorganisms. For a disaccharide not used as a primary energy source, the disaccharide can often be accumulated to sufficient levels even in the presence of endogenous metabolic pathways. Where endogenous degradation pathways specific for the target fermentable sugar, the photosynthetic microorganism can be engineered to reduce or eliminate such activity. For example, a cyanobacterium engineered to accumulate sucrose can be further engineered to reduce or eliminate sucrose invertase activity. In various embodiments, strains of photosynthetic microorganisms that synthesize fermentable disaccharide sugar in response to osmotic or matric water stress can be used. In other embodiments transgenic strains of photosynthetic microorganisms engineered to accumulate fermentable disaccharide sugar in the absence of, or reduced levels of, osmotic stress. Advantageously, the foregoing methods of synthesizing fermentable disaccharide sugar can be adapted to occur within photobioreactors described herein.

Because of the greater efficiency and lower environmental impact of growing photosynthetic microorganisms compared to higher plants, compositions, devices, and methods described herein represent important improvements in sustainability over current biofuel production practices.

Photosynthetic Microorganism

Provided herein is a photosynthetic microorganism genetically engineered to accumulate a dissaccharide sugar. The photosynthetic microorganism can be, for example, a naturally photosynthetic microorganism, such as a cyanobacterium, or an engineered photosynthetic microorganism, such as an artificially photosynthetic bacterium. Examples of the accumulated dissaccharide sugar include, but are not limited to sucrose, trehalose, gluocosylglycerol, and mannosylfructose. In various embodiments, one or more genes encoding the protein(s) responsible for producing the desired dissaccharide from corresponding phosphorylated monomers is engineered in a host photosynthetic microorganism (e.g., cyanobacterium) so as to result in the accumulation of the desired dissaccharide. In some embodiments, an endogenous pathway of the host photosynthetic microorganism is engineered so as to accumulate a dissaccharide sugar. For example, the osmotic sucrose pathway in cyanobacteria can be engineered to accumulate sucrose in the absence of osmotic stress. In some embodiments, an exogenous dissaccharide pathway is engineered in cyanobacteria so as to accumulate a dissaccharide sugar. For example, the osmotic trehalose pathway from *E. coli* can be engineered to accumulate trehalose in cyanobacteria.

Synthase and Phosphotase

A photosynthetic microorganism can be transformed so as to have a synthase activity and a phosphotase activity for the desired dissaccharide. For example, a cyanobacterium can be engineered to have sucrose phosphate synthase activity and sucrose phosphate phosphatase activity. As another example, a cyanobacterium can be engineered to have trehalose phosphate synthase activity and trehalose phosphate phosphatase activity. As another example, a cyanobacterium can be engineered to have gluocosylglycerol phosphate synthase activity and gluocosylglycerol phosphate phosphatase activity. As another example, a cyanobacterium can be engineered to have mannosylfructose phosphate synthase activity and mannosylfructose phosphate phosphatase activity. It is contemplated these activities can likewise be engineered in other photosynthetic microorganisms.

Synthase activity and phosphotase activity can be engineered into a photosynthetic microorganism by way of the individual genes, one encoding a polypeptide having synthase activity and the other encoding a polypeptide having phosphatase activity; or by one gene encoding both synthase activity and phosphatase activity. For example, synthase activity and phosphatase activity can be present in a fusion polypeptide.

The monomeric sugars of the desired dissaccharide can be endogenous or exogenous to the photosynthetic microorganism. Where monomeric sugars of the desired dissaccharide are endogenous, the photosynthetic microorganism can be engineered to produce increased levels of such monomers. Where monomeric sugars of the desired dissaccharide are exogenous, the photosynthetic microorganism can be engineered to produce such exogenous monomers.

The photosynthetic microorganism can be engineered to synthesize and accumulate the desired dissaccharide continuously, after some developmental state, or upon being induced to do so. Induction of dissaccharide synthesis can be according to the actions of an inducible promoter associated with the encoded synthase or phosphotase and an inducing agent, as discussed in further detail herein.

In some embodiments, transformed cyanobacteria, as described herein, can accumulate at least about 0.1 micrograms of a dissaccharide (e.g., sucrose, trehalose, glucosylglycerol, or mannosylfructose) per minute per gram dry biomass. In some embodiments, transformed cyanobacteria can accumulate at least about 0.1 up to about 10 micrograms of a dissaccharide (e.g., sucrose, trehalose, glucosylglycerol, or mannosylfructose) per minute per gram dry biomass. For example, transformed cyanobacteria can accumulate at least about 0.2, at least about 0.3, at least about 0.4, at least about 0.5, at least about 0.6, at least about 0.7, at least about 0.8, or at least about 0.9 micrograms of a dissaccharide (e.g., sucrose, trehalose, glucosylglycerol, or mannosylfructose) per minute per gram dry biomass. In other embodiments, various transformed photosynthetic microorganisms accumulate similar amounts of a dissaccharide.

It is contemplated that that various embodiments will accumulate a disaccharide (e.g., sucrose, trehalose, glucosylglycerol, or mannosylfructose) at defined ranges of the values above. For example, some transformed cyanobacteria can accumulate at least about 0.1 up to about 0.9 micrograms of a disaccharide (e.g., sucrose, trehalose, glucosylglycerol, or mannosylfructose) per minute per gram dry biomass; at least about 0.1 up to about 0.8 micrograms of a disaccharide (e.g., sucrose, trehalose, glucosylglycerol, or mannosylfructose) per minute per gram dry biomass; at least about 0.1 up to about 0.7 micrograms of a disaccharide (e.g., sucrose, trehalose, glucosylglycerol, or mannosylfructose) per minute per gram dry biomass; etc. Similarly, some transformed cyanobacteria can accumulate at least about 0.2 up to about 1.0 micrograms of a disaccharide (e.g., sucrose, trehalose, glucosylglycerol, or mannosylfructose) per minute per gram dry biomass; at least about 0.3 up to about 1.0 micrograms of a disaccharide (e.g., sucrose, trehalose, glucosylglycerol, or mannosylfructose) per minute per gram dry biomass; at least about 0.4 up to about 1.0 micrograms of a disaccharide (e.g., sucrose, trehalose, glucosylglycerol, or mannosylfructose)

per minute per gram dry biomass; at least about 0.5 up to about 1.0 micrograms of a disaccharide (e.g., sucrose, trehalose, glucosylglycerol, or mannosylfructose) per minute per gram dry biomass; at least about 0.6 up to about 1.0 micrograms of a disaccharide (e.g., sucrose, trehalose, glucosylglycerol, or mannosylfructose) per minute per gram dry biomass; at least about 0.7 up to about 1.0 micrograms of a disaccharide (e.g., sucrose, trehalose, glucosylglycerol, or mannosylfructose) per minute per gram dry biomass; at least about 0.8 up to about 1.0 micrograms of a disaccharide (e.g., sucrose, trehalose, glucosylglycerol, or mannosylfructose) per minute per gram dry biomass; or at least about 0.9 up to about 1.0 micrograms of a disaccharide (e.g., sucrose, trehalose, glucosylglycerol, or mannosylfructose) per minute per gram dry biomass. Methods for assaying sugar accumulation is host cells are well-known to those of skill in the art (see e.g., Example 10).

Host

The host genetically engineered to accumulate a dissaccharide sugar can be any photosynthetic microorganism. The photosynthetic microorganism can be, for example, a naturally photosynthetic microorganism, such as a cyanobacterium, or an engineered photosynthetic microorganism, such as an artificially photosynthetic bacterium. Exemplary microorgansims that are either naturally photosynthetic or can be engineered to be photosynthetic include, but are not limited to, bacteria; fungi; archaea; protists; microscopic plants, such as a green algae; and animals such as plankton, planarian, and amoeba. Examples of naturally occurring photosynthetic microorganisms include, but are not limited to, *Spirulina maximum, Spirulina platensis, Dunaliella salina, Botrycoccus braunii, Chlorella vulgaris, Chlorella pyrenoidosa, Serenastrum capricomutum, Scenedesmus auadricauda, Porphyridium cruentum, Scenedesmus acutus, Dunaliella sp., Scenedesmus obliquus, Anabaenopsis, Aulosira, Cylindrospermum, Synechoccus sp., Synechocystis sp.,* and/or *Tolypothrix.*

Preferably, the host photosynthetic microorganism is a cyanobacterium. Cyanobacteria, also known as blue-green algae, are a broad range of oxygengenic photoautotophs. The host cyanobacterium can be any photosynthetic microorganism from the phylum Cyanophyta. The host cyanobacterium can have a unicellular or colonial (e.g., filaments, sheets, or balls) morphology. Preferably, the host cyanobacterium is a unicellular cyanobacterium. Examples of cyanobacteria that can be engineered to accumulate a disaccharide sugar include, but are not limited to, the genus *Synechocystis, Synechococcus, Thermosynechococcus, Nostoc, Prochlorococcu, Microcystis, Anabaena, Spirulina,* and *Gloeobacter.* Preferably the host cyanobacterium is a *Synechocystis* spp. or *Synechococcus* spp. More preferably, the host cyanobacterium is *Synechococcus elongatus* PCC 7942 (ATCC 33912) and/or *Synechocystis* spp. PCC 6803 (ATCC 27184).

Sucrose

Biosynthesis of sucrose in a photosynthetic microorganism, such as cyanobacteria, can be accomplished through the catalytic action of two enzyme activities, sucrose phosphate synthase (sps) and sucrose phosphate phosphatase (spp), functioning in sequence (see e.g., FIG. 4). Such activities are present in some cyanobacteria for acclimation to osmotic and matric water stress (see e.g., Lunn, J. E. 2002. Plant Physiol 128, 1490-1500). Either or both of these activities can be engineered in a cyanobacterium so as to result in accumulation of sucrose.

A gene of particular interest for engineering a photosynthetic microorganism to accumulate sucrose is the active sps/spp fusion (asf) gene from *Synechococcus elongatus* PCC 7942. Asf has both sps and spp biosynthetic functions (see e.g., Example 4). In some embodiments, an ASF-encoding nucleotide sequence is cloned from its native source (e.g., *Synechococcus elongatus* PCC 7942) and inserted into a host cyanobacterium (see e.g., Examples 4-9). In some embodiments, a transformed host photosynthetic microorganism comprises an asf polynucleotide of SEQ ID NO: 1. In some embodiments, a photosynthetic microorganism is transformed with a nucleotide sequence encoding ASF polypeptide of SEQ ID NO: 2. In further embodiments, a transformed host photosynthetic microorganism comprises a nucleotide sequence having at least about 80% sequence identity to SEQ ID NO: 1 or a nucleotide sequence encoding a polypeptide having sps and spp activity and at least about 80% sequence identity to SEQ ID NO: 2. As an example, a transformed host photosynthetic microorganism, such as a cyanobacterium, can comprise a nucleotide sequence having at least about 85%, at least about 90%, at least about 95%, or at least about 99% sequence identity to SEQ ID NO: 1, wherein the transformed host exhibits ASF, SPS, and/or SPP activity and/or accumulation of sucrose. As an example, a transformed host photosynthetic microorganism can comprise a nucleotide sequence encoding a polypeptide having at least about 85%, at least about 90%, at least about 95%, or at least about 99% sequence identity to SEQ ID NO: 2, wherein the transformed host exhibits ASF, SPS, and/or SPP activity and/or accumulation of sucrose. As another example, a transformed host photosynthetic microorganism can comprise a nucleotide sequence that hybridizes under stringent conditions to SEQ ID NO: 1 over the entire length of SEQ ID NO: 1, and which encodes an active SPS/SPP fusion (ASF) polypeptide. As a further example, a transformed host photosynthetic microorganism can comprise the complement to any of the above sequences.

In some embodiments, a sucrose phosphate synthase (sps) (see e.g., SEQ ID NO: 3 encoding sps gene and SEQ ID NO: 4 encoding SPS polypeptide), or homologue thereof, is engineered to be expressed or overexpressed in a transformed photosynthetic microorganism. For example, a photosynthetic microorganism can be transformed with a nucleotide having a sequence of SEQ ID NO: 3 so as to express sucrose phosphate synthase. As another example, a photosynthetic microorganism can be transformed with a nucleotide having at least about 80%, at least about 85%, at least about 90%, at least about 95%, or at least about 99% percent identity to SEQ ID NO: 3 encoding a polypeptide having sucrose phosphate synthase. As another example, a transformed host photosynthetic microorganism can comprise a nucleotide sequence encoding a polypeptide having at least about 85%, at least about 90%, at least about 95%, or at least about 99% sequence identity to SEQ ID NO: 4, wherein the transformed host exhibits SPS activity and/or accumulation of sucrose.

In some embodiments, sucrose phosphate phosphatase (spp) (see e.g., SEQ ID NO: 5 encoding spp gene and SEQ ID NO: 6 encoding SPP polypeptide), or homologue thereof, is engineered to be expressed or overexpressed in a transformed photosynthetic microorganism. For example, a photosynthetic microorganism, such as a cyanobacterium, can be transformed with a nucleotide having a sequence of SEQ ID NO: 5 so as to express sucrose phosphate phosphatase. As another example, a photosynthetic microorganism can be transformed with a nucleotide having at least about 80%, at least about 85%, at least about 90%, at least about 95%, or at least about 99% percent identity to SEQ ID NO: 5 encoding a polypeptide having sucrose phosphate phosphatase activity. As another example, a transformed host photosynthetic microorganism can comprise a nucleotide sequence encoding a polypeptide having at least about 85%, at least about 90%, at least about 95%, or at least about 99% sequence identity to SEQ ID NO: 6, wherein the transformed host exhibits SPP activity and/or accumulation of sucrose.

In some embodiments, a photosynthetic microorganism is engineered to express one or more of ASF, SPS, and/or SPP. For example, a photosynthetic microorganism, such as a cyanobacterium, can be engineered to express ASF and SPS; ASF and SPP; SPS and SPP; or ASF, SPS, and SPP.

Trehalose

Biosynthesis of trehalose can be accomplished through the catalytic action of two enzyme activities, trehalose phosphate synthase (tps) and trehalose phosphate phosphatase (tpp), functioning in sequence. Either or both of these activities can be engineered in a photosynthetic microorganism so as to result in accumulation of trehalose. Biosynthesis of trehalose does not naturally occur in some photosynthetic microorganisms, such as cyanobacteria.

In some embodiments, a trehalose phosphate synthase (tps) (see e.g., SEQ ID NO: 76 encoding tps gene and SEQ ID NO: 77 encoding TPS polypeptide), or homologue thereof, is engineered to be expressed or overexpressed in a transformed photosynthetic microorganism. For example, a photosynthetic microorganism, such as cyanobacterium, can be transformed with a nucleotide having a sequence of SEQ ID NO: 76 so as to express trehalose phosphate synthase. As another example, a photosynthetic microorganism can be transformed with a nucleotide having at least about 80%, at least about 85%, at least about 90%, at least about 95%, or at least about 99% percent identity to SEQ ID NO: 76 encoding a polypeptide having trehalose phosphate synthase. As another example, a transformed host photosynthetic microorganism can comprise a nucleotide sequence encoding a polypeptide having at least about 85%, at least about 90%, at least about 95%, or at least about 99% sequence identity to SEQ ID NO: 77, wherein the transformed host exhibits TPS activity and/or accumulation of trehalose.

In some embodiments, trehalose phosphate phosphatase (tpp) (see e.g., SEQ ID NO: 78 encoding tpp gene and SEQ ID NO: 79 encoding TPP polypeptide), or homologue thereof, is engineered to be expressed or overexpressed in a transformed photosynthetic microorganism. For example, a photosynthetic microorganism, such as a cyanobacterium, can be transformed with a nucleotide having a sequence of SEQ ID NO: 78 so as to express trehalose phosphate phosphatase. As another example, a photosynthetic microorganism can be transformed with a nucleotide having at least about 80%, at least about 85%, at least about 90%, at least about 95%, or at least about 99% percent identity to SEQ ID NO: 78 encoding a polypeptide having trehalose phosphate phosphatase activity. As another example, a transformed host photosynthetic microorganism can comprise a nucleotide sequence encoding a polypeptide having at least about 85%, at least about 90%, at least about 95%, or at least about 99% sequence identity to SEQ ID NO: 79, wherein the transformed host exhibits TPP activity and/or accumulation of trehalose.

Glucosylglycerol

In some embodiments, a glucosylglycerolphosphate synthase (gps) (see e.g., SEQ ID NO: 80 encoding gps gene and SEQ ID NO: 81 encoding GPS polypeptide), or homologue thereof, is engineered to be expressed or overexpressed in a transformed photosynthetic microorganism. For example, a photosynthetic microorganism, such as a cyanobacterium, can be transformed with a nucleotide having a sequence of SEQ ID NO: 80 so as to express glucosylglycerolphosphate synthase. As another example, a photosynthetic microorganism can be transformed with a nucleotide having at least about 80%, at least about 85%, at least about 90%, at least about 95%, or at least about 99% percent identity to SEQ ID NO: 80 encoding a polypeptide having glucosylglycerolphosphate synthase. As another example, a transformed host photosynthetic microorganism can comprise a nucleotide sequence encoding a polypeptide having at least about 85%, at least about 90%, at least about 95%, or at least about 99% sequence identity to SEQ ID NO: 81, wherein the transformed host exhibits GPS activity and/or accumulation of glucosylgycerol.

In some embodiments, glucosylglycerolphosphate phosphatase (gpp) (see e.g., SEQ ID NO: 82 encoding gpp gene and SEQ ID NO: 83 encoding GPP polypeptide), or homologue thereof, is engineered to be expressed or overexpressed in a transformed photosynthetic microorganism. For example, a photosynthetic microorganism, such as a cyanobacterium, can be transformed with a nucleotide having a sequence of SEQ ID NO: 82 so as to express glucosylglycerolphosphate phosphatase. As another example, a photosynthetic microorganism can be transformed with a nucleotide having at least about 80%, at least about 85%, at least about 90%, at least about 95%, or at least about 99% percent identity to SEQ ID NO: 82 encoding a polypeptide having glucosylglycerolphosphate phosphatase activity. As another example, a transformed host photosynthetic microorganism can comprise a nucleotide sequence encoding a polypeptide having at least about 85%, at least about 90%, at least about 95%, or at least about 99% sequence identity to SEQ ID NO: 83, wherein the transformed host exhibits GPP activity and/or accumulation of glucosylglycerol.

Mannosylfructose

In some embodiments, a mannosylfructose phosphate synthase (mps) (see e.g., SEQ ID NO: 84 encoding mps gene and SEQ ID NO: 85 encoding MPS polypeptide), or homologue thereof, is engineered to be expressed or overexpressed in a transformed photosynthetic microorganism. For example, a photosynthetic microorganism, such as a cyanobacterium, can be transformed with a nucleotide having a sequence of SEQ ID NO: 84 so as to express mannosylfructose phosphate synthase. As another example, a photosynthetic microorganism can be transformed with a nucleotide having at least about 80%, at least about 85%, at least about 90%, at least about 95%, or at least about 99% percent identity to SEQ ID NO: 84 encoding a polypeptide having mannosylfructose phosphate synthase. As another example, a transformed host photosynthetic microorganism can comprise a nucleotide sequence encoding a polypeptide having at least about 85%, at least about 90%, at least about 95%, or at least about 99% sequence identity to SEQ ID NO: 85, wherein the transformed host exhibits MPS activity and/or accumulation of mannosylfructose.

In some embodiments, mannosylfructose phosphate phosphatase (mpp) (see e.g., SEQ ID NO: 86 encoding mpp gene and SEQ ID NO: 87 encoding MPP polypeptide), or homologue thereof, is engineered to be expressed or overexpressed in a transformed photosynthetic microorganism. For example, a photosynthetic microorganism, such as a cyanobacterium, can be transformed with a nucleotide having a sequence of SEQ ID NO: 86 so as to express mannosylfructose phosphate phosphatase. As another example, a photosynthetic microorganism can be transformed with a nucleotide having at least about 80%, at least about 85%, at least about 90%, at least about 95%, or at least about 99% percent identity to SEQ ID NO: 86 encoding a polypeptide having mannosylfructose phosphate phosphatase activity. As another example, a transformed host photosynthetic microorganism can comprise a nucleotide sequence encoding a polypeptide having at least about 85%, at least about 90%, at least about 95%, or at least about 99% sequence identity to SEQ ID NO: 87, wherein the transformed host exhibits MPP activity and/or accumulation of mannosylfructose.

Molecular Engineering

Design, generation, and testing of the variant nucleotides, and their encoded polypeptides, having the above required percent identities to an asf sequence and retaining a required activity of the expressed protein and/or sugar accumulation phenotype is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide (e.g., asf, sps, spp, tps, tpp, gps, gpp, mps, or mpp) and/or polypeptide (e.g., ASF, SPS, SPP, TPS, TPP, GPS, GPP, MPS, or MPP) variants having, for example, at least 95-99% identity to the reference sequence described herein and screen such for phenotypes including disaccharide accumulation according to methods routine in the art. Generally, conservative substitutions can be made at any position so long as the required activity is retained.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m=81.5°$ C.$+16.6(\log_{10}[Na^+])+0.41$ (fraction G/C content)$-0.63$(% formamide)$-(600/1)$. Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Promoter

One or more of the nucleotide sequences discussed above (e.g., asf, sps, spp, tps, tpp, mps, mpp, gps, gpp) can be operably linked to a promoter that can function in the host photosynthetic microorganism. Where the host is cyanobacteria, preferably, the promoter can function efficiently in both cyanobacteria and a bacteria, such as E. coli. Promoter selection can allow expression of a desired gene product under a variety of conditions.

Promoters can be selected for optimal function in a photosynthetic microorganism host cell, such as a cyanobacterium, into which the vector construct will be inserted. Promoters can also be selected on the basis of their regulatory features. Examples of such features include enhancement of transcriptional activity and inducibility.

The promoter can be an inducible promoter. For example, the promoter can be induced according to temperature, pH, a hormone, a metabolite (e.g., lactose, mannitol, an amino acid), light (e.g., wavelength specific), osmotic potential (e.g., salt induced), a heavy metal, or an antibiotic. Numerous standard inducible promoters will be known to one of skill in the art.

In some embodiments, the promoter is a temperature inducible promoter. For example, the Lambda promoter is a temperature inducible promoter that can function in cyanobacteria. Surprisingly, the Lambda promoter functions at a temperature different than when utilized in E. coli. In E. coli, the Lambda promoter is most active at 42° C., a temperature above the normal viability range for cyanobacteria. Generally, in E. coli, the Lambda promoter has about a 5% to 10% increased expression from about 30° C. to 35° C. and at about 37° C. has about a 20% increased expression; but from about 37° C. to 42° C. provides about 100% increased expression. In cyanobacteria, the Lambda promoter is most active at around 30° C. to 35° C., an ideal growth temperature range for cyanobacteria and a range much lower than optimal expression of the Lambda promoter in E. coli. So, the Lambda promoter provides for effective expression of disaccharide biotsynthetic activity in cyanabctaria.

Examples of promoters that can be inserted into the plasmid include, but are not limited to, carB, nirA, psbAII, dnaK, kaiA, and $\lambda_{PR}$ (see e.g., Example 6). In some embodiments, the promoter can function efficiently in both cyanobacteria and E. coli. In some embodiments, the asf coding region comprises a promoter with said coding region (see e.g., Example 8). For example, the asf coding region can comprise a promoter in front of the SPP domain of asf (see e.g., FIG.

10). Such an internal promoter can occur with or without a promoter at the start of the asf coding region.

The term "chimeric" is understood to refer to the product of the fusion of portions of two or more different polynucleotide molecules. "Chimeric promoter" is understood to refer to a promoter produced through the manipulation of known promoters or other polynucleotide molecules. Such chimeric promoters can combine enhancer domains that can confer or modulate gene expression from one or more promoters or regulatory elements, for example, by fusing a heterologous enhancer domain from a first promoter to a second promoter with its own partial or complete regulatory elements. Thus, the design, construction, and use of chimeric promoters according to the methods disclosed herein for modulating the expression of operably linked polynucleotide sequences are encompassed by the present invention.

Novel chimeric promoters can be designed or engineered by a number of methods. For example, a chimeric promoter may be produced by fusing an enhancer domain from a first promoter to a second promoter. The resultant chimeric promoter may have novel expression properties relative to the first or second promoters. Novel chimeric promoters can be constructed such that the enhancer domain from a first promoter is fused at the 5' end, at the 3' end, or at any position internal to the second promoter.

Constructs

Any of the transcribable polynucleotide molecule sequences described above can be provided in a construct. Constructs of the present invention generally include a promoter functional in the host photosynthetic microorganism, such as cyanobacteria, operably linked to a transcribable polynucleotide molecule for disaccharide biosynthesis (e.g., asf, sps, spp, tps, tpp, mps, mpp, gps, gpp), such as provided in SEQ ID NO: 1, 3, 5, 76, 78, 80, 82, 84, and 86, and variants thereof as discussed above.

Exemplary promoters are discussed above. One or more additional promoters may also be provided in the recombinant construct. These promoters can be operably linked to any of the transcribable polynucleotide molecule sequences described above.

The term "construct" is understood to refer to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. The term "vector" or "vector construct" is understood to refer to any recombinant polynucleotide construct that may be used for the purpose of transformation, i.e., the introduction of heterologous DNA into a host photosynthetic microorganism, such as a cyanobacterium.

In addition, constructs may include, but are not limited to, additional polynucleotide molecules from an untranslated region of the gene of interest. These additional polynucleotide molecules can be derived from a source that is native or heterologous with respect to the other elements present in the construct.

Plasmid

In some embodiments, a host photosynthetic microorganism, such as a cyanobacterium, is transformed with a plasmid-based expression system (see e.g., Example 5). Preferably the plasmid encoding the gene of interest comprises a promoter, such as one or more of those discussed above. For plasmid based transformation, preferred is a broad host range plasmid that enables function in both *E. coli* and cyanobacteria, which provides the advantage of working in a convenient fast growing well understood system (*E. coli*) that can be efficiently transferred to the final host (cyanobacteria). In some embodiments, plasmid based transformation and chromosomal integration are used in conjunction, where the plasmid protocol is used for design and testing of gene variants followed by chromosomal integration of identified variants.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Provided herein are nucleotide sequences for plasmid constructs encoding sps, spp, and/or asf. Examples of plasmid constructs encoding sps, spp, and/or asf include, but are not limited to, pLybAL11 (SEQ ID NO: 19) (see e.g., FIG. 6) and pLybAL12 (SEQ ID NO: 20) (see e.g., FIG. 7). Also provided herein are nucleotide sequences for plasmid constructs encoding tps and tpp. Examples of plasmid constructs encoding tps and tpp include, but are not limited to, pLybAL23 (SEQ ID NO: 118). A skilled artisan will understand that similar contructs can be generated for biosynthetic genes necessary for accumulation of other disaccharides, such as glucosylglycerol and mannosylfructose.

In some embodiments, the transformed host photosynthetic microorganism comprises pLybAL11 (SEQ ID NO: 19) or pLybAL12 (SEQ ID NO: 20). In some embodiments, the transformed host photosynthetic microorganism comprises pLybAL23 (SEQ ID NO: 118). For example, a transformed cyanobacterium can comprise pLybAL11 (SEQ ID NO: 19), pLybAL12 (SEQ ID NO: 20), or pLybAL23 (SEQ ID NO: 118).

A plasmid construct comprising a disaccharide biosynthetic gene(s) can also include a promoter. Examples of plasmid constructs comprising sps, spp, and/or asf and a promoter include, but are not limited to, pLybAL7f (SEQ ID NO: 65); pLybAL8f, including kanamycin resistance (SEQ ID NO: 69); pLybAL13f (SEQ ID NO: 51), pLyAL13r (SEQ ID NO: 52), pLybAL14f (SEQ ID NO: 53), pLybAL14r (SEQ ID NO: 54), pLybAL15 (SEQ ID NO: 44), pLybAL16 (SEQ ID NO: 45), pLybAL17 (SEQ ID NO: 46), pLybAL18 (SEQ ID NO: 47), pLybAL19 (SEQ ID NO: 48), pLybAL21 (SEQ ID NO: 49), and pLybAL22 (SEQ ID NO: 50). Examples of plasmid constructs comprising tps and tpp and a promoter include, but are not limited to, pLybAL23 (SEQ ID NO: 118), pLybAL28 (SEQ ID NO: 121), pLybAL29 (SEQ ID NO: 122), and pLybAL30 (SEQ ID NO: 123). A skilled artisan will understand that similar promoter containing contructs can be generated for biosynthetic genes necessary for accumulation of other disaccharides, such as glucosylglycerol and mannosylfructose.

In some embodiments, the transformed host cyanobacterium comprises pLybAL7f (SEQ ID NO: 65); pLybAL8f (SEQ ID NO: 69); pLybAL13f (SEQ ID NO: 51), pLyAL13r (SEQ ID NO: 52), pLybAL14f (SEQ ID NO: 53), pLybAL14r (SEQ ID NO: 54), pLybAL15 (SEQ ID NO: 44), pLybAL16 (SEQ ID NO: 45), pLybAL17 (SEQ ID NO: 46), pLybAL18 (SEQ ID NO: 47), pLybAL19 (SEQ ID NO: 48), pLybAL21 (SEQ ID NO: 49), and pLybAL22 (SEQ ID NO: 50). In some embodiments, the transformed host cyanobacterium comprises pLybAL28 (SEQ ID NO: 121), pLybAL29 (SEQ ID NO: 122), pLybAL30 (SEQ ID NO: 123), and pLybAL23 (SEQ ID NO: 118).

Sugar Secretion

In various embodiments, a transformed disaccharide-accumulating photosynthetic microorganism can secrete the accumulated disaccharide from within the cell into its growth environment. Secretion of the disaccharide can be an inherent effect of transforming the photosynthetic microorganism to accumulate a disaccharide or the photosynthetic microorganism can be further engineered to secrete the disaccharide. For example, some cyanobacteria transformed to accumulate trehalose inherently secrete trehalose from the cell (see e.g., Examples 19-20). As another example, a cyanobacterium transformed to accumulate sucrose can be further engineered to secrete sucrose from the cell (see e.g., Example 16).

A host photosynthetic microorganism, such as a cyanobacterium, can be further engineered to secrete a disaccharide. In some embodiment, a transformed host photosynthetic microorganism is engineered to express a porin specific for the accumulated disaccharide. For example, a cyanobacterium engineered to accumulate sucrose can be further engineered to express a sucrose porin (see e.g., Example 16). In one embodiment, the transformed disaccharide-accumulating cyanobacterium comprises an scrY nucleic acid, such as SEQ ID NO: 94. In one embodiment, the transformed disaccharide-accumulating cyanobacterium comprises a nucleic acid encoding a scrY polypeptide, such as SEQ ID NO: 95. In one embodiment, the transformed disaccharide-accumulating cyanobacterium comprises a plasmid containing scrY, such as pLybAL32 (SEQ ID NO: 91). It is contemplated that a similar approach can be applied to other photosynthetic microorganisms or other target disaccharides.

Modulation of Sugar Degradation

In some embodiments, a host photosynthetic microorganism, such as a cyanobacterium, is further engineered to improve disaccharide production by modulation of degradation activity (see e.g., Example 14). In some embodiments, an invertase homologue can be down-regulated or eliminated in a transformed photosynthetic microorganism. For example an invertase homologue from *Synechocystis* spp. PCC 6803 (nucleotide sequence SEQ ID NO: 70; polypeptide sequence SEQ ID NO: 71) can be down-regulated or eliminated in a transformed cyanobacterium. As another example, an invertase homologue from *Synechococcus elongatus* PCC 7942 (nucleotide sequence SEQ ID NO: 72; polypeptide sequence SEQ ID NO: 73) can be down-regulated or eliminated in a transformed cyanobacterium. In some embodiments, a sucraseferredoxin-like protein is down-regulated or eliminated in a transformed cyanobacteriuma. For example, a sucraseferredoxin-like protein from *Synechocystis* spp. PCC 6803 (nucleotide sequence SEQ ID NO: 74; polypeptide sequence SEQ ID NO: 75) (Machray G. C. et al. 1994. FEBS Lett 354, 123-127) can be down-regulated or eliminated in a transformed cyanobacterium. These genes can be deleted using the markerless deletion protocol described in, for example, FIG. 11 (see e.g., Examples 12-13) A similar approach can be taken for other disaccharides engineered to be accumulated in a cyanobacterium.

Other methods of down-regulation or silencing the above genes are known in the art. For example, disaccharide degradative activity can be down-regulated or eliminated using antisense oligonucleotides, protein aptamers, nucleotide aptamers, and RNA interference (RNAi) (e.g., small interfering RNAs (siRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem. Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, Tex.; Sigma Aldrich, Mo.; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinformatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

In some embodiments, a host photosynthetic microorganism can be further engineered to promote disaccharide secretion from the cells. For example, a cyanobacterium can be further engineered to promote sucrose secretion from the cells (see e.g., Example 15-16). When in a low osmotic environment, the sucrose can be automatically expunged from the cells, as done with osmoprotectants by some organisms when transitioning from high to low salt environments (Schleyer, M., Schmidt, R. and Bakker, E. P. 1993. Arch Microbiol 160, 424-43; Koo, S. P., Higgins, C. F. and Booth, I. R. 1991. J Gen Microbiol 137, 2617-2625; Lamark, T., Styrvold, O. B. and Strgim, A. R. 1992. FEMS Microbiol. Lett 96, 149-154). Sucrose porins can be engineered to be expressed in a transformed cyanobacterium (see e.g., Example 16). These genes can be cloned and transformed into cyanobacteria according to techniques described above. Such approaches can be adapted to other photosynthetic microorganisms.

In some embodiments, a host photosynthetic microorganism is transformed by stable integration into a chromosome of the host. For example, a host cyanobacterium can be transformed by stable integration into a chromosome of the host (see e.g., Examples 11-13). Chromosomal integration can insure that the target gene(s) is installed into the organism without risk of expulsion as sometimes occurs with plasmid-based gene expression. Chromosomal integration can also reduce or eliminate the need for antibiotics to maintain target genes.

Preferably, the strategy for chromosomal integration targets gene insertion into what is termed the upp locus on the chromosome (see e.g., Example 11-13). This site codes for the enzyme uracil phosphoribosyltransferase (UPRTase) which is a scavenger enzyme in pyrimidine biosynthesis. Using this strategy allows candidate selection by 5-fluorouracil (5-FU), which can eliminate non-integrated organisms. Segregation methods are generally used in cyanobacterial systems because these organisms contain multiple copies of their chromosomes (e.g., up to 12 for *Synechocystis* spp. PCC 6803 and 16 for *Synechococcus elongatus* PCC 7942). This strategy is particularly attractive for cyanobacteria, because this approach can avoid the use of traditional segregation techniques that rely on selective pressure and statistical integration for successful segregation. Using 5-FU as a screening agent can be more efficient because it can prevent growth for any organism that contains even a single active upp gene. In this manner, fully integrated candidates can be selected rapidly over fewer generation cycles compared to the processes required of traditional techniques.

Solid Phase Photosynthetic Bioreactor

Provided herein is a photobioreactor for culturing photosynthetic microorganisms comprising a solid phase cultivation support for the growth of photosynthetic microorganisms. A solid phase cultivation support, or solid cultivation support, or solid support, or the like, is generally understood to mean a cultivation support that is neither a liquid nor a gas. Although the support itself is a solid, the support structure may be selected so that it absorbs a liquid (e.g., growth media), a gas, or both. In certain preferred embodiments, as described more fully below, the solid support can absorb moisture for use by the microorganisms during cultivation.

Various embodiments of the photobioreactor(s) described herein can support the growth a photosynthetic microorganism. The photosynthetic microorganism grown in the photobioreactor can be, for example, a naturally photosynthetic microorganism, such as a cyanobacterium, or an engineered photosynthetic microorganism, such as an artificially photosynthetic bacterium. Exemplary microorganisms that are either naturally photosynthetic or can be engineered to be photosynthetic include, but are not limited to, bacteria; fungi; archaea; protists; microscopic plants, such as a green algae; and animals such as plankton, planarian, and amoeba. Examples of naturally occurring photosynthetic microorganisms include, but are not limited to, *Spirulina maximum*, *Spirulina platensis*, *Dunaliella salina*, *Botrycoccus braunii*, *Chlorella vulgaris*, *Chlorella pyrenoidosa*, *Serenastrum capricornutum*, *Scenedesmus auadricauda*, *Porphyridium cruentum*, *Scenedesmus acutus*, *Dunaliella* sp., *Scenedesmus obliquus*, *Anabaenopsis*, *Aulosira*, *Cylindrospermum*, *Synechoccus* sp., *Synechocystis* sp., and/or *Tolypothrix*.

Preferably, the bioreactor is configured to support innoculation, growth, and/or harvesting of cyanobacteria transformed to accumulate a disaccharide, as described above.

The photobioreactor can be an open or a closed system, as described more fully below. In various embodiments, the photobioreactor includes a solid phase cultivation support, a protective barrier layer, and a suspension element. Some embodiments of the photobioreactor can contain a system for delivery and/or removal of gas, fluids, nutrients, and/or photosynthetic microorganisms. Delivery systems can be, for example, standard plumbing fixtures. Any of the various lines can include quick-connect plumbing fixtures. The photobioreactor can have a gas delivery line, which can deliver, for example, delivering carbon dioxide or normal atmospheric air. The photobioreactor can have a fluid delivery line. Preferably, the fluid delivery line connects to a trickle or drip system which conveys a fluid (e.g., water) to the solid phase cultivation support. The photobioreactor can have a nutrient delivery line. Formulation of a nutrient composition for the growth and maintenance of a photosynthetic microorganism is within the ordinary skill of the art. In some embodiments, the nutrient and fluid delivery lines can be combined, for example to supply a fluid-based nutrient mixture. In some embodiments, the fluid delivery line or the nutrient delivery line can be a spray device for distributing a liquid medium over the growth surface. In such spray devices, the photobioreactor is large enough to accommodate, for example, a spray device between an outer layer, such as a barrier layer, and the solid phase cultivation support. Usually, nutrients are supplied in a water-based composition. It can be advantageous to provide for different water delivery line(s) and nutrient delivery line(s) so as to provide for independent control of moisture and nutrient levels. The photobioreactor can have a product harvest line so as to provide for collection of photosynthetic microorganisms and/or liquid suspended/soluble products. The photobioreactor can have an inoculation line so as to provide for inoculation of photosynthetic microorganisms. In some embodiments, the fluid, nutrient, and/or inoculation lines can be combined.

One embodiment of a solid-phase photobioreactor is depicted in FIG. 1 (front view) and FIG. 2 (side view). In these embodiments, a solid phase cultivation support 2 is enclosed by protective barrier 7. FIG. 2 shows that the solid cultivation support is between protective barrier layers 3 that comprise the protective barrier 7. The solid cultivation support 2 provides the surface upon which photosynthetic microorganisms are cultivated. The protective barrier layers 3 that make up the protective barrier 7 are transparent to allow actinic radiation to reach the surface of the solid cultivation support 2 to support the growth of photosynthetic microorganisms. Resealable closures 4 allow for a protective barrier 7 that is releasably sealed. Exchange of gases and vapor occurs through a selective panel 5 of material that is incorporated into the protective barrier 7. The photobioreactor 1 can be suspended by support elements 6 to allow for a vertical or non-horizontal orientation.

Another embodiment of a solid-phase photobioreactor is depicted in FIG. 12A (front view) and FIG. 12B (side view). The reactor 1 can be designed in a segmented format, which can aid in servicing and minimizes potential contamination of the surface and/or plumbing. Each segment can be connected to the reactor through plumbing (e.g., quick connect type plumbing) of the various supply and product harvest lines. The reactor can be supported by a suspension element 6 from, for example, rails, which allows the reactor 1 to hang in space and aid in rapid servicing of each segment. The outer protective barrier 7 can be a transparent material that enables light penetration facilitating photosynthesis on the growth surface 2, while preventing environmental contamination and moisture loss from evaporation. The growth surface 2 can be composed of a material that retains moisture, supplies nutrients, removes products, and/or enables high density growth of photosynthetic microorganisms. The growth surface 2 can be serviced by plumbing that provides continuous feeding/product harvest from the surface by liquid culture media. The media tubing 8 can be a porous hose that seeps liquid to the surface 2, which can percolate through the growth surface 2 by gravity. The liquid can be harvested at the bottom of the reactor by a harvesting tube 9, which collects products and excess liquid media for transport from the reactor 1. Gases, such as carbon dioxide and air, can be supplied to the reactor by a gas dispersion tube 10. The gas supply tube 10 can provide a positive pressure environment and is expected to supply gases necessary for growth in a controlled, efficient manner. The gas supply line 10 can also assist in minimizing moisture loss by humidifying incoming gas streams. Excess gas from the reactor can be vented by a breathable panel 5 (on the reverse side, not shown) that is a porous material that allows for gas passage but minimizes or eliminates environmental contamination. Contamination is expected to be minimized by the positive pressure configuration of the reactor 1 through filtration of the incoming gas delivered by the supply line 10. Positive pressure can also prevent contamination from the environment by providing an inside out pathway for gas flow.

In the embodiment depicted in FIG. 12B, features of the reactor 1 are depicted in an orientation relative to the growth surface. The breathable panel 5 allowing for excess gas to escape the reactor 1 can be located toward the bottom of the device to provide a path for gas to migrate across the growth surface 2. Location of the breathable panel 5 on the bottom of the barrier surface 7 also minimizes or prevents the possibility of carbon dioxide segregation and build up resulting from its higher density relative to air. The dimensions of the breathable panel 5 can be determined based on gas flow rate requirements for optimal growth on the cultivation surface 2.

Solid Phase Cultivation Support

The solid phase cultivation support of a photobioreactor as described herein provides a surface on and/or in which a photosynthetic microorganism can grow.

Preferably, the solid phase cultivation support comprises a material that provides or facilitates the provision and/or retention of moisture and/or nutrients to the organisms, so as to promote and sustain growth. Embodiments of the invention are not limited to the type or strain of photosynthetic microorganisms that can be cultivated. One of ordinary skill in the art will recognize that the amount of moisture and the amount and composition of nutrients desirable for cell growth will vary with the type or strain of photosynthetic microorganism and the application for which it is to be grown. Materials (or the substances contained within or on those materials) that may have a deleterious effect on the growth of photosynthetic microorganisms are generally avoided.

A single photobioreactor can be used to cultivate a single type or multiple types or strains of photosynthetic microorganisms. Further, the solid cultivation support can comprise material(s) such that it is suitable for a single cultivation cycle or multiple cycles of cultivation, with or without sterilization between cultivation cycles. Still further, a photobioreactor can be configured to cultivate a single type or strain of microorganism or multiple types or strains of microorganisms on a single or multiple solid supports. In some embodiments, instead of an axenic culture, a community of different photosynthetic microorganisms, or a community of photosynthetic and non-photosynthetic microorganisms, can be grown together simultaneously on one cultivation support. A single photobioreactor can also comprise multiple cultivation supports. Thus in another embodiment, multiple cultivation supports within a single protective barrier can cultivate one or more types or strains of photosynthetic microorganisms simultaneously.

The solid cultivation support preferably comprises a relatively porous material. A relatively porous material generally has increased surface area and can retain and/or absorb more moisture than a relatively non-porous material. Also preferred is a solid cultivation support that has a textured or topographical surface(s). A textured or topographical surface can enhance cell density compared to a relatively non-textured or smooth surface. Although the choice of support material and surface topography are typically selected to enhance the adhesion of microorganisms to the support, it generally is desirable that the organisms not so tightly adhere so as to impede their removal or harvest. In some embodiments, the solid cultivation support comprises a material suitable for adhesion and growth of microorganisms. In some embodiments, the solid cultivation support comprises a material that reduces or eliminates biofilm formation.

The solid-phase supports of the photobioreactors described herein are believed to be different from solid supports that have been utilized in the art (e.g., the most commonly used solid phase support for the growth of microorganisms is agar). Agar is generally cast into rigid forms, such as a petri dish, and used while therein to maintain its physical integrity because agar tends to break or tear when subjected to minimal levels of stress, strain, or both. In contrast, various embodiments of the cultivation support is sufficiently strong and durable that it can be used in a photobioreactor while maintaining its physical integrity without the need of a stronger, more durable "frame". Or stated another way, the prior art involved a sufficient portion of the weak agar support in contact with a substantially stronger, more durable material (e.g., a petri dish) such that a composite is formed. Thus, the solid-phase supports of various embodiments of the photobioreactor are suitable in themselves for the cultivation of microorganisms and are sufficiently strong and durable.

Other desirable physical characteristics and/or operation parameters of the solid-phase support are described below. For example, the support can be relatively flat and rigid (like a plate) or it may consist of a multiplicity of flat and rigid sections flexibly connected by, e.g., hinges, springs, wires, threads, etc. Suitable rigid materials include, but are not limited to, various metals, polymers, ceramics, and composites thereof. The rigid materials preferably have surface topographies that enhance the adherence of the photosynthetic microorganisms thereto. Further, the rigid materials may be formed with a desired level of porosity to enhance the ability to deliver moisture and/or nutrients to the photosynthetic microorganisms. Still further, the rigid materials may be coated with absorbent or super absorbent polymer formulations (see below). Alternatively, the support may consist essentially of flexible material, such as a fabric. Fabrics for use in a solid-phase support include, but are not limited to, cotton, polyester, and/or cotton polyester blends, optionally coated with absorbent or super absorbent polymer formulations. Flexibility of the cultivation support can be greatly advantageous because it allows for the cultivation support to be folded, twisted, draped, or rolled for storage, transport, or handling.

In addition, the solid-phase cultivation support is preferably structurally stable at elevated temperatures (e.g., about 120° C. and above), such as would be typically encountered during autoclave sterilization, and will not melt like agar. Thus, in one embodiment, the cultivation support may be sterilized by autoclaving and then placed within the protective barrier of the invention. In another embodiment, the cultivation support can be placed within the protective barrier, and the entire photobioreactor may then be autoclaved. Although autoclaving is one method for sterilization, one of skill in the art will recognize that any other appropriate method of sterilization may be utilized.

The solid cultivation support of the present invention can comprise or be made of any material appropriate for supporting the growth of photosynthetic microorganisms. For example, the support may be composed of natural materials, modified natural materials, synthetic materials, or any combination thereof. Natural materials can include, but are not limited to cotton, wool, processed woven plant fibers, and natural polysaccharides (e.g., agar, starches, cellulosics). Modified natural materials can include, but are not limited to, chemically modified plant fibers such as nitrocellulose or cellulose esters, in addition to natural fibers co-woven or blended with polyester or polyamide fibers. Synthetic materials can include, but are not limited to, fibers composed of nylon, fiberglass, polysiloxanes, polyester, polyolefins, polyamide, copolyester polyethylene, polyacrylates, or polysulfonates. Further examples of solid cultivation support materials include wire mesh, polyurethane foams, polyethylene foams, vitreous carbon foams, polyester/polyethylene foams, polyimide foams, polyisocyanate foams, polystyrene foams, and polyether foams, or combinations thereof.

In various embodiments, the solid cultivation support is a fabric. The fabric can be formed by methods such as, but not limited to, weaving, knitting, felting, and the bonding or cross-linking of fibers or polymers together. The construction of the fabric can be loose or open. Alternatively, the fabric can be tightly constructed. That said, fabrics that have a significant texture, surface area, topographical variability, and/or roughness may provide more mechanical bonding or adherence of the photosynthetic microorganisms to the cultivation support and thus may be preferable, especially in embodiments wherein the photobioreactor is handled, transported, or otherwise moved during the process for inoculating the support with, and/or growing and/or harvesting the organisms. Preferably, in most applications the adherence of the organisms to the substrate should not be so great as to unduly hinder their removal during a harvesting operation. Still further, the ability of a fabric to retain moisture and/or nutrients for use by the organisms can be controlled by selecting fibers that are generally hydrophobic, hydrophilic, or a mixture of such fibers. These properties allow for moisture and/or nutrients dissolved therein to be retained and/or transported by the solid support so that they are available to the microorganisms growing on the surface.

The properties of the cultivation support, especially moisture and/or nutrient retention, can be enhanced by coating the support with a material selected to enhance photosynthetic microorganism growth. For example, the cultivation support can be coated with agar or a super absorbent polymer such as modified cellulose ester, acrylate or acrylate/polyamine copolymer blends. These coating materials are typically able to absorb and retain greater than 10 to 100 times their dry weight in water. In some embodiments, these materials are formulated such that they would retain their superabsorbent properties in the presence of ionic culture media components. The coating material can coat the surface of the cultivation support, or the fibers of a fabric if used, or both. In one embodiment, a swatch of terrycloth serving as the cultivation support is coated in agar. When a solid cultivation support is coated as such, the "surface" of the cultivation support includes the surface of the coating if photosynthetic microorganisms attach to such. To keep the cultivation support thin, pliable, and light, the coating is preferably thin, for example, no greater than about 100 microns. However, thicker coatings can also be used depending on the application desired, or on the combination of solid cultivation support and coating material selected.

The solid-phase cultivation support can be a composite, layered structure. The solid-phase cultivation support can comprise at least two layers arranged so as to be adjacent. Multiple layers of the solid-phase cultivation support can be coupled, such as by bonding, stitching, adhesive, compression, or any other suitable means. The various layers can each independently be selected from among the several materials discussed above. For example, the solid-phase cultivation support can comprise a first material layer of fabric bonded to a second material layer of synthetic foam. An another example, the solid-phase cultivation support can comprise a first material layer of synthetic foam bonded to a second material layer of synthetic foam of the same or different density. Preferably, the solid-phase cultivation support is a composite, layered structure comprising at least a first layer, which is composed of a high surface area growth material, and a second layer, which is composed of a permeable type material.

In addition to supplying moisture, nutrients, and a surface for attachment, the cultivation support can provide a surface for capturing actinic radiation. Thus, in some embodiments, the dimensions of the solid cultivation support are sheet-like. That is, the depth of the support is small relative to the length and width of the support. In one embodiment, the cultivation support is a sheet-like layer between film-like layers of a protective barrier. Such a flat bioreactor can be suspended like a flat panel. In another embodiment, just the cultivation support is suspended like a curtain enclosed by the outer barrier of the photobioreactor. A thin sheet of a traditional solid phase support such as agar would easily rip apart, and would likely not be able to be suspended as such. Therefore, it is preferable that the solid cultivation support alone be able to maintain its integrity when suspended, even when saturated with liquid.

As shown herein, a fabric with a terrycloth-type weave can provide a suitable solid support (see e.g., Example 1). One of skill in the art will understand that other natural, modified-natural, and synthetic materials may also be acceptable. Terrycloth provides many of the attributes believed to be desirable in a solid support of the present invention. For example, it is flexible, and not prone to tearing, ripping, breaking, or cracking when handled in accordance with non-destructive techniques (e.g., bending, folding, twisting, or rolling) under conventional conditions (e.g., temperature). Likewise, terrycloth is typically not prone to tearing, ripping, or breaking when modestly stretched (even when saturated with liquid). Additionally, terrycloth tends to be highly textured because it is composed of the many loops of fibers. This provides a large amount of surface area for the attachment of microorganisms thereby increasing the amount of microorganisms that can be grown on a support of any given size. Further, a cotton terrycloth typically absorbs at least about three times its own weight, which allows for moisture and any nutrients dissolved therein to be retained by the fabric support so that they are available to the microorganisms growing on the surface of the support. Thus, various embodiments provide for a solid cultivation support that is thin or sheet-like in dimension, able to support its own wet weight while suspended, flexible, pliable, absorbent, highly textured, or any combination thereof.

The above-described supports can be, and in many applications preferably are, used repeatedly and more preferably for so long as they are structurally sound and provide a surface adequate to support the growth of the microorganisms disposed of after a single use thereby reducing operational costs and waste. That said, there can be certain applications in which single-use supports would be desirable, such as cultivation of recombinant photosynthetic microorganisms useful in producing pharmaceutical products such as small organic molecules or therapeutic proteins and peptides. To reduce the costs of such single-use supports and in view of the fact that that they will not be reused, such supports need not be as durable and therefore can be made or constructed using methods and/or materials that are less costly and less durable. For example, supports comprised of paper fibers similar to that of paper towels may be appropriate.

Several embodiments of a solid phase cultivation support are depicted in FIG. 13. The solid phase cultivation support material depicted in FIG. 13A is a single material that can provide sustainable surface for organism growth, access to moisture and nutrients, point of organism attachment, and/or removal of cultivation products. The material can allow for liquid percolation and equilibrium diffusion to exchange nutrients, moisture, and products between the surface and organisms. The rendering of the structure configuration is an example of a high surface area material, which can be optimized for dimension and shape. The solid phase cultivation support material depicted in FIG. 13B is a hybrid material that is composed of multiple layers of materials, each having specific functions for the growth surface. The base layer can be a porous material that efficiently allows for supply of nutrients and moisture as well as removal of products that are percolated through the material. The base material can also provide physical support for the growth surface. The outer layer(s) is expected to be attached to the base layer and can be optimized to provide point of attachment for the organisms. The surface layer can achieve more control of the surface growth environment in terms of surface area and compatibility with the cultivated organism.

Protective Barrier

A photobioreactor as described herein can comprise a barrier that protects the solid cultivation support and growth surface from contamination and/or moisture loss. At the same time, the photobioreactor provides for actinic radiation, either sunlight or artificial light, and carbon dioxide reaching the photosynthetic microorganisms. In various embodiments, the photobioreactor comprises at least one solid support and a protective barrier for the cultivation of photosynthetic microorganisms.

Protection from Physical Handling and/or Contamination

To prevent contamination, a protective physical barrier can at least partially cover the solid cultivation support. In certain embodiments, the physical barrier can enclose the cultivation support. The protective barrier can also control, at least in part, the loss of the moisture from the support and/or the atmosphere within the photobioreactor to the atmosphere outside the photobioreactor. One of skill in the art will recognize that the protective barrier can be constructed from any of numerous types of materials depending on the embodiment of the invention desired.

The protective barrier can completely enclose the cultivation support. If the protective barrier is permanently sealed, the barrier must be breached, cut, torn, or the like to access the cultivation support within. Thus, in some embodiments, access is provided through the protective barrier to the cultivation support and the surface on which the microorganisms are grown.

In preferred embodiments, the protective barrier is releasably sealed. The releasable seal can be any of a number of closure types including, but not limited to zipper-type closures such as found in Ziploc® storage bags (SC Johnson Company), hook-and-loop type fasteners (e.g., Velcro USA, Inc.), twist ties, zipties, snaps, clips, pressure sensitive adhesive backed surfaces, and all art recognized equivalents thereto. A complete seal, however, is not necessarily required; and it may be more efficient not to completely seal the outer barrier to allow for easier access to the cultivation support.

The photobioreactor can comprise a single cultivation support or multiple cultivation supports within a protective barrier. In some embodiments, a single cultivation support is enclosed within a single protective barrier. For example, a plastic bag may form a protective barrier within which a single solid cultivation support is enclosed (see e.g., FIG. 1). In other embodiments, a single protective barrier may enclose multiple solid cultivation supports. For example, a greenhouse-type structure may form a protective barrier within which multiple solid cultivation supports are enclosed.

Transmission of Actinic Radiation

The photobioreactor can provide for transmission of actinic radiation, either sunlight or artificial light, to the photosynthetic microorganisms. But the protective barrier of the invention need not necessarily be transparent to light. Some embodiments can comprise a cultivation support enclosed within a non-transparent protective barrier if a sufficient light source for the growth of photosynthetic microorganisms is provided within. It may be desirable, simpler, more economical, and the like to provide a transparent barrier to utilize sunlight, for instance, as a light source.

Preferred embodiments provide for a transparent barrier comprising a material such as, but not limited, glass or any type of transparent or generally visible light transmitting polymer such as polyethylene, acrylic polymers, polyethylene terephthalate, polystyrene, polytetrafluoroethylene, or co-polymers thereof, or combinations thereof. The transparent barrier can be selected from materials that are durable and not prone to ripping, tearing, cracking, fraying, shredding, or other such physical damage. The transparent barrier material can be selected for its ability to withstand autoclave sterilization or other exposure to temperature extremes. Further, the transparent barrier materials can be selected to withstand prolonged exposure to sunlight or other radiation without discoloring or deteriorating. One of skill in the art will recognize that certain coatings or formulations that resist photooxidation can be particularly useful. In addition, infrared reflecting or absorbing coatings can be selected to reduce and/or otherwise regulate the buildup of temperature within the photobioreactor of the invention.

One of skill in the art will recognize that the thickness of the transparent barrier material will vary depending on mechanical properties of scale. For example, the transparent barrier material may be of an industrial/marine type plastic about 10 mil thick or it may be of the type used in a household plastic bag, i.e., around 2 mil thick. In one embodiment, the transparent barrier material is thin and flexible. For example, the transparent barrier material can be less than about 10 mil.

In some embodiments, the barrier forms a protective layer or film covering the two sides of a thin, flexible, solid cultivation support. The assembled photobioreactor of this embodiment would be flexible, and could be bent, rolled, folded, twisted, or the like for storage, transport, conveying, or handling. In another embodiment, the transparent barrier material is rigid. For example, the barrier can be a glass greenhouse. Most likely, the thickness of the greenhouse glass would preferably be consistent with building practices but it is possible that it could be altered. The photobioreactor of such an embodiment would be for practical purposes immovable, but multiple solid supports could be handled, transported, conveyed and the like within the confines of one protective, transparent barrier.

Although a protective barrier can be selected to provide sufficient light for the growth of photosynthetic microorganisms, it is not necessary that the entire barrier be transparent. Thus, in some embodiments, portions of the barrier, such as one or more edges, are made from a non-transparent material. The non-transparent material can be composed of materials including, but not limited to polyethylene fiber material (Tyvek®), polytetrafluoroethylene filtration media, cellulosic filter material, fiberglass filter material, polyester filter material and polyacrylate filter material, and combinations thereof. The non-transparent material can be selected for durability. In such an embodiment, a transparent portion of the barrier would be further protected from tearing, ripping, fraying, shredding, and the like by a durable, non-transparent portion. In one embodiment, a non-transparent portion provides or comprises an attachment structure and/or reinforcement for suspending the photobioreactor by further comprising mounting or attachment points (e.g., holes, loops, hooks, grommets, or other art equivalent device, opening or, recess) and/or or a mechanism for securing the photobioreactor to a structure. Although it is not required that any such mounting points, etc., be located in or on the non-transparent portion, they can be contained within or on a non-transparent portion of the barrier, within or on a transparent portion of the barrier, or within or on a non-transparent and a transparent portion of the barrier. The attaching structure may also be contained within or on, or pass through, the solid cultivation support.

In some embodiments, the device has a discernable front side and back side. The front side of this device is meant to face a light source, and thus the portion of the barrier on the front side is preferably transparent, while the portion of the protective barrier on the side facing away from the light source is not necessarily transparent.

Provision of Gas Exchange

During photosynthesis, photosynthetic microorganisms consume carbon dioxide and release oxygen. A photobioreactor as described herein can provide carbon dioxide sufficient for a desired amount of photosynthesis to occur. One way to supply carbon dioxide to the inside of the photobioreactor is to allow direct gas exchange between the air inside and the air surrounding the photobioreactor. For example, holes, vents, windows, or other such openings can be provided in the protective barrier so that the system is open to the surrounding atmosphere.

But such an open configuration may not be desirable when contamination of the photosynthetic microorganisms is a concern. To address this concern, the protective barrier can completely seal off the solid support or supports enclosed within from the outside air. In such an embodiment, the desired concentration of carbon dioxide can be maintained by introducing it into the enclosure. For example, one of skill in the art would recognize that plumbing or tubing from a tank of compressed carbon dioxide would allow for carbon dioxide to be mixed into the air enclosed within the photobioreactor. In addition, it is known that the emissions from factories, industrial plants, power plants, or the like can be harnessed as a source of carbon dioxide for photosynthetic microorganisms, thus reducing carbon emissions. In one embodiment, a gas supply line can provide carbon dioxide to the growth surface local area.

It may be desirable, simpler, more economical, and the like to provide a selective barrier that is gas permeable to utilize atmospheric carbon dioxide. Thus, some photobioreactor embodiments provide for a selective barrier that allows gas and vapor exchange between the environment enclosed within the protective barrier and the surrounding air, while still providing a sealed physical barrier against contamination. Such barrier can be at least partially gas/vapor permeable (e.g., much less permeable than conventional textile fabrics, higher than that of plastic films, and/or similar to that of coated papers), thus allowing the exchange of gases such as carbon dioxide and oxygen but is additionally at least partially and preferably considered to be impermeable to solids and liquids. In some embodiments, the photobioreactor can contain a semi-permeable barrier layer and a gas supply line to maintain an elevated carbon dioxide concentration in the area around or near the growth surface.

In some embodiments, a selective barrier can have an average pore size or diameter of no greater than about 10 micrometers and a gas exchange rate that is at least about 5 and no greater than about 10,000 Gurley seconds (a Gurley second or Gurley is a unit describing the number of seconds required for 100 cubic centimeters of gas to pass through 1.0 square inch of a given material at a given pressure differential). Therefore, in addition to allowing gas exchange, the selective barrier can prevent loss of moisture from the enclosed system.

The selective barrier portion of the protective barrier can be composed of any appropriate polymer-based material, such as spunbonded olefin barriers. Spunbonded olefin barriers (very fine polyethylene fibers) with various properties are readily available from DuPont under the brand name Tyvek®. Such materials are particularly advantageous because of their combination of physical properties, i.e., they tend to resist the transmission of liquids such as water yet they have a sufficiently high degree of gas/vapor permeability; they are relatively strong, absorb little or no moisture, are rip-resistant, have a significant degree of elasticity, and are highly flexible. Spunbonded olefin can exceed 20,000 cycles when tested on an MIT flex tester (TAPPI method T-423). In addition, they are inert to most acids, bases and salts although a prolonged exposure to oxidizing substances, such as concentrated nitric acid or sodium persulfate, will cause some loss of strength. Spunbonded olefin barriers have good dimensional stability in that sheet dimensions tend to change less than 0.01% between 0 and 100% relative humidity at constant temperature. Certain products meet the requirements of Title 21 of the United States Code of Federal Regulations (21 CFR 177.1520) for direct food contact applications. They also have excellent mold and mildew resistance; and are of a neutral pH. Unfortunately, however, their UV resistance is not exceptional. That said, at least one to three months of useful outdoor life can usually be expected. Additionally, their UV resistance can be improved with opaque coatings or by including UV inhibitors in the polymer fibers. Additionally, because the spunbonded oelefins produced to date are opaque, the portion of the protective barrier that would comprise such material is preferably not situated and/or so extensive as to compromise the cultivation of the photosynthetic microorganisms.

In particular, spunbonded olefin can be produced in "hard" and "soft" structure types. Type 10, a "hard," area-bonded product, is a smooth, stiff non-directional paper-like form. Types 14 and 16 are "soft," point-bonded products with an embossed pattern, providing a fabric-like flexible substrate. Type 14 styles (or the equivalent thereof) can be used, for example, where barrier, durability, and breathability are required. Type 16 styles are pin perforated with 5-20 mil (0.13-0.51 mm) holes, giving them much higher air and moisture permeability, additional softness, and greater flexibility and drape than Type 14 styles, but at the expense of lower tear strength and barrier properties. Thus, the particular properties of the selective barrier can be customized by selecting one or more types of spunbonded olefin products.

Other examples of selective polymer barriers include, but are not limited to nylon, polysulfone, polytetrafluoroethylene, cellulosic, fiberglass, polyester and polyacrylate membranes and filter material, and combinations thereof.

The entirety of the protective barrier need not be gas permeable to provide for a barrier that is sufficiently selective for the growth of photosynthetic microorganisms. Only a portion of the protective barrier sufficient to allow for adequate gas exchange need be gas permeable. In one embodiment, the selective portion is a panel of the protective barrier (see e.g., FIG. 1). The size and placement of the selective panel in relation to the area of the support surface can be altered to achieve a desired amount of gas exchange for a particular application without unduly hindering the cultivation of the microorganisms. One of skill in the art will recognize that the percentage of the area of the outer barrier composed of the gas permeable selective material will depend on the gas permeability rate of the material. In fact, because the gas permeable portion will still allow the transport of water vapor across it, in various embodiments, the size of the gas permeable portion of the protective barrier is selected so as to allow for sufficient transport of oxygen and carbon dioxide while minimizing the loss of moisture.

Suspension and Conveyance System

Photobioreactors described herein can be configured for large scale production and/or harvesting through, for example, integration into a handling and conveyance system. FIG. 3 shows an above view of an exemplary design of a photobioreactor farm for handling large numbers of photobioreactors in a continuous process. The photobioreactors or cultivation panels (not individually shown) are attached to conveyor systems 8. The conveyor systems 8 move the cultivation panels along their paths. Multiple conveyor systems converge at centrally located inoculation and harvesting centers 9. Thus, the cultivation panels are moved into the inoculation and harvesting centers 9 where they can be processed (e.g., harvested and/or inoculated) and then the panels are moved away from the centers following inoculation and during the period of cultivation of the biomass. The panels are then moved back towards the centers during the latter period of cultivation prior to harvesting, eventually arriving back at the centers with mature biomass for harvest. The cycle is then repeated. Harvested biomass can be transported through a pipeline 10 for further processing. The capacity of the photobioreactor farm can be increased by adding additional conveyor systems or additional inoculation and harvest centers to form large arrays dedicated to biomass production.

Suspension of Photobioreactor

To supply light to photosynthetic microorganisms, a favored embodiment of the photobioreactor is one in which the cultivation support is thin and sheet-like. When oriented horizontally, the efficient utilization of floor space tends to decrease, therefore in certain embodiments of the invention the cultivation support is oriented non-horizontally, preferably substantially vertically, or more preferably vertically. Nevertheless, the cultivation support may be oriented in essentially any manner so long as a sufficient amount of actinic radiation can reach the microorganisms. Thus, when the photobioreactor is of the type where the protective barrier forms a closely associated film or layer around the solid support, a preferred orientation of the entire photobioreactor is vertical, but any orientation is acceptable. To be clear, the aforementioned orientations (e.g., vertical, horizontal, substantially vertical, non-horizontal, etc.) are relative to the floor or ground beneath the cultivation support, assuming that the floor or ground is horizontal.

Various structures, scaffolding, stands, racks, etc. may be used to hold or suspend a cultivation support or an entire photobioreactor in a desired orientation. In particular, the cultivation support and/or the protective barrier can be suspended from, or attached to a rope, line, hook, cable, track, rail, chain, shelf, pole, tube, scaffold, stand, beam or any other such structure capable of suspending the solid cultivation support and/or photobioreactor. Multiple cultivation supports and/or photobioreactors may be suspended from a common structure, like sheets hanging from a clothes line. The cultivation support(s) and/or photobioreactor(s) may be suspended statically, or in a manner that allows for their movement. The position of the holes, loops, hooks, or the like will preferably distribute the weight of the cultivation support and/or photobioreactor substantially evenly.

Suspension of the photobioreactor or cultivation support, especially in a vertical orientation, is space efficient and may provide advantages in handling. However, the bioreactor or cultivation support of the invention need not be suspended. For example, in certain embodiments of the present invention, the cultivation support is sufficiently rigid that if oriented non-horizontally, vertically, or substantially vertically (e.g., by securing or placing its base to/on a surface, in an embodiment in which the support is like a rigid plate, panel, grid, etc.) it can support its own weight and will remain so oriented. In another embodiment, the protective barrier is free standing, such as a greenhouse, and multiple cultivation supports are suspended and/or free-standing within.

Suspension of the photobioreactor and/or cultivation support, especially in a vertical orientation, is space efficient and may provide advantages in handling. However, the bioreactor or cultivation support of the invention need not be suspended. For example, in certain embodiments of the present invention, the cultivation support is sufficiently rigid that if oriented non-horizontally, vertically, or substantially vertically (e.g., by securing or placing its base to/on a surface, in an embodiment in which the support is like a rigid plate, panel, grid, etc.) it can support its own weight and will remain so oriented. In another embodiment, the protective barrier is free standing, such as a greenhouse, and multiple cultivation supports are suspended and/or free-standing within.

Conveyance

Also described herein is a system for conveying photobioreactors, cultivation supports within the protective barrier of a photobioreactor, or some combination thereof from one location to another. The ability to transport a photobioreactor and/or cultivation support can be advantageous for a variety of reasons. For example, it may allow for optimizing their position(s) for receiving light, and for maintaining a desired temperature or gas content. The transportability can be particularly advantageous when multiple photobioreactors or cultivation supports are to be subject to discrete steps, such as inoculating, cultivating, inducing, and/or harvesting, because it is likely to be more efficient to move the photobioreactors or cultivation supports to several assigned locations in a continuous-type process instead of transporting the necessary materials and equipment to stationary photobioreactors or cultivation supports.

Thus, the growing surface, whether the cultivation support alone, or the cultivation support enclosed in a protective barrier, can be conveyed, even after inoculation. One of skill in the art will be familiar with numerous types of conveyor systems frequently used in industrial applications. The conveyance system is not limited to any particular type so long as it is capable of moving one or more photobioreactors or cultivation supports. One skilled in the art will recognize that the type of attachment between the photobioreactor or cultivation support and the conveyor system will vary with the type of conveyance system employed and will be selected to work cooperatively with any mounting points that are part of the cultivation support and/or the protective barrier. Although it is envisioned that the cultivation support(s) or photobioreactor(s) will be conveyed in a mechanized manner powered by one or more motors (e.g., through the action of a chain and gears), it is also possible for them to be conveyed with human effort (e.g., by simply pushing suspended bioreactors that are attached to a rail by a bearing mechanism that slides along the rail).

A conveyor system that suspends photobioreactor(s) and/or cultivation support(s), especially in a vertical orientation, is space efficient and may provide advantages in handling. But the conveyor system need not rely on suspending photobioreactor(s) or cultivation support(s). For example, a photobioreactor may move along on top of the conveyor system, such as by sliding over a roller conveyor. In one embodiment, the conveyor system may move photobioreactors comprising a cultivation support enclosed in a protective barrier. Alternatively, the protective barrier of a photobioreactor may be a large enclosure protecting one or more conveyor systems moving multiple cultivation supports.

Photobioreactor Farm

For large scale applications, it may be impractical to construct a single cultivation support of sufficient size. Thus is provided use of two or several or tens or hundreds or thousands or more cultivation supports to cultivate photosynthetic microorganisms in a photobioreactor "farm." These cultivation supports can all reside within a single protective barrier, thus comprising a single photobioreactor, or multiple cultivation supports may be part of multiple photobioreactors. In either case, it can be beneficial to organize the multiple photobioreactors or cultivation supports within a photobioreactor farm for ease and efficiency of handling and processing. It can also be beneficial to organize their arrangement to maximize the amount of energy captured from a light source such as the sun. Such organization can consist of arranging numerous photobioreactors or cultivation supports in an orderly fashion such as, but not limited to, rows, columns, concentric circles, in grids, radiating outward from a central point, and so forth.

In various embodiments, the farm comprises multiple photobioreactors or cultivation supports suspended from a common structure such as a track, rail, chain, line, or the like. In further embodiments, the structure is part of a conveyor system and the photobioreactors or cultivation supports move along the path of the conveyor system from one location to another.

A photobioreactor farm can comprise one or an arrangement of multiple conveyor systems handling numerous photobioreactors or cultivation supports. Such an arrangement could be scaled up to comprise two or several or tens or hundreds or thousands or more conveyor systems together handling two or several or tens or hundreds or thousands or more photobioreactors or cultivation supports. In addition to the conveyor system(s), a photobioreactor farm can include defined areas, stations, or centers for performing steps such as inoculating, cultivating, inducing, and/or harvesting photosynthetic microorganisms. Such centers can be the location of specialized equipment for performing certain steps. The paths of the conveyor systems can bring the photobioreactors or cultivation supports to such centers where a particular step is performed. The photobioreactor or cultivation support can then be moved along to the next area or center in the sequence. Different photobioreactors or cultivation supports along the conveyor system can reside at different centers along the path and thus be subject to different steps simultaneously. In one embodiment, the path of the conveyor system is a loop. Once a photobioreactor or cultivation support completes one round of steps in the cultivation process, it can repeat the process. Allowing for some units to be damaged or otherwise eventually needing replacement, essentially the same set of photobioreactors or solid cultivation supports can be used repeatedly.

In a further embodiment, cultivation and harvest can occur at the same or nearly the same location. This location is termed an inoculation and harvest center (see e.g., FIG. 3). Inoculation of the photobioreactors and/or solid cultivation supports occurs at the inoculation and harvest center. The conveyor system forms a loop that then transports the photobioreactors or cultivation supports away from the inoculation and harvest center. The photobioreactors or cultivation supports then travel along the path of the conveyor system for an amount of time sufficient for the desired amount of cell growth. The conveyor system then returns the photobioreactors or cultivation supports back to the inoculation and harvest center for harvest. Multiple conveyor systems can share a common inoculation and harvest center from which they radiate out from. If even more capacity is needed, a photobioreactor farm can comprise multiple inoculation and harvest centers handling the photobioreactors or cultivation supports from multiple conveyor systems. Although increased efficiencies may be realized, it is not necessary that the location of inoculation and of harvest be the same or nearly the same location.

Methods of Using a Photobioreactor

Cultivation of Photosynthetic Microorganisms

A solid phase photobioreactor, as described herein, can be used for cultivating photosynthetic microorganisms. Photosynthetic microorganisms that can be grown in the solid phase photobioreactor include, but are not limited to, a naturally photosynthetic microorganism, such as a cyanobacterium, or an engineered photosynthetic microorganism, such as an artificially photosynthetic bacterium. Exemplary microorganisms that are either naturally photosynthetic or can be engineered to be photosynthetic include, but are not limited to, bacteria; fungi; archaea; protists; microscopic plants, such as a green algae; and animals such as plankton, planarian, and amoeba. Examples of naturally occurring photosynthetic microorganisms that can be grown in the bioreactor include, but are not limited to, *Spirulina maximum, Spirulina platensis, Dunaliella salina, Botrycoccus braunii, Chlorella vulgaris, pyrenoidosa, Serenastrum capricomutum, Scenedesmus auadricauda, Porphyridium cruentum, Scenedesmus acutus, Dunaliella* sp., *Scenedesmus obliquus, Anabaenopsis, Aulosira, Cylindrospermum, Synechoccus* sp., *Synechocystis* sp., and/or *Tolypothrix*.

Preferably, the photosynthetic microorganisms grown in the solid phase photobioreactor comprise cyanobacteria. The cyanobacterium grown in the bioreactor can be any photosynthetic microorganism from the phylum Cyanophyta. The cyanobacterium grown in the bioreactor can have a unicellular or colonial (e.g., filaments, sheets, or balls) morphology. Preferably, the cyanobacterium grown in the bioreactor is a unicellular cyanobacterium. Examples of cyanobacteria that can be grown in the bioreactor include, but are not limited to, the genus *Synechocystis, Synechococcus, Thermosynechococcus, Nostoc, Prochlorococcu, Microcystis, Anabaena, Spirulina*, and *Gloeobacter*. Preferably the cyanobacterium grown in the bioreactor is a *Synechocystis* spp. or *Synechococcus* spp. (e.g., *Synechococcus elongatus* PCC 7942 (ATCC 33912) and/or *Synechocystis* spp. PCC 6803 (ATCC 27184)). More preferably, the photosynthetic microorganism grown in the bioreactor is a transgenic photosynthetic microorganism engineered to accumulate a disaccharide, as disclosed herein.

A solid cultivation support of a photobioreactor can be inoculated with a photosynthetic microorganism, along with addition of moisture and other components including, but not limited to, nutrients, salts, buffers, metals, nitrogen, phosphate, sulfur, etc. The photobioreactor can then be releasably sealed with the cultivation support within the protective barrier. The sealed photobioreactor can be placed, for example by suspending it, in a location and manner to allow for control of illumination and temperature. The placement can be static, or the photobioreactor can be moved, such as to ensure maximum exposure to the sun's radiation over the course of a day. The photosynthetic microorganisms can be cultivated for a desired amount of time. One of skill in the art will recognize that the length of time will vary according to the type of microorganism and the density of cell growth desired. For example, for certain strains of cyanobacteria, a cultivation period that is within the range of about four to about seven days can provide a yield of cells that is within the range of about 50 to about 250 grams of dry biomass per liter equivalent. Following a period for cultivation, the releasable seal can be opened and the photosynthetic microorganisms can be harvested.

As used herein, "grams of dry biomass per liter equivalent" is a unit determined by calculating the average depth of the biomass layer (e.g., about 150 microns) growing on the cultivation surface and multiplying that value by the length and the width of the cultivation surface. This calculation provides a volume. The weight of the collected biomass from the cultivation surface can then be correlated to the volume and expressed as "grams of dry biomass per liter equivalent."

Method of Continuous Cultivation

Greater efficiencies can be realized if the process of cultivating photosynthetic microorganisms were to be made continuous, for example, like an assembly line. Instead of requiring the equipment and capacity to handle a large amount of biomass all at once that then sits idle in between batches, a continuous system would require less total capacity, but would utilize that capacity more efficiently through continuous operation. By dividing cultivation into smaller but more numerous components, the components can be organized in a spatially continuous arrangement. Different discrete steps of the overall production process can then occur simultaneously. After a cultivation component is subjected to a process step, the component moves forward in the process while another component replaces it in that step. Therefore, production of the end product would not be limited to the maturation of a large batch, but can occur regularly as individual components complete the assembly line-like process. Further, following the completion of one round of the process, the components can immediately start the process over and do so repeatedly.

More specifically, continuous cultivation relates to methods of using conveyable photobioreactors or cultivation supports for cultivating photosynthetic microorganisms in a continuous manner. Continuous or continuous process is understood as the spatial relationship that can allow the photobioreactors or solid cultivation supports to progress from one step of the cultivation process to another. Alternatively, it is possible for a single large structural support to be utilized in a continuous process. Specifically, the support can be a loop of material (e.g., terry cloth fabric) that is made to travel along a circuit (e.g., like a conveyor belt that is arranged preferably vertically). The end result is that biomass production can be achieved regularly as multiple photobioreactors or solid cultivation supports finish the process sequentially and repeatedly. This type of process presents opportunities in large scale applications for increased efficiencies over producing biomass in large, but infrequent batches.

In a preferred embodiment, the continuous spatial relationship is along the path of a conveyor system. The manner of operation is analogous to an assembly line. Such a conveyor system can operate in a number of ways. For example, the conveyor system can operate without interruption while moving the photobioreactors or cultivation supports from one location to another. In such an embodiment, inoculation, harvesting, and the like occur while the photobioreactors or cultivation supports are in motion. Alternatively, the conveyor system can stop to allow for steps to be performed, and then resume to move the photobioreactors or cultivation supports to the location of the next step. Further, the conveyor system can operate without interruption, and the photobioreactors or cultivation supports can be detached from the movement of the conveyor system for processing, and then reattached to re-enter into the stream of conveyance. One skilled in the art will realize that other permutations of this general theme are also possible.

In one embodiment of a method of continuous cultivation, multiple photobioreactors are inoculated at one location along the conveyor system. The conveyor system then moves the photobioreactors to an area where cultivation of the photosynthetic microorganisms occurs. During this portion of conveyance, the photobioreactors can be positioned to allow for optimal illumination to promote growth and photosynthesis. Next, the photobioreactors would arrive at a location where the photosynthetic microorganisms can be harvested. The photobioreactors can then return along the path of the conveyor system to the point of inoculation to begin the process again. To improve efficiency, the time between when the photobioreactors leave the location of inoculation and arrive at the location of harvest can be made to coincide with the time it takes for the desired amount of growth of the photosynthetic microorganisms to occur. The steps of the process are not limited to inoculation, cultivation, and harvest; additional steps can include inducement of the cells to synthesize a desired product or sterilization. Although the above embodiment describes a system of conveyable photobioreactors, it will be appreciated that the same type of continuous cultivation can be practiced within a single protective barrier to convey and process multiple solid cultivation supports.

Method of Producing Fermentable Sugars

One technology that can benefit from the ability to more efficiently grow photosynthetic microorganisms is the production of biomass for alternative fuels such as ethanol or biodiesel. Relative to plants currently grown to produce biomass such as corn, sugarcane, soybeans, canola, jatropha, and so forth, photosynthetic microorganisms, such as cyanobacteria, produce biomass at a much faster rate, which may lead to much greater productivity. In addition, direct production of disaccharides by microorganisms avoids much of the extensive energy-intensive pre-processing of using plant biomass to produce fermentable sugar. Further, the use of phototrophic microorganisms instead of plants can lead to higher yields of fermentable sugars without soil depletion, erosion, and diversion of the food supply. Relative to other microorganisms, preference is given to phototrophic microorganisms because their sources of carbon ($CO_2$) and energy (light) can be supplied from the environment, making them far less expensive to cultivate. In addition, phototrophic microorganisms can be utilized to consume carbon emissions from industrial processes, thus providing further benefits to the environment.

One obstacle to producing high quantities of fermentable sugars from photosynthetic microorganisms is that they generally consume produced carbohydrates rather than accumulating them. While some sugars, such as sucrose or trehalose, are not utilized as a primary carbon source by photosynthetic microorganisms, there are mechanisms for slow assimilation. In spite of reprocessing mechanisms, such material can accumulate without being metabolized. If the organism is engineered appropriately, the assimilation mechanism can be inactivated, which enables high yields of sugars to be produced.

Provided herein is a method for producing fermentable sugars, especially disaccharide sugars, by photosynthetic microorganisms. Examples of fermentable sugars include, but are not limited to, sucrose, trehalose, glucosylglycerol, and mannosylfructose. Preferably, the fermentable sugar is sucrose or trehalose. The method can be adapted to occur in a continuous manner to improve the cost effectiveness of production.

Various embodiments of this method can be practiced using a photosynthetic microorganism capable of synthesizing fermentable sugars. Some embodiments harness and control the natural phenomena of osmo- and matric water protection for the generation of fermentation feedstocks. In one embodiment, synthesis of fermentable sugars is inducible. In another embodiment, synthesis of fermentable sugars can be modified by genetic manipulation to be produced constitutively.

Fermentable sugar-producing photosynthetic microorganisms are preferably cyanobacteria. In some embodiments, a cyanobacterium accumulates a disaccharide according to inducible endogenous pathways. In some embodiments, a transgenic cyanobacterium accumulates a disaccharide according to engineered exogenous pathways. Both endogenous and exogenous pathways are discussed in further detail above.

Preferably, the transgenic photosynthetic microorganisms are one or more of those discussed above.

Two non-limiting examples of strains of cyanobacteria capable of accumulating a disaccharide are *Synechococcus elongatus* PCC 7942 and *Synechocystis* sp. PCC 6803. Naturally occurring *Synechococcus elongatus* PCC 7942 synthesizes sucrose upon exposure to salt concentrations of up to about 700 mM, its tolerance limit. When glucosylglycerol biosynthesis is blocked by deletion of the agp gene, *Synechocystis* sp. PCC 6803 produces sucrose as its osmoprotectant upon exposure to salt concentrations up to its tolerance limit which may approach 900 mM. In some embodiments, salt induction can be accomplished by introducing aerosolized saline solution applied directly to the cultivation surface. One advantage of this process is application can be controllably introduced along the growing surface depending on growth time of the cultivar thereby balancing accumulation of biomass and production of a disaccharide such as sucrose.

For producing fermentable sugars, the photosynthetic microorganisms can be cultured and grown on a solid medium or in a liquid or gel medium. Culture and growth of photosynthetic microorganisms are well known in the art. Except as otherwise noted herein, therefore, culture and growth of photosynthetic microorganisms can be carried out in accordance with such known processes. For example, a transgenic cyanobacteria engineered to accumulate a disaccharide can be cultured and grown in a liquid medium. The accumulated sugar can be isolated from such liquid medium if excreted from the cell. The accumulated sugar can be isolated from photosynthetic microorganisms harvested from the liquid medium. In one embodiment, a transgenic cyanobacteria engineered to accumulate trehalose, as discussed above, is cultured and grown in a liquid medium. Trehalose secreted from the transgenic cyanobacteria can be isolated directly from the liquid medium. In one embodiment, a transgenic cyanobacteria engineered to accumulate sucrose, as discussed above, is cultured and grown in a liquid medium. Sucrose can be isolated directly from engineered cyanobactria harvested from the liquid medium. In one embodiment, a transgenic cyanobacteria engineered to accumulate and secrete sucrose, as discussed above, is cultured and grown in a liquid medium. Sucrose secreted from the transgenic cyanobacteria can be isolated directly from the liquid medium.

Preferably, photosynthetic microorganisms are cultivated to a relatively high cell density of at least about 50 grams of dry biomass per liter equivalent prior to induction. Such relatively high cell densities can be achieved using a solid phase photobioreactor, as described herein. Disaccharide (e.g., sucrose) production can then be initiated/induced by treating the accumulated biomass with defined concentrations of suitable salt compounds effective at altering the activity of water in the culture media as measured by solution conductivity. In a further preferred embodiment, sodium chloride is the salt used. Following an appropriate response time period (e.g., at least about 1 hour to no greater than about 48 hours), the sucrose laden cells can be harvested and processed to isolate and recover the sucrose produced. Typically, an appropriate response period is within the range of at least about 5 hours to no greater than about 24 hours. More typically, the appropriate response period is within the range of at least about 10 hours to no greater than about 20 hours.

In one embodiment, the majority of disaccharide (e.g., sucrose, trehalose, glucosylglycerol, mannosylfructose) synthesized accumulates within the cells. In another embodiment, the disaccharide is secreted by the cells which can then be recovered from the photobioreactor. Regardless of whether the disaccharide is within the cells or secreted, the disaccharide can be obtained using any appropriate harvesting process including, but not limited to, an aqueous spray wash applied to the cultivation surface. The wash comprising cells and/or disaccharide can be collected and processed to isolate and recover the disaccharide.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Solid Phase Photobioreactor

A static prototype device was constructed composed of a 2 mil polyethylene barrier layer with a Ziploc® resealable closure. A 60 sq. cm breathable panel was incorporated into one surface, and a 225 sq. cm woven cotton fabric cultivation support surface was placed inside. The device was sterilized by treatment with 70% volume aqueous ethanol followed by drying of the device at 50° C. with a stream of sterile filtered air. 30 ml of sterile BG-11 culture media was absorbed onto the cultivation support followed by inoculation of the growing surface with a pre-culture of *Synechococcus elongates* PCC 7942, using an aerosol applicator. The preculture was grown in BG-11 media at 26° C. for 2 days prior to inoculation. The photobioreactor was placed in an incubation chamber maintained at 33° C. and illuminated at 300 microeinsteins with cool white fluorescent lamps. After 2 days, the reactor displayed active growth of organisms and was allowed to continue growth for an additional 2 days whereupon the reactor was removed from the incubator and the growth surface washed with deionized water. The water was removed by evaporation to afford 254 mg dry weight biomass.

Example 2

Production of Sucrose by Photosynthetic Microorganisms

The following is a prophetic example to illustrate a method for production of sucrose by photosynthetic microorganism in combination with a photobioreactor. At least one photobioreactor, for example a photobioreactor of the current invention such as described in Example 1 or Example 3, may be run for approximately 4-7 days with either *Synechocystis* sp. PCC6803, or engineered *Synechocystis* sp. at a temperature range of between about 15 and 40° C., under illumination of between about 60 and 300 microeinsteins, and carbon dioxide concentration of between about 0.2 and 15 volume %. Following the initial cultivation period the growth surface may be treated with an aqueous salt solution in the concentration range of between about 0.01 and 1.5 M, more preferably between about 0.2 and 0.9 M, using an aerosol spray. The cultivation may be allowed to continue for approximately an additional one to two days to allow sucrose production. The growth surface may then be harvested by washing the surface with deionized water. In a further embodiment the wash water is sterile fresh cultivation media and the washing stringency is such that between about 70 and 90% of the cell mass is collected. The biomass remaining on the cultivation support may then be allowed to continue growth as a subsequent cycle. It is anticipated that the yield for these cultivations should be between about 200 and 600 mg dry biomass depending on the growth surface material and organism employed.

Example 3

Solid Cultivation Support Coated with an Absorbent Polymer

The growth surface of a static photobioreactor of the type described in Example 1 was prepared by dip coating the sterile dry surface of the material with a heated solution of sterile 1.5 weight percent agar dispersed in BG-11 culture media. The coated growth surface was allowed to cool and harden upon which the surface was inserted into a sterilized protective barrier to form a photobioreactor device and inoculated with *Synechococcus* sp. grown in preculture as described in Example 1. Cultivation and harvesting were performed essentially as described in Example 1.

Example 4

ASF Gene Target

Biosynthesis of sucrose in cyanobacteria was explored through modulation of sucrose phosphate synthase (sps) and sucrose phosphate phosphatase (spp) activities. Such activities are already present in many cyanobacteria for acclimation to osmotic and matric water stress (see e.g., Lunn, J. E. 2002. Plant Physiol 128, 1490-1500).

Lunn, J. E. (2002. Plant Physiol 128, 1490-1500) analyzed the genomic organization of the sps and spp genes of several organisms, including *Synechocystis* spp. PCC 6803 and *Synechococcus elongatus* PCC 7942. Lunn proposed that the sucrose phosphate synthase (SPS) of *Synechocystis* spp. PCC 6803 (SEQ ID NO: 3) has an inactive sucrose phosphate phosphatase (SPP-like) domain and a distinct SPP activity. The SPP-like domain has a high level of identity with the spp, but is missing many of the conserved active site residues of the haloacid dehalogenase (HAD) superfamily. While no work has yet been done on *Synechococcus elongatus* PCC 7942, Lunn proposed that both activities are contained within a single enzyme. An alignment of these enzymes is shown in FIG. 5.

Searches of the *Synechococcus elongatus* PCC 7942 genome did not reveal a distinct sps gene elsewhere on the chromosome. The *Synechococcus elongatus* PCC 7942 enzyme (SEQ ID NO: 2) was utilized so as to avoid the necessity of multiple gene expression. While the gene from PCC 7942 has been termed sps, because it is a single enzyme fusion bearing both SPS and SPP activities, it was termed asf for active SPS/SPP fusion (SEQ ID NO: 1) (see below for further information on the possible expression of a distinct SPP enzyme.)

There are two approaches to expressing the *Synechococcus elongatus* PCC 7942 asf gene product (SEQ ID NO: 2).

The first approach is a plasmid-based expression system built upon the broad host range vector pMMB67EH (Furste, J. P., Pansegrau, W., Frank, R., Blocker, H., Scholz, P., Bagdasarian, M. and Lanka, E. 1986. Gene 48, 119-131). Plasmid pMMB67EH is a derivative of RSF1010, which replicates in most Gram-negative and even some Gram-positive organisms, thus allowing for plasmid-based analysis of sucrose production in *E. coli*, *Synechocystis* spp. PCC 6803, *Synechococcus elongatus* PCC 7942 and a variety of other cyanobacteria (Kreps, S., Ferino, F., Mosrin, C., Gerits, J., Mergeay, M. and Thuriaux, P. 1990. Mol Gen Genet. 221, 129-133; Marraccini, P., Bulteau, S., Cassier-Chauvat, C., Mermet-Bouvier, P. and Chauvat, F. 1993. Plant Molecular Biology 23, 905-909; Gormley, E. P. and Davies, J. 1991. J Bacteriology 173, 6705-8).

The second approach is stable integration into the chromosome of *Synechocystis* spp. PCC 6803 and *Synechococcus elongatus* PCC 7942 at the upp (uracil phosphoribosyltransferase) locus. The upp locus was chosen for reasons described below.

Example 5

Plasmid-Based Expression

Figure 6:
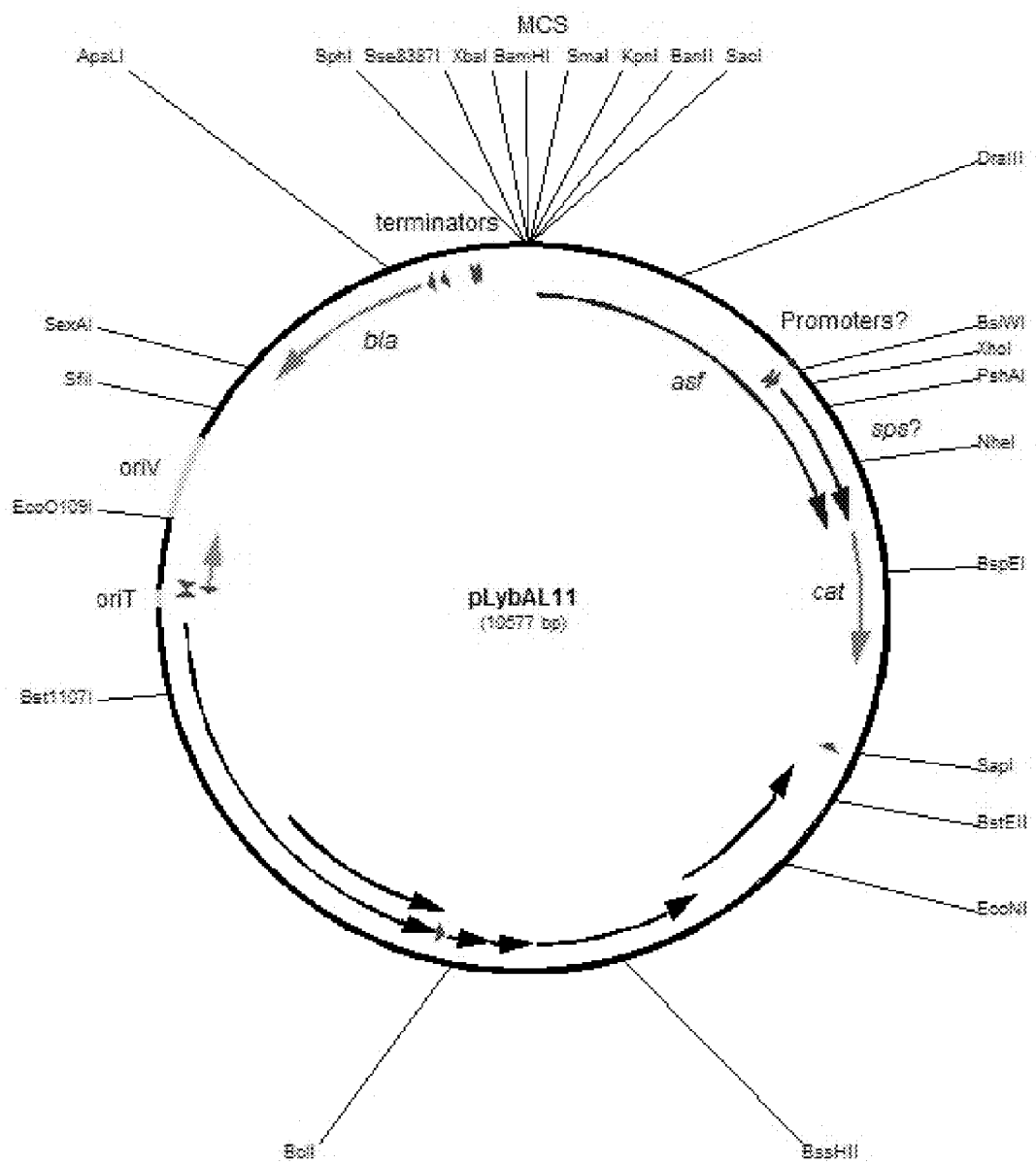
FIG. 6 is schematic depiction of pLybAL11. pLybAL11 allows construction of libraries of cyanobacterial DNA and selection for promoter sequences. The promoterless asf gene is behind bidirectional terminators, separated by a multiple cloning site (MCS). oriV allows for plasmid replication in most Gram-negative organisms. oriT allows for conjugal transfer of the plasmid from *E. coli* to a chosen cyanobacterium (or other organism) with the assistance of the pRK2013 helper plasmid. The β-lactamase gene (bla) is present for selection in *E. coli*. DNA libraries can be constructed in *E. coli* by cloning cyanobacterial genomic DNA into the MCS. The plasmid library can then be transferred to cyanobacteria by conjugation or direct transformation. Active promoters can then be isolated by selection for resistance to chloramphenicol through expression of the chloramphenicol acetyltransferase gene (cat). The strength of the promoters can be assessed by both assay for chloramphenicol acetyltransferase activity and direct examination of sucrose production. Further details regarding methodology are provided in Example 5.
Figure 7:
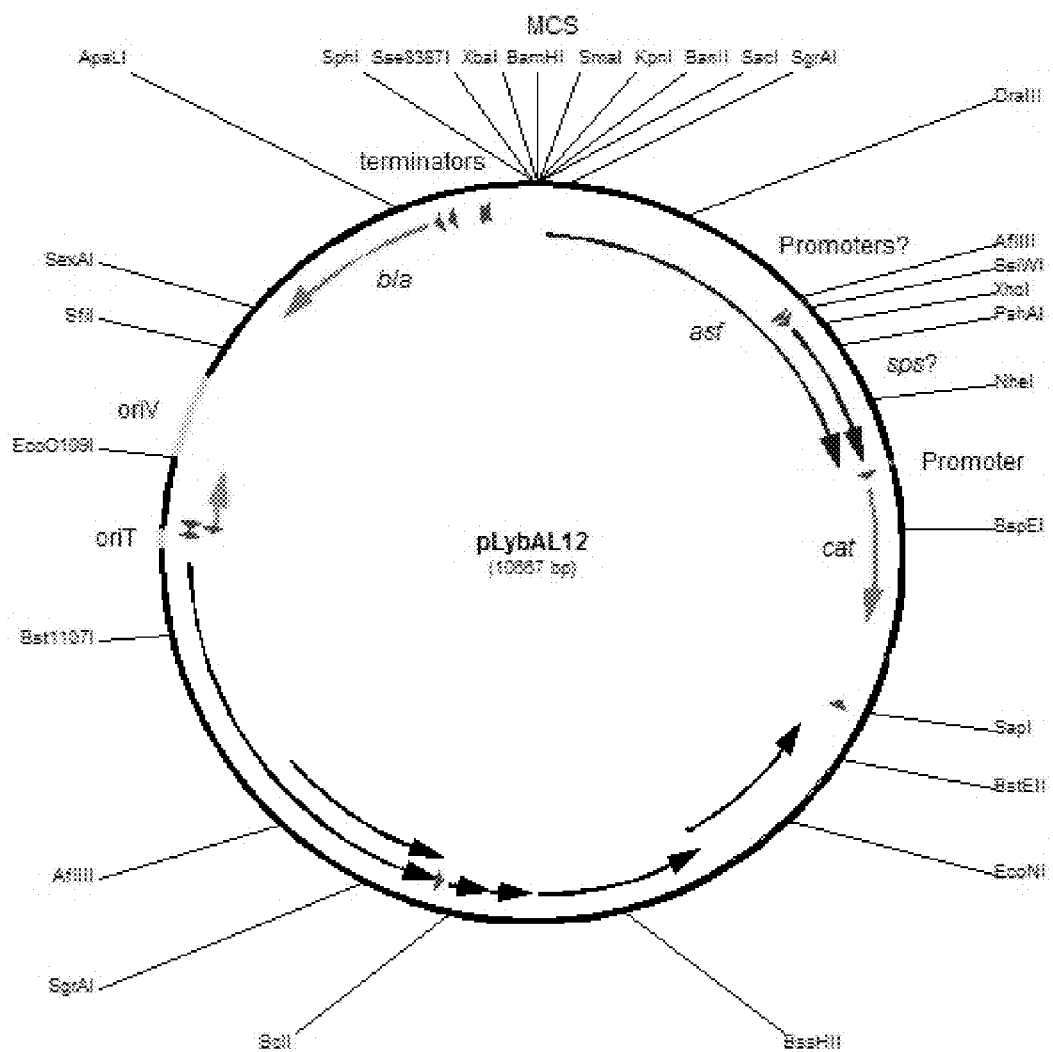
FIG. 7 is schematic depiction of pLybAL12. pLybAL12 allows analysis of the capacity of preselected promoters to drive asf expression. The only difference between pLybAL12 and pLybAL11 is the presence of an active promoter in front of the chloramphenicol acetyltransferase gene (cat). Specific DNA sequences isolated from cyanobacterial chromosomal DNA amplified by PCR can be cloned into the MCS. Both chloramphenicol and ampicillin can be used for selection in *E. coli*. The plasmid library can then be transferred to cyanobacteria by conjugation or direct transformation. Plasmid bearing cyanobacteria can then be isolated by selection for resistance to chloramphenicol through expression of the chloramphenicol acetyltransferase gene (cat). The strength of the promoters can be assessed by both assay for chloramphenicol acetyltransferase activity and direct examination of sucrose production. Further details regarding methodology are provided in Example 5.

Two plasmids were designed for plasmid-based expression of the asf gene product, pLybAL11 (see e.g., FIG. 6; SEQ ID NO: 19) and pLybAL12 (see e.g., FIG. 7; SEQ ID NO: 20). Plasmid pLybAL12 was constructed for expression from predetermined promoters and pLybAL11 was constructed for expression from promoters selected at random.

Both plasmids were constructed as follows. The asf gene from *Synechococcus elongatus* PCC 7942 was amplified by PCR with the oligonucleotides 5'-AGACTACAATTG-GGGCGTTTTCTGTGAG-3' (the MfeI restriction endonuclease site is nucleotide positions 7-12) (SEQ ID NO: 7) and 5'-CTTACGTGCCGATCAACGTCTCATTCTGAAAAGG-TTAAGCGATCGCCTC-3' (SEQ ID NO: 8) using whole cells as the template, yielding the product of SEQ ID NO: 1.

The gene encoding for chloramphenicol acetylransferase (cat), both with and without the upstream promoter, was amplified from pBeloBAC11 (GENBANK™ Accession U51113).

The cat gene lacking the promoter was amplified from pBeloBAC11 by PCR with the oligonucleotides 5'-TTA-TCGCGATCGTCAGGAGCTAAGGAAGCTAAAATGG-AG-3' (SEQ ID NO: 9) and 5'-CGACCAATT-CACGTGTTTGACAGCTTATC-3' (SEQ ID NO: 10) (the PvuI and PmlI restriction endonuclease sites are at nucleotide positions 4-9 and 10-15, respectively) to yield the product of SEQ ID NO: 11.

The cat gene bearing the promoter was amplified from pBeloBAC11 by PCR with the oligonucleotides 5'-TTTTGG-CGATCGTGAGACGTTGATCGGCACGTAAG-3' (SEQ ID NO: 12) and 5'-CGACCAATTCACGTGTTTGAC-AGCTTATC-3' (SEQ ID NO: 13) (the PvuI and PmlI restriction endonuclease sites are at nucleotide positions 7-12 and 10-15, respectively) to yield the product of SEQ ID NO: 14.

The PCR products bearing the cat gene were digested with PvuI and the ends blunted with T4 DNA polymerase. They were then individually ligated to the asf PCR product. The resultant products were purified by agarose gel electrophoresis, digested with MfeI and PmlI and then ligated with T4 DNA ligase to the 6.6 Kbp product of pMMB67EH digested with EcoRI and HpaI. The ligation products were transformed into chemically competent NEB5α (New England Biolabs; Ipswich, Mass.) and selected for at 37° C. on LB agar supplemented with 100 µg/ml ampicillin. Selected candidates were grown at 37° C. in LB supplemented with 100 µg/ml ampicillin for miniprep, analyzed by restriction endonuclease digest and then verified by sequence analysis with the oligonucleotides 5'-GCTTCTGCGTTCTGATTTAATCTGTATCAG-3' (SEQ ID NO: 15), 5'-TATCACTTATTCAGGCGTAGCAACCAG-3' (SEQ ID NO: 16), 5'-GTCGTTAGTGACATCGACAACACACTG-3' (SEQ ID NO: 17), and 5'-GATCGCGATACTGATCGAGATAGGTC-3' (SEQ ID NO: 18). Candidate number 5 of pLybAL11 (pLybAL11-5) (SEQ ID NO: 19) and Candidate number 1 of pLybAL12 (pLybAL12-1) (SEQ ID NO: 20) were chosen for further study.

Based upon plasmid yield during minipreps, it appears that the copy number of these plasmids is greatly reduced when propagated in the *E. coli* strain NEB Turbo (New England Biolabs; Ipswich, Mass.), suggesting the importance in choice of host strain for these plasmids.

Example 6

Promoter Insertion

Six promoters were chosen for insertion into pLybAL12-5. The presumed promoter for *Synechocystis* spp. PCC 6803 carB encoding carbamoyl phosphate synthase, which is likely to be immediately upstream of the gene pyrR where they would be co-transcribed as an operon, was chosen because it is likely to be strong due to its role in both pyrimidine and arginine biosynthesis. The nitrate reductase (nirA) promoters from both *Synechocystis* spp. PCC 6803 (Aichi, M., Takatani, N. and Omata, T. 2001. J. Bacteriol. 183, 5840-5847) and *Synechococcus elongatus* PCC 7942 (Maeda, S-I. et al. 1998. J Bacteriol 180, 4080-4088) were chosen for their ability to be regulated by the source of nitrogen. The strong light-phase promoter for the photosystem II D1 protein (psbAII) from *Synechococcus elongatus* PCC 7942 (Golden, S. S., Brusslan, J. and Haselkorn, R. 1986. EMBO Journal 5, 2789-2798) and two dark-phase promoters from *Synechocystis* spp. PCC 6803 [dnaK (Aoki, S., Kondo, T. and Ishiura M. 1995. J Bacteriol 177, 5606-11) and kaiA (Kucho, K-I. et al. 2005. J Bacteriol 187, 2190-2199)] were also selected as regulated cyanobacterial derived promoters. Lastly, the $\lambda_{PR}$ temperature-regulated promoter, which has been shown to be active in cyanobacteria, was chosen (Ferino, F. and Chauvat, F. 1989. Gene 84, 257-66; Mermet-Bouvier, P. and Chauvat, F. 1994. Current Microbiology 28, 145-148).

The following oligonucleotides were used to amplify the promoters by PCR using whole cells as the template, yielding the products shown. The restriction endonuclease sites incorporated for cloning are provided in the sequence.

*Synechocystis* spp. PCC 6803 pyrR (SphI/KpnI) (SEQ ID NO: 23) was amplified from whole cells by PCR with the oligonucleotides 5'-CGGTGTGCATGCCGTTATTGATGGAATG-3' (SEQ ID NO: 21) and 5'-TCACTAGGTACCTAAATTACCTGGGAAGCCAG-3' (SEQ ID NO: 22), having restriction endonuclease sites at nucleotide positions 7-12 for both.

*Synechocystis* spp. PCC 6803 nirA (SphI/KpnI) (SEQ ID NO: 26) was amplified from whole cells by PCR with the oligonucleotides 5'-CCCAAGGCATGCAGGAAAACAAGCTCAGAATGCTG-3' (SEQ ID NO: 24) and 5'-TTTATTGGTACCAACGCTTCAAGCCAGATAACAGTAGAGATC-3' (SEQ ID NO: 25), having restriction endonuclease sites at nucleotide positions 7-12 for both.

*Synechococcus elongatus* PCC 7942 psbAII (SphI/KpnI) (SEQ ID NO: 29) was amplified from whole cells by PCR with the oligonucleotides 5'-ATCTTTGCGTTCCGTGACGGCTACTG-3' (SEQ ID NO: 27) and 5'-GCAGATGGTACCGGTCAGCAGAGTG-3' (having restriction endonuclease sites at nucleotide positions 7-12) (SEQ ID NO: 28).

*Synechococcus elongatus* PCC 7942 nirA (SphI/KpnI) (SEQ ID NO: 32) was amplified from whole cells by PCR with the oligonucleotides 5'-CAGCCAGCATGCATAAATTTCTGTTTTGACCAAACCATCC-3' (SEQ ID NO: 30) and 5'-GTGGCTGGTACCATGGATTCATCTGCCTACAAAG-3' (SEQ ID NO: 31), having restriction endonuclease sites at nucleotide positions 7-12 for both.

$\lambda_{PR}$ (XbaI/KpnI) (SEQ ID NO: 35) was amplified from whole cells by PCR with the oligonucleotides 5'-GTGCATTCTAGATGGCTACGAGGGCAGACAGTAAG-3' (SEQ ID NO: 33) and 5'-TTCTGTGGTACCATATGGATCCTCCTTCTTAAGATGCAACCATTATCACC-3' (SEQ ID NO: 34), having restriction endonuclease sites at nucleotide positions 7-12 for both.

*Synechocystis* spp. PCC 6803 dnaK (SphI/KpnI) (SEQ ID NO: 38) was amplified from whole cells by PCR with the oligonucleotides 5'-GCCCCAGCATGCACCAGTAAACATAAATCTC-3' (SEQ ID NO: 36) and 5'-ATTGGTGGTACCGAGGTCAATCCCAACAAC-3' (SEQ ID NO: 37), having restriction endonuclease sites at nucleotide positions 7-12 for both.

*Synechocystis* spp. PCC 6803 kiaA (SphI/KpnI) (SEQ ID NO: 41) was amplified from whole cells by PCR with the oligonucleotides 5'-GCCAGAGCATGCAAAGCTCACTAACTGG-3' (SEQ ID NO: 39) and 5'-GGAAAAGGTACCTGAGTCTATGGGCAACGTG-3' (SEQ ID NO: 40), having restriction endonuclease sites at nucleotide positions 7-12 for both.

After amplification, the PCR products were digested with the restriction endonucleases shown above, gel purified, and ligated into similarly digested pLybAL12-1 to yield plasmids pLybAL15 (SEQ ID NO: 44), pLybAL16 (SEQ ID NO: 45), pLybAL17 (SEQ ID NO: 46), pLybAL18 (SEQ ID NO: 47), pLybAL19 (SEQ ID NO: 48), pLybAL21 (SEQ ID NO: 49), and pLybAL21 (SEQ ID NO: 50), respectively. The ligation products were transformed into electrocompetent NEB5α (New England Biolabs; Ipswich, Mass.) and selected for at 30° C. on LB agar supplemented with 100 µg/ml ampicillin, 34 µg/ml chloramphenicol, and 5% sucrose. Selected candidates were grown at 30° C. in LB supplemented with 100 µg/ml ampicillin, 34 µg/ml chloramphenicol and 5% sucrose for miniprep, analyzed by restriction endonuclease digest, and then verified by sequence analysis with the oligonucleotides 5'-GCTTCTGCGTTCTGATTTAATCTGTATCAG-3" (SEQ ID NO: 42) and 5'-ATGGGTCTGAATGTGCAGAATGTAGAG-3' (SEQ ID NO: 43). Candidates 6 and 7 (pLybAL15-6 and pLybAL15-7), 2 (pLybAL16-2), 4 and 5 (pLybAL17-4 and pLybAL17-5), 1 and 2 (pLybAL18-1 and pLybAL18-2), 1 and 2 (pLybAL19-1 and pLybAL19-2), 3 and 5 (pLybAL21-3 and pLybAL21-5) and 4 and 8 (pLybAL22-4 and pLybAL22-8) were chosen for plasmids pLybAL15 (SEQ ID NO: 44), pLybAL16 (SEQ ID NO: 45), pLybAL17 (SEQ ID NO: 46), pLybAL18 (SEQ ID NO: 47), pLybAL19 (SEQ ID NO: 48), pLybAL21 (SEQ ID NO: 49), and pLybAL21 (SEQ ID NO: 50), respectively.

Selection and growth of these plasmids on LB supplemented with sucrose and both antibiotics was essential to obtaining clones. Selection was originally conducted on LB supplemented with ampicillin alone, but plasmids containing a promoter could not be isolated. Isolates were either re-ligation of the vector alone or of varying size and lacking the ability to be propagated in the presence chloramphenicol. It is thought that internal sucrose was being produced, creating an osmotic shock for the cells that leads to deletions preventing sucrose production. Subsequent experiments indicated that, once isolated, the plasmids may be stable in the absence of sucrose, possibly through the eventual induction of osmotic stress machinery and/or sucrose consumption enzymes.

Example 7

Transformation of Synechocystis and Synechococcus

The promoter-containing plasmids, pLybAL15 (SEQ ID NO: 44), pLybAL16 (SEQ ID NO: 45), pLybAL17 (SEQ ID NO: 46), pLybAL18 (SEQ ID NO: 47), pLybAL19 (SEQ ID NO: 48), pLybAL21 (SEQ ID NO: 49), and pLybAL21 (SEQ ID NO: 50), as well as the promoterless pLybAL12-1 vector (SEQ ID NO: 20) (see Examples 5-6), were placed into both Synechocystis spp. PCC 6803 and Synechococcus elongatus PCC 7942 by triparental conjugation, performed consistent with Elhai, J. and Wolk, C. P. 1988. Methods in Enzymology 167, 747-754, unless indicated otherwise.

Overnight cultures of the cargo strains (NEB5α bearing the plasmids to be transferred), as well as an overnight culture of HB101 bearing the helper plasmid pRK2013 (ATCC 37159) grown at 30° C. were pelleted by centrifugation, washed twice with LB and then resuspended in LB in one-tenth the original volume. Each cyanobacterium was grown at 30° C. in BG11-A, which is the same as BG11 except the trace elements have been replaced with Nitsch's trace elements (Nitsch, J. P. and Nitsch, C. 1956. American Journal of Botany 43, 839-851) under constant illumination to an $OD_{730}$ of approximately 0.5. The cells were pelleted by centrifugation, washed twice with BG11-A, and resuspended in BG11-A with a 7.5-fold increase in concentration. A series of 10-fold dilutions of the cyanobacteria in BG11-A were prepared down to $10^{-5}$. At each dilution, 100 µl of the cyanobacterium was combined with 50 µl each of the cargo and helper strains of E. coli. 150 µl of each mixture was then plated onto BG11-A agar (1.5%) plates supplemented with 5% LB. The plates were incubated at 26-28° C. under constant illumination for 16 to 24 hours. The agar (app. 30 ml) on each plate was lifted and 300 µl of a 100× chloramphenicol solution were added. The final concentration of chloramphenicol was 25 µg/ml for Synechocystis spp. PCC 6803 and 7.5 µg/ml for Synechococcus elongatus PCC 7942. Incubation continued for 8-12 days. Individual colonies of transconjugants were purified away from contaminating E. coli by restreaking onto BG11-A supplemented with the appropriate amount of chloramphenicol to, again, obtain isolated colonies.

Example 8

Promoter Library in PLybAL11-5

Figure 8:
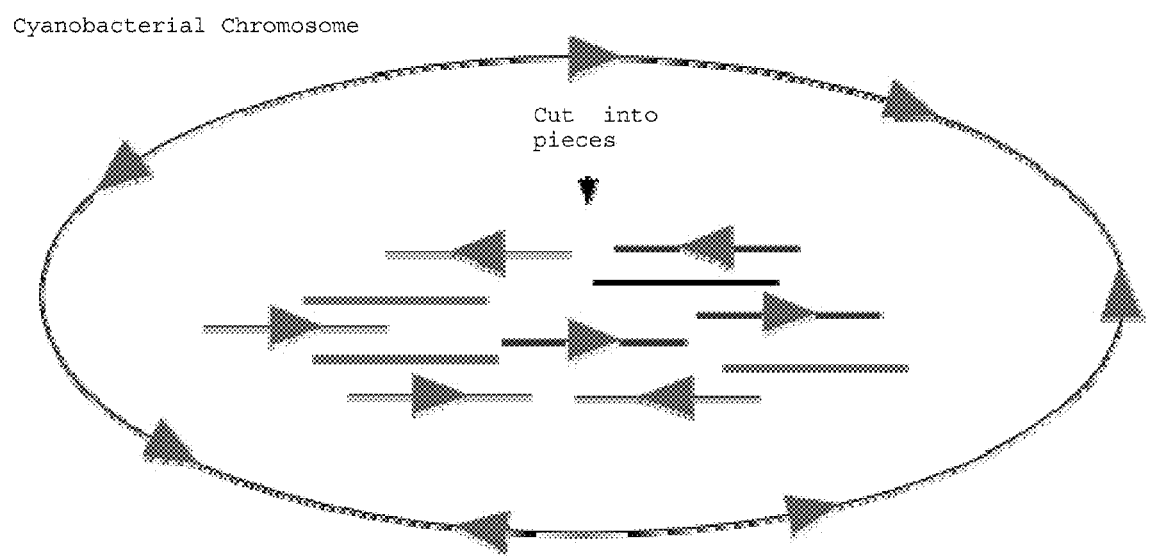
FIG. 8 is a cartoon depicting construction of a cyanobacterial promoter library. Further details regarding methodology are provided in Example 8.

The following example describes construction of a library of cyanobacterial DNA for promoter selection using pLybAL11-5 (SEQ ID NO: 19) (see Example 5). A modified, scaled up version of the chromosomal DNA isolation protocol of Wilson, K. (1997. Preparation of Genomic DNA from Bacteria. In Current Protocols in Molecular Biology. John Wiley and Sons Vol. 1, pp. 2.4.1-2.4.5) was employed, where the primary differences were much longer incubation times and the replacement of SDS with Sarkosyl. The DNA isolated was of sufficient quality for partial Sau3AI digest for insertion into the BamHI site of pLybAL11-5. As shown in FIG. 8, some of the fragments would have promoters and others would not.

During the process of library construction, a possible promoter within the asf gene was discovered. To function as a promoter cloning vector, plasmid pLybAL11-5 (SEQ ID NO: 19) is supposed to only be resistant to chloramphenicol when a promoter has been inserted in front of the asf gene, as the marker lacks its normal promoter and the promoter upstream of asf was not included. Once constructed, however, the chloramphenicol resistance conferred by this plasmid was examined in E. coli. When NEB5α bearing pLybAL11-5 was cultured on LB agar (1.5%) supplemented with 34 µg/ml chloramphenicol at 37° C., growth was observed. When cultured in liquid LB medium supplemented with 34 µg/ml chloramphenicol, however, little-to-no growth was observed. NEB5α bearing pLybAL12-1 (SEQ ID NO: 20) grows in the presence of chloramphenicol on both solid and in liquid LB medium.

Figure 9:
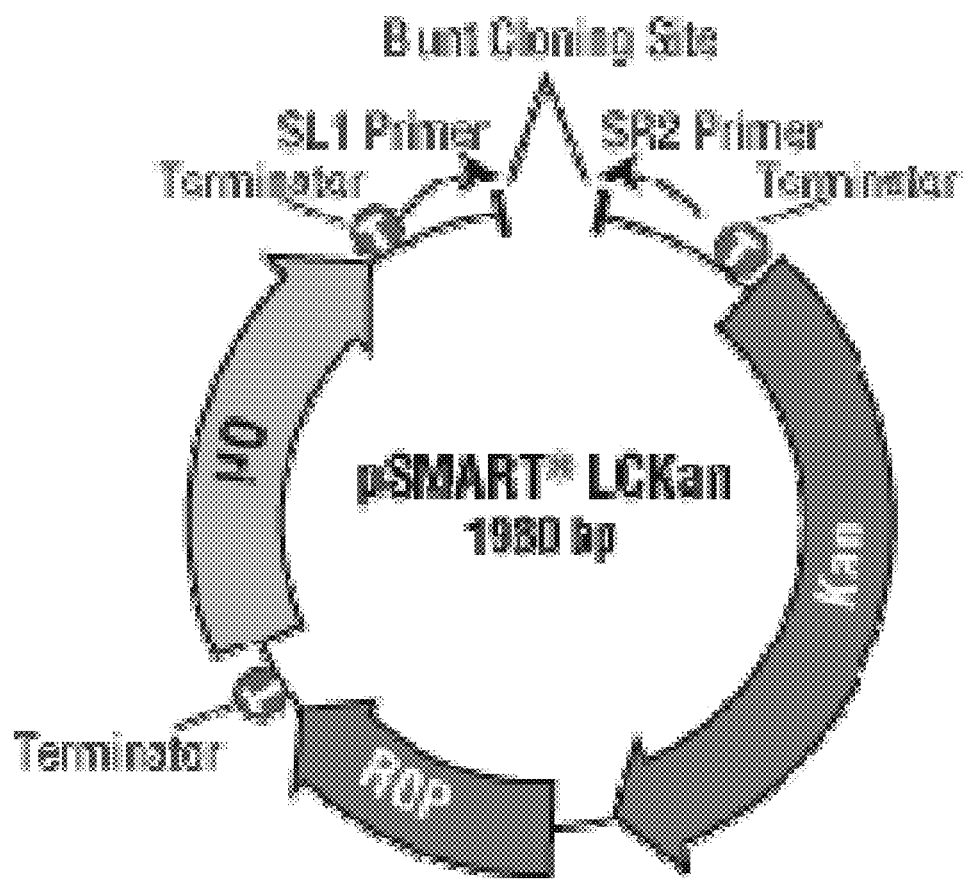
FIG. 9 is a schematic diagram depicting pSMART-LCKan. Further details regarding methodology are provided in Example 8.

To verify there was no missed promoter upstream of the asf gene but downstream of the transcription terminators, the insert placed into pMMB67EH to make pLybAL11 was cloned into Lucigen Corp.'s (Middleton, Wis.) pSMART-LCKan blunt-end cloning vector using Lucigen's CloneSmart kit with the Lucigen strain of E. coli (E. coli 10G) competent cells (see e.g., FIG. 9). Because it was blunt-ended cloning, the inserts could ligate to the plasmid in either direction to create pLybAL13f (SEQ ID NO: 51) and pLyAL13r (SEQ ID NO: 52). This vector is specifically designed to eliminate transcription read through from the vector by surrounding the cloning site with terminators. As a control, the insert used to construct pLybAL12 was also placed into this vector, creating pLybAL14f (SEQ ID NO: 53) and pLybAL14r (SEQ ID NO: 54). The plasmids looked to be the appropriate size on an agarose gel but inserts were not verified by DNA sequencing to confirm the integrity of the clones. Similar results, however, were seen for E. coli 10G bearing pLybAL13 and pLybAL14 (with the cloned DNA ligated in either direction f or r) as were seen for NEB5α bearing pLybAL11(SEQ ID NO: 19) and pLybAL12 (SEQ ID NO: 20), respectively. This indicates that the activity of this promoter is weak in E. coli.

Many E. coli promoters do not function in cyanobacteria, and vice versa. It is possible that this promoter activity would not be observed in Synechocystis spp. PCC 6803 or Synechococcus elongatus PCC 7942. To check this, pLybAL11-5 (SEQ ID NO: 19) was inserted into both organisms by conjugation, as described above. On BG11-A agar (1.5%) supplemented with chloramphenicol (25 µg/ml and 7.5 µg/ml for Synechocystis spp. PCC 6803 and Synechococcus elongatus PCC 7942, respectively), growth was observed.

Growth of these organisms bearing pLybAL11-5 (SEQ ID NO: 19) on liquid BG11-A supplemented with chloramphenicol was examined. It is possible that this activity is very weak and is only observable when present on a multiple-copy plasmid. This may be the case with E. coli, but is not likely with the cyanobacteria. RSF 1010 is a relatively low-copy plasmid, having only 12 copies in E. coli (Frey, J., Bagdasarian, M. M. and Bagdasarian, M. 1992). Gene 113, 101-106). E. coli undergoing rapid division has at most 2 copies of its chromosome, thus at least a 6-fold increase in copy number. A comparable copy number in cyanobacteria for this plasmid is likely. The chromosomal copy numbers of Synechocystis spp. PCC 6803 and Synechococcus elongatus PCC 7942 of 10-12 and 16, respectively, are similar (Labarre, J., Chauvat, F. and Thuriaux, P. 1989. J Bacteriol 171, 3449-57). The results above suggest the presence of a promoter within the asf gene of cyanobacteria.

FIG. 10 shows a possible location of a promoter (or promoters) within the asf gene. Transcription initiation elements have been described by Curtis, S. E. [1994. The transcription apparatus and the regulation of transcription initiation. In The Molecular Biology of Cyanobacteria. Bryant, D. A. (ed). Kluwer Academic Publishers pp. 613-699]. Translation initiation elements have been defined by Sazuka, T. and Ohara, O. (1996. DNA Research 3, 225-232).

Based upon alignment to known SPS enzymes and the presence of a stop codon only two codons upstream, the translation initiation of the asf gene is predicted to start at a GTG start codon. While ATG start codons are the most common, GTG and TTG are less common, but not rare. A typical E. coli-like Shine-Delgarno sequence (GGAG or GAGG) complementary the 3'-end of the 16S rRNA for which the adenine nucleotide is optimally 9-12 bp away from the first nucleotide of the start codon is also present, except with somewhat longer spacing. This sequence is found in about half the genes studied by Sazuka and Ohara. Less optimal spacing is not uncommon, but often leads to reduced levels of expression. There is too little sequence upstream of the Shine-Delgarno sequence but downstream of the MfeI site to incorporate a promoter. It is possible that a partial promoter may be incorporated, but the rest of the promoter would have to produced by the vector sequence of all three plasmids (pLybAL11-5 (SEQ ID NO: 19); pLybAL13f (SEQ ID NO: 51); and pLybAL13r (SEQ ID NO: 52)), which is improbable.

Thus it likely that the promoter activity is located within the asf gene. If the promoter is within the asf gene, one potential position is in front of the SPP domain of asf. This would give the sucrose biosynthetic enzymes of Synechococcus elongatus PCC 7942 a similar quaternary structure to those from Synechocystis spp. PCC 6803. Each organism would have two proteins, an SPS domain with a translationally fused SPP or SPP-like domain and a distinct SPP that may (or may not) interact with each other.

First, it was determined whether the SPP domain of asf could even be translated separately. As can be seen in FIG. 10 and Table 1, there is a TTG start codon immediately upstream of the SPP domain that is preceded by a Shine-Delgarno sequence.

The region surrounding the start codon matches the consensus determined by Sazuka and Ohara for 72 cyanobacterial genes almost as well as the native start codon. While determining cyanobacterial promoters based upon rules established for E. coli promoters, the typical −35 and −10 elements were searched for since the promoter does appear to be active in E. coli. Two possible promoters were identified, as seen in FIG. 10. There remains the possibility of an additional promoter(s) elsewhere in asf.

Example 9

Transfer of Plasmids from E. Coli to Cyanobacteria

Conjugation was used for transfer of the pMMB67EH-based plasmids into cyanobacteria. Protocols exist for the transformation of these organisms (Zang, X., Liu, B., Liu, S., Arunakumara, K. K. I. U. and Zhang, X. 2007. Journal of Microbiology 45, 241-245; Golden, S. S, and Sherman, L. A. 1984. Journal of Bacteriology 158, 36-42), but such approaches were unsuccessful for placing these plasmids into Synechocystis spp. PCC 6803 and Synechococcus elongatus PCC 7942 using natural transformation.

The presence of the plasmids in the cyanobacteria was verified. Transconjugants were analyzed for the presence of plasmid by PCR of the asf/cat gene combination with the oligonucleotides 5'-AGACTACAATTGGGGCGTTTTCT-GTGAG-3" (SEQ ID NO: 7) and 5'-GGTGGTTGT-GTTTGACAGCTTATC-3' (SEQ ID NO: 55), yielding a 3.1 kb product. In addition, plasmids were isolated and analyzed. Cultures of cells grown in BG11-A supplemented with chloramphenicol (at the concentrations described above) are pelleted by centrifugation, resuspended in TE, heat-treated and miniprepped by the Promega Wizard SV Plus miniprep kit. But with poor yield, direct plasmid analysis is difficult. As such, the isolated DNA is transformed into E. coli NEB5α, re-isolated using the Promega Wizard SV Plus miniprep kit, and then subjected to restriction endonuclease analysis.

Example 10

Sucrose Production Assay and Analysis

Synechococcus transformed with pLybAL19 or pLybAL17 (see Example 7) was assayed for sucrose accumulation. Sucrose is measured with BioVision, Inc.'s (Mountain View, Calif.) sucrose assay kit. Assays were run following a 4 hour induction period (increased light to 180 microeinsteins from 50 microeinsteins for pLybAL17 (SEQ ID NO: 46) and increased temperature from 26 to 39° C. for pLybAL19 (SEQ ID NO: 48)). Data was corrected for background glucose present in the cells.

TABLE 1

Nucleotides immediately surrounding the proposed spp start codon. The nucleotides immediately surrounding the proposed spp start codon are compared to the consensus of 72 cyanobacterial genes. Nucleotides matching the consensus are italicized, whereas nucleotides that do not match the consensus are underlined. Nucleotide numbers are relative to the first nucleotide of the start codon.

| | NT# | | | | | | | | | | | | | |
|---|---|---|---|---|---|---|---|---|---|---|---|---|---|---|
| | −10 | −9 | −8 | −7 | −6 | −5 | −4 | −3 | −2 | −1 | 123 | 4 | 5 | 6 |
| Consensus | A/G | A/G | A/T | A/T | A/T | A/T | A/T | A/T | C/T | T/C | ATG | A/G | C | C/T |
| Selo7942 asf | T | G | A | C | T | A | G | C | G | C | GTG | G | C | A |
| Selo7942 spp | T | C | G | C | A | A | A | C | G | C | TTG | A | T | T |

Results showed Synechococcus transformed with pLybAL19 (SEQ ID NO: 48) accumulated 0.78 nanomoles of sucrose per mg of dry biomass. Results also showed that Synechococcus transformed with pLybAL17 (SEQ ID NO: 46) accumulated 0.95 nanomoles of sucrose per mg of dry biomass.

Further analysis for plasmid-based sucrose production in E. coli, Synechocystis spp. PCC 6803, and Synechococcus elongatus PCC 7942 was performed. Because bacteria can consume sucrose, detection may be difficult. As such, cells are grown under suppressing conditions and then assayed shortly after induction. The pyrR promoter may be suppressed by growth with uracil and induced by transfer medium lacking uracil. The nirA promoters can be suppressed by growth with ammonium ions as the nitrogen source and induced by transfer to medium with nitrate as the nitrogen source. The psbAII promoter can be shifted from low light to high light. The dark phase promoters can be shifted from light to dark. And, the $\lambda_{PR}$ promoter can be shifted from low (25° C.) to high (39° C.) temperature.

Example 11

Expression Through Stable Chromosomal Integration

Insertion of sucrose biosynthetic genes can cause a negative impact on cell growth, leading to difficulties in obtaining complete segregation of the 10-16 chromosomes. With normal selection for an antibiotic resistance marker, having additional copies of the marker does not dramatically impact the cells ability to survive in the presence of antibiotic. Therefore, complete chromosomal segregation can be difficult to achieve using antibiotic selection when faced with a negative phenotype.

Deletion of the upp gene (encoding for uracil phosphoribosyltransferase) in most organisms leads to resistance to the otherwise toxic 5-fluorouracil. To obtain complete resistance, all copies of the upp gene must be deleted. Thus integrating into the upp locus of Synechocystis spp. PCC 6803 (SEQ ID NO: 56) and Synechococcus elongatus PCC 7942 (SEQ ID NO: 58) will lead to 5-fluorouracil resistance and allow for positive selection of complete segregation, even in the presence of a negative phenotype.

Example 12

The Upp/Kanamycin Resistance Cassette

Figure 11:
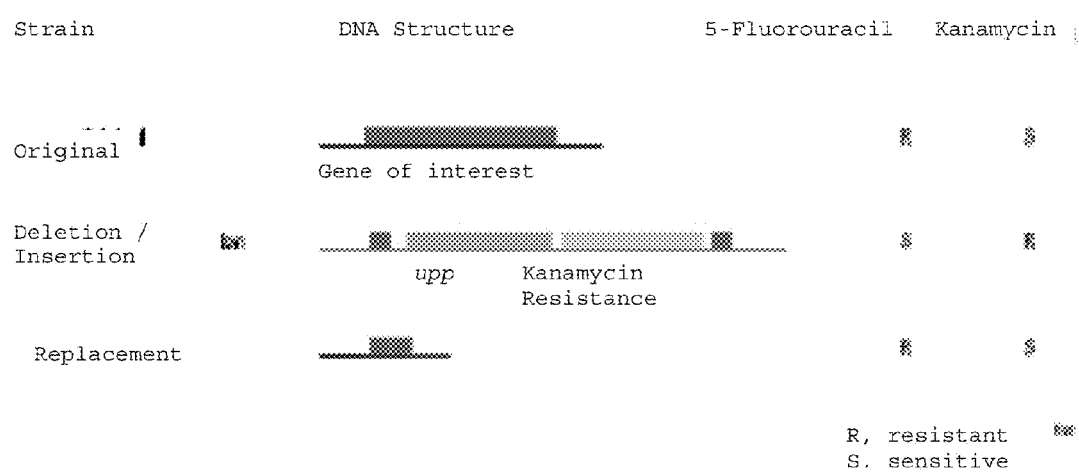
FIG. 11 is a schematic diagram depicting a two-step protocol for markerless deletion of genes in the cyanobacterial genome. This strategy assumes that the cyanobacterial strain being used has had its upp gene deleted. The upp gene will have been deleted during the sucrose biosynthetic insertions. The gene of interest that has been targeted for deletion must be identified. The starting strain is resistant to 5-fluorouracil, but sensitive to kanamycin. The gene is either completely or partially deleted by the insertion of a cassette containing a kanamycin resistance marker and an active upp, making the strain resistant to kanamycin, but sensitive to 5-fluorouracil. The upp and kanamycin resistance markers can then be removed, making the strain once again resistant to 5-fluorouracil, but sensitive to kanamycin. Further details regarding methodology are provided in Example 12.

A general strategy for genomic manipulation using a upp/kanamycin resistance cassette is outlined in FIG. 11. Deletion of a gene is depicted, but the strategy can easily be modified at the "replacement" step for insertions and mutations.

An upp/kanamycin resistance cassette was constructed. The cassette was constructed in Epicentre Biotechnologies CopyControl cloning kit with blunt-end cloning vector pCC1 and *E. coli* strain EPI300 according to manufacturer protocols. The upp gene from *Bacillus subtilis* 168 was amplified from whole cells using the oligonucleotides 5'-AAGAAG-CAAGACAGCGTGTAGCTGCTCTGACTG-3' (SEQ ID NO: 60) and 5'-TCCCGGGATTTGGTACCTTATTTTGT-TCCAAACATGCGGTCACCCGCATC-3' (having restriction endonuclease sites at nucleotide positions 2-7 and 12-17) (SEQ ID NO: 61), yielding the product of SEQ ID NO: 62.

The PCR product was cloned into pCC1 and those bearing the insert were selected for on LB supplemented with chloramphenicol as described in Epicentre Biotechnologies' protocol. The forward orientation, relative to lacZ, was screened for by restriction endonuclease digest, yielding pLybAL7f (SEQ ID NO: 65). The exact sequence of the insert was verified by DNA sequencing with the oligonucleotides 5'-GTAATACGACTCACTATAGGGC-3' (SEQ ID NO: 63) and 5'-CACACAGGAAACAGCTATGACCAT-3' (SEQ ID NO: 64) for candidates 3 and 8 (pLybAL7-3 and pLybAL7-8).

The kanamycin resistance marker from the Lybradyn vector pLybAA1 [originally derived from pACYC177 (Rose, R. E. 1988. Nucleic Acids Res. 16, 356] was amplified with the oligonucleotides 5'-GTCAGTGCACTGCTCTGCCAGT-GTTACAACC-3' (having ApaLI restriction endonuclease sites at nucleotide positions 5-10) (SEQ ID NO: 66) and 5'-CTCAGTGGCGCCAAAACTCACGTTAAGGGATTT-TGGTC-3' (SEQ ID NO: 67) (having NarI restriction endonuclease sites at nucleotide positions 7-12), yielding the product of SEQ ID NO: 68.

The PCR product was digested with ApaLI and NarI and ligated into similarly digested pLybAL7f, creating pLybAL8f (SEQ ID NO: 69). The proper plasmid was selected for on LB supplemented with 50 µg/ml neomycin and examined by restriction endonuclease digestion.

Example 13

Upp Deletion

One strategy to force segregation of chromosomal inserts for the expression of sugars, including sucrose, trehalose, glucosylglycerol, and mannosylfructose, utilizes deletion of upp from the chromosome leading to resistance to 5-fluorouracil. While this has been established in many organisms (such as *E. coli* and *B. subtilis*), it has not previously been established for cyanobacteria, such as Synechocystis spp. PCC 6803 and Synechococcus elongatus PCC 7942.

Testing showed that growth of each of these organisms was completely inhibited by 1 µg/ml, 5-fluorouracil. Growth of Synechocystis spp. PCC 6803 is completely inhibited by 0.5 µg/ml, 5-fluorouracil and is sensitive to as little as little as 0.1 µg/ml, 5-fluorouracil.

The upp gene and surrounding sequences of both Synechocystis spp. PCC 6803 was amplified with the oligonucleotides Sspupp-F (SEQ ID NO: 96) and Sspupp-R (SEQ ID NO: 97). The upp gene and surrounding sequences of Synechococcus elongatus PCC 7942 was amplified with the oligonucleotides Seloupp-F (SEQ ID NO: 98) and Seloupp-R (SEQ ID NO: 99). The PCR products (upp of Synechocystis spp. PCC 6803, SEQ ID NO: 100; upp of Synechococcus elongatus PCC 7942, SEQ ID NO: 101) were then cloned into the Epicentre Biotechnologies' (Madison, Wis.) blunt cloning vector pCC1, as per the manufacturer's instructions.

While the PCR product (SEQ ID NO: 100 or SEQ ID NO: 101) can ligate into pCC1 in either direction, the forward orientation relative to the lac promoter was chosen, generating pLybAL3f (SEQ ID NO: 102) (containing upp of Synechocystis spp. PCC 6803) and pLybAL5f (SEQ ID NO: 103) (containing upp of Synechococcus elongatus PCC 7942), respectively. The inserts were sequenced using oligonucleotides T7long (SEQ ID NO: 104) and M13rev (SEQ ID NO: 105). The nucleotide sequence of upp of Synechocystis spp. PCC 6803 is represented by SEQ ID NO: 111 and the polypeptide sequence by SEQ ID NO: 112. The nucleotide sequence of upp of Synechococcus elongatus PCC 7942 is represented by SEQ ID NO: 113 and the polypeptide sequence by SEQ ID NO: 114.

Plasmid pLybAL4f (SEQ ID NO: 106) was created from pLybAL3f (SEQ ID NO: 102) by removal of the BlpI and ApaLI fragment, blunt ending with T4 DNA polymerase and then recircularizing with T4 DNA ligase. Part of the Synechocystis spp. PCC 6803 upp gene was then deleted by digesting pLybAL4f with AvrII and SgfI, blunt ending with T4 DNA polymerase and then recircularizing with T4 DNA ligase, creating pLybAL9f (SEQ ID NO: 107). The SacI/SphI fragment (SEQ ID NO: 108) bearing the cyanobacterial DNA was excised from pLybAL9f (SEQ ID NO: 107) and ligated into similarly digested pARO180 (sequence not completely known; Parke, D. 1990. Construction of mobilizable vectors derived from plasmids RP4, pUC18 and pUC19. Gene 93:135-137; ATCC 77123), creating pLybAL25. Plasmid pLybAL6fb (SEQ ID NO: 109) was created from pLybAL5f by removal of the SapI and ApaLI fragment, blunt ending with T4 DNA polymerase and then recircularizing with T4 DNA ligase. Part of the *Synechococcus elongatus* PCC 7942 upp gene was then deleted by digesting pLybAL6fb with BssHII and BsaI, blunt ending with T4 DNA polymerase and then recircularizing with T4 DNA ligase, creating pLybAL10fb (SEQ ID NO: 110). The SacI/SphI fragment (SEQ ID NO: 138) bearing the cyanobacterial DNA was excised from pLybAL10fb and ligated into similarly digested pARO180, creating pLybAL26.

Plasmids pLybAL25 and pLybAL26 were placed in *E. coli* 517-1 (ATCC 47055). Plasmids pLybAL25 and pLybAL26 are to be transferred to *Synechocystis* spp. PCC 6803 and *Synechococcus elongatus* PCC 7942 by biparental conjugation. Since these plasmids do not replicate in cyanobacteria, they should function as suicide vectors and cross over into the chromosome, deleting upp on one of the copies of the chromosome. An optimized protocol will enable speeding of segregation without killing the cells by premature exposure to too much 5-fluorouracil.

Example 14

Modification of Sucrose Degradation Enzymes

Cyanobacteria transformed with asf are further engineered to improve sucrose production by modulation of sucrose degradation activity.

The inventors have identified genes encoding invertase homologues in both *Synechocystis* spp. PCC 6803 (nucleotide sequence SEQ ID NO: 70; polypeptide sequence SEQ ID NO: 71) and *Synechococcus elongatus* PCC 7942 (nucleotide sequence SEQ ID NO: 72; polypeptide sequence SEQ ID NO: 73). *Synechocystis* spp. PCC 6803 also encodes a sucraseferredoxin-like protein (nucleotide sequence SEQ ID NO: 74; polypeptide sequence SEQ ID NO: 75) (Machray G. C. et al. 1994. FEBS Lett 354, 123-127).

These genes are deleted using the markerless deletion protocol described in FIG. 11.

Example 15

Modification of Sucrose Degradation Enzymes

Cyanobacteria transformed with asf are further engineered to promote sucrose secretion from the cells.

When in a low osmotic environment, the sucrose may be automatically expunged from the cells, as done with osomoprotectants by some organisms when transitioning from high to low salt environments (Schleyer, M., Schmidt, R. and Bakker, E. P. 1993. Arch Microbiol 160, 424-43; Koo, S. P., Higgins, C. F. and Booth, I. R. 1991. J Gen Microbiol 137, 2617-2625; Lamark, T., Styrvold, O. B. and Strgim, A. R. 1992. FEMS Microbiol. Lett 96, 149-154). Engineering of cyanobacteria can promote such a process.

Cyanobacteria transformed with asf are further engineered to express sucrose permease, such as those used by *E. coli* and *Salmonella* or in the transport of sucrose to nitrogen-fixing cysts of certain cyanobacteria (Jahreis K. et al. 2002. J Bacteriol 184, 5307-5316; Cumino, A. C. 2007. Plant Physiol 143, 1385-97). These genes are cloned and transformed into cyanobacteria according to techniques described above.

Example 16

Sucrose Secretion by Cyanobacteria Transformed with Porin

Sucrose secretion from *Synechocystis* spp. PCC 6803 and *Synechococcus elongatus* PCC 7942 can be facilitated by transformation with sucrose porin.

The gene encoding sucrose porin (scrY) from *Enterobacter sakazakii* ATCC BAA-894 was cloned for expression in *Synechocystis* spp. PCC 6803 and *Synechococcus elongatus* PCC 7942. The function of this gene has been inferred from its sequence and those of its neighbors. *Enterobacter sakazakii* scrY was amplified from chromosomal DNA by PCR with the oligonucleotides EsscrYBamHI-F (SEQ ID NO: 88) and EsscrYSacI-R (SEQ ID NO: 89). The PCR product (SEQ ID NO: 90) was digested with BamHI and SacI and ligated into similarly digested pLybAL19 and cloned into NEB5α, creating pLybAL32 (SEQ ID NO: 91). The scrY gene (nucleic acid SEQ ID NO: 94; polypeptide sequence, SEQ ID NO: 95) was then sequenced with the oligonucleotides EsscrYmidseq-F (SEQ ID NO: 92) and EsscrYmidseq-R (SEQ ID NO: 93). When introduced into the host, this construct allows for the co-expression of the genes scrY and asf under the control of the temperature-inducible promoter. This plasmid was transferred by tri-parental conjugation (as described above) into *Synechocystis* spp. PCC 6803. The transformed *Synechocystis* spp. PCC 6803 is tested for efficacy in the secretion of sucrose. Similar transformation and testing of *Synechococcus elongatus* PCC 7942 follows.

Example 17

Generation of Trehalose Accumulating Cyanobacteria

The trehalose biosynthetic genes encoding trehalose phosphate synthase and trehalose phosphate phosphatase (otsA and otsB, respectively) from *E. coli* are found in a two gene operon, otsBA (SEQ ID NO: 115). The operon was cloned by PCR amplification of *E. coli* K12 genomic DNA with the oligonucleotides EcotsBA-F (SEQ ID NO: 116) and EcotsBA-R (SEQ ID NO: 117). The PCR product was digested with AflII and NheI and was cloned into pLybAL19 (SEQ ID NO: 48), replacing most of the asf gene. The new plasmid, pLybAL23 (SEQ ID NO: 118), places the trehalose biosynthetic genes under the control of the temperature-inducible $\lambda_{PR}$ promoter. The genes were sequenced to verify their integrity with the oligonucleotides EcotsBAmidseq-F (SEQ ID NO: 119) and EcotsBAmidseq-R (SEQ ID NO: 120). Expression of the otsBA operon was then placed under control of the pyrR, psbAII, dnaK and kiaA promoters (as described above) by ligating the AflII (blunt-ended with T4 DNA polymerase)/NheI fragment of pLybAL23 bearing the otsBA operon, into pLybAL15, pLybAL17, pLybAL21 and pLybAL22 digested with SacI (blunt-ended with T4 DNA polymerase) and NheI, creating pLybAL28 (SEQ ID NO: 121), pLybAL29 (SEQ ID NO: 122), pLybAL30 (SEQ ID NO: 123), and pLybAL31 (SEQ ID NO: 124), respectively.

Each of plasmids pLybAL28 (SEQ ID NO: 121), pLybAL29 (SEQ ID NO: 122), pLybAL30 (SEQ ID NO: 123), and pLybAL31 (SEQ ID NO: 124) were moved into *Synechocystis* spp. PCC 6803 by tri-parental conjugation (as described above). Expression of the otsBA operon from pLybAL23 was placed under the control of the *Synechocystis* spp. PCC 6803 and *Synechococcus elongatus* PCC 7942 nirA promoters (as described above) in pLybAL16 and pLybAL18 in the same way as just described for the other promoters, creating pLybAL36 (SEQ ID NO: 125) and pLybAL37 (SEQ ID NO: 126), respectively.

Example 18

Trehalose Assay

Biomass was separated from the culture broth as necessary by centrifugation and residual biomass was removed from the clarified culture broth by filtration through 0.2 micron filter. The culture broth was concentrated to a residue by evaporation under reduced pressure. The concentrated culture broth was dissolved in 1 ml of de-ionized water and then 10 microliters of solution was sampled in a trehalose assay. The biomass collected by centrifugation was transferred to a weigh dish and heated to 100° C. to remove residual moisture. The dry biomass was weighed and then a 100 mg sample was dissolved in 1 ml of de-ionized water. The mixture was then ground and the solids were removed by centrifugation. A 10 microliter sample of the clarified supernatant was diluted 100 fold with de-ionized water and 10 microliters of the diluted sample were tested for trehalose.

The assay for trehalose used a modified procedure of a commercially supplied sucrose assay kit available through Biovision, Inc. The modification to the standard protocol was the substitution of trehalase for the kit supplied invertase enzyme solution.

The kit involves the hydrolysis of trehalose with trehalase to release glucose. The glucose is oxidized by glucose oxidase to produce hydrogen peroxide which is detected by the action of peroxidase in the presence of a colored indicator. The colored indicator is quantitatively measured by its characteristic absorbance at 570 nm to afford the concentration of glucose originally present in the sample.

Trehalase (treA nucleic acid SEQ ID NO: 134 encoding trehalase polypeptide SEQ ID NO: 135) was prepared from the recombinant $E.\ coli$ treA gene which has been engineered into a plasmid and transformed into an $E.\ coli$ host by a similar method as described by Gutierrez C, Ardourel M, Bremer E, Middendorf A, Boos W, Ehmann U. Mol Gen Genet. 1989 June; 217(2-3):347-54. Periplasmic trehalase was cloned from $E.\ coli$ K12, encoded by treA. The treA PCR product (SEQ ID NO: 127) was digested with AflII/XbaI and then ligated into similarly digested pLybCB6, a proprietary plasmid with a constitutive version of the strong $E.\ coli$ trp promoter, creating pLybAL24 (SEQ ID NO: 130). The integrity of the insert was analyzed by sequencing with the oligonucleotides EctreAmidseq-F and EctreAmidseq-R.

A C-terminal $His_6$-tagged version of the trehalase was constructed. The gene was amplified by PCR with the oligonucleotides EctreA-F2 (SEQ ID NO: 131) and EctreA-R2 (SEQ ID NO: 132). The PCR product (SEQ ID NO: 136) was then digested with AflII/XbaI and then ligated into similarly digested pLybAL24, creating pLybAL33 (SEQ ID NO: 133).

Strong constitutive expression of the periplasmic trehalase is detrimental to the cells, causing a strong growth defect at 37° C. This can be significantly alleviated by growing the cells at 30° C.

The protein was expressed in $E.\ coli$ BW25113 on a plasmid pLYBAL24 (SEQ ID NO: 130) which was grown in 2×YT media containing kanamycin. The protein was produced constitutively using the Trp promoter and contains a signal peptide which allows the protein to be transported to the periplasm. Following fermentation and harvesting of the biomass, the enzyme was purified by selective periplasmic release by treatment of the washed and resuspended cell pellet with 2% v/v dichloromethane in 50 mM Tris buffer pH 8. The lysate was separated from cell debris by centrifugation and further processed by concentration using an Amicon ultrafilter fitted with a 10,000 Dalton membrane. The concentrated lysate may be used in assays directly or the enzyme can be further purified by metal ion affinity chromatography using the engineered 6× poly histidine tag on the C-terminus of the enzyme (SEQ ID NO: 137).

Example 19

Solid Phase Trehalose Production

A solid composite fabric covered hydrophilic foam composed of a substrate foam used as a media/moisture reservoir (Foamex Aquazone) was bound to a fabric layer (DuPont Sontara) used as a growth surface measuring 15 cm by 15 cm. The composite material was sterilized by soaking in 70% ethanol in water and then hung in a vertical bioreactor plumbed to deliver solutions to the top of the composite material. The solutions were allowed to percolate through the growing composite surface by gravity. Residual ethanol was removed from the sterilized growing surface by passage of 1 liter of sterile de-ionized water flowing at 0.2 ml/min. The growing surface was equilibrated with culture media by flowing 0.5 liters of BG11A growth medium containing 10 micrograms/ml chloramphenicol through the composite material at 0.2 ml/min.

The equilibrated, sterile growth surface was inoculated by flooding the surface with 10 ml of a 4 day pre-culture of $Synechocystis$ spp. PCC 6803 transformed by plasmid pLYBAL23. Following 30 minute incubation the reactor was turned to a vertical position and the fermentation was begun. The reactor was illuminated with 80 microeisteins of light from a white LED array. Temperature was maintained at 28° C., by a resistive heating device attached to the bioreactor. The reactor was continuously purged with 0.2 micron filtered air at 0.2 L/min and fresh culture media was supplied by pump and gravity percolation through the foam layer of the growth composite at a rate of 0.2 ml/min for 30 minutes every 6 hours. The reactor was run continuously for 4-7 days during which the growth surface of the composite was overspread with a dense lawn of cyanobacteria. Following the initial cultivation period the temperature of the bioreactor was increased to 40° C. and maintained at this temperature for an additional 24 hours. During the elevated temperature period spent culture broth was collected and processed for trehalose determination. At the completion of the fermentation run the biomass was collected by rinsing the growth surface with de-ionized water which can be processed for trehalose assay.

The amount of trehalose produced and retained in the biomass grown on the solid surface was up to 2.5 wt % of the total dry weight biomass recovered from the bioreactor following temperature induction. 0.8 wt % of the dry biomass equivalent weight of trehalose was recovered from the culture medium following temperature induction.

Example 20

Trehalose Production Liquid Phase 1 liter of sterile BG11A media was prepared in a Bioflow reactor to which chloramphenicol was added to a concentration of 10 micrograms/ml. The reactor was then inoculated with a 5% by volume, 4 day pre-culture of $Synechocystis$ spp. PCC 6803 transformed with plasmid pLYBAL23. The reactor was run at 28° C., 300 RPM, 0.2 L/min 0.2 micron filtered air purge and illuminated at 80 microeinsteins of light using a fluorescent bulb array. The cultivation was maintained for 4-7 days following which a 200 ml sample was removed for processing and trehalose assay. The temperature of the fermentation was then elevated to 40° C. for 24 hours. A 200 ml sample was then removed from the bioreactor for processing and trehalose assay.

Following temperature induction the dried biomass produced up to 3 wt % trehalose while the spent culture broth contained 0.3 wt % trehalose equivalent relative to biomass.

REFERENCES

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:

1. A method of producing a fermentable sugar using a photobioreactor, the method comprising:
   (A) inoculating a photobioreactor with a transgenic cyanobacteria engineered to accumulate at least one fermentable sugar selected from the group consisting of sucrose and trehalose, wherein the transgenic cyanobacteria comprises an artificial DNA construct comprising
      (i) a promoter functional in the transgenic cyanobacteria;
      (ii) a nucleotide sequence encoding
         (a) a first polypeptide comprising SEQ ID NO: 2 or a sequence 95% identical thereto having sucrose phosphate synthase and sucrose phosphate phosphatase (ASF) activity; or
         (b) a second polypeptide and a third polypeptide, wherein (1) the second polypeptide comprises SEQ ID NO: 4 or a polypeptide that is 95% identical to SEQ ID NO: 4 having sucrose phosphate synthase (SPS) activity and the third polypeptide comprises SEQ ID NO: 6 or a polypeptide that is 95% identical to SEQ ID NO: 6 having sucrose phosphate phosphatase (SPP) activity; or (2) the second polypeptide comprises SEQ ID NO: 77 or a polypeptide that is 95% identical to SEQ ID NO: 77 having trehalose phosphate synthase (TPS) activity and the third polypeptide comprises SEQ ID NO: 79 or a polypeptide that is 95% identical to SEQ ID NO: 79 having trehalose phosphate phosphatase (TPP) activity; and
      (iii) a transcriptional termination sequence,
      wherein the transgenic cyanobacteria accumulates increased levels of the fermentable sugar compared to a cyanobacteria cell not comprising the DNA construct;
   (B) cultivating the transgenic cyanobacteria in or on the photobioreactor; and
   (C) isolating accumulated fermentable sugar.

2. The method of claim 1, wherein the fermentable sugar accumulates within the transgenic cyanobacteria.

3. The method of claim 1, wherein isolating the accumulated fermentable sugar comprises:
   harvesting at least a portion of the transgenic cyanobacteria from the photobioreactor; and
   recovering the fermentable sugars from the harvest.

4. The method of claim 1, wherein the accumulated fermentable sugar is secreted from the transgenic cyanobacteria and isolated from a cultivation media.

5. The method of claim 1, wherein isolating the accumulated fermentable sugar comprises isolating the accumulated fermentable sugar from the photobioreactor.

6. The method of claim 1, wherein the transgenic cyanobacteria are cultivated to a density of at least about 50 grams of dry biomass per liter equivalent.

7. The method of claim 1, wherein the fermentable sugar comprises at least one sugar selected from the group consisting of sucrose and trehalose.

8. The method of claim 1, wherein the transgenic cyanobacteria comprises a cyanobacteria selected from the group consisting of *Synechococcus* or *Synechocystis*.

9. The method of claim 1, further comprising inducing synthesis of the fermentable sugar by the transgenic cyanobacteria.

10. The method of claim 9, wherein inducing synthesis of the fermentable sugar comprises exposing the transgenic cyanobacteria to an inducing agent selected from the group consisting of temperature, pH, a metabolite, light, an osmotic agent, a heavy metal, and an antibiotic.

11. The method of claim 10, wherein the inducing agent is applied to the photobioreactor by aerosol spray.

12. The method of claim 9, wherein inducing synthesis of the fermentable sugar comprises treating the transgenic cyanobacteria with a salt compound.

13. The method of claim 9, wherein the salt compound is sodium chloride.

14. The method of claim 9, wherein the salt compound is added at a concentration of between about 0.01 mM and 1.5 M or between about 0.2 M and 0.9 M.

15. The method of claim 1, wherein,
   the photobioreactor comprises
      (a) a cultivation support, the cultivation support being non-gelatinous, solid, and suitable for providing nutrients and moisture to the cyanobacteria on at least a portion of a surface thereof, wherein said portion of the surface has a topography that allows the cyanobacteria to adhere thereto when said portion of the surface is oriented non-horizontally; and
      (b) a physical barrier disposed over at least said portion of the surface of the cultivation support; and inoculating the photobioreactor with the cyanobacteria comprises inoculating the cultivation support of the photobioreactor.

16. The method of claim 15, wherein the physical barrier is configured so as to allow inoculation of said portion of the surface of the cultivation support, formation and maintenance of an environment suitable for the cultivation and harvesting of the transgenic cyanobacteria.

17. The method of claim 15, further comprising releasably sealing the physical barrier of the photobioreactor after the inoculation of the cultivation support, wherein the cultivation of the transgenic cyanobacteria occurs while the physical barrier is sealed or unsealed.

18. The method of claim 15, further comprising at least one of: supplying fluid to the cultivation support; supplying nutrients to the cultivation support; or supplying gas to the cultivation support.

19. The method of claim 15, further comprising conveying the photobioreactor to at least one of an inoculation station, a cultivation station, and a harvesting station.

20. A method of producing a fermentable sugar using a photobioreactor, the method comprising:
(A) inoculating a cultivation support of a photobioreactor with a cyanobacteria transformed with the nucleotide sequence of claim 1 that produces a fermentable sugar, wherein the photobioreactor comprises
   (i) the cultivation support, the cultivation support being non-gelatinous, solid, and suitable for providing nutrients and moisture to the photosynthetic microorganisms on at least a portion of a surface thereof, wherein said portion of the surface has a topography that allows the transgenic cyanobacteria to adhere thereto when said portion of the surface is oriented non-horizontally; and
   (ii) a physical barrier disposed over at least said portion of the surface of the cultivation support; and
(B) cultivating the cyanobacteria on the cultivation support; and
(C) isolating the fermentable sugar.

* * * * *